United States Patent
Tada et al.

(10) Patent No.: US 7,652,141 B2
(45) Date of Patent: Jan. 26, 2010

(54) PYRIDONE DERIVATIVES HAVING A BINDING ACTIVITY TO THE CANNABINOID TYPE 2 RECEPTOR

(75) Inventors: Yukio Tada, Osaka (JP); Yasuyoshi Iso, Osaka (JP); Kohji Hanasaki, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 489 days.

(21) Appl. No.: 11/168,640

(22) Filed: Jun. 29, 2005

(65) Prior Publication Data

US 2006/0052411 A1 Mar. 9, 2006

Related U.S. Application Data

(62) Division of application No. 10/250,421, filed as application No. PCT/JP01/11427 on Dec. 26, 2001, now Pat. No. 6,977,266.

(30) Foreign Application Priority Data

Dec. 28, 2000 (JP) ............................. 2000-400768

(51) Int. Cl.
    C07D 215/38 (2006.01)
(52) U.S. Cl. ..................... 546/167; 546/153; 546/159
(58) Field of Classification Search .................. 546/153, 546/159, 167
    See application file for complete search history.

(56) References Cited

U.S. PATENT DOCUMENTS

| | | | |
|---|---|---|---|
| 4,542,139 | A | 9/1985 | Hitzel et al. |
| 6,017,919 | A | 1/2000 | Inaba et al. |
| 6,509,352 | B1 | 1/2003 | Inaba et al. |
| 6,977,266 | B2 | 12/2005 | Tada et al. |
| 6,997,266 | B2 * | 2/2006 | Jackson et al. ............... 166/384 |
| 2005/0101590 | A1 | 5/2005 | Yasui et al. |
| 2008/0103139 | A1 | 5/2008 | Ishizuka et al. |
| 2008/0312292 | A1 | 12/2008 | Yasui et al. |

FOREIGN PATENT DOCUMENTS

| | | | |
|---|---|---|---|
| DE | 3209866 | * | 9/1983 |
| EP | 0 481 802 | | 4/1992 |
| EP | 481802 | * | 4/1992 |
| WO | 99/02499 | | 1/1999 |
| WO | 99/18096 | | 4/1999 |
| WO | 99/31066 | | 6/1999 |
| WO | 00/69826 | | 11/2000 |
| WO | 03/070277 | | 8/2003 |
| WO | 2006/046778 | | 5/2006 |

OTHER PUBLICATIONS

Walfred S. Saari et al., "Synthesis and Evaluation of 2-Pyridinone Derivatives as HIV-1-Specific Reverse Transcriptase Inhibitors. 2. Analogues of 3-Aminopyridin-2(1H)-one", J. Med. Chem., vol. 35, pp. 3792-3802, 1992.
Lars G. Beholz et al., "Formation of Dihydropyridone- and Pyridone-Based Peptide Analogs through Aza-Annulation of β-Enamino Ester and Amide Substrates with α-Amido Acrylate Derivates", J. Org. Chem., vol. 62, pp. 1033-1042, 1997.
Takuo Chiba et al., "Studies on Amino Acid Derivatives. IV. [1)] Synthesis of 3-Amino-2(1H)-pyridone Derivatives Using 4-Ethoxymethylene-2-phenyl-5-oxazolone", Chem. Pharm. Bull., vol. 33, No. 7, pp. 2731-2734, 1985.
Daniela Parolaro, "Presence and Functional Regulation of Cannabinoid Receptors in Immune Cells", Life Science, vol. 65, Nos. 6/7, pp. 637-644, 1999.
Kristy D. Lake et al., "Cardiovascular Effects of Anandamide in Anesthetized and Conscious Normotensive and Hypertensive Rats", Hypertension, vol. 29, pp. 1204-1210, 1997.
Sean Munro et al., "Molecular characterization of a peripheral receptor for cannabinoids", Nature, vol. 365, pp. 61-65, 1993.
Jacob M. Hoffman et al., "Synthesis and Evaluation of 2-Pyridinone Derivatives as HIV-1-Specific Reverse Transcriptase Inhibitors. 4. 3[2-(Benzoxazol-2-yl)ethyl]-5-ethyl-6-methylpyridin-2(1H)-one and Analogues", J. Med. Chem., vol. 36, pp. 953-966, 1993.
Otto Meth-Cohn et al., "A Versatile New Synthesis of Quinolines and Related Fused Pyridines. Part 12. [1] A General Synthesis of 2-Chloropyridines and 2-Pyridones", J. Chem. Soc. Perkin. Trans., vol. 1, pp. 1173-1182, 1984.
Canadian Office Action dated Feb. 14, 2008 issued in connection with Canadian application No. 2,433,158 corresponding to parent application of present U.S. application.
Japanese Office Action mailed Mar. 4, 2008 issued in connection with Japanese application No. 2002-554662 corresponding to the present U.S. application.

* cited by examiner

Primary Examiner—D. Margaret Seaman
(74) Attorney, Agent, or Firm—Wenderoth, Lind & Ponack, L.L.P.

(57) ABSTRACT

It was found that the compound having a binding activity to the cannabinoid type 2 receptor represented by the formula (I):

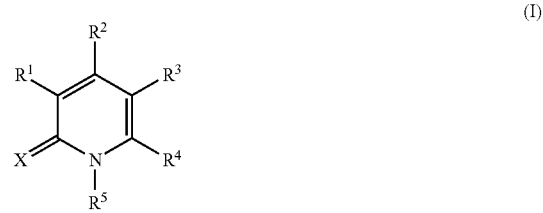

wherein $R^1$ is a group represented by the formula: —$Y^1$—$Y^2$—$Y^3$—$R^a$ wherein $Y^1$ is single bond or the like; $Y^2$ is —C(=O)—NH— or the like; $Y^3$ is optionally substituted aryl or the like; $R^2$ is hydrogen or the like; $R^3$ is alkyl or the like; $R^4$ is alkyl or the like; $R^5$ is optionally substituted alkyl or the like; or $R^3$ and $R^4$ taken together with the adjacent atom form cyclic group or the like.

7 Claims, No Drawings

PYRIDONE DERIVATIVES HAVING A BINDING ACTIVITY TO THE CANNABINOID TYPE 2 RECEPTOR

This application is a divisional application of Ser. No. 10/250,421, filed Jun. 30, 2003, which is a 371 application of PCT/JP01/11427, filed Dec. 26, 2001, now U.S. Pat. No. 6,977,266.

TECHNICAL FIELD

The present invention relates to pyridone derivatives. In detail, the present invention relates to pharmaceutical compositions having a binding activity to the cannabinoid type 2 receptor (pharmaceutical compositions containing pyridone derivatives having an antagonistic activity or an agonistic activity to the cannabinoid type 2 receptor).

BACKGROUND ART

Cannabinoid was discovered as the main active substance contained in marijuana in 1960 and found to exhibit an activity in the central nervous system (illusion, euphoria, sensory confusion of time and space) and in the peripheral cell system (immunosuppressive activity, anti-inflammatory activity, analgesic activity).

After that, anandamide and 2-arachidonoylglycerol produced from arachidonic acid-containing phospholipids were discovered as endogenous agonists to the cannabinoid receptor. These endogenous agonists are known to exhibit an activity to the central nervous system and an activity to the peripheral cell system. It is disclosed in Hypertension (1997) 29, 1204-1210 that anandamide exhibits an activity to the cardiovascular system.

A cannabinoid type 1 receptor discovered in 1990 was found to be distributed over the central nervous system such as the brain. Agonists to this receptor were found to suppress the release of neurotransmitters to cause central actions such as analgesic effect or illusion. A cannabinoid type 2 receptor discovered in 1993 was found to be distributed over immune tissues such as the spleen. Agonists to this receptor were found to suppress an activation of immunocyte or inflammatory cells to exhibit an immunosuppressive activity, an anti-inflammatory activity and an analgesic activity (Nature, 1993, 365, 61-65).

Therefore, antagonists or agonists to the cannabinoid type 2 receptor are expected as immunosuppressive agents, anti-inflammatory agents, and analgesic agents (Nature, 1998, 349, 277-281).

In WO99/02499 and WO00/40562, described as a compound having an antagonistic activity or an agonistic activity to the cannabinoid type 2 receptor are quinolone derivatives. These quinolone derivatives are the compounds having a benzene ring substituted with dialkoxy and a nitrogen atom of the quinolone ring substituted with a hydrogen atom or methyl as shown below.

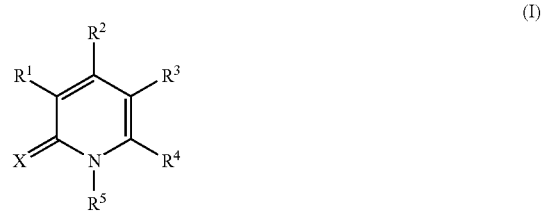

On the other hand, disclosed in EP0481802 and J. Med. Chem. 1998, 36, 953-066 are pyridone derivatives having anti-HIV activity.

Furthermore, disclosed in Japanese Patent Publication Kokai 1983-46068 is a quinolone derivative represented by (A) as an intermediate of medicament, and in J. Chem. Soc. Perkin. Trans. I (1984), p1173-1182 discloses a pyridone derivative represented by (B).

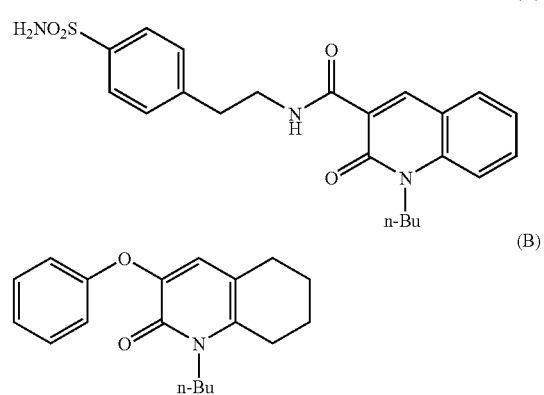

DISCLOSURE OF INVENTION

The present invention provides pyridone derivatives explained below as novel compounds having an antagonistic activity or an agonistic activity to the cannabinoid type 2 receptor.

That is, the present invention relates to:

(1) a pharmaceutical composition having a binding activity to the cannabinoid type 2 receptor which contains as an active ingredient a compound of the formula (I):

wherein $R^1$ is hydrogen, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro, or a group represented by the formula: $-Y^1-Y^2-Y^3-R^a$ wherein $Y^1$ and $Y^3$ each is independently single bond or optionally substituted alkylene; $Y^2$ is single bond, $-O-$, $-O-C(=O)-$, $-O-C(=O)-O-$, $-O-C(=O)-NR^b-$, $-O-SO_2-$, $-NR^b-$, $-NR^b-C(=O)-$, $-NR^b-SO_2-$, $-NR^b-C(=NH)-$, $-NR^b-C(=O)-O-$, $-NR^b-C(=O)-NR^b-$, $-NR^b-C(=O)-NR^b-SO_2-$, $-NR^b-C(=S)-$, $-NR^b-C(=S)-NR^b-$, $-NR^b-SO_2-NR^b-$, $-NR^b-C(=NH)-NR^b-$, $-S-$, $-SO_2-O-$, $-SO_2-NR^b-$, $-SO_2-NR^b-C(=O)-NR^b-$, $-C(=O)-O-$, $C(=O)-NR^b-$, $-C(=O)NR^b-C(=O)-$, $C(=O)-NR^b-C(=S)-$, $-C(=S)-NR^b-$, —C(=S)—NR$^b$—C(=O)—, —C(=NH)—NR$^b$—, —C(=O)—, —C(=O)—NR$^b$—C(=NR$^b$)—, or —C(=O)—NR$^b$—NR$^b$—; R$^a$ is optionally substituted alkyl, optionally substituted alkenyl, optionally substituted alkynyl, optionally substituted carbocyclic group, optionally substituted heterocyclic group, or acyl; R$^b$ each is independently hydrogen, optionally substituted alkyl, optionally substituted alkenyl, optionally substituted alkynyl, optionally substituted carbocyclic group, optionally substituted heterocyclic group, acyl, hydroxy, or alkoxy;

R$^2$ is hydrogen, optionally substituted alkyl, optionally substituted alkenyl, optionally substituted alkynyl, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro, or a group represented by the formula: —Y$^4$—R$^c$ wherein Y$^4$ is single bond, —O—, —S—, —SO—, —SO$_2$—, —NH—, —C(=O)—, —CH$_2$—, —C(=O)—NH—, or —NH—C(=O)—; R$^c$ is optionally substituted carbocyclic group or optionally substituted heterocyclic group;

R$^3$ and R$^4$ each is independently hydrogen, optionally substituted alkyl, optionally substituted alkenyl, optionally substituted alkynyl, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro or a group represented by the formula: —Y$^5$—R$^d$ wherein Y$^5$ is single bond, optionally substituted alkylene, alkenylene, alkynylene, —O—, —S—, —SO—, —SO$_2$—, —NH—, —C(=O)—, —CH$_2$—, —C(=O)—NH-E-, or —NH—C(=O)—; E is single bond or optionally substituted alkylene; R$^d$ is optionally substituted carbocyclic group or optionally substituted heterocyclic group;

R$^5$ is hydrogen, optionally substituted alkyl which may have heteroatom and/or unsaturated bond or a group represented by the formula: —Y$^6$—R$^e$ wherein Y$^6$ is single bond, optionally substituted alkylene, alkenylene, alkynylene, —O—, —S—, —SO—, —SO$_2$—, —NH—, —C(=O)—, —CH$_2$—, —C(=O)—NH-E-, or —NH—C(=O)—; E is single bond or optionally substituted alkylene; R$^e$ is optionally substituted carbocyclic group or optionally substituted heterocyclic group; or any one of combinations of R$^2$ and R$^3$, R$^3$ and R$^4$, and R$^4$ and R$^5$, taken together with the adjacent atoms form optionally substituted cyclic group which may have heteroatom and/or unsaturated bond;

X is S or O;

provided that the case wherein R$^3$ and R$^4$ taken together with the adjacent atoms form a benzene ring di-substituted with alkoxy, and R$^5$ is hydrogen or methyl is excluded;

a prodrug, a pharmaceutically acceptable salt or solvate thereof, (2) the pharmaceutical composition according to (1) which has a binding activity to the cannabinoid type 2 receptor wherein R$^5$ is optionally substituted C$_2$ or more alkyl which may have heteroatom and/or unsaturated bond or a group represented by —Y$^6$—R$^e$ wherein Y$^6$ and R$^e$ are as defined in (1), (3) the pharmaceutical composition according to (2) which has a binding activity to the cannabinoid type 2 receptor wherein R$^5$ is optionally substituted C$_3$ or more alkyl which may have heteroatom and/or unsaturated bond or a group represented by the formula: —Y$^6$—R$^e$ wherein Y$^6$ is optionally substituted alkylene; R$^e$ is optionally substituted aryl, optionally substituted cycloalkyl, optionally substituted heteroaryl, or optionally substituted heterocyclic group, (4) the pharmaceutical composition according to any one of (1) to (3) which has a binding activity to the cannabinoid type 2 receptor wherein R$^1$ is a group represented by the formula: —Y$^1$—Y$^2$—Y$^3$—R$^a$ wherein Y$^1$, Y$^2$, Y$^3$, R$^a$, and R$^b$ are as defined in (1), (5) the pharmaceutical composition according to (4) which has a binding activity to the cannabinoid type 2 receptor wherein R$^1$ is a group represented by the formula: —Y$^1$—Y$^2$—Y$^3$—R$^a$ wherein Y$^1$, Y$^2$, Y$^3$, and R$^a$ are as defined in (1); Y$^2$ is —O—, —NR$^b$—C(=O)— or —C(=O)—NR$^b$—; R$^b$ is hydrogen or optionally substituted alkyl, (6) the pharmaceutical composition according to any one of (1) to (5) which has a binding activity to the cannabinoid type 2 receptor wherein R$^3$ and R$^4$ are not taken together, (7) the pharmaceutical composition according to (6) which has a binding activity to the cannabinoid type 2 receptor wherein R$^3$ is hydrogen, optionally substituted alkyl, halogen, or a group represented by the formula: —Y$^5$—R$^d$ wherein Y$^5$ is single bond, optionally substituted alkylene, alkenylene, alkynylene; R$^d$ is optionally substituted aryl or optionally substituted heteroaryl;

R$^4$ is hydrogen or optionally substituted alkyl;

provided that the case wherein R$^3$ and R$^4$ are hydrogen at the same time is excluded, (8) the pharmaceutical composition according to any one of (1) to (5) which has a binding activity to the cannabinoid type 2 receptor wherein R$^3$ and R$^4$ taken together with the adjacent atoms form optionally substituted cyclic group which may have heteroatom and/or unsaturated bond;

provided that the case wherein the optionally substituted cyclic group is optionally substituted benzene ring is excluded, (9) the pharmaceutical composition according to (1) which has a binding activity to the cannabinoid type 2 receptor wherein R$^1$ is hydrogen, cyano, formyl, carboxy, isothiocyanato, amino, hydroxy, carbamoyl, or a group represented by the formula: —Y$^1$—Y$^2$—Y$^3$—R$^a$ wherein Y$^1$ and Y$^3$ each is independently single bond or optionally substituted alkylene (the substituent is halogen, alkenylene, hydroxy, azide, amino, acylamino, alkylsulfonylamino, alkenyloxycarbonylamino, alkoxycarbonylamino, alkenylamino, arylcarbonylamino, heteroarylcarbonylamino, cyano, alkoxy, alkylsulfonyloxy, trialkylsilyloxy, oxo, methylene, halogenated alkoxycarbonyloxy formyloxy and/or acylthio); Y$^2$ is single bond, —O—, —O—C(=O)—, —O—C(=O)—O—, —O—C(=O)—NH—, —NR$^b$—C(=O)—, —NH—C(=O)—O—, —NH—C(=O)—NH—, —NH—C(=S)—NH—, —S—, —SO$_2$—O—, —SO$_2$—NH—, —SO$_2$—NH—C(=O)—NH—, —C(=O)—O—, —C(=O)—NR$^b$—; —C(=S)—NH—, —C(=O)—NH—C(=O)—, —C(=O)—NH—C(=S)—O—, —C(=O)—, —C(=O)—NR$^b$—C(=NR$^b$)—, or —C(=O)—NH—NR$^b$—; R$^a$ is optionally substituted alkyl (the substituent is hydroxy and/or aralkyl), alkenyl, optionally substituted aryl (the substituent is carboxy, optionally substituted amino, alkoxy, alkylthio, alkylenedioxy, halogen, alkyl, hydroxy, halogenated alkyl and/or halogenated alkoxy), optionally substituted cycloalkyl (the substituent is aryl and/or hydroxy), optionally substituted cycloalkenyl (the substituent is alkenylene, hydroxy, alkylsulfonyloxy, azide, amino and/or acylamino), optionally substituted heteroaryl (the substituent is oxo, heteroaryl, halogen, aryl and/or alkyl), or optionally substituted heterocyclic group (the substituent is aryl optionally substituted halogen, aralkyl, acyl, arylcarbonyl, cycloalkylcarbonyl, alkylsulfonyl, arylsulfonyl, alkyl and/or halogenated alkylcarbonyl); $R^b$ is hydrogen, alkyl, acyl, hydroxy and/or alkoxy;

$R^2$ is hydrogen, alkyl, alkenyl, or a group represented by the formula: —$Y^4R^c$ wherein $Y^4$ is —O—; $R^c$ is heteroaryl;

$R^3$ is hydrogen, alkyl, halogen, or a group represented by the formula: —$Y^5$—$R^d$ wherein $Y^5$ is single bond, alkylene, —C(=O)—NH-alkylene-; $R^d$ is optionally substituted aryl (the substituent is halogen, alkyl, alkoxy, alkylenedioxy and/or halogenated alkyl) or optionally substituted heteraryl (the substituent is halogen, alkyl, alkoxy, alkylenedioxy and/or halogenated alkyl);

$R^4$ is hydrogen, alkyl, or a group represented by the formula: —$Y^5$—$R^d$ wherein $Y^5$ is single bond; $R^d$ is aryl;

$R^5$ is hydrogen, optionally substituted $C_3$ or more alkyl which may have heteroatom and/or unsaturated bond (the substituent is halogen, hydroxy, azide, amino, alkoxy, alkenyloxy, alkylsulfonyloxy, acylthio, acylamino, arylcarbonylamino, cycloalkylcarbonylamino, halogenated alkylcarbonylamino, alkylsulfonylamino, arylsulfonylamino, formyl, oxo and/or cyano) or a group represented by the formula: —$Y^6$—$R^e$ wherein $Y^6$ is alkylene; $R^e$ is optionally substituted aryl, optionally substituted cycloalkyl, optionally substituted heteroaryl or optionally substituted heterocyclic group; or $R^2$ and $R^3$ taken together with the adjacent atoms form optionally substituted cyclic group (the substituent is oxo and/or hydroxy), $R^3$ and $R^4$ taken together with the adjacent atoms form optionally substituted cyclic group which may have heteroatom and/or unsaturated bond (the substituent is acyl, aralkyl, alkenylene and/or alkylene), or $R^4$ and $R^5$ taken together with the adjacent atoms form optionally substituted carbocyclic group which may have unsaturated bond (the substituent is alkenylene),

(10) the pharmaceutical composition according to any one of (1) to (9) which has a binding activity to the cannabinoid type 2 receptor as an anti-inflammatory agent,

(11) the pharmaceutical composition according to any one of (1) to (9) which has a binding activity to the cannabinoid type 2 receptor as an immunosuppressive agent,

(12) the pharmaceutical composition according to any one of (1) to (9) which has a binding activity to the cannabinoid type 2 receptor as a nephritis treating agent,

(13) the pharmaceutical composition according to any one of (1) to (9) which has a binding activity to the cannabinoid type 2 receptor of any one of (1) to (9) as an analgesic agent,

(14) a compound of the formula (I):

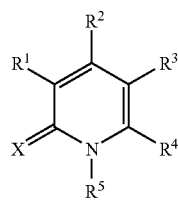

wherein $R^1$ is a group represented by the formula: —$Y^1$—$Y^2$—$Y^3$—$R^a$ wherein $Y^1$, $Y^2$, $Y^3$ and $R^b$ are as defined in (1); $R^a$ is optionally substituted carbocyclic group, optionally substituted heterocyclic group or acyl;

$R^2$ is hydrogen or optionally substituted alkyl;

$R^3$ is optionally substituted alkyl, halogen or a group represented by the formula: —$Y^5$—$R^d$ wherein $Y^6$ is single bond or alkylene; $R^d$ is as defined in (1);

$R^4$ is hydrogen or optionally substituted alkyl;

$R^5$ is optionally substituted $C_3$ or more alkyl which may have heteroatom and/or unsaturated bond or a group represented by the formula: —$Y^6$—R wherein $Y^6$ and $R^e$ are as defined in (1);

or $R^3$ and $R^4$ taken together with the adjacent atoms form optionally substituted cyclic group which may have heteroatom and/or unsaturated bond;

X is as defined in (1);

provided that when $R^3$ and $R^4$ taken together with adjacent atoms form optionally substituted benzene ring, $R^1$ is a group represented by the formula: —$Y^1$—$Y^2$—$Y^3$—$R^a$ wherein $Y^1$ is single bond; $Y^3$ is optionally substituted alkylene; $Y^2$ is —$NR^b$—C(=O)—, —C(=O)—$NR^b$—; $R^a$ is optionally substituted carbocyclic group, optionally substituted heterocyclic group; and $R^b$ is hydrogen or optionally substituted alkyl; and the followings are excluded: the case wherein $R^3$ and $R^4$ taken together with adjacent atoms form unsubstituted carbocyclic group (provided that the bond between carbon atom substituted with $R^3$ and carbon atom substituted $R^4$ is the double bond, and the other bonds between carbon atoms are single bond), and $R^1$ is a group represented by the formula: —$Y^1$—$Y^2$—$Y^3$—$R^a$ wherein $Y^1$ and $Y^3$ are single bond; $Y^2$ is —O—; Re is phenyl), and the case wherein $R^3$ and $R^4$ taken together with adjacent atoms form benzene and $R^1$ is a group represented by the formula: —$Y^1$—$Y^2$—$Y^3$—$R^a$ wherein $Y^1$ is single bond; $Y^3$ is ethylene; $Y^2$ is —C(=O)—$NR^b$—; and $R^a$ is phenyl substituted with sulfamoyl; a prodrug, a pharmaceutically acceptable salt or solvate thereof,

(15) the compound according to (14) wherein $R^1$ is a group represented by the formula: —$Y^1$—$Y^2$—$Y^3$—$R^a$ wherein $Y^1$, $Y^3$, $R^a$ are as defined in (14); $Y^2$ is —O—, —$NR^b$—C(=O)— or —C(=O)—$NR^b$—; $R^b$ is hydrogen or optionally substituted alkyl; a prodrug, a pharmaceutically acceptable salt or solvate thereof,

(16) the compound according to (14) or (15) wherein $R^3$ and $R^4$ are not taken together;

a prodrug, a pharmaceutically acceptable salt or solvate thereof,

(17) the compound according to (14) or (15) wherein $R^3$ and $R^4$ taken together with the adjacent atoms form cyclic group which may have heteroatom and/or unsaturated bond;

a prodrug, a pharmaceutically acceptable salt or solvate thereof,

(18) the compound according to (14) wherein $R^1$ is a group represented by the formula: —$Y^1$—$Y^2$—$Y^1$—$R^a$ wherein $Y^1$ is single bond; $Y^3$ is optionally substituted alkylene; $Y^2$ is —O—, —NH—C(=O)—, or —C(=O)—NH—; $R^a$ is optionally substituted carbocyclic group or optionally substituted heterocyclic group;

$R^2$ is hydrogen;

$R^3$ is alkyl, halogen or a group represented by the formula: —$Y^5$—$R^d$ wherein $Y^5$ is single bond; $R^d$ is optionally substituted carbocyclic group or optionally substituted heterocyclic group;

$R^4$ is hydrogen or alkyl;

$R^5$ is optionally substituted $C_3$ or more alkyl or a group represented by the formula: —$Y^6$—$R^e$ wherein $Y^6$ is optionally substituted alkylene; $R^e$ is optionally substituted aryl, optionally substituted cycloalkyl or optionally substituted heteroaryl; or $R^3$ and $R^4$ taken together with the adjacent atoms form cyclic group which may have heteroatom and/or unsaturated bond;

a prodrug, a pharmaceutically acceptable salt or solvate thereof,

(19) a library of compound of the formula (I):

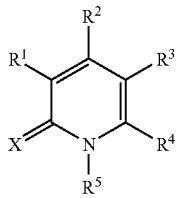

(I)

wherein $R^1$ is a group represented by the formula: $-Y^1-Y^2-Y^3-R^a$ wherein $Y^1$ is single bond; $Y^3$ is single bond or optionally substituted alkylene; $Y^2$ is $-C(=O)-NR^b-$; $R^a$ is optionally substituted carbocyclic group or optionally substituted heterocyclic group; $R^b$ is hydrogen;

$R^2$ is hydrogen;

$R^3$ and $R^4$ taken together with adjacent atoms form unsubstituted carbocyclic group (provided that the bond between carbon atom substituted with $R^3$ and carbon atom substituted $R^4$ is the double bond, and the other bonds between carbon atoms are single bond)

$R^5$ is $C_3$ or more alkyl or a group represented by the formula: $-Y^6-R^e$ wherein $Y^6$ is optionally substituted alkylene; $R^e$ is optionally substituted aryl optionally substituted cycloalkyl or optionally substituted heteroaryl;

X is S or O,

(20) the compound according to (19);

provided that the case wherein $R^3$ and $R^4$ taken together with adjacent atoms form 6-membered carbocyclic group (provided that the bond between carbon atom substituted with $R^3$ and carbon atom substituted $R^4$ is the double bond, and the other bonds between carbon atoms are single bond), and $R^1$ is a group represented by the formula: $-Y^1-Y^2-Y^3-R^a$ wherein $Y^1$ and $Y^3$ are single bond; $Y_2$ is $-O-$; $R^a$ is phenyl is excluded;

a prodrug, a pharmaceutically acceptable salt or solvate thereof,

(21) a library of compound of the formula (I):

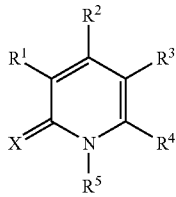

(I)

wherein $R^1$ is a group represented by the formula: $-Y^1-Y^2-Y^3-R^a$ wherein $Y^1$ is single bond; $Y^2$ is $-C(=O)-NR^b-$; $Y^3$ is single bond or optionally substituted alkylene; $R^a$ is optionally substituted carbocyclic group or optionally substituted heterocyclic group; $R^b$ is hydrogen;

$R^2$ is hydrogen;

$R^3$ is a group represented by the formula: $-Y^5-R^d$ wherein $Y^5$ is single bond; $R^d$ is optionally substituted aryl optionally substituted cycloalkyl or optionally substituted heteroaryl $R^4$ is hydrogen or alkyl;

$R^5$ is $C_3$ or more alkyl or a group represented by the formula: $-Y_6-R^e$ wherein $Y^6$ is optionally substituted alkylene; $R^e$ is optionally substituted aryl optionally substituted cycloalkyl or optionally substituted heteroaryl;

X is S or O

(22) the compound according to (21);

a prodrug, a pharmaceutically acceptable salt or solvate thereof,

(23) a library of compound of the formula (I):

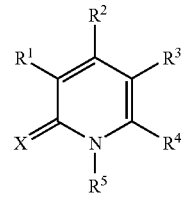

(I)

wherein $R^1$ is a group represented by the formula: $-Y^1-Y^2-Y^3-R^a$ wherein $Y^1$ and $Y^3$ are single bond; $Y^2$ is $-NR^b-C(=O)-$; $R^a$ is optionally substituted carbocyclic group; $R^b$ is hydrogen;

$R^2$ is hydrogen;

$R^3$ and $R^4$ each is independently alkyl;

$R^5$ is $C_3$ or more alkyl;

X is O,

(24) the compound according to (23);

a prodrug, a pharmaceutically acceptable salt or solvate thereof,

(25) a compound of the formula:

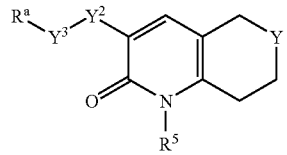

wherein Y is single bond, $-NH-$, $-O-$, or $-(CH_2)_{1,5}-$;

$Y^2$ is $-C(=O)-NH-$ or $-NH-C(=O)-$;

$Y^3$ is single bond or optionally substituted alkylene;

$R^a$ is optionally substituted aryl, optionally substituted cycloalkyl, optionally substituted cycloalkenyl, optionally substituted heteroaryl or optionally substituted heterocyclic group;

$R^5$ is $C_3$ or more alkyl or a group represented by the formula: $-Y^6-R^e-$ wherein $Y^6$ is alkylene, $R^e$ is optionally substituted aryl, optionally substituted cycloalkyl, optionally substituted heteroaryl, or optionally substituted heterocyclic group; a prodrug, a pharmaceutically acceptable salt or solvate thereof,

(26) the compound according to (25) wherein Y is $-(CH_2)_3-$; a prodrug, a pharmaceutically acceptable salt or solvate thereof,

(27) a compound of the formula:

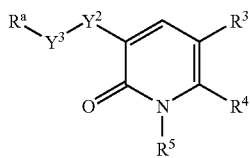

wherein $R^3$ and $R^4$ each is independently alkyl;
$Y^2$ is —C(=O)—NH— or —NH—C(=O)—;
$Y^3$ is single bond or optionally substituted alkylene;
$R^a$ is optionally substituted aryl, optionally substituted cycloalkyl, optionally substituted cycloalkenyl, optionally substituted heteroaryl or optionally substituted heterocyclic group;
$R^5$ is $C_3$ or more alkyl or a group represented by the formula: —$Y^6$—$R^e$— wherein $Y^6$ is alkylene; $R^e$ is optionally substituted aryl, optionally substituted cycloalkyl, optionally substituted heteroaryl, or optionally substituted heterocyclic group; a prodrug, a pharmaceutically acceptable salt or solvate thereof,

(28) the compound according to any one of (25) to (27) wherein $Y^3$ is optionally substituted alkylene;

a prodrug, a pharmaceutically acceptable salt or solvate thereof,

(29) a pharmaceutical composition which contains as an active ingredient a compound of (14) to (18), (20), (22), and (24) to (28),

(30) the pharmaceutical composition according to (29) which has a binding activity to the cannabinoid type 2 receptor,

(31) the pharmaceutical composition according to (29) which is useful as an anti-inflammatory agent,

(32) the pharmaceutical composition according to (29) which is useful as an immunosuppressive agent,

(33) the pharmaceutical composition according to (29) which is useful as a nephritis treating agent,

(34) the pharmaceutical composition according to (29) which is useful as an analgesic agent,

(35) a method for treating the diseases related to the cannabinoid type 2 receptor which comprises the administration of a compound of any one of (1) to (13),

(36) use of the compound according to (1) to (13) for the preparation of a treating agent against the diseases related to the cannabinoid type 2 receptor, Furthermore, the present invention includes the following invention.

[1] A pharmaceutical composition having a binding activity to the cannabinoid type 2 receptor which contains as an active ingredient a compound of the formula (I):

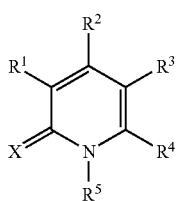

(I)

wherein $R^1$ is hydrogen, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro, or a group represented by the formula: —$Y^1$—$Y^2$—$Y^3$—$R^a$ wherein $Y^1$ and $Y^3$ each is independently single bond or optionally substituted alkylene; $Y^2$ is single bond, —O—, —O—C(=O)—, —O—C(=O)—O—, —O—C(=O)—$NR^b$—, —O—$SO_2$—, —$NR^b$—, —$NR^b$—C(=O)—, —$NR^b$—$SO_2$—, —$NR^b$—C(=NH)—, —$NR^b$—C(=O)—O—, —$NR^b$—C(=O)—$NR^b$—, —$NR^b$—C(=O)—$NR^b$—$SO_2$—, —$NR^b$—C(=S)—, —$NR^b$—C(=S)—$NR^b$—, —$NR^b$—$SO_2$—$NR^b$—, —$NR^b$—C(=NH)—$N^b$—, —S—, —$SO_2$—O—, —$SO_2$—$NR^b$—, —$SO_2$—$NR^b$—C(=O)—$NR^b$—, —C(=O)—O—, —C(=O)—$NR^b$—, C(=O)—$NR^b$—C(=O)—, —C(=O)—$NR^b$—C(=S)—, —C(=S)—$NR^b$—, —C(=S)—$NR^b$—C(=O)—, or —C(=NH)—$NR^b$—; $R^a$ is optionally substituted alkyl, optionally substituted alkenyl, optionally substituted alkynyl, optionally substituted carbocyclic group, optionally substituted heterocyclic group, or acyl; $R^b$ each is independently hydrogen, optionally substituted alkyl, optionally substituted alkenyl, optionally substituted alkynyl, optionally substituted carbocyclic group, optionally substituted heterocyclic group, or acyl;

$R^2$ is hydrogen, optionally substituted alkyl, optionally substituted alkenyl, optionally substituted alkynyl, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro, or a group represented by the formula: —$Y^4$—$R^c$ wherein $Y^4$ is single bond, —O—, —S—, —SO—, —$SO_2$—, —NH—, —C(=O)—, —$CH_2$—, —C(=O)—NH—, or —NH—C(=O)—; $R^c$ is optionally substituted carbocyclic group or optionally substituted heterocyclic group;

$R^3$ is hydrogen, optionally substituted alkyl, optionally substituted alkenyl, optionally substituted alkynyl, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro or a group represented by the formula: —$Y^5$—$R^d$ wherein $Y^5$ is single bond, optionally substituted alkylene, alkenylene, alkynylene, —O—, —S—, —SO—, —$SO_2$—, —NH—, —C(=O)—, —$CH_2$—, —C(=O)—NH—, —NH—C(=O)— or —C(=O)—NH-(optionally substituted alkylene)-; $R^d$ is optionally substituted carbocyclic group or optionally substituted heterocyclic group;

$R^4$ is hydrogen, optionally substituted alkyl, optionally substituted alkenyl, optionally substituted alkynyl, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, or nitro;

$R^5$ is hydrogen, optionally substituted alkyl which may have heteroatom and/or unsaturated bond or a group represented by the formula: —$Y^6$—$R^e$ wherein $Y^6$ is single bond, optionally substituted alkylene, alkenylene, alkynyl ene, —O—, —S—, —SO—, —$SO_2$—, —NH—, —C(=O)—, —$CH_2$—, —C(=O)—NH—, —NH—C(=O)—, or —C(=O)—NH-(optionally substituted alkylene)-; $R^e$ is optionally substituted carbocyclic group or optionally substituted heterocyclic group; or any one of combination of $R^2$ and $R^3$, $R^3$ and $R^4$, and $R^4$ and $R^5$, taken together form optionally substituted alkylene which may have heteroatom and/or unsaturated bond;

X is S or O;

provided that the case wherein all of $R^2$, $R^3$, $R^4$ and $R^5$ are hydrogen at same time, the case wherein $R^3$ and $R^4$ taken together form butadienylene di-substituted with alkoxy, and the case wherein $R^5$ is hydrogen or methyl are excluded;

a prodrug, a pharmaceutically acceptable salt or solvate thereof,

[2] the pharmaceutical composition according to [1] which has a binding activity to the cannabinoid type 2 receptor wherein $R^5$ is optionally substituted $C_2$ or more alkyl which may have heteroatom and/or unsaturated bond or a group represented by the formula: —$Y^6$—$R^e$ wherein $Y^6$ and $R^e$ are as defined in [1],

[3] the pharmaceutical composition according to [2] which has a binding activity to the cannabinoid type 2 receptor wherein $R^5$ is optionally substituted $C_3$ or more alkyl which may have heteroatom and/or unsaturated bond or a group represented by the formula: —$Y^6$—$R^e$ wherein $Y^6$ is optionally substituted alkylene; $R^e$ is optionally substituted aryl, optionally substituted cycloalkyl, optionally substituted heteroaryl, or optionally substituted heterocyclic group,

[4] the pharmaceutical composition according to any one of [1] to [3] which has a binding activity to the cannabinoid type 2 receptor wherein $R^1$ is a group represented by the formula: —$Y^1$—$Y^2$—$Y^3$—$R^a$ wherein $Y^1$, $Y^2$, $Y^3$, $R^a$, and $R^b$ are as defined in [1],

[5] the pharmaceutical composition according to (4) which has a binding activity to the cannabinoid type 2 receptor wherein $R^1$ is a group represented by the formula: —$Y^1$—$Y^2$—$Y^3$—$R^a$ wherein $Y^1$, $Y^3$, and $R^a$ are as defined in [1]; $Y^2$ is —O—, —$NR^b$—C(=O)— or —C(=O)—$NR^b$—; $R^b$ is hydrogen or optionally substituted alkyl,

[6] the pharmaceutical composition according to any one of [1] to [5] which has a binding activity to the cannabinoid type 2 receptor wherein $R^3$ and $R^4$ are not taken together,

[7] the pharmaceutical composition according to [6] which has a binding activity to the cannabinoid type 2 receptor wherein $R^3$ is hydrogen, optionally substituted alkyl, halogen, or a group represented by the formula: —$Y^5$—$R^d$ wherein $Y^6$ is single bond, optionally substituted alkylene, alkenylene, alkynylene; $R^d$ is optionally substituted aryl or optionally substituted heteroaryl; $R^4$ is hydrogen or optionally substituted alkyl;

provided that the case wherein $R^3$ and $R^4$ are hydrogen at the same time is excluded,

[8] the pharmaceutical composition according to any one of [1] to [5] which has a binding activity to the cannabinoid type 2 receptor wherein $R^3$ and $R^4$ taken together form optionally substituted alkylene which may have heteroatom and/or unsaturated bond;

provided that the case wherein the optionally substituted alkylene is optionally substituted butadienylene is excluded,

[9] the pharmaceutical composition according to [1] which has a binding activity to the cannabinoid type 2 receptor wherein $R^1$ is hydrogen, cyano, formyl, carboxy, isothiocyanato, amino, hydroxy, or a group represented by the formula: —$Y^1$—$Y^2$—$Y^3$—$R^a$ wherein $Y^1$ and $Y^3$ each is independently single bond or optionally substituted alkylene (as substituent thereof are halogen, alkenylene, hydroxy, or azide); $Y^2$ is single bond, —O—, —O—C(=O)—, —O—C(=O)—O—, —O—C(=O)—NH—, —NH—, —$NR^b$—C(=O)—, —NH—C(=O)—O—, —NH—C(=O)—NH—, —NH—C(=S)—NH—, —S—, —$SO_2$—O—, —$SO_2$—NH—, —$SO_2$—NH—C(=O)—NH—, —C(=O)—O—, —C(=O)—$NR^b$—, or —C(=S)—NH—; $R^a$ is optionally substituted alkyl (the substituent is hydroxy), alkenyl, optionally substituted aryl (the substituent is carboxy, optionally substituted amino, alkoxy, alkylthio, alkylenedioxy, halogen, alkyl, or hydroxy), optionally substituted cycloalkyl (the substituent is aryl), optionally substituted cycloalkenyl (the substituent is alkenylene), or optionally substituted heteroaryl (the substituent is oxo); $R^b$ is hydrogen, alkyl, or acyl;

$R^2$ is hydrogen, alkyl, alkenyl, or a group represented by the formula: —$Y^4$—$R^c$ wherein $Y^4$ is —O—; $R^c$ is heteroaryl;

$R^3$ is hydrogen, alkyl, halogen, or a group represented by the formula: —$Y^5$—Rd wherein $Y^5$ is single bond, alkylene, or —C(=O)—NH-alkylene-; $R^d$ is aryl optionally substituted with halogen (the substituent is halogen, alkyl, alkoxy, alkylenedioxy, or halogenated alkyl) or optionally substituted heteraryl (the substituent is halogen, alkyl, alkoxy, alkylenedioxy, or halogenated alkyl);

$R^4$ is hydrogen or alkyl;

$R^5$ is hydrogen, optionally substituted $C_3$ or more alkyl which may have heteroatom and/or unsaturated bond (the substituent is halogen, hydroxy, or azide) or a group represented by the formula: —$Y^6$—$R^e$ wherein $Y^6$ is alkylene; $R^e$ is optionally substituted aryl, optionally substituted cycloalkyl, optionally substituted heteroaryl or optionally substituted heterocyclic group; or $R^2$ and $R^3$ taken together with the adjacent atoms form optionally substituted cyclic group (the substituent is oxo or hydroxy), $R^3$ and $R^4$ taken together with the adjacent atoms form optionally substituted cyclic group which may have heteroatom and/or unsaturated bond (the substituent is acyl, aralkyl, or alkenylene), or $R^4$ and $R^5$ taken together with the adjacent atoms form optionally substituted carbocyclic group which may have unsaturated bond (the substituent is alkenylene),

[10] the pharmaceutical composition according to any one of [1] to [9] which has a binding activity to the cannabinoid type 2 receptor as an anti-inflammatory agent,

[11] the pharmaceutical composition according to any one of [1] to [9] which has a binding activity to the cannabinoid type 2-receptor as an immunosuppressive agent,

[12] the pharmaceutical composition according to any one of [1] to [9] which has a binding activity to the cannabinoid type 2 receptor as a nephritis treating agent,

[13] the pharmaceutical composition according to any one of [1] to [9]which has a binding activity to the cannabinoid type 2 receptor as an analgesic agent,

[14] a compound of the formula (I):

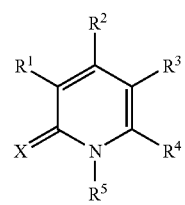

wherein $R^1$ is a group represented by the formula: —$Y^1$—$Y^2$—$Y^3$—$R^a$ wherein $Y^1$, $Y^2$, $Y^3$ and $R^b$ are as defined in [1]; $R^a$ is optionally substituted carbocyclic group, optionally substituted heterocyclic group or acyl;

$R^2$ is hydrogen or optionally substituted alkyl;

$R^3$ is optionally substituted alkyl, halogen or a group represented by the formula: —$Y^5$—$R^d$ wherein $Y^5$ is single bond or alkylene; $R^d$ is as defined in [1];

$R^4$ is hydrogen or optionally substituted alkyl;

$R^5$ is optionally substituted $C_3$ or more alkyl which may have heteroatom and/or unsaturated bond or a group represented by the formula: —$Y^6$—$R^e$ wherein $Y^6$ and $R^e$ are as defined in [1];

or $R^3$ and $R^4$ taken together with the adjacent atoms form optionally substituted cyclic group which may have heteroatom and/or unsaturated bond;

X is as defined in [1];

provided that when $R^1$ and $R^4$ taken together form optionally substituted butadienylene, $R^1$ is a group represented by the formula: —$Y^1$—$Y^2$—$Y^3$—$R^a$ wherein $Y^1$ is single bond; $Y^8$ is optionally substituted alkylene; $Y^2$ is —$NR^b$—C(=O)—, —C(=O)—$NR^b$—; $R^a$ is optionally substituted carbocyclic group, optionally substituted heterocyclic group; and $R^b$ is hydrogen or optionally substituted alkyl; and the followings are excluded: the case wherein $R^3$ and $R^4$ taken together form tetramethylene and $R^1$ is a group represented by the formula: —$Y^1$—$Y^2$—$Y^3$—$R^a$ wherein $Y^1$ and $Y^3$ are single bond; $Y^2$ is —O—; $R^a$ is phenyl, and the case wherein $R^3$ and $R^4$ taken together form butadienylene and $R^1$ is a group represented by the formula: —$Y^1$—$Y^2$—$Y^3$—$R^a$ wherein $Y^1$ is single bond; $Y^3$ is ethylene; $Y^2$ is —C(=O)—$NR^b$—; and $R^a$ is phenyl substituted with sulfamoyl are excluded;

a prodrug, a pharmaceutically acceptable salt or solvate thereof,

[15] the compound according to [14] wherein $R^1$ is a group represented by the formula: —$Y^1$—$Y^2$—$Y^3$—$R^a$ wherein $Y^1$, $Y^3$, and $R^a$ are as defined in [14]; $Y^2$ is —O—, —$NR_b$—C(=O)— or —C(=O)—$NR^b$—; $R^b$ is hydrogen or optionally substituted alkyl;

a prodrug, a pharmaceutically acceptable salt or solvate thereof,

[16] the compound according to [14] or [15] wherein $R^3$ and $R^4$ are not taken together;

a prodrug, a pharmaceutically acceptable salt or solvate thereof,

[17] the compound according to [14] or [15] wherein $R^3$ and $R^4$ taken together form alkylene which may have heteroatom and/or unsaturated bond;

a prodrug, a pharmaceutically acceptable salt or solvate thereof,

[18] the compound according to [14] wherein $R^1$ is a group represented by the formula: —$Y_{-}$—$Y^2$—$Y^3$—$R^a$ wherein $Y^1$ is single bond; $Y^3$ is optionally substituted alkylene; $Y^2$ is —O—, —NH—C(=O)—, or —C(=O)—NH—; $R^a$ is optionally substituted carbocyclic group or optionally substituted heterocyclic group; $R^1$ is hydrogen; $R^3$ is alkyl, halogen or a group represented by the formula: —$Y^5$—$R^d$ wherein $Y^5$ is single bond; $R^d$ is optionally substituted carbocyclic group or optionally substituted heterocyclic group; $R^4$ is hydrogen or alkyl; $R^5$ is optionally substituted $C_3$ or more alkyl or a group represented by the formula: —$Y^6$—$R^e$ wherein $Y^6$ is optionally substituted alkylene; $R^e$ is optionally substituted aryl, optionally substituted cycloalkyl or optionally substituted heteroaryl; or $R^3$ and $R^4$ taken together form alkylene which may have heteroatom and/or unsaturated bond;

a prodrug, a pharmaceutically acceptable salt or solvate thereof,

[19] a library of compound of the formula (I):

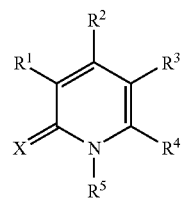

wherein $R^1$ is a group represented by the formula: —$Y^1$—$Y^2$—$Y^3$—$R^a$ wherein $Y^1$ is single bond; $Y^3$ is single bond or optionally substituted alkylene; $Y^2$ is —C(=O)—$NR^b$—; $R^a$ is optionally substituted carbocyclic group or optionally substituted heterocyclic group; $R^b$ is hydrogen;

$R^2$ is hydrogen;

$R^3$ and $R^4$ taken together form alkylene;

$R^5$ is $C_3$ or more alkyl or a group represented by the formula: —$Y^6$—$R^e$ wherein $Y^6$ is optionally substituted alkylene; $R^e$ is optionally substituted aryl, optionally substituted cycloalkyl or optionally substituted heteroaryl;

X is S or 0,

[20] the compound according to [19];

provided that the case wherein $R^3$ and $R^4$ taken together form tetramethylene and $R^1$ is a group represented by the formula: —$Y^1$—$Y^2$—$Y^3$—$R^a$ wherein $Y^1$ and $Y^3$ are single bond; $Y^2$ is —O—; $R^a$ is phenyl is excluded;

a prodrug, a pharmaceutically acceptable salt or solvate thereof,

[21] a library of compound of the formula (I):

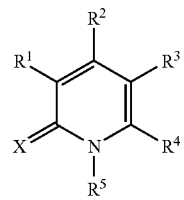

wherein $R^1$ is a group represented by the formula: —$Y^1$—$Y^2$—$Y^3$—$R^a$ wherein $Y^1$ is single bond; $Y^2$ is —C(=O)—$NR^b$—; $Y^3$ is single bond or optionally substituted alkylene; $R^a$ is optionally substituted carbocyclic group or optionally substituted heterocyclic group; $R^b$ is hydrogen;

$R^2$ is hydrogen;

$R^3$ is a group represented by the formula: —$Y^5$—$R^d$ wherein $Y^5$ is single bond; $R^d$ is optionally substituted carbocyclic group or optionally substituted heterocyclic group;

$R^4$ is hydrogen or alkyl;

$R^5$ is $C_3$ or more alkyl or a group represented by the formula: —$Y^6$—$R^e$ wherein $Y^6$ is optionally substituted alkylene; $R^e$ is optionally substituted aryl, optionally substituted cycloalkyl or optionally substituted heteroaryl;

X is S or O,

[22] the compound according to [21];

a prodrug, a pharmaceutically acceptable salt or solvate thereof,

[23] a pharmaceutical composition which contains as an active ingredient a compound of [14] to [18], [20], or [22],

[24] the pharmaceutical composition according to [23] which has a binding activity to the cannabinoid type 2 receptor,

[25] the pharmaceutical composition according to [23] which is useful as an anti-inflammatory agent,

[26] the pharmaceutical composition according to [23] which is useful as an immunosuppressive agent,

[27] the pharmaceutical composition according to [23] which is useful as a nephritis treating agent,

[28] the pharmaceutical composition according to [23] which is useful as an analgesic agent.

The phrase "taken together form optionally substituted alkylene which may have heteroatom and/or unsaturated bond" means "taken together with the adjacent atoms form optionally substituted cyclic group which may have heteroatom and/or unsaturated bond".

The present invention includes a method for treating inflammation or nephritis which comprises administrating the compound of the present invention a method of immunosuppression which comprises administrating the compound of present invention, a method of painkiller which comprises administrating the compound of the present invention, and a use of the compound of the present invention for the preparation of anti-inflammatory agent, immunosuppressive agent, nephritis treating agent, or analgesic agent.

Furthermore, the present invention includes a treating agent for diseases related to the cannabinoid type 2 receptor which contains the compound of the present invention as an active ingredient, a method for treating diseases related to the cannabinoid type 2 receptor which comprises administrating the compound of the present invention, and a use of the compound of the present invention for the preparation of treating agent for diseases related to the cannabinoid type 2 receptor.

The compounds of the present invention are pyridone derivatives represented by the following formula (I). Position number of pyridone derivatives is shown as follows.

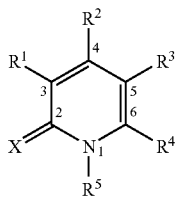

(I)

wherein $R^1$ is hydrogen, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro, or a group represented by the formula: —$Y^1$—$Y^2$—$Y^3$—$R^a$ wherein $Y^1$ and $Y^3$ each is independently single bond or optionally substituted alkylene; $Y^2$ is single bond, —O—, —O—C(=O)—, —O—C(=O)—O—, —O—C(=O)—$NR^b$—, —O—SO$_2$—, —$NR^b$—, —$NR^b$—C(=O)—, —$NR^b$—SO$_2$—, —$NR_b$—C(=NH)—, —$NR^b$—C(=O)—O—, —$NR^b$—C(=O)—$NR^b$—, —$NR^b$—C(=O)—$NR^b$—SO$_2$—, —$NR^b$—C(=S)—, —$NR^b$—C(=S)—$NR^b$—, —$NR^b$—SO$_2$—$NR^b$—, —$NR^b$—C(=NH)—$NR^b$—, —S—, SO$_2$—O—, —SO$_2$—$NR^b$—, —SO$_2$—$NR^b$—C(=O)—$NR^b$, —C(=)—, (=S), —C(=S)—$NR^b$—, —C(=S)—$NR^b$—C(=O)—, —C(=NH)—$NR^b$—, —C(=O)—, —C(=O)—$NR^b$—C(=$NR^b$)—, or —C(=O)—$NR^b$—$NR^b$—; $R^a$ is optionally substituted alkyl, optionally substituted alkenyl, optionally substituted alkynyl, optionally substituted carbocyclic group, optionally substituted heterocyclic group, or acyl; $R^b$ each is independently hydrogen, optionally substituted alkyl, optionally substituted alkenyl, optionally substituted alkynyl, optionally substituted carbocyclic group, optionally substituted heterocyclic group, acyl, hydroxy, or alkoxy;

$R^2$ is hydrogen, optionally substituted alkyl, optionally substituted alkenyl, optionally substituted alkynyl, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro, or a group represented by the formula: —$Y^4$—$R^c$ wherein $Y^4$ is single bond, —O—, —S—, —SO—, —SO$_2$—, —NH—, —C(=O)—, —CH$_2$—, —C(=O)—NH—, or —NH—C(=O)—; $R^c$ is optionally substituted carbocyclic group or optionally substituted heterocyclic group;

$R^3$ and $R^4$ each is independently hydrogen, optionally substituted alkyl, optionally substituted alkenyl, optionally substituted alkynyl, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro or a group represented by the formula: —$Y^5$—$R^d$ wherein $Y^5$ is single bond, optionally substituted alkylene, alkenylene, alkynylene, —O—, —S—, —SO—, —SO$_2$—, —NH—, —C(=O)—, —CH$_2$—, —C(=O)—NH-E-, or —NH—C(=O)—; E is single bond or optionally substituted alkylene; $R^d$ is optionally substituted carbocyclic group or optionally substituted heterocyclic group;

$R^5$ is hydrogen, optionally substituted alkyl which may have heteroatom and/or unsaturated bond or a group represented by the formula: —$Y^6$—$R^e$ wherein $Y^6$ is single bond, optionally substituted alkylene, alkenylene, alkynylene, —O—, —S—, —SO—, —SO$_2$—, —NH—, —C(=O)—, —CH$_2$—, —C(=O)—NH-E-, or —NH—C(=O)—; E is single bond or optionally substituted alkylene; $R^e$ is optionally substituted carbocyclic group or optionally substituted heterocyclic group; or any one of combinations of $R^2$ and $R^3$, $R^3$ and $R^4$, and $R^4$ and $R^5$, taken together with the adjacent atoms form optionally substituted cyclic group which may have heteroatom and/or unsaturated bond;

X is S or O;

provided that the case wherein $R^1$ and $R^4$ taken together with the adjacent atoms form benzene ring di-substituted with alkoxy, and $R^5$ is hydrogen or methyl is excluded;

It is characterized that the compounds of the present invention have pyridone skeleton, especially, having one or more of $R^2$, $R^3$, $R^4$, and $R^5$ substituted.

Preferable embodiments of the compounds of the present invention are exampled as follows.

In the case of $R^1$,

1) $R^1$ is a group represented by the formula: —$Y^1$—$Y^2$—$Y^3$—$R^a$ wherein $Y^1$, $Y^2$, $Y^3$, $R^a$ and $R^b$ are as defined in (1);

2) $R^1$ is hydrogen, cyano, formyl, carboxy, isothiocyanato, amino, hydroxy, carbamoyl, or a group represented by the formula: —$Y^1$—$Y^2$—$Y^3$—$R^a$ wherein $Y^1$ and $Y^3$ each is independently single bond or optionally substituted alkylene (the substituent is halogen, alkenylene, hydroxy, azide, amino, acylamino, alkylsulfonylamino, alkenyloxycarbonylamino, alkoxycarbonylamino, alkenylamino, arylcarbonylamino, heteroarylcarbonylamino, cyano, alkoxy, alkylsulfonyloxy, trialkylsilyloxy, oxo, methylene, halogenated alkoxycarbonyloxy, formyloxy, and/or acylthio; $Y^2$ is single bond, —O—, —O—C(=O)—, —O—C(=O)—O—, —O—C(=O)—NH—, —NH—, —$NR^b$—C(=O)—, —NH—C(=O)—O—, NH—C(=O)—NH—, —NH—C(=S)—NH—, —S—, —SO$_2$—O—, —SO$_2$—NH—, —SO$_2$—NH—C(=O)—NH—, —C(=O)—O—, —C(=O)—NR$^b$—, —C(=S)—NH—, —C(=O)—NH—C(=O)—, —C(=O)—NH—C(=S)—, —C(=O)—NR$^b$—C(=NR$^b$)—, or —C(=O)—NH—NR$^b$—; R$^a$ is optionally substituted alkyl (the substituent is hydroxy and/or aralkyl), alkenyl, optionally substituted aryl (the substituent is carboxy, optionally substituted amino, alkoxy, alkylthio, alkylenedioxy, halogen, alkyl, hydroxy, halogenated alkyl and/or halogenated alkoxy), optionally substituted cycloalkyl (the substituent is aryl and/or hydroxy), optionally substituted cycloalkenyl (the substituent is alkenylene, hydroxy, alkylsulfonyloxy, azide, amino and/or acylamino), optionally substituted heteroaryl (the substituent is oxo, heteroaryl, halogen, aryl and/or alkyl), or optionally substituted heterocyclic group (the substituent is aryl substituted with halogen, aralkyl, acyl, arylcarbonyl, cycloalkylcarbonyl, alkylsulfonyl, arylsulfonyl, alkyl, and/or halogenated alkylcarbonyl); R$^b$ is hydrogen, alkyl, acyl, hydroxy and/or alkoxy;

3) R$^1$ is a group represented by the formula: —Y$^1$—Y$^2$—Y$^3$—R$^a$ wherein Y$^1$, Y$^3$, and R$^a$ are as defined (1); Y$^2$ is —O—, —NR$^b$—C(=O) or —C(=O)—NR$^b$—; R$^b$ is hydrogen or optionally substituted alkyl;

4) R$^1$ is a group represented by the formula: —Y$^1$—Y$^2$—Y$^3$—R$^a$ wherein Y$^1$, Y$^2$, Y$^3$, and R$^b$ are as defined (1); R$^a$ is optionally substituted carbocyclic group, optionally substituted heterocyclic group, or acyl;

5) R$^1$ is a group represented by the formula: —Y$^1$—Y$^2$—Y$^3$—R$^a$ wherein Y$^1$ is single bond; Y$^3$ is optionally substituted alkylene; Y$^2$ is —O—, —NH—C(=O)— or —C(=O)—NH—; R$^a$ is optionally substituted carbocyclic group or optionally substituted heterocyclic group;

6) R$^1$ is a group represented by the formula: —Y$^1$—Y$^2$—Y$^3$—R$^a$ wherein Y$^1$ is single bond; Y$^3$ is single bond or optionally substituted alkylene; y is —C(=O)—NR$^b$—; R$^a$ is optionally substituted carbocyclic group or optionally substituted heterocyclic group; R$^b$ is hydrogen;

7) R$^1$ is a group represented by the formula: —Y$^1$—Y$^2$—Y$^3$—R$^a$ wherein Y$^1$ is single bond; Y$^3$ is optionally substituted alkylene; Y$^2$ is —C(=O)—NR$^b$— or —NR$^b$—C(=O)—; R$^a$ is optionally substituted aryl or optionally substituted heteroaryl; R$^b$ is hydrogen;

8) R$^1$ is a group represented by the formula: —Y$^1$—Y$^2$—Y$^3$—R$^a$ wherein Y$^1$ is single bond; Y$^3$ is optionally substituted branched alkylene; Y$^2$ is —O—, —NH—C(=O)—, or —C(=O)—NH—; R$^a$ is optionally substituted carbocyclic group or optionally substituted heterocyclic group;

in the case of R$^2$,

1) R$^2$ is hydrogen, alkyl, alkenyl, or a group represented by the formula: —Y$^4$—Rc wherein Y$^4$ is —O—; R$^c$ is heteroaryl;

2) R$^2$ is hydrogen or optionally substituted alkyl;

3) R$^2$ is hydrogen;

in the case of R$^3$,

1) R$^3$ is a group represented by the formula: —Y$^5$—R$^d$ wherein Y$^5$ is single bond; R$^d$ is optionally substituted carbocyclic group or optionally substituted heterocyclic group;

2) R$^3$ is hydrogen, optionally substituted alkyl, halogen, or a group represented by the formula: —Y$^5$—R$^d$ wherein Y$^5$ is single bond, optionally substituted alkylene, alkenylene, or alkynylene; R$^d$ is optionally substituted aryl or optionally substituted heteroaryl;

3) R$^3$ is alkyl, halogen, or a group represented by the formula: —Y$^5$—R$^d$ wherein Y$^6$ is single bond; R$^d$ is optionally substituted carbocyclic group or optionally substituted heterocyclic group;

4) R$^3$ is hydrogen, alkyl, halogen, or a group represented by the formula: —Y$^5$—Rd wherein Y$^6$ is single bond, alkylene, or —C(O)—NH-alkylene; R$^d$ is optionally substituted aryl (as a substituent halogen, alkyl, alkoxy, alkylenedioxy, and/or halogenated alkyl) or optionally substituted heteroaryl (as a substituent halogen, alkyl, alkoxy, alkylenedioxy, and/or halogenated alkyl);

5) R$^3$ is optionally substituted alkyl, halogen, or a group represented by the formula: —Y$^5$-R$^d$ wherein Y$^5$ is single bond or alkylene; R$^d$ is as defined in (1);

6) R$^3$ is hydrogen, alkyl, or a group represented by the formula: —Y$^5$—R$^d$ wherein Y$^5$ is single bond or alkylene; R$^d$ is optionally substituted aryl or optionally substituted heteroaryl;

7) R$^3$ is alkyl;

in the case of R$^4$,

1) R$^4$ is hydrogen or optionally substituted alkyl;

2) R$^4$ is hydrogen, alkyl, or a group represented by the formula: —Y$^5$—R$^d$ wherein Y$^5$ is single bond; R$^d$ is aryl;

3) R$^4$ is hydrogen;

4) R$^4$ is alkyl;

in the case of R$^5$,

1) R$^5$ is optionally substituted C$_2$ or more alkyl which may have heteroatom and/or unsaturated bond or a group represented by the formula: —Y$^6$—R$^e$ wherein Y$^6$ and R$^e$ are as defined in (1);

2) R$^5$ is C$_3$ or more alkyl or a group represented by —Y$^6$—R$^e$ wherein Y$^6$ is optionally substituted alkylene; R$^e$ is optionally substituted aryl, optionally substituted cycloalkyl, or optionally substituted heteroaryl;

3) R$^5$ is optionally substituted C$_3$ or more or a group represented by the formula: —Y$^6$—R$^e$ wherein Y$^6$ is optionally substituted alkylene; R$^e$ is optionally substituted aryl, optionally substituted cycloalkyl, or optionally substituted heteroaryl;

4). R$^5$ is optionally substituted C$_3$ or more alkyl which may have heteroatom and/or unsaturated bond or a group represented by the formula: —Y$^6$—R$^e$ wherein Y$^6$ is optionally substituted alkylene; R$^e$ is optionally substituted aryl, optionally substituted cycloalkyl, optionally substituted heteroaryl or optionally substituted heterocyclic group;

5) R$^6$ is hydrogen, optionally substituted C$_3$ or more alkyl which may have heteroatom and/or unsaturated bond (the substituent is halogen, hydroxy, azide, amino, alkoxy, alkenyloxy, alkylsulfonyloxy, acylthio, acylamino, arylcarbonylamino, cycloalkylcarbonylamino, halogenated alkylcarbonylamino, alkylsulfonylamino, arylsulfonylamino, formyl, oxo and/or cyano) or a group represented by the formula: —Y$^6$—R$^e$ wherein Y$^6$ is alkylene; R$^e$ is optionally substituted aryl, optionally substituted cycloalkyl, optionally substituted heteroaryl or optionally substituted heterocyclic group;

6) R$^5$ is C$_3$ or more alkyl which may have heteroatom and/or unsaturated bond or a group represented by the formula: —Y$^6$—R wherein Y$^6$ and R$^e$ are as defined in (1);

7) R$^5$ is C$_3$ or more alkyl or a group represented by the formula: —Y$^6$—R$^e$ wherein Y$^6$ is alkylene;

$R^e$ is optionally substituted aryl;
8) $R^5$ is $C_3$ or more alkyl;
9) $R^5$ is a group represented by the formula: —$Y^6$—$R^e$ wherein $Y^6$ is alkylene; $R^e$ is optionally substituted aryl, optionally substituted cycloalkyl, or optionally substituted heteroaryl;

in the case of $R^1$ and $R^4$,
1) $R^3$ and $R^4$ taken together;
2) $R^3$ and $R^4$ taken together with the adjacent atoms form optionally substituted cyclic group which may have heteroatom and/or unsaturated bond, provided that cyclic group is not optionally substituted benzene ring;
3) $R^3$ and $R^4$ taken together with the adjacent atoms form carbocyclic group, provided that one bond among carbon atom substituted with $R^3$ and carbon atom substituted with $R^4$ is only double bond, other bond among another carbon atom is single bond;
4) $R^3$ and $R^4$ taken together with the adjacent atoms form optionally substituted cyclic group (the substituent is acyl, aralkyl, alkenylene and/or alkylene) which may have heteroatom and/or unsaturated bond;
5) $R^3$ and $R^4$ taken together with the adjacent atoms form optionally substituted cyclic group which may have heteroatom and/or unsaturated bond;
6) $R^3$ and $R^4$ taken together with the adjacent atoms form optionally substituted cyclic group which may have heteroatom, provided that one bond among carbon atom substituted with $R^3$ and carbon atom substituted with $R^4$ is only double bond, other bond among another carbon atom is single bond;
7) $R^3$ and $R^4$ taken together with the adjacent atoms form unsubstituted carbocyclic group, provided that one bond among carbon atom substituted with $R^3$ and carbon atom substituted with $R^4$ is only double bond, other bond among another carbon atom is single bond;

in the case of $R^2$ and $R^3$,
1) $R^2$ and $R^3$ taken together with the adjacent atoms form optionally substituted carbocyclic group (the substituent is oxo and/or hydroxy);

in the case of $R^4$ and $R^5$,
1) $R^4$ and $R^5$ taken together with the adjacent atoms form optionally substituted cyclic group (the substituent is alkenylene) which may have unsaturated bond;

in the case of X,
1) X is oxygen atom;
2) X is sulfur atom.

Furthermore, as the compounds of the present invention especially above (25) to (28) are preferable terms.

The meanings of each term used in the present specification are explained below. Each term employed alone or in combination with other terms is used in the present specification expresses the same meaning.

The term "halogen" includes fluoro, chloro, bromo and iodo.

The term "heteroatom" includes nitrogen atom, oxygen atom, or sulfur atom.

The term "cyclic group (or alkyl) which may have heteroatom" includes cyclic group (or alkyl) which may be intervined with one or more of a group consisting of —NR—, —N=, =N—, —O—, and —S— wherein R is hydrogen or organic residue (e.g., alkyl).

The term "unsaturated bond" includes double bond or triple bond.

The term "cyclic group (or alkyl) which may have unsaturated bond" includes cyclic group (or alkyl) which may be intervined with one or more of a group consisting of —CR=CR—, —C=N—, —C≡C— wherein R each is independently organic residue (e.g., alkyl).

The term "alkyl" includes a $C_1$-$C_{12}$ straight or branched alkyl, for example, methyl, ethyl, n-propyl, isopropyl, n-butyl, isobutyl, sec-butyl, tert-butyl, n-pentyl, isopentyl, neopentyl, n-hexyl, n-heptyl, n-octyl, n-noyl, n-decyl or the like. Preferred is a C1-C4 straight or branched alkyl as alkyl of $R^a$, $R^b$, $R^2$, $R^3$, and $R^4$, for example, methyl, ethyl, n-propyl, isopropyl, n-butyl, isobutyl, sec-butyl and tert-butyl.

The term "alkyl which may have heteroatom and/or unsaturated bond of $R^5$" includes the above "alkyl" which may have heteroatom and/or unsaturated bond, especially preferred is C2 or more alkyl, more preferred is C3 or more alkyl. For example, n-propyl, isopropyl, n-butyl, isobutyl, sec-butyl, tert-butyl, n-pentyl, isopentyl, neopentyl, n-hexyl, n-heptyl, n-octyl, n-noyl, n-decyl, undexyl, dodecyl or the like As "the above alkyl containing heteroatom" preferred is C3-C12 straight or branched alkyl containing 1 to 3 heteroatom(s). Especially, preferred is C3-C8 alkyl containing one heteroatom, for example, "alkoxyalkyl", "alkylthioalkyl", "alkylaminoalkyl" or the like.

The term "alkoxy" includes an oxygen atom substituted with the above "alkyl", for example, methoxy, ethoxy, n-propoxy, isopropoxy, n-butoxy, isobutoxy, sec-butoxy, tert-butoxy, n-pentyloxy, n-hexyloxy, n-heptyloxy, n-octyloxy or the like. Preferred is a C1-C4 straight or branched alkoxy, for example, methoxy, ethoxy, n-propoxy, isopropoxy, n-butoxy, isobutoxy, sec-butoxy and tert-butoxy.

The term "alkylthio" includes a sulfur atom substituted with the above "alkyl", for example, methylthio, ethylthio, n-propylthio, isopropylthio, n-butylthio, isobutylthio, sec-butylthio, tert-butylthio, n-pentylthio, n-hexylthio or the like. Preferred is a C1-C4 straight or branched alkylthio, for example, methylthio, ethylthio, n-propylthio, isopropylthio, n-butylthio, isobutylthio, sec-butylthio and tert-butylthio.

The term "alkylamino" includes an amino group substituted with the above "alkyl", for example, methylamino, ethylamino, n-propylamino, isopropylamino, n-butylamino, isobutylamino, sec-butylamino, tert-butylamino, n-pentylamino, n-hexylamino or the like. Preferred is a C1-C4 straight or branched alkylamino, for example, methylamino, ethylamino, n-propylamino, isopropylamino, n-butylamino, isobutylamino, sec-butylamino and tert-butylamino.

The term "alkoxyalkyl" includes the above "alkyl" substituted with the above "alkoxy", for example, methoxymethyl, ethoxymethyl, n-propoxymethyl, 1-methoxyethyl, 2-methoxyethyl, 1-ethoxyethyl, 2-ethoxyethyl, 1-n-propoxyethyl, 2-n-propoxyethyl, 1-methoxy-n-propyl, 2-methoxy-n-propyl, 3-methoxy-n-propyl, 1-ethoxy-n-propyl, 2-ethoxy-n-propyl, 3-ethoxy-n-propyl, 1-n-propoxy-n-propyl, 2-n-propoxy-n-propyl, 3-n-propoxy-n-propyl or the like.

The term "alkylthioalkyl" includes the above "alkyl" substituted with the above "alkylthio", for example, methylthiomethyl, ethylthiomethyl, n-propylthiomethyl, 1-methylthioethyl, 2-methylthioethyl, 1-ethylthioethyl, 2-ethylthioethyl, 1-n-propylthioethyl, 2-n-propylthioethyl, 3-n-propylthioethyl, 1-methylthio-n-propyl, 2-methylthio-n-propyl, 3-methylthio-n-propyl, 1-ethylthio-n-propyl, 2-ethylthio-n-propyl, 3-ethylthio-n-propyl, 1-n-propylthio-n-propyl, 2-n-propylthio-n-propyl, 3-n-propylthio-n-propyl or the like.

The term "alkylaminoalkyl" includes the above "alkyl" substituted with the above "alkylamino", for example, methylaminomethyl, ethylaminomethyl, n-propylaminomethyl, 1-methylaminoethyl, 2-methylaminoethyl, 1-ethylaminoethyl, 2-ethylaminoethyl, 1-n-propylaminoethyl, 2-n-propylaminoethyl, 3-n-propylaminoethyl, 1-methylamino-n-propyl, 2-methylamino-n-propyl, 3-methylamino-n-propyl, 1-ethylamino-n-propyl, 2-ethylamino-n-propyl, 3-ethylamino-n-propyl, 1-n-propylamino-n-propyl, 2-n-propylamino-n-propyl, 3-n-propylamino-n-propyl or the like.

As "the above alkyl containing unsaturated bond" preferred is $C_3$-$C_{12}$ straight or branched alkyl containing 1 or 2 unsaturated bond(s). Especially, preferred is C3-C8 alkyl containing one unsaturated bond, for example, "alkenyl", "alkynyl" or the like.

The term "alkenyl" includes C2-C12 straight or branched alkenyl which is the above "alkyl" having one or more double bond, for example, vinyl, 1-propenyl, 2-propenyl, 1-butenyl, 2-butenyl, 3-butenyl, 1,3-butadienyl, 3-methyl-2-butenyl or the like.

The term "alkynyl" includes $C_2$-$C_{12}$ straight or branched alkynyl which is the above "alkyl" having one or more triple bond, for example, etynyl, 1-propynyl, 2-propynyl, 1-butynyl, 2-butynyl, 3-butynyl or the like.

The term "halogenated alkyl" includes the above "alkyl" substituted with one or more halogen, for example, chloromethyl, dichloromethyl, difluoromethyl, trifluoromethyl, chloroethyl (e.g., 1-chloroethyl, 2-chloroethyl or the like), dichloroethyl (e.g., 1,1-dichloroethyl, 1,2-dichloroethyl, 2,2-dichloroethyl or the like) or the like.

The term "halogenated alkoxy" includes the above "alkoxy" substituted with one or more halogen, for example, dichloromethoxy, difluoromethoxy, trifluoromethoxy, trifluoroethoxy (e.g., 2,2,2-trifluoroethoxy or the like) or the like.

The term "alkylene" includes a $C_1$-$C_{12}$ straight or branched alkylene, for example, methylene, ethylene, trimethylene, tetramethylene, pentamethylene, hexamethylene, heptamethylene, 1-methylethylene, 1-ethylethylene, 1,1-dimethylethylene, 1,2-dimethylethylene, 1,1-diethylethylene, 1,2-diethylethylene, 1-ethyl-2-methylethylene, 1-methyltrimethylene, 2-methyltrimethylene, 1,1-dimethyltrimethylene, 1,2-dimethyltrimethylene, 2,2-dimethyltrimethylene, 1-ethyltrimethylene, 2-ethyltrimethylene, 1,1-diethyltrimethylene, 1,2-diethyltrimethylene, 2,2-diethyltrimethylene, 2-ethyl-2-methyltrimethylene, 1-methyltetramethylene, 2-methyltetramethylene, 1,1-dimethyltetramethylene, 1,2-dimethyltetramethylene, 2,2-dimethyltetramethylene, 2,2-di-n-propyltrimethylene or the like.

As the "alkylene" of $Y^1, Y^3, Y^5$, y6, —C(=O)—NH-alkylene-, includes $C_1$-$C_{10}$ straight alkylene, especially, preferred is C1-C4 straight alkylene (e.g., methylene, ethylene, trimethylene, tetramethylene), more preferred is C1 or C2 straight alkylene (e.g., methylene, ethylene).

In the case of any one of combination of $R^2$ and $R^3$, $R^3$ and $R^4$, $R^4$ and $R^5$ taken together with the adjacent atom form optionally substituted cyclic group which may have heteroatom and/or unsaturated bond, the term "cyclic group" includes the above "alkyl" which may have heteroatom and/or unsaturated bond. Especially, preferred is C2 or more alkylene, more preferred is C3 or more alkylene. Especially, preferred is C3 or more straight alkylene.

That is, the terms "containing heteroatom" and "containing unsaturated bond" mean as defined above.

The term "alkenylene" includes $C_2$-$C_{12}$ straight or branched alkenylene which is the above "alkylene" having one or more double bond(s), for example, vinylene, propenylene, or butenylene. Preferred is $C_2$-$C_6$ straight alkenylene, for example, vinylene, propenylene, butenylene, pentenylene, hexenylene, butadienylene or the like.

The term "alkynylene" includes $C_2$-$C_{12}$ straight or branched alkynylene which is the above "alkylene" having one or more triple bond(s).

The term "acyl" includes a carbonyl group substituted with a group except hydrogen, for example, alkylcarbonyl (e.g., acetyl, propionyl, butyryl, isobtyryl, valeryl, isovaleryl, pivaloyl, hexanoyl, octanoyl, lauroyl or the like), alkenylcarbonyl (e.g., acryloyl, methacryloyl), cycloalkylcarbonyl (e.g., cyclopropanecarbonyl, cyclobutanecarbonyl, cyclopentanecarbonyl, cyclohexanecarbonyl or the like), arylcarbonyl (e.g., benzoyl, naphthoyl or the like), heteroarylcarbonyl (e.g., pyridinecarbonyl or the like). These group may be optionally substituted with alkyl, halogen or and like. For example, as arylcarbonyl substituted with alkyl is toluoyl, and as alkylcarbonyl substituted with halogen is trifluoroacetyl or the like.

The term "alkenyloxy" includes an oxygen atom substituted with the above "alkenyl", for example, vinyloxy, 1-propenyloxy, 2-propenyloxy, 1-butenyloxy, 2-butenyloxy, 3-butenyloxy, 1,3-butadienyloxy, 3-methyl-2-butenyloxy or the like.

The term "alkynyloxy" includes an oxygen atom substituted with the above "alkynyl", for example, ethynyloxy, 1-propynyloxy, 2-propynyloxy, 1-butynyloxy, 2-butynyloxy, 3-butynyloxy or the like.

The term "alkoxycarbonyl" includes carbonyl substituted with the above "alkoxy", for example, methoxycarbonyl, ethoxycarbonyl, n-propoxycarbonyl, i-propoxycarbonyl, n-butoxycarbonyl, i-butoxycarbonyl, sec-butoxycarbonyl, tert-butoxycarbonyl, n-pentyloxyearbonyl, n-hexyloxycarbonyl, n-heptyloxycarbonyl, n-octyloxycarbonyl or the like. Especially, preferred is methoxycarbonyl, ethoxycarbonyl or the like.

The term "alkylsulfinyl" includes sulfinyl substituted with the above "alkyl". Especially, preferred is methanesulfinyl, ethanesulfinyl or the like.

The term "alkylsulfonyl" includes sulfonyl substituted with the above "alkyl". Especially, preferred is methanesulfonyl, ethanesulfonyl or the like.

The acyl of "acylamino" is as defined the above "acyl". Especially, as "acylamino" preferred is acetylamino, propionylamino or benzoylamino.

The alkylsulfonyl of "alkylsulfonylamino" is as defined the above "alkylsulfonyl". Especially, as "alkylsulfonylamino" preferred is methanesulfonylamino or ethanesulfonylamino.

The alkenyloxy of "alkeyloxycarbonylamino" is as defined the above "alkeyloxy". Especially, as "alkeyloxycarbonylamino" preferred is vinyloxycarbonylamino or allyoxycarbonylamino.

The alkoxycarbonyl of "alkoxycarbonylamino" is as defined the above "alkoxycarbonyl". Especially, as "alkoxycarbonylamino" preferred is methoxycarbonylamino, ethoxycarbonylamino or tert-butoxycarbonylamino.

The alkenyl of "alkenylamino" is as defined the above "alkenyl". Especially, as "alkenylamino" preferred is vinylamino or allylamino.

The aryl of "arylcarbonylamino" is as defined the above "aryl". Especially, as "arylcarbonylamino" preferred is benzoylamino or naphthoylamino.

The heteroaryl of "heteroarylcarbonylamino" is as defined the above "heteroaryl". Especially, as "heteroarylcarbonylamino" preferred is pyridinecarboylamino.

The alkylsulfonyl of "alkylsulfonyloxy" is as defined the above "alkylsulfonyl". Especially, as "alkylsulfonyloxy" preferred is methanesulfonyloxy or ethanesulfonyloxy.

As "trialkylsilyloxy" preferred is tert-butyldimethylsilyloxy.

The halogenated alkoxy of "halogenated alkoxycarbonyloxy" is as defined the above "halogenated alkoxy". Especially, as "halogenated alkoxycarbonyloxy" preferred is trifluoromethoxycarbonyloxy or trichloromethoxycarbonyloxy.

The acyl of "acylthio" is as defined the above "acyl". Especially, as "acylthio" preferred is acetylthio.

The aryl of "arylcarbonyl" is as defined the above "aryl". Especially, as "arylcarbonyl" preferred is benzoyl or naphthoyl.

The cycloalkyl of "cycloalkylcarbonyl" is as defined the above "cycloalkyl". Especially, as "cycloalkylcarbonyl" preferred is cyclopropylcarbonyl, cyclobutylcarbonyl or cyclohexylcarbonyl.

The aryl of "arylsulfonyl" is as defined the above "aryl". Especially, as "arylsulfonyl" preferred is benzenesulfonyl.

The halogenated alkyl of "halogenated alkylcarbonyl" is as defined the above "halogenated alkyl". Especially, as "halogenated alkylcarbonyl" preferred is trifluoromethylcarbonyl.

The alkylene of "alkylenedioxy" is as defined the above "alkylene". Especially, as "alkylenedioxy" preferred is methylenedioxy, ethylenedioxy, trimethylenedioxy, or tetramethylenedioxy.

The term "aralkyl" includes the above "alkyl" substituted with the above "aryl", for example, benzyl, phenethyl, phenylpropyl, naphthylmethyl, naphthylethyl or the like.

The cycloalkyl of "cycloalkylcarbonylamino" is as defined the above "cycloalkyl". Especially, as "cycloalkylcarbonylamino" preferred is cyclopropylcarbonylamino, cyclobutylcarbonylamino or cyclohexylcarbonylamino.

The halogenated alkyl of "halogenated alkylcarbonylamino" is as defined the above "halogenated alkyl". Especially, as "halogenated alkylcarbonylamino" preferred is trifluoromethylcarbonylamino.

The aryl of "arylsulfonylamino" is as defined the above "aryl". Especially, as "arylsulfonylamino" preferred is benzenesulfonylamino.

Examples of substituents of "optionally substituted amino" include alkyl (e.g., methyl, ethyl, n-propyl, i-propyl or the like), acyl (e.g., formyl, acetyl, propionyl, benzoyl or the like), aralkyl (e.g., benzyl, phenylethyl, phenylpropyl, naphthylmethyl or the like) or the like. A nitrogen atom of an amino group may be mono- or di-substituted with these substituents.

Examples of "optionally substituted amino" include unsubstituted amino, alkylamino (e.g., methylamino, ethylamino, n-propylamino, i-propylamino, dimethylamino, diethylamino, ethylmethylamino, propylmethylamino), acylamino (e.g., acetylamino, formylamino, propionylamino, benzoylamino), acylalkylamino (e.g., N-acetylmethylamino), aralkylamino (e.g., benzylamino, 1-phenylethylamino, 2-phenylethylamino, 3-phenylethylamino, 1-naphthylmethylamino, 2-naphthylmethylamino, dibenzylamino or the like), alkylsulfonylamino (e.g., methanesulfonylaimino, ethanesulfonylamino or the like), alkenyloxycarbonylamino (e.g., vinyloxycarbonylamino, allyloxycarbonylamino or the like), alkoxycarbonylamino (e.g., methoxycarbonylamino, ethoxycarbonylamino, tert-butoxycarbonylamino or the like), alkenylamino (e.g., vinylamino, allylamino or the like), arylcarbonylamino (e.g., benzoylamino or the like), heteroarylcarbonylamino (e.g., pyridinecarbonylamino or the like).

Examples of the substituents of "optionally substituted carbamoyl" include alkyl (e.g., methyl, ethyl, n-propyl, i-propyl or the like), acyl (e.g., formyl, acetyl, propionyl, benzoyl or the like) or the like. The nitrogen atom of carbamoyl group may be mono- or di-substituted with these substituents.

As "optionally substituted carbamoyl" preferred are carbamoyl, N-methylcarbamoyl, N-ethylcarbamoyl or the like.

The term "carbocyclic group" includes a cyclic substituent consisting of carbon atom and hydrogen atom, and the cyclic part may be saturated cycle or unsaturated cycle, for example, aryl, cycloalkyl, cycloalkenyl or the like. Preferred is $C_3$-$C_{14}$ cyclic group.

The term "aryl" includes $C_6$-$C_{14}$ aromatic carbocyclic group, for eaxample, phenyl, naphthyl, anthryl, phenanthryl or the like.

The ternm "cycloalkyl" includes $C_3$-$C_7$ cycloalkyl, for example, cyclopropyl, cyclobutyl, cyclopentyl, cyclohexyl or the like.

The term "cycloalkenyl" includes $C_3$-$C_{12}$ alkenyl which is the above "cycloalkyl" having one or more double bond, for example, cyclopropenyl (e.g., 1-cyclopropenyl), cyclobutenyl (e.g., 1-cyclobutenyl), cyclopentenyl (e.g., 1-cyclopenten-1-yl, 2-cyclopenten-1-yl, and 3-cyclopenten-1-yl), cyclohexenyl (e.g., 1-cyclohexen-1-yl, 2-cyclohexen-1-yl, and 3-cyclohexen-1-yl), cycloheptenyl (e.g., 1-cycloheptenyl), cyclooctenyl (e.g., 1-cyclooctenyl) or the like. Especially, preferred is 1-cyclohexen-1-yl, 2-cyclohexen-1-yl, or 3-cyclohexen-1-yl.

The term "heterocyclic group" includes a group derived from a ring wherein carbon atom and hydrogen atom of the cyclic part of the above "carbocyclic group" is substituted with one to five heteroatom(s), and the cyclic part may be saturated cycle or unsaturated cycle, for example, heteroaryl, heterocycle or the like.

The term "heteroaryl" includes a $C_1$-$C_9$ heteroaryl having one to four nitrogen atom(s), oxygen atom(s) and/or sulfur atom(s), for example, furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl) tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl) pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl (e.g., 2-benzoxazolyl, 4-benzoxazolyl, 5-benzoxazolyl, 6-benzoxazolyl, 7-benzoxazolyl, 8-benzoxazolyl), quinoxalyl (e.g., 2-quinoxalyl, 5-quinoxalyl, 6-quinoxalyl), cinnolyl (e.g., 3-cinnolyl, 4-cinnolyl, 5-cinnolyl, 6-cinnolyl, 7-cinnolyl, 8-cinnolyl), quinazolyl (e.g., 2-quinazolyl, 4-quinazolyl, 5-quinazolyl, 6-quinazolyl, 7-quinazolyl, 8-quinazolyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl), phenothiadinyl (e.g., 1-phenothiadinyl, 2-phenothiadinyl, 3-phenothiadinyl, 4-phenothiadinyl) or the like.

The term "heterocycle" includes a $C_1$-$C_9$ non-aromatic ring having one to four nitrogen atom(s), oxygen atom(s) and/or sulfur atom(s), for example, 1-pyrrolinyl, 2-pyrrolinyl, 3-pyrrolinyl, pyrrolidino, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidyl, 3-piperidyl, 4-piperidyl, piperazino, 2-piperazinyl, 2-morpholinyl, 3-morpholinyl, morpholino, tetrahydropyranyl or the like. Especially, preferred is morpholino, pyrrolidino, piperidino or piperazino.

When "optionally substituted "optionally substituted alkyl", "optionally substituted alkenyl", "optionally substituted alkynyl", optionally substituted carbocyclic group", "optionally substituted heterocyclic group", "optionally substituted alkyl which may have heteroatom and/or unsaturated bond", or "optionally substituted cyclic group which may have heteroatom and/or unsaturated bond" have substituent, these may be substituted with same or different one to four substituent(s) at any position.

Examples of these substituents include hydroxy, carboxy, halogen (fluoro, chloro, bromo, iodo), halogenated alkyl (e.g., $CF_3$, $CH_2CF_3$, $CH_2CCl_3$ or the like), alkyl (e.g., methyl, ethyl, isopropyl, tert-butyl or the like), alkenyl (e.g., vinyl), formyl, acyl (e.g., asectyl, propionyl, butyryl, pivaloyl, benzoyl, piridinecarbonyl, cyclopentanecarbonyl, cyclohexanecarbonyl or the like), alkynyl (e.g., ethynyl), cycloalkyl (e.g., cyclopropyl, cyclobutyl, cyclopentyl, cyclohexyl or the like), cycloalkenyl (e.g., cyclopropenyl or the like), alkoxy (e.g., methoxy, ethoxy, propoxy, butoxy or the like), alkoxycarbonyl (e.g., methoxycarbonyl, ethoxycarbonyl, tert-butoxycarbonyl or the like), nitro, nitroso, oxo, optionally substituted amino (e.g., amino, alkylamino (e.g., methylamino, ethylamino, dimethylamino or the like), formylamino, acylamino (e.g., acetylamino, benzoylamino or the like), aralkylamino (e.g., benzylamino, tritylamino), hydroxyamino, alkylsulfonylamino, alkenyloxycarbonylamino, alkoxycarbonylamino, alkenylamino, arylcarbonylamino, heteroarylcarbonylamino or the like), azide, aryl (e.g., phenyl or the like), aryloxy (e.g., phenoxy), aralkyl (e.g., benzyl, phenethyl, phenylpropyl or the like), alkylenedioxy (e.g., methylenedioxy), alkylene (e.g., methylene, ethylene, trimethylene, tetramethylene, pentamethylene or the like), alkenylene (e.g., propenylene, butenylene, butadienylen or the like), cyano, isocyano, isocyanato, thiocyanato, isothiocyanato, mercapto, alkylthio (e.g., methylthio, ethylthio or the like), alkylsulfonyl (e.g., methanesuilfonyl, ethanesulfonyl), arylsulfonyl (e.g., benzenesulfonyl or the like), optionally substituted carbamoyl, sulfamoyl, formyloxy, haloformyl, oxalo, mercapto, thioformyl, thiocarboxy, dithiocarboxy, thiocarbamoyl, sulfino, sulfo, sulfoamino, hydrazido, ureido, amidino, guanidino, alkylsulfonyloxy, trialkylsilyloxy, halogenated alkoxycarbonyloxy, formyloxy, acylthio, thioxo or the like.

Furthermore, in the case substituent is divalent such as alkylene, alkenylene or alkylenedioxy, and when such a substituent locates at the same atom, can be formed a spiro ring, and a fused ring formed when such a substituent locates at different.

As the substituent of "optionally substituted alkylene" of $Y^1$ or $Y^3$, for example, preferred is halogen, alkenylene, hydroxy, azide, optionally substitited amino (e.g., amino, acylamino, alkylsulfonylamino, alkenyloxycarbonylamino, alkoxycarbonylamino, alkenylamino, arylcarbonylamino, heteroarylcarbonylamino), cyano, alkoxy, alkylsulfonyloxy, trialkylsilyloxy, oxo, methylene, halogenated alkoxycarbonyloxy, formyloxy or acylthio.

As the substituent of "optionally substituted alkyl", "optionally substituted alkenyl", or "optionally substituted alkynyl" of $R^a$ or $R^b$, for example, preferred is hydroxy or aralkyl.

Examples of preferable substituent of "optionally substituted carbocyclic group" or "optionally substituted heterocyclic group" include carboxy, optionally substituted amino (e.g., amino, alkylamino (e.g., methylamino, ethylamino, dimethylamino or the like), acylamino (e.g., acetylamino, benzoylamino or the like), aralkyamino (e.g., benzylamino, tritylamino, hydroxyamino or the like), alkoxy (e.g., methoxy, ethoxy, propoxy, butoxy or the like), alkylthio (e.g., methylthio, ethylthio or the like), alkylene (e.g., methylene, ethylene, trimethylene, tetramethylene or the like), alkylenedioxy (e.g., methylenedioxy or the like), halogen (fluoro, chloro, bromo, iodo), alkyl (e.g., methyl, ethyl, isopropyl, tert-butyl or the like), hydroxy, oxo, thioxo or the like.

As "optionally substituted carbocyclic group" of $R^a$, preferred is optionally substituted aryl (the substituent is carboxy, optionally substituted amino, alkoxy, alkylthio, alkylenedioxy, halogen, alkyl, hydroxy, halogenated alkyl and/or halogenated alkoxy), optionally substituted cycloalkyl (the substituent is aryl and/or hydroxy), or optionally substituted cycloalkeyl (the substituent is alkenylene, hydroxy, alkylsulfonyloxy, azide, amino and/or acylamino).

As "optionally substituted heterocyclic group" of $R^a$, preferred is optionally substituted heteroaryl (the substituent is oxo, heteroaryl, halogen, aryl and/or alkyl) or optionally substituted heterocycle (the substituent is aryl optionally substituted with halogen; aralkyl, acyl, arylcarbonyl, cycloalkylcarbonyl, alkylsulfonyl, arylsulfonyl, alkyl and/or halogenated alkylcarbonyl).

Examples of preferable substituent of "cyclic group optionally containig heteroatom and/or unsaturated bond" include oxo, hydroxy, alkenylene (e.g., propenylene, butenylene, butadienylene), acyl (e.g., acetyl, propionyl, butyryl, pivaloyl, benzoyl, pyridinecarbonyl, cyclopentanecarbonyl, cyclohexanecarbonyl or the like), aralkyl (e.g., benzyl or the like), alkylene (e.g., methylene, ethylene, trimethylene, tetramethylene, pentamethylene or the like).

As a substituent of "alkyl which may have heteroatom and/or unsaturated bond" of $R^5$, preferred is halogen, hydroxy, azide, amino, alkoxy, alkenyloxy, alkylsulfonyloxy, acylthio, acylamino, arylcarbonylamino, cycloalkylcarbonylamino, halogenated alkylcarbonylamino, alkylsulfonylamino, arylsulfonylamino, formyl, oxo or cyano.

Examples of "any one of combinations of $R^2$ and $R^3$, $R^3$ and $R^4$, and $R^4$ and $R^5$, taken together with the adjacent atoms form optionally substituted cyclic group which may have heteroatom and/or unsaturated bond" include the following structure.

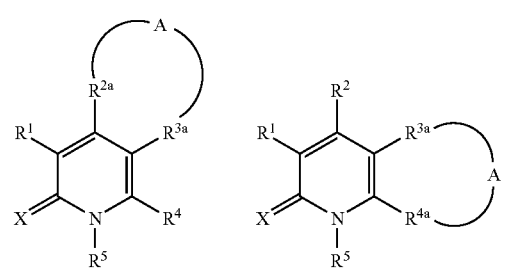

-continued

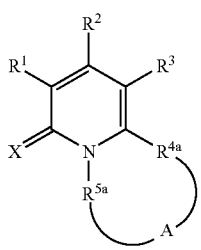

wherein $R^1$, $R^2$, $R^3$, $R^4$, and $R^5$ are as defined above; —$R^{2a}$-A-$R^{3a}$—, —$R^{3a}$-A-$R^{4a}$—, and —$R^{4a}$-A-$R^{5a}$— each is independently optionally substituted alkylene which may have heteroatom and/or unsaturated bond.

Especially, preferred is when an atom bonding to pyridone ring is carbon atom, that is, $R^{2a}$, $R^{3a}$, $R^{4a}$, and $R^{5a}$ are carbon atom. Furthermore, this carbon atom may bond to the above substituent (e.g., alkyl, alkoxy, hydroxy, oxo, halogen, amino or the like).

The term "cyclic group" includes 4-12 membered ring, especially preferred is 5-10 membered ring, more preferred is 5-8 membered ring. The atom structuring the ring includes carbon atom, heteroatom (nitrogen atom, sulfur atom, oxygen atom), hydrogen atom or the like.

When $R^2$ and $R^3$ taken together with the adjacent atoms form optionally substituted cyclic group which may have heteroatom and/or unsaturated bond, for example, include the following compound.

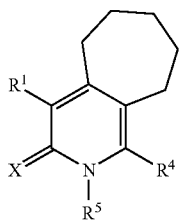 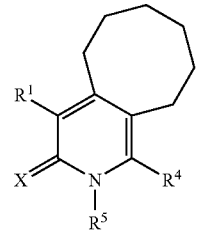

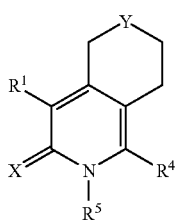

Y = O, S, NR

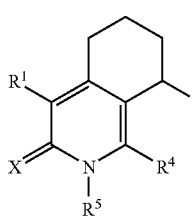 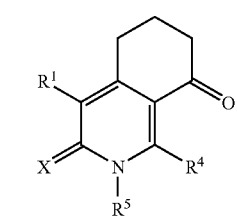

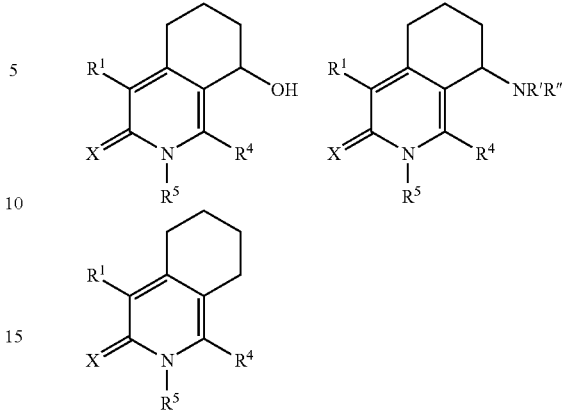

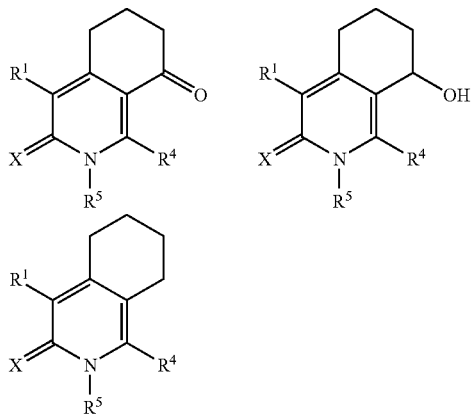

Especially, preferred is the following compound.

wherein $R^1$, $R^4$, $R^5$ and X are as defined above; Y is oxygen atom, sulfur atom or —NR—; R, R' and R" are hydrogen, alkyl, aralkyl or the like.

When $R^3$ and $R^4$ taken together with the adjacent atoms form optionally substituted cyclic group which may have heteroatom (especially oxygen atom, nitrogen atom) and/or unsaturated bond (especially double bond), especially, preferred is the following compound.

1) The cyclic group is unsubstituted carbocyclic group,
2) different positions of the cyclic group are substituted with alkenylene,
3) the cyclic group contains oxygen atom or nitrogen atom,
4) the cyclic group contains nitrogen atom, and the nitrogen atom is substituted with substituent (especially, alkyl, acyl, aralkyl or the like),
5) the cyclic group is unsubstituted carbocyclic group, provide that the bond between carbon atom substituted with $R^a$ and carbon atom substituted with $R^4$ is the double bond, and the other bonds between carbon atoms are single bond,
6) the cyclic group is unsubstituted ring containing heteroatom, provide that the bond between carbon atom substituted with $R^3$ and carbon atom substituted with $R^4$ is the double bond, and the other bonds between carbon atoms are single bond.

Examples include the following compound.
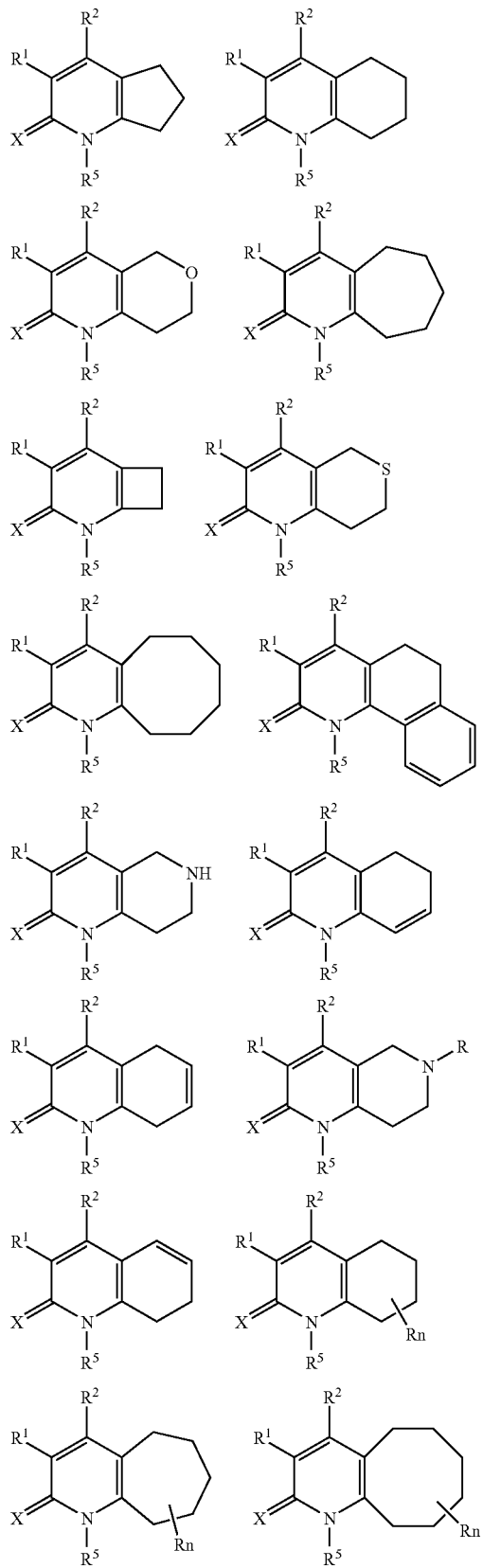
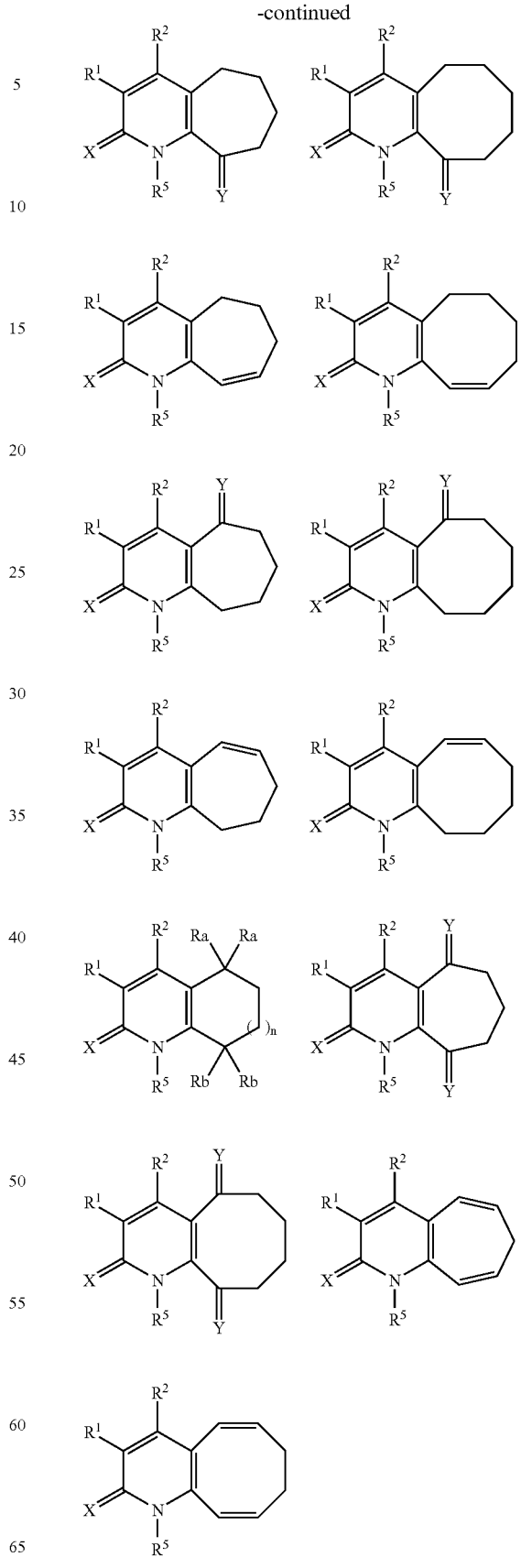

Especially, preferred is the following structure.

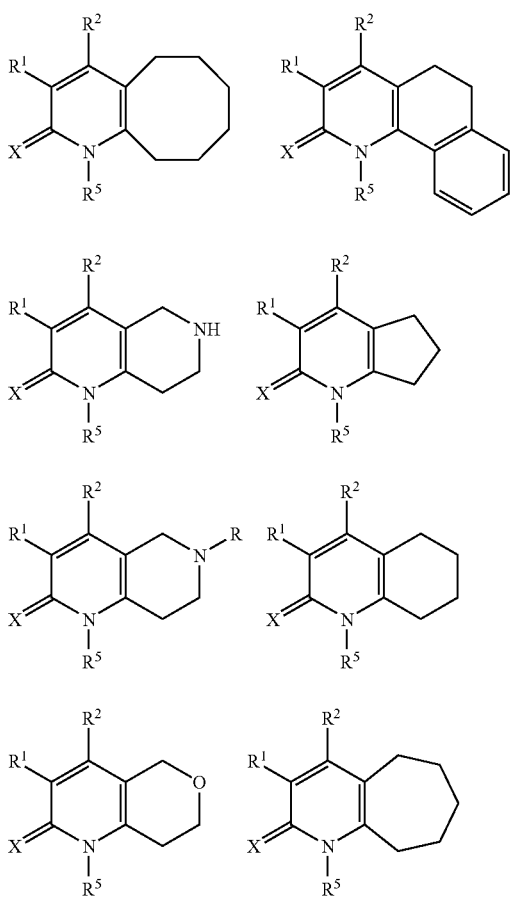

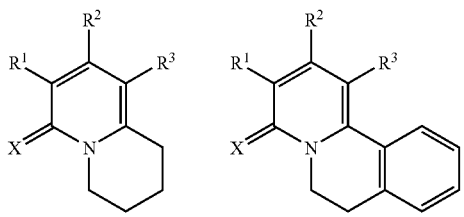

wherein $R^1$, $R^2$, $R^5$ and X are as defined above; Y is oxygen atom or sulfur atom; R, $R^a$ and $R^b$ are acyl, aralkyl, alkyl, alkoxy, oxo or the like; n is an integer of 0 to 5.

Furthermore, the present invention includes the case that $R^3$ and $R^4$ taken together with the adjacent atoms form cyclic group which may have unsaturated bond. In this case, preferred is double bond as unsaturated bond, and preferred is cyclic group having a double bond between carbon atom substituted with $R^3$ and carbon atom substituted with $R^4$ and another double bond.

The case that $R^1$ and $R^4$ taken together with the adjacent atoms form benzene ring is included in the present invention, provided that the compound wherein benzene ring is substituted with dialkoxy and $R^5$ is hydrogen or methyl is excluded.

When $R^4$ and $R^5$ taken together with the adjacent atoms form optionally substituted cyclic group which may have heteroatom (especially oxygen atom, nitrogen atom) and/or unsaturated bond (especially double bond), especially, preferred is the following compound.

1) The cyclic group is optionally substituted carbocyclic group which may have unsaturated bond (especially, double bond),
2) the cyclic group is unsubstituted,
3) different positions of the cyclic group are substituted with substituent (especially, alkenylene or the like). Examples include the following compound.

Furthermore, among the combinations of $R^2$ and $R^3$, $R^3$ and $R^4$, and $R^4$ and $R^5$, preferred is the combination of $R^3$ and $R^4$ taken together with the adjacent atoms form optionally substituted cyclic group which may have heteroatom and/or unsaturated bond;

When $R^1$ is represented by the formula: $-Y^1-Y^2-Y^3-R^a$ wherein $Y^1$, $Y^2$, $Y^3$ and $R^a$ are as defined above, especially, preferred is the formula: $-Y^1-Y^2-Y^3-R^a$ wherein $Y^1$ is single bond; $Y^2$ is $-O-$, $-NR^b-C(=O)-$ or $-C(=O)-NR^b-$; $Y^3$ is optionally substituted alkylene;

$R^a$ is optionally substituted aryl, optionally substituted cycloalkyl, or optionally substituted heteroaryl.

The term "$R^3$ and $R^4$ are not taken together" includes that $R^3$ and $R^4$ are not taken together with the adjacent atoms and does not form optionally substituted cyclic group which may have heteroatom and unsubstituted bond, and $R^3$ and $R^4$ each is independently hydrogen, optionally substituted alkyl, optionally substituted alkenyl, optionally substituted alkynyl, halogen, cyano, formyl, acyl, carboxy, alkoxycarbonyl, optionally substituted carbamoyl, isothiocyanato, optionally substituted amino, hydroxy, alkoxy, alkylthio, alkenyloxy, alkynyloxy, alkylsulfinyl, alkylsulfonyl, nitro or a group represented by $-Y^5-R^d$ wherein $Y^5$ is single bond, optionally substituted alkylene, alkenylene, alkynylene, $-O-$, $-S-$, $-SO-$, $-SO_2-$, $-NH-$, $-C(=O)-$, $-CH_2-$, $-C(=O)-NH-E-$, or $-NH-C(=O)-$; E is single bond or optionally substituted alkylene; $R^d$ is optionally substituted carbocyclic group or optionally substituted heterocyclic group.

BEST MODE FOR CARRYING OUT THE INVENTION

The general preparations are shown as follows.

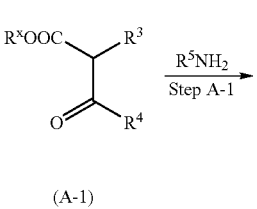

(A-1)

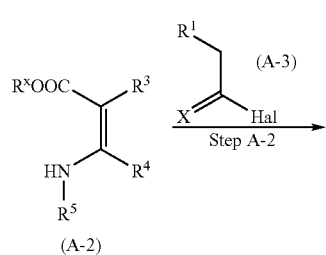

(A-2)

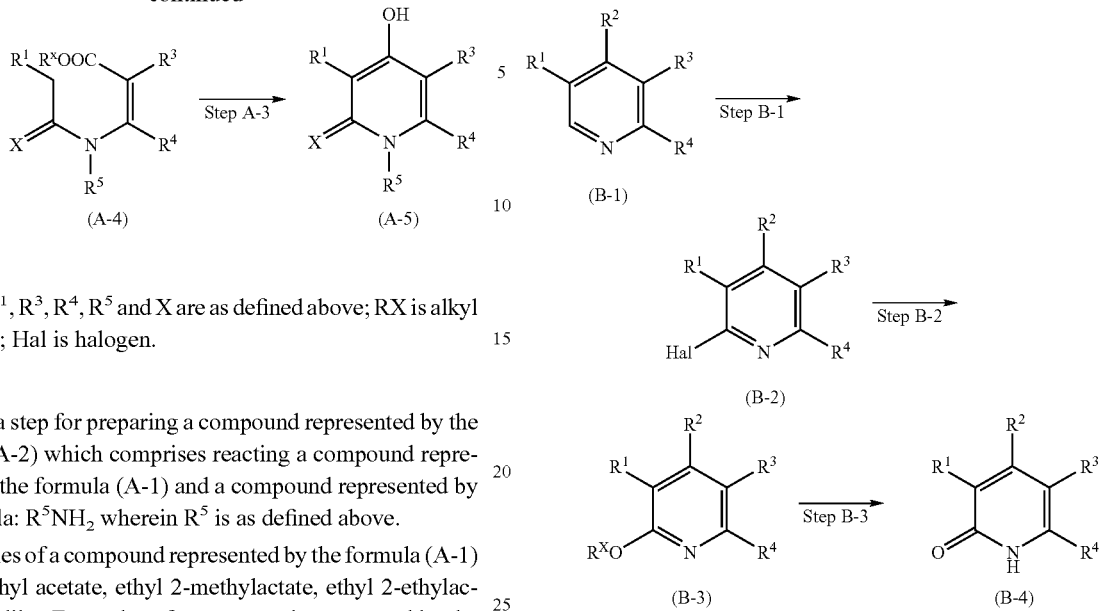

wherein $R^1$, $R^3$, $R^4$, $R^5$ and X are as defined above; RX is alkyl or the like; Hal is halogen.

Step A-1

This is a step for preparing a compound represented by the formula (A-2) which comprises reacting a compound represented by the formula (A-1) and a compound represented by the formula: $R^5NH_2$ wherein $R^5$ is as defined above.

Examples of a compound represented by the formula (A-1) include ethyl acetate, ethyl 2-methylactate, ethyl 2-ethylactate or the like. Examples of a compound represented by the formula: $R^5NH_2$ include alkylamine (e.g., methylamine, ethylamine, n-propylamine, n-butylamine or the like), aralkylamine (e.g., benzylamine, phenethylamine or the like) or the like. Examples of a reaction solvent include benzene, toluene, xylene or the like, especially, preferred is toluene or xylene. Example of the reaction temperature includes room temperature to 200° C., especially preferred is 80 to 180° C. This step can be carried out by azeotropical dehydration and the obtained product represented by the formula (A-2) can be purified by distillation under reduced or atmosphere pressure or the like.

Step A-2

This is a step for preparing a compound represented by the formula (A-4) which comprises reacting a compound represented by the formula (A-2) and a compound represented by the formula (A-3) in the presence of a base.

Examples of a base include pyridine, dimethylaminopyridine, triethylamine or the like, especially preferred is pyridine. Examples of a reaction solvent include diethyl ether, tetrahydrofuran; ethylene chloride, tluene or the like, especially, preferred is diethyl ether. Example of the reaction temperature includes 0 to 200° C., especially preferred is room temperature to 100° C.

Step A-3

This is a step for preparing a compound represented by the formula (A-5) which comprises cyclizing a compound represented by the formula (A-4) in the presence of a base.

Examples of a base used include sodium metal, metal alkoxide (e.g., sodium methoxide or the like). As a reaction solvent, preferred is a mixture of alcohol (e.g., methanol or ethanol) and benzene, toluene or the like. Example of the reaction temperature includes 0 to 200° C., especially preferred is room temperature to 100° C.

wherein $R^1$, $R^2$, $R^3$ and $R^4$ are as defined above; $R^x$ is alkyl or the like.

Step B-1

This is a step for preparing a compound represented by the formula (B-2) which comprises reacting a compound represented by the formula (B-1) with a halogenated reagent.

Examples of a halogenated reagent include chlorine gass, bromine, iodine or the like, especially preferred is iodine. Preferred is to be carried out in the presence of an acid. Examples of an acid include hydrochloric acid (conc. hydrochloric acid or diluted hydrochloric acid), hydrobromic acid, sulfuric acid or the like. Furthermore, this step can be carried out in the presence of a base. Examples of a base can be used include potassium carbonate, sodium carbonate or the like. Furthermore, this step can be carried out in the presence of a halogen potassium salt. When as a halogenated reagent was used iodine, preferred is to be carried out in the presence of potassium iodide. Examples of a reaction solvent include methylene chloride, chloroform, carbon teterachloride or the like. Example of the reaction temperature includes —10 to 150° C., especially preferred is room temperature to 100° C.

Furthermore, as a halogenated reagent can be used N-halosuccinimide. Examples of N-halosuccinimide include N-chlorosuccinimide, N-bromosuccinimide or the like, especially preferred is N-bromosuccinimide. Examples of a reaction solvent include benzene, toluene, xylene, methylene chloride, chloroform, carbon teterachloride or the like.

Step B-2

This is a step for preparing a compound represented by the formula (B-3) which comprises reacting a compound represented by the formula (B-2) with a sodium alcoholate.

Examples of a sodium alcoholate include sodium methoxide, sodium ethoxide or the like, especially preferred is sodium methoxide. As a reaction solvent, preferred is alcohol (e.g., methanol, ethanol or the like). Example of the reaction temperature includes 0 to 200° C., especially preferred is room temperature to 170° C. Preferred is to be carried out under heating in a sealed tube.

Step B-3

This is a step for preparing a compound represented by the formula (B-4) which comprises heating a compound represented by the formula (B-3) in the presence of pyridium chloride.

The step can be carried out without a reaction solvent, to be used pyridium chloride as a reaction solvent. Example of the reaction temperature includes 80 to 250° C., especially preferred is 100 to 210° C. Furthermore, this step can be carried out to be used boron tribromide. In this case, as a reaction solvent can be used methylene chloride or the like.

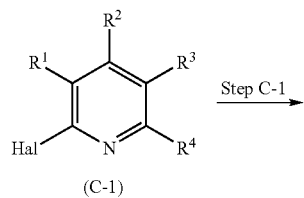

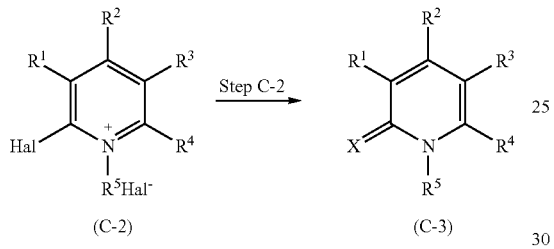

wherein $R^1$, $R^2$, $R^3$, $R^4$ and $R^5$ are as defined above; Hal is halogen.

Step C-1

This is a step for preparing a compound represented by the formula (C-2) which comprises reacting a compound represented by the formula (C-1) and a compound represented by the formula: $R^5Hal$ wherein $R^5$ is as defined above; Hal is halogen.

Example of the reaction temperature includes 0 to 200° C., especially preferred is 100 to 150° C. Furthermore, a reaction solvent may not be used. Preferred is to be carried out in a sealed tube.

Step C-2

This is a step for preparing a compound represented by the formula (C-3) from a compound represented by the formula (C-2).

When preparing of a compound wherein X is S, 1,3-diphenylurea. Examples of a reaction solvent include acetonitrile, toluene, methylene chloride or the like. Example of the reaction temperature includes room temperature to 100° C., especially preferred is under heating at reflux. Furthermore, preferred is to be carried out in the presence of a base. As a base can be used triethylamine or the like.

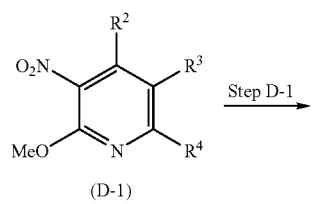

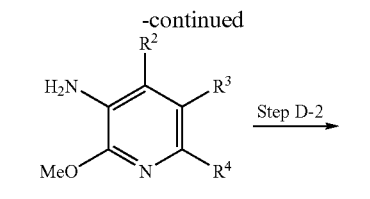

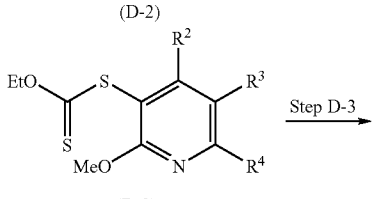

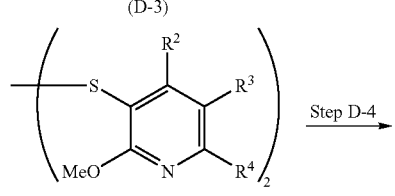

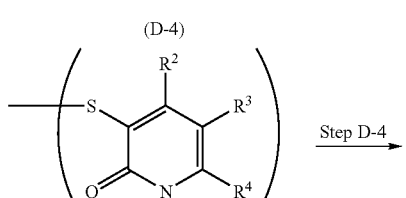

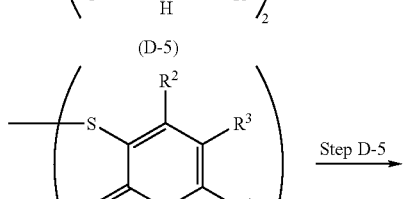

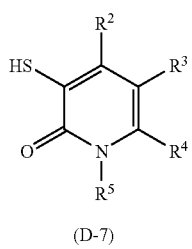

wherein $R^2$, $R^3$, $R^4$ and $R^5$ are as defined above.

Step D-1

This is a step for preparing a compound represented by the formula (D-2) from a compound represented by the formula (D-1).

This step can be carried out by an usual hydrogenation reaction (catalytic reduction). Examples of a catalyst include palladium on carbon, platinum oxide, palladium dioxide or the like. Example of a reaction solvent includes alcohol (methanol or ethanol). As a reaction temperature preferred is room temperature. Furthermore, this reduction can be carried out under atmosphere or medium pressure.

Step D-2

This is a step for preparing a compound represented by the formula (D-3) which comprises diazotizating a compound represented by the formula (D-2) followed by thiocarbonylating.

Diazotization can be carried out at −40 to 20° C., preferred is 0 to 10° C., and a diazonium salt can be obtained under acidic condition. As a reaction solvent preferred is water or alcohol (methanol or the like). The thiocarbonylation of the obtained diazonium salt can be carried out reacting with ethyl potassium xanthate, and preferred is to be reacted in water. Example of the reaction temperature includes room temperature to 80° C., preferred is 40° C.

Step D-3

This is a step for preparing a compound represented by the formula (D-4) which comprises reacting a compound represented by the formula D-3) in the presence of a base followed by oxidating by dimethylsulfoxide.

Examples of a base include lithium hydroxide, sodium hydroxide, potassium hydroxide or the like, especially preferred is sodium hydroxide. Examples of a reaction solvent include alcohol (e.g., ethanol, propanol, butanol or the like), tetrahydrofuran or the like, preferred is ethanol. Example of the reaction temperature includes 0 to 60° C., preferred is room temperature.

Step D-4

This is a step for preparing a compound represented by the formula (D-5) which comprises heating in the presence of pyridium chloride a compound represented by the formula (D-4). This step is carried out in a similar manner to Step B-3.

Step D-5

This is a step for preparing a compound represented by the formula (D-6) which comprises reacting a compound represented by the formula (D-5) and a compound represented by the formula: $R^5Hal$ wherein $R^5$ is as defined above: Hal is halogen in the presence of a base.

When as a base are used sodium hydroxide, potassium hydroxide, potassium carbonate, sodium carbonate, DBU or the like, as a reaction solvent cam be used dimethylformamide, tetrahydrofuran, alcohol (e.g., methanol, etahnol or n-butanol) or the like. Furthermore, when as a base lithium hydride or the like, preferred is sodium hydride, as a reaction solvent can be used dimethylformamide, tetrahydrofuran or the like. Examples of a compound represented by the formula: $R^5Hal$ include halogenated alkyl (e.g., methyl iodide, ethyl iodide, propyl iodide, butyl iodide or the like), halogenated aralkyl (e.g., benzyl bromide, phenethyl bromide or the like) or the like. Example of the reaction temperature includes 0 to 0.200° C., preferred is room temperature to 150° C.

Step D-6

This is a step for preparing a compound represented by the formula (D-7) which comprises reducing a compound represented by the formula (D-6).

This step can be carried out in the presence of trialkylphosphine (e.g., trin-butylphosphine), triphenylphosphine or, the like. Examples of a reaction solvent include a water containing organic solvent (e.g., acetone, tetrahydrofuran, toluene, methylene chloride or the like). Example of the reaction temperature includes 0 to 150° C., preferred is room temperature to 100° C.

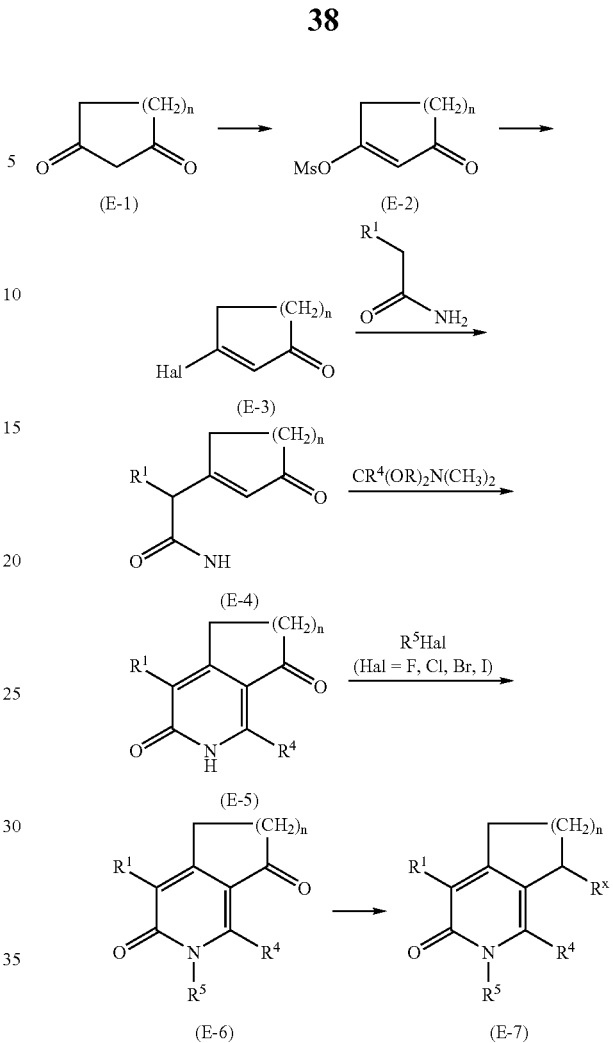

wherein $R^1$, $R^4$ and $R^5$ are as defined above; n is 1 or more; Hal is halogen.

Step E-1

This is a step for preparing a compound represented by the formula (E-2) which comprises reacting a compound represented by the formula (E-1) with methanesulfonyl halide (e.g., methanesulfonyl chloride).

Examples of a reaction solvent include methylene chloride, toluene, tetrahydrofuran, especially preferred is methylene chloride. Example of the reaction temperature includes 0 to 150° C., preferred is room temperature to 100° C.

Step E-2

This is a step for preparing % a compound represented by the formula (E-3) which comprises reacting a compound represented by the formula (E-2) with a benzyltrialkylammonium halide in the presence of borontrifluoride ether complex ($BF_3.Et_2O$).

Examples of a benzyltrialkylammonium halide include benzyltriethylammonium chloride, benzyltributylammonium chloride or the like, especially preferred is benzyltriethylammonium chloride. Example of the reaction temperature includes 0 to 180° C., preferred is room temperature. Examples of a reaction solvent include methylene chloride, toluene or the like. TMS triflate or the like can be used instead of borontrifluoride ether complex ($BF_3.Et_2O$).

Step E-3

This is a step for preparing a compound represented by the formula (E-4) which comprises reacting a compound represented by the formula (E-3) and a compound represented by the formula: $R^1CH_2C(=O)NH_2$ in the presence of base.

Examples of a base include lithium hydride, sodium hydride or the like, especially preferred is sodium hydride. Examples of a reaction solvent include dimethylformamide, tetrahydrofuran, toluene, diglyme or the like, especially preferred is diglyme. Example of the reaction temperature includes 0 to 150° C., preferred is room temperature to 100° C.

Step E-4

This is a step for preparing a compound represented by the formula (E-5) which comprises reacting a compound represented by the formula (E-4) and a compound represented by the formula: $CR^4(OR)_2N(CH_3)_2$ wherein $R^4$ is as defined above; R is alkyl or the like.

Examples of a compound represented by the formula: $CR^4(OR)_2N(CH_3)_2$ include N,N-dimethylformamide dimethyl acetal, N,N-dimethylformamide diethyl acetal, N,N-dimethylformamide dipropyl acetal, N,N-dimethylacetamide dibutyl acetal or the like. Examples of a reaction solvent include dimethylformamide, tetrahydrofuran or the like. Example of the reaction temperature includes 0 to 150° C., preferred is room temperature to 100° C.

Step E-5

This is a step for preparing a compound represented by the formula (E-6) which comprises reacting a compound represented by the formula (E-5) and a compound represented by the formula: $R^5Hal$ wherein $R^5$ is as defined above; Hal is halogen in the presence of a base. This step can be carried out in a similar manner to Step D-5.

Step E-6

This is a step for preparing a compound represented by the formula (E-7) which comprises reacting a compound represented by the formula (E-6) with a reducing reagent.

Examples of a reaction solvent include diethyl ether, tetrahydrofuran, methylene chloride or the like. When a reducing reagent is sodium cyanoborohydride or trialkylsilane, can be prepared a compound represented by the formula (E-7) wherein Rx is hydrogen, and the reaction can be carried out in the presence of boron trifluoride-diethyl ether complex. When a reducing reagent is sodium borohydride, can be prepared a compound represented by the formula (E-7) wherein Rx is hydroxy.

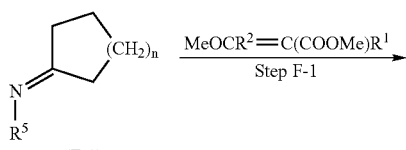

(F-1)

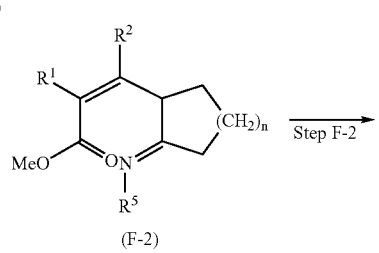

(F-2)

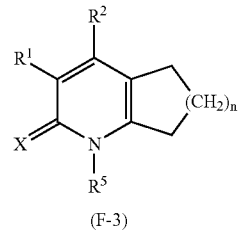

(F-3)

wherein $R^1$, $R^2$ and $R^5$ are as defined above; n is 1 or more.

Step F-1

This is a step for preparing a compound represented by the formula (F-2) which comprises reacting a compound represented by the formula (F-1) and a compound represented by the formula $MeOCR^2=C(COOMe)R^1$.

Examples of a compound represented by the formula: $MeOCR^2=C(COOMe)R^1$ include dimethyl methoxymethylenemalonate, diethyl methoxymethylenemalonate or the like. Examples of a reaction solvent include diglyme, toluene or the like. Example of the reaction temperature includes room temperature to 200° C., preferred is 100 to 150° C.

Step F-2

This is a step for preparing a compound represented by the formula (F-3) which comprises heating a compound represented by the formula (F-2).

This step using as a reaction solvent diglyme or toluene, is carried out at room temperature to 200° C., preferred is 100 to 150° C. Step F-1 and Step F-2 may be carried out continuously, without isolation of a compound represented by the formula (F-2).

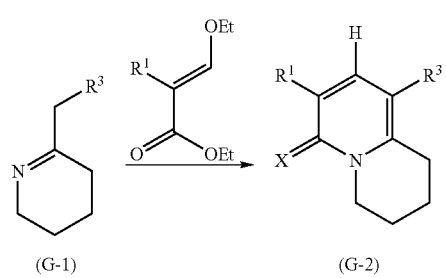

(G-1)                    (G-2)

wherein $R^1$, $R^3$ and X are as defined above

Step G-1

This is a step for preparing a compound represented by the formula (G-2) which comprises reacting a compound represented by the formula (G-1) and a compound represented by the formula $EtOCH=C(COOEt)R^1$.

Examples of a compound represented by the formula: $EtOCH=C(COOEt)R^1$ include diethyl ethoxymethylenemalonate or the like. As a reaction solvent preferred is terahydrofuran or diethyl erther. Example of the reaction temperature includes −100° C. to room temperature, preferred is −78 to 0° C. As a base can be used LDA or butyl lithium. After the reaction, the reaction mixture may de neutralized with acetic acid or the like.

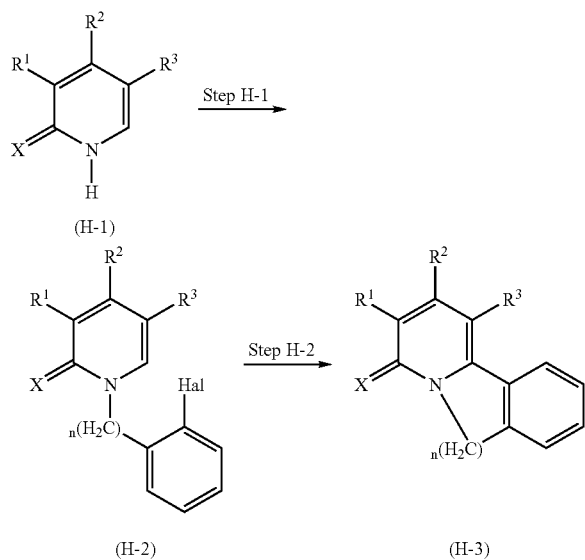

(H-1)

(H-2)            (H-3)

wherein R¹, R², R³, and X are as defined above; n is 1 or more integer; Hal is halogen.

Step H-1

This is a step for preparing a compound represented by the formula (H-2) which comprises reacting a compound represented by the formula (H-1) with o-halogenoaralkyl halide.

Examples of o-halogenoaralkyl halide include o-bromobenzyl bromide, o-bromophenethyl bromide, o-bromophenylpropylbromide or the like. Examples of a reaction solvent include terahydrofuran, dimethylformamide or the like, especially preferred is dimethylformamide. Examples of a base used include sodium hydride, potassium carbonate or the like. Example of the reaction temperature includes 0 to 200-C, preferred is room temperature to 100° C.

Step H-2

This is a step for preparing a compound represented by the formula (H-3) which comprises reacting a compound represented by the formula (H-2) in the presence of palladium catalyst, triphenylphosphine, base, and quaternary ammonium salt.

Examples of palladium catalyst include palladium dibenzylideneacetone (or chloroform complex therof) or tetraxistriphenylphosphinepalladium. Examples of a base include potassium carbonate, sodium carbonate, triethylamine or the like, especially potassium carbonate. Especially preferred is to be carried out in the presence of quaternary ammonium chloride, example of quaternary ammonium chloride include tetraethylammonium chloride, tetrabutylammonium chloride or the like. Lithium chloride may be used instead of it. Examples of a reaction solvent include dimethylformamide, dimethoxyethane, terahydrofuran or the like. Example of the reaction temperature includes 0 to 150° C., preferred is 80 to 130° C.

Various compounds of the present invention can be prepared by conversion of functional group of the above obtained compounds of the present invention as follows.

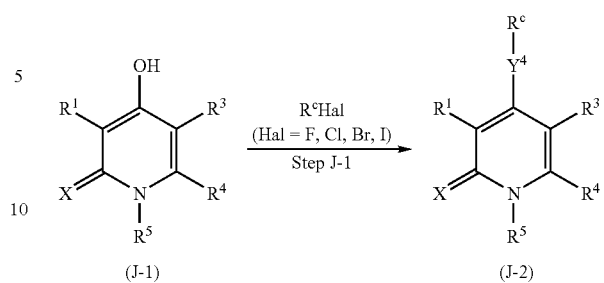

(J-1)            (J-2)

Step J-1

This is a step for preparing a compound represented by the formula (J-2) which comprises reacting a compound represented by the formula (J-1) and a compound represented by the formula: R$^c$Hal wherein R¹ is as defined above; Hal is halogen in the presence of a base.

Examples of a compound represented by the formula: R$^c$Hal include alkyl halide (e.g., methyl iodide or ethyl iodide), acyl chloride (e.g., acetyl chloride, propionyl chloride), aryl halide (e.g., bromobenzene), heteroaryl halide (e.g., 2-chlorobenzoxazole or the like), aralkyl halide (e.g., benzyl bromide, phenethyl bromide or the like), heteroaralkyl halide (e.g., 2-picolyl chloride, 3-picolyl chloride or the like), arylsulfonyl halide (e.g., benzenesulfonyl chloride or the like) or the like. Examples of a base include lithium hydride, sodium hydride or the like, especially sodium hydride. Examples of a reaction solvent include terahydrofuran, dimethylformamide, or the like, especially preferred is dimethylformamide.

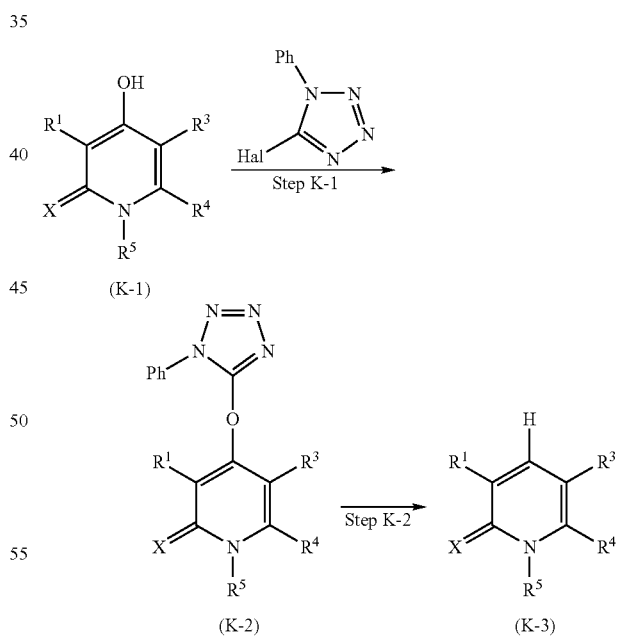

(K-1)

(K-2)            (K-3)

Step K-1

This is a step for preparing a compound represented by the formula (K-2) which comprises reacting a compound represented by the formula (K-1) with chloro-1-phenyl-1H-tetrazole in the presence of a base.

Examples of a base include potassium carbonate, sodium carbonate, sodium hydroxide or the like, especially potassium carbonate. Examples of a reaction solvent include dimethylformamide, terahydrofuran or the like, especially preferred is dimethylformamide. Example of the reaction temperature includes 0 to 100° C., especially preferred is room temperature.

Step K-2

This is a step for preparing a compound represented by the formula (K-3) which comprises catalytically reducing a compound represented by the formula (K-2) in the presence of a catalyst.

Examples of a catalyst include palladium on carbon, platinum oxide or the like, especially 10% palladium on carbon. Examples of a reaction solvent include alcohol (e.g., ethanol), dimethylformamide, a mixture of these and water, especially preferred is a mixture of dimethylformamide and water. The reaction may be carried out under atmosphere pressure or medium pressure (e.g., 5 kg/cm$^2$), especially preferred is medium-pressure (e.g., 5 kg/cm$^2$).

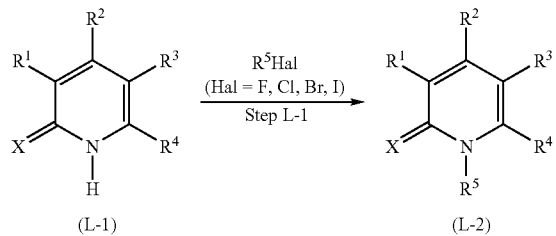

wherein $R^1$, $R^2$, $R^3$, $R^4$, and $R^5$ are as defined above; Hal is halogen.

Step L-1

This is a step for preparing a compound represented by the formula (L-2) which comprises reacting a compound represented by the formula (L-1) and a compound represented by the formula: $R^5$Hal wherein $R^5$ is as defined above; Hal is halogen in the presence of a base. This step can be carried out in a similar manner to Step D-5.

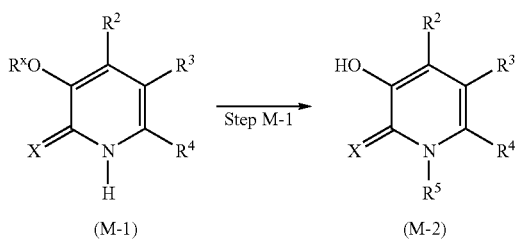

wherein $R^2$, $R^3$, $R^4$, $R^5$, and X are as defined above; $R^x$ is alkyl or the like.

Step M-1

This is a step for preparing a compound represented by the formula (M-2) which comprises heacting a compound represented by the formula (M-1) in the presence of pyridinium chloride. This step can be carried out in a similar manner to Step B-3.

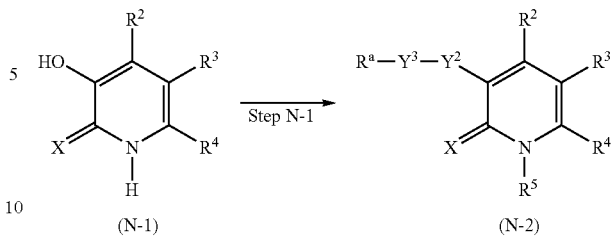

Step N-1

This is a step for preparing a compound represented by the formula (N-2) which comprises reacting a compound represented by the formula (N-1) with a various kind of reagent.

In this step, can be used any kind of reagent which can be reacted with phenolic hydroxy of a compound represented by the formula (N-1). Furthermore, can be used if necessary, a base, a condensing reagent, a catalyst or the like. The reaction temperature may be selected according to a kind of reaction, a used reagent, a base, a condensing reagent, a catalyst or the like.

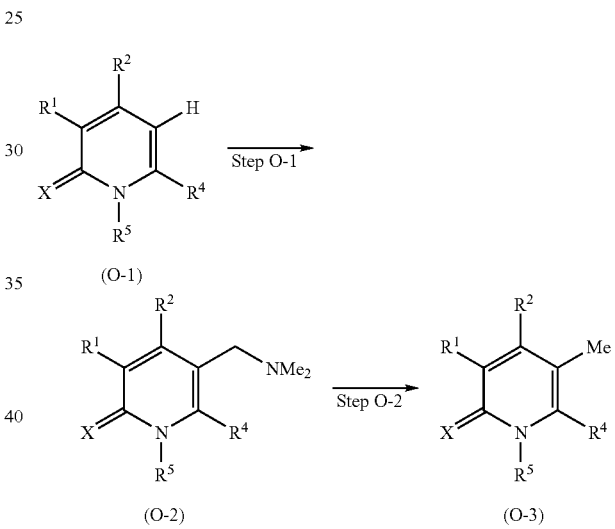

wherein $R^1$, $R^2$, $R^4$, and $R^5$ are as defined above.

Step O-1

This is a step for preparing a compound represented by the formula (0-2) which comprises reacting a compound represented by the formula (0-1) with N,NN',N'-teteramethyl-diaminomethane.

Examples of a reaction solvent include toluene, ethanol, water containing etahnol or the like, especially preferred is water containing ethanol. Example of the reaction temperature includes room temperature to 100° C., especially preferred is 60 to 80° C. Preferred is to be carried out under heating at reflux.

Step O-2

This is a step for preparing a compound represented by the formula (0-3) which comprises reacting a compound represented by the formula (0-2) with a halogenated alkyl, followed by triphenylphosphine and finally treating with sodium hydroxide.

Examples of a halogenated alkyl include ethyl bromide, iodomethane or the like. As a reaction solvent preferred is methylene chloride, alcohol, toluene, and as a reaction temperature preferred is room temperature.

In the step of conversion to phosphonium salt reacting with triphenylphosphine, as a reaction solvent is used alcohol (ethanol) or teterahydrofuran, and as a reaction temperature at 50 to 100° C., especially preferred is 70° C.

The above obtained phosphonium salt can be converted to a methyl derivative by treating with a base. Examples of a base include sodium hydroxide or potassium hydroxide.

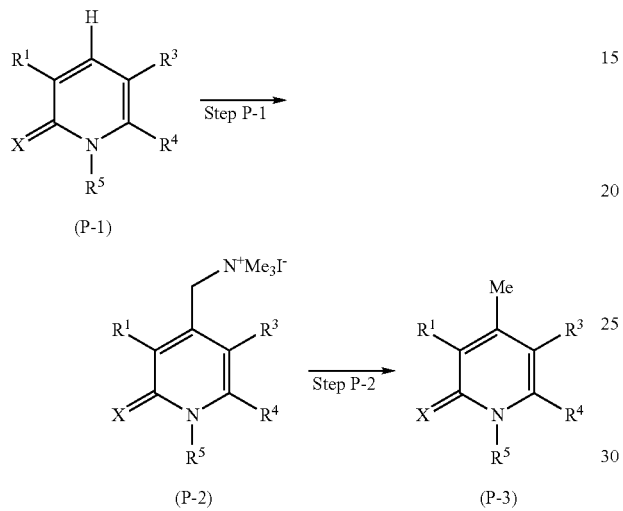

wherein $R^1$, $R^3$, $R^4$, and $R^5$ are as defined above.

A compound represented by the formula (P-2) is obtained by reacting a compound represented by the formula (P-1) with N,NN',N'-teteramethyldiaminomethane, followed by treatment with iodomethane in a similar manner to Step O-1.

A compound represented by the formula P-3) can be prepared by treating with triphenylphosphine, followed by a base in a similar manner to Step O-2.

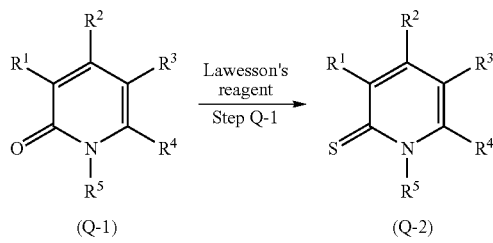

wherein $R^1$, $R^2$, $R^3$, $R^4$, and $R^5$ are as defined above.

Step Q-1

This is a step for preparing a compound represented by the formula (Q-2) which comprises reacting a compound represented by the formula (Q-1) with Lawesson's reagent.

Examples of a reaction solvent include benzene, toluene, xylene or the like, especially preferred is toluene. Example of the reaction temperature includes 80 to 250° C., especially preferred is to be carried out in toluene under heating at reflux.

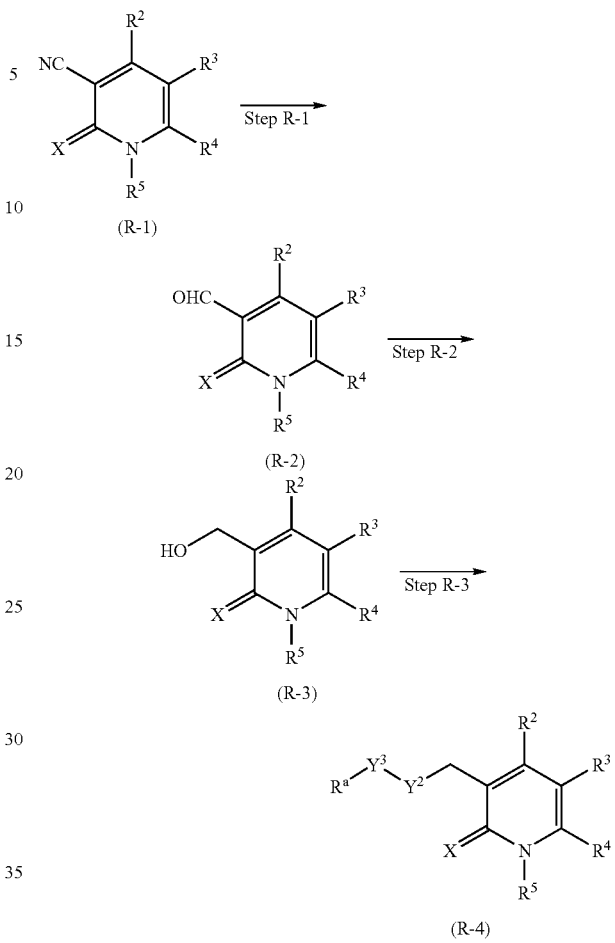

wherein $R^2$, $R^3$, $R^4$, $R^5$, X, $R^a$, Y, and $Y^2$ are as defined above.

Step R-1

This is a step for preparing a compound represented by the formula (R-2) which comprises reacting a compound represented by the formula (R-1) with diisobutylaluminum hydride.

Examples of a reaction solvent include toluene, tetrahydrofuran or the like. Preferred is to be carried out under ice-cooling.

Step R-2

This is a step for preparing a compound represented by the formula (R-3) which comprises reacting a compound represented by the formula (R-2) with sodium borohydride.

Examples of a reaction solvent include alcohol (e.g., ethanol, methanol or the like). The reaction may be carried out at room temperature.

Step R-3

This is a step for preparing a compound represented by the formula (R-4) which comprises reacting a compound represented by the formula (R-3) with a various kinds of reagent.

In this step, can be used any kind of reagent which can be reacted with phenolic hydroxy of a compound represented by the formula (R-3). Furthermore, can be used if necessary, a base, a condensing-reagent, a catalyst or the like. The reaction temperature may be selected according to a kind of reaction, a used reagent, a base, a condensing reagent, a catalyst or the like.

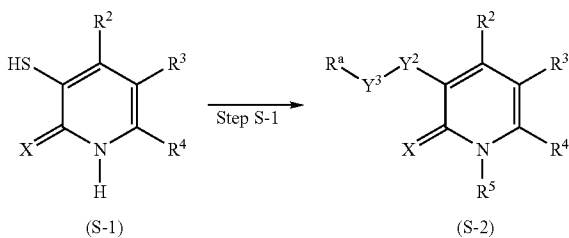

wherein $R^2$, $R^3$, $R^4$, $R^5$, X, $R^a$, X, $Y^2$, and $Y^3$ are as defined above.

Step S-1

This is a step for preparing a compound represented by the formula (S-2) which comprises reacting a compound represented by the formula (S-1) with various kinds of reagent.

In this step, can be used any kind of reagent which can be reacted with mercapto group of a compound represented by the formula (S-1). Furthermore, can be used at need a base, a condensing reagent, a catalyst or the like. The reaction temperature may be selected according to a kind of reaction, a used reagent, a base, a condensing reagent, a catalyst or the like.

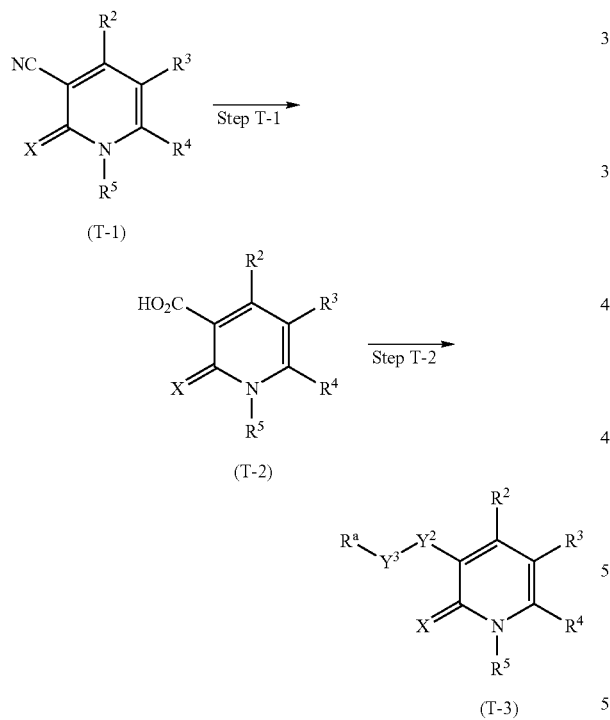

wherein $R^2$, $R^3$, $R^4$, $R^5$, X, R—, X, $Y^2$, and $Y^3$ are as defined above.

Step T-1

This is a step for preparing a compound represented by the formula (T-2) which comprises hydrolyzing a compound represented by the formula (T-1) with sodium borohydride.

In the hydrolysis of this step, can be used a base or an acid. Examples of a base include sodium hydroxide or potassium hydroxide. Examples of an acid conc. hydrochloric acid or conc. sulfuric acid. Examples of a reaction solvent include ethanol, water or mixture of them. Example of the reaction temperature includes 80 to 150° C., especially preferred is 100° C.

Step T-2

This is a step for preparing a compound represented by the formula (T-3) which comprises reacting a compound represented by the formula (T-2) with a various kind of reagent.

In this step, can be used any kind of reagent which can be reacted with carboxyl of a compound represented by the formula (T-2). Furthermore, can be used at need a base, a condensing reagent, a catalyst or the like. The reaction temperature may be selected according to a kind of reaction, a used reagent, a base, a condensing reagent, a catalyst or the like.

For example, a reaction when $Y^2$ is —C(=O)—NH—; $Y^3$ is alkylene; $R^a$ is aryl or heteroaryl, is explained as follows.

A compound represented by the formula (T-3) can be prepared by reacting a compound represented by the formula (T-2) with methanesulfonyl chloride in the presence of a base, followed by a compound represented by the formula: $R^aY^3NH_2$. Examples of a base include trialkylamine (e.g., triethylamine), pyridine or the like, especially preferred is triethylamine. Examples of a reaction solvent include dimethylformamide or the like. Example of the reaction temperature includes 0 to 150° C., especially preferred is room temperature to 100° C.

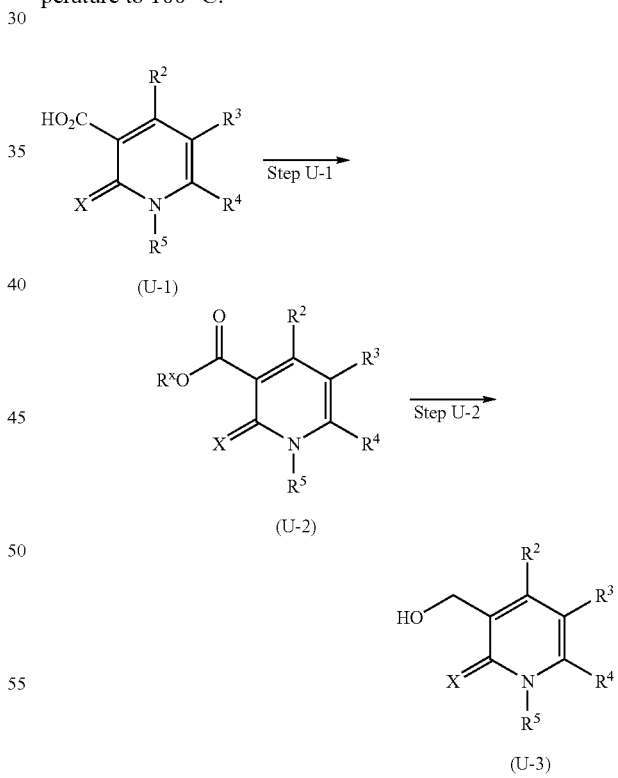

wherein $R^2$, $R^3$, $R^4$, $R^5$, and X are as defined above; $R^x$ is methyl, mesyl, trimethylsilyl or the like.

Step U-1

This is a step for preparing a compound represented by the formula (U-2) which comprises esterification of a compound represented by the formula (U-1).

As an ester, preferred is methyl ester, mesyl ester, trialkylsilyl ester (e.g., trimethylsilyl ester or the like). It can be carried out under an usual esterfication condition.

For example, when preparing trialkylsilyl ester, a compound represented by the formula (U-2) may be prepared by reacting a compound represented by the formula (U-1) with a trialkylsilyl halide. Examples of a trialkylsilyl halide include trimethylsilyl chloride or the like. In this step, preferred is to be carried out in the presence of hexamethyldisilazane. Examples of a reaction solvent include benzene, toluene, xylene or the like, especially preferred is toluene. Example of the reaction temperature includes room temperature to 200° C., especially preferred is to be carried out in toluene under heating at reflux.

Step U-2

This is a step for preparing a compound represented by the formula (U-3) which comprises reacting a compound represented by the formula (U-2) with a reducing reagent.

Examples of a redecing reagent include lithiumaluminum hydride, lithium borohydride, DIBAL or the like. This step can be carried out in the presence of cerium chloride. Examples of a reaction solvent include alcohol (methanol or ethanol), tetrahydrofuran, diethyl ether. As the reaction temperature preferred is room temperature.

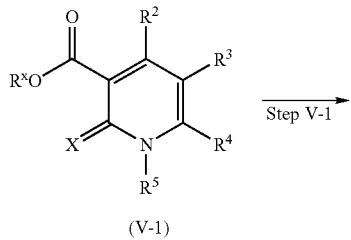

(V-1)

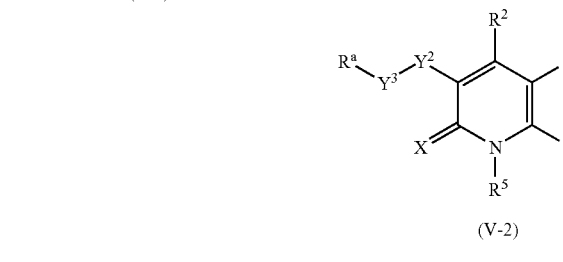

(V-2)

wherein $R^2$, $R^3$, $R^4$, $R^5$, X, $R^a$, $Y^2$, and $Y^3$ are as defined above; $R^x$ is alkyl or the like.

Step V-1

This is a step for preparing a compound represented by the formula (V-2) which comprises reacting a compound represented by the formula (V-1) with a various kind of reagent.

In this step, can be used any kind of reagent which can be reacted with the group represented by the formula: —C(=O)—$OR^x$ of a compound represented by the formula (V-2). Furthermore, can be used at need a base, a condensing reagent, a catalyst or the like. The reaction temperature may be selected according to a kind of reaction, a used reagent, a base, a condensing reagent, a catalyst or the like.

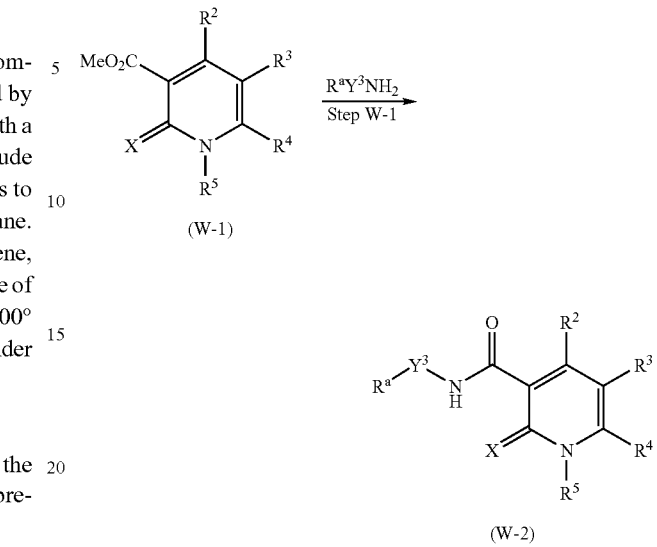

(W-1)

(W-2)

wherein $R^2$, $R^3$, $R^4$, $R^5$, X, $R^a$, and $Y^3$ are as defined above.

Step W-1

This is a step for preparing a compound represented by the formula (W-2) which comprises reacting a compound represented by the formula (W-1) and a compound represented by the formula: $R^aY^3NH_2$.

Examples of a compound represented by the formula: $R^aY^3NH_2$ include optionally substituted aralkylamine (e.g., benzylamine, phenethylamine, p-aminophenethylamine or the like), optionally substituted heteroaralkylamine (e.g., 2-(pyridin-4-yl)ethylamine or the like) or the like. Examples of a reaction solvent include xylene, diglyme or the like, especially preferred is diglyme. Examples of the reaction temperature includes 100 to 250° C., especially preferred is 150 to 200° C.

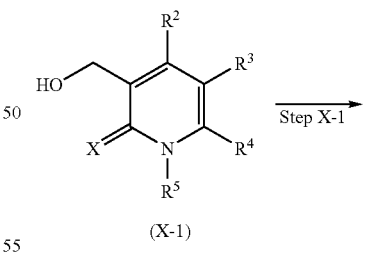

(X-1)

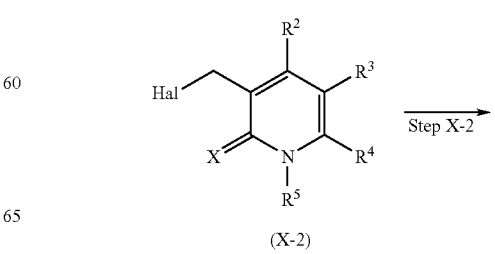

(X-2)

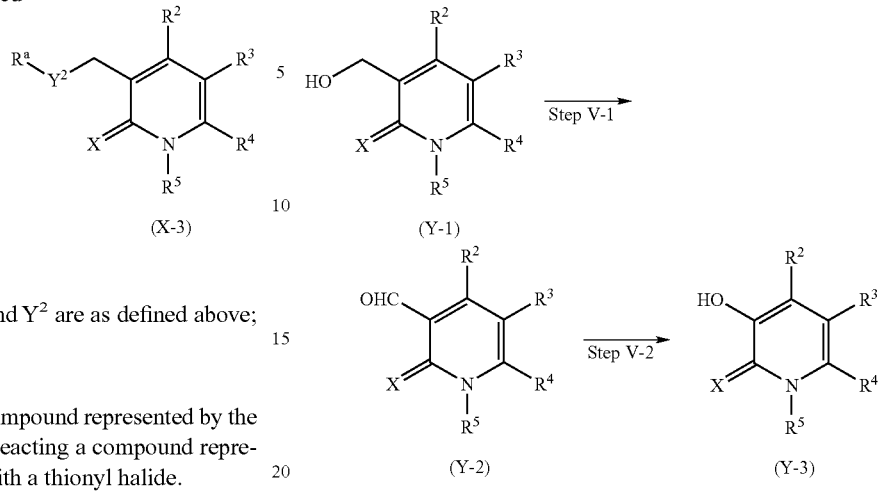

wherein $R^2$, $R^3$, $R^4$, $R^5$, X, $R^a$, and $Y^2$ are as defined above; Hal is halogen.

Step X-1

This is a step for preparing a compound represented by the formula (X-2) which comprises reacting a compound represented by the formula (—X-1) with a thionyl halide.

Examples of a thionyl halide include thienyl bromide, thienyl chloride or the like. Examples of a reaction solvent include methylene chloride, chloroform, crabon teterachloride or the like, especially preferred is methylene chloride. Examples of the reaction temperature includes 0 to 100° C., especially preferred is 10° C. to room temperature.

As another method, a compound represented by the formula (X-2) can be prepared by reacting a compound represented by the formula (X-1) with a N-halogenosuccinimide in the presence of triphenylphosphine. Examples of a N-halogenosuccinimide include N-chlorosuccinimide, N-bromosuccinimide or the like, especially preferred is N-bromosuccinimide. Examples of a reaction solvent include benzene, toluene, xylene, methylene chloride, chloroform, crabon teterachloride or the like.

Step X-2

This is a step for preparing a compound represented by the formula (X-3) which comprises reacting a compound represented by the formula (X-2) with a various kind of reagent.

In this step, can be used any kind of reagent which can be reacted with halogenomethyl of a compound represented by the formula (X-2). Furthermore, can be used if necessary, a base, a condensing reagent, a catalyst or the like. The reaction temperature may be selected according to a kind of reaction, a used reagent, a base, a condensing reagent, a catalyst or the like.

For example, a reaction when $Y^2$ is —S—; $Y^3$ is single bond, $R^a$ is aryl or heteroaryl, is explained as follows.

A compound represented by the formula (X-3) can be prepared by reacting a compound represented by the formula (X-2) with an arylmercaptane (e.g., benzenethiol or the like) or a heteroarylmercaptane (e.g., 2-mercaptobenzoxazole or the like) in the presence of a base.

Examples of a base include sodium carbonate, potassium carbonate or the like, especially preferred is potassium carbonate: Examples of a reaction solvent include dimethylformamide or the like. Examples of the reaction temperature includes 0 to 100° C., especially preferred is room temperature to 100° C.

wherein $R^2$, $R^3$, $R^4$, $R^5$, and X are as defined above.

Step Y-1

This is a step for preparing a compound represented by the formula (Y-2) which comprises Swern oxidation reacting a compound represented by the formula (Y-1) with dimethylsulfoxide and a oxalyl halide.

Examples of an oxalyl halide include an oxalyl chloride or the like. Examples of a reaction solvent include methylene chloride or the like. Examples of the reaction temperature includes −78 to 0° C., especially preferred is −60 to −40° C.

Step Y-2

This is a step for preparing a compound represented by the formula (Y-3) which comprises reacting a compound represented by the formula (Y-2) with an oxidizing reagent.

Examples of an oxidizing reagent include meta-chloroperbenzoic acid or the like. In this step, may be added sodium hydrogen phosphate. Examples of a reaction solvent include methylene chloride, tetrahydrofuran or the like. This reaction may be carried out at room temperature.

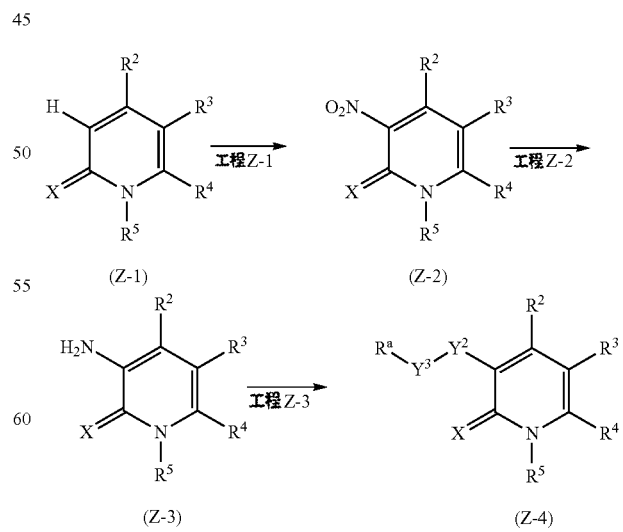

wherein $R^2$, $R^3$, $R^4$, X, $R^a$, $Y^2$, and $Y^3$ are as defined above.

Step Z-1

This is a step for preparing a compound represented by the formula (Z-2) from a compound represented by the formula (Z-1). An usual nitration reaction may be carried, out. For example, the nitration reaction may be carried out using nitrating acid (sulfuric acid and nitric acid).

Step Z-2

This is a step for preparing a compound represented by the formula (Z-3) which comprises reducing a compound represented by the formula (Z-2). This step can be carried out in a similar manner to Step D-1.

Step Z-3

This is a step for preparing a compound represented by the formula (Z-4) which comprises reacting a compound represented by the formula (Z-3) with a various kind of reagent.

In this step, can be used any kind of reagent which can be reacted with an amino group of a compound represented by the formula (Z-3). Furthermore, can be used if necessary, a base, a condensing reagent, a catalyst or the like. The reaction temperature may be selected according to a kind of reaction, a used reagent, a base, a condensing reagent, a catalyst or the like.

For example, when $Y^2$ is —NH—C(=O)—; $Y^3$ is single bond, $R^a$ is alkyl or aryl, is explained as follows.

A compound represented by the formula (Z-4) can be prepared by reacting a compound represented by the formula (Z-3) with an acylation reagent (e.g., acetyl chloride, benzoyl chloride or the like).

In this step, preferred is to be carried out in the presence of a base. For example, can be used pyridine or the like. Examples of a reaction solvent include dimethylformamide or the like. Examples of the reaction temperature includes 0 to 150° C., especially preferred is room temperature to 100° C.

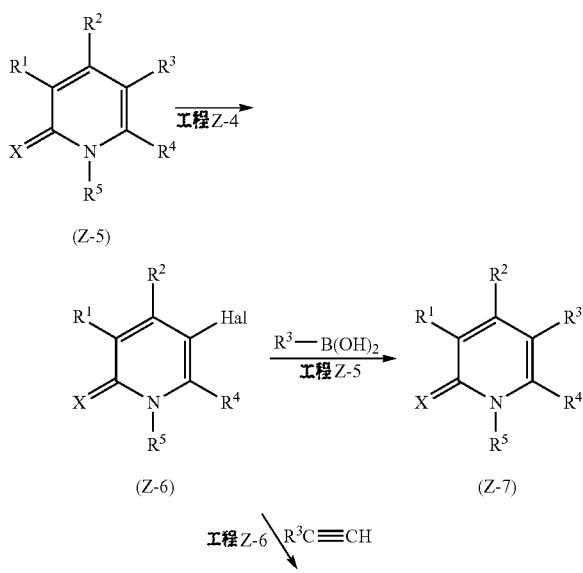

(Z-5)

(Z-6)

(Z-7)

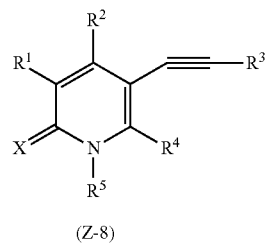

(Z-8)

wherein $R^1$, $R^2$, $R^3$, $R^4$, $R^5$, and X are as defined above; Hal is halogen.

Step Z-4

This is a step for preparing a compound represented by the formula (Z-6) which comprises reacting a compound represented by the formula (Z-5) with a N-halogenosuccinimide.

This step can be carried out in a similar manner to Step B-1.

Step Z-5

This is a step for preparing a compound represented by the formula (Z-7) which comprises reacting a compound represented by the formula (Z-6) with a compound represented by the formula: $R^3$—B(OH)$_2$ in the presence of a palladium catalyst.

Examples of $R^3$ of a compound represented by the formula: $R^3$—B(OH)$_2$ include optionally substituted alkenyl, optionally substituted alkynyl, optionally substituted arylalkenyl, optionally substituted arylalkynyl, optionally substituted aryl, optionally substituted heteroaryl or the like. Examples of a palladium catalyst include Pd(PPh$_3$)$_4$, PdCl$_2$(PPh$_3$)$_2$ or the like. In this step, preferred is to be carried out in the presence of a base. Examples of a base include triethylamine, potassium carbonate, sodium carbonate, a sodium alcoholate (e.g., NaOMe, NaOEt or the like). Examples of a reaction solvent include dimethylformamide, benzene, toluene, xylene or the like, especially preferred is dimethylformamide. Examples of the reaction temperature includes room temperature to 200° C., especially preferred is 50 to 100° C.

Step Z-6

This is a step for preparing a compound represented by the formula (Z-8) which comprises reacting a compound represented by the formula (Z-6) with a compound represented by the formula: $R^3C\equiv CH$ in the presence of a palladium catalyst.

Examples of $R^3$ of a compound represented by the formula: $R^3C\equiv CH$ include optionally substituted alkenyl, optionally substituted alkynyl, optionally substituted arylalkenyl, optionally substituted arylalkynyl, optionally substituted aryl, optionally substituted heteroaryl or the like. This step can be carried out in a similar manner to Step Z-5. This step may be carried out in the presence of copper iodide or the like.

When preparing the compound of the present invention, can be used a solid phase reaction as follows.

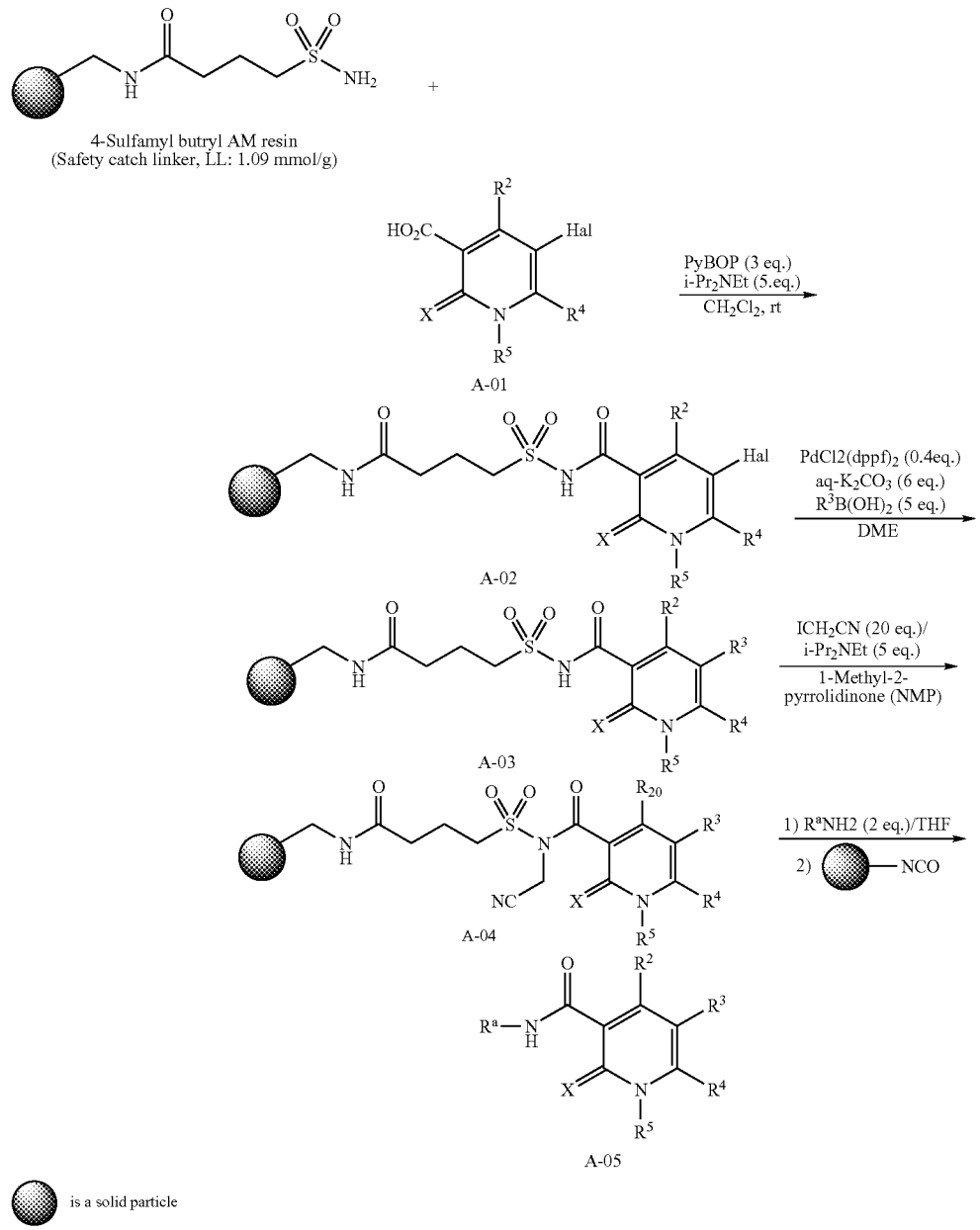

is a solid particle wherein $R^2$, $R^3$, $R^4$, $R^5$, and $R^a$ are as defined above.

Preparation of a Resin A-02

This is step for bonding a resin to a carboxylic acid.

Examples of a resin include 4-sulfamylbutyryl AM resin or the like. Example of a carboxylic acid can be used includes a compound represented by A-01. In this case, can be selected $R^2$, $R^4$, $R^5$ and X, and carboxylic acid.

For example, can be used 4-n-butyl-5-iodo-2-oxo-1,2-dihydropyridine-3-carboxylic acid (a carboxylic acid X-1 wherein $R^2$ and $R^4$ are hydrogen; $R^5$ is n-butyl; X is oxygen atom). Examples of a reaction solvent include methylene chloride or the like. As the reaction temperature preferred is room temperature. In this step, preferred is to be carried out in the presence of N,N-diisopropylethylamine and PyBOP.

Example of the reaction time includes several hours to several tens hours, especially preferred is ten and several hours. After the reaction, Resin (A-02) can be prepared by filtrating of resin, followed by washing with a washing solvent (e.g., water, THF, methylene chloride, diethyl ether or the like), succesively.

Preparation of a Resin A-03

This is step for preparing a resin A-03 from the above obtained resin A-02. A resin A-03 is prepared by reacting a resin A-02 and a compound represented by the formula: $R^3$—$B(OH)_2$ in the presence of a palladium catalyst and a base.

Examples of a reaction solvent include DME or the like. Examples of a palladium catalyst include $PdCl_2(dppf)$ or the like. It is desirable to use about 5 chemical equivalent of a compound represented by the formula: $R^3$—$B(OH)_2$ to a solid particle. Examples of a compound represented by the formula: $R^3$—$B(OH)_2$ include a compound represented by the formula: $R^3$—$B(OH)_2$ wherein $R^3$ is optionally substituted aryl or optionally substituted aryl. In this case, can be widely selected a substituent. Examples of a base include potassium carbonate or the like. As the reaction temperature preferred is about 80° C. Example of the reaction time includes several hours to several tens hours, especially preferred is ten and several hours. After the reaction, resin (A-03) can be prepared by filtrating of resin, followed by washing with a washing solvent (e.g., water, THF, N-methylpyrrolidone, methylene chloride, diethyl ether or the like), succesively.

Preparation of Resin a A-04

This is step for preparing a resin A-04 by reacting a resin A-03 with iodoacetonitrile in the presence of a base.

Examples of a reaction solvent include N-mathylpyrrolidone or the like. Examples of a base N,N-diisopropylethylamine or the like. As the reaction temperature preferred is room temperature. Example of the reaction time includes several hours to several tens hours, especially preferred is ten and several hours. After the reaction, resin (A-04) can be prepare by filtrating of resin, followed by washing with a washing solvent (e.g., A-methylpyrrolidone, methylene chloride, diethyl ether or the like), succesively.

Preparation of a Compound (A-05) of the Present Invention

This is step for preparing a compound (A-05) of the present invention by reacting a resin A-04 with an amine, after the reaction, followed by cutting off the compound from a solid particle.

Examples of a reaction solvent include THF or the like. In this step, can be used a various amine. By this way, can be prepared a compound possessing various $R^a$ of the present invention. The reaction is carried out for about 24 h, to which is added macromolecule immobilized isocyanate resin. After shaking the mixture for several hours, excess of amine is filtered off, and can be cut off the compound (A-05) from the solid particle. The compound (A-05) can be prepared by filtering off the resin, followed by eluting with an eluting solvent (e.g., methylene chloride), and evaporating the filtrate under reduced pressure.

The compound of the present invention can be prepared another solid phase synthesis shown below.

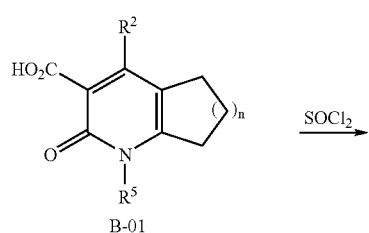
B-01

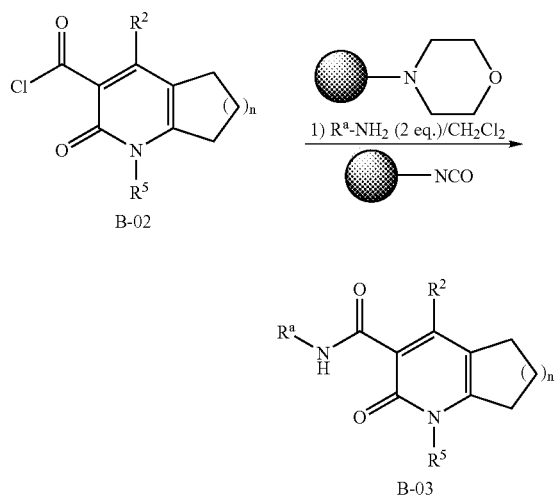
B-02

B-03 wherein $R^1$, $R^5$, and $R^a$ are as defined above; n is 1 or more integer.

Preparation of Compound B-02

This is step for preparing a compound (B-$_{02}$) by reacting a compound (B-01) with thiony chloride.

Examples of a compound (B-01) include 1-butyl-2-oxo-1,2,5,6,7,8,9,10-octahydrocyclooocta[b]pyridine-3-carboxylic acid wherein $R^2$ is hydrogen; $R^5$ is n-butyl, or the like. Examples of a reaction solvent include toluene or the like. As the reaction temperature, preferrred is about 65° C. The reaction is progressed for comparatively short time, e.g., about 20 min. The compound (B-02) can be prepared by evaporating the reaction mixture under reduced pressure.

Preparation of Compound B-03

This is step for preparing a compound (B-03) of the present invention by reacting an amine ($R^a$—$NH_2$) and a compound (B-02) in the presence of macromolecule immobilized N-methylmorpholine resin (1.93 mmol/g).

Examples of a reaction solvent include methylene chloride or the like. In this step, can be used various amines. By this way, can be prepared a compound possessing various $R^a$ of the present invention. The reaction is carried out for about 24 h, to which is added macromolecule-immobilized isocyanate resin. After shaking for several hours, excess of amine is filtered off, and can be cut off the compound (B-03) from the solid particle. That is to say, the compound (B-03) can be prepared by filtering off the resin, followed by eluting with a eluting solvent (e.g., methylene chloride), and evaporating the filtrate under reduced pressure.

In above mentioned reaction, the case is exemplified that $R^1$ and $R^4$ are taken together with an adjacent atom to form ring, though another case taht $R^3$ and $R^4$ are not taken together can be carried out as well.

The compound of the present invention can be prepared by another solid phase synthesis shown below.

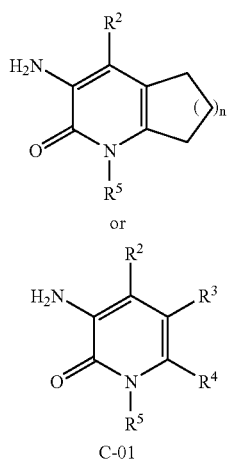

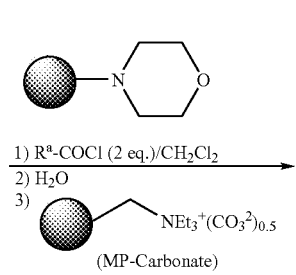

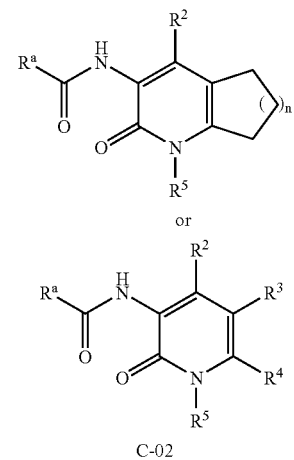

wherein $R^2$, $R^4$, $R^5$, and $R^a$ are as defined above; n is 1 or more integer.

Preparation of Compound C-02

This is step for preparing a compound (C-02) of the present invention by reacting an acyl chloride ($R^a$—COCl) and a compound (C-01) in the presence of macromolecule immobilized N-methylmorpholine resin (1.93 mmol/g).

Examples of a reaction solvent include methylene chloride or the like. In this step, can be used various acyl chloride. By this way, can be prepared a compound possessing various $R^a$ of the present invention. The reaction is carried out for about 24 h, to which is added macromolecule-immobilized carbonate resin (MP-Carbonate). After shaking for several hours, excess of amine is filtered off, and can be cut off the compound (C-02) from the solid particle. That is to say, the compound (C-02) can be prepared by filtering off the resin, followed by eluting with a eluting solvent (e.g., methylene chloride), and evaporating the filtrate under reduced pressure. Furthermore, the compound having higher purity can be obtained by fixing these obtained product on the full automatic purifier or the like.

In above mentioned reaction, the case is exemplified that $R^1$ and $R^4$ are taken together with an adjacent atom to form ring, furthermore when $R^1$ and $R^4$ are not taken together this solid phase synthesis can be carried out.

A compound represented by the formula: $R^3$—B(OH)$_2$ and a compound represented by the formula: $R^a$NH$_2$ used in these solid phase synthesis may be a commercially obtainable compound or synthesized.

Since this preparation is a solid phase synthesis, a purification operation is washing a solid particle. This can usually be carried out as a routine work, and tsynthesis is useful for prepaing many compounds having a various substituents for a short time. Therefore, taking the advantage of solid phase synthesis, can be reacted a compound having the fixed skeleton or the like with a compound represented by the various kinds of formula: $R^3$—B(OH)$_2$ or $R^a$NH$_2$ to obtain several tens to several tens thousands compounds. Among them a compound having the most suitable substituent can be selected to find the compound of the present invention having high activity.

Furthermore, a library of the compound of the present invention can be prepared from a group consisting of two or more compounds obtained by this preparation. In this case, the split synthesis described above or parallel synthesis may be carried out. Furthermore, a compound prepared by usual organic synthesis may be used. The term of compound library means a group consisting of two or more compounds having a common partial structure.

Example of the common partial structure of the compound of the present invention includes a pyridone skeletone. Furthermore, a more preferable embodiment includes that the nitrogen atom of the pyridone skeletone is substituted with C2 or more alkyl or the like. Furthermore, a more preferable embodiment includes that an amido bond (—C(=O)—NH or —NH—C(=O)—) is at 3-position of the pyridone skeletone.

These compounds having such a common partial structure exhibit a binding activity to the cannabinoid type 2 receptor, and a library thereof is useful to search an anti-inflammatory agent, an analgesic agent, a nephritis treating agent or the like.

Furthermore, the library of the present compound can be used not only to search a compound exhibiting a binding activity to the cannabinoid type 2 receptor (especially, a compound exhibiting an agonistic activity to the cannabinoid type 2 receptor), but also useful for the screening for other medical use. In order to obtain especially useful structure activity relationship (SAR), the library is preferably a group consisting of at least 10 compounds, more preferably a group consisting of at least 50 compounds.

The above-mentioned library includes that consisting of at least one compound of the present invension.

The term of a binding activity to the cannabinoid type 2 receptor means an agonistic activity or an antagonistic activity to the cannabinoid type 2 receptor via binding to the receptor. The term of an agonistic activity to the cannabinoid type 2 receptor means to exhibit an agonistic effect. The term of an antagonistic activity to the cannabinoid type 2 receptor means to exhibit an antagonistic effect.

A prodrug is a derivative which is converted to a pharmaceutically active compound of the present invention in vivo under a physiological condition. Method for the selection and process of an appropriate prodrug derivative are described in the literature such as Design of Prodrugs, Elsevier, Amsterdam 1985.

A prodrug of the present invention can be prepared by introducing a leaving group to substituents on ring A which are substitutable (e.g., amino, hydroxy or the like). Examples of a prodrug derived form a compound having an amino group includes carbamate derivatives (e.g., methylcarbamate, cyclopropylmethylcarbamate, t-butylcarbamate, benzylcarbamate or the like), amide derivatives (e.g., formamide, acetamide or the like), N-alkyl derivative (e.g.; N-allylamine, N-methoxymethylamine or the like) or the like. Examples of a prodrug derived form a compound having hydroxy group include ether derivatives (methoxymethylether, methoxyethoxymethylether or the like), ester derivatives (e.g., acetate, pivaloate, benzoate or the like) or the like.

Examples of a pharmaceutically acceptable salt include basic salts (e.g., alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aralkyl amine salts such as N,N-dibenzylethylenediamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts). Acid addition salts include, for example, mineral acid salts such as hydrochlorides salts, sulfates salts, nitrate salts, phosphates salts, carbonates salts, hydrogen carbonates salts or perchlorates salts; organic acid salts such as acetates, propionates, lactates, maleates, fumarates, tartrates, malates, succinates, or ascorbates; sulfonates such as methanesulfonates, isethionates, benzenesulfonates, or p-toluenesulfonates; and acidic amino acid salts such as aspartates or glutamates.

A solvate includes a solvate of the compound of the present invention, a prodrug of itself or a pharmaceutically acceptable salt thereof, for example, monosolvate, disolvate, monohydrate, dihydrate or the like.

The compound of the present invention has a binding activity to the cannabinoid type 2 receptor, and binds to the cannabinoid type 2 receptor to exhibit an antagonistic activity or agonistic activity to the cannabinoid type 2 receptor, especially an agonistic activity to the cannabinoid type 2 receptor.

Therefore, the compound of the present invention can be used for treating or preventing diseases related to the cannabinoid type 2 receptor. For example, Proc. Natl. Acad. Sci. USA 96, 14228-14233. discloses that cannabinoid type 2 receptor agonists have an anti-inflammatory activity and analgesic activity. Nature, 1998, 349, 277-281 discloses that cannabinoid type 2 receptor agonists have an analgesic activity. Cancer Research 61 (2001) 5784-5789 discloses that cannabinoid type 2 receptor agonists have a degeneracy activity to encephaloma. European Journal of Pharmacology 396 (2000) 85-92 discloses that cannabinoid type 2 receptor antagonists have an analgesic activity. Furthermore, J. Pharmacol Exp. Ther., 2001, 296, 420-425 discloses that the compound having a binding activity (agonistic activity and/or antagonistic activity) to the cannabinoid type 2 receptor has an anti-inflammatory activity.

The compound of the present invention is thought to suppresses the activation of immunocyte, inflammatory cells and peripheral neurons to exhibit an activity to the peripheral cell system (e.g., an immunosuppressive activity, an anti-inflammatory activity and an analgesic activity). Thus, the present compounds can be used as anti-inflammatory agents, antiallergenic agents, analgesic agents, immunedeficiency treating agents, immunosuppressive agents, immunomodulating agents, autoimmune disease treating agents, chronic rheumatoid arthritis treating agents, multiple sclerosis treating agents, encephaloma treating agents, glaucoma treating agents or the like.

Agonists to the cannabinoid type 2 receptor are known to suppress nephritis caused by rat Thy-1 antibody in WO97/29079. Therefore, the present compounds are useful as nephritis treating agents.

When using the compound of the present invention in treatment, it can be formulated into ordinary formulations for oral and parenteral administration. A pharmaceutical composition containing the compound of the present invention can be in the form for oral and parenteral administration. Specifically, it can be formulated into formulations for oral administration such as tablets, capsules, granules, powders, syrup, and the like; those for parenteral administration such as injectable solution or suspension for intravenous, intramuscular or subcutaneous injection, inhalant, eye drops, nasal drops, suppositories, or percutaneous formulations such as ointment.

In preparing the formulations, carriers, excipients, solvents and bases known to one ordinary skilled in the art may be used. Tablets are prepared by compressing or formulating an active ingredient together with auxiliary components. Examples of usable auxiliary components include pharmaceutically acceptable excipients such as binders (e.g., cornstarch), fillers (e.g., lactose, microcrystalline cellulose), disintegrates (e.g., starch sodium glycolate) or lubricants (e.g., magnesium stearate). Tablets may be coated appropriately. In the case of liquid formulations such as syrups, solutions or suspensions, they may contain suspending agents (e.g., methyl cellulose), emulsifiers (e.g., lecithin), preservatives and the like. In the case of injectable formulations, it may be in the form of solution or suspension, or oily or aqueous emulsion, which may contain suspension-stabilizing agent or dispensing agent, and the like. In the case of an inhalant, it is formulated into a liquid formulation applicable to an inhaler. In the case of eye drops, it is formulated into a solution or a suspension.

Although an appropriate dosage of the present compound varies depending on the administration route, age, body weight, sex, or conditions of the patient, and the kind of drug(s) used together, if any, and should be determined by the physician in the end, in the case of oral administration, the daily dosage can generally be between about 0.01-100 mg, preferably about 0.01-10 mg, more preferably about 0.1-10 mg, per kg body weight. In the case of parenteral administration, the daily dosage can generally be between about 0.001-100 mg, preferably about 0.001-1 mg, more preferably about 0.01-1 mg, per kg body weight. The daily dosage can be administered in 1-4 divisions.

EXAMPLE

The following Examples are provided to further illustrate the present invention and are not to be construed as limiting the scope. Example number is same as compound number as shown in Table.

The meaning of each abbreviation are shown as follows.

Me: methyl, Et: ethyl, nPr: n-propyl, iPr: isopropyl,
nBu: n-butyl, iBu: isobutyl, sBu: sec-butyl, tBu: tert-butyl
Ph: phenyl, Ac: acetyl, Bn: benzyl
DMF: N,N-dimethylformamide, THF: tetrahydrofuran,
Ms: mesyl, TBDMD: tert-butyldimethylsilyl

Example 1-004

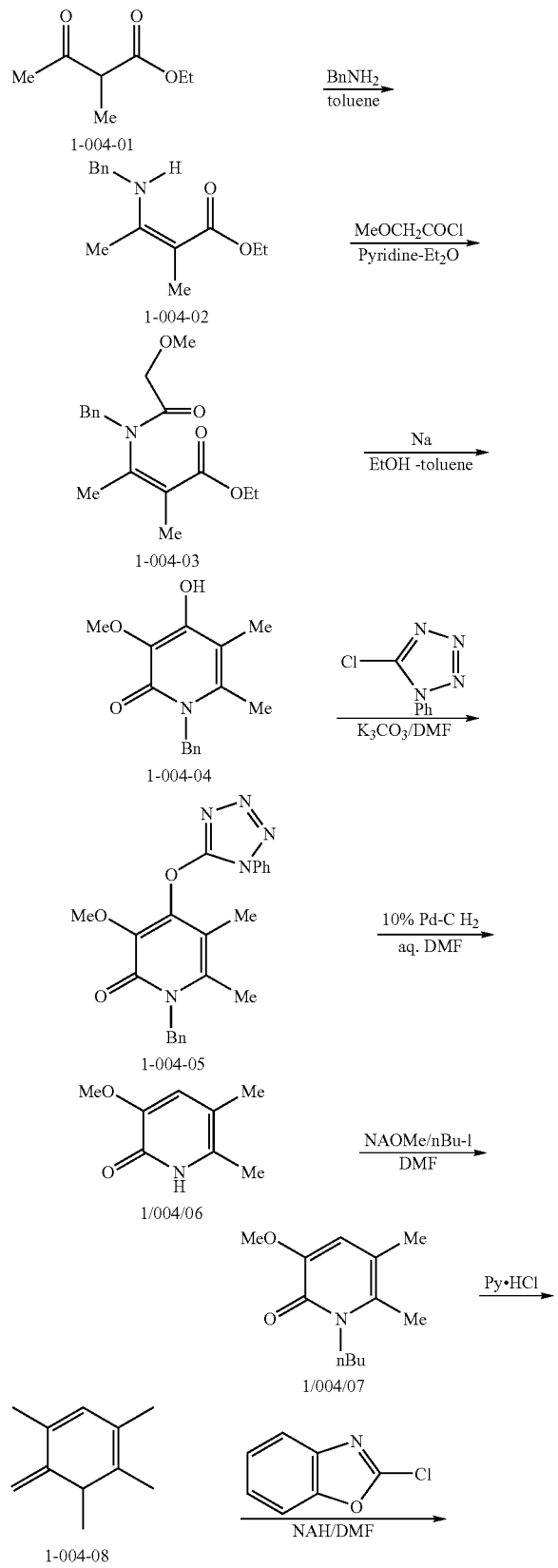

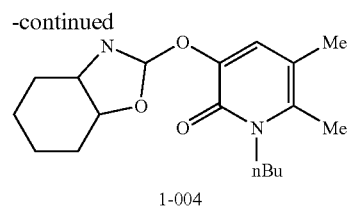

a) Preparation of ethyl 3-benzylamino-2-methylcrotonate (1-004-02)

A solution of ethyl 2-methylacetoaceate (1-004-01) (115.34 g) and benzylamine (85.73 g) in toluene (1.6 L) was azeotropically dehydrated in an oil bath at 145° C. for 8 h under nitrogen atmosphere. Benzylamine was added to the reaction mixture and the reaction mixture was dehydrated again. After 6 h, the reaction mixture was distilled under atmospheric pressure to remove about 600 mL of the solvent, and evaporated under reduced pressure to give ethyl 3-benzylamino-2-methylcrotonate (1-004-02) (195.66 g).

$^1$H NMR (300 MHz, CDCl$_3$): δ 1.28 (t, J=7.2 Hz, 3H), 1.80 (s, 3H), 1.93 (s, 3H), 4.13 (q, J=7.2 Hz, 2H), 4.43 (d, J=6.3 Hz, 2H), 7.20-7.40 (m, 5H), 9.65 (br s, 1H).

b) Preparation of ethyl N-benzylmethoxyacetamide-2-methylcrotonate (1-004-03)

Ethyl 3-benzylamino-2-methylcrotonate (1-004-02) (97.83 g) was dissolved in diethyl ether (2 L). The reaction mixture was stirred under ice-cooling and nitrogen atmosphere. After pyridine (35.6 mL) was added to the reaction mixture, a solution of methoxyacetyl chloride (40.2 mL) in diethyl ether was added dropwise to the reaction mixture at 5 to 6° C. as internal temperature for 45 min. After 2 h, the reaction mixture was poured into ice-water (1.5 L), extracted twice with diethyl ether, and washed with water (1 L) and an aqueous solution of sodium bicarbonate. The extract was dried over magnesium sulfate, and evaporated under reduced pressure to give ethyl 1-benzylmethoxyacetamide-2-methylcrotonate (1-004-03) (111.47 g, 91.3%) as an oil.

$^1$H NMR (300 MHz, CDCl$_3$): δ 1.21 (t, J=7.2 Hz, 3H), 1.74 (s, 3H), 1.89 (s, 3H), 3.44 (s, 3H), 3.97 (d, J=14.7 Hz, 1H), 3.98 (q, J=7.2 Hz, 2H), 4.12 (d, J=14.7 Hz, 1H), 4.31 (d, J=14.4 Hz, 1H), 4.95 (d, J=14.4 Hz, 1H), 7.20-7.40 (m, 5H).

c) Preparation of 1-benzyl-5,6-dimethyl-4-hydroxy-3-methoxy-2-pyridone (1-004-04)

To a solution of toluene (1.39 L) and ethanol (2.08 mL) was added sodium metal (7.98 g) under nitrogen atmosphere, and the reaction mixture was stirred in an oil bath at 140° C. A solution of ethyl 1-benzylmethoxyacetamide-2-methylcrotonate (1-004-03) (105.93 g) in toluene (340 mL) was added dropwise to the reaction mixture over 1 h and 20 min, and the reaction mixture was stirred under reflux. After 2 h, the reaction mixture was stirred under ice-cooling and 4 mole/L hydrochloric acid/dioxane (86.8 mL) was added dropwise over 10 min to the reaction mixture, and the reaction mixture was stirred at room temperature. After 2 h, the resulting precipitate was filtered, and washed with toluene to give the precipitate (73.16 g). To the obtained precipitate (73.16 g) were added chloroform (500 mL) and water (500 mL), and the reaction mixture was dissolved in a water bath at 65° C., and shaken to separate. Further the reaction mixture was extracted with chloroform (250 mL), washed with water (250 mL), dried over magnesium sulfite, and evaporated under reduced pressure to give the residue (54.95 g). The obtained residue (54.95 g) was washed with ethyl acetate (50 mL) and diethyl ether (50 mL) to give 1-benzyl-5,6-dimethyl-4-hydroxy-3-methoxy-2-pyridone (1-004-04) (53.95 g, 60.0%) as a skin-colored crystal.

m.p.: 212° C.

$^1$H NMR (300 MHz, CDCl$_3$): δ 2.03 (s, 3H), 2.19 (s, 3H), 3.99 (s, 3H), 5.38 (br s, 2H), 6.41 (br s, 1H), 7.11-7.33 (m, 5H).

d) Preparation of 1-benzyl-5,6-dimethyl-3-methoxy-4-O-(1-phenyl-1H-tetrazolyl)-2-pyridone (1-004-05)

DMF (300 mL) was added to a mixture of 1-benzyl-5,6-dimethyl-4-hydroxy-3-methoxy-2-pyridone (1-004-04) (25.93 g), 5-chloro-1-phenyl-1H-tetrazole (21.67 g) and potassium carbonate (27.64 g) under nitrogen atmosphere, and the suspension was stirred at room temperature. After 4 and half hour, the reaction mixture was poured into-ice-water (1 L), extracted three times with ethyl acetate (500 mL), washed twice with water (500 mL), dried over magnesium sulfate, and evaporated under reduced pressure. The obtained residue (42.4 g) was dissolved in acetone (300 mL). After concentration under reduced pressure, diethyl ether (300 mL) was added to the residue. The resulting crystal was filtered to give 1-benzyl-5,6-dimethyl-3-methoxy-4-O-(1-phenyl-1H-tetrazolyl)-2-pyridone (1-004-05) (29.87 g, 74.0%, m.p.: 178° C.). Further the filtrate was purified by silica gel column chromatography (150 g, CHCl$_3$) to give an additional 1-004-05 (4.3 g, 10.7%).

$^1$H NMR (300 MHz, CDCl$_3$): δ 2.07 (s, 3H), 2.28 (s, 3H), 3.79 (s, 3H), 5.41 (br s, 2H), 7.15-7.84 (m, 10H).

e) Preparation of 5,6-dimethyl-3-methoxy-2-pyridone (1-004-06)

A solution of 1-benzyl-5,6-dimethyl-3-methoxy-4-O-(1-phenyl-1H-tetrazolyl)-2-pyridone (1-004-05) (27.15 g) in DMF (272 mL) was added a suspension of 10% palladium on carbon (5.43 g) in water (27 mL). The reaction mixture was reduced under medium hydrogen pressure (5 kg/cm) at room temperature. In the course of the reaction, 10% palladium on carbon (2.72 g) was added to the reaction mixture. After 48 h, catalyst was filtered off on Celite and washed with methanol, and the filtrate was evaporated under reduced pressure. After water (160 mL) was added to the obtained residue and the reaction mixture was heated at 85° C. in a water bath, the insoluble substance was filtered off. The insoluble substance was washed with hot water to give an insoluble substance (8.77 g). The filtrate was evaporated under reduced pressure, and acetone (110 mL) was added to the obtained residue (11.55 g). After the mixture was stirred at room temperature, a colorless powder was filtered to give 1-004-06 (8.23 g, 79.8%, m.p.: 215-9° C.). 1-004-06 (0.31 g, 3.0%) was obtained from the filtrate in a similar manner to the treatment described above.

$^1$H NMR (300 MHz, CDCl$_3$): δ 2.07 (s, 31H), 2.28 (s, 3H), 3.79 (s, 3H), 5.41 (br s, 2H), 7.15-7.84 (m, 10H).

f) Preparation of 1-butyl-5,6-dimethyl-3-methoxy-2-pyridone (1-004-07)

n-Butanol (13 mL) was added to a mixture of 5,6-dimethyl-3-methoxy-pyridone (1-004-06) (306 mg) and potassium hydroxide (157 mg). 1-Iodobutane (0.44 mL) was added to the suspension, and the reaction mixture was heated with stirring in an oil bath at 85° C. under nitrogen atmosphere. After 24 h, the reaction mixture was evaporated under reduced pressure, and the residue was dissolved in acetyl acetate and water. The reaction mixture was extracted twice with ethyl acetate, and once with water, dried over magnesium sulfate, and evaporated under reduced pressure. The obtained residue (300 mg) was purified by silica gel column chromatography (Lobar column B, toluene/acetone (3/1)) to give 1-butyl-5,6-dimethyl-3-methoxy-2-pyridone (1-004-07) (124 mg, 29.6%).

$^1$H NMR (300 MHz, CDCl$_3$): δ 0.96 (t, J=7.2 hz, 3H), 1.36-1.48 (m, 2H), 1.60-1.70 (m, 2H), 2.09 (s, 3H), 2.26 (s, 3H), 3.78 (s, 3H), 4.08 (t, J=7.8 Hz, 2H), 6.44 (s, 2H).

g) Preparation of 1-butyl-5,6-dimethyl-3-hydroxy-2-pyridone (1-004-08)

Pyridinium chloride (293 mg) was added to 1-butyl-5,6-dimethyl-3-methoxy-2-pyridone (1-004-07) (124 mg), and the reaction mixture was heated with stirring in an oil bath at 200° C. under nitrogen atmosphere. After 30 min, the reaction mixture was dissolved in diethyl ether and water, extracted twice with diethyl ether, washed once with water, and dried over magnesium sulfate. The solvent was evaporated under reduced pressure to give 1-butyl-5,6-dimethyl-3-hydroxy-2-pyridone (1-004-08) (94 mg, 81%, m.p.: 112-116° C.)

$^1$H NMR (300 MHz, CDCl$_3$): δ 0.98 (t, J=7.2 hz, 3H), 1.37-1.50 (m, 2H), 1.61-1.72 (m, 2H), 2.08 (s, 3H), 2.26 (s, 3H), 4.10 (t, J=7.8 Hz, 2H), 6.66 (br s, 2H).

h) Preparation of 3-(benzoxazole-2-yloxy)-1-butyl-5,6-dimethyl-1H-pyridine-2-one (1-004)

3-(Benzoxazole-2-yloxy)-1-butyl-5,6-dimethyl-1H-pyridine-2-one (1-004) (66.7%, m.p. 106-8° C.) was synthesized in a similar manner to the preparation of 1-015.

Examples 1-001 to 1-003 and 1-005 were synthesized in a similar manner to Example 1-004.

Example 1-013

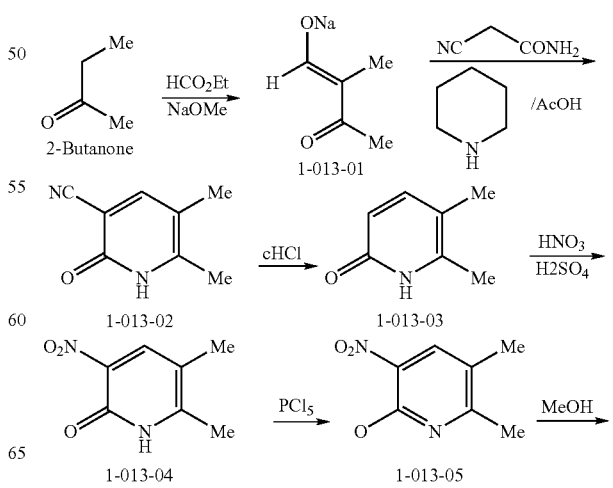

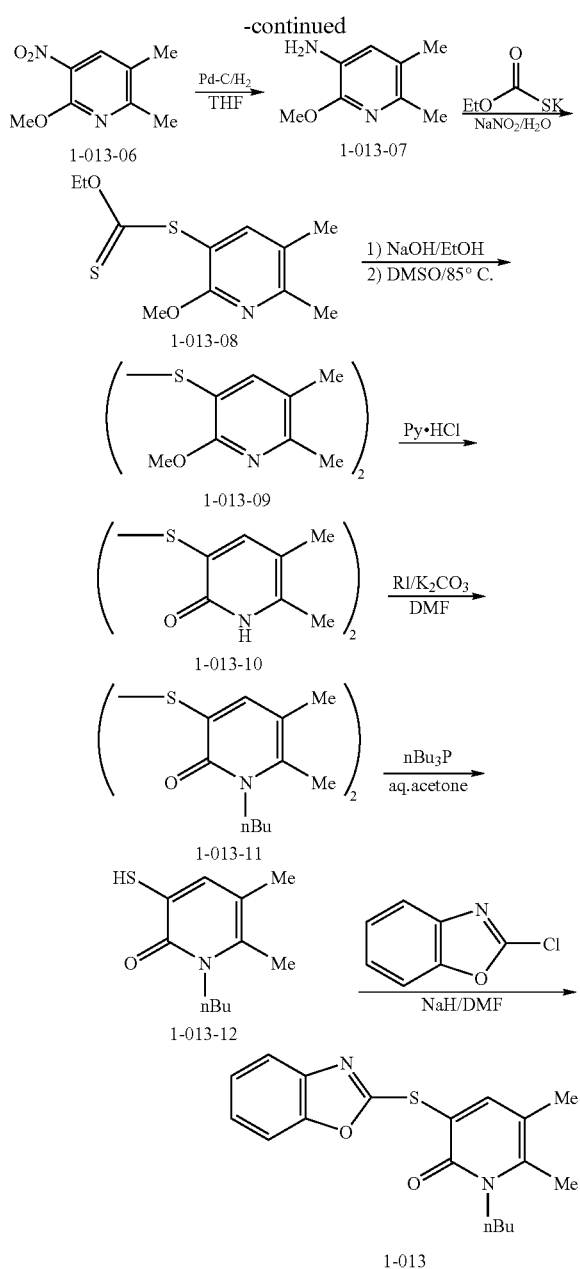

b) Preparation of 3-cyano-5,6-dimethyl-2-pyridone (1-013-02)

Water was added to 2-methyl-3-oxobutanal sodium salt (1-013-01) (34.73 g), and to the reaction mixture was added 2-cyanoacetamide (23.91 g) and 1.76 mol/L piperidinium acetate (119.4 mL), and the reaction mixture was stirred under reflux in an oil bath at 127° C. After 21 h, to the reaction mixture was added gradually dropwise acetic acid (42.7 mL) at 65° C. as internal temperature for 15 min. After the stirring was continued until internal temperature became to 24° C., the resulting crystal was filtered, and washed with water to give 3-cyano-5,6-dimethyl-2-pyridone (1-013-02) (27.76 g, 65.9%, m.p. 258-263° C.).

$^1$H NMR (300 MHz, DMSO): δ 1.98 (s, 3H), 2.23 (s, 3H), 7.95 (s, 1H), 12.45 (br s, 1H).

c) Preparation of 5,6-dimethyl-2-pyridone (1-013-03)

To a suspension of 3-cyano-5,6-dimethyl-2-pyridone (1-013-02) (12.0 g) in water (293 mL) was added conc. hydrochloric acid (293 mL), and the reaction mixture was reflux with stirring in oil-bath at 135° C. After 3 days, the reaction mixture was cooled, and evaporated under reduced pressure. To the residue (24.75 g) were added chloroform (300 mL) and methanol (15 mL), and the reaction mixture was heated in a water bath at 65° C., and the dissolble material was filtered off. Furthermore, the dissolble material was treated by chloroform (200 mL) and methanol (10 mL) in a similar manner to described above. The combined filtrates were evaporated under reduced pressure. To the obtained residue (13.26 g) were added methanol (150 mL) and potassium carbonate (10 g). After stirred at room temperature for 30 min, the dissolble material was filtered off. The filtrate was evaporated under reduced pressure. To the obtained residue (14.7 g) was added chloroform (200 mL), and the dissolble material was filtered off again. The filtrate was evaporated under reduced pressure to give 5,6-dimethyl-2-pyridone (1-013-03) (9.41 g, 94.3%, m.p.: 202-207° C.)

$^1$H NMR (300 MHz, CDCl$_3$): δ 2.05 (s, 3H), 2.31 (s, 3H), 6.38 (d, J=9.0 Hz, 1H), 7.26 (d, J=9.0 Hz, 1H), 13.17 (br s, 1H).

d) Preparation of 5,6-dimethyl-3-nitro-2-pyridone (1-013-04)

5,6-Dimethyl-2-pyridone (1-013-03) (3.695 g) was dissolved in conc. sulfuric acid (38 mL) under ice-cooling, and the reaction mixture was stirred under ice-cooling, and then to the reaction mixture was added dropwise 70% nitric acid (3.53 mL) at 3 to 5° C. as internal temperature for 50 min, and then the reaction mixture was stirred. After 2 h, the reaction mixture was poured gradually into ice and the resulting crystal was filtered. The crystal was washed with water to give 5,6-dimethyl-3-nitro-2-pyridone (1-013-04) (3.102 g, 61.5%, m.p.: 251-257 (dec)). Furthermore the aqueous layer was extracted five times with chloroform, the organic layer was dried over magnesium sulfate, and evaporated under reduced pressure. The resulting crystal was filtered to give an additional 5,6-dimethyl-3-nitro-2-pyridone (1-013-04)(271 mg, 5.4%).

$^1$H-NMR (300 MHz, DMSO): 2.06 (s, 3H), 2.29 (s, 3H), 8.35 (s, 1H), 12.79 (br s, 1H).

a) Preparation of 2-methyl-3-oxobutanal sodium salt (1-013-01)

A solution of 28% sodium methoxide/methanol (138 mL) was diluted with diethyl ether (920 mL) and the reaction mixture was stirred under ice-cooling, and to the reaction mixture was added dropwise a mixture of 2-butanone (51.2 g) and ethyl formate (57.2 g) at 4 to 6° C. as internal temperature for 45 min. After the reaction mixture was stirred at the same temperature for an additional 30 min, and at room temperature overnight. The resulting colorless powder was filtered to give 2-methyl-3-oxobutanal sodium salt (1-013-010) (60.66 G, 70%).

$^1$H NMR (300 MHz, CDCl$_3$): δ 1.62 (s, 3H), 2.13 (s, 3H), 8.99 (s, 1H).

e) Preparation of 2-chloro-5,6-dimethyl-3-nitropyridine (1-013-05)

5,6-Dimethyl-3-nitro-2-pyridone (1-013-04)(841 mg) and phosphorus pentachloride (1.25 g) was heated with stirring in an oil bath at 140° C. under nitrogen atmosphere. After 35 min, the reaction mixture was cooled under ice-cooling, poured into ice-water, extracted with twice with chloroform, and washed once with water and a saturated aqueous solution of sodium bicarbonate. To the extract was added a decolorzing charcoal, and the extract was dried over magnesium sulfate, and evaporated under reduced pressure to give 2-chloro-5,6-dimethyl-3-nitropyridine (1-013-05) (842 mg, 90.2%) as a crystalline residue.

$^1$H NMR (300 MHz, CDCl$_3$): δ 2.38 (s, 3H), 2.58 (s, 3H), 8.01 (s, 1H).

f) Preparation of 5,6-dimethyl-2-methoxy-3-nitropyridine (1-013-06)

To a solution of 28% sodium methoxide (1.11 mL) and methanol (5.5 mL) was added dropwise a solution of 2-chloro-5,6-dimethyl-3-nitropyridine (1-013-05) (837 mg) in methanol (6.6 mL) for 5 min at room temperature under nitrogen atmosphere, and the reaction mixture was heated with stirring, in oil-bath at 50° C. for 7 h. To the reaction mixture was added diethyl ether and the reaction mixture was poured into water, extracted with twice with diethyl ether, washed once with water, and dried over magnesium sulfate. The solvent was evaporated under reduced pressure to give 5,6-dimethyl-2-methoxy-3-nitropyridine (1-013-06) (675 mg, 82.6%, m.p.: 71-73° C.) as an orange crystal.

$^1$H NMR (300 MHz, CDCl$_3$): δ 2.28 (s, 3H), 2.48 (s, 3H), 4.08 (s, 3H), 8.07 (s, 1H).

g) Preparation of 3-amino-5,6-dimethyl-2-methoxypyridine (1-013-07)

5,6-Dimethyl-2-methoxy-3-nitropyridine (1-013-06) (2.56 g) was dissolved in tetrahydrofuran (41 mL), and to the reaction mixture was added a suspension of 5% palladium on carbon (450 mg) in methanol (41 mL), and then the catalytic reduction was carried out. After 3 h, catalyst was filtered off, and the filtrate was evaporated under reduced pressure to give 3-amino-5,6-dimethyl-2-methoxypyridine (1-013-07) (2.096 g, 97.9%, m.p.: 56-58° C.) as a blackish brown crystal.

$^1$H NMR (300 MHz, CDCl$_3$): δ 2.12 (s, 3H), 2.30 (s, 3H), 2.48-3.49 (br s, 2H), 3.95 (s, 3H), 6.70 (s, 1H). I, h) Preparation of 5,6-dimethyl-3-[[ethoxy(thiocarbonyl)]thio]-2-methoxypyridine (1-013-08)

3-Amino-5,6-dimethyl-2-methoxypyridine (1-013-07) (1.787 g) was dissolved in water (3 mL) and conc. hydrochloric acid (3 mL), and the reaction mixture was cooled under ice-acetone bath, and stirred under cooling. To the reaction mixture was added dropwise a solution of sodium nitrite (4.81 g) in water (27.1 mL) at 4 to 5° C. as internal temperature for 45 min, and the reaction mixture was stirred at the same temperature. On the other hand, potassium ethylxanthrate (12.64 g) was dissolved in water (17.3 mL), and the reaction mixture was heated with stirring in an oil bath at 40° C. To the reaction mixture was added dropwise a cooling solution of the above prepared diazonium salt for 35 min, and the reaction mixture was heated with stirring for 40 min. The reaction mixture was cooled, extracted three times with chloroform, washed once with a saturated aqueous solution of sodium bicarbonate and brine, and dried over magnesium sulfate. The extract was evaporated under reduced pressure. The red oily residue (12.49 g) was purified by silica gel column chromatography (300 g, toluene/hexane=2/3) to give 5,6-dimethyl-3-[[ethoxy(thiocarbonyl)]thio]-2-methoxypyridine (1-013-08) (6.281 g, 36%) as an red oil. The obtained compound contained 2 isomers caused by rotatory hindrance.

$^1$H NMR (300 MHz, CDCl$_3$): δ 1.45 (t, J=7.2 Hz, 3H), 2.18 (s, 3H), 2.39 (s, 3H), 3.98 (s, 3H), 4.70 (q, J=7.2 Hz, 2H), 7.47 (s, 1H).

$^1$H NMR (300 MHz, CDCl$_3$): δ 1.33 (t, J=7.2 Hz, 3H), 2.21 (s, 3H), 2.44 (s, 3H), 3.94 (s, 3H), 4.60 (q, J=7.2 Hz, 2H), 7.43 (s, 1H).

i) Preparation of (5,6-dimethyl-2-methoxypyridin-3-yl)disulfide (1-013-09)

5,6-Dimethyl-3-[[ethoxy(thiocarbonyl)]thio]-2-methoxypyridine (1-013-08) (6.275 g) was dissolved in ethanol (200 mL) and the reaction mixture was stirred at room temperature. To the reaction mixture was added 1 mole/L sodium hydroxide solution (67 mL) at a time under nitrogen atmosphere, and the reaction mixture was stirred overnight. After 15 h, the resulting precipitate was filtered, and washed with water to give the precipitate (543 mg). Furthermore, the filtrate was adjusted with 5 mole/L hydrochloric acid to pH 3, and evaporated under reduced pressure. To the residue was added methylene chloride (100 mL), and the mixture was stirred at room temperature. The insoluble material was filtered off and the filtrate was evaporated under reduced pressure to give the residue (2.00 g).

The combined the residue (2.00 g+543 mg) was suspended with dimethylsulfoxide (20 mL), and the mixture was heated with stirring in an oil bath at 85° C. under nitrogen atmosphere. After 7 h, the reaction mixture was stirred at room temperature, and to the reaction mixture was added water (100 mL). The reaction mixture was stirred under ice-cooling for 30 min to give (5,6-dimethyl-2-methoxypyridin-3-yl)disulfide (1-013-09) (2.23 g, 54.4%) as a yellow powder.

$^1$H NMR (300 MHz, CDCl$_3$): δ 2.16 (s, 3H), 2.36 (s, 3H), 3.96 (s, 3H), 7.53 (s, 1H).

j) Preparation of (5,6-dimethyl-2-pyridon-3-yl)disulfide (1-013-10)

Pyridium chloride (7.69 g) was added to (5,6-dimethyl-2-methoxypyridin-3-yl)disulfide (1-013-09) (2.225 g) and the reaction mixture was heated with stirring in an oil bath at 160° C. under nitrogen atmosphere. After 40 min, the reaction mixture was cooled and water (100 mL) was added to the reaction mixture. The reaction mixture was stirred at room temperature, and the resulting precipitate was filtered, and washed with water to give (5,6-dimethyl-2-pyridon-3-yl)disulfide (1-013-10) (1.736 g, 85.1%) as a blackish brown powder.

$^1$H NMR (300 MHz, CDCl$_3$): δ 1.95 (s, 3H), 2.13 (s, 3H), 7.42 (s, 1H), 11.89 (br s, 1H).

k) Preparation of (1-butyl-5,6-dimethyl-2-pyridon-3-yl)disulfide (1-013-11)

(5,6-Dimethyl-2-pyridon-3-yl)disulfide (1-013-1.0) (31 mg) was suspended with DMF (1 mL), and to the reaction mixture were added 1-iodobutane (78 mg) and potassium carbonate (42 mg). The reaction mixture was stirred at room temperature for 3 days under nitrogen atmosphere. Ethyl acetate was added to the reaction mixture and the reaction mixture was poured into water, extracted twice with ethyl acetate, washed once with water, dried over magnesium sulfate, and evaporated to give the residue (39 mg, 92.9%). The obtained compound contained a 1-butyl derivative (1-013-11) at the rate of 20% judging from NMR data.

1) Preparation of (1-butyl-5,6-dimethyl-3-mercapto-2-pyridone (1-013-12)

(1-Butyl-5,6-dimethyl-2-pyridon-3-yl)disulfide (1-013-11) (123 mg) was dissolved in acetone (8 mL) and the reaction mixture was stirred at room temperature, to the reaction mixture was added tri-n-butylphosphine (0.16 mL), and added gradually water (4 ml). The reaction mixture was stirred at the same temperature for 2 h, and then was stirred at room temperature overnight. The reaction mixture was diluted with methylene chloride, and water, extracted twice with mathylene chloride, washed once with water, dried over magnesium sulfate, and evaporated under reduced pressure. The obtained residue (277 mg) was subjected to preparative thin-layer chromatography (toluene/acetone=39/1) to give (1-butyl-5,6-dimethyl-3-mercapto-2-pyridone (1-013-12) (11 mg, 8.9%) as a crystal.

$^1$H NMR (300 MHz, CDCl$_3$): δ 0.93 (t, J=7.2 Hz, 3H), 1.32-1.45 (m, 2H), 1.62-1.72 (m, 2H), 2.11 (s, 3H), 2.32 (s, 3H), 4.20 (t, J=7.8 Hz, 2H), 7.68 (s, 1H).

m) Preparation of N-1-butyl-5,6-dimethyl-3-(benzoxazol-2-yl)thio-2-pyridone (1-013)

1-013 (4.5 mg, 26.5%) as a crystal was obtained from (1-butyl-5,6-dimethyl-3-mercapto-2-pyridone (11 mg) in a similar manner to Example 1-015.

Example 1-012 was synthesized in similar manner as Example 1-013.

Example 1-014

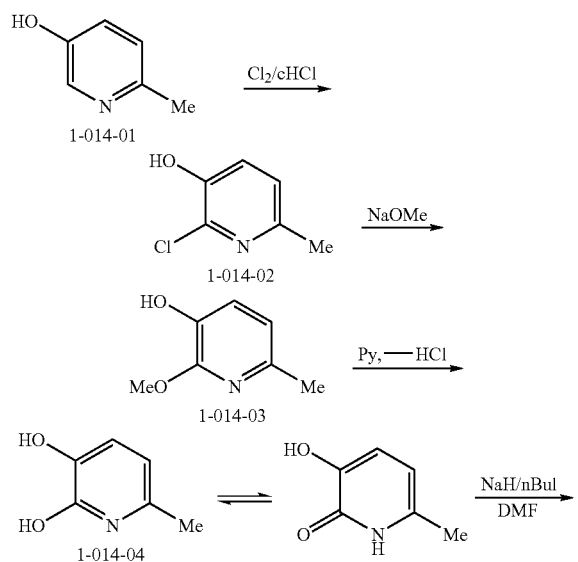

-continued

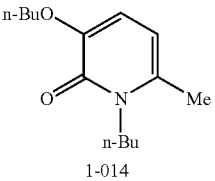

1-014 a) Preparation of 2-chloro-3-hyroxy-6-methylpyridine (1-014-02)

5-Hydroxy-2-methylpyridine (1-014-01) (27.01 g) was dissolved in conc. hydrochloric acid (200 mL) and to the reaction mixture was bubbled chlorine gass at 68 to 74° C. After the reaction mixture was stood overnight, the volatile was removed by bubbling nitrogen gas. The reaction mixture was evaporated under reduced pressure to give the crystal residue. The crystal residue was dissolved in methanol, and treated with active charcoal. After recrystallization, the desired 2-chloro-3-hyroxy-6-methylpyridine (1-014-02) (23.96 g, 67.3%) was obtained.

b) Preparation of 2-methoxy-3-hyroxy-6-methylpyridine (1-014-03)

In metal sealed tube were added 2-chloro-3-hyroxy-6-methylpyridine (1-014-02) (22.91 g) and 28% sodium methoxide/methanol solution (120 mL) and the reaction mixture was reacted at 150° C. for 3 days. To the reaction mixture was added ice and water (100 mL) and the reaction mixture was neutralized with acetic acid, and evaporated completely. The residue was purified by silica gel column chromatography (chloroform) to give the desired 2-methoxy-3-hyroxy-6-methylpyridine (1-014-03) (10.44 g, 48.1%). Furthermore, the fraction contained the starting material was reacted in sealed tube again.

$^1$H-NMR (300 MHz, CDCl$_3$): δ 2.35 (s, 3H), 3.97 (s, 3H), 6.60 (d, J=7.8 Hz, 1H), 6.98 (d, J=7.8 Hz, 1H).

c) Preparation of 2,3-dihyroxy-6-methylpyridine (1-014-04)

Pyridine hydrochloride salt (43.3 g) was added to 2-methoxy-3-hyroxy-6-methylpyridine (1-014-03) obtained above, the reaction mixture was heated at 160° C. for 1 h and at 170 C for 20 min. To the reaction mixture was added water (50 mL) and the reaction mixture was extracted repeatingly with 5% methanol/ethyl acetate and ethyl acetate. The combined extracts were evaporated completely to give the light gray residue. This 2,3-dihyroxy-6-methylpyridine (1-014-04) was used in the next reaction without purification.

d) Preparation of 1-butyl-3-butyl-6-methyl-2-pyridone (1-014-05)

The crude 2,3-dihyroxy-6-methylpyridine (1-014-04) (16.04 g) was dissolved in dry DMF (70 mL) and 60% solid sodium hydride (10.25 g) was added gradually to the reaction mixture. The reaction mixture was stirred at room temperature for 30 min under nitrogen atmosphere. A solution of 1-iodobutane (29.1 mL) in DMF (30 mL) was added dropwise to the reaction mixture for 20 min and the reaction mixture was stirred at room temperature for 3 h. To the reaction mixture was added a saturated aqueous solution of ammonium chloride, and the reaction mixture was extracted three times with 150 ml of ethyl acetate. The aqueous layer was extracted repeatedly with chloroform and the combined organic layers were treated with active charcoal, and evaporated under reduced pressure. The obtained residue was purified by silica gel column chromatography (n-hexane/ethyl acetate) to give 1-butyl-3-O-butyl-6-methyl-2-pyridone (1-014) (8.915 g). Total yield of two steps was 50.1%.

$^1$H-NMR (300 MHz, CDCl$_3$): δ0.96 (t, J=7.5 Hz, 6H), 1.43 (m, 4H), 1.67 (m, 2H), 1.82 (m, 2H), 2.31 (s, 3H), 3.88 (t, J=6:6 Hz, 2H), 4.01 (t, J=7.8 Hz, 2H), 5.87 (d, J=7.8 Hz, 1H), 6.52 (d, J=7.8 Hz, 1H).

Example 1-015

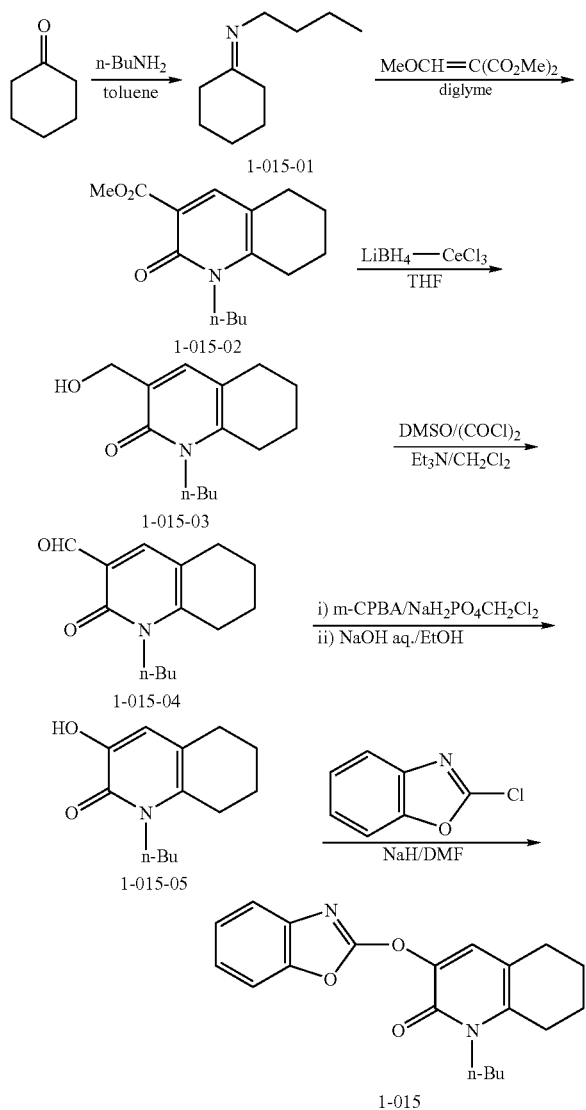

a) Preparation of butyl-cyclohexylideneamine (1-015-01)

1-Butylamine (9.88 mL, 0.1 mol) and toluene (15 mL) was added to cyclohexanone (10.36 mL, 0.1 mol) and the reaction mixture was heated under reflux for 24 h under dehydration condition by using Dienstark reflux condenser packing molecular sieves 4A. After the reaction mixture was cooled to room temperature, evaporated under reduced pressure. The residue was distilled under reduced pressure (2 mmHg) at 64° C. to give butyl-cyclohexylideneamine (1-015-01) (12.8 g, 84%) as a colorless oil.

$^1$H NMR (300 MHz, CDCl): δ 0.93 (t, J=7.5 Hz, 3H), 1.35 (sextet, J=7.5 Hz, 2H), 1.58 (quint, J=7.5 Hz, 2H), 1.61-1.70 (m, 4H), 1.71-1.77 (m, 2H), 2.30 (t, J=6.0 Hz, 2H), 2.34 (t, J=6.0 Hz, 2H), 3.30 (t, J=7.5 Hz, 2H).

b) Preparation of 1-butyl-2-oxo-1,2,5,6,7,8-hexahydroisoquinoline-3-carboxylic acid methyl ester (1-015-02)

Butyl-cyclohexylideneamine (1-015-01) (12.8 g, 83.6 mmol) was dissolved in diglyme (75 mL) and the reaction mixture was heated at 120° C. To the reaction mixture was added dropwise a solution of dimethyl methoxymethylenemalonate (14 g, 80.4 mmol) in diglyme (75 mL) for 1 h and the reaction mixture was reacted at 120° C. for 3 h. After cooling, the diglyme was evaporated under reduced pressure. The obtained residue was purified by silica gel column chromatography (toluene/ethyl acetate) to give 1-buthyl-2-oxo-1,2,5,6,7,8-hexahydroisoquinoline-3-carboxylic acid methyl ester (1-015-O$_2$) (15 g, 71%) as an yellow oil.

$^1$H NMR (300 MHz, CDCl$_3$): δ 0.97 (t, J=7.5 Hz, 3H), 1.43 (sextet, J=7.5 Hz, 2H), 1.63-1.78 (m, 4H), 1.87 (quint, J=6.0 Hz, 2H), 2.57 (t, J=6.0 Hz, 2H), 2.73 (t, J=6.0 Hz, 2H), 3.90 (s, 3H), 4.02 (t, J=7.8 Hz, 2H), 7.92 (s, 1H).

c) Preparation of 1-butyl-3-hydroxymethyl-5,6,7,8-tetrahydro-1H-quinoline-2-one (1-015-03)

1-Buthyl-2-oxo-1,2,5,6,7,8-hexahydroisoquinoline-3-carboxylic acid methyl ester (1-015-02) (130 mg, 0.5 mmol) was dissolved in THF (12 mL), and to the reaction mixture were added CeCl$_3$ 7H$_2$O (372.6 mg, 1 mmol) and lithium borohydride (21.8 mg, 1 mmol). The reaction mixture was stirred at room temperature for 20 min and to the reaction mixture was added 1 mol/L diluted hydrochloric acid (20 mL). The reaction mixture was extracted with ethyl acetate (40 mL), washed with brine (30 mL), dried over anhydrous magnesium sulfate, and evaporated under reduced pressure. The residue was reacted once more under the same conditions described above and the similar post treatment was performed. The obtained residue was purified by silica gel column chromatography (toluene/ethyl acetate) to give 1-butyl-3-hydroxymethyl-5,6,7,8-tetrahydro-1H-quinoline-2-one (1-015-03) (80 mg, 68%) as a colorless oil.

$^1$H NMR (300 MHz, CDCl$_3$): δ 0.98 (t, J=7.5 Hz, 3H), 1.43 (sextet, J=7.5 Hz, 2H), 1.65 (quint, J=7.5 Hz, 2H), 1.71 (quint, J=6.0 Hz, 2H), 1.85 (quint, J=6.0 Hz, 2H), 2.52 (t, J=6.0 Hz, 2H), 2.68 (t, J=6.0 Hz, 2H), 4.00 (t, J=7.8 Hz, 2H), 4.53 (s, 2H), 7.02 (s, 1H).

d) Preparation of 1-butyl-2-oxo-1,2,5,6,7,8-hexahydroquinoline-3-carboaldehyde (1-015-04)

DMSO (0.54 mL, 7.64 mmol) was dissolved in methylene chloride (27 mL) and the solvent was cooled at −78° C. To the solvent were added dropwise oxalyl chloride (0.4 mL, 4.58 mL), a solution of 1-butyl-3-hydroxymethyl-5,6,7,8-tetrahydro-1H-quinoline-2-one (1-015-03) (0.9 g, 3.82 mmol) in methylene chloride (20 mL) and triethylamine (1.33 mL, 9.55 mmol), and then the reaction mixture was stirred at −78° C. for 5 min; The reaction mixture was gradually warmed to room temperature, and stirred at room temperature for 20 min. To the reaction mixture was added 1 mol/L diluted hydrochloric acid (50 mL), and the reaction mixture was extracted with ethyl acetate (200 mL), washed with aqueous saturated sodium hydrogen carbonate solution (50 mL) and brine (50 mL), dried over anhydrous magnesium sulfate, and evaporated under reduced pressure. The obtained residue was purified by silica gel column chromatography (toluene/ethyl acetate) to give 1-butyl-2-oxo-1,2,5,6,7,8-hexahydroquinoline-3-carboaldehyde (1-015-04) (0.5 g, 56%) as a pale yellow bubbly substance.

$^1$H NMR (300 MHz, CDCl$_3$): δ 0.99 (t, J=7.5 Hz, 3H), 1.46 (sextet, J=7.5 Hz, 2H), 1.68 (quint, J=7.5 Hz, 2H), 1.74 (quint, J=6.0 Hz, 2H), 1.88 (quint, J=6.0 Hz, 2H), 2.59 (t, J=6.0 Hz, 2H), 2.76 (t, J=6.0 Hz, 2H), 4.05 (t, J=7.8 Hz, 2H), 7.76 (s, 1H), 10.34 (s, 1H).

e) Preparation of 1-butyl-3-hydroxy-5,6,7,8-tetrahydro-1H-quinoline-2-one (1-015-05)

1-Butyl-2-oxo-1,2,5,6,7,8-hexahydroquinoline-3-carboaldehyde (1-015-04) (160 mg, 0.69 mmol) was dissolved in methylene chloride (10 mL), and to the reaction mixture were added NaH$_2$PO$_4$—H$_2$O (190 mg, 1.38 mmol) and meta-chloroperbenzoic acid (237 mg, 1.38 mmol). The reaction mixture was stirred at room temperature for 30 min, and to the reaction mixture was added 5% aqueous sodium thiosulfate solution (20 mL). The reaction mixture was extracted with ethyl acetate (50 mL), washed with aqueous saturated sodium hydrogen carbonate solution (20 mL) and brine (20 mL), dried over anhydrous magnesium sulfate, and evaporated under reduced pressure. The residue was dissolved in ethanol (5 mL), 2 mol/L aqueous sodium hydroxide solution (0.35 mL, 0.7 mmol) was added to the reaction mixture, and the reaction mixture was stirred at room temperature for 30 min. To the reaction mixture was added 0.2 mol/L diluted hydrochloric acid (7 mL), and the reaction mixture was extracted with ethyl acetate (25 ml), washed brine (10 mL), dried over anhydrous magnesium sulfate, and evaporated under reduced pressure. The obtained residue was purified by silica gel column chromatography (toluene/ethyl acetate) to give 1-butyl-3-hydroxy-5,6,7,8-tetrahydro-1H-quinoline-2-one (1-015-05) (82 mg, 54%) as a pale brown color crystal.

$^1$H NMR (300 MHz, CDCl$_3$): δ 0.97 (t, J=7.5 Hz, 3H), 1.42 (sextet, J=7.5 Hz, 2H), 1.60-1.74 (m, 4H), 1.83 (quint, J=6.0 Hz, 2H), 2.50 (t, J=6.0 Hz, 2H), 2.62 (t, J=6.0 Hz, 2H), 4.02 (t, J=7.8 Hz, 2H), 6.57 (s, 1H).

f) Preparation of 3-(benzoxazole-2-yloxy)-1-butyl-5,6,7,8-tetrahydro-1H-quinoline-2-one (1-015)

1-Butyl-3-hydroxy-5,6,7,8-tetrahydro-1H-quinoline-2-one (1-015-05) (10 mg, 0.045 mmol) was dissolved in DMF (1 mL), and to the reaction mixture was added sodium hydride (60% oil suspension, 2.7 mg, 0.068 mmol). The reaction mixture was stirred at room temperature for 5 min, and to the reaction mixture was added 2-chlorobenzoxazole (7.7 μL, 0.068 mmol). The reaction mixture was stirred at room temperature for 20 min and extracted with ethyl acetate (50 mL), washed with aqueous saturated sodium hydrogen carbonate solution (20 mL) and brine (20 mL), dried over anhydrous magnesium sulfate, and evaporated under reduced pressure. The residue was dissolved in ethanol (5 mL), 2 mol/L aqueous sodium hydroxide solution (0.35 mL, 0.7 mmol) was added to the reaction mixture, and the reaction mixture was stirred at room temperature for 30 min. To the reaction mixture was added 0.2 mol/L diluted hydrochloric acid (7 mL), and the reaction mixture was extracted with ethyl acetate (25 ml), washed brine (10 mL), dried over anhydrous magnesium sulfate, and evaporated under reduced pressure. The obtained residue was purified by silica gel column chromatography (toluene/ethyl acetate) to give 1-butyl-3-hydroxy-5,6,7,8-tetrahydro-1H-quinoline-2-one (1-015-05) (82 mg, 54%) as a pale brown color crystal.

$^1$H NMR (300 MHz, CDCl$_3$): δ 0.94 (t, J=7.5 Hz, 3H), 1.40 (sextet, J=7.5 Hz, 2H), 1.66 (quint, J=7.5 Hz, 2H), 1.74 (quint, J=6.0 Hz, 2H), 1.87 (quint, J=6.0 Hz, 2H), 2.58 (t, J=6.0 Hz, 0.2H), 2.69 (t, J=6.0 Hz, 2H), 4.02 (t, J=7.8 Hz, 2H), 7.16-7.26 (m, 2H), 7.24 (s, 1H), 7.40 (dd, J=6.9 Hz, 2.4 Hz, 1H), 7.48 (dd, J=6.9 Hz, 2.4 Hz, 1H).

Example 1-017

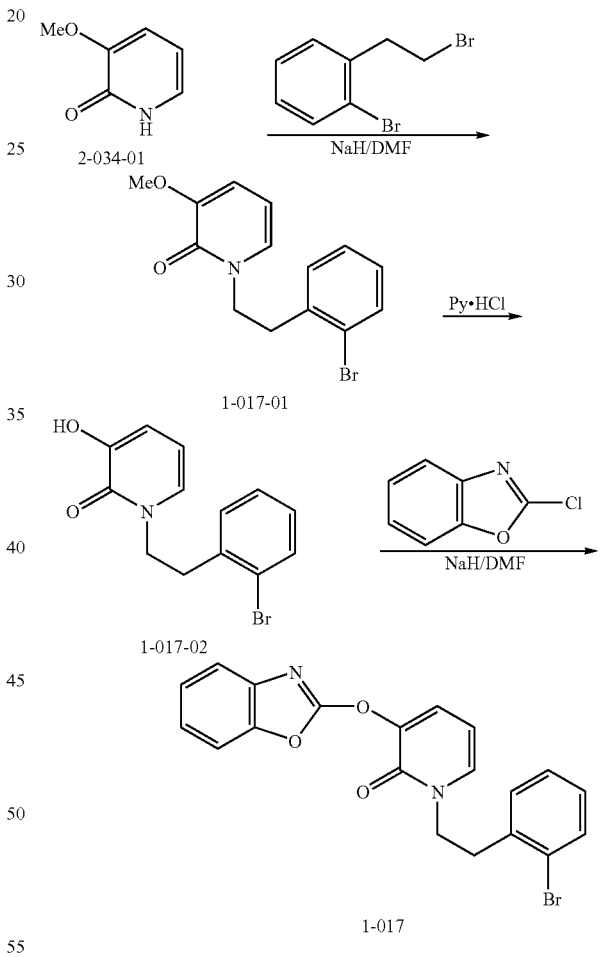

a) Preparation of 1-(2-bromophenethyl)-3-methoxy-2-pyridone (1-017-01)

1-(2-Bromophenethyl)-3-methoxy-2-pyridone (1-017-01) (44%) was synthesized in a similar manner to the preparation of 2-034-02.

$^1$H NMR (300 MHz, CDCl$_3$): δ 3.22 (t, J=7.3 Hz, 2H), 3.83 (s, 3H), 4.21 (t, J=7.6 Hz, 2H), 5.96 (t, J=7.3 Hz, 1H), 6.60 (m, 2H), 7.07-7.22 (m, 3H), 7.55 (d, J=7.6 Hz, 1H).

b) Preparation of 1-(2-bromophenethyl)-3-hydroxy-2-pyridone (1-017-02)

1-(2-Bromophenethyl)-3-hydroxy-2-pyridone (1-017-02) (100%) was synthesized in a similar manner to the preparation of 1-004-08.

$^1$H NMR (300 MHz, CDCl): a 3.23 (t, J=7.3 Hz, 2H), 4.23 (t, J=7.3 Hz, 2H), 6.02 (t, J=7.0 Hz, 1H), 6.57 (dd, J=7.0, 1.2 Hz, 1H), 6.78 (dd, J=7.3, 1.8 Hz, 1H), 7.08-7.14 (m, 2H), 7.18-7.23 (m, 1H), 7.56 (dd, J=7.0, 1.2 Hz, 1H).

c) Preparation of 3-(benzoxazol-2-yloxy)-1-(2-bromophenethyl)-3-hydroxy-2-pyridone (1-017)

3-(Benzoxazol-2-yloxy)-1-(2-Bromophenethyl)-3-hydroxy-2-pyridone (1-017-02) (70%) was synthesized in a similar manner to the preparation of 1-015.

Example 1-018

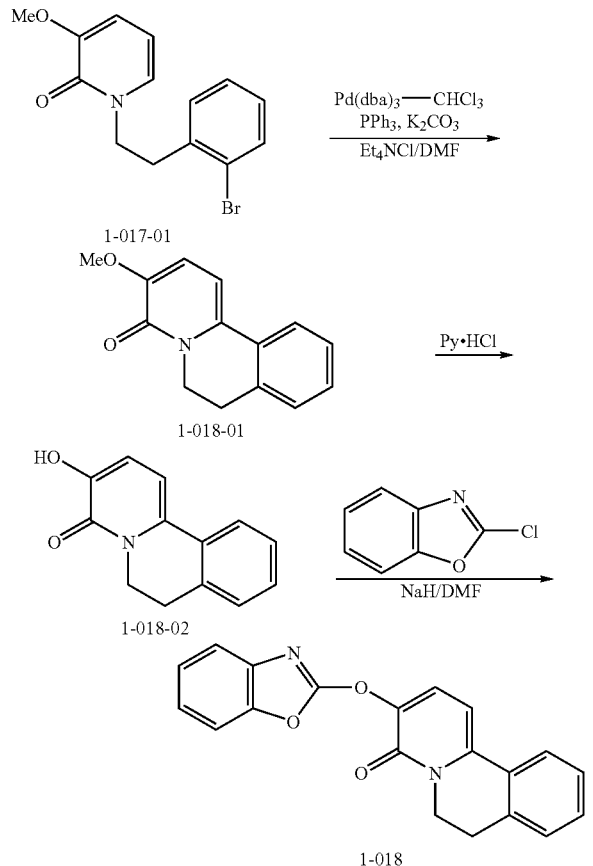

a) Preparation of 3-methoxy-6,7-dihydroxypyrido[2,1,a]isoquinolin-4-one (1-018-01)

To a solution of 1-(2-bromophenethyl)-3-methoxy-2-pyridone (1-017-01) (100 mg) in DMF (4 mL) were added Pd(dba) CHCl$_3$ (30 mg), Et$_3$NCl (54 mg), and potassium carbonate (67 mg) at room temperature. After the reaction mixture was stirred at 120° C. for 3 h, the solvent was evaporated. To the residue were added aqueous saturated ammonium chloride solution and ethyl acetate, and organic layer was separated. The aqueous layer was extracted three times with ethyl acetate, and combined organic layers were washed successively with successive water and brain, dried over anhydrous magnesium sulfate, and evaporated under reduced pressure. The obtained crude product was purified by preparative thin-layer chromatography (toluene/acetone=1/1) to give 3-methoxy-6,7-dihydroxypyrido[2,1,a]isoquinolin-4-one (1-018-01) (50.6 mg, 69%) as an oil.

$^1$H NMR (300 MHz, CDCl$_3$): δ 2.97 (t, J=6.4 Hz, 2H), 3.88 (s, 3H), 4.34 (t, J=6.3 Hz, 2H), 6.64 (d, J=7.9 Hz, 1H), 6.74 (d, J=7.9 Hz, 1H), 7.23-7.34 (m, 3H), 7.64-7.67 (m, 1H).

b) Preparation of 3-hydroxy-6,7-dihydroxypyrido[2,1,a]isoquinolin-4-one (1-018-02)

3-Hydroxy-6,7-dihydroxypyrido[2,1, a]isoquinolin-4-one (1-018-02) (98%) was synthesized in a similar manner to the preparation of 1-004-08.

$^1$H NMR (300 MHz, CDCl$_3$): δ 3.00 (t, J=6.6 Hz, 2H), 4.35 (t, J=6.6 Hz, 2H), 6.71 (d, J=7.8 Hz, 1H), 6.93 (d, J=7.8 Hz, 1H), 7.24-7.34 (m, 3H), 7.64-7.68 (m, 1H).

d) Preparation of 3-(benzoxazole-2-yloxy)-6,7-dihydroxypyrido[2,1,a]isoquinolin-4-one (1-018)

3-(Benzoxazole-2-yloxy)-6,7-dihydroxypyrido[2,1,a]isoquinolin-4-one (1-018) (47%) was synthesized in a similar manner to the preparation of 1-004.

Example 2-004

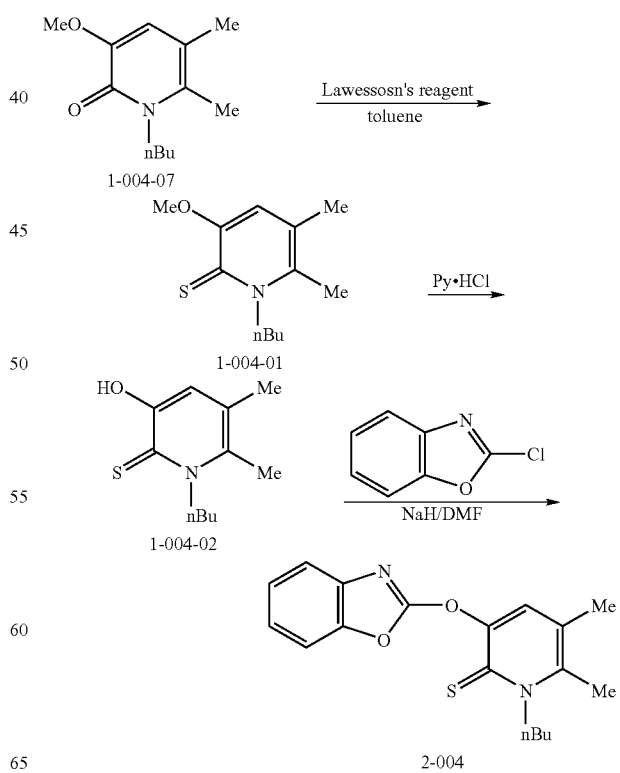

a) Preparation of 1-butyl-5,6-dimethyl-3-methoxy-2-thiopyridone (2-004-01)

To a mixture of 1-butyl-5,6-dimethyl-3-methoxy-2-pyridone (1-004-07) (222 mg) and Lawesson's reagent (502 mg) was added toluene (8 mL), and the suspension was refluxed with stirring for 7 h under nitrogen atmosphere. To a reaction mixture was added methanol (25 mL) and the reaction mixture was stirred at room temperature for 1 h, and evaporated under reduced pressure. The residue (0.80 g) was purified by silica gel column chromatography (toluene/acetone=4/1) using by Lobar column B to give 1-butyl-5,6-dimethyl-3-methoxy-2-thiopyridone (2-004-01) (177 mg, 74.1%, m.p. 111-112° C.)

$^1$H NMR (300 MHz, CDCl$_3$): δ 1.00 (t, J=7.2 Hz, 3H), 1.43-1.55 (m, 2H), 1.70-1.95 (br s, 2H), 2.22 (s, 3H), 2.46 (s, 3H), 3.89 (s, 3H), 4.90 (br s, 2H), 6.54 (s, 1H).

b) Preparation of N-1-butyl-5,6-dimethyl-3-hydroxy-2-thiopyridone (2-004-02)

N-1-Butyl-5,6-dimethyl-3-hydroxy-2-thiopyridone (2-004-02) (118 mg, 74.2%, m.p. 81-88° C.) was synthesized from 2-004-01 (170 mg) in a similar manner to the preparation of 1-013-10.

$^1$H NMR (300 MHz, CDCl$_3$): δ 1.02 (t, J=7.2 Hz, 3H), 1.45-1.57 (m, 2H), 1.70-1.90 (m, 2H), 2.21 (s, 3H), 2.45 (s, 3H), 4.72 (br s, 2H), 6.87 (s, 1H), 8.44 (br s, 1H).

c) Preparation of 1-butyl-5,6-dimethyl-3-O-(benzoxazol-2-yl)-2-thiopyridone (2-004)

1-Butyl-5,6-dimethyl-3-O-(benzoxazol-2-yl)-2-thiopyridone (2-004) (84 mg, 45.9%, m.p. 185-187° C.) was synthesized from 2-004-02 (118 mg) in a similar manner to the preparation of Example 1-004.

Examples 2-001 to 2-013 were synthesized in a similar manner to the preparation of Example 2-004.

Example 2-014

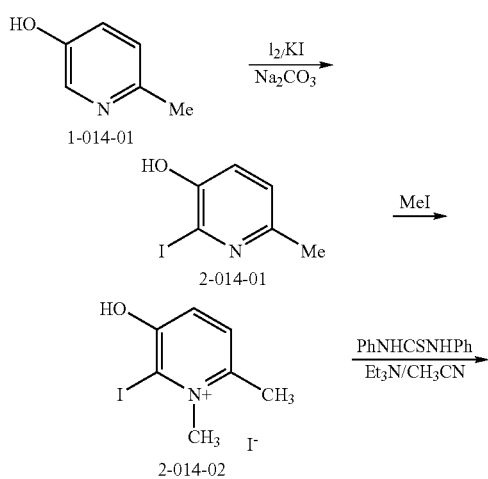

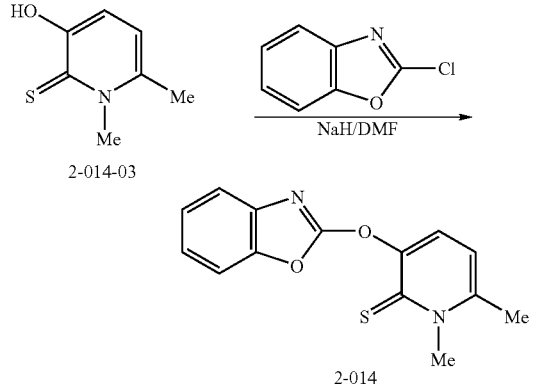

a) Preparation of 2-iodo-3-hydroxy-6-methylpyridine (2-014-01)

Sodium carbonate (68.0 g) and water (810 mL) were added to 5-hydroxy-2-methylpyridine (1-014-01) (36.11 g), and the reaction mixture was stirred at room temperature, dissolved. To the reaction mixture was added dropwise a solution of iodine (117 g) and potassium iodide (117 g) in water (810 mL) for 35 min. The resulting pink-yellow crystal was filtered and dried under reduced pressure to give 2-iodo-3-hydroxy-6-methylpyridine (2-014-01) (34.1 g, 43.9%, m.p. 187-190° C.)

$^1$H-NMR (300 MHz, CDCl$_3$+CD$_3$OD): δ 2.45 (s, 3H), 6.45 (d, J=6.9 Hz, 1H), 7.02 (dd, J=6.6, 1.5 Hz, 1H)

b) Preparation of 3-hydroxy-2-iodo-1,6-dimethylpyridinium iodide (2-014-02)

2-Iodo-3-hydroxy-6-methylpyridine (835 mg) and iodomethane (3 mL) were added in glass sealed cube, and the reaction mixture was reacted at 130° C. for 4 h and at 180° C. for 1 h. The reaction mixture was completely evaporated to give 3-hydroxy-2-iodo-1,6-dimethylpyridinium iodide (2-014-02) (1.42 g).

c) Preparation of 1,6-dimethyl-3-hydroxy-2-thiopyridone (2-014-03)

To a solution of 3-hydroxy-2-iodo-1,6-dimethylpyridinium iodide (2-014-02) (852 mg) and triethylamine (457 mg) in acetonitrile (10 mL) was added 1,3-diphenylthiourea (517 mg), and the reaction mixture was refluxed for 2 h, and evaporated. The residue was purified by silica gel column chromatography (n-hexane/ethyl acetate) to give 1,6-dimethyl-3-hydroxy-2-thiopyridone (2-014-03) (279 mg).

$^1$H NMR (300 MHz, CDCl$_3$): δ 2.47 (s, 3H), 4.12 (s, 3H), 6.53 (d, J=8.1 Hz, 1H), 6.95 (d, J=8.1 Hz, 1H), 8.35 (br s, 1H).

d) Preparation of 3-(benzoxazol-2-yloxy)-1,6-dimethyl-1H-pyridine-2-thione (2-014)

1,6-Dimethyl-3-hydroxy-2-thiopyridone (2-014-03) (157 mg) was dissolved in DMP (3 mL), and to the reaction mixture was added 60% sodium hydride (52 mg), and the reaction mixture was reacted at room temperature for 7 min. 2-Chlorobenzoxazole (184 mg) was added to the reaction mixture by washing with DMF (0.5 mL), and the reaction mixture was reacted at room temperature for 2 h. The reaction mixture was repeatedly extracted with aqueous saturated ammonium chloride solution and ethyl acetate, and evaporated under reduced pressure. The residue was purified by silica gel column chromatography and recrystallized from chloroform to give 3-(benzoxazol-2-yloky)-1,6-dimethyl-1H-pyridine-2-thione (2-014) (182 mg, 66.8%, m.p. 245-247° C.)

Example 2-015, 2-018, 2-026

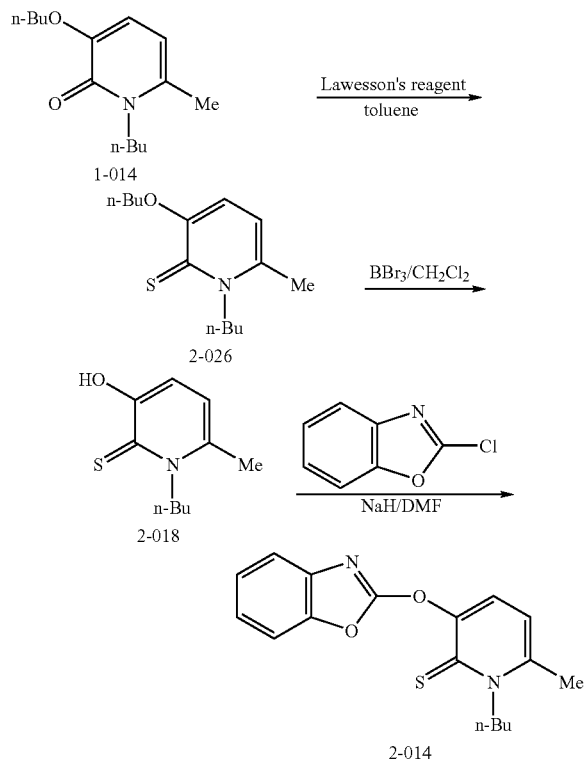

a) Preparation of 1-butyl-3-butyl-6-methyl-2-thiopyridone (2-026)

1-Butyl-3-butyl-6-methyl-2-pyridone (1-014) (8.91 g) was dissloved in dry toluene (200 mL), and to the reaction mixture was added Lawesson's reagent (19.41 g), and the reaction mixture was reacted under reflux for 3.5 h under nitrogen atmosphere. To a reaction mixture was added methanol (80 mL) and the reaction mixture was stirred at room temperature for 1.5 h, and evaporated. The residual solution was purified by silica gel column chromatography (n-hexane/ethyl acetate) to give 1-butyl-3-butyl-6-methyl-2-thiopyridone (2-026) (12.97 g). The product was used at next reaction without further purification.

$^1$H-NMR (300 MHz, CDCl$_3$): b 0.94 (t, J=7.5 Hz, 3H), 0.99 (t, J=7.5 Hz, 3H), 1.46 (m, 4H), 1.87 (m, 4H), 2.50 (s, 3H), 3.98 (t, J=6.9 Hz, 2H), 4.75 (brs, 2H), 6.40 (d, J=7.8 Hz, 1H), 7.80 (d, J=7.8 Hz, 1H)

b) Preparation of 1-butyl-3-hydroxy-6-methyl-2-thiopyridone (2-018)

1-Butyl-3-butyl-6-methyl-2-thiopyridone (2-026) (12.97 g) was dissolved in dry methylene chloride (200 mL), and to the reaction mixture was slowly added a solution of 1 mmol/mL boron tribromide in methylene chloride (5.6 mL), and the reaction mixture was stirred at room temperature for 5 h. The reaction mixture was poured into ice and water, adjusted at pH 8 to 9 with conc. aqueous ammonia, extracted with chloroform, washed with brine, purified by alumina (150 g) column chromatography, eluted with chloroform to give 1-butyl-3-hydroxy-6-methyl-2-thiopyridone (2-018) (5.439 g, 73.4%) as an orange oil.

$^1$H-NMR (300 MHz, CDCl): δ 1.02 (t, J=7.8 Hz), 1.50 (m, 2H), 1.85 (m, 2H), 2.51 (s, 3H), 4.66 (br s, 2H), 6.49 (d, J=7.8 Hz, 1H), 6.91 (d, J=7.8 Hz, 1H), 8.44(brs. 1H).

c) Preparation of 1-butyl-3-(benzoxazol-2-yl)-6-methyl-2-thiopyridone (2-014)

1-Butyl-3-hydroxy-6-methyl-2-thiopyridone (2-018) (113 mg) was dissolved in dry DMF (1.1 mL), and to the reaction mixture was added 60% sodium hydride (36 mg), and the reaction mixture was stirred at room temperature for 30 min. To the reaction mixture was added 2-chlorobenzoxazole (112 mg), and the reaction mixture was reacted for 2 h and 40 min. The reaction mixture was poured into ice-water (20 mL), extracted twice with ethyl acetate (30 mL), washed with brine, and evaporated. The residue was purified by preparative thin-layer chromatography using chloroform as a developing solvent to give 1-butyl-3-(benzoxazol-2-yl)-6-methyl-2-thiopyridone (2-014) (117 mg, m.p. 125-127.5° C.)

Examples 2-025 to 2-029 were synthesized in a similar manner to the preparation of Example 2-014.

Example 2-034

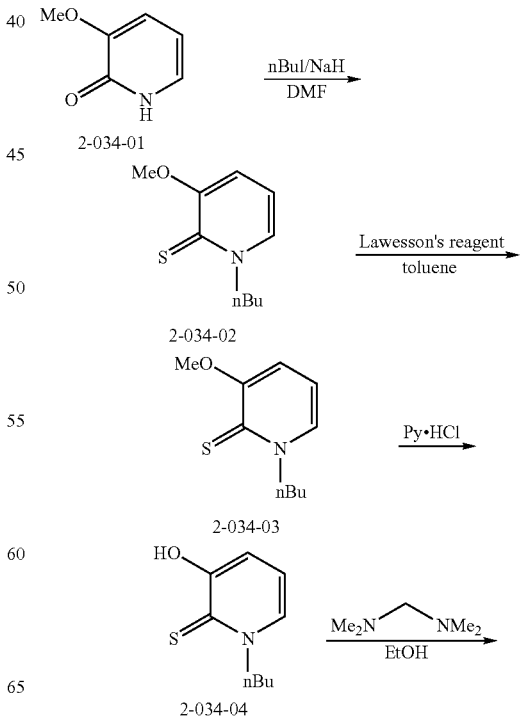

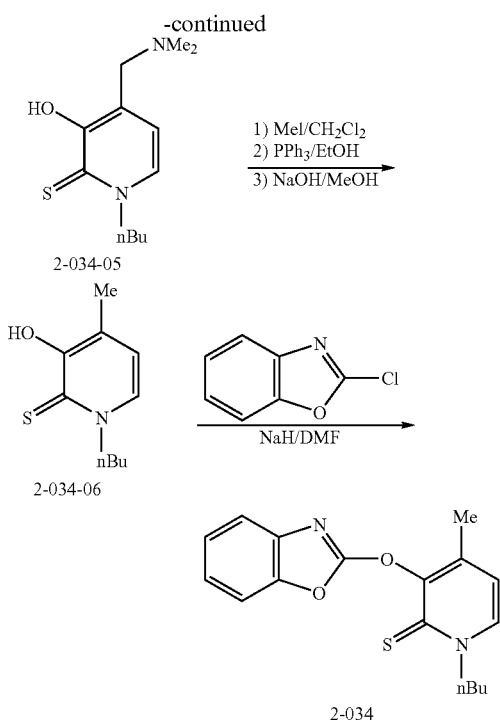

a) Preparation of 1-butyl-3-methoxy-2-pyridone (2-034-02)

To a solution of 3-methoxy-2(1H)-pyridone (2-034-01) (5.0 g) in DMF (40 mL) was added sodium hydride (60% wt, 2.2 g) at room temperature. After the reaction mixture was stirred for 20 min, 1-iodobutane (15.5 g) was added to the reaction mixture, and the reaction mixture was stirred for 40 min. After the reaction was quenched with water, the solvent was removed. To the residue were added a saturated aqueous solution of ammonium chloride and ethyl acetate, and the organic layer was separated, and the aqueous layer was extracted three times with ethyl acetate. The combined organic layers were washed water and brine, dried over anhydrous magnesium sulfate, and evaporated under reduced pressure. The crude product was purified by silica gel column chromatography (toluene/acetone=4/1) to give 1-butyl-3-methoxy-2-pyridone (2-034-02) (6.7 g, 93%) as an oil.

$^1$H NMR (300 MHz, CDCl$_3$): δ 0.93 (t, J=7.2 Hz, 2H), 1.30-1.42 (m, 2H), 1.68-1.78 (m, 2H), 3.81 (s, 3H), 3.97 (t, J=7.2 Hz, 2H), 6.09 (t, J=7.2 Hz, 1H), 6.59 (dd, J=7.2, 1.5 Hz, 1H), 6.88 (dd, J=7.2, 1.5 Hz, 1H).

b) Preparation of 1-butyl-3-methoxypyridine-2-thione (2-034-03)

To a solution of 1-butyl-3-methoxy-2-pyridone (2-034-02) (6.4 g) in toluene (150 mL) was added Lawesson's reagent (16.8 g), and the reaction mixture was heated under reflux. After the reaction mixture was stirred for 3 h, to the reaction mixture was added methanol (100 mL), and the reaction mixture was stirred for 30 min. After the solvent was evaporated under reduced pressure, to the reaction mixture were added water and ethyl acetate, and the organic layer was separated. The aqueous layer was extracted three times with ethyl acetate, and the combined organic layers were washed with water and brine, dried over anhydrous magnesium sulfate, and evaporated under reduced pressure. The crude product was purified by silica gel column chromatography to give 1-butyl-3-methoxypyridine-2-thione (2-034-03) (5.6 g, 80%) as an oil.

$^1$H NMR (300 MHz, CDCl): δ 0.98 (t, J=7.3 Hz, 3H), 1.36-1.48 (m, 2H), 1.84-1.94 (m, 2H), 3.92 (s, 3H), 4.62 (t, J=7.6 Hz, 2H), 6.61 (dd, J=7.9, 6.2 Hz, 1H), 6.69 (dd, J=7.9, 1.23 Hz, 1H), 7.38 (dd, J=6.2, 1.2 Hz, 1H).

c) Preparation of 1-butyl-3-hydroxypyridine-2-thione (2-034-04)

Pyridine hydrochloride salt (3.6 g) was added to 1-butyl-3-methoxypyridine-2-thione (2-034-03) (1.4 g), and the reaction mixture was stirred at 190° C. for 40 min. To the reaction mixture were added water and ethyl acetate, and the organic layer was separated, and the organic layer was extracted three times with ethyl acetate. The combined organic layers were washed with water and brine, dried over anhydrous magnesium sulfate, and evaporated under reduced pressure to give 1-butyl-3-hydroxypyridine-2-thione (2-034-04) (1.02 g, 0.78%) as an oil.

$^1$H NMR (300 MHz, CDCl$_3$): δ 0.99 (t, J=7.3 Hz, 3H), 1.43 (m, 2H), 1.91 (m, 2H), 4.53 (t, J=7.6 Hz, 2H), 6.66 (dd, J=7.6, 6.7 Hz, 1H), 6.97 (dd, J=7.6, 1.2 Hz, 1H), 7.34 (dd, J=6.7, 1.2 Hz, 1H), 8.61 (br s, 1H).

d) Preparation of 1-butyl-3-hydroxy-4(N,N-dimethylaminomethyl)pyridine-2-thione (2-034-05)

To a solution of 1-butyl-3-hydroxypyridine-2-thione (2-034-04) (1.0 g) in ethanol containing 10% water (20 mL) was added N,N,N',N'-teteramethyldiaminomethane (1.70 g) at room temperature. After the reaction mixture was stirred at 75° C. for 24 h, the solvent was evaporated under reduced pressure to give 1-butyl-3-hydroxy-4(N,N-dimethylaminomethyl)pyridine-2-thione (2-034-05) (1.3 g, 95%) as an oil.

$^1$H NMR (300 MHz, CDCl): δ 0.99 (t, J=7.3 Hz, 3H), 1.39-1.47 (m, 2H), 1.86-1.93 (m, 2H), 2.29 (s, 6H), 3.48 (s, 2H), 4.51 (t, J=7.3 Hz, 2H), 6.87 (d, J=6.7 Hz, 1H), 7.32 (d, J=6.7 Hz, 1H).

d) Preparation of 1-butyl-3-hydroxy-4-methylpyridine-2-thione (2-034-06)

To a solution of 1-butyl-3-hydroxy-4(N,N-dimethylaminomethyl)pyridine-2-thione (2-034-05) (1.0 g) in methylene chloride (20 mL) was added iodomethane (2.1 g) at room temperature. After the reaction mixture was stirred for 1 h, the solvent was evaporated under reduced pressure. To the residue were added ethanol (20 mL) and triphenylphosphine (1.6 g), and the reaction mixture was stirred at 75° C. for 20 h, and evaporated under reduced pressure. To the residue were added methanol (10 mL) and 1 mol/L aqueous sodium hydroxide solution (8 mL), and the reaction mixture was stirred at 60° C. for 2 h, and evaporated under reduced pressure. The crude product was purified by silica gel column chromatography (toluene/acetone=4/1) to give 1-butyl-3-hydroxy-4-methylpyridine-2-thione (2-034-06) (0.57 g, 70%) as an oil.

$^1$H NMR (300 MHz, CDCl$_3$): δ 0.98 (t, J=7.3 Hz, 3H), 1.36-1.48 (m, 2H), 1.84-1.94 (m, 2H), 2.25 (s, 3H), 4.50 (t, J=7.6 Hz, 2H), 6.55 (d, J=6.7 Hz, 1H), 7.25 (d, J=6.7 Hz, 1H), 8.67 (s, 1H).

f) Preparation of 3-(benzoxazol-2-yloxy)-1-butyl-4-methoxypyridine-2-thione (2-034)

To a solution of 1-butyl-3-hydroxy-4-methylpyridine-2-thione (2-034-06) (50 mg) in DMF (1.0 mL) was added sodium hydride (60% wt, 15 mg) at room temperature. After the reaction mixture was stirred for 20 min, to the reaction mixture was added 2-chlorobenzoxazole (85 mg), and the reaction mixture was stirred at 75° C. for 17 h. After the reaction was quenched with water, the solvent was evaporated. To the residue were added aqueous saturated ammonium chloride solution and ethyl acetate, and the organic layer was separated, and the aqueous layer was extracted three times with ethyl acetate. The combined organic layers were washed water and brine, dried over anhydrous magnesium sulfate, and evaporated under reduced pressure. The crude product was purified by column chromatography (toluene/acetone=4/1) to give 3-(benzoxazol-2-yloxy)-1-butyl-4-methoxypyridine-2-thione (2-034) (73 mg, 92%) as a yellow crystal. The obtained crystal was purified by recrystallization from methylene chloride and diethyl ether.

Example 2-035

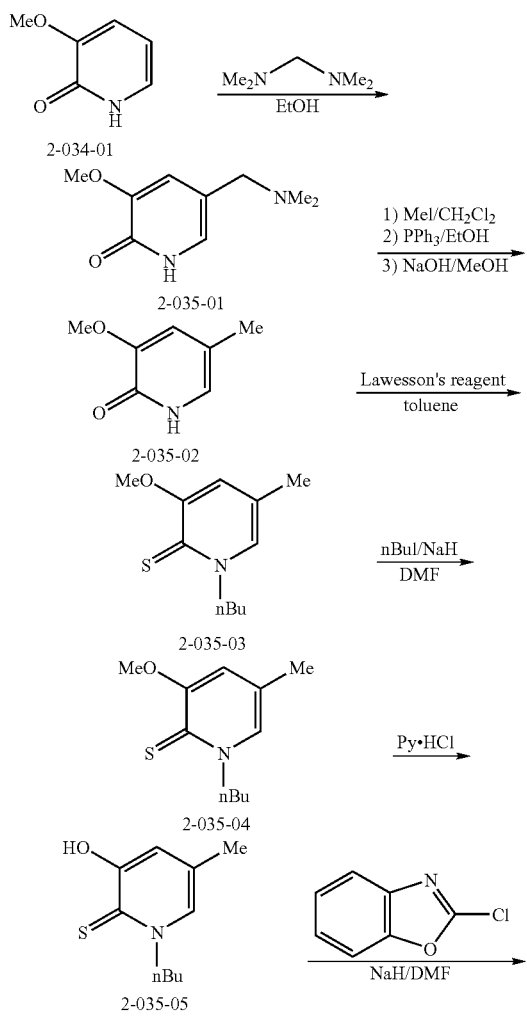

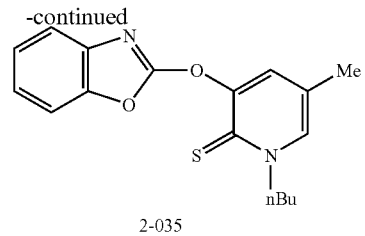

2-035 a) Preparation of 5-(N,N-dimethylaminomethyl)-3-methoxy-2(1)-pyridone (2-035-01)

To a solution of 3-methoxy-2(1H)-pyridone (2-034-01) (5.0 g) in ethanol containing 10% water (150 mL) was added N,N,N',N'-teteramethyldiaminomethane (54 mL) at room temperature, and the reaction mixture was heated under reflux. After the reaction mixture was stirred for 48 h, the solvent was removed under reduced pressure, and the obtained crude product was purified by silica gel column chromatography (chloroform/methanol/water=6/14/1) to give 5-(N,N-dimethylaminomethyl)-3-methoxy-2(1H)-pyridone (2-035-01) (4.5 g, 53%) as an oil.

$^1$H NMR (300 MHz, CDCl$_3$): δ 2.21 (s, 6H), 3.17 (s, 2H), 3.87 (s, 3H), 6.86 (d, J=1.8 Hz, 1H), 6.90 (d, J=1.8 Hz, 1H).

b) Preparation of 3-methoxy-5-methyl-2(1 h)-pyridone (2-035-02)

3-Methoxy-5-methyl-2(12)-pyridone (2-035-02) (71%) was synthesized in a similar manner to the preparation of 2-034-06.

$^1$H NMR (300 MHz, CDCl$_3$): δ 2.11 (d, J=1.2 Hz, 3H), 3.84 (s, 3H), 6.62 (d, J=2.1 Hz, 1H), 6.80 (dd, J=2.1, 1.2 Hz, 11).

c) Preparation of 1-butyl-3-methoxy-5-methyl-2-pyridone (2-035-03)

1-Butyl-3-methoxy-5-methyl-2-pyridone (2-035-03) (63%) was synthesized in a similar manner to the preparation of 2-034-02.

$^1$H NMR (300 MHz, CDCl$_3$): δ 0.94 (t, J=7.3 Hz, 3H), 1.29-1.42 (m, 2H), 1.66-1.76 (m, 2H), 2.08 (d, J=1.2 Hz, 3H), 3.80 (s, 3H), 3.92 (t, J=7.3 Hz, 2H), 6.45 (d, J=1.2 Hz, 1H), 6.65 (dd, J=2.1, 1.2 Hz, 1H).

d) Preparation of 1-butyl-3-methoxy-5-methylpyridine-2-thione (2-035-04)

1-Butyl-3-methoxy-5-methylpyridine-2-thione (2-035-04) (100%) was synthesized in a similar manner to the preparation of 2-034-03

$^1$H NMR (300 MHz, CDCl$_3$): δ 0.97 (t, J=7.4 Hz, 3H), 1.35-1.48 (m, 2H), 1.83-1.93 (m, 2H), 2.21 (s, 3H), 3.91 (s, 3H), 4.59 (t, J=7.7 Hz, 2H), 6.55 (s, 1H), 7.21 (s, 1H).

d) Preparation of 1-butyl-3-hydroxy-5-methylpyridine-2-thione (2-035-05)

1-Butyl-3-hydroxy-5-methylpyridine-2-thione (2-035-05) (76%) was synthesized in a similar manner to the preparation of 2-034-04.

$^1$H-NMR (CDCl$_3$, 300 MHz): δ 0.99 (t, J=7.3 Hz, 3H), 1.37-1.50 (m, 2H), 1.85-1.95 (m, 2H), 2.19 (d, J=0.9 Hz, 3H), 4.49 (t, J=7.6 Hz, 2H), 6.86 (d, J=1.2 Hz, 1H), 7.16 (dd, J=1.9, 0.9 Hz, 1H), 8.55 (s, 1H).

f) Preparation of 3-(benzoxazol-2-yloxy)-1-butyl-5-methylpyridine-2-thione (2-035)

To a solution of 1-butyl-3-hydroxy-5-methylpyridine-2-thione (2-035-05) (300 mg) in DMF (6.0 mL) was added sodium hydride (60% wt, 79 mg) at room temperature. After the reaction mixture was stirred for 20 min, to the reaction mixture was added 2-chlorobanzoxazole (432 mg), and the reaction mixture was stirred at room temperature for 2 h. After the reaction was quenched with water, the solvent was removed. To the residue were added aqueous saturated ammonium chloride solution and ethyl acetate, and the organic layer was separated, and the aqueous layer was extracted three times with ethyl acetate. The combined organic layers were washed with water and brine, dried over anhydrous magnesium sulfate, and evaporated under reduced pressure. The crude product was purified by silica gel column chromatography (toluene/acetone=4/1) to give 3-(benzoxazol-2-yloxy)-1-butyl-4-methylpyridine-2-thione (2-035) 372 mg, 73%) as a yellow crystal. The obtained crystal was purified by recrystallization from methylene chloride and diethyl ether.

Examples 2-030 to 2-037 were synthesized in the similar manner as Examples 2-034 and 2-035.

Example 3-003

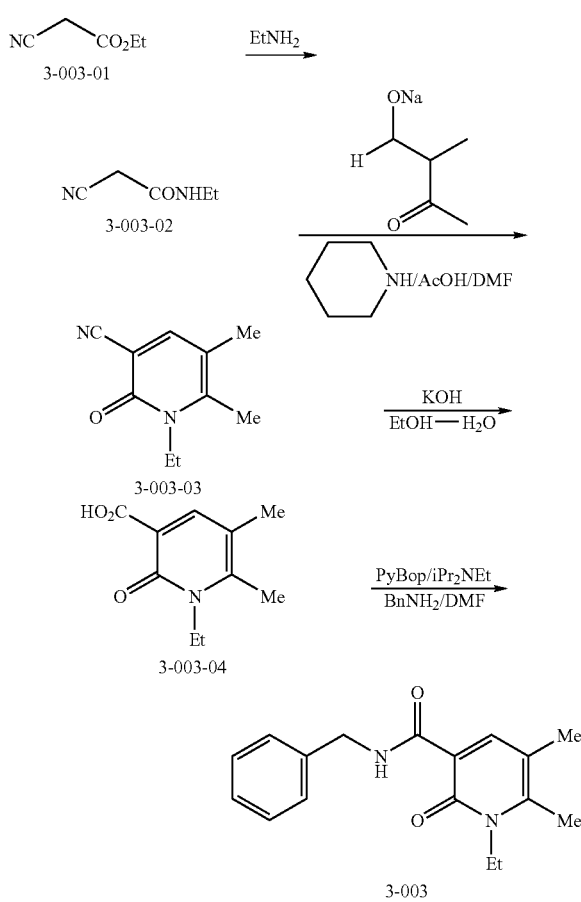

a) Preparation of N-ethyl cyanoacetamide (3-003-02)

Aqueous 70% ethylamine solution (15.5 mL) was added dropwise to ethylcyanoacetete (3-003-01) (11.31 g) at room temperature. Since the inner temperature rose up to 44° C., the reaction mixture was stirred at 32 to 37° C. for 15 min under ice-cooling. After the reaction mixture was stirred for 9 h at the same temperature, stood overnight. The reaction mixture was evaporated under reduced pressure, and to the obtained brown crystalloid residue (11.93 g) were diethyl ether (20 mL) and n-hexane (10 mL). The orange crystal was filtered to give N-ethyl cyanoacetamide (3-003-02) (9.05 g, 80.7%, m.p. 54-59° C.)

$^1$H NMR (300 MHz, CDCl$_3$): δ 1.20 (t, J=7.2 Hz, 3H), 3.31-3.40 (m, 4H), 6.22 (br s, 1H).

b) Preparation of 1-ethyl-3-cyano-5,6-dimethyl-2-pyridone (3-003-03)

To a suspension of 2-methyl-3-oxobutanal sodium salt (3.18 g) and N-ethylcyanoacetamide (3-0003-02) (2.243 g) in DMF (20 mL) were added acetic acid (1.49 mL) and piperidine (0.40 mL) at room temperature, and the reaction mixture was refluxed with stirring in an oil bath at 135° C. for 5 h. The reaction mixture was dissolved in chloroform and water, extracted three times with chloroform, dried over magnesium sulfate, and evaporated under reduced pressure. The obtained crystal residue (4.07 g) was washed three times with n-hexane (1 mL) to give 1-ethyl-3-cyano-5,6-dimethyl-2-pyridone (3-003-03) (3.38 g, 96%) as a brown crystal.

$^1$H NMR (300 MHz, CDCl$_3$): δ 1.33 (t, J=7.2 Hz, 3H), 2.13 (s, 3H), 2.43 (s, 3H), 4.19 (q, J=7.2 Hz, 2H), 7.59 (s, 1H).

c) Preparation of 1-ethyl-3-carboxy-5,6-dimethyl-2-pyridone (3-003-04)

1-Ethyl-3-cyano-5,6-dimethyl-2-pyridone (3-003-03) (3.37 g) was dissolved in 80% ethanol (65 mL), and to the reaction mixture was added potassium hydroxide (7.96 g), and the reaction mixture was refluxed with stirring in oil bath at 102° C. for 24 h. The reaction mixture was evaporated under reduced pressure, and to the residue were added water (50 mL) and ethyl acetate (50 mL). After the reaction mixture was stirred under ice-cooling, and was separated by shaking, and to the aqueous layer was conc. hydrochloric acid (13 mL). The resulting crystal was filtered, and washed with cooled water to give 1-ethyl-3-carboxy-5,6-dimethyl-2-pyridone (3-003-04) (2.734 g, 73.3%, m.p. 164-165° C.) as a yellow ocher crystal.

$^1$H NMR (300 MHz, CDCl$_3$): δ 1.38 (t, J=7.2 Hz, 3H), 2.20 (s, 3H), 2.49 (s, 3H), 4.28 (q, J=7.2 Hz, 2H), 8.28 (s, 1H), 14.73 (br s, 1H).

d) Preparation of 1-ethyl-2-oxo-5,6-dimethyl-1,2-dihydropyridine-3-carboxylic acid benzylamide (3-003)

1-Ethyl-3-carboxy-5,6-dimethyl-2-pyridone (3-003-04) (195 mg) was dissolved in DMF (3 mL), and to the reaction mixture were added benzylamine (0.17 mL), diisopropylethylamine (0.35 mL), and benzotriazol-1-yloxytripyrrolidinophosphonium hexafluorophosphate (PyBOP, 624 mg), and the reaction mixture was stirred at room temperature for 1 h. The reaction mixture was diluted with ethyl acetate, washed twice with hydrochloric acid and aqueous sodium bicarbonate solution, respectively, and water, dried over magnesium sulfate, and evaporated under reduced pressure. The residue (0.40 g) was subjected to silica gel (30 g) column chromatography (chloroform) to give 1-ethyl-2-oxo-5,6-dimethyl-1,2-dihydropyridine-3-carboxylic acid benzylamide (3-003) (259 mg, 91.1%) as a crystal, followed by recrystallization from methylene/n-hexane to give colorless needle crystal (207 mg, 72.9%, m.p. 117° C.)

Examples 3-001 to 3-036 were synthesized in similar manner as Example 3-004.

Example 3-067, 3-068, 3-069

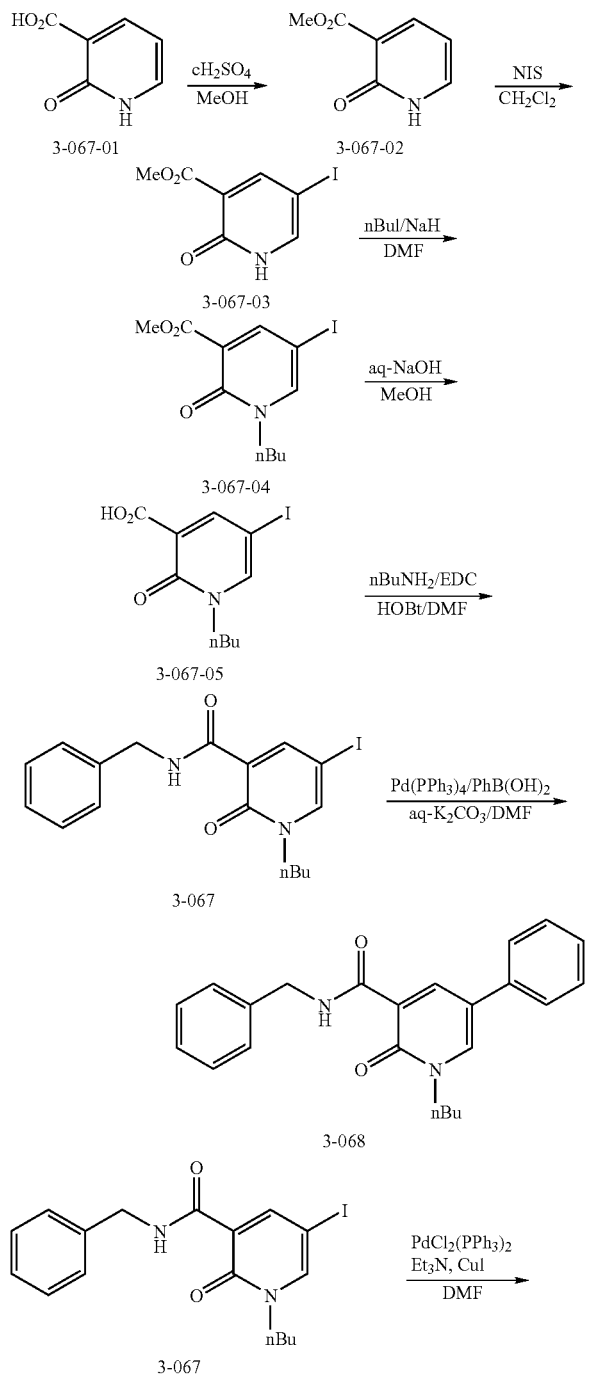

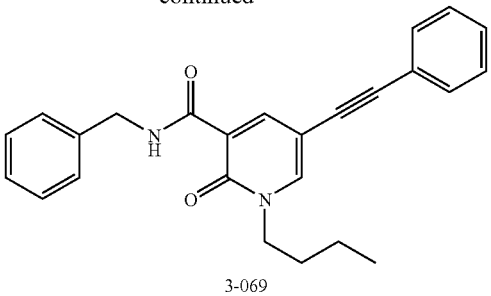

a) Preparation of 2-hydroxynicotinic acid methyl ester (3-067-02)

To a solution of 2-hydroxynicotinic acid (3-067-01) (50 g) in methanol (500 ml) were added conc. sulfuric acid (15 ml) and toluene (100 mL) at room temperature. After the reaction mixture was stirred for 28 h attached Dienstark reflux tube and neutralized with an aqueous potassium carbonate solution, the solvent was evaporated. To the residue were added aqueous saturated ammonium chloride solution and chloroform, and the organic layer was separated, and the aqueous layer was extracted with chloroform. The combined organic layers were dried over anhydrous magnesium sulfate, and evaporated under reduced pressure to give 2-hydroxynicotinic acid methyl ester (3-067-02) (46 g, 84%) as a white solid.

$^1$H NMR (300 MHz, CDCl$_3$): δ 3.92 (s, 3H), 6.45 (dd, J=7.3, 6.4 Hz, 1H), 7.78 (dd, J=6.4, 2.4 Hz, 1H), 8.29 (dd, J=7.3, 2.4 Hz, 1H).

b) Preparation of 2-hydroxy-5-iodonicotinic acid methyl ester (3-067-03)

To a solution of 2-hydroxynicotinic acid methyl ester (3-067-02) (20 g) in methylene chloride (500 mL) was added N-iodosuccinimide (NIS, 38 g) at room temperature, and the reaction mixture was heated under reflux for 16 h, and evaporated. To the residue was added ethyl acetate (200 mL) and the reaction mixture was heated under reflux for 2 h. The insoluble solid was filtered to give 2-hydroxy-5-iodonicotinic acid methyl ester (3-067-03) (30 g, 81%) as a white solid.

$^1$H NMR (300 MHz, CDCl$_3$): δ 3.97 (s, 3H), 8.33 (brs, 1H), 8.43 (d, J=2.4 Hz, 1H).

c) Preparation of 1-butyl-5-iodo-2-oxo-1,2-dihydropridine-3-carboxylic acid methyl ester (3-067-04)

1-Butyl-5-iodo-2-oxo-1,2-dihydropridine-3-carboxylic acid methyl ester (3-067-04) (89%) was synthesized in a similar manner to the preparation of 2-034-O$_2$.

$^1$H NMR (300 MHz, CDCl$_3$): δ 0.96 (t, J=7.4 Hz, 3H), 1.31-1.44 (m, 2H), 1.69-1.79 (m, 2H), 3.90 (s, 3H), 3.94 (t, J=7.4 Hz, 2H), 7.71 (d, J=2.8 Hz, 1H), 8.24 (d, J=2.8 Hz, 1H).

c) Preparation of 1-butyl-5-iodo-2-oxo-1,2-dihydropridine-3-carboxylic acid (3-067-05)

1-Butyl-5-iodo-2-oxo-1,2-dihydropridine-3-carboxylic acid (3-067-05) was synthesized in a similar manner to the preparation of 3-003-04.

¹H NMR (300 MHz, CDCl₃): δ 0.99 (t, J=7.4 Hz, 3H), 1.35-1.47 (m, 2H), 1.74-1.84 (m, 2H), 4.05 (t, J=7.5 Hz, 2H), 7.83 (d, J=2.7 Hz, 1H), 8.63 (d, J=2.7 Hz, 1H), 14.13 (s, 1H).

d) Preparation of 1-butyl-5-iodo-2-oxo-1,2-dihydropridine-3-carboxylic acid benzylamide (3-067)

1-Butyl-5-iodo-2-oxo-1,2-dihydropridine-3-carboxylic acid benzylamide (3-067) (82%) was synthesized in a similar manner to the preparation of 3-003.

e) Preparation of 1-butyl-2-oxo-5-phenyl-1,2-dihydropridine-3-carboxylic acid benzylamide (3-068)

To a solution of 1-butyl-5-iodo-2-oxo-1,2-dihydropridine-3-carboxylic acid benzylamide (3-067) (100 mg) in DMF (2.0 mL) were added Pd(PPh₃)₄ (20 mg), phenyl boric acid (89 mg), and an aqueous solution of potassium carbonate (2 mole/L, 0.24 mL) at room temperature. After stirred at 90° C. for 18 h, to the reaction mixture were added a saturated aqueous solution of ammonium chloride and ethyl acetate. The organic layer was separated and the aqueous layer was extracted three times with ethyl acetate, and the combined organic layers were washed with water and brine, dried over anhydrous magnesium sulfate, and evaporated under reduced pressure. The obtained crude product was purified by the preparative thin-layer chromatography (toluene/acetone=7/1) to give 1-butyl-2-oxo-5-phenyl-1,2-dihydropridine-3-carboxylic acid benzylamide (3-068) (77 mg, 88%) as an oil.

f) Preparation of 1-butyl-2-oxo-5-phenylethynyl-1,2-dihydiopridine-3-carboxylic acid benzylamide (3-069)

To a solution of 1-butyl-5-iodo-2-oxo-1,2-dihydropridine-3-carboxylic acid benzylamide (3-067) (78 mg) in DMF (2.0 mL) were added PdCl₂(PPh₃)₂ (15 mg), phenylacetylene (89 mg), CuI (11 mg), and triethylamine (48 mg) at room temperature. After stirred at 90° C. for 18 h, to the reaction mixture were added a saturated aqueous solution of ammonium chloride and ethyl acetate. The organic layer was separated and the aqueous layer was extracted three times with ethyl acetate, and the combined organic layers were washed with water and brine, dried over anhydrous magnesium sulfate, and evaporated under reduced pressure. The obtained crude product was purified by the preparative thin-layer chromatography (toluene/acetone=7/1) to give 1-butyl-2-oxo-5-phenylethynyl-1,2-dihydropridine-3-carboxylic acid benzylamide (3-069) (65 mg, 89%) as an oil.

Examples 3-039 to 3-044 and 3-061 to 3-066 were synthesized in a similar manner to Example 3-067 and 3-068.

Example 3-101

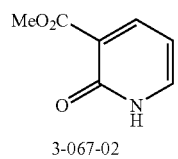
3-067-02

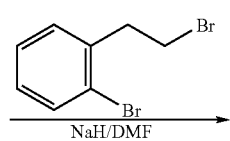

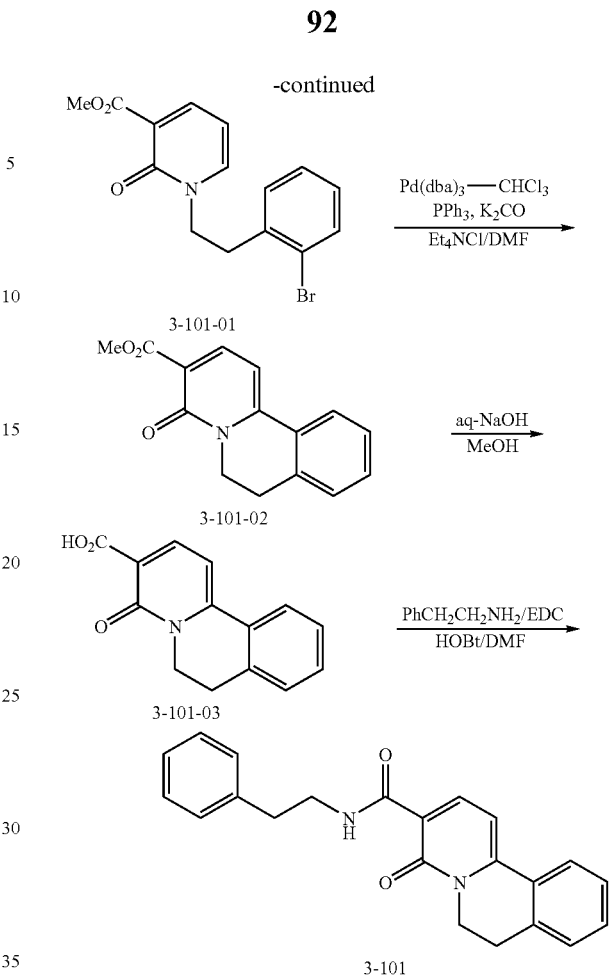

a) Preparation of 2-hydroxy-1-(2-bromophenethyl) nicotinic acid methyl ester (3-101-01)

2-Hydroxy-1-(2-bromophenethyl)nicotinic acid methyl ester (3-101-01) (59%) was synthesized in a similar manner to the preparation of 2-034-O₂.

¹H NMR (300 MHz, CDCl₃): δ 3.25 (t, J=7.2 Hz, 2H), 3.93 (s, 3H), 4.23 (t, J=7.2 Hz, 2H), 6.09 (t, J=7.5 Hz, 1H), 7.08-7.23 (m, 4H), 7.56 (dd, J=8.1, 2.1 Hz, 1H), 8.15 (dd, J=7.5, 2.4 Hz, 1H).

b) Preparation of 4-oxo-6,7-dihydropyrido[2,1,a]isoquinoline-3-carboxylic acid methyl ester (3-101-02)

4-Oxo-6,7-dihydropyrido[2,1,a]isoquinoline-3-carboxylic acid methyl ester (3-101-02) (42%) was synthesized in a similar manner to the preparation of 1-018-01.

¹H NMR (300 MHz, CDCl₃): δ 3.01 (t, J=6.7 Hz, 2H), 3.93 (s, 3H), 4.35 (t, J=6.7 Hz, 2H), 6.76 (d, J=7.6 Hz, 1H), 7.32 (dd, J=7.3, 1.2 Hz, 1H), 7.39 (ddd, J=7.6, 7.3, 1.5 Hz, 1H), 7.46 (ddd, J=7.9, 7.6, 1.2 Hz, 1H), 7.78 (dd, J=7.9, 1.5 Hz, 1H), 8.25 (d, J=7.6 Hz, 1H).

c) Preparation of 4-oxo-6,7-dihydropyrido[2,1,a]isoquinoline-3-carboxylic acid (3-101-03)

To a solution of 4-oxo-6,7-dihydropyrido[2,1,a]isoquinoline-3-carboxylic acid methyl ester (3-101-02) (252 mg) in dioxane (2.0 mL) was 2 mol/L aqueous sodium hydroxide solution (2.0 mL) at room temperature. After the reaction mixture was stirred for 1 h, and washed with diethyl ether, adjusted to be acidic with conc. hydrochloric acid. To the reaction mixture were added water and ethyl acetate, and the organic layer was separated. The aqueous layer was extracted three times with ethyl acetate and the combined organic layers were washed with water and brine, dried over anhydrous magnesium sulfate, and evaporated under reduced pressure to give 4-oxo-6,7-dihydropyrido[2,1,a]isoquinoline-3-carboxylic acid (3-101-03) (209 mg, 88%) as a white solid.

$^1$H NMR (300 MHz, CDCl$_3$): δ 3.10 (t, J=6.7 Hz, 2H), 4.42 (t, J=6.7 Hz, 2H), 7.05 (d, J=7.6 Hz, 1H), 7.36 (d, J=7.3 Hz, 1H), 7.41-7.56 (m, 2H), 7.84 (d, J=7.3 Hz, 1H), 8.56 (d, J=7.6 Hz, 1H), 14.40 (s, 1H).

d) Preparation of 4-oxo-6,7-dihydropyrido[2,1,a]isoquinoline-3-carboxylic acid phenethylamide (3-101)

To a solution of 4-oxo-6,7-dihydropyrido[2,1;a]isoquinoline-3-carboxylic acid (3-101-03) (76 mg) in DMF (2.0 mL) were added 1-ethyl-3-(3-dimethylaminopropyl)carbodiimide hydrochloric acid salt (EDC, 83 mg), 1-hydroxybenzotriazole (HOBt, 58 mg), and phenethylamine (80 mg) at room temperature. After the reaction mixture was stirred for 18 h, the reaction was quenched with 0.5 mol/L hydrochloric acid. To the reaction mixture was added ethyl acetate and the organic layer was separated. The aqueous layer was extracted three times with ethyl acetate, and the combined organic layers were washed with water and brine, dried over anhydrous magnesium sulfate, and evaporated under reduced pressure. The obtained crude crystal was recrystallized to give 4-oxo-6,7-dihydropyrido[2,1,a]isoquinoline-3-carboxylic acid phenethylamide (3-101) (84 mg, 74%) as an yellow crystal.

Example 4-002

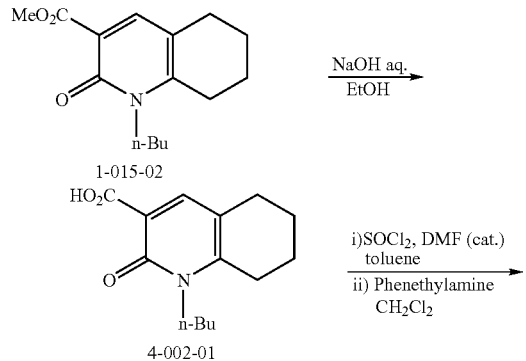

a) Preparation of 1-butyl-2-oxo-1,2,5,6,7,8-hexahydroquinoline-3-carboxylic acid (4-002-01)

1-Butyl-2-oxo-1,2,5,6,7,8-hexahydroquinoline-3-carboxylic acid methyl ester (1-015-02) (263 mg, 1 mmol) was dissolved in ethanol (6 mL), and to the reaction mixture was added an aqueous solution of sodium hydroxide (2 mol/L, 0.6 mL, 1.2 mmol), and the reaction mixture was stirred at room temperature for 30 min. To the reaction mixture was added diluted hydrochloric acid (0.4 N, 6 mL) and the reaction mixture was extracted with ethyl acetate (25 mL). To the aqueous layer was added sodium chloride, followed by extraction with ethyl acetate (25 mL), and the combined organic layers were dried over anhydrous magnesium sulfate, and evaporated under reduced pressure. The obtained crystal residue was recrystallized from hexane to give 1-butyl-2-oxo-1,2,5,6,7,8-hexahydroquinoline-3-carboxylic acid (4-002-01) (220 mg, 88%) as a white crystal.

$^1$H-NMR (300 MHz, CDCl$_3$): δ 1.00 (t, J=7.5 Hz, 3H), 1.46 (sextet, J=7.5 Hz, 2H), 1.68-1.73 (m, 2H), 1.77 (quint, J=6.0 Hz, 2H), 1.92 (quint, J=6.0 Hz, 2H), 2.65 (t, J=6.0 Hz, 2H), 2.80 (t, J=6.0 Hz, 2H), 4.10 (t, J=7.8 Hz, 2H), 8.22 (s, 1H), 14.82 (s, 1H).

b) Preparation of 1-butyl-2-oxo-1,2,5,6,7,8-hexahydroquinoline-3-carboxylic acid phenethylamide (4-002)

1-Butyl-2-oxo-1,2,5,6,7,8-hexahydroquinoline-3-carboxylic; acid (4-002-01) (100 mg, 0.38 mmol) was dissloved in toluene (10 mL), and to the reaction mixture were added thionyl chloride (83 μL, 1.14 mmol) and catalytic amount of DMF, and the reaction mixture was reacted at 75° C. for 30 min. The reaction mixture was evaporated under reduced pressure and the residue was dissolved in methylene chloride (5 mL). To the reaction mixture was added phenethylamine (143 μL, 1.14 mmol) and the reaction mixture was stirred at room temperature for 10 min. To the reaction mixture was added diluted hydrochloric acid (1 mol/L, 10 mL) and the reaction mixture was extracted with ethyl acetate (30 mL), washed with brine (10 mL), dried over anhydrous magnesium sulfate, and evaporated under reduced pressure. The residue was purified by silica gel column chromatography (toluene/ethyl acetate), followed by recrystallization from diethyl ether to give 1-butyl-2-oxo-1,2,5,6,7,8-hexahydroquinoline-3-carboxylic acid phenethylamide (4-002) (100 mg, 74%) as white crystal.

$^1$H NMR (300 MHz, CDCl$_3$): δ 0.99 (t, J=7.5 Hz, 3H), 1.45 (sextet, J=7.5 Hz, 2H), 1.63 (quint, J=7.5 Hz, 2H), 1.74 (quint, J=6.0 Hz, 2H), 1.88 (quint, J=6.0 Hz, 2H), 2.62 (t, J=6.0 Hz, 2H), 2.74 (t, J=6.0 Hz, 2H), 2.93 (t, J=7.8 Hz, 2H), 3.66 (dt, J=9.0 Hz, 6.0 Hz, 2H), 4.03 (t, J=7.8 Hz, 2H), 7.20-7.33 (m, 5H), 8.25 (s, 1H), 10.05 (br t, J=6.0 Hz, 1H).

Examples 4-001 to 4-310 were synthesized in a similar manner to Example 3-002.

Example 4-501

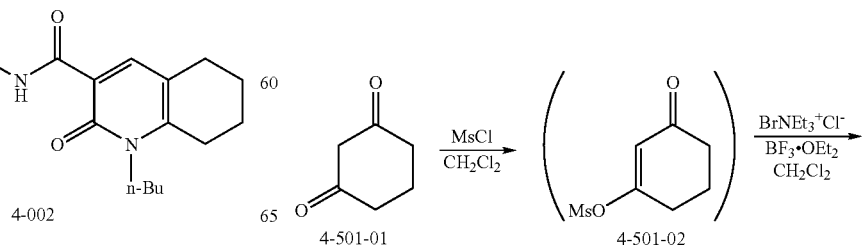

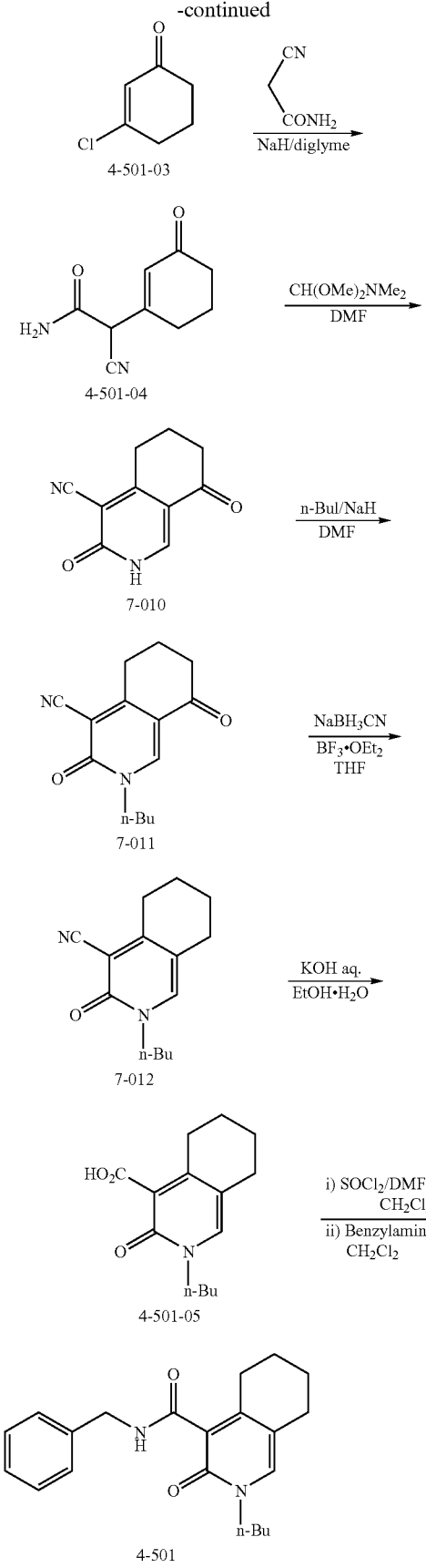

a) Preparation of 3-chloro-2-cyclohexene-1-one (4-501-03)

1,3-cyclohexanedione (4-501-01) (8.72 g, 77.6 mmol) was dissolved in methylene chloride (400 mL) and to the reaction mixture were added methanesulfonyl chloride (6 mL; 77.6 mmol) and potassium carbonate (32 g, 232 mmol), and the reaction mixture was stirred at room temperature for 2 h. The reaction mixture was poured into a mixture of methylene chloride (1.4 L) and water (400 mL), separated, and the organic layer was washed with brine (400 mL), dried over anhydrous magnesium sulfate, and evaporated until the total amount became 300 mL under reduced pressure. To a solution of the mesylate derivative (4-501-02) were benzyltriethylammonium chloride (25 g, 110 mmol) and boron trifluoride diethyl ether complex (1.9 mL, 15.4 mmol), and the reaction mixture was stirred at room temperature for 1.5 h, poured into a mixture of methylene chloride (0.8 L) and water (400 mL), and separated. The organic layer was washed with brine (400 mL), dried over anhydrous magnesium sulfate, and evaporated under reduced pressure. The obtained residue was subjected to silica gel column chromatography (toluene/ethyl acetate) to give 3-chloro-2-cyclohexene-1-one (4-501-03) (7.24 g, 72%) as an yellow oil.

$^1$H NMR (300 MHz, CDCl$_3$): δ 2.09 (quint, J=6.0 Hz, 2H), 2.40 (t, J=6.6 Hz, 2H), 2.69 (td, J=6.0 Hz, 1.5 Hz, 2H), 6.23 (t, J=1.5 Hz, 1H).

b) Preparation of 3-cyanoacetamide-2-cyclohexene-1-one (4-501-04)

2-Cyanoacetamide (4.42 g, 52.8 mmol) was dissolved in diglyme (50 mL) and to the reaction mixture was added sodium hydride (60% oil suspension, 2.1 g, 52.8 mmol), and the reaction mixture was vigorously stirred at room temperature for 5 min. To the reaction mixture was gradually added a solution of 3-chloro-2-cyclohexen-1-one (4-501-03) (6.24 g, 48 mmol) in diglyme (60 ml), and the reaction mixture was stirred at room temperature for 2.5 h. Then to the reaction mixture were 2-cyanoacetamide (1.6 g, 19.2 mmol) and sodium hydride (60% oil suspension, 0.76 g, 19.2 mmol), and the reaction mixture was stirred at room temperature for 1.5 h. To the reaction mixture was added diluted hydrochloric acid (1 mol/L, 100 mL) and the reaction mixture was extracted with ethyl acetate (300 mL). To the aqueous layer was added sodium chloride, followed by extraction with ethyl acetate (300 mL). The combined organic layers were dried over anhydrous magnesium sulfate, and evaporated under reduced pressure. The obtained crystal residue purified by silica gel column chromatography (toluene/ethyl acetate), followed by recrystallization from hexane to give 3-cyanoacetamide-2-cyclohexene-1-one (4-501-04) (6.5 g, 76%) as a white crystal.

$^1$H NMR (300 MHz, d$_6$-DMSO): δ 1.71 (quint, J=6.0 Hz, 2H), 1.79 (quint, J=6.0 Hz, 2H), 2.78 (t, J=6.0 Hz, 2H), 5.90 (s, 1H), 6.90 (s, 1H), 11.16 (br d, J=1.5 Hz, 2H).

c) Preparation of 3,8-dioxo-2,3,5,6,7,8-hexahydroisoquinoline-4-carbonitrile (7-010)

3-Cyanoacetamide-2-cyclohexene-1-one (4-501-04) (1.25 g, 7 mmol) was dissolved in DMF (25 mL) and to the reaction mixture was added N N-dimethylformamidedimethylacetal (1.1 mL, 8.4 mmol), and the reaction mixture was stirred at room temperature for 70 h. To the reaction mixture was added diluted hydrochloric acid (1 mol/L, 100 mL), the reaction mixture was extracted with ethyl acetate (300 mL). To the aqueous layer was added sodium chloride, followed by extraction with ethyl acetate (300 mL). The combined organic layers were dried over anhydrous magnesium sulfate, and evaporated under reduced pressure. The obtained crystal residue purified by silica gel column chromatography (toluene/ethyl acetate), followed by recrystallized from toluene to give 3,8-dioxo-2,3,5,6,7,8-hexahydroisoquinoline-4-carbonitrile (7-010) (0.92 g, 70%) as white crystal.

$^1$H NMR (300 MHz, CDCl$_3$+(a small amount of CD$_3$OD)): δ 2.17 (quint, J=6.3 Hz, 2H), 2.63 (t, J=6.3 Hz, 2H), 3.09 (t, J=6.3 Hz, 2H), 8.34 (s, 1H).

d) Preparation of 2-butyl-3,8-dioxo-2,3,5,6,7,8-hexahydroisoquinoline-4-carbonitrile (7-011)

3,8-Dioxo-2,3,5,6,7,8-hexahydroisoquinoline-4-carbonitrile (7-010) (770 mg, 4.1 mmol) was dissolved in DMF (15 mL) and to the reaction mixture was added 1-iodobutane (0.51 mL, 4.5 mmol) and sodium hydride (60% oil suspension, 180 mg, 4.5 mmol), and the reaction mixture was stirred at room temperature for 3 h. To the reaction mixture was added dilute hydrochloric acid (1 mol/L, 60 mL) and the reaction mixture was extracted with ethyl acetate (150 mL), washed with brine (50 mL), dried over anhydrous magnesium sulfate, and evaporated under reduced pressure. The obtained residue was subjected to silica gel column chromatography (toluene/ethyl acetate) to give 2-butyl-3,8-dioxo-2,3,5,6,7,8-hexahydroisoquinoline-4-carbonitrile (7-011) (610 mg, 61%) as a white crystal.

$^1$H NMR (300 MHz, CDCl$_3$): δ 0.97 (t, J=7.5 Hz, 3H), 1.38 (sextet, J=7.5 Hz, 2H), 1.76 (quint, J=7.5 Hz, 2H), 2.15 (quint, J=6.3 Hz, 2H), 2.61 (t, J=6.3 Hz, 2H), 3.06 (t, J=6.3 Hz, 2H), 4.03 (t, J=7.5 Hz, 2H), 8.39 (s, 1H).

e) Preparation of 2-butyl-3-oxo-2,3,5,6,7,8-hexahydroisoquinoline-4-carbonitrile (7-012)

2-Butyl-3,8-dioxo-2,3,5,6,7,8-hexahydroisoquinoline-4-carbonitrile (7-011) (100 mg, 0.41 mmol) was dissolved in THF (7 mL) and to the reaction mixture were added boron trifluoride diethyl ether complex (0.21 mL, 1.64 mmol) and sodium cyanoborohydried (90 mg, 1.44 mmol), and the reaction mixture was stirred at room temperature for 30 min. To the reaction mixture was added an saturated aqueous solution of sodium hydrogencarbaonate (30 mL) and the reaction mixture was extracted with ethyl acetate (60 mL), washed with brine (30 mL), dried over anhydrous magnesium sulfate, and evaporated under reduced pressure. The obtained residue was subjected to silica gel column chromatography (toluene/ethyl acetate) to give 2-butyl-3-oxo-2,3,5,6,7,8-hexahydroisoquinoline-4-carbonitrile (7-012) (70 mg, 75%) as a white solid.

$^1$H NMR (300 MHz, CDCl$_3$): δ 0.96 (t, J=7.5 Hz, 3H), 1.37 (sextet, J=7.5 Hz, 2H), 1.67-1.86 (m, 6H), 2.54 (t, J=6.3 Hz, 2H), 2.87 (t, J=6.3 Hz, 2H), 3.93 (t, J=7.5 Hz, 2H), 7.22 (s, 1H).

f) Preparation of 2-butyl-3-oxo-2,3,5,6,7,8-hexahydroisoquinoline-4-carboxylic acid (4-501-05)

2-Butyl-3-oxo-2,3,5,6,7,8-hexahydroisoquinoline-4-carbonitrile (7-012) (260 mg, 1.13 mmol) was dissolved in water (6 mL)/ethanol (26 mL), to the reaction mixture was added potassium hydroxide (444 mg, 7.91 mmol), and the reaction mixture was heated under reflux for 24 h, and then cooled under ice-cooling. To the reaction mixture was added dropwise diluted hydrochloric acid (2 mol/L, 8 mL) and the reaction mixture was extracted with ethyl acetate (70 mL), dried over anhydrous magnesium sulfate, and evaporated under reduced pressure. The crystal residue was recrystallized from hexane to give 2-butyl-3-oxo-2,3,5,6,7,8-hexahydroisoquinoline-4-carboxylic acid (4-501-05) (197 mg, 70%) as a white crystal.

$^1$H NMR (300 MHz, CDCl$_3$): δ 0.97 (t, J=7.5 Hz, 3H), 1.37 (sextet, J=7.5 Hz, 2H), 1.70-1.82 (m, 6H), 2.56 (t, J=6.0 Hz, 2H), 2.87 (t, J=6.0 Hz, 2H), 3.95 (t, J=7.5 Hz, 2H), 7.27 (s, 1H).

g) Preparation of 2-butyl-3-oxo-2,3,5,6,7,8-hexahydroisoquinoline-4-carboxylic acid benzylamide (4-501)

2-Butyl-3-oxo-2,3,5,6,7,8-hexahydroisoquinoline-4-carboxylic acid (4-501-05) (5 mg, 0.02 mmol) was dissolved in toluene (1 mL), and to the reaction mixture were added thionyl chloride (4.4 μL, 0.06 mmol) and catalytic amount of DMF, and the reaction mixture was reacted at 75° C. for 30 min. After concentration of the reaction mixture under reduced pressure, the residue was dissolved in methylene chloride (1 mL), and then benzylamine (6.2 μL, 0.06 mmol) was added to the reaction mixture, and the reaction mixture was stirred at room temperature for 10 min. To the reaction mixture was added diluted hydrochloric acid (1 mol/L, 3 mL), and the reaction mixture was extracted with ethyl acetate (8 mL), washed with brine (4 mL), dried over anhydrous magnesium sulfate, and evaporated under reduced pressure. The obtained residue was purified by silica gel column chromatography (toluene/ethyl acetate) to give 2-butyl-3-oxo-2,3,5,6,7,8-hexahydroisoquinoline-4-carboxylic acid benzylamide (4-501) (5 mg, 74%) as a white crystal.

$^1$H-NMR (CDCl$_3$, 300 MHz): δ 0.95 (t, J=7.5 Hz, 3H), 1.37 (sextet, J=7.5 Hz, 2H), 1.66-1.77 (m, 6H), 2.57 (br t, J=6.3 Hz, 2H), 3.27 (br t, J=6.3 Hz, 2H), 3.92 (t, J=7.5 Hz, 2H), 4.60 (d, J=5.7 Hz, 2H), 7.12 (s, 1H), 7.23-7.40 (m, 5H), 9.58 (br t, J=5.7 Hz, 1H).

Examples 4-502 to 4-504 were synthesized in a similar manner to Example 4-501.

Example 5-004

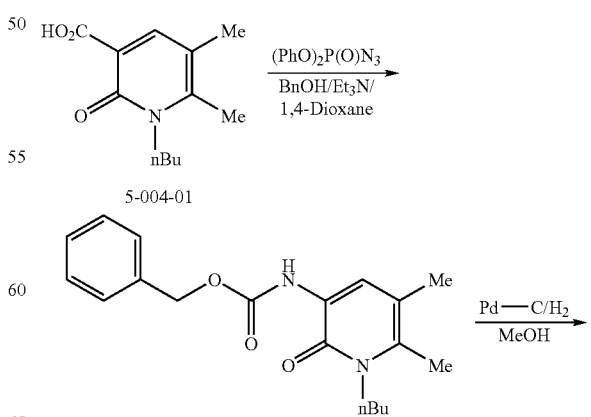

-continued

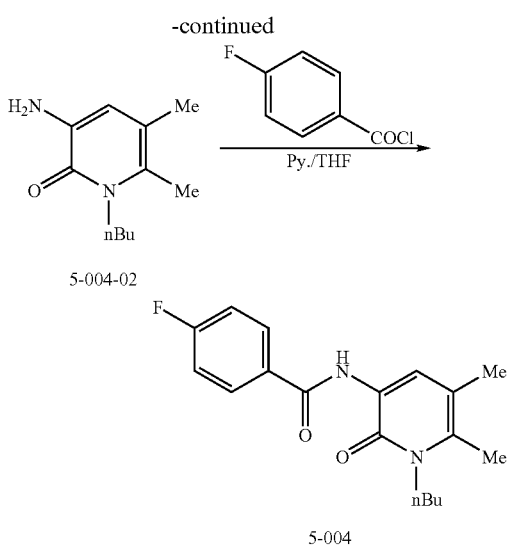

a) Preparation of 3-benzyloxycarbonylamino-1-butyl-5,6-dimethyl-2-pyridone (5-017)

1-Butyl-3-carboxy-5,6-dimethyl-2-pyridone (5-004-01) (2.233 g) was dissolved in dioxane (50 mL), and to the reaction mixture were added triethylamine (4.2 mL) and diphenylphosphoryl azide (2.4 mL), and the reaction mixture was refluxed with stirring in an oil bath at 110° C. under nitrogen atmosphere. After 4 h, the reaction mixture was poured into ice-water, and to the reaction mixture were added ethyl acetate and aqueous hydrochloric acid solution, and then shaken to separate. The organic layer was washed each once with an aqueous solution of sodium bicarbonate and water, dried over magnesium sulfate, and evaporated under reduced pressure. The obtained residue was purified by silica gel column chromatography (Lobar column B, toluene/acetone=29/1) to give 3-benzyloxycarbonylamino-1-butyl-5,6-dimethyl-2-pyridone (5-017) (2.477 g, 75.4%, m.p. 65 to 66° C.) as an yellow crystal.

b) Preparation of 3-amino-1-butyl-5,6-dimethyl-2-pyridone (5-004-02)

3-Benzyloxycarbonylamino-1-butyl-5,6-dimethyl-2-pyridone (5-017) (2.487 g) was dissolved in methanol (25 mL), and to the reaction mixture was added a suspension of 10% palladium on carbon (373 mg) in water (2.5 mL), and the reaction mixture was reacted in catalytic reduction under atmospheric pressure. After 4 h, the reaction mixture filtered off on Celite, washed with methanol, and evaporated under reduced pressure to give 3-amino-1-butyl-5,6-dimethyl-2-pyridone (5-004-02) (1.438 g, 97.8%, m.p. 94 to 97° C.) as a brown crystal.

$^1$H NMR (300 MHz, CDCl): δ 0.97 (t, J=7.2 Hz, 3H), 1.37-1.49 (m, 2H), 1.60-1.71 (m, 2H), 4.08 (d, J=7.8 Hz, 2H), 6.42 (s, 1H).

c) Preparation of N-1-butyl-3-(4-fluorobenzoyl)amino-5,6-dimethyl-2-pyridone (5-004)

3-Amino-1-butyl-5,6-dimethyl-2-pyridone (5-004-02) (117 mg) was dissolved in pyridine, (1 mL), and the reaction mixture was stirred under ice-cooling and nitrogen atmosphere, and to the reaction mixture was added dropwise a solution of 4-fluorobenzoyl chloride (0.08 mL) in tetrahydrofuran (1 mL) over 10 min, followed by stirring at the same condition. After 3 h, the reaction mixture was diluted with ethyl acetate and poured into ice-water, extracted once with ethyl acetate, washed with aqueous hydrochloric acid solution, water, an aqueous solution of sodium bicarbonate, and water, dried over magnesium sulfate, and evaporated under reduced pressure. The obtained crystal residue (202 mg) was recrystallized from methylene chloride/n-hexane to give 1-butyl-3-(4-fluorobenzoyl)amino-5,6-dimethyl-2-pyridone (5-004) (103 mg, 54.2%, m.p. 129 to 130° C.) as a colorless needle.

Examples 5-001 to 5-017 were synthesized in a similar manner to Example 5-001.

Example 5-018

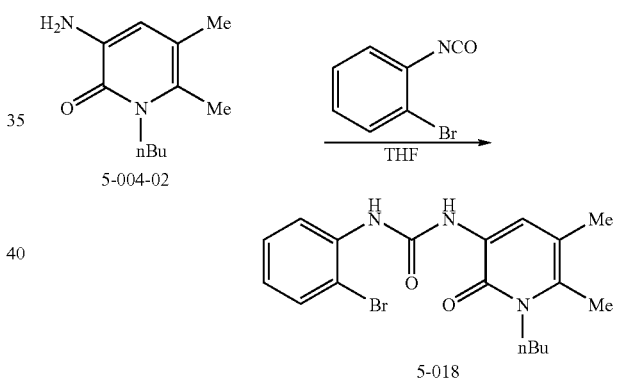

a) Preparation of 4-(benzoxazol-2-yloxy)-1-benzyl-3-methoxy-5,6-dimethyl-1H-pyridin-2-one (5-018)

2-Bromophenylisocyanate (80 mg) was dissolved in tetrahydrofuran (2 mL), and the reaction mixture was stirred at room temperature under nitrogen atmosphere, and to the reaction mixture was added dropwise a solution of 3-amino-1-butyl-5,6-dimethyl-2-pyridone (5-004-02) (78 mg) in teterahydrofuran (2 mL) over 10 min, and the reaction mixture was stirred at room temperature overnight. The reaction mixture was evaporated under reduced pressure, and the obtained crystal was recrystallized from dichloromethne/diethyl ether to give 4-(benzoxazol-2-yloxy)-1-benzyl-3-methoxy-5,6-dimethyl-1H-pyridin-2-one (5-018) (142 mg, 89.9%, m.p. 197 to 8° C.).

Example 5-019 was synthesized in a similar manner to Example 5-018.

Example 6-001, 6-005, 6-007

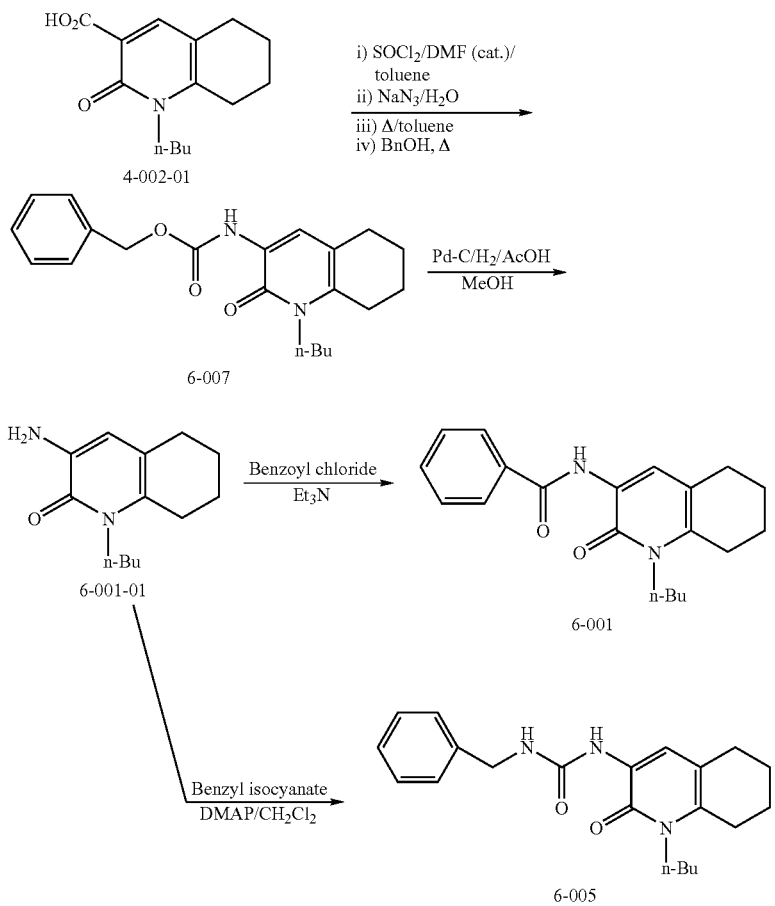

a) Preparation of (1-butyl-2-oxo-1,2,5,6,7,8-hexahydroquinolin-3-yl)carbamic acid benzyl ester (6-007)

1-Butyl-2-oxo-1,2,5,6,7,8-hexahydroquinoline-3-carboxylic acid (4-002-01) (100 mg, 0.38 mmol) was dissolved in toluene (5 mL), and to the reaction mixture were added thionyl chloride (57 mL, 0.76 mmol) and catalytic amount of DMF, and the reaction mixture was reacted at 75° C. for 30 min. The reaction mixture was concentrated under reduced pressure, and the residue was dissolved in acetone (5 mL), and then to the reaction mixture was added an aqueous solution of sodium azide (29 mg, 0.42 mmol) (0.5 mL), and the reaction mixture was stirred at room temperature for 15 min. To the reaction mixture was added water (5 mL), the reaction mixture was extracted with ethyl acetate (10 mL), washed with brine (5 mL), dried over anhydrous magnesium sulfate, and evaporated under reduced pressure. The residue was dissolved in toluene (5 mL), and the reaction mixture was reacted at 120° C. for 30 min, and then benzyl alcohol (46 μL, 0.44 mmol) was added to the reaction mixture, and the reaction mixture was stirred at 120° C. for 2 h. The reaction mixture was purified by silica gel column chromatography (toluene/ethyl acetate), to give (1-butyl-2-oxo-1,2,5,6,7,8-hexahydroquinolin-3-yl)carbamic acid benzyl ester (6-007) (90 mg, 63%) as a white foamy substance.

$^1$H NMR (300 MHz, CDCl$_3$): δ 0.96 (t, J=7.5 Hz, 3H), 1.41 (sextet, J=7.5 Hz, 2H), 1.63 (quint, J=7.5 Hz, 2H), 1.70 (quint, J=6.0 Hz, 2H), 1.83 (quint, J=6.0 Hz, 2H), 2.53 (t, J=6.0 Hz, 2H), 2.63 (t, J=6.0 Hz, 2H), 4.01 (t, J=7.8 Hz, 2H), 5.19 (s, 2H), 7.29-7.41 (m, 5H), 7.76 (s, 1H), 7.86 (br s, 1H).

b) Preparation of 3-amino-1-butyl-5,6,7,8-tetrahydroquinolin-2-one acetic acid salt (6-001-01)

(1-Butyl-2-oxo-1,2,5,6,7,8-hexahydroquinolin-3-yl)carbamic acid benzyl ester (6-007) (100 mg, 0.28 mmol) was dissolved in methanol (7 mL), and to the reaction mixture were added acetic acid (16 μL, 0.28 mmol) and palladium on carbon (10%, 30 mg), and the reaction mixture was stirred vigorously under hydrogen atmosphere for 1.5 h. Palladium on carbon was filtered off, and the filtrate was concentrated under reduced pressure, and the crystalloid residue was recrystallized from hexane to give 3-amino-1-butyl-5,6,7,8-tetrahydro-1H-quinolin-2-one acetic acid salt (6-001-01) (60 mg, 76%) as a white crystal.

$^1$H NMR (300 MHz, CDCl$_3$): δ 0.98 (t, J=7.5 Hz, 3H), 1.43 (sextet, J=7.5 Hz, 2H), 1.67 (quint, J=7.5 Hz, 2H), 1.76 (quint, J=6.0 Hz, 2H), 1.88 (quint, J=6.0 Hz, 2H), 2.05 (s, 3H), 2.58 (t, J=6.0 Hz, 2H), 2.67 (t, J=6.0 Hz, 2H), 4.04 (t, J=7.8 Hz, 2H), 8.27 (s, 1H).

c) Preparation of N-(1-butyl-2-oxo-1,2,5,6,7,8-hexahydroquinolin-3-yl)banzamide (6-001)

3-Amino-1-butyl-5,6,7,8-tetrahydroquinolin-2-one acetic acid salt (6-001-01) (5 mg, 0.018 mmol) was dissolved in methylene chloride (1 mL), and to the reaction mixture were added benzoyl chloride (2.3 μL, 0.02 mmol) and triethylamine (5.6 μL, 0.04 mmol), followed by stirring at room temperature for 10 min. To the reaction mixture was added diluted hydrochloric acid (0.1 mol/L, 3 mL), and the reaction mixture was extracted with ethyl acetate (10 mL), washed with brine (3 mL), dried over anhydrous magnesium sulfate, and evaporated under reduced pressure. The obtained residue was purified by silica gel column chromatography (toluene/ethyl acetate) to give N-(1-butyl-2-oxo-1,2,5,6,7,8-hexahydroquinolin-3-yl)banzamide (6-001) (4.9 mg, 83%) as a white foamy crystal.

$^1$H NMR (300 MHz, CDCl$_3$): δ 0.99 (t, J=7.5 Hz, 3H), 1.45 (sextet, J=7.5 Hz, 2H), 1.66 (quint, J=7.5 Hz, 2H), 1.74 (quint, J=6.0 Hz, 2H), 1.87 (quint, J=6.0 Hz, 2H), 2.60 (t, J=6.0 Hz, 2H), 2.69 (t, J=6.0 Hz, 2H), 4.06 (t, J=7.8 Hz, 2H), 7.43-7.56 (m, 3H), 7.94 (d, J=6.9 Hz, 2H), 8.31 (s, 1H), 9.26 (br s, 1H).

Examples 6-002 to 6-004 were synthesized in a similar manner to Example 6-001.

d) Preparation of 1-benzyl-3-(1-butyl-2-oxo-1,2,5,6,7,8-hexahydroquinolin-3-yl)urea (6-005)

3-Amino-1-butyl-5,6,7,8-tetrahydro-1H-quinolin-2-one acetic acid salt (6-001-01) (5 mg, 0.018 mmol) was dissolved in methylene chloride (1 mL), and to the reaction mixture were added benzylisocyanate (2.5 μL, 0.02 mmol) and 4-dimethylaminopyridine (2.4 mg, 0.02 mmol), and the reaction mixture was stirred at room temperature for 4 h. To the reaction mixture was added diluted hydrochloric acid (0.1 mol/L, 3 mL), and the reaction mixture was extracted with ethyl acetate (10 mL), washed with brine (3 mL), dried over anhydrous magnesium sulfate, and evaporated under reduced pressure. The obtained residue was purified by silica gel column chromatography (toluene/ethyl acetate) to give 1-benzyl-3-(1-butyl-2-oxo-1,2,5,6,7,8-hexahydroquinolin-3-yl)urea (6-005) (5.0 mg, 79%) as a white crystal.

$^1$H NMR (300 MHz, CDCl$_3$): δ 0.92 (t, J=7.5 Hz, 3H), 1.32 (sextet, J=7.5 Hz, 2H), 1.57-1.65 (m, 2H), 1.69 (quint, J=6.0 Hz, 2H), 1.82 (quint, J=6.0 Hz, 2H), 2.55 (t, J=6.0 Hz, 2H), 2.59 (t, J=6.0 Hz, 2H), 3.90 (t, J=7.8 Hz, 2H), 4.46 (d, J=6.0 Hz, 2H), 5.72 (br s, 1H), 7.24-7.32 (m, 5H), 7.95 (s, 1H), 8.00 (br s, 1H).

Example 7-004

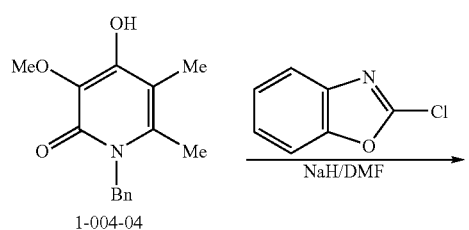

-continued

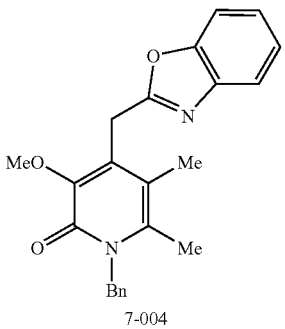

7-004 a) Preparation of 1-(2-bromophenyl)-3-(1-butyl-5,6-dimethyl-2-oxo-1,2-dihydropyridin-3-yl)urea (7-004)

1-Benzyl-5,6-dimethyl-4-hydroxy-3-methoxy-2-pyridone (1-004-04) (259 mg) was dissolved in DMF (3 mL), and to the reaction mixture was added 60% sodium hydride (48 mg) at a time, after 10 min, added a solution of 2-chlorobenzoxazole (261 mg) in DMF (0.5 mL), and the reaction mixture was stirred at room temperature for 5 h and overnight. The reaction mixture was poured into an ice water, extracted twice with ethyl acetate, washed twice with water, dried over magnesium sulfate, and evaporated under reduced pressure. The obtained crystal residue was dissolved in acetone, after decolorization treatment, diethyl ether added to reaction mixture, followed by stand at room temperature. The resulting crystal wsa filtered to give 1-(2-bromophenyl)-3-(1-butyl-5,6-dimethyl-2-oxo-1,2-dihydropyridin-3-yl)urea (7-004) (144 mg, 38.3%, m.p. 154 to 155° C.) as colorless prism.

$^1$H NMR (300 MHz, CDCl$_3$): δ 2.07 (s, 3H), 2.28 (s, 3H), 3.88 (s, 3H), 5.42 (br s, 2H), 7.19-7.54 (m, 9H).

Example 7-008

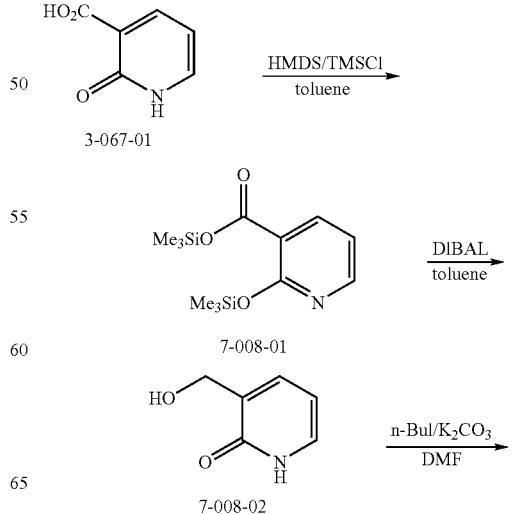

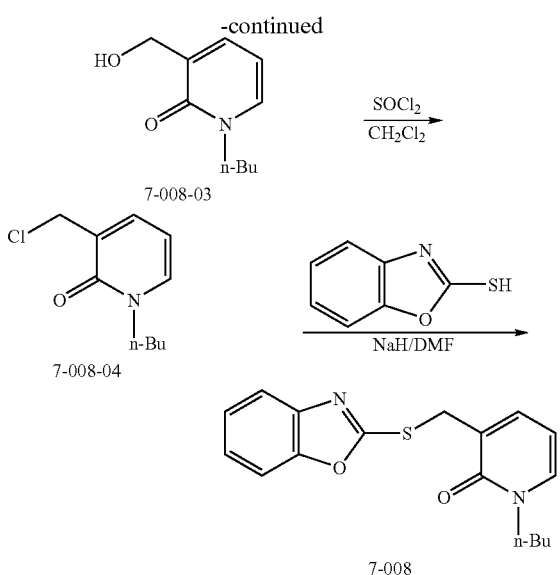

a) Preparation of 3-hydroxymethyl-2(1H)-pyridone (7-008-01)

To a solution of 2-hydroxynicotinic acid (3-067-01) (5.0 g) in toluene (70 mL), and to the reaction mixture were added hexamethyldisilazane (HMDS, 19 mL) and chlorotrimethylsilane (TMSCl, 0.23 mL), and the reaction mixture was heated under reflux. After stirring for 2 h, the solvent was removed, and toluene was added to the residue. To the reaction mixture was added diisobutylaluminium hydride (DIBAL, 2 M toluene solution, 90 mL) at −78° C., after stirring for 4 h, the reaction was quenched with methanol. The insoluble substance was filtered off on Celite, and the filtrate was evaporated under reduced pressure. To the residue were added water and ethyl acetate, and the organic layer was separated, and then the aqueous layer was extracted with three times with ethyl acetate. The combined organic layers were washed with water, brine, dried over anhydrous magnesium sulfate, and evaporated to give 3-hydroxymethyl-2(11)-pyridone (7-008-01) (2.6 g, 59%) as a white solid.

$^1$H NMR (300 MHz, CDCl$_3$): δ 4.50 (s, 2H), 6.43 (t, J=6.7 Hz, 1H), 7.33-7.36 (m, 1H), 7.64-7.67 (m, 1H).

b) Preparation of 1-butyl-3-hydroxymethyl-2-pyridone (7-008-02)

To a solution of 3-hydroxymethyl-2(11)-pyridone (7-008-01) (0.63 g) in DMF (15 mL), and to the reaction mixture were added potassium carbonate (1.4 g) and 1-iodobutane (1.86 g). After stirring at 70° C. for 2 h, the solvent was removed. To the residue were added a saturated aqueous solution of ammonium chloride and ethyl acetate, and the organic layer was separated, and then the aqueous layer was extracted three times with ethyl acetate. The combined organic layers were washed with water and brine, dried over anhydrous magnesium sulfate, and evaporated under reduced pressure. The obtained crude product was purified by column chromatography (toluene/ethyl acetone=2/1) to give 1-butyl-3-hydroxymethyl-2-pyridone (7-008-02) (0.56 g, 61%) as an oil.

$^1$H NMR (300 MHz, CDCl$_3$): δ 0.96 (t, J=7.3 Hz, 311), 1.32-1.45 (m, 2H), 1.69-1.79 (m, 2H), 3.95 (t, J=7.6 Hz, 2H), 4.57 (s, 2H), 6.20 (t, J=6.7 Hz, 1H), 7.24 (dd, J=6.7, 1.2 Hz, 1H), 7.28-7.31 (m, 1H).

c) Preparation of 3-(benzoxazol-2-yloxymethyl)-1-butyl-2-pyridone (7-008-03)

3-(Benzoxazol-2-yloxymethyl)-1-butyl-2-pyridone (7-008-03) (50%) was synthesized in a similar manner to the preparation of 2-034-03.

d) Preparation of 1-butyl-3-chloromethyl-2-pyridone (7-008-04)

To a solution of 3-(benzoxazol-2-yloxymethyl)-1-butyl-2-pyridone (7-008-03) (169 mg) in methylene chloride (4.0 mL) was added thionyl chloride (122 mg) at room temperature. After stirring for 1 h, the solvent was removed to 1-butyl-3-chloromethyl-2-pyridone (7-008-04) as an oil.

$^1$H NMR (300 MHz, CDCl$_3$): δ 0.96 (t, J=7.3 Hz, 3H), 1.32-1.45 (m, 2H), 1.69-1.79 (m, 2H), 3.96 (t, J=7.3 Hz, 2H), 6.19 (t, J=6.7 Hz, 1H), 7.27 (dd, J=6.7, 2.1 Hz, 1H), 7.49-7.53 (m, 1H).

e) Preparation of 3-(benzoxazol-2-ylsulfanylmethyl)-1-butyl-2-pyridone (7-008)

3-(Benzoxazol-2-ylsulfanylmethyl)-1-butyl-2-pyridone (7-008) (97%) was synthesized in a similar manner to the preparation of 2-035.

Example 7-009

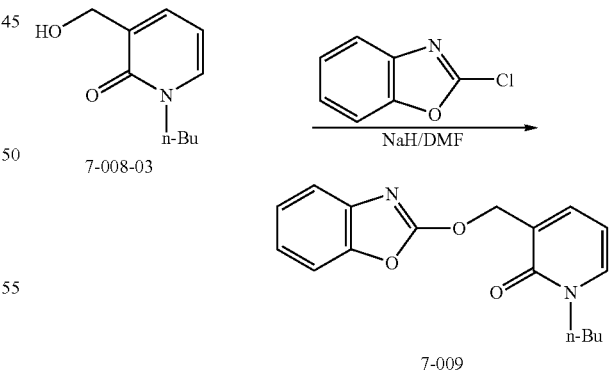

a) Preparation of 3-(benzoxazol-2-yloxymethyl)-1-butyl-2-pyridone (7-009)

3-(Benzoxazol-2-yloxymethyl)-1-butyl-2-pyridone (7-009) (50%) was synthesized in a similar manner to the preparation of 2-035.

Example 7-013 to Example 7-107

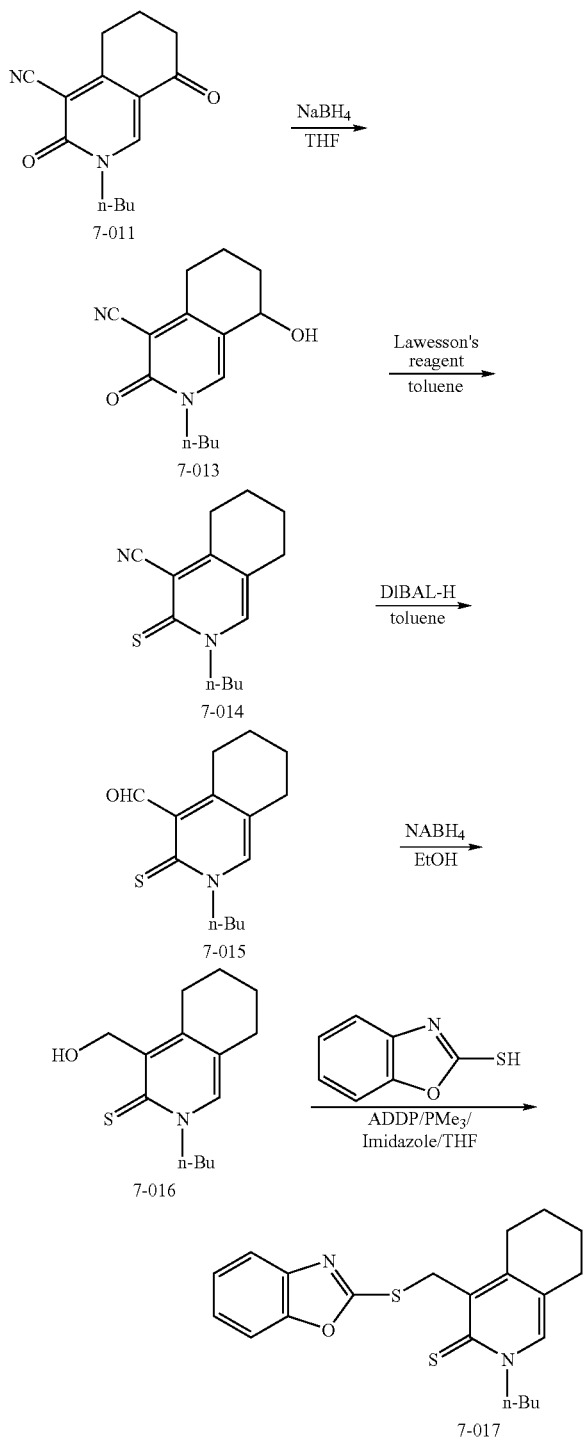

a) Preparation of 2-butyl-8-hydroxy-3-oxo-2,3,5,6,7,8-hexahydroisoquinoline-4-carbonitrile (7-013)

2-Butyl-3,8-dioxo-2,3,5,6,7,8-hexahydroisoquinoline-4-carbonitrile (7-011) (10 mg, 0.04 mmol) was dissolved in THF (1 mL), and to the reaction mixture was added sodium borohydride (2.1 mg, 0.056 mmol), and the reaction mixture was stirred at room temperature for 10 min. To the reaction mixture was added diluted hydrochloric acid (1 mol/L, 3 mL), and the reaction mixture was extracted with ethyl acetate (10 mL), washed with brine (5 mL), dried over anhydrous magnesium sulfate, and evaporated under reduced pressure. The obtained crystalloid residue was recrystallized from methylene chloride to give 2-butyl-8-hydroxy-3-oxo-2,3,5,6,7,8-hexahydroisoquinoline-4-carbonitrile (7-013) (7.4 mg, 75%) as a white crystal.

$^1$H NMR (300 MHz, CDCl$_3$): δ 0.97 (t, J=7.5 Hz, 3H), 1.38 (sextet, J=7.5 Hz, 2H), 1.76 (quint, J=7.5 Hz, 2H), 2.15 (quint, J=6.0 Hz, 2H), 2.61 (t, J=6.0 Hz, 2H), 3.06 (t, J=6.0 Hz, 2H), 3.45-3.58 (m, 1H), 4.03 (t, J=7.5 Hz, 2H), 8.39 (s, 1H).

b) Preparation of 2-butyl-3-thioxo-2,3,5,6,7,8-hexahydroisoquinoline-4-carbonitrile (7-014)

2-Butyl-3-oxo-2,3,5,6,7,8-hexahydroisoquinoline-4-carbonitrile (7-013) (80 mg, 0.35 mmol) was dissolved in toluene (8 mL), and to the reaction mixture was added Lawesson's reagent (169 mg, 0.42 mmol), the reaction mixture was heated under reflux for 12 h. The reaction mixture was cooled to room temperature, and methanol was added to the reaction mixture, and the reaction mixture was stirred at room temperature for 1 h, and evaporated under reduced pressure. The obtained residue was purified by silica gel column chromatography to give 2-butyl-3-thioxo-2,3,5,6,7,8-hexahydroisoquinoline-4-carbonitrile (7-014) (63 mg, 73%) as a pale brown powder.

$^1$H NMR (300 MHz, CDCl): δ 0.98 (t, J=7.5 Hz, 3H), 1.41 (sextet, J=7.5 Hz, 2H), 1.75-1.90 (m, 6H), 2.60 (t, J=6.3 Hz, 2H), 2.87 (t, J=6.3 Hz, 2H), 4.81 (t, J=7.5 Hz, 2H), 7.50 (s, 1H).

c) Preparation of 2-butyl-3-thioxo-2,3,5,6,7,8-hexahydroisoquinoline-4-carboaldehyde (7-015)

2-Butyl-3-thioxo-2,3,5,6,7,88-hexahydroisoquinoline-4-carbonitrile (7-014) (220 mg, 0.89 mmol) was dissolved in toluene (20 mL), and to the reaction mixture was added 1 M diisobutylaluminium hydride toluene solution (1.7 mL, 1.7 mmol) under ice-cooling, and the reaction mixture was stirred for 30 min. To the reaction mixture was added 1 mol/L diluted hydrochloric acid (5 mL), and the reaction mixture was extracted with ethyl acetate (10 mL), washed with brine (10 mL), dried over anhydrous magnesium sulfate, and evaporated under reduced pressure. The obtained residue was purified by silica gel column chromatography (toluene/ethyl acetate) to give 2-butyl-3-thioxo-2,3,5,6,7,8-hexahydroisoquinoline-4-carboaldehyde (7-015) (44 mg, 20%) as a pale brown crystal.

$^1$H NMR (300 MHz, CDCl$_3$): δ 0.99 (t, J=7.5 Hz, 3H), 1.44 (sextet, J=7.5 Hz, 2H), 1.74 (quint, J=3.3 Hz, 4H), 1.87 (quint, J=7.5 Hz, 21H), 2.62 (br t, J=6.3 Hz, 2H), 2.95 (br t, J=6.3 Hz, 2H), 4.51 (t, J=7.5 Hz, 2H), 7.53(s, 1H), 10.60 (s, 1H).

d) Preparation of 2-butyl-3-hydroxymethyl-5,6,7,8-tetrahydroisoquinoline-3-thione (7-016)

2-Butyl-3-thioxo-2,3,5,6,7,8-hexahydroisoquinoline-4-carboaldehyde (7-015) (10 mg, 0.04 mmol) was dissolved in methanol (2 mL), and to the reaction mixture was added sodium borohydride (4.6 mg, 0.12 mmol), and the reaction mixture was stirred at room temperature for 10 min. To the reaction mixture was added 1 mol/L diluted hydrochloric acid (4 mL), and the reaction mixture was extracted with ethyl acetate (10 mL), washed with brine (5 mL), dried over anhydrous magnesium sulfate, and evaporated under reduced pressure. The obtained residue was purified by silica gel column chromatography (toluene/ethyl acetate) to give 2-butyl-3-hydroxymethyl-5,6,7,8-tetrahydroisoquinoline-3-thione (7-016) (9 mg, 90%) as a pale brown powder.

$^1$H NMR (300 MHz, CDCl$_3$): δ 0.99 (t, J=7.2 Hz, 3H), 1.43 (sextet, J=7.2 Hz, 2H), 1.71-1.95 (m, 6H), 2.66 (br t, J=6.3 Hz, 2H), 2.83 (t, J=6.3 Hz, 2H), 4.58 (br t, J=7.2 Hz, 2H), 4.79 (s, 2H), 7.61 (s, 1H).

e) Preparation of 4-(benzoxazol-2-ylthiomethyl)-2-butyl-5,6,7,8-tetrahydro-2H-isoquinoline-3-thione (7-017)

2-Butyl-3-hydroxymethyl-5,6,7,8-tetrahydroisoquinoline-3-thione (7-016) (14 mg, 0.056 mmol) was dissolved in THF (1 mL), and to the reaction mixture were added 2-mercaptobenzoxazole (16.3 mg, 0.11 mmol), 1,1'-(azodicarbonyl)dipiperidine (28.1 mg, 0.11 mmol), imidazole (7.6 mg, 0.11 mmol), and 1 M trimethylphosphine toluene solution (0.11 mL, 0.11 mmol), and the reaction mixture was stirred at room temperature for 18 h. The reaction mixture was concentrated under reduced pressure, and to the reaction mixture was added toluene (2 mL). After the resulting insoluble substance was filtered off, the filtrate was purified by silica gel column chromatography (toluene/ethyl acetate) to give 4-(benzoxazol-2-ylthiomethyl)-2-butyl-5,6,7,8-tetrahydro-2H-isoquinoline-3-thione (7-017) (6.5 mg, 30%) as a pale brown powder.

$^1$H NMR (300 MHz, CDCl$_3$): δ 0.99 (t, J=7.5 Hz, 3H), 1.43 (sextet, J=7.5 Hz, 2H), 1.70-1.95 (m, 6H), 2.62 (t, J=6.3 Hz, 2H), 3.01 (t, J=6.3 Hz, 2H), 4.58 (t, J=7.5 Hz, 2H), 5.05 (s, 2H), 7.15-7.30 (m, 2H), 7.42 (dd, J=7.2 Hz, J=1.8 Hz, 1H), 7.48 (br s, 1H), 7.60 (dd, J=7.2 Hz, J=1.8 Hz, 1H).

Example 7-018

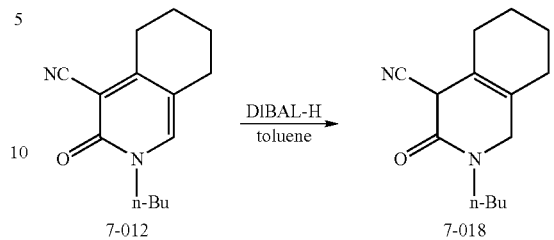

a) Preparation of 2-butyl-3-oxo-1,2,3,4,5,6,7,8-octahydroisoquinoline-4-carbonitrile (7-018)

2-Butyl-3-oxol-2,3,5,6,7,8-hexahydroisoquinoline-4-carbonitrile (7-012) (100 mg, 0.43 mmol) was dissolved in toluene (10 mL), and to the reaction mixture was added 1 M diisobutylaluminium hydride toluene solution (0.8 mL, 0.8 mmol) under ice-cooling, and the reaction mixture was stirred for 10 min. To the reaction mixture was added 1 mol/L diluted hydrochloric acid (5 mL), and the reaction mixture was extracted with ethyl acetate (10 mL), washed with brine (5 mL), dried over anhydrous magnesium sulfate, and evaporated under reduced pressure. The obtained residue was purified by silica gel column chromatography (toluene/ethyl acetate) to give 2-butyl-3-oxo-1,2,3,4,5,6,7,8-octahydroisoquinoline-4-carbonitrile (7-018) (70 mg, 70%) as a white powder.

$^1$H NMR (300 MHz, CDCl$_3$): δ 0.93 (t, J=7.5 Hz, 3H), 1.32 (sextet, J=7.5 Hz, 2H), 1.42-1.59 (m, 5H), 1.88 (s, 1H), 1.97-2.08 (m, 2H), 2.20-2.32 (m, 1H), 2.54-2.66 (m, 1H), 3.06-3.19 (m, 2H), 3.33-3.43 (m, 3H).

Structures and NMR data of the compounds were described in following Tables.

TABLE 1

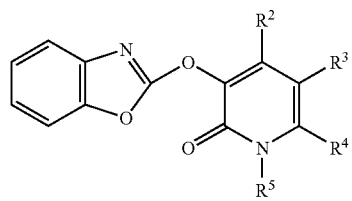

| Compound No. | R$^2$ | R$^3$ | R$^4$ | R$^5$ | $^1$H-NMR (CDCl$_3$) |
|---|---|---|---|---|---|
| 1-0001 | H | Me | Me | Me | 2.16 (s, 3H), 2.33 (s, 3H), 3.62 (s, 3H). 7.17-7.26 (m, 2H), 7.34 (s, 1H), 7.34-7.43 (m, 1H), 7.46-7.50 (m, 1H). |
| 1-0002 | H | Me | Me | Et | 1.32 (t, J =7.2 Hz, 3H), 2.15 (s, 3H), 2.36 (s, 3H), 4.19 (q, J = 7.2 Hz, 2H), 7.19-7.25 (m, 2H), 7.34 (s, 1H), 7.39-7.42 (m, 1H), 7.46-7.49 (m, 1H). |
| 1-0003 | H | Me | Me | nPr | 0.98 (t, J =7.2 Hz, 3H), 1.65-1.78 (m, 2H), 2.15 (s, 3H), 2.34 (s, 3H), 4.03-4.08 (m, 2H), 7.16-7.26 (m, 2H), 7.33 (s, 1H), 7.38-7.41 (m, 1H), 7.46-7.49 (m, 1H). |
| 1-0004 | H | Me | Me | nBu | 0.95 (t, J =7.5 Hz, 3H), 1.35-1.48 (m, 2H), 1.62-1.72 (m, 2H), 2.15 (s, 3H), 2.35 (s, 3H), 4.10 (t, J'= 7.8 Hz, 2H), 7.19-7.25 (m, 2H), |

TABLE 1-continued

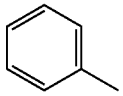

| Compound No. | R² | R³ | R⁴ | R⁵ | ¹H-NMR (CDCl₃) |
|---|---|---|---|---|---|
| | | | | | 7.33 (s, 1H), 7.38-7.42 (m, 1H), 7.46-7.49 (m, 1H). |
| 1-0005 | H | Me | Me | Bn | 2.14 (s, 3H), 2.25 (s, 3H), 5.42 (br s, 2H), 7.17-7.51 (m, 10H). |
| 1-0006 | H | 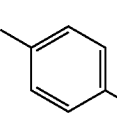 | H | nBu | 0.94 (t, J = 7.4 Hz, 3H), 1.35-1.48 (m, 2H), 1.76-1.86 (m, 2H), 4.06 (t, J = 7.4 Hz, 2H), 7.22-7.28 (m, 3H), 7.34-7.51 (m, 7H), 7.81 (d, J = 2.5 Hz, 1H). |
| 1-0007 | H | 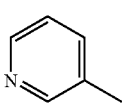 | H | nBu | 0.96 (t, J = 7.3 Hz, 3H), 1.35-1.48 (m, 2H), 1.75-1.85 (m, 2H), 4.05 (t, J = 7.3 Hz, 2H), 7.10-7.17 (m, 2H), 7.22-7.24 (m, 3H), 7.37-7.44 (m, 3H), 7.48-7.52 (m, 1H), 7.76 (d, J = 2.7 Hz, 1H). |
| 1-0008 | H | 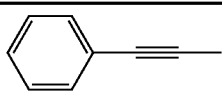 | H | nBu | 0.97 (t, J = 7.3 Hz, 3H), 1.36-1.49 (m, 2H), 1.79-1.87 (m, 2H), 4.08 (t, J = 7.3 Hz, 2H), 7.23-7.27 (m, 2H), 7.37-7.44 (m, 2H), 7.45-7.52 (m, 1H), 7.50 (d, J = 2.7 Hz, 1H), 7.75-7.78 (m, 1H), 7.81 (d, J = 2.7 Hz, 1H), 8.61 (d, J = 3.7 Hz, 1H), 8.74 (s, 1H). |

TABLE 2

| Compound No. | R² | R³ | R⁴ | R⁵ | ¹H-NMR (CDCl₃) |
|---|---|---|---|---|---|
| 1-0009 | H | Ph-C≡C- | H | nBu | 0.97 (t, J = 7.4 Hz, 3H), 1.38-1.48 (m, 2H), 1.75-1.85 (m, 2H), 4.05 (t, J = 7.4 Hz, 2H), 6.92 (s, 1H), 7.23-7.52 (m, 6H), 7.67-7.69 (m, 2H), 7.71 (d, J = 2.7 Hz, 1H), 7.89 (d, J = 2.7 Hz, 1H). |
| 1-010 | Me | H | Me | nBu | 0.94 (t, J = 7.5 Hz, 3H), 1.39 (sextet, J = 7.5 Hz, 2H), 1.61-1.71 (m, 2H), 2.21 (s, 3H), 2.37 (s, 3H), 3.99 (t, J = 7.8 Hz, 2H), 5.95 (s, 1H), 7.18 (ddd, J = 7.5, 7.5, 1.8 Hz), 7.23 (ddd, J = 7.5, 7.5, 1.8 Hz, 1H), 7.40 (m, 1H), 7.47 (m, 1H). |

TABLE 2-continued

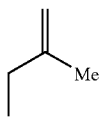

| Compound No. | R² | R³ | R⁴ | R⁵ | ¹H-NMR (CDCl₃) |
|---|---|---|---|---|---|
| 1-011 | 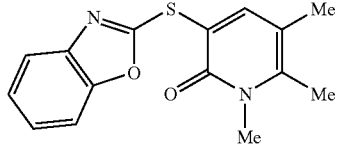 | H | Me | nBu | 0.94 (t, J = 7.5 Hz, 3H), 1.37 (sextet, J = 7.5 Hz, 2H), 1.68-1.78 (m, 2H), 1.73 (d, J = 1.0 Hz, 3H), 3.32 (s, 2H), 3.94 (t, J = 7.5 Hz, 2H), 4.82 (s, 1H), 4.88 (s, 1H), 6.13 (d, J = 7.2 Hz, 1H), 7.17 (d, J = 7.2 Hz, 1H), 7.19 (ddd, J = 7.5, 7.5, 1.5 Hz, 1H), 7.23 (ddd, J = 7.5, 7.5, 1.5 Hz, 1H), 7.40 (m, 1H), 7.48 (m, 1H). |

TABLE 3

| Compound No. | Structure | ¹H-NMR (CDCl₃) |
|---|---|---|
| 1-012 | 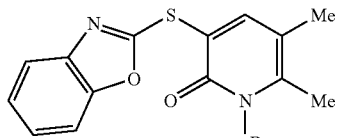 | 2.16 (s, 3H), 2.36 (s, 3H), 7.20-7.29 (m, 2H), 7.40-7.44 (m, 1H9, 7.58-7.61 (m, 1H), 7.83 (s, 1H). |
| 1-013 | 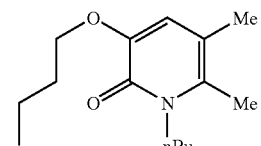 | 0.95 (t, J = 7.2 Hz), 1.35-1.48 (m, 2H), 1.60-1.72 (m, 2H), 2.15 (s, 3H), 2.39 (s, 3H), 4.11 (t, J = 7.8 Hz, 2H), 7.22-7.29 (m, 2H), 7.41-7.44 (m, 1H), 7.57-7.61 (m, 1H), 7.81 (s, 1H). |
| 1-014 | 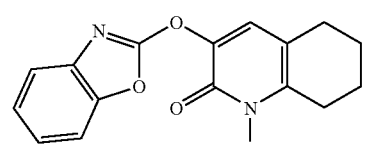 | 0.96 (t, J = 7.2 Hz, 6H), 1.30-1.60 (m, 4H), 1.60-1.75 (m, 2H), 1.76-1.90 (m, 2H), 2.31 (s, 3H), 3.89 (t, J = 6.9 Hz, 2H), 4.02 (t, J = 8.1 Hz, 2H), 5.88 (d, J = 7.8 Hz, 1H), 6.52 (d, J = 7.2 Hz, 1H). |
| 1-015 | 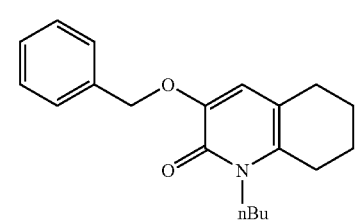 | 0.94 (t, J = 7.5 Hz, 3H), 1.40 (sextet, J = 7.5 Hz, 2H), 1.66 (quint, J = 7.5 Hz, 2H), 1.74 (quint, J = 6.0 Hz, 2H), 1.87 (quint, J = 6.0 6.0 Hz, 2H), 2.58 (t, J = 6.0 Hz, 2H), 2.69 (t, J = 6.0 Hz, 2H), 4.02 (t, J = 7.8 Hz, 2H), 7.16-7.26 (m, 2H), 7.24 (s, 1H), 7.40 (dd, J = 6.9 Hz, 2.4 Hz, 1H), 7.48 (dd, J = 6.9 Hz, 2.4 Hz, 1H). |
| 1-016 | 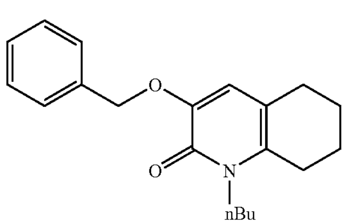 | 0.96 (t, J = 7.5 Hz, 3H), 1.42 (sextet, J = 7.5 Hz, 2H), 1.60-1.76 (m, 4H), 1.81 (quint, J = 6.0 Hz, 2H), 2.43 (t, J = 6.0 Hz, 2H), 2.61 (t, J = 6.0 Hz, 2H), 4.01 (t, J = 7.8 Hz, 2H), 5.07 (s, 2H), 6.43 (s, 1H), 7.28-7.39 (m, 1H), 7.34 (d, J = 7.5 Hz, 2H), 7.45 (d, J = 7.5 Hz, 2H). |

TABLE 3-continued

| Compound No. | Structure | 1H-NMR (CDCl3) |
|---|---|---|
| 1-017 | (benzoxazole-O-pyridinone with N-CH2CH2-(2-bromophenyl)) | 3.23 (t, J = 7.5 Hz, 2H), 4.24 (t, J = 7.5 Hz, 2H), 6.10 (t, J = 6.9 Hz, 1H), 6.99 (dd, J = 1.8, 6.9 Hz, 1H), 7.08-7.29 (m, 5H), 7.42-7.45 (m, 1H), 7.49-7.52 (m, 2H), 7.56 (dd, J = 1.2, 7.8 Hz, 1H). |
| 1-018 | (benzoxazole-O-fused tricyclic pyridinone) | 3.03 (t, J = 6.1 Hz, 2H), 4.34 (t, J = 6.1 Hz, 2H), 6.74 (d, J = 7.9 Hz, 1H), 7.19-7.45 (m, 6H), 7.50 (d, J = 6.4 Hz, 1H), 7.61 (d, J = 7.9 Hz, 1H), 7.73 (d, J = 7.3 Hz, 1H). |
| 1-019 | (phenethyloxy-tetrahydroquinolinone N-nBu) | 0.96 (t, J = 7.5 Hz, 3H), 1.41 (sextet, J = 7.5 Hz, 2H), 1.58-1.73 (m, 4H), 1.81 (quint, J = 6.0 Hz, 2H), 2.45 (t, J = 6.0 Hz, 2H), 2.61 (t, J = 6.0 Hz, 2H), 3.18 (t, J = 7.5 Hz, 2H), 4.00 (t, J = 7.8 Hz, 2H), 4.07 (t, J = 7.5 Hz, 2H), 6.34 (s, 1H), 7.21-7.33 (m, 5H). |

TABLE 4

Structure: benzoxazol-2-yloxy pyridine-2-thione with R³ at 5-position, Me at 6-position, R⁵ on N.

| Compound No. | R³ | R⁵ | 1H-NMR (CDCl3) |
|---|---|---|---|
| 2-001 | Me | Me | 2.28 (s, 3H), 2.49 (s, 3H), 4.17 (s, 3H), 7.19-7.24 (m, 2H), 7.40 (s, 1H), 7.43-7.49 (m, 2H). |
| 2-002 | Me | Et | 1.46 (t, J = 7.2 Hz, 3H), 2.25 (s, 3H), 2.55 (s, 3H), 4.92 (br s, 2H), 7.18-7.24 (m, 2H), 7.37 (s, 1H), 7.42-7.49 (m, 2H). |
| 2-003 | Me | nPr | 1.04 (t, J = 7.2 Hz, 3H), 1.89 (br s, 2H), 2.25 (s, 3H), 2:52 (s, 3H), 4.71 (br s, 2H), 7.19-7.26 (m, 2H), 7.36 (s, 1H), 7.42-7.49 (m, 2H). |
| 2-004 | Me | nBu | 0.99 (t, J = 7.2 Hz, 3H), 1.42-1.54 (m, 2H), 1.83 (br s, 2H), 2.25 (s, 3H), 2.53 (s, 3H), 4.80 (br s, 2H), 7.18-7.26 (m, 2H), 7.36 (s, 1H), 7.42-7.49 (m, 2H). |
| 2-005 | Me | iBu | 0.97-0.99 (m, 6H), 2.27 (s, 3H), 2.51 (s, 3H), 2.51-2.66 (m, 1H), 3.81 (br s, 1H), 5.64 (br s, 1H), 7.20-7.24 (m, 2H), 7.39 (s, 1H), 7.42-7.48 (m, 2H). |
| 2-006 | Me | nPent | 0.92 (t, J = 7.2 Hz, 3H), 1.36-1.48 (m, 4H), 1.85 (br s, 2H), 2.25 (s, 3H), 2.53 (s, 3H), 4.76 (br s, 2H), 7.18-7.26 (m, 2H), 7.36 (s, 1H), 7.42-7.49 (m, 2H). |
| 2-007 | Me | nHexyl | 0.89 (t, J = 7.2 Hz, 3H), 1.30-1.50 (m, 6H), 1.84 (br s, 2H), 2.25 (s, 3H), 2.52 (s, 3H), 4.79 (br s, 2H), 7.17-7.26 (m, 2H), 7.35 (s, 1H), 7.42-7.49 (m, 2H). |
| 2-008 | Me | Bn | 2.24 (s, 3H), 2.38 (s, 3H), 6.27 (br s, 2H), 7.14-7.52 (m, 10H). |
| 2-009 | Et | Me | 1.23 (t, J = 7.8 Hz, 3H), 2.50 (s, 3H), 2.61 (q, J = 7.8 Hz, 2H), 4.17 (s, 3H), 7.19-7.24 (m, 2H), 7.42 (s, 1H), 7.42-7.49 (m, 2H). |
| 2-010 | Et | Et | 1.23 (t, J = 7.5 Hz, 3H), 1.47 (t, J = 7.2 Hz, 3H), 2.57 (s, 3H), 2.59 (q, J = 7.5 Hz, 2H), 4.92 (br s, 2H), 7.18-7.24 (m, 2H), 7.39 (s, 1H), 7.43-7.49 (m, 2H). |
| 2-011 | Et | nPr | 1.04 (t, J = 7.2 Hz, 3H), 1.22 (t, J = 7.5 Hz, 3H), 1.89 (br s, 2H), 2.54 (s, 3H), 2.59 (q, J = 7.5 Hz, 2H), 4.72 (br s, 2H), 7.18-7.24 (m, 2H), 7.38 (s, 1H), 7.42-7.49 (m, 2H). |
| 2-012 | Et | nBu | 0.99 (t, J = 7.2 Hz, 3H), 1.22 (t, J = 7.5 Hz, 3H), 1.42-1.54 (m, 2H), 1.83 (br s, 2H), 2.55 (s, 3H), 2.59 (q, J = 7.5 Hz, 2H), 4.77 (br s, 2H), 7.20-7.24 (m, 2H), 7.38 (s, 1H), 7.42-7.49 (m, 2H). |
| 2-013 | Et | Bn | 1.22 (t, J = 7.5 Hz, 3H), 2.40 (s, 3H), 2.57 (q, J = 7.5 Hz, 2H), 6.27 (br s, 2H), 7.13-7.51 (m, 10H). |

TABLE 5

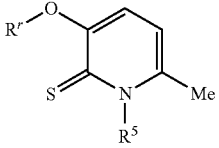

| Compound No. | R<sup>r</sup> | R<sup>5</sup> | $^1$H-NMR (CDCl$_3$) |
|---|---|---|---|
| 2-014 | 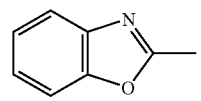 | Me | 2.55 (s, 3H), 4.10 (s, 3H), 6.57 (d, J = 7.8 Hz, 1H), 7.20-7.26 (m, 2H), 7.40-7.50 (m, 3H). |
| 2-015 | 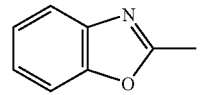 | nBu | 0.99 (t, J = 7.2 Hz, 3H), 1.47 (sextet, J = 7.5 Hz, 2H), 1.84 (m, 2H), 2.58 (s, 3H), 4.69 (br s, 2H), 6.52 (d, J = 7.8 Hz, 1H), 7.20-7.26 (m, 2H), 7.30-7.50 (m, 3H). |
| 2-016 | 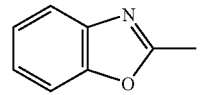 | nBu | 0.82 (t, J = 7.5 Hz, 3H), 1.32 (sextet, J = 7.5 Hz, 2H), 1.47-1.52 (m, 2H), 2.46 (s, 3H), 4.37 (br s, 2H), 4.80 (s, 2H), 7.06 (d, J = 9.0 Hz, 1H), 7.26-7.35 (m, 3H), 7.38-7.44 (m, 1H), 7.60-7.67 (m, 1H). |
| 2-017 | Ac | nBu | 0.99 (t, J = 7.5 Hz, 3H), 1.47 (sextet, J = 7.5 Hz, 2H), 1.83 (m, 2H), 2.38 (s, 3H), 2.54 (s, 3H), 4.70 (br s, 2H), 6.44 (d, J = 7.8 Hz, 1H), 7.04 (d, J = 7.5 Hz, 1H). |
| 2-018 | H | nBu | 1.02 (t, J = 7.8 Hz, 3H), 1.50 (sextet, J = 7.8 Hz, 2H), 1.80-1.90 (m, 2H), 2.51 (s, 3H), 4.66 (br s, 2H), 6.49 (d, J = 8.1 Hz, 1H), 6.91 (d, J = 7.8 Hz, 1H), 8.44 (br s, 1H). |
| 2-019 | 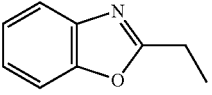 | nBu | 0.96 (t, J=7.5 Hz, 3H), 1.41 (sextet, J = 7.5 Hz, 2H), 1.70 (m, 2H), 2.43 (s, 3H), 2.52 (s, 3H), 4.61 (brs, 2H), 6.38 (d, J = 8.1 Hz, 1H), 7.26-7.35 (m, 3H), 7.97 (d, J = 8.7 Hz, 1H). |
| 2-020 | H$_3$C—SO$_2$— | nBu | 1.01 (t, J = 7.5 Hz, 3H), 1.49 (sextet, J = 7.2 Hz, 2H), 1.82 (m, 2H), 2.57 (s, 3H), 3.48 (dd, J = 3.0, 1.5 Hz, 3H), 4.70 (brs, 2H), 6.47 (d, J = 7.8 Hz, 1H), 7.31 (dd, J = 7.8, 1.8 Hz, 1H). |
| 2-021 | 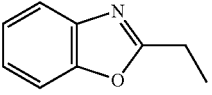 | nBu | 0.98 (t, J = 7.2 Hz, 3H), 1.46 (sextet, J = 7.5 Hz, 2H), 1.81 (m, 2H), 2.51 (s, 3H), 4.00 (s, 2H), 4.67 (brs, 2H), 6.39 (d, J = 7.8 Hz, 1H), 6.98 (d, J = 7.8 Hz, 1H), 7.10-7.50 (m, 5H). |
| 2-022 | 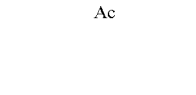 | nBu | 0.99 (t, J = 7.2 Hz, 3H), 1.47 (sextet, J = 7.2 Hz, 2H), 1.85 (m, 2H), 2.54 (s, 3H), 2.90-3.00 (m, 2H), 3.10-3.20 (m, 2H), 4.70 (brs, 2H), 3.10-3.20 (m, 2H), 4.70 (brs, 2H), 6.42 (d, J = 8.1 Hz, 1H), 6.97 (d, J = 8.1 Hz, 1H), 7.18-7.34 (m, 5H). |

TABLE 6

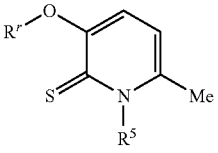

| Compound No. | R<sup>r</sup> | R<sup>5</sup> | $^1$H-NMR (CDCl$_3$) |
|---|---|---|---|
| 2-023 | 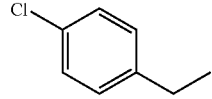 | nBu | 0.92 (t, J = 6.9 Hz, 3H), 1.37 (m, 4H), 2.41 (s, 3H), 4.17 (brs, 2H), 4.47 (s, 2H), 6.99 (d, J = 9.0 Hz, 1H), 7.00-7.30 (m, 5H). |
| 2-024 | 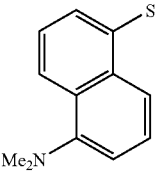 | nBu | 0.94 (t, J = 6.9 Hz, 3H), 1.40 (sextet, J = 7.8 Hz, 2H), 1.70 (m, 2H), 2.48 (s, 3H) 2.89 (s, 6H), 4.60 (br s, 2H), 6.27 (d, J = 8.1 Hz, 1H), 6.97 (dd, J = 8.1, 1.2 Hz, 1H), 7.21 (d, J = 7.8 Hz, 1H), 7.51 (dd, J = 8.1, 7.8 Hz, 1H), 7.61 (dd, J = 8.4, 7.8 Hz, 1H), 8.28 (dd, J = 7.2, 0.9 Hz, 1H), 8.61 (t, J = 8.4 Hz, 2H). |
| 2-025 | 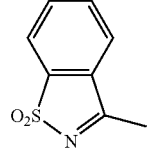 | nBu | 1.02 (t, J = 7.5 Hz, 3H), 1.50 (sextet, J = 7.5 Hz, 2H), 1.80-1.85 (m, 2H), 2.51 (s, 3H), 4.67 (br s, 2H), 6.51 (dd, J = 5.1, 4.8 Hz, 1H), 6.57 (d, J = 7.8 Hz, 1H), 7.38 (d, J = 8.1 Hz, 1H), 7.70-7.85 (m, 2H). |
| 2-026 | nBu | nBu | 0.90-1.03 (m, 6H), 1.4-1.6 (m, 4H), 1.8-1.9 (m, 4H), 2.50 (s, 3H), 3.98 (t, J = 6.9 Hz, 2H), 4.76 (brs, 2H), 6.40 (d, J = 8.1 Hz, 1H), 6.60 (d, J = 7.8 Hz, 1H). |
| 2-027 | 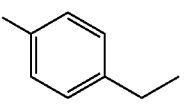 | nBu | 0.91 (t, J = 7.2 Hz, 3H), 1.25-1.44 (m, 4H,), 1.25-1.44 (m, 4H), 2.40 (s, 3H), 3.75 (s, 3H), 4.18 (brs, 2H), 4.44 (s, 2H), 6.73 (A$_2$B$_2$-type, J = 8.7 Hz, 2H), 6.98 (d, J = 9.3 Hz, 1H), 7.09 (A$_2$B$_2$-type, J = 8.4 Hz, 2H), 7.25 (d, J = 9.0 Hz, 1H). |
| 2-028 | EtO$_2$C— | nBu | 0.99 (t, J = 7.2 Hz, 3H), 1.40 (t, J = 7.2 Hz, 3H), 1.47 (sextet, J = 7.5 Hz, 2H), 1.84 (m, 2H), 2.55 (s, 3H), 4.35 (q, J = 7.5 Hz, 2H), 4.69 (brs, 2H), 6.45 (dd, J = 7.5, 0.6 Hz, 1H), 7.12 (d, J = 7.5 Hz, 1H). |
| 2-029 | 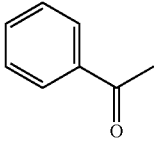 | nBu | 0.99 (t, J = 7.2 Hz, 3H), 1.48 (sextet, J = 7.2 Hz, 2H), 1.85 (m, 2H), 2.57 (s, 3H), 4.73 (brs, 2H), 6.48 (d, J = 7.8 Hz, 1H), 7.18 (d, J = 7.5 Hz, 1H), 7.20-7.70 (m, 3H), 8.20-8.30 (m, 2H). |

TABLE 7

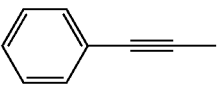

| Compound No. | R² | R³ | R⁴ | R⁵ | ¹H-NMR (CDCl₃) |
|---|---|---|---|---|---|
| 2-030 | H | H | H | iPr | 1.45 (s, 3H), 1.48 (s, 3H), 6.31-6.45 (m, 1H), 6.76 (t, J = 7.0 Hz, 1H), 7.03-7.29 (m, 3H), 7.43-7.29 (m, 3H), 7.43-7.54 (m, 2H), 7.74 (dd, J = 1.5, 7.0 Hz, 1H). |
| 2-031 | Me | H | H | nPr | 1.00 (t, J = 7.3 Hz, 3H), 1.83-2.02 (m, 2H), 4.48 (t, J = 7.7 Hz, 2H), 6.56 (d, J = 6.6 Hz, 1H), 7.20-7.28 (m, 2H), 7.43-7.49 (m, 2H), 7.57 (d, J = 6.6 Hz, 1H). |
| 2-032 | —CH₂OMe | H | H | nPr | 0.96 (t, J = 7.3 Hz, 3H), 1.35-1.47 (m, 2H), 1.8-1.91 (m, 2H), 3.43 (s, 3H), 4.48-4.56 (m, 3H), 6.89 (d, J = 6.7 Hz, 1H), 6.97-7.48 (m, 4H), 7.68 (d, J = 6.7 Hz, 1H). |
| 2-033 | H | H | H | nBu | 0.98 (t, J = 7.3 Hz, 3H), 1.37-1.49 (m, 2H), 1.83-1.94 (m, 2H), 4.57 (t, J = 7.6 Hz, 2H), 6.65-6.70 (m, 1H), 7.22-7.27 (m, 2H), 7.43-7.51 (m, 3H), 7.68 (dd, J = 1.5, 6.4 Hz, 1H). |
| 2-034 | Me | H | H | nBu | 0.95 (t, J = 7.3 Hz, 3H), 1.34-1.46 (m, 2H), 1.79-1.90 (m, 2H), 2.29 (s, 3H), 4.51 (t, J = 7.4 Hz, 2H), 6.55 (d, J = 6.6 Hz, 1H), 7.20-7.28 (m, 2H), 7.43-7.48 (m, 2H), 7.59 (d, J = 6.6 Hz, 1H). |
| 2-035 | H | Me | H | nBu | 0.97 (t, J = 7.3 Hz, 3H), 1.36-1.46 (m, 2H), 1.82-1.92 (m, 2H), 4.54 (t, J = 7.6 Hz, 2H), 7.19-7.27 (m, 2H), 7.40-7.52 (m, 4H). |
| 2-036 | H | Br | H | nBu | 0.99 (t, J = 7.5 Hz, 3H), 1.43 (sextet, J = 7.5 Hz, 2H), 1.83-1.93 (m, 2H), 4.53 (t, J = 7.5 Hz, 2H), 7.21-7.30 (m, 2H), 7.42-7.52 (m, 2H), 7.64 (d, J = 2.1 Hz, 1H), 7.79 (d, J = 2.1 Hz, 1H). |
| 2-037 | H | ![phenylethynyl] | H | nBu | 1.00 (t, J = 7.3 Hz, 3H), 1.45 (sextet, J = 7.3 Hz, 2H), 1.85-1.97 (m, 2H), 4.57 (t, J = 7.6 Hz, 2H), 7.22-7.28 (m, 2H), 7.34-7.44 (m, 3H), 7.44-7.52 (m, 4H), 7.61 (d, J = 1.8 Hz, 1H), 7.89 (d, J = 1.8 Hz, 1H). |

TABLE 8

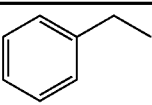

| Compound No. | Rʳ | R⁵ | ¹H-NMR (CDCl₃) |
|---|---|---|---|
| 3-001 | ![benzyl] | Me | 2.20 (s, 3H), 2.39 (s, 3H), 3.62 (s, 3H), 4.65 (d, J = 6.0 Hz, 2H), 7.21-7.38 (m, 5H), 8.37 (s, 1H), 10.28 (br s, 1H). |

TABLE 8-continued

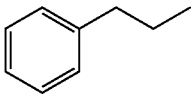

| Compound No. | R<sup>r</sup> | R<sup>5</sup> | <sup>1</sup>H-NMR (CDCl<sub>3</sub>) |
|---|---|---|---|
| 3-002 | 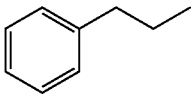 | Me | 2.19 (s, 3H), 2.38 (s, 3H), 2.93 (t, J = 7.2 Hz, 2H), 3.62 (s, 3H), 3.65-3.72 (m, 2H), 7.21-7.33 (m, 5H), 8.34 (s, 1H), 9.99 (br s, 1H). |
| 3-003 | 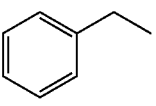 | Et | 1.32 (t, J = 7.2 Hz, 3H), 2.18 (s, 3H), 2.42 (s, 3H), 4.20 (q, J = 7.2 Hz, 2H), 4.64 (d, J = 6.0 Hz, 2H), 7.24-7.38 (m, 5H), 8.35 (s, 1H), 10.30 (br s, 1H). |
| 3-004 | 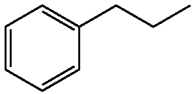 | Et | 1.33 (t, J = 7.2 Hz, 3H), 2.18 (s, 3H), 2.42 (s, 3H), 2.93 (t, J = 7.5 Hz, 2H), 3.64-3.71 (m, 2H), 4.21 (q, J = 7.2 Hz, 2H), 7.18-7.33 (m, 5H), 8.32 (s, 1H), 10.03 (br s, 1H). |
| 3-005 | 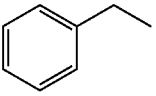 | nPr | 1.03 (t, J = 7.8 Hz, 3H), 1.65-1.78 (m, 2H), 2.19 (s, 3H), 2.42 (s, 3H), 4.07 (t, J = 8.1 Hz, 2H), 4.65 (d, J = 6.0 Hz, 2H), 7.24-7.38 (m, 5H), 8.36 (s, 1H), 10.30 (br s, 1H). |
| 3-006 | 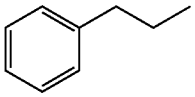 | nPr | 1.05 (t, J = 7.5 Hz, 3H), 1.67-1.80 (m, 2H), 2.19 (s, 3H), 2.42 (s, 3H), 2.92-2.97 (m, 2H), 3.64-3.72 (m, 2H), 4.09 (t, J = 7.8 Hz, 2H), 7.20-7.35 (m, 5H), 8.33 (s, 1H), 10.05 (br s, 1H). |
| 3-007 | 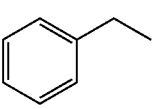 | iPr | 1.60 (s, 3H), 1.63 (s, 3H), 2.17 (s, 3H), 2.40 (s, 3H), 4.64 (d, J = 6.0 Hz, 3H), 7.24-7.34 (m, 5H), 8.31 (s, 1H), 10.31 (br s, 1H). |
| 3-008 | 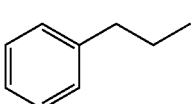 | iPr | 1.62 (s, 3H), 1.64 (s, 3H), 2.17 (s, 3H), 2.40 (s, 3H), 2.93 (d, J = 7.8 Hz, 2H), 3.62-3.69 (m, 2H), 4.64 (br s, 1H), 7.18-7.33 (m, 5H), 8.28 (s, 1H), 10.04 (br s, 1H). |
| 3-009 | 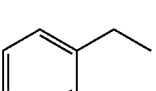 | nBu | 0.98 (t, J = 7.2 Hz, 3H), 1.3-1.51 (m, 2H), 1.61-1.71 (m, 2H), 2.18 (s, 3H), 2.41 (s, 3H), 4.10 (t, J = 8.1 Hz, 2H), 4.64 (d, J = 6.0 Hz, 2H), 7.21-7.38 (m, 5H), 8.35 (s, 1H), 10.30 (br s, 1H). |
| 3-010 | 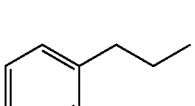 | nBu | 1.00 (t, J = 7.2 Hz, 3H), 1.40 (m, 2H), 1.61-1.72 (m, 2H), 2.93 (t, J = 7.2 Hz, 2H), 3.63-3.70 (m, 2H), 4.11 (t, J = 7.8 Hz, 2H), 7.18-7.32 (m, 5H), 8.32 (s, 1H), 10.03 (br s, 1H). |

TABLE 9

| Compound No. | R<sup>r</sup> | R<sup>5</sup> | $^1$H-NMR (CDCl$_3$) |
|---|---|---|---|
| 3-011 | benzyl-CH$_2$ (PhCH$_2$CH$_2$-) | nHexyl | 0.89 (t, J = 7.2 Hz, 3H), 1.30-1.50 (m, 6H), 1.60-1.75 (m, 2H), 2.18 (s, 3H), 2.41 (s, 3H), 4.09 (t, J = 7.8 Hz, 2H), 4.64 (d, J = 5.7 Hz, 2H), 7.23-7.38 (m, 5H), 8.35 (s, 1H). |
| 3-012 | PhCH$_2$CH$_2$- | nHexyl | 0.91 (t, J = 6.9 Hz, 3H), 1.32-1.45 (m, 6H), 1.63-1.70 (m, 2H), 2.18 (s, 3H), 2.40 (s, 3H), 2.93 (t, J = 7.5 Hz, 2H), 3.63-3.70 (m, 2H), 4.10 (t, J = 7.8 Hz, 2H), 7.18-7.32 (m, 5H), 8.31 (s, 1H), 10.04 (br s, 1H). |
| 3-013 | PhCH$_2$- | Bn | 2.19 (s, 3H), 2.31 (s, 3H), 4.64 (d, J = 5.7 Hz, 2H), 5.44 (br s, 2H), 7.07-7.38 (m, 10H), 8.44 (s, 1H), 10.24 (br s, 1H). |
| 3-014 | PhCH$_2$CH$_2$- | Bn | 2.18 (s, 3H), 2.31 (s, 3H), 2.93 (t, J = 7.5 Hz, 2H), 3.64-3.71 (m, 2H), 5.45 (br s, 2H), 7.08-7.36 (m, 10H), 8.41 (s, 1H), 9.98 (br s, 1H). |
| 3-015 | PhCH$_2$- | Ph | 2.00 (s, 3H), 2.22 (s, 3H), 4.58 (d, J = 5.7 Hz, 2H), 7.15-7.32 (m, 7H), 7.49-7.58 (m, 3H), 8.49 (s, 1H), 10.02 (br s, 1H). |
| 3-016 | PhCH$_2$CH$_2$- | Ph | 2.00 (s, 3H), 2.22 (s, 3H), 2.88 (t, J = 7.8 Hz, 2H), 3.59-3.66 (m, 2H), 7.16-7.29 (m, 7H), 7.51-7.61 (m, 3H), 8.46 (s, 1H), 9.82 (brs, 1H). |

TABLE 10

| Compound No. | R<sup>r</sup> | R<sup>3</sup> | $^1$H-NMR (CDCl$_3$) |
|---|---|---|---|
| 3-033 | PhCH$_2$- | nBu | 0.93 (t, J = 7.2 Hz, 3H), 0.98 (t, J = 7.2 Hz, 3H), 1.32-1.51 (m, 6H), 1.61-1.69 (m, 2H), 2.41 (s, 3H), 2.48 (t, J = 7.8 Hz, 2H), 4.09 (t, J = 7.8 Hz, 2H), 4.64 (d, J =6.0 Hz, 2H), 7.23-7.38 (m, 5H), 8.35 (s, 1H), 10.30 (br s, 1H). |
| 3-034 | PhCH$_2$CH$_2$- | nBu | 0.93 (t, J = 7.2 Hz, 3H), 1.00 (t, J = 7.2 Hz, 3H), 1.30-1.54 (m, 6H), 1.63-1.72 (m, 2H), 2.42 (s, 3H), 2.48 (t, J = 7.8 Hz, 2H), 2.93 (m, 2H), 3.62-3.70 (m, 2H), 4.10 (t, J = 7.8 Hz, 2H), 7.16-7.32 (m, 5H), 8.32 (s, 1H), 10.04 (br s, 1H). |

TABLE 10-continued

Structure: R<sup>r</sup>-NH-C(=O)- attached to a 2-oxo-1-nBu-6-Me-pyridine with R³ at 5-position.

| Compound No. | R<sup>r</sup> | R³ | ¹H-NMR (CDCl₃) |
|---|---|---|---|
| 3-035 | benzyl-CH₂ (PhCH₂CH₂-) | nPentyl | 0.90 (t, J = 6.9 Hz, 3H), 0.98 (t, J = 7.2 Hz, 3H), 1.30-1.53 (m, 8H), 1.62-1.69 (m, 2H), 2.47 (s, 3H), 2.48 (t, J = 7.5 Hz, 2H), 4.09 (t, J = 7.8 Hz, 2H), 4.64 (d, J = 5.7 Hz, 2H), 7.23-7.38 (m, 5H), 8.35 (s, 1H), 10.31 (br s, 1H). |
| 3-036 | Ph(CH₂)₂- | nPentyl | 0.90 (t, J = 6.9 Hz, 3H), 1.00 (t, J = 7.2 Hz, 3H), 1.28-1.39 (m, 4H), 1.40-1.55 (m, 4H), 1.62-1.72 (m, 2H), 2.42 (s, 3H), 2.47 (t, J = 7.5 Hz, 2H), 2.93 (t, J = 7.2 Hz, 2H), 3.63-3.70 (m, 2H), 4.10 (t, J = 7.8 Hz, 2H), 7.20-7.32 (m, 5H), 8.32 (s, 1H), 10.04 (br s, 1H). |
| 3-037 | PhCH₂- | I | 0.98 (t, J = 7.3 Hz, 3H), 1.38-1.50 (m, 2H), 1.61-1.71 (m, 2H), 2.71 (s, 3H), 4.16 (t, J = 7.9 Hz, 2H), 4.63 (d, J = 5.8 Hz, 2H), 7.22-7.37 (m, 5H), 8.78 (s, 1H), 10.4 (br s, 1H). |
| 3-038 | Ph(CH₂)₂- | I | 1.00 (t, J = 7.3 Hz, 3H), 1.39-1.51 (m, 2H), 1.59 (s, 3H), 1.61-1.71 (m, 2H), 2.71 (s, 3H), 2.92 (t, J = 7.6 Hz, 2H), 3.62-3.69 (m, 2H), 4.17 (t, J = 7.9 Hz, 2H), 7.19-7.33 (m, 5H), 8.74 (s, 1H), 9.77 (br s, 1H). |
| 3-039 | PhCH₂- | m-tolyl | 1.00 (t, J = 7.3 Hz, 3H), 1.41-1.53 (m, 2H), 1.68-1.78 (m, 2H), 4.15 (t, J = 7.6 Hz, 2H), 4.65 (d, J = 5.8 Hz, 2H), 7.22-7.45 (m, 10H), 8.46 (s, 1H), 10.25 (br s, 1H). |
| 3-040 | Ph(CH₂)₂- | m-tolyl | 1.02 (t, J = 7.3 Hz, 3H), 1.43-1.55 (m, 2H), 1.69-1.79 (m, 2H), 2.41 (s, 3H), 2.94 (t, J = 7.9 Hz, 2H), 3.65-3.72 (m, 2H), 4.16 (t, J = 7.6 Hz, 2H), 7.19-7.45 (m, 10H), 8.43 (s, 1H), 9.98 (br s, 1H). |

TABLE 11

Structure: R<sup>r</sup>-NH-C(=O)- attached to a 2-oxo-1-nBu-6-Me-pyridine with R³ at 5-position.

| Compound No. | R<sup>r</sup> | R³ | ¹H-NMR (CDCl₃) |
|---|---|---|---|
| 3-044 | Ph(CH₂)₂- | CF₃ | 1.02 (t, J=6.7 Hz, 3H), 1.42-1.54 (m, 2H), 1.66-1.74 (m, 2H), 2.61 (s, 3H), 2.93 (t, J= 7.3 Hz, 2H), 3.64-3.69 (m, 2H), 4.14 (t, J= 7.9 Hz, 2H), 7.20-7.33 (m, 5H), 8.69 (s, 1H), 9.61 (brs, 1H). |

TABLE 12

| Compound No. | R^r | R^3 | ^1H-NMR(CDCl_3) |
|---|---|---|---|
| 3-061 | n-Hexyl | —C(O)NH—(CH_2)_5CH_3 | 0.86-0.91(m, 6H), 0.95(t, J=7.3 Hz, 3H), 1.26-1.47(m, 16H), 1.54-1.65 (m, 4H), 1.73-1.83(m, 2H), 3.38-3.45 (m, 4H), 4.07(t, J=7.3 Hz, 2H), 6.72 (t, J=5.5 Hz, 1H), 8.40(d, J=2.7 Hz, 1H), 8.83(d, J=2.7 Hz, 1H), 9.69(t, J=5.5 Hz, 1H). |
| 3-062 | —CH_2—Ph | —C(O)NH—CH_2—Ph | 1.02(t, J=7.3 Hz, 3H), 1.33-1.45(m, 2H), 1.72-1.82(m, 2H), 4.06(t, J= 7.6 Hz, 2H), 4.58(d, J=5.5 Hz, 4H), 6.81(br s, 1H, 7.24-7.36(m, 10H), 7.42(d, J=2.7 Hz, 1H), 8.78(d, J= 2.7 Hz, 1H), 10.00(br s, 1H). |
| 3-063 | —(CH_2)_2—Ph | —C(O)NH—(CH_2)_2—Ph | 0.97(t, J=7.3 Hz, 3H), 1.33-1.46(m, 2H), 1.72-1.82(m, 2H), 2.88-2.94(m, 4H), 3.63-3.72(m, 4H), 4.06(t, J= 7.6Hz, 2H), 7.20-7.34(m, 10H), 8.37 (d, J=2.7 Hz, 1H), 8.65(d, J=2.7 Hz, 1H), 9.52(br s, 1H). |
| 3-064 | —CH_2—Ph | —C(O)N((CH_2)_3CH_3)_2 | 0.91-0.96(m, 6H), 0.93(t, J=7.3 Hz, 3H), 1.32-1.44(m, 4H), 1.54-1.65(m, 6H), 1.71-1.81(m, 2H), 3.38(br s, 4H), 4.02(t, J=7.3 Hz, 2H), 4.64(d, J=5.8 Hz, 2H), 7.23-7.39(m, 5H), 7.85(d, J=2.7 Hz, 1H), 8.58(d, J= 2.7 Hz, 1H), 10.04(t, J=5.5 Hz, 1H). |
| 3-065 | —CH_2—Ph | —C(O)NH-(piperidinyl) | 0.96(t, J=7.3 Hz, 3H), 1.15-1.49(m, 6H), 1.64-1.81(m, 6H), 1.96-2.05(m, 2H), 3.87-3.99(m, 1H), 4.05(t, J= 7.3 Hz, 2H), 4.64(d, J=5.8 Hz, 2H), 6.10(d, J=7.9 Hz, 2H), 6.92-7.38 (m, 5H), 8.38(d, J=2.7 Hz, 1H), 8.72(d, J=2.7 Hz, 1H), 10.05(t, J= 5.8 Hz, 1H). |
| 3-066 | —(CH_2)_2—Ph | —C(O)NH—(CH_2)_5CH_3 | 0.89(t, J=6.7 Hz, 3H), 0.97(t, J= 7.3 Hz, 3H)1.27-1.45(m, 8H), 1.54-1.63(m, 2H), 1.73-1.82(m, 2H), 2.93 (t, J=7.6 Hz, 2H), 3.38-3.45(m, 2H), 3.65-3.72(m, 2H), 4.06(t, J= 7.6 Hz, 2H), 6.44(t, J=5.5 Hz, 1H), 7.20-7.34(m, 5H), 8.39(d, J=2.7 Hz, 1H), 8.74(d, J=2.7 Hz, 1H), 9.78(t, J=5.5 Hz, 1H). |

TABLE 13

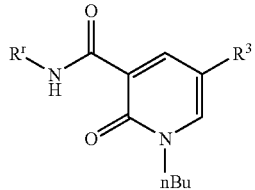

| Compound No. | R<sup>r</sup> | R³ | ¹H-NMR(CDCl₃) |
|---|---|---|---|
| 3-067 | 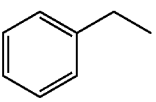 | I | 0.96(t, J=7.3 Hz, 3H), 1.31-1.44(m, 2H), 1.68-1.78(m, 2H), 3.95(t, J=7.3 Hz, 2H), 4.62(d, J=7.3 Hz, 2H), 7.23-7.36(m, 5H), 7.70(d, J=2.6 Hz, 1H), 8.67(d, J=2.6 Hz, 1H), 10.03(br s, 1H). |
| 3-068 | 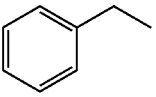 | 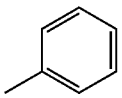 | 0.98(t, J=7.3 Hz, 3H), 1.36-1.48(m, 2H), 1.75-1.85(m, 2H), 4.08(t, J=7.6 Hz, 2H), 4.67(d, J=5.8 Hz, 2H), 7.22-7.50(m, 10H), 7.69(d, J=2.7 Hz, 1H), 8.87(d, J=2.7 Hz, 1H), 10.25(brs, 1H). |
| 3-069 | 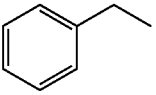 | 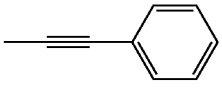 | 0.98(t, J=7.6 Hz, 3H), 1.34-1.46(m, 2H), 1.72-1.82(m, 2H), 4.01(t, J=7.6 Hz, 2H), 4.65(d, J=5.8 Hz, 2H), 7.23-7.40(m, 8H), 7.45-7.51(m, 2H), 7.73(d, J=2.7 Hz, 1H), 8.66(d, J=2.7 Hz, 1H), 10.03(t, J=5.8 Hz, 1H). |
| 3-070 | nBuO | H | 0.95(t, J=7.5 Hz, 3H), 1.38(sextet, J=7.8 Hz, 2H), 1.73-1.79(m, 2H), 3.90(s, 3H), 3.98(t, J=7.5 Hz, 2H), 6.24(d, J=6.9 Hz, 1H), 7.53(dd, J=6.7, 2.1 Hz, 1H), 8.14(dd, J=7.5, 2.4 Hz, 1H). |
| 3-071 | 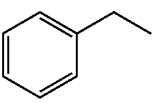 | H | 0.95(t, J=6.9 Hz, 3H), 1.36(sextet, J=7.8 Hz, 2H), 1.66-1.80(m, 2H), 3.96(t, J=7.2 Hz, 2H), 4.60(d, J=6.0 Hz, 2H), 6.36(t, J=7.5 Hz, 1H), 7.20-7.40(m, 5H), 7.46(dd, J=6.3, 2.1 Hz, 1H), 8.47(dd, J=7.2, 2.4 Hz, 1H). |
| 3-072 | 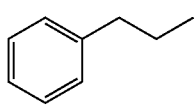 | CF₃ | 0.99(t, J=7.3 Hz, 3H), 1.34-1.47(m, 2H), 1.72-1.82 (m, 2H), 2.93(t, J=7.3 Hz, 2H), 3.66-3.73(m, 2H), 7.20-7.34(m, 5H), 7.83 (m, 1H), 8.69(d, J=2.7 Hz, 1H), 9.62(br s, 1H). |
| 3-073 | 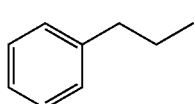 | 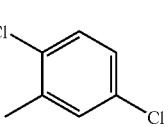 | 0.99(t, J=7.3 Hz, 3H), 1.37-1.49(m, 2H), 2.95(t, J7.3 Hz, 2H), 3.66-3.73(m, 2H), 4.07(t, J7.3 Hz, 2H), 7.19-7.31(m, 6H), 7.34(d, J=2.4 Hz, 1H), 7.42(d, J=8.5 Hz, 1H), 7.65(d, J=2.7 Hz, 1H), 8.63(dd, J=2.7, 0.6 Hz, 1H), 9.89(t, J=5.8 Hz, 1H). |

TABLE 14

[Structure: pyridinone with R'-NH-C(=O)- at 3-position, R³ at 5-position, nBu on N]

| Compound No. | R' | R³ | ¹H-NMR(CDCl₃) |
|---|---|---|---|
| 3-074 | phenethyl (PhCH₂CH₂−) | 5-methyl-1H-indol-3-yl | 1.00(t, J=7.3 Hz, 3H), 1.38-1.50(m, 2H), 1.70-1.87(m, 2H), 2.97(t, J=7.3 Hz, 2H), 3.69-3.76(m, 2H), 4.09(t, J=7.3 Hz, 2H), 6.58(brs, 1H), 7.20-7.34(m, 6H), 7.44-7.47(m, 2H), 8.63(s, 1H), 8.89(d, J=2.4 Hz, 1H), 10.11(t, J=5.8 Hz, 1H). |

TABLE 15

[Structure: pyridinone with R'-NH-C(=O)- at 3-position, R₄ at 6-position, nBu on N]

| Compound No. | R' | R³ | ¹H-NMR(CDCl₃) |
|---|---|---|---|
| 3-081 | phenethyl | Me | 0.98(t, J=7.2 Hz, 3H), 1.43(sextet, J=7.5 Hz, 2H), 1.60-1.70(m, 2H), 2.46(s, 3H), 4.05(t, J=8.1 Hz, 2H), 4.27(dd, J=7.2, 6.6 Hz, 1H), 4.64(d, J=5.7 Hz, 2H), 7.20-7.40(m, 5H), 8.41(d, J=7.5 Hz, 1H), 10.2(br s, 1H). |
| 3-082 | benzyl | nPentyl | 0.93(t, J=7.2 Hz, 3H), 0.98(t, J=7.2 Hz, 3H), 1.37-1.50(m, 6H), 1.62-1.70(m, 4H), 2.67(t, J=7.8 Hz, 2H), 4.05(t, J=7.8 Hz, 2H), 4.64(d, J=6.0Hz, 2H), 6.27(d, J=7.5 Hz, 1H), 7.20-7.40(m, 5H), 8.44(d, J=7.5 Hz, 1H), 10.21(br s, 1H). |
| 3-083 | phenethyl | nPentyl | 0.93(t, J=6.9 Hz, 3H), 1.00(t, J=7.2 Hz, 3H), 1.38-1.49(m, 6H), 1.63-1.70(m, 4H), 2.66(t, J=7.8 Hz, 2H), 2.93(t, J=7.5 Hz, 2H), 3.63-3.68(m, 2H), 4.06(t, J=7.8 Hz, 2H), 6.27(d, Jz 7.5 Hz, 1H), 7.17-7.32(m, 5H), 8.40(d, J=7.5 Hz, 1H), 9.94(br s, 1H). |
| 3-084 | benzyl | nHexyl | 0.91(t, J=7.2 Hz, 3H), 0.98(t, J=7.2 Hz, 3H), 1.30-1.50(m, 8H), 1.60-1.72(m, 4H), 2.67(t, J=7.8 Hz, 2H), 4.05(t, J=8.1 Hz, 2H), 4.64(d, J=5.7 Hz, 2H), 6.28(d, J=7.8 Hz, 1H), 7.20-7.40(m, 5H), 8.44(d, J=7.8 Hz, 1H), 10.21(br s, 1H). |
| 3-085 | phenethyl | nHexyl | 0.91(t, J=7.2 Hz, 3H), 1.00(t, J=7.2 Hz, 3H), 1.31-1.49(m, 8H), 1.61-1.71(m, 4H), 2.67(t, J=7.8 Hz, 2H), 2.93(t, J=7.2 Hz, 2H), 3.63-3.70(m, 2H), 4.06(t, J=7.8 Hz, 2H), 6.27(d, J=7.8 Hz, 1H), 7.18-7.33(m, 5H), 8.41(d, J=7.8 Hz, 1H), 9.94(t, J=5.1 Hz, 1H). |

TABLE 16

| Compound No. | Structure | ¹H-NMR(CDCl₃) |
|---|---|---|
| 3-101 | 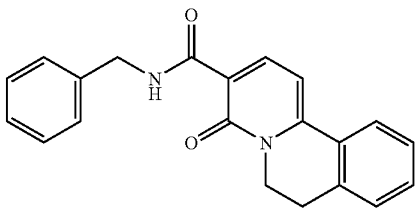 | 3.03(t, J=6.4 Hz, 2H), 4.35(t, J=6.4 Hz, 2H), 4.68(d, J=5.8 Hz, 2H), 6.94(d, 7.9 Hz, 1H), 7.23-7.49(m, 8H), 7.81 (d, J=7.3 Hz, 1H), 8.63(d, J=7.9 Hz, 1H), 10.22(br s, 1H). |
| 3-102 | 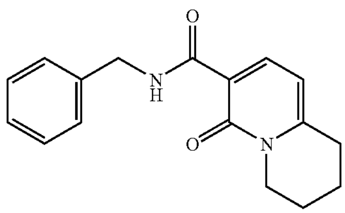 | 1.79-1.88(m, 2H), 1.95-2.03(m, 2H), 2.88 (t, J=6.4 Hz, 2H), 4.04(t, J=6.1 Hz, 2H), 4.65(d, Jz 5.8 Hz, 2H), 6.26(d, J=7.3 Hz, 1H), 7.20-7.38(m, 5H), 8.46(d, J=7.3 Hz, 1H), 10.19(br s, 1H). |
| 3-103 | 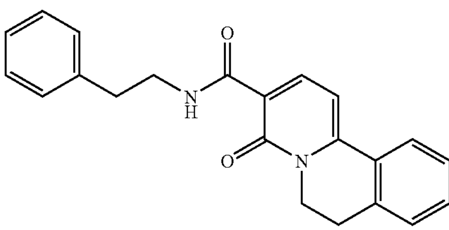 | 2.97(t, Jz 7.3 Hz, 2H), 3.04(t, J=6.4 Hz, 2H), 3.68-3.75(m, 2H), 4.35(t, J=6.4 Hz, 2H), 6.92(d, J=7.9 Hz, 1H), 7.19-7.35(m, 5H), 7.37-7.43(m, 3H), 7.80 (dd, J=1.5, 7.3 Hz, 1H), 8.59(d, J=7.9 Hz, 1H), 9.93(brs, 1H). |
| 3-104 | 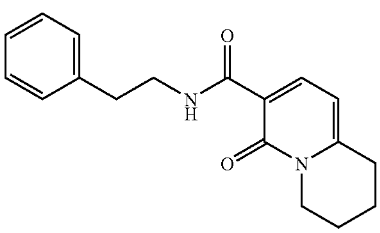 | 1.79-1.88(m, 2H), 1.95-2.04(m, 2H), 2.87 (t, J=6.4 Hz, 2H), 2.93(t, J=7.3 Hz, 2H), 3.65-3.72(m, 2H), 4.04(t, J=6.4 Hz, 2H), 6.24(d, J=7.3 Hz, 1H), 7.18-7.33(m, 5H), 8.42(d, J=7.3 Hz, 1H), 9.90(br s, 1H). |
| 3-105 | 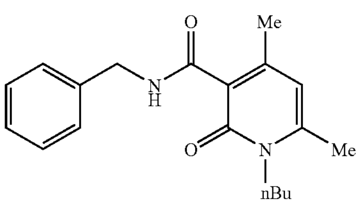 | 0.97(t, J=7.5 Hz, 3H), 1.42(sextet, J=7.5 Hz, 2H), 1.60-1.70(m, 2H), 2.39(s, 3H), 2.63(s, 3H), 3.91(t, J=7.9 Hz, 2H), 4.60(s, 2H), 6.05(s, 1H), 7.20-7.40(m, 5H). |
| 3-106 | 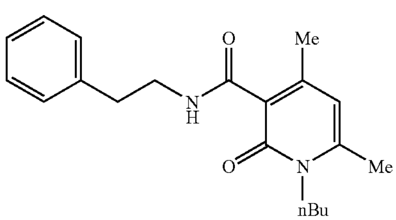 | 0.98(t, J=7.5 Hz, 3H), 1.43(sextet, J=7.5 Hz, 2H), 1.60-1.72(m, 2H), 2.39(s, 3H), 2.61(s, 3H), 2.93(t-like, 2H), 3.63 (t-like, 2H), 4.00(t, J=7.9 Hz, 2H), 6.04 (s, 1H), 7.17-7.33(m, 5H). |
| 3-107 | 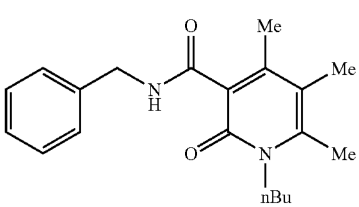 | 0.97(t, J=7.5 Hz, 3H), 1.42(sextet, J=7.5 Hz, 2H), 1.58-1.72(m, 2H), 2.08(s, 3H), 2.41(s, 3H), 2.52(s, 3H), 4.08(t, J=7.5 Hz, 2H), 4.62(s, 2H), 7.20-7.42(m, 5H), 9.02(br s, 1H). |

TABLE 16-continued

| Compound No. | Structure | ¹H-NMR(CDCl₃) |
|---|---|---|
| 3-108 | 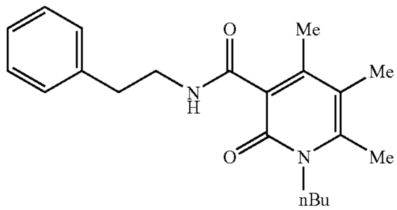 | 0.98(t, J=7.5 Hz, 3H), 1.43(sextet, J= 7.5 Hz, 2H), p.58-1.72(m, 2H), 2.07(s, 3H), 2.40(s, 3H), 2.44(s, 3H), 2.93(t, J= 7.5 Hz, 2H), 3.67(t, J=7.5 Hz, 2H), 4.07 (t, J=7.8 Hz, 2H), 7.16-7.34(m, 5H), 8.47(br s, 1H). |

TABLE 17

| Compound No. | Structure | ¹H-NMR(CDCl₃) |
|---|---|---|
| 3-109 | 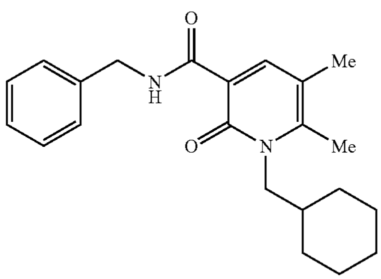 | 1.00-1.28(m, 4H), 1.56-1.90(m, 7H), 2.18(s, 3H), 2.39(s, 3H), 4.00(br s, 2H), 4.64(d, J=6.0 Hz, 2H), 7.20-7.40(m, 5H), 8.35(s, 1H), 10.3(br s, 1H). |
| 3-110 | 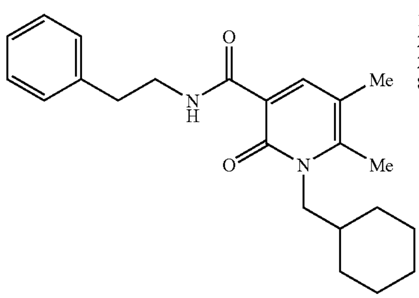 | 1.00-1.30(m, 4H), 1.58-1.90(m, 7H), 2.93(t, J=7.5 Hz, 2H), 3.62-3.69(m, 2H), 4.01(br s, 2H), 7.18-7.35(m, 5H), 8.32(s, 1H), 10.3(br s, 1H). |
| 3-111 | 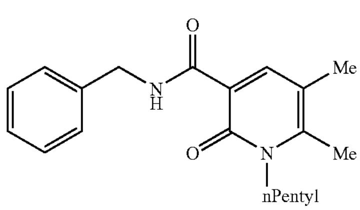 | 0.92(t, J=7.2 Hz, 3H), 1.37-1.42(m, 4H), 1.60-1.75(m, 2H), 2.18(s, 3H), 2.40 (s, 3H), 4.08(t, J=8.1 Hz, 2H), 4.64(d, J= 5.7 Hz, 2H), 7.20-7.40(m, 5H), 8.35(s, 1H), 10.3(br s, 1H). |
| 3-112 | 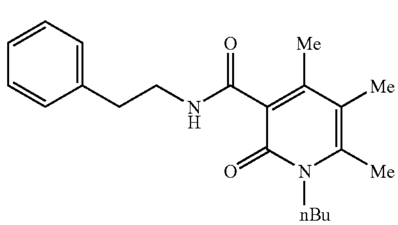 | 0.94(t, J=7.2 Hz, 3H), 1.38-1.42(m, 4H), 1.60-1.75(m, 2H), 2.18(s, 3H), 2.40 (s, 3H), 2.93(t, J=7.8 Hz, 2H), 3.60-3.70 (m, 2H), 4.10(t, J=7.8 Hz, 2H), 7.20-7.35(m, 5H), 8.31(s, 1H), 10.03(br s, 1H). |

TABLE 18

| Compound No. | R<sup>r</sup> | Y | ¹H-NMR(CDCl₃) |
|---|---|---|---|
| 4-001 | 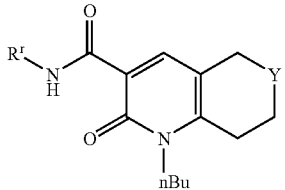 | —CH₂— | 0.97(t, J=7.5 Hz, 3H), 1.43(sextet, J=7.5 Hz, 2H), 1.62(quint, J=7.5 Hz, 2H), 1.74 (quint, J=6.0 Hz, 2H), 1.88(quint, J=6.0 Hz, 2H), 2.62(t, J=6.0 Hz, 2H), 2.74(t, J=6.0 Hz, 2H), 4.03(t, J=7.8 Hz, 2H), 4.64(d, J=6.0 Hz, 2H), 7.23-7.38(m, SF1), 8.28(s, 1H), 10.32(br t, J=6.0 Hz, 1H). |
| 4-002 | 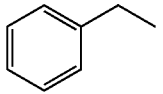 | —CH₂— | 0.99(t, J=7.5 Hz, 3H), 1.45(sextet, J=7.5 Hz, 2H), 1.63(quint, J=7.5 Hz, 2H), 1.74 (quint, J=6.0 Hz, 2H5, 1.88(quint, J6.0 Hz, 2H), 2.62(t, J=6.0 Hz, 2H), 2.74(t, J=6.0 Hz, 2H), 2.93(t, J=7.8 Hz, 2H), 3.66(dt, J=9.0 Hz, 6.0 Hz, 2H), 4.03(t, J=7.8 Hz, 2H), 7.20-7.33(m, 5H), 8.25(s, 1H), 10.05(br t, J=6.0 Hz, 1H). |
| 4-003 | 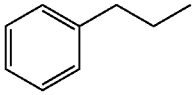 | —CH₂— | 0.99(t, J=7.5 Hz, 3H), 1.45(sextet, J=7.5 Hz, 2H), 1.66(quint, J=7.5 Hz, 2H), 1.73 (quint, J=6.0 Hz, 2H), 1.87(quint, J=6.0 Hz, 2H), 2.61(t, J=6.0 Hz, 2H), 2.73(t, J=6.0 Hz, 2H), 2.82(t, J=7.8 Hz, 2H), 3.60(dt, J=9.0 Hz, 6.0 Hz, 2H), 4.03(t, J=7.5 Hz, 2H), 6.65(dd, J=6.3 Hz, 1H), 2.1(Hz, 2H), 7.05(dd, J=6.3 Hz, 2.1 Hz, 2H), 8.23(s, 1H), 10.01(br t, J=6.0 Hz, 1H). |
| 4-004 | 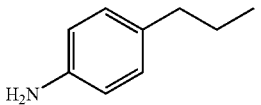 | —CH₂— | 0.99(t, J=7.2 Hz, 3H), 1.44(sextet, J=7.2 Hz, 2H), 1.65(quint, J=7.2 Hz, 2H), 1.74 (quint, J=6.0 Hz, 2H), 1.88(quint, J=6.0 Hz, 2H), 2.64(t, J=6.0 Hz, 2H), 2.74(t, J=6.0 Hz, 2H), 2.94(t, Jz 7.5 Hz, 2H), 3.70(q, J=6.9 Hz, 2H), 4.03(t, J=7.8 Hz, 2H), 7.20(d, J=4.8 Hz, 2H), 8.22(s, 1H), 8.51(br s, 2H), 10.10(br t, J=6.0 Hz, 1H). |
| 4-005 | 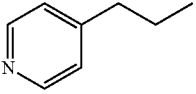 | —CH₂— | 1.01(t, J=7.5 Hz, 3H), 1.44(sextet, J=7.5 Hz, 2H), 1.70(quint, J=7.S Hz, 2H), 1.76 (quint, J6.0 Hz, 2H), 1.91(quint, J6.0 Hz, 2H), 2.66(t, J=6.0 Hz, 2H), 2.78(t, J=6.0 Hz, 2H), 4.09(t, J=7.8 Hz, 2H), 7.09(t, J=7.5 Hz, 1H), 7.34(t, J=7.5 Hz, 2H), 7.77(d, J=7.5 Hz, 2H), 8.34(s, 1H), 12.18(br s, 1H). |

TABLE 19

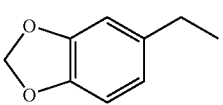

| Compound No. | R<sup>r</sup> | Y | $^1$H-NMR(CDCl$_3$) |
|---|---|---|---|
| 4-006 |  | —CH$_2$— | 0.98(t, J=7.5 Hz, 3H), 1.43(sextet, J=7.5 Hz, 2H), 1.65(quint, J=7.5 Hz, 2H), 1.74 (quint, J=6.0 Hz, 2H), 1.88(quint, J=6.0 Hz, 2H), 2.62(t, J=6.0 Hz, 2H), 2.74(t, J=6.0 Hz, 2H), 4.02(t, J=7.8 Hz, 2H), 4.53(d, J=6.0 Hz, 2H), 5.02(s, 2H), 6.74(d, J=7.8 Hz, H), 6.81(dd, J=7.8 Hz, 1.8 Hz, 1H), 6.86(d,J=1.8 Hz, 1H), 8.27(s, 1H), 10.26(br t, J=6.0 Hz, 1H). |
| 4-007 | 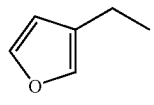 | —CH$_2$— | 0.98(t, J=7.5 Hz, 3H), 1.44(sextet, J=7.5 Hz, 2H), 1.63(quint, J=7.5 Hz, 2H), 1.73 (quint, J=6.0 Hz, 2H), 1.88(quint, J6.0 Hz, 2H), 2.62(t, J=6.0 Hz, 2H), 2.74(t, J=6.0 Hz, 2H), 4.03(t, J=7.8 Hz, 2H), 4.62(d, J=5.4 Hz, 2H), 6.25(dd, J=3.0 Hz, 0.9 Hz, 1H), 6.28-6.31(m, 1H), 7.35(d, J=0.9 Hz, 1H), 8.26(s, 1H), 10.25(br t, J=5.4 Hz, 1H). |

TABLE 20

| Compound No. | R<sup>r</sup> | Y | $^1$H-NMR(CDCl$_3$) |
|---|---|---|---|
| 4-008 | 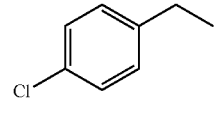 | —CH$_2$— | 0.98(t, J=7.5 Hz, 3H), 1.43(sextet, J=7.5 Hz, 2H), 1.62(quint, J=7.5 Hz, 2H), 1.74(quint, J=6.0 Hz, 2H), 1.88(quint, J=6.0 Hz, 2H), 2.62(t, J6.0 Hz, 2H), 2.74(t, J=6.0 Hz, 2H), 4.03(t, J=7.8 Hz, 2H), 4.59(d, J=6.0 Hz, 2H), 7.26(s, 2H), 7.28(s, 2H), 8.26(s, 1H), 10.35(br t, J=6.0 Hz, 1H). |
| 4-009 |  | —CH$_2$— | 0.97(t, J=7.5 Hz, 3H), 1.43(sextet, J=7.5 Hz, 2H), 1.64(quint, J=7.5 Hz, 2H), 1.74(quint, J=6.0 Hz, 2H), 1.88(quint, J=6.0 Hz, 2H), 2.62(t, J6.0 Hz, 2H), 2.73(t, J6.0 Hz, 2H), 3.78(s, 3H), 4.01 (t, J=7.8 Hz, 2H), 4.57(d, J=6.0 Hz, 2H), 6.85(d, J=9.0 Hz, 2H), 7.29(d, J=9.0 Hz, 2H), 8.27(s, 1H), 10.24(br t, J=6.0 Hz, 1H). |
| 4-010 | 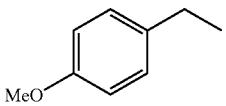 | —O— | 0.98(t, J=7.5 Hz, 3H), 1.43(sextet, J=7.5 Hz, 2H), 1.66(quint, J=7.5 Hz, 2H), 2.82(t, J=6.0 Hz, 2H), 4.01(t, J=6.0 Hz, 2H), 4.02(t, J=7.5 Hz, 2H), 4.60(s, 2H), 4.64(d, J=6.0 Hz, 2H), 7.24-7.38 (m, 5H), 8.22(s, 1H), 10.22(br t, J=6.0 Hz, 1H). |

TABLE 20-continued

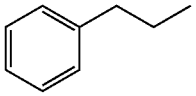

| Compound No. | R<sup>r</sup> | Y | ¹H-NMR(CDCl₃) |
|---|---|---|---|
| 4-011 | 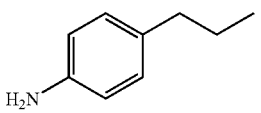 | —O— | 1.00(t, J=7.5 Hz, 3H), 1.45(sextet, J=7.5 Hz, 2H), 1.69(quint, J=7.5 Hz, 2H), 2.83(t, J=6.0 Hz, 2H), 2.93(t, J=7.5 Hz, 2H), 3.67(dt, J=9.0 Hz, 6.0 Hz, 2H), 4.01(t, J=6.0 Hz, 2H), 7.18-7.36(m, 5H), 8.19(s, 1H), 9.96(br t, J=6.0 Hz, 1H). |
| 4-012 | 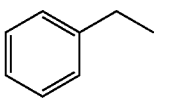 | —O— | 0.99(t, J=7.5 Hz, 3H), 1.45(sextet, J=7.5 Hz, 2H), 1.69(quint, J=7.5 Hz, 2H), 2.82(t, J=6.0 Hz, 2H), 2.83(t, J=7.5 Hz, 2H), 3.61(dt, J=9.0 Hz, 6.0 Hz, 2H), 4.01(t, J=6.0 Hz, 2H), 4.03(t, J=7.5 Hz, 2H), 4.59(s, 2H), 6.71(d, J=7.5 Hz, 2H), 7.07(d, J=7.5 Hz, 2H), 8.17(s, 1H), 9.92(br t, J=6.0 Hz, 1H). |

TABLE 21

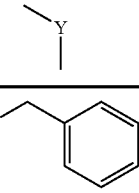

| Compound No. | R<sup>r</sup> | Y | ¹H-NMR (CDCl₃) |
|---|---|---|---|
| 4-013 | 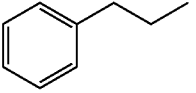 | 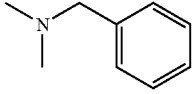 | 0.96 (t, J = 7.5 Hz, 3H), 1.41 (sextet, J = 7.5 Hz, 2H), 1.60-1.73 (m, 2H), 2.78 (d, J = 4.2 Hz, 2H), 2.84 (d, J = 4.2 Hz, 2H), 3.48 (s, 2H), 3.69 (s, 2H), 3.99 (t, J = 7.5 Hz, 2H), 4.63 (d, J = 6.0 Hz, 2H), 7.26-7.37 (m, 10H), 8.21 (s, 1H), 10.24 (br t, J = 6.0 Hz, 1H). |
| 4-014 | | | 0.98 (t, J = 7.5 Hz, 3H), 1.43 (sextet, J = 7.5 Hz, 2H), 1.65 (quint, J = 7.5 Hz, 2H), 2.78 (d, J = 4.5 Hz, 2H), 2.85 (d, J = 4.5 Hz, 2H), 2.92 (t, J = 7.5 Hz, 2H), 3.48 (s, 2H), 3.66 (dt, J = 9.0 Hz, 6.0 Hz, 2H), 3.69 (s, 2H), 4.01 (t, J = 7.8 Hz, 2H), 7.23-7.38 (m, 10H), 8.18 (s, 1H), 9.99 (br t, J = 6.0 Hz, 1H). |

TABLE 22

| Compound No. | R'' | Y | ¹H-NMR (CDCl₃) |
|---|---|---|---|
| 4-015 | 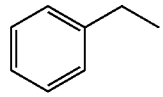 |  | 0.97 (t, J = 7.5 Hz, 3H), 1.43 (sextet, J = 7.5 Hz, 2H), 1.65 (quint, J = 7.5 Hz, 2H), 2.77 (t, J = 6.0 Hz, 2H), 3.19 (t, J = 6.0 Hz, 2H), 3.86 (s, 2H), 4.01 (t, J = 7.8 Hz, 2H), 4.64 (d, J = 6.0 Hz, 2H), 7.23-7.38 (m, 5H), 8.24 (s, 1H), 10.27 (br t, J = 6.0 Hz, 1H). |
| 4-016 | 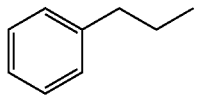 |  | 0.99 (t, J = 7.5 Hz, 3H), 1.45 (sextet, J = 7.5 Hz, 2H), 1.66 (quint, J = 7.5 Hz, 2H), 2.78 (t, J = 6.0 Hz, 2H), 2.93 (t, J = 7.5 Hz, 2H), 3.19 (t, J = 6.0 Hz, 2H), 3.67 (dt, J = 9.0 Hz, 6.0 Hz, 2H), 3.86 (s, 2H), 4.02 (t, J = 7.8 Hz, 2H), 7.18-7.34 (m, 5H), 8.21 (s, 1H), 10.01 (br t, J = 6.0 Hz, 1H). |
| 4-017 | 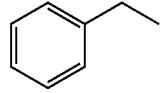 | 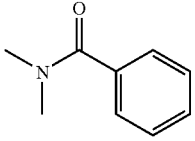 | 0.98 (t, J = 7.5 Hz, 3H), 1.44 (sextet, J = 7.5 Hz, 2H), 1.66 (quint, J = 7.5 Hz, 2H), 2.93 (br t, J = 6.0 Hz, 2H), 3.80 (br t, J = 6.0 Hz, 2H), 4.02 (t, J = 7.8 Hz, 2H), 4.49 (s, 2H), 4.62 (d, J = 6.0 Hz, 2H), 7.23-7.35 (m, 5H), 7.43-7.51 (m, 5H), 8.10 (s, 1H), 10.16 (br t, J = 6.0 Hz, 1H). |
| 4-018 | 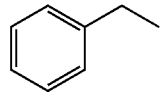 | 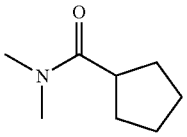 | 0.98 (t, J = 7.5 Hz, 3H), 1.43 (sextet, J = 7.5 Hz, 2H), 1.55-1.90 (m, 10H), 2.84 (quint, J = 6.0 Hz, 1H), 2.91 (t, J = 7.5 Hz, 2H), 3.82 (t, J = 6.0 Hz, 1/3 × 2H), 3.91 (t, J = 6.0 Hz, 2/3 × 2H), 4.01 (t, J = 7.8 Hz, 2H), 4.52 (s, 2/3 × 2H), 4.59 (s, 1/3 × 2H), 4.65 (d, J = 6.0 Hz, 2H), 7.24-7.39 (m, 5H), 8.31 (s, 2/3 × 1H), 8.33 (s, 1/3 × 1H), 10.20 (br t, J = 6.0 Hz, 1H). |

TABLE 23

| Compound No. | R'' | Y | ¹H-NMR (CDCl₃) |
|---|---|---|---|
| 4-019 | 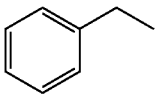 | 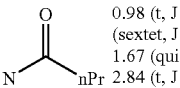 | 0.98 (t, J = 7.5 Hz, 3H), 0.99 (t, J = 7.5 Hz, 3H), 1.43 (sextet, J = 7.5 Hz, 2H), 1.66 (quint, J = 7.5 Hz, 2H), 1.67 (quint, J = 7.5 Hz, 2H), 2.37 (t, J = 7.5 Hz, 2H), 2.84 (t, J = 6.0 Hz, 2/3 × 2H), 2.89 (t, J = 6.0 Hz, 1/3 × 2H), 3.77 (t, J = 6.0 Hz, 1/3 × 2H), 3.90 (t, J = 6.0 Hz, 2/3 × 2H), 4.01 (t, J = 7.8 Hz, 2H), 4.47 (s, 2/3 × 2H), (s, 1/3 × 2H), 4.65 (d, J = 6.0 Hz, 2H), 7.24-7.39 (m, 5H), 8.30 (s, 2/3 × 1H), 8.33 (s, 1/3 × 1H), 10.19 (br t, J = 6.0 Hz, 1H). |

TABLE 23-continued

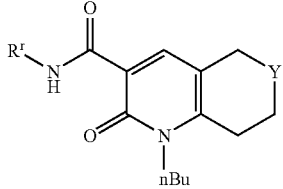

| Compound No. | R^r | Y | ^1H-NMR (CDCl_3) |
|---|---|---|---|
| 4-020 | 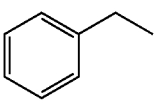 | 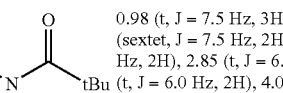 | 0.98 (t, J = 7.5 Hz, 3H), 1.29 (s, 9H), 1.43 (sextet, J = 7.5 Hz, 2H), 1.65 (quint, J = 7.5 Hz, 2H), 2.85 (t, J = 6.0 Hz, 2H), 3.90 (t, J = 6.0 Hz, 2H), 4.00 (t, J = 7.8 Hz, 2H), 4.62 (s, 2H), 4.64 (d, J = 6.0 Hz, 2H), 7.24-7.38 (m, 5H), 8.31 (s, 1H), 10.20 (br t, J = 6.0 Hz, 1H). |

TABLE 24

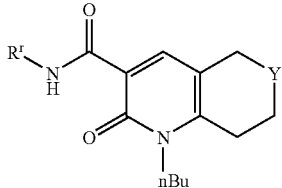

| Compound No. | R^r | Y | ^1H-NMR (CDCl_3) |
|---|---|---|---|
| 4-021 | 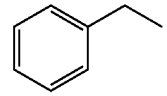 | 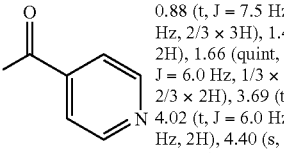 | 0.88 (t, J = 7.5 Hz, 1/3 × 3H), 0.99 (t, J = 7.5 Hz, 2/3 × 3H), 1.44 (sextet, J = 7.5 Hz, 2H), 1.66 (quint, J = 7.5 Hz, 2H), 2.86 (t, J = 6.0 Hz, 1/3 × 2H), 2.99 (t, J = 6.0 Hz, 2/3 × 2H), 3.69 (t, J = 6.0 Hz, 1/3 × 2H), 4.02 (t, J = 6.0 Hz, 2/3 × 2H), 4.06 (t, J = 7.8 Hz, 2H), 4.40 (s, 1/3 × 2H), 4.62 (s, 2/3 × 2H), 4.63 (d, J = 6.0 Hz, 2H), 7.24-7.38 (m, 7H), 8.11 (s, 2/3 × 1H), 8.39 (s, 1/3 × 1H), 8.76 (d, J = 5.4 Hz, 2H), 10.12 (br t, J = 6.0 Hz, 1H). |
| 4-022 | 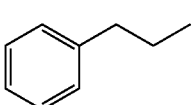 | 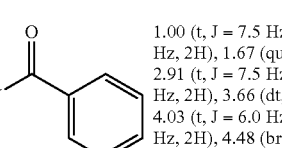 | 1.00 (t, J = 7.5 Hz, 3H), 1.46 (sextet, J = 7.5 Hz, 2H), 1.67 (quint, J = 7.5 Hz, 2H), 2.91 (t, J = 7.5 Hz, 2H), 2.92 (t, J = 6.0 Hz, 2H), 3.66 (dt, J = 6.3 Hz, 6.9 Hz, 2H), 4.03 (t, J = 6.0 Hz, 2H), 4.04 (t, J = 7.5 Hz, 2H), 4.48 (br s, 2/3 × 2H), 4.68 (br s, 1/3 × 2H), 7.20-7.32 (m, 5H), 7.44-7.51 (m, 5H), 8.08 (br s, 2/3 × 1H), 8.37 (br s, 1/3 × 1H), 9.89 (br t, J × 6.0 Hz, 1H) |
| 4-023 | 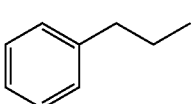 | 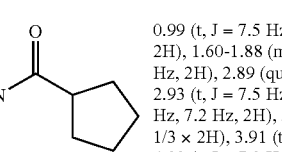 | 0.99 (t, J = 7.5 Hz, 3H), 1.44 (sextet, J = 7.5 Hz, 2H), 1.60-1.88 (m, 10H), 2.83 (t, J = 6.0 Hz, 2H), 2.89 (quint, J = 6.0 Hz, 1H), 2.93 (t, J = 7.5 Hz, 2H), 3.68 (dt, J = 6.6 Hz, 7.2 Hz, 2H), 3.82 (t, J = 6.0 Hz, 1/3 × 2H), 3.91 (t, J = 6.0 Hz, 2/3 × 2H), 4.02 (t, J = 7.8 Hz, 2H), 4.52 (s, 2/3 × 2H), 4.58 (s, 1/3 × 2H), 7.18-7.34 (m, 5H), 8.27 (s, 2/3 × 1H), 8.30 (s, 1/3 × 1H), 9.93 (br t, J = 6.0 Hz, 1H). |

TABLE 25

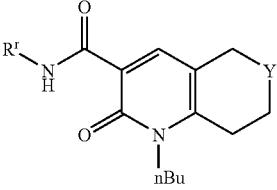

| Compound No. | R<sup>r</sup> | Y | ¹H—NMR (CDCl₃) |
|---|---|---|---|
| 4-024 | 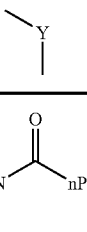 | 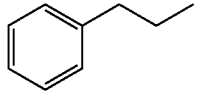 | 0.98 (t, J = 7.5 Hz, 3H), 0.99 (t, J = 7.5 Hz, 3H), 1.45 (sextet, J = 7.5 Hz, 2H), 1.66 (quint, J = 7.5 Hz, 2H), 1.67 (quint, J = 7.5 Hz, 2H), 2.37 (t, J = 7.5 Hz, 2H), 2.84 (t, J = 6.0 Hz, 2H), 2.93 (t, J = 7.5 Hz, 2H), 3.68 (q, J = 6.9 Hz, 2H), 3.77 (t, J = 6.0 Hz, 1/3 × 2H), 3.90 (t, J = 6.0 Hz, 2/3 × 2H), 4.03 (t, J = 7.8 Hz, 2H), 4.47 (s, 2/3 × 2H), 4.58 (s, 1/3 × 2H), 7.20-7.33 (m, 5H), 8.27 (s, 2/3 × 1H), 8.30 (s, 1/3 × 1H), 9.81 (br t, J = 6.0 Hz, 1/3 × 1H), 9.93 (br t, J = 6.0 Hz, 2/3 × 1H). |
| 4-025 | 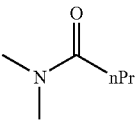 | 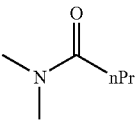 | 1.00 (t, J = 7.5 Hz, 3H), 1.30 (s, 9H), 1.45 (sextet, J = 7.5 Hz, 2H), 1.66 (quint, J = 7.5 Hz, 2H), 2.85 (t, J = 6.0 Hz, 2H), 2.93 (t, J = 7.5 Hz, 2H), 3.68 (dt, J = 9.0 Hz, 6.0 Hz, 2H), 3.90 (t, J = 6.0 Hz, 2H), 4.01 (t, J = 7.8 Hz, 2H), 4.62 (s, 2H), 7.18-7.33 (m, 5H), 8.28 (s, 1H), 9.94 (br t, J = 6.0 Hz, 1H). |
| 4-026 | 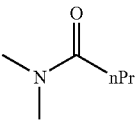 | 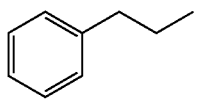 | 0.88 (t, J = 7.5 Hz, 1/3 × 3H), 1.00 (t, J = 7.5 Hz, 2/3 × 3H), 1.46 (sextet, J = 7.5 Hz, 2H), 1.65 (quint, J = 7.5 Hz, 2H), 2.82-3.01 (m, 4H), 3.66 (dt, J = 9.0 Hz, 6.0 Hz, 2H), 4.04 (t, J = 6.0 Hz, 2H), 4.07 (t, J = 7.8 Hz, 2H), 4.39 (br s, 2/3 × 2H), 4.73 (br s, 1/3 × 2H), 7.20-7.37 (m, 7H), 8.07 (s, 2/3 × 1H), 8.35 (s, 1/3 × 1H), 8.76 (d, J = 4.8 Hz, 2H), 9.85 (br t, J = 6.0 Hz, 1H). |

TABLE 26

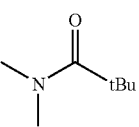

| Compound No. | R<sup>r</sup> | n | ¹H-NMR (CDCl₃) |
|---|---|---|---|
| 4-051 | 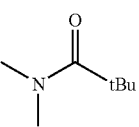 | 1 | 0.97 (t, J = 7.5 Hz, 3H), 1.41 (sextet, J = 7.5 Hz, 2H), 1.69 (quint, J = 7.5 Hz, 2H), 2.19 (quint, J = 7.5 Hz, 2H), 2.85 (t, J = 7.5 Hz, 2H), 3.00 (t, J = 7.5 Hz, 2H), 3.98 (t, J = 7.8 Hz, 2H), 4.64 (d, J = 6.0 Hz, 2H), 7.23-7.39 (m, 5H), 8.46 (s, 1H), 10.31 (br t, J = 6.0 Hz, 1H). |
| 4-052 | 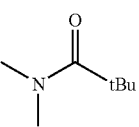 | 1 | 0.98 (t, J = 7.5 Hz, 3H), 1.41 (sextet, J = 7.5 Hz, 2H), 1.70 (quint, J = 7.5 Hz, 2H), 2.19 (quint, J = 7.5 Hz, 2H), 2.85 (t, J = 7.5 Hz, 2H), 2.93 (t, J = 7.5 Hz, 2H), 3.00 (t, J = 7.5 Hz, 2H), 3.67 (dt, J = 9.0 Hz, 6.0 Hz, 2H), 3.99 (t, J = 7.8 Hz, 2H), 7.18-7.34 (m, 5H), 8.43 (s, 1H), 10.05 (br t, J = 6.0 Hz, 1H). |

TABLE 26-continued

| Compound No. | R' | n | ¹H-NMR (CDCl₃) |
|---|---|---|---|
| 4-053 | (benzyl / phenylmethyl) | 3 | 0.98 (t, J = 7.5 Hz, 3H), 1.44 (sextet, J = 7.5 Hz, 2H), 1.57-1.65 (m, 4H), 1.68 (quint, J = 6.0 Hz, 2H), 1.86 (quint, J = 6.0 Hz, 2H), 2.71 (t, J = 6.0 Hz, 2H), 2.94 (t, J = 6.0 Hz, 2H), 4.15 (br t, J = 7.8 Hz, 2H), 4.64 (d, J = 6.0 Hz, 2H), 7.22-7.38 (m, 5H), 8.33 (s, 1H), 10.31 (br t, J = 6.0 Hz, 1H). |
| 4-054 | (phenethyl) | 3 | 0.99 (t, J = 7.5 Hz, 3H), 1.46 (sextet, J = 7.5 Hz, 2H), 1.60-1.67 (m, 4H), 1.69 (quint, J = 6.0 Hz, 2H), 1.86 (quint, J = 6.0 Hz, 2H), 2.71 (t, J = 6.0 Hz, 2H), 2.71 (t, J = 7.5 Hz, 2H), 2.72 (t, J = 6.0 Hz, 2H), 3.66 (dt, J = 9.0 Hz, 6.0 Hz, 2H), 4.17 (br t, J = 7.8 Hz, 2H), 7.19-7.34 (m, 5H), 8.29 (s, 1H), 10.05 (br t, J = 6.0 Hz, 1H). |
| 4-055 | (4-fluorobenzyl) | 3 | 0.98 (t, J = 7.5 Hz, 3H), 1.44 (sextet, J = 7.5 Hz, 2H), 1.58-1.65 (m, 4H), 1.69 (quint, J = 6.0 Hz, 2H), 1.86 (quint, J = 6.0 Hz, 2H), 2.71 (t, J = 6.0 Hz, 2H), 2.94 (t, J = 6.0 Hz, 2H), 4.15 (br t, J = 7.8 Hz, 2H), 4.59 (d, J = 6.0 Hz, 2H), 6.99 (t, J = 9.0 Hz, 2H), 7.32 (dd, J = 9.0 Hz, 6.0 Hz, 2H), 8.32 (s, 1H), 10.32 (brt, J = 6.0 Hz, 1H). |
| 4-056 | (4-fluorophenethyl) | 3 | 0.99 (t, J = 7.5 Hz, 3H), 1.45 (sextet, J = 7.5 Hz, 2H), 1.57-1.66 (m, 4H), 1.69 (quint, J = 6.0 Hz, 2H), 1.86 (quint, J = 6.0 Hz, 2H), 2.71 (t, J = 6.0 Hz, 2H), 2.89 (t, J = 7.5 Hz, 2H), 2.94 (t, J = 6.0 Hz, 2H), 3.63 (dt, J = 9.0 Hz, 6.0 Hz, 2H), 4.16 (br t, J = 7.8 Hz, 2H), 6.97 (t, J = 9.0 Hz, 2H), 7.20 (dd, J = 9.0 Hz, 6.0 Hz, 2H), 8.29 (s, 1H), 10.04 (br t, J = 6.0 Hz, 1H) |

TABLE 27

| Compound No. | R' | n | ¹H-NMR (CDCl₃) |
|---|---|---|---|
| 4-057 | (4-hydroxyphenethyl) | 3 | 0.99 (t, J = 7.5 Hz, 3H), 1.45 (sextet, J = 7.5 Hz, 2H), 1.57-1.68 (m, 4H), 1.69 (quint, J = 6.0 Hz, 2H), 1.86 (quint, J = 6.0 Hz, 2H), 2.70 (t, J = 6.0 Hz, 2H), 2.84 (t, J = 7.5 Hz, 2H), 2.94 (t, J = 6.0 Hz, 2H), 3.63 (dt, J = 9.0 Hz, 6.0 Hz, 2H), 4.16 (br t, J = 7.8 Hz, 2H), 6.22 (br s, 1H), 6.76 (d, J = 8.4 Hz, 2H), 7.06 (d, J = 8.4 Hz, 2H), 8.29 (s, 1H), 10.10 (br t, J = 6.0 Hz, 1H). |

TABLE 28

| Compound No. | R<sup>r</sup> | n | ¹H-NMR (CDCl₃) |
|---|---|---|---|
| 4-058 | 4-aminophenethyl (H₂N-C₆H₄-CH₂CH₂-) | 3 | 0.99 (t, J = 7.5 Hz, 3H), 1.45 (sextet, J = 7.5 Hz, 2H), 1.57-1.68 (m, 4H), 1.69 (quint, J = 6.0 Hz, 2H), 1.86 (quint, J = 6.0 Hz, 2H), 2.70 (t, J = 6.0 Hz, 2H), 2.81 (t, J = 7.5 Hz, 2H), 2.93 (t, J = 6.0 Hz, 2H), 3.60 (dt, J = 9.0 Hz, 6.0 Hz, 2H), 4.16 (br t, J = 7.8 Hz, 2H), 6.40 (d, J = 8.4 Hz, 2H), 7.05 (d, J = 8.4 Hz, 2H), 8.29 (s, 1H), 10.00 (br t, J = 6.0 Hz, 1H). |
| 4-059 | 3,4-dihydroxyphenethyl | 3 | 0.98 (t, J = 7.5 Hz, 3H), 1.44 (sextet, J = 7.5 Hz, 2H), 1.56-1.68 (m, 4H), 1.69 (quint, J = 6.0 Hz, 2H), 1.87 (quint, J = 6.0 Hz, 2H), 2.71 (t, J = 6.0 Hz, 2H), 2.94 (t, J = 6.0 Hz, 2H), 4.16 (br t, J = 7.8 Hz, 2H), 4.48 (d, J = 6.0 Hz, 2H), 6.05 (br s, 1H), 6.53 (br s, 1H), 6.74 (s, 2H), 6.87 (s, 1H), 8.30 (s, 1H), 10.35 (br t, J = 6.0 Hz, 1H). |
| 4-060 | 4-carboxybenzyl (HO₂C-C₆H₄-CH₂-) | 3 | 0.99 (t, J = 7.5 Hz, 3H), 1.45 (sextet, J = 7.5 Hz, 2H), 1.56-1.69 (m, 4H), 1.70 (quint, J = 6.0 Hz, 2H), 1.87 (quint, J = Hz, 2H), 2.72 (t, J = 6.0 Hz, 2H), 2.95 (t, J = 6.0 Hz, 2H), 4.18 (br t, J = 7.8 Hz, 2H), 4.70 (d, J = 6.0 Hz, 2H), 7.43 (d, J = 8.1 Hz, 2H), 8.00 (d, J = 8.1 Hz, 2H), 8.33 (s, 1H), 10.44 (br t, J = 6.0 Hz, 1H). |
| 4-061 | benzyl | 6 | 0.97 (t, J = 7.5 Hz, 3H), 1.26-1.34 (m, 4H), 1.42 (sextet, J = 7.5 Hz, 2H), 1.46-1.60 (m, 4H), 1.65 (quint, J = 7.5 Hz, 2H), 1.80 (quint, J = 6.0 Hz, 2H), 1.87 (quint, J = 6.0 Hz, 2H), 2.73 (t, J = 6.0 Hz, 2H), 2.93 (br t, J = 6.0 Hz, 2H), 4.12 (br t, J = 7.8 Hz, 2H), 4.64 (d, J = 6.0 Hz, 2H), 7.23-7.41 (m, 5H), 8.38 (s, 1H), 10.36 (br t, J = 6.0 Hz, 1H |
| 4-062 | phenethyl | 6 | 0.98 (t, J = 7.5 Hz, 3H), 1.24-1.33 (m, 4H), 1.46 (sextet, J = 7.5 Hz, 2H), 1.47-1.58 (m, 4H), 1.66 (quint, J = 7.5 Hz, 2H), 1.80 (quint, J = 6.0 Hz, 2H), 1.86 (quint, J = 6.0 Hz, 2H), 2.73 (t, J = 6.0 Hz, 2H), 2.94 (t, J = 7.5 Hz, 2H), 2.95 (t, J = 6.0 Hz, 2H), 3.67 (dt, J = 9.0 Hz, 6.0 Hz, 2H), 4.14 (br t, J = 7.8 Hz, 2H), 7.21-7.34 (m, 5H), 8.35 (s, 1H), 10.10 (br t, J = 6.0 Hz, 1H). |

TABLE 29

| Compound No. | R<sup>r</sup> | ¹H-NMR (CDCl₃) |
|---|---|---|
| 4-101 | phenethyl | 0.97 (t, J = 7.5 Hz, 3H), 1.35-1.53 (m, 4H), 1.44 (sextet, J = 7.5 Hz, 2H), 1.60-1.78 (m, 6H), 2.64 (t, J = 6.0 Hz, 2H), 2.88 (t, J = 6.0 Hz, 2H), 4.09 (br t, J = 7.8 Hz, 2H), 4.64 (d, J = 6.0 Hz, 2H), 7.17-7.39 (m, 5H), 8.34 (s, 1H), 10.34 (br t, J = 6.0 Hz, 1H). |

TABLE 29-continued

[Structure: cycloocta-fused 2-oxo-1-nBu-pyridine-3-carboxamide with R'NH-C(=O)-]

| Compound No. | R' | $^1$H-NMR (CDCl$_3$) |
|---|---|---|
| 4-0102 | phenethyl | 0.99 (t, J = 7.5 Hz, 3H), 1.34-1.53 (m, 4H), 1.46 (sextet, J = 7.5 Hz, 2H), 1.62-1.80 (m, 6H), 2.64 (t, J = 6.0 Hz, 2H), 2.89 (t, J = 6.0 Hz, 2H), 2.94 (t, J = 7.5 Hz, 2H), 3.67 (dt, J = 9.0 Hz, 6.0 Hz, 2H), 4.10 (br t, J = 7.8 Hz, 2H), 7.18-7.34 (m, 5H), 8.31 (s, 1H), 10.07 (br t, J = 6.0 Hz, 1H). |
| 4-0103 | 4-F-phenethyl | 0.99 (t, J = 7.5 Hz, 3H), 1.36-1.58 (m, 4H), 1.46 (sextet, J = 7.5 Hz, 2H); 1.59-1.74 (m, 4H), 1.76 (quint, J = 6.0 Hz, 2H), 2.64 (t, J = 6.0 Hz, 2H), 2.89 (t, J = 6.0 Hz, 2H), 2.90 (t, J = 7.5 Hz, 2H), 3.64 (dt, J = 9.0 Hz, 6.0 Hz, 2H), 4.09 (br t, J = 7.8Hz, 2H), 6.98 (t, J = 8.4 Hz, 2H), 7.21 (dt, J = 9.0 Hz, 6.0 Hz, 2H), 8.30 (s, 1H), 10.06 (br t, J =6.0 Hz, 1H). |
| 4-104 | 4-H$_2$N-phenethyl | 0.99 (t, J = 7.5 Hz, 3H), 1.37-1.52 (m, 4H), 1.46 (sextet, J = 7.5 Hz, 2H), 1.61-1.73 (m, 4H), 1.76 (quint, J = 6.0 Hz, 2H), 2.64 (t, J = 6.0 Hz, 2H), 2.82 (t, J = 7.5 Hz, 2H), 2.88 (t, J = 6.0 Hz, 2H), 3.61 (dt, J = 9.0 Hz, 6.0 Hz, 2H), 4.09 (br t, J = 7.8 Hz, 2H), 6.64 (d, J = 8.4 Hz, 2H), 7.05 (d, J =8.4 Hz, 2H), 8.30 (s, 1H), 10.02 (br t, J = 6.0 Hz, 1H). |
| 4-105 | 4-HO-phenethyl | 0.99 (t, J = 7.5 Hz, 3H), 1.36-1.52 (m, 4H), 1.45 (sextet, J = 7.5 Hz, 2H), 1.60-1.72 (m, 4H), 1.76 (quint, J = 6.0 Hz, 2H), 2.63 (t, J = 6.0 Hz, 2H), 2.85 (t, J = 7.5 Hz, 2H), 2.88 (t, J = 6.0 Hz, 2H), 3.63 (dt, J = 9.0 Hz, 6.0 Hz, 2H), 4.10 (br t, J = 7.8 Hz, 2H), 6.76 (d, J = 8.4 Hz, 2H), 7.08 (d, J =8.4 Hz, 2H), 8.31 (s, 1H), 10.10 (br t, J = 6.0 Hz, 1H). |

TABLE 30

[Structure: cycloocta-fused 2-oxo-1-R$^5$-pyridine-3-carboxamide with R'NH-C(=O)-]

| Compound No. | R' | R$^5$ | $^1$H-NMR (CDCl$_3$) |
|---|---|---|---|
| 4-301 | benzyl | -(CH$_2$)$_3$-OMe | 1.36 (quint, J = 6.0 Hz, 2H), 1.49 (quint, J = 6.0 Hz, 2H), 1.61-1.68 (m, 2H), 1.69 (quint, J = 6.0 Hz, 2H), 2.66 (t, J = 6.0 Hz, 2H), 3.03 (t, J = 6.0 Hz, 2H), 3.30 (s, 3H), 3.67 (t, J = 5.4 Hz, 2H), 4.32 (t, J = 5.4 Hz, 2H), 4.64 (d, J = 6.0 Hz, 2H), 7.26-7.40 (m, 5H), 8.36 (s, 1H), 10.25 (br t, J = 6.0 Hz, 1H). |
| 4-302 | phenethyl | -(CH$_2$)$_3$-OMe | 1.38 (quint, J = 4.8 Hz, 2H), 1.49 (quint, J = 4.8 Hz, 2H), 1.60-1.67 (m, 2H), 1.70 (quint, J = 6.0 Hz, 2H), 2.66 (t, J = 6.0 Hz, 2H), 2.94 (t, J = 7.5 Hz, 2H), 3.03 (t, J = 6.0 Hz, 2H), 3.31 (s, 3H), 3.67 (dt, J = 9.0 Hz, 6.0 Hz, 2H), 3.68 (t, J = 5.4 Hz, 2H), 4.33 (t, J = 5.4 Hz, 2H), 7.24-7.34 (m, 5H), 8.33 (s,1H), 9.98 (br t, J = 6.0 1H). |

TABLE 30-continued

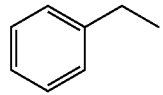

| Compound No. | R$^r$ | R$^5$ | $^1$H-NMR (CDCl$_3$) |
|---|---|---|---|
| 4-303 | benzyl (CH$_2$Ph) | 4-methylpentyl | 0.99 (d, J = 6.7 Hz, 6H), 1.32-1.82 (m, 11H), 2.64 (t, J = 6.3 Hz, 2H), 2.87 (t, J = 6.3 Hz, 2H), 3.98-4.20 (br s, 2H), 4.64 (d, J = 5.8 Hz, 2H), 7.23-7.40 (m, 5H), 8.34 (s, 1H), 10.3 (t-like). |
| 4-304 | benzyl | 3-(4-pyridyl)propyl | (CD$_3$OD): 1.24-1.57 (m, 2H), 1.64-1.85 (m, 2H), 2.70 (t-like, 2H), 2.94 (t-like, 2H), 3.06 (t, J = 7.5 Hz, 2H), 4.41 (t, J = 7.5 Hz, 2H), 4.61 (s, 2H), 7.22-7.40 (m, 7H), 8.44 (A$_2$B$_2$, J = 5.2 Hz), 8.26 (d, J = 0.9 Hz, 1H). |
| 4-305 | benzyl | 3-(piperidin-1-yl)propyl | 1.32-1.82 (m, 14H), 2.38-2.53 (m, 4H), 2.57 (t, J = 7.5 Hz, 2H), 2.64 (t, J = 6.0 Hz, 2H), 2.94 (t, J = 6.4 Hz, 2H), 4.26 (t-like, 1H), 4.64 (d, J = 5.8 Hz, 2H), 7.22-7.39 (m, 5H), 8.34 (s, 1H), 10.29 (d, J = 5.8 Hz, 2H). |
| 4-306 | benzyl | 4-(imidazol-1-yl)butyl | 1.32-1.50 (m, 4H), 1.52-1.72 (m, 4H), 2.17 (quint, J = 6.7 Hz, 2H), 2.52-2.70 (m, 4H), 3.98-4.10 (m, 2H), 4.10 (t, J = 6.7 Hz, 2H), 4.65 (d, J = 5.8 Hz, 2H), 6.98 (s, 1H), 7.10 (s, 1H), 7.22-7.40 (m, 5H), 7.54 (s, 1H), 8.35 (s, 1H), 10.19 (t, J = 5.8 Hz, 1H). |

TABLE 31

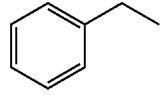

| Compound No. | R$^r$ | R$^5$ | $^1$H-NMR (CDCl$_3$) |
|---|---|---|---|
| 4-307 | benzyl | 4-(morpholin-4-yl)butyl | 1.34-1.54 (m, 4H), 1.60-1.81 (m, 4H), 1.82-1.94 (m, 2H), 2.28-2.50 (m, 6H), 2.64 (t, J=6.4 Hz, 2H), 2.93 (t, J=6.4 Hz, 2H), 3.70 (t, J=4.5 Hz, 2H), 4.17 (t, J=7.5 Hz, 2H), 4.64 (d, J=5.8 Hz, 2H), 7.20-7.39 (m, 5H), 8.34 (s, 1H), 10.29 (t-like, 1H). |
| 4-308 | benzyl | 3-(3-pyridyl)propyl | 1.30-1.42 (m, 2H), 1.42-1.52 (m, 2H), 1.60-1.80 (m, 4H), 2.64 (t, J=5.9 Hz, 2H), 2.79 (t, J=6.1 Hz, 2H), 3.01 (t, J=7.7 Hz, 2H), 4.31 (t, J=7.7 Hz, 2H), 4.87 (t, J=5.8 Hz, 2H), 7.14-7.28 (m, 2H), 7.30-7.42 (m, 4H), 7.57 (ddd, J=6.0, 1.9, 1.9 Hz, 2H), 8.38 (s, 1H), 8.51 (d-like, 2H), 10.3 (t, J=5.8 Hz, 1H). |

TABLE 31-continued

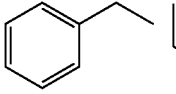

| Compound No. | R^r | R^5 | $^1$H-NMR (CDCl$_3$) |
|---|---|---|---|
| 4-309 | 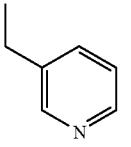 | 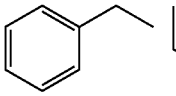 | 1.37-1.53 (m, 4H), 1.60-1.80 (m, 4H), 2.66 (t, J=6.1 Hz, 2H), 2.81 (t, J=6.4 Hz, 2H), 4.64 (t, J=5.8 Hz, 2H), 5.44 (br s, 2H), 7.20-7.42 (m, 7H), 8.45 (s, 1H), 8.45-8.58 (m, 2H), 10.1 (t, J=5.8 Hz, 1H). |
| 4-310 | 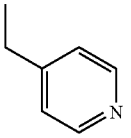 | 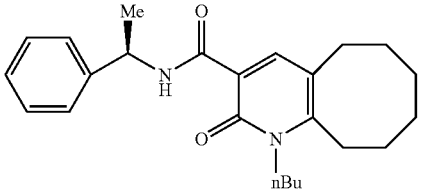 | 1.35-1.55 (m, 4H), 1.60-1.80 (m, 4H), 2.68 (t, J=5.9 Hz, 2H), 2.74 (t, J=6.1 Hz, 2H), 4.62 (t, J=5.8 Hz, 2H), 5.42 (br s, 2H), 6.97 (A$_2$B$_2$, J=6.1 Hz, 2H), 7.19-7.37 (m, 5H), 8.47 (s, 1H), 8.54-8.58 (m, 2H), 10.1 (t-like, 1H). |

TABLE 32

| Compound No. | Structure | $^1$H-NMR (CDCl$_3$) |
|---|---|---|
| 4-311 | 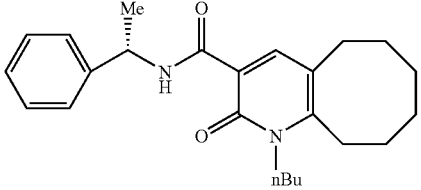 | 0.99 (t, J=7.4 Hz, 3H), 1.36-1.75 (m, 12H), 2.62 (t, J=5.9 Hz, 2H), 2.88 (t, J=6.3 Hz, 2H), 4.08 (brs, 2H), 5.31 (m, 1H), 7.14-7.42 (m, 5H), 8.29 (s, 1H), 10.35 (d, J=7.5 Hz, 1H). |
| 4-312 | 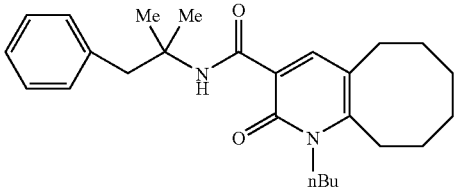 | 0.99 (t, J=7.4 Hz, 3H), 1.36-1.75 (m, 12H), 2.62 (t, J=5.9 Hz, 2H), 2.88 (t, J=6.3 Hz, 2H), 4.08 (brs, 2H), 5.31 (m, 1H), 7.14-7.42 (m, 5H), 8.29 (s, 1H), 10.35 (d, J=7.5 Hz, 1H). |
| 4-313 | 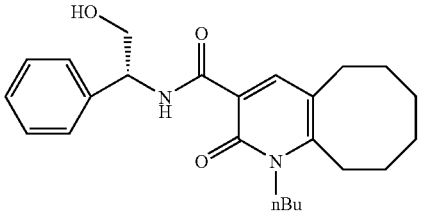 | 0.98 (t, J=7.1 Hz, 3H), 1.40-1.76 (m, 12H), 1.42 (s, 6H), 2.64 (t, J=6.0 Hz, 2H), 2.88 (t, J=6.5 Hz, 2H), 3.19 (s, 2H), 4.07 (brs, 2H), 7.16-7.26 (m, 5H), 8.33 (s, 1H), 9.87 (s, 1H). |
| 4-314 | 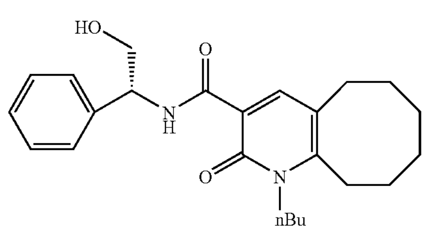 | 0.98 (t, J=7.4 Hz, 3H), 1.39-1.76 (m, 12H), 2.64 (t, J=5.9 Hz, 2H), 2.89 (t, J=6.3 Hz, 2H), 3.93 (dd, J=11.4, 4.5 Hz, 1H), 3.97 (dd, J=11.4, 6.9 Hz, 1H), 4.10 (brs, 2H), 5.31 (m, 1H), 7.27-7.46 (m, 5H), 8.31 (s, 1H), 10.75 (d, J=6.3 Hz, 1H). |

TABLE 32-continued

| Compound No. | Structure | ¹H-NMR (CDCl₃) |
|---|---|---|
| 4-315 | 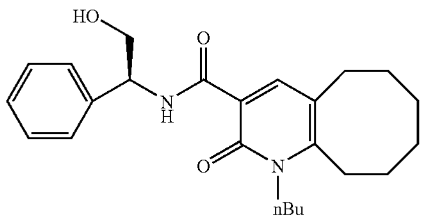 | 0.98 (t, J=7.4 Hz, 3H), 1.39-1.76 (m, 12H), 2.64 (t, J=5.9 Hz, 2H), 2.89 (t, J= 6.3 Hz, 2H), 3.93 (dd, J=11.4, 4.5 Hz, 1H), 3.97 (dd, J=11.4, 6.9 Hz, 1H), 4.10 (brs, 2H), 5.31 (m, 1H), 7.27-7.46 (m, 5H), 8.31 (s, 1H), 10.75 (d, J=6.3 Hz, 1H). |
| 4-316 | 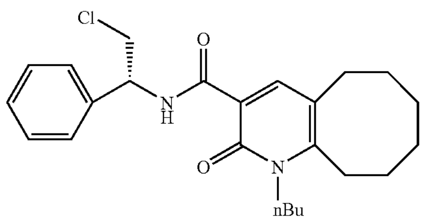 | 0.99 (t, J=7.2 Hz, 3H), 1.32-1.76 (m, 12H), 2.63 (t, J=5.9 Hz, 2H), 2.89 (t, J= 6.0 Hz, 2H), 3.91 (d, J=5.7 Hz, 2H), 4.12 (brs, 2H), 5.54 (m, 1H), 7.28-7.45 (m, 5H), 8.29 (s, 1H), 10.77 (d, J=7.5 Hz, 1H). |
| 4-317 | 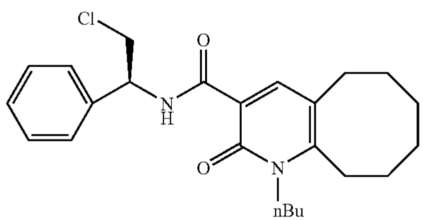 | 0.99 (t, J=7.2 Hz, 3H), 1.32-1.76 (m, 12H), 2.63 (t, J=5.9 Hz, 2H), 2.89 (t, J= 6.0 Hz, 2H), 3.91 (d, J=5.7 Hz, 2H), 4.12 (brs, 2H), 5.54 (m, 1H), 7.28-7.45 (m, 5H), 8.29 (s, 1H), 10.77 (d, J=7.5 Hz, 1H). |
| 4-318 | 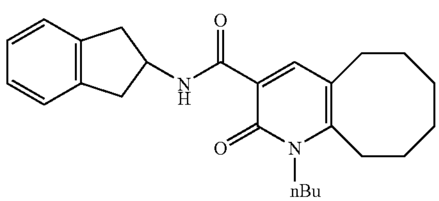 | 0.97 (t, J=7.4 Hz, 3H), 1.38-1.75 (m, 12H), 2.64 (t, J =6.0 Hz, 2H), 2.88 (t, J= 6.2 Hz, 2H), 2.99 (dd, J=16.0, 6.6 Hz, 2H), 3.41 (dd, J=16.0, 7.5 Hz, 2H), 4.07 (brs, 2H), 4.88 (m, 1H), 7.15-7.24 (m, 4H), 8.32 (s, 1H), 10.17 (d, J=6.0 Hz, 1H). |

TABLE 33

| Compound No. | Structure | ¹H-NMR (CDCl₃) |
|---|---|---|
| 4-319 | 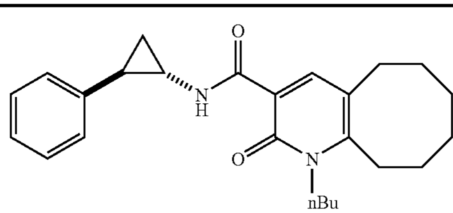 | 0.99 (t, J=7.2 Hz, 3H), 1.25-1.77 (m, 12H), 2.18 (m, 1H), 2.64 (t, J=6.0 Hz, 2H), 2.89 (t, J=6.4 Hz, 2H), 3.14 (m, 1H), 4.10 (brs, 2H), 7.16-7.30 (m, 5H), 8.33 (s, 1H), 10.12 (d, J=3.6 Hz, 1H). |
| 4-320 | 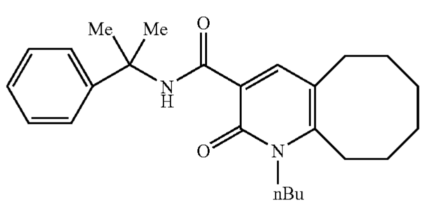 | 1.00 (t, J=7.2 Hz, 3H), 1.30-1.55 (m, 6H), 1.59 (s, 6H), 1.56-1.89 (m, 6H), 2.58 (t, J=6.0 Hz, 2H), 2.88 (t, J=6.3 Hz, 2H), 4.00-4.23 (m, 2H), 7.10-7.40 (m, 5H), 7.46 (d, J=8.4 Hz, 2H), 8.23 (s, 1H). |

TABLE 33-continued

| Compound No. | Structure | $^1$H-NMR (CDCl$_3$) |
|---|---|---|
| 4-321 | 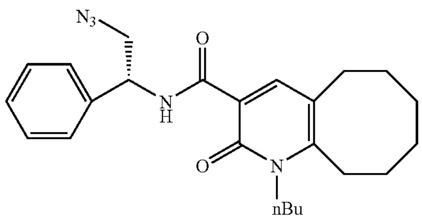 | 1.35-2.04 (m, 8H), 2.03-2.15 (m, 2H), 2.64 (t, J=6.0 Hz, 2H), 2.88-2.96 (m, 4H), 3.63-3.71 (m, 2H), 3.78 (t, J=6.0 Hz, 2H), 4.05 (dd, J=6.9, 2.1 Hz, 2H), 4.18-4.27 (m, 3H), 6.49 (dd, J=14.1, 6.6 Hz, 1H), 7.15-7.35 (m, 5H), 8.32 (s, 1H), 10.01 (brs, 1H). |
| 4-322 | 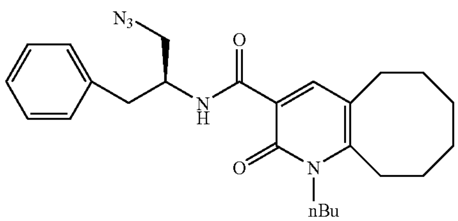 | 1.35-2.04 (m, 8H), 2.03-2.15 (m, 2H), 2.64 (t, J=6.0 Hz,: 2H), 2.88-2.96 (m, 4H), 3.63-3.71 (m, 2H), 3.78 (t, J=6.0 Hz, 2H), 4.05 (dd, J=6.9, 2.1 Hz, 2H), 4.18-4.27 (m, 3H), 6.49 (dd, J=14.1, 6.6 Hz, 1H), 7.15-7.35 (m, 5H), 8.32 (s, 1H), 10.01 (brs, 1H). |
| 4-323 | 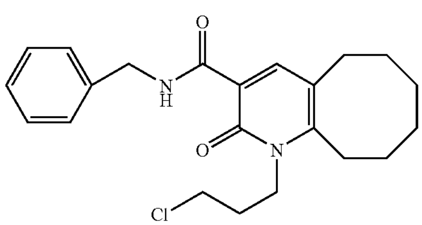 | 1.20-1.90 (m, 8H), 2.13-2.28 (m, 2H), 2.55-2.72 (m, 2H), 2.82-3.02 (m, 2H), 3.62-3.78 (m, 2H), 4.20-4.38 (m, 2H), 4.64 (d, J=6.3 Hz, 2H), 7.18-7.43 (m, 5H), 8.36 (s, 1H). |
| 4-324 | 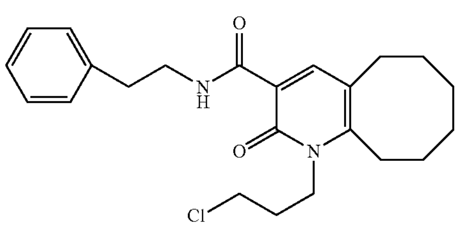 | 1.20-1.90 (m, 8H), 2.12-2.28 (m, 2H), 2.65 (t, J=6.6 Hz, 2H), 2.92-3.02 (m, 4H), 3.60 3.78 (m, 4H), 4.29 (t, J=9.0 Hz, 2H), 7.10-7.40 (m, 5H), 8.33 (s, 1H). |
| 4-325 | 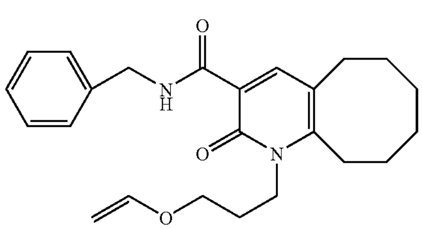 | 1.37-1.80 (m, 8H), 2.02 (m, 2H), 2.65 (t, J=6.3 Hz, 2H), 2.92 (t, J=6.6 Hz, 2H), 3.77 (t, J=5.4 Hz, 2H), 4.04 (dd, J=6.9, 2.1 Hz, 1H), 4.16-4.26 (m, 3H), 4.65 (d, J=6.0 Hz, 2H), 6.48 (dd, J=14.1, 6.6 hz, 1H), 7.21-7.42 (m, 5H), 8.35 (s, 1H), 10.29 (brs, 1H). |
| 4-326 | 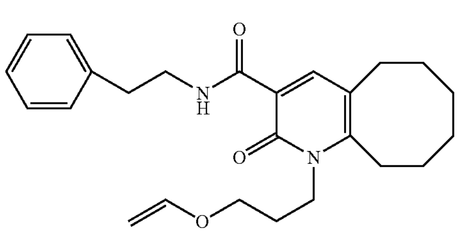 | 1.37 (m, 8H), 2.07 (m, 2H), 2.64 (t, J=6.0 Hz, 2H), 2.64 (t, J=6.0 Hz, 2H), 2.90-2.96 (m, 4H), 3.63-3.71 (m, 2H), 3.78 (t, J=6.0 Hz, 2H),4.05 (dd, J=6.9 Hz, 2.1 Hz, 1H), 4.18-4.27 (m, 3H), 6.49 (dd, J=14.1, 6.6 Hz, 1H), 7.18-7.33 (m, 5H), 8.32 (s, 1H), 10.01 (brs, 1H). |

TABLE 34

| Compound No. | Structure | $^1$H-NMR (CDCl$_3$) |
|---|---|---|
| 4-327 | 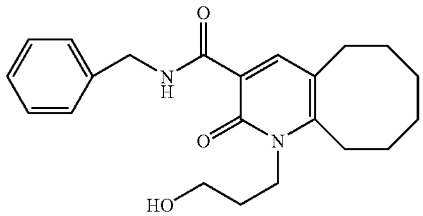 | 1.38-1.81 (m, 8H), 1.88-1.96 (m, 2H), 2.66 (t, J=6.3 Hz, 2H), 2.93 (t, J=6.3 Hz, 2H), 3.52 (t, J=5.1 Hz, 2H), 3.72 (brs, 1H), 4.65 (d, J=6.3 Hz, 2H), 7.22-7.38 (m, 5H), 8.40 (s, 1H), 10.18 (brs, 1H). |
| 4-328 | 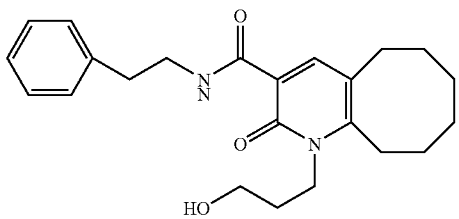 | 1.38-1.95 (m, 10H), 2.65 (t, J=6.0 Hz, 2H), 2.90-2.94 (m, 4H), 3.45-3.52 (m, 2H), 3.65-3.72 (m, 2H), 3.91 (brs, 1H), 4.34 (brs, 2H), 7.20-7.35 (m, 5H), 8.37 (s, 1H), 9.88 (brs, 1H). |
| 4-329 | 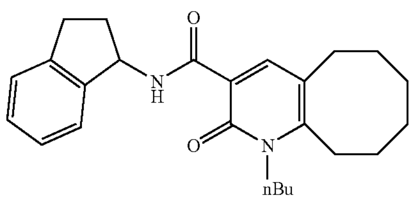 | 0.96 (t, J=6.9 Hz, 3H), 1.30-1.55 (m, 6H), 1.55-1.82 (m, 6H), 1.97 (ddd, J=16.5, 12.9, 8.4 Hz, 1H), 2.60-2.73 (m, 3H), 2.84-2.96 (m, 3H), 3.03 (ddd, J=16.5, 9.3, 3.6 Hz, 1H), 3.93-4.20 (m, 2H), 5.67 (q-like, 1H), 7.10-7.35 (m, 3H), 7.38 (m, 1H), 8.37 (s, 1H). |
| 4-330 | 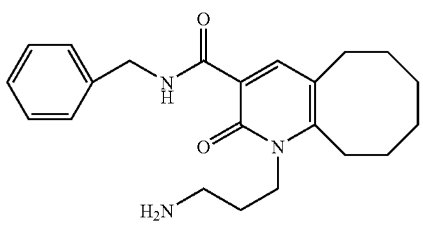 | 1.25-1.28 (m, 14H), 2.65 (t, J=6.0 Hz, 2H), 2.80 (brs, 2H), 2.92 (t, J=6.0 Hz, 2H), 4.22 (m, 2H), 4.65 (d, J=6.0 Hz, 2H), 7.24-7.39 (m, 5H), 8.36 (s, 1H), 10.25 (brs, 1H). |
| 433-1 | 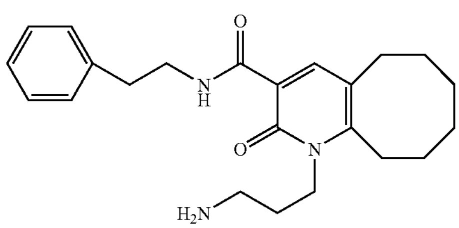 | 1.37-1.90 (m, 12H), 2.64 (t, J=6.3 Hz, 2H), 2.80 (m, 2H), 2.90-2.96 (m, 4H), 3.68 (q, J=6.3 Hz, 2H), 4.23 (brs, 2H), 7.21-7.33 (m, 5H), 8.33 (s, 1H), 9.98 (brs, 1H). |
| 4-332 | 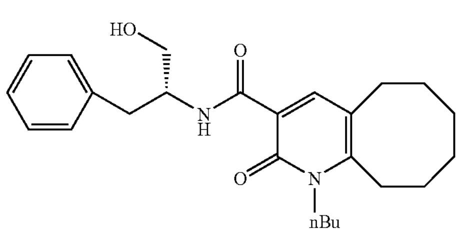 | 1.00 (t, J=7.5 Hz, 3H), 1.33-1.54 (m, 6H), 1.55-1.79 (m, 6H), 2.63 (t, J=6.0 Hz, 2H), 2.89 (t, J=6.3 Hz, 2H), 2.98 (d, J=7.5 Hz, 2H), 3.66 (dd, J=10.1, 6.3 Hz, 1H), 3.79 (dd, J=10.1, 3.6 Hz, 1H), 4.33 (m, 1H), 7.18-7.40 (m, 5H), 8.27 (s, 1H). |
| 4-333 | 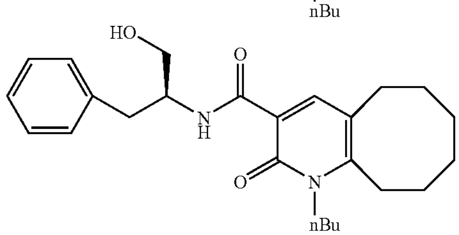 | 1.00 (t, J=7.5 Hz, 3H), 1.33-1.54 (m, 6H), 1.55-1.79 (m, 6H), 2.63 (t, J=6.0 Hz, 2H), 2.89 (t, J=6.3 Hz, 2H), 2.98 (d, J=7.5 Hz, 2H), 3.66 (dd, J=10.1, 6.3 Hz, 1H), 3.79 (dd, J=10.1, 3.6 Hz, 1H), 4.33 (m, 1H), 7.18-7.40 (m, 5H), 8.27 (s, 1H). |

TABLE 35

| Compound No. | Structure | ¹H-NMR (CDCl₃) |
|---|---|---|
| 4-501 | 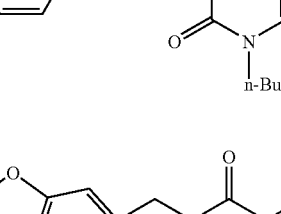 | 0.95 (t, J=7.5 Hz, 3H), 1.37 (sextet, J= 7.5 Hz, 2H), 1.66-1.77 (m, 6H), 2.57 (br t, J=6.3 Hz, 2H), 3.27 (br t, J=6.3 Hz, 2H), 3.92 (t, J=7.5 Hz, 2H), 4.60 (d, J= 5.7 Hz, 2H), 7.12 (s, 1H), 7.23-7.40 (m, 5H), 9.58 (br t, J=5.7 Hz, 1H). |
| 4-502 | 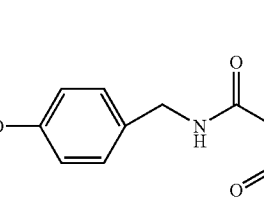 | 0.95 (t, J=7.5 Hz, 3H), 1.37 (sextet, J= 7.5 Hz, 2H), 1.66-1.77 (m, 6H), 2.56 (br t, J=6.3 Hz, 2H), 3.27 (br t, J=6.3 Hz, 2H), 3.92 (t, J=7.5 Hz, 2H), 4.50 (d, J=7.5 Hz, 2H), 5.92 (s, 2H), 6.75 (d, J=8.4 Hz, 1H), 6.83 (d, J=8.4 Hz, 1H), 6.88 (s, 1H), 7.13 (s, 1H), 9.58 (br s, 1H). |
| 4-503 | 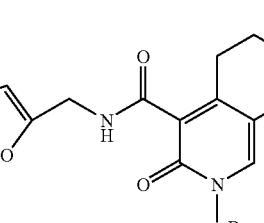 | 0.95 (t, J=7.5 Hz, 3H), 1.37 (sextet, J= 7.5 Hz, 2H), 1.65-1.77 (m, 6H), 2.56 (br t, J=6.3 Hz, 2H), 3.27 (br t, J=6.3 Hz, 2H), 3.79 (s, 3H), 3.91 (t, J=7.5 Hz, 2H), 4.53 (s, 2H), 6.86 (d, J=8.4 Hz, 2H), 7.12 (s, 1H), 7.30 (d, J=8.4 Hz, 2H), 9.54 (br s, 1H). |
| 4-504 | 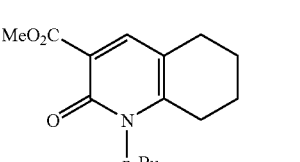 | 0.95 (t, J=7.2 Hz, 3H), 1.37 (sextet, J= 7.2 Hz, 2H), 1.66-1.78 (m, 6H), 2.56 (br t, J=6.3 Hz, 2H), 3.27 (br t, J=6.3 Hz, 2H), 3.92 (t, J=7.2 Hz, 2H), 4.58 (s, 2H), 6.27 (dd, J=3.0 Hz, 0.9 Hz, 1H), 6.30 (dd, J=3.0 Hz, 1.8 Hz, 1H), 7.13 (s, 1H), 7.35 (dd, J=1.8 Hz, 0.9 Hz, 1H), 9.65 (br s, 1H). |
| 4-505 | 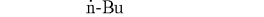 | 0.97 (t, J=7.5 Hz, 3H), 1.43 (sextet, J= 7.5 Hz, 2H), 1.63-1.78 (m, 4H), 1.87 (quint, J=6.0 Hz, 2H), 2.57 (t, J=6.0 Hz, 2H), 2.73 (t, J=6.0 Hz, 2H), 3.90 (s, 3H), 4.02 (t, J=7.8 Hz, 2H), 7.92 (s, 1H). |

TABLE 36

| Compound No. | Structure | ¹H-NMR (CDCl₃) |
|---|---|---|
| 4-506 | 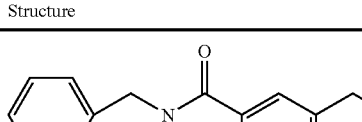 | 0.96 (t, J=7.5 Hz, 3H), 1.42 (sextet, J=7.5 Hz, 2H), 1.60-1.77 (m, 4H), 1.84 (quint, J= 6.0 Hz, 2H), 2.54 (t, J=6.0 Hz, 2H), 2.70 (t, J=6.0 Hz, 2H), 2.88 (s, 3H), 4.02 (t, J=7.8 Hz, 2H), 4.75 (s, 2H), 7.17-7.40 (m, 6H). (minor isomer): δ0.95 (t, J=7.5 Hz, 3H), 1.41 (sextet, J=7.5 Hz, 2H), 1.60-1.77 (m, 4H), 1.83 (quint, J=6.0 Hz, 2H), 2.50 (t, J= 6.0 Hz, 2H), 2.68 (t, J=6.0 Hz, 2H), 2.97 (s, 3H), 4.01 (t, J=7.8 Hz, 2H), 4.49 (s, 2H), 7.17-7.40 (m, 6H). |

TABLE 36-continued

| Compound No. | Structure | $^1$H-NMR (CDCl$_3$) |
|---|---|---|
| 4-507 | MeO$_2$C, n-Bu | 0.89 (t, J=7.5 Hz, 3H), 1.30 (sextet, J=7.5 Hz, 2H), 1.92 (quint, J=6.9 Hz, 2H), 2.57, 2.77 (ABq, J=9.0 Hz, 2H), 2.58, 2.76 (ABq, J=7.5 Hz, 2H), 3.93 (s, 3H), 4.30 (t, J=7.5 Hz, 2H), 7.31-7.41 (m, 3H), 7.56 (dd, J=7.2 Hz, 2.4 Hz, 1H), 8.10 (s, 1H). |
| 4-508 | HO$_2$C, n-Bu | 0.91 (t, J=7.5 Hz, 3H), 1.30 (sextet, J=7.5 Hz, 2H), 1.91 (quint, J=6.6 Hz, 2H), 2.65, 2.80 (ABq, J=9.0 Hz, 2H), 2.66, 2.79 (ABq, J=7.5 Hz, 2H), 4.42 (t, J=7.5 Hz, 2H), 7.38-7.46 (m, 3H), 7.57 (d, J=7.5 Hz, 1H), 8.39 (s, 1H), 14.77 (br s, 1H). |
| 4-509 | n-Bu | 0.88 (t, J=7.5 Hz, 3H), 1.27 (sextet, J=7.5 Hz, 2H), 1.87 (quint, J=6.0 Hz, 2H), 2.62, 2.78 (ABq, J=9.0 Hz, 2H), 2.64, 2.76 (ABq, J=7.5 Hz, 2H), 4.35 (t, J=7.5 Hz, 2H), 4.68 (d, J=6.0 Hz, 2H), 7.21-7.41 (m, 8H), 7.53 (dd, J=6.9 Hz, 2.4 Hz, 1H), 8.46 (s, 1H), 10.33 (br t, J=6.0 Hz, 1H). |
| 4-510 | n-Bu | 0.90 (t, J=7.5 Hz, 3H), 1.29 (sextet, J=7.5 Hz, 2H), 1.87 (quint, J=6.6 Hz, 2H), 2.62, 2.78 (ABq, J=9.0 Hz, 2H), 2.63, 2.76 (ABq, J=7.5 Hz, 2H), 2.96 (t, J=7.5 Hz, 2H), 3.66-3.74 (m, 2H), 4.36 (t, J=7.5 Hz, 2H), 7.19-7.37 (m, 8H), 7.53 (dd, J=6.9 Hz, 2.4 Hz, 1H), 8.42 (s, 1H), 10.06 (br t, J=6.0 Hz, 1H). |

TABLE 37

R$^r$—C(O)—NH—[pyridinone with Me, Me, nBu substituents]

| Compound No. | R$^r$ | $^1$H-NMR (CDCl$_3$) |
|---|---|---|
| 5-001 | Me | 0.98 (t, J=7.5 Hz, 3H), 1.37-1.50 (m, 2H), 1.60-1.70 (m, 2H), 2.12 (s, 3H), 2.17 (s, 3H), 2.30 (s, 3H), 4.10 (t, J=7.8 Hz, 2H), 8.20 (s, 1H), 8.35 (br s, 1H). |
| 5-002 | phenyl | 1.00 (t, J=7.2 Hz, 3H), 1.40-1.52 (m, 2H), 1.64-1.74 (m, 2H), 2.17 (s, 3H), 2.34 (s, 3H), 4.14 (t, J=7.8 Hz, 2H), 7.44-7.57 (m, 3H), 7.92-7.95 (m, 2H), 8.41 (s, 1H), 9.22 br s, 1H). |
| 5-003 | 2-fluorophenyl | 0.99 (t, J=7.2 Hz, 3H), 1.39-1.52 (m, 2H), 1.64-1.74 (m, 2H), 2.16 (s, 3H), 2.34 (s, 3H), 4.13 (t, J=7.8 Hz, 2H), 7.15-7.24 (m, 1H), 7.30 (dd, 1.8, 8.4 Hz, 1H), 7.47-7.54 (m, 1H), 8.12 (dt, 1.8, 7.8 Hz, 1H), 8.42 (s, 1H), 9.75 (br s) 1H). |

TABLE 37-continued

| Compound No. | R^r | ¹H-NMR (CDCl₃) |
|---|---|---|
| 5-004 | 4-F-C₆H₄- | 1.00 (t, J=7.2 Hz, 3H), 1.40-1.52 (m, 2H), 1.63-1.74 (m, 2H), 2.17 (s, 3H), 2.34 (s, 3H), 4.13 (t, J=7.8 Hz, 2H), 7.12-7.18 (m, 2H), 7.93-7.97 (m, 2H), 8.37 (s, 1H), 9.16 (br s, 1H). |
| 5-005 | 2-Cl-C₆H₄- | 0.98 (t, J=7.2 Hz, 3H), 1.38-1.50 (m, 2H), 1.64-1.72 (m, 2H), 2.17 (s, 3H), 2.34 (s, 3H), 4.11 (t, J=7.8 Hz, 2H), 7.31-7.47, (m, 3H), 7.73 (dd, J=2.1, 7.2 Hz, 1H), 8.41 (s, 1H), 9.13 (br s, 1H). |
| 5-006 | 2-Me-C₆H₄- | 0.98 (t, J=7.2 Hz, 3H), 1.38-1.50 (m, 2H), 1.61-1.72 (m, 2H), 2.17 (s, 3H), 2.34 (s, 3H), 2.53 (s, 3H), 4.11 (t, J=7.8 Hz, 2H), 7.20-7.26 (m, 2H), 7.32-7.37 (m, 1H), 7.54 (d, J=7.8 Hz, 1H), 8.39 (s, 1H), 8.74 (br s, 1H). |
| 5-007 | 3-Me-C₆H₄- | 1.00 (t, J=7.2 Hz, 3H), 1.40-1.52 (m, 2H), 1.64-1.74 (m, 2H), 2.17 (s, 3H), 2.34 (s, 3H), 2.42 (s, 3H), 4.13 (t, J=7.8 Hz, 2H), 7.35 (m, 2H), 7.74 (m, 2H), 8.41 (s, 1H), 9.21 (br s, 1H). |
| 5-008 | 4-Me-C₆H₄- | 0.99 (t, J=7.2 Hz, 3H), 1.40-1.52 (m, 2H), 1.64-1.74 (m, 2H), 2.16 (s, 3H), 2.34 (s, 3H), 2.41 (s, 3H), 4.13 (t, J=7.8 Hz, 2H), 7.27 (d, J=8.1 Hz, 2H), 7.84 (d, J=8.1 Hz, 2H), 8.40 (s, 1H), 9.20 (br s, 1H). |
| 5-009 | 3-F-C₆H₄- | 1.00 (t, J=7.2 Hz, 3H), 1.40-1.52 (m, 2H), 1.64-1.74 (m, 2H), 2.17 (s, 3H), 2.35 (s, 3H), 4.13 (t, J=7.8 Hz, 2H), 7.20-7.27 (m, 1H), 7.41-7.48 (m, 1H), 7.63-7.70 (m, 2H), 8.38 (s, 1H), 9.19 (br s, 1H). |
| 5-010 | 1-naphthyl | 0.98 (t, J=7.2 Hz, 3H), 1.38-1.50 (m, 2H), 1.62-1.73 (m, 2H), 2.20 (s, 3H), 2.36 (s, 3H), 4.12 (t, J=7.8 Hz, 2H), 7.46-7.59 (m, 3H), 7.79 (dd, J=1.2, 7.2 Hz, 1H), 7.88 (dd, 1.5, 7.2 Hz, 1H), 7.95 (d, J=8.1 Hz, 1H), 8.45 (dd, J=1.5, 7.5 Hz, 1H), 8.50 (s, 1H), 8.95 (br s, 1H). |
| 5-011 | 2-naphthyl | 1.01 (t, J=7.2 Hz, 3H), 1.42-1.54 (m, 2H), 1.66-1.76 (m, 2H), 2.19 (s, 3H), 2.36 (s, 3H), 4.16 (t, J=7.8 Hz, 2H), 7.53-7.62 (m, 2H), 7.88-8.03 (m, 4H), 8.47 (s, 2H), 9.41 (br s, 1H). |

TABLE 38

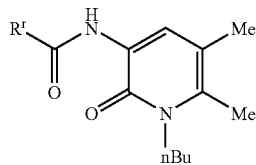

| Compound No. | R<sup>r</sup> | <sup>1</sup>H-NMR (CDCl₃) |
|---|---|---|
| 5-012 | (benzyl) | 0.96 (t, J=7.2 Hz, 3H), 1.35-1.47 (m, 2H), 1.57-1.67 (m, 2H), 2.09 (s, 3H), 2.28 (s, 3H), 3.72 (s, 2H), 4.05 (t, J=7.8 Hz,2H), 7.28-7.40 (m, 5H), 8.22 (s, 1H), 8.40 (br s, 1H). |
| 5-013 | (phenethyl) | 0.98 (t, J=7.2 Hz, 3H), 1.37-1.49 (m, 2H), 1.60-1.70 (m, 2H), 2.12 (s, 3H), 2.31 (s, 3H), 2.69 (t, J=7.5 Hz, 2H), 3.04 (t, J=7.5 Hz, 2H), 4.09 (t, J=7.8 Hz, 2H), 7.17-7.34 (m, 5H), 8.23 (s, 1H), 8.35 (br s, 1H). |
| 5-014 | (2-methyl-6-CO₂H-phenyl) | 0.92 (t, J=7.2 Hz, 3H), 1.31-1.39 (m, 2H), 1.51-1.62 (m, 2H), 2.11 (s, 3H), 2.33 (s, 3H), 4.05 (t, J=7.8 Hz, 2H), 7.54-7.64 (m, 3H), 7.83 (d, J=7.5 Hz, 1H), 8.14 (s, 1H), 8.99 (s, 1H), 13.06 (br s, 1H). |
| 5-015 | nBuO— | 0.94 (t, J=7.5 Hz, 3H), 1.35-1.49 (m, 4H), 1.60-1.70 (m, 4H), 2.11 (s, 3H), 2.29 (s, 3H), 4.09 (t, J=7.8 Hz, 2H), 4.15 (t, J=6.6 Hz, 2H), 7.73 (br s, 1H), 7.85 (br s, 1H). |
| 5-016 | (phenoxymethyl) | 0.99 (t, J=7.2 Hz, 3H), 1.39-1.51 (m, 2H), 1.62-1.73 (m, 2H), 2.11 (s, 3H), 2.31 (s, 3H), 4.13 (t, J=7.8 Hz, 2H), 7.16-7.41 (m, 5H), 7.88 (s, 1H), 8.09 (br s, 1H). |
| 5-017 | BnO— | 0.97 (t, J=7.2 Hz, 3H), 1.36-1.48 (m, 2H), 1.59-1.69 (m, 2H), 2.11 (s, 3H), 2.29 (s, 3H), 4.08 (t, J=7.8 Hz, 2H), 5.19 (s, 2H), 7.26-7.41 (m, 5H), 7.83 (s, 1H), 7.86 (s, 1H). |
| 5-018 | (2-bromophenylamino) | 0.90 (t, J=7.2 Hz, 3H), 1.27-1.40 (m, 2H), 1.57-1.67 (m, 2H), 2.14 (s, 3H), 2.31 (s, 3H), 4.09 (t, J=7.8 Hz, 2H), 6.91-6.97 (m, 1H), 7.28-7.34 (m, 1H), 7.49 (br s, 1H), 7.50-7.54 (m, 1H), 8.08-8.11 (m, 1H), 8.10 (s, 1H), 8.38 (br s, 1H). |
| 5-019 | (phenylamino) | 1.00 (t, J=7.2 Hz, 3H), 1.39-1.51 (m, 2H), 1.61-1.71 (m, 2H), 2.15 (s, 3H), 2.35 (s, 3H), 4.15 (t, J=7.8 Hz, 2H), 6.98-7.03 (m, 1H), 7.25-7.30 (m, 2H), 7.41-7.45 m, 2H), 8.03 (s, 1H). |
| 5-020 | PhSO₂NH— | 0.98 (t, J=7.2 Hz, 3H), 1.42-1.75 (m, 4H), 2.12 (s, 3H), 4.27 (t, J=7.8 Hz, 2H), 7.48-7.61 (m, 3H), 8.04-8.09 (m, 3H), 8.98 (s, 1H), 10.35 (br s, 1H). |

TABLE 39

| Compound No. | Structure | $^1$H-NMR (CDCl$_3$) |
|---|---|---|
| 5-101 | 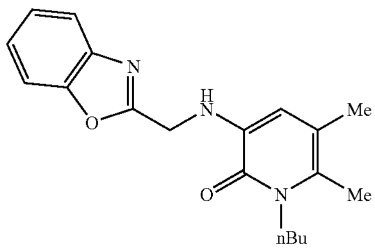 | 0.97 (t, J=7.2 Hz, 3H), 1.36-1.49 (m, 2H), 1.60-1.70 (m, 2H), 2.04 (s, 3H), 2.22 (s, 3H), 4.08 (t, J=7.5 Hz, 2H), 4.51 (s, 2H), 6.27 (s, 1H), 7.30-7.35 (m, 2H), 7.48-7.52 (m, 1H), 7.69-7.72 (m, 1H). |
| 5-102 | 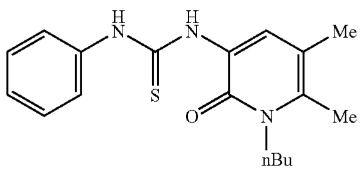 | 0.98 (t, J=7.2 Hz, 3H), 1.37-1.49 (m, 2H), 1.59-1.69 (m, 2H), 2.18 (s, 3H), 2.38 (s, 3H), 4.10 (t, J=7.8 Hz, 2H), 7.23-7.43 (m, 1H), 7.42-7.43 (m, 4H), 8.86 (s, 1H). |
| 5-103 | 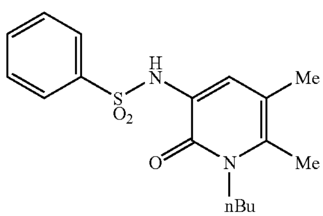 | 0.92 (t, J=7.2 Hz, 3H), 1.25-1.37 (m, 2H), 1.45-1.55 (m, 2H), 2.08 (s, 3H), 2.23 (s, 3H), 3.97 (t, J=7.8 Hz, 2H), 7.35 (s, 1H), 7.41-7.55 (n, 2H), 7.65 (br s, 1H), 7.83-7.87 (m, 2H). |
| 5-104 | 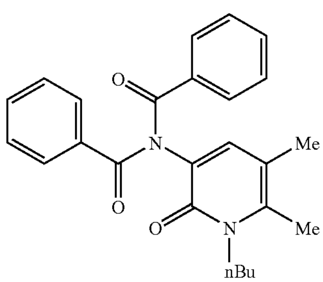 | 0.95 (t, J=7.2 Hz, 3H), 1.33-1.45 (m, 2H), 1.59-1.70 (m, 2H), 2.00 (s, 3H), 2.30 (s, 3H), 4.10 (t, J=7.8 Hz, 2H), 7.03 (s, 1H), 7.28-7.44 (m, 6H), 7.79-7.82 (m, 4H). |
| 5-105 | 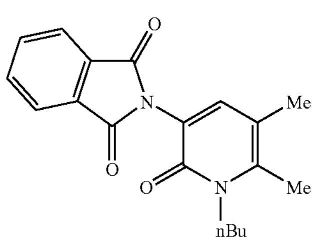 | 0.96 (t, J=7.2 Hz, 3H), 1.37-1.49 (m, 2H), 1.62-1.73 (m, 2H), 2.16 (s, 3H), 2.39 (s, 3H), 4.11 (t, J=8.1 Hz, 2H), 7.30 (s, 1H), 7.72-7.77 (m, 2H), 7.88-7.94 (m, 2H). |
| 5-106 | 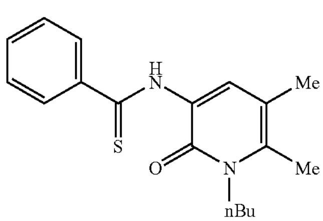 | 0.99 (t, J=7.2 Hz 3H), 1.40-1.52 (m, 2H), 1.64-1.75 (m, 2H), 2.20 (s, 3H), 2.37 (s, 3H), 4.15 (t, J=7.8 Hz, 2H), 7.38-7.50 (m, 3H), 7.89-7.92 (m, 2H), 9.57 (s, 1H), 10.60 (br s, 1H). |

TABLE 40

[Structure: R'-C(=O)-NH- attached to 3-position of 1-nBu-2-oxo-5,6,7,8-tetrahydroquinoline]

| Compound No. | R' | $^1$H-NMR (CDCl$_3$) |
|---|---|---|
| 6-001 | 4-methylphenyl | 0.99 (t, J=7.5 Hz, 3H), 1.45 (sextet, J=7.5 Hz, 2H), 1.66 (quint, J=7.5 Hz, 2H), 1.74 (quint, J=6.0 Hz, 2H), 1.87 (quint, J=6.0 Hz, 2H), 2.60 (t, J=6.0 Hz, 2H), 2.69 (t, J=6.0 Hz, 2H), 4.06 (t, J=7.8 Hz, 2H), 7.43-7.56 (m, 3H), 7.94 (d, J=6.9 Hz, 2H), 8.31 (s, 1H), 9.26 (br s, 1H). |
| 6-002 | benzyl (PhCH$_2$-) | 0.95 (t, J=7.5 Hz, 3H), 1.40 (sextet, J=7.5 Hz, 2H), 1.56-1.65 (m, 2H), 1.69 (quint, J=6.0 Hz, 2H), 1.82 (quint, J=6.0 Hz, 2H), 2.52 (t, J=6.0 Hz, 2H), 2.62 (t, J=6.0 Hz, 2H), 3.72 (s, 2H), 3.98 (t, J=7.8 Hz, 2H), 7.27-7.39 (m, 5H), 8.13 (s, 1H), 8.44 (br s, 1H). |
| 6-003 | phenethyl (PhCH$_2$CH$_2$-) | 0.97 (t, J=7.5 Hz, 3H), 1.42 (sextet, J=7.5 Hz, 2H), 1.61 (quint, J=7.5 Hz, 2H), 1.71 (quint, J=6.0 Hz, 2H), 1.84 (quint, J=6.0 Hz, 2H), 2.55 (t, J=6.0 Hz, 2H), 2.65 (t, J=6.0 Hz, 2H), 2.70 (t, J=7.8 Hz, 2H), 3.04 (t, J=7.8 Hz, 2H), 4.02 (t, J=7.8 Hz, 2H), 7.18-7.33 (m, 5H), 8.15 (s, 1H), 8.41 (br s, 1H). |
| 6-004 | phenoxymethyl (PhO-CH$_2$-) | 0.98 (t, J=7.5 Hz, 3H), 1.41 (sextet, J=7.5 Hz, 2H), 1.64 (quint, J=7.5 Hz, 2H), 1.72 (quint, J=6.0 Hz, 2H), 1.85 (quint, J=6.0 Hz, 2H), 2.57 (t, J=6.0 Hz, 2H), 2.67 (t, J=6.0 Hz, 2H), 4.03 (t, J=7.8 Hz, 2H), 4.60 (s, 2H), 7.03 (d, J=7.8 Hz, 2H), 7.32 (d, J=7.8 Hz, 3H), 8.19 (s, 1H), 9.49 (br s, 1H). |
| 6-005 | benzylaminomethyl (PhCH$_2$-NH-) | 0.92 (t, J=7.5 Hz, 3H), 1.32 (sextet, J=7.5 Hz, 2H), 1.57-1.65 (m, 2H), 1.69 (quint, J=6.0 Hz, 2H), 1.82 (quint, J=6.0 Hz, 2H), 2.55 (t, J=6.0 Hz, 2H), 2.59 (t, J=6.0 Hz, 2H), 3.90 (t, J=7.8 Hz, 2H), 4.46 (d, J=6.0 Hz, 2H), 5.72 (br s, 1H), 7.24-7.32 (m, 5H), 7.95 (s, 1H), 8.00 (br s, 1H). |
| 6-006 | phenylamino (Ph-NH-) | (in d$_6$-DMSO): 0.93 (t, J=7.5 Hz, 3H), 1.35 (sextet, J=7.5 Hz, 2H), 1.56 (quint, J=7.5 Hz, 2H), 1.60-1.70 (m, 2H), 1.71-1.80 (m, 2H), 2.51 (t, J=6.0 Hz, 2H), 2.67 (t, J=6.0 Hz, 2H), 4.00 (t, J=7.5 Hz, 2H), 6.96 (t, J=7.2 Hz, 1H), 7.27 (t, J=7.5 Hz, 2H), 7.43 (d, J=7.5 Hz, 2H), 7.84 (s, 1H), 8.53 (br s, 1H), 9.51 (br s, 1H). |
| 6-007 | benzyloxy (PhCH$_2$-O-) | 0.96 (t, J=7.5 Hz, 3H), 1.41 (sextet, J=7.5 Hz, 2H), 1.63 (quint, J=7.5 Hz, 2H), 1.70 (quint, J=6.0 Hz, 2H), 1.83 (quint, J=6.0 Hz, 2H), 2.53 (t, J=6.0 Hz, 2H), 2.63 (t, J=6.0 Hz, 2H), 4.01 (t, J=7.8 Hz, 2H), 5.19 (s, 2H), 7.29-7.41 (m, 5H), 7.76 (s, 1H), 7.86 (br s, 1H). |

TABLE 41

| Compound No. | Structure | $^1$H-NMR (CDCl$_3$) |
|---|---|---|
| 7-001 | [Structure: 2-(benzoxazol-2-ylthio)-3-substituted pyridine bearing nBuO, Me groups] | 0.71 (t, J = 7.2 Hz, 3H), 1.10-1.23 (m, 2H), 1.46-1.55 (m, 2H), 2.22 (s, 3H), 2.43 (s, 3H), 4.28 (t, J = 6.3 Hz, 2H), 7.20-7.29 (m, 2H), 7.38-7.41 (m, 1H), 7.58-7.60 (m, 1H), 7.67 (s, 1H). |

TABLE 41-continued

| Compound No. | Structure | ¹H-NMR (CDCl₃) |
|---|---|---|
| 7-002 | (structure) | 0.97 (t, J = 7.2 Hz, 3H), 1.37-1.49 (m, 2H), 1.60-1.80 (m, 2H), 2.21 (s, 3H), 2.44 (s, 3H), 2.48 (s, 3H), 4.71 (br s, 2H), 7.30-7.35 (m, 3H), 8.01 (s, 1H), 8.04 (s, 1H). |
| 7-003 | (structure) | 0.97 (t, J = 7.5 Hz, 3H), 1.37-1.50 (m, 2H), 1.62-1.73 (m, 2H), 2.07 (s, 3H), 2.33 (s, 3H), 4.09 (t, J = 7.8 Hz, 2H), 6.96 (s, 1H). |
| 7-004 | (structure) | 2.07 (s, 3H), 2.28 (s, 3H), 3.88 (s, 3H), 5.42 (br s, 2H), 7.19-7.54 (m, 9H). |
| 7-005 | (structure) | 1.10 (t, J = 7.5 Hz, 3H), 2.30 (s, 3H), 2.53 (q, J = 7.5 Hz, 2H), 3.85 (s, 3H), 5.41 (br s, 2H), 7.18-7.55 (m, 9H). |
| 7-006 | (structure) | 0.84 (t, J = 7.2 Hz, 3H), 1.28 (sextet, J = 7.5 Hz, 2H), 1.61-1.68 (m, 2H), 2.46 (s, 3H), 4.42 (t, J = 6.6 Hz, 2H), 4.64 (d, J = 5.1 Hz, 1H), 6.87 (d, J = 6.0 Hz, 1H), 7.26-7.37 (m, 5H), 8.32 (br s, 1H), 8.42 (d, J = 7.5 Hz, 1H). |
| 7-007 | (structure) | 0.95 (t, J = 7.2 Hz, 3H), 1.39 (m, 2H), 1.74 (m, 2H), 3.98 (t, J = 7.5 Hz, 2H), 4.50 (d, J = 5.7 Hz, 1H), 4.60 (d, 5.7 Hz, 1H), 5.9 (brs, 1H), 6.36 (brs, 1H), 6.56 (dd, J = 9.6, 3.6 Hz, 1H), 7.25-7.36 (m, 5H), 7.86 (m, 1H), 8.22 (m, 2H). |
| 7-008 | (structure) | 0.96 (t, J = 7.3 Hz, 3H), 1.32-1.45 (m, 2H), 1.69-1.79 (m, 2H), 3.96 (t, J = 7.6 Hz, 2H), 4.44 (s, 2H), 7.19-7.30 (m, 3H), 7.40-7.43 (m, 1H), 7.59-7.62 (m, 1H), 7.66 (dd, J = 7.0 Hz, 1H). |

TABLE 41-continued

| Compound No. | Structure | $^1$H-NMR (CDCl$_3$) |
|---|---|---|
| 7-009 | 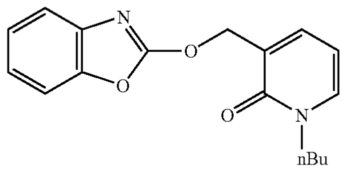 | 0.96 (t, J = 7.3 Hz, 3H), 1.32-1.44 (m, 2H), 1.68-1.79 (m, 2H), 3.96 (t, J = 7.6 Hz, 2H), 6.14 (t, J = 7.0 Hz, 1H), 7.06-7.27 (m, 5H), 7.39 (dd, J = 1.8, 7.0 Hz, 1H). |

TABLE 42

| Compound No. | Structure | $^1$H-NMR (CDCl$_3$) |
|---|---|---|
| 7-010 | 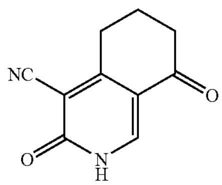 | (in CDCl$_3$ + CD$_3$OD): 2.17 (quint, J = 6.3 Hz, 2H), 2.63 (t, J = 6.3 Hz, 2H), 3.09 (t, J = 6.3 Hz, 2H), 8.34 (s, 1H). |

TABLE 43

| Compound No. | Structure | $^1$H-NMR (CDCl$_3$) |
|---|---|---|
| 7-011 | 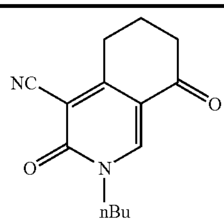 | 0.97 (t, J = 7.5 Hz, 3H), 1.38 (sextet, J = 7.5 Hz, 2H), 1.76 (quint, J = 7.5 Hz, 2H), 2.15 (quint, J = 6.3 Hz, 2H), 2.61 (t, J = 6.3 Hz, 2H), 3.06 (t, J = 6.3 Hz, 2H), 4.03 (t, J = 7.5 Hz, 2H), 8.39 (s, 1H). |
| 7-012 | 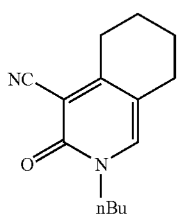 | 0.96 (t, J = 7.5 Hz, 3H), 1.37 (sextet, J = 7.5 Hz, 2H), 1.67-1.86 (m, 6H), 2.54 (t, J = 6.3 Hz, 2H), 2.87 (t, J = 6.3 Hz, 2H), 3.93 (t, J = 7.5 Hz, 2H), 7.22 (s, 1H). |
| 7-013 | 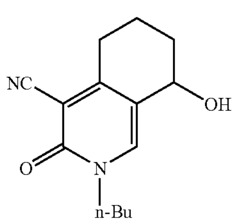 | 0.97 (t, J = 7.5 Hz, 3H), 1.38 (sextet, J = 7.5 Hz, 2H), 1.76 (quint, J = 7.5 Hz, 2H), 2.15 (quint, J = 6.0 Hz, 2H), 2.61 (t, J = 6.0 Hz, 2H), 3.06 (t, J = 6.0 Hz, 2H), 3.45-3.58 (m, 1H), 4.03 (t, J = 7.5 Hz, 2H), 8.39 (s, 1H). |
| 7-014 | 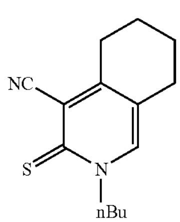 | 0.98 (t, J = 7.5 Hz, 3H), 1.41 (sextet, J = 7.5 Hz, 2H), 1.75-1.90 (m, 6H), 2.60 (t, J = 6.3 Hz, 2H), 2.87 (t, J = 6.3 Hz, 2H), 4.81 (t, J = 7.5 Hz, 2H), 7.50 (s, 1H). |

TABLE 43-continued

| Compound No. | Structure | $^1$H-NMR (CDCl$_3$) |
|---|---|---|
| 7-015 | 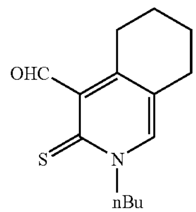 | 0.99 (t, J = 7.5 Hz, 3H), 1.44 (sextet, J = 7.5 Hz, 2H), 1.74 (quint, J = 3.3 Hz, 4H), 1.87 (quint, J = 7.5 Hz, 2H), 2.62 (br t, J = 6.3 Hz, 2H), 2.95 (br t, J = 6.3 Hz, 2H), 4.51 (t, J = 7.5 Hz, 2H), 7.53 (s, 1H), 10.60 (s, 1H). |
| 7-016 | 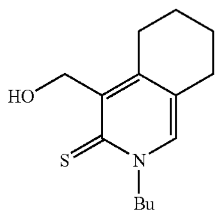 | 0.99 (t, J = 7.2 Hz, 3H), 1.43 (sextet, J = 7.2 Hz, 2H), 1.71-1.95 (m, 6H), 2.66 (br t, J = 6.3 Hz, 2H), 2.83 (t, J = 6.3 Hz, 2H), 4.58 (br t, J = 7.2 Hz, 2H), 4.79 (s, 2H), 7.61 (s, 1H). |
| 7-017 | 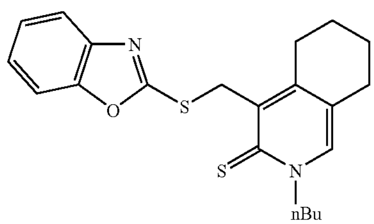 | 0.99 (t, J = 7.5 Hz, 3H), 1.43 (sextet, J = 7.5 Hz, 2H), 1.70-1.95 (m, 6H), 2.62 (t, J = 6.3 Hz, 2H), 3.01 (t, J = 6.3 Hz, 2H), 4.58 (t, J = 7.5 Hz, 2H), 5.05 (s, 2H), 7.15-7.30 (m, 2H), 7.42 (dd, J = 7.2 Hz, J = 1.8 Hz, 1H), 7.48 (br s, 1H), 7.60 (dd, J = 7.2 Hz, J = 1.8 Hz, 1H). |
| 7-018 | 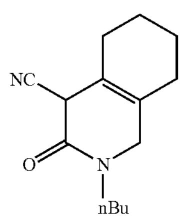 | 0.93 (t, J = 7.5 Hz, 3H), 1.32 (sextet, J = 7.5 Hz, 2H), 1.42-1.59 (m, 5H), 1.88 (s, 1H), 1.97-2.08 (m, 2H), 2.20-2.32 (m, 1H), 2.54-2.66 (m, 1H), 3.06-3.19 (m, 2H), 3.33-3.43 (m, 3H). |
| 7-019 | 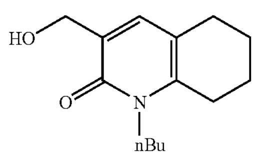 | 0.98 (t, J = 7.5 Hz, 3H), 1.43 (sextet, J = 7.5 Hz, 2H), 1.65 (quint, J = 7.5 Hz, 2H), 1.71 (quint, J = 6.0 Hz, 2H), 1.85 (quint, J = 6.0 Hz, 2H), 2.52 (t, J = 6.0 Hz, 2H), 2.68 (t, J = 6.0 Hz, 2H), 4.00 (t, J = 7.8 Hz, 2H), 4.53 (s, 2H), 7.02 (s, 1H). |

TABLE 43

| Compound No. | Structure | $^1$H-NMR (CDCl$_3$) |
|---|---|---|
| 7-020 | 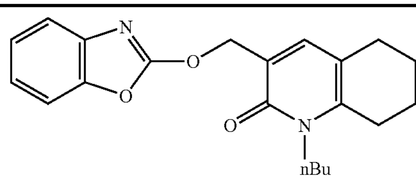 | 0.97 (t, J = 7.5 Hz, 3H), 1.43 (sextet, J = 7.5 Hz, 2H), 1.57-1.72 (m, 4H), 1.81 (quint, J = 6.0 Hz, 2H), 2.45 (t, J = 6.0 Hz, 2H), 2.65 (t, J = 6.0 Hz, 2H), 4.01 (t, J = 7.8 Hz, 2H), 4.93 (s, 2H), 7.08-7.30 (m, 4H), 7.13 (s, 1H). |
| 7-021 | 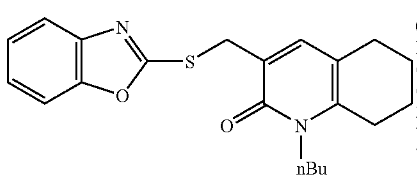 | 0.97 (t, J = 7.5 Hz, 3H), 1.43 (sextet, J = 7.5 Hz, 2H), 1.59-1.73 (m, 4H), 1.81 (quint, J = 6.0 Hz, 2H), 2.49 (t, J = 6.0 Hz, 2H), 2.66 (t, J = 6.0 Hz, 2H), 4.01 (t, J = 7.8 Hz, 2H), 4.43 (s, 2H), 7.24 (quint d, J = 7.5 Hz, 1.5 Hz, 2H), 7.40 (s, 1H), 7.42 (dd, J = 7.5 Hz, 1.5 Hz, 1H), 7.60 (dd, J = 7.5 Hz, 1.5 Hz, 1H). |

TABLE 43-continued

| Compound No. | Structure | ¹H-NMR (CDCl₃) |
|---|---|---|
| 7-022 | ![structure with allyloxymethyl group on bicyclic quinolinone with nBu] | 0.96 (t, J = 7.5 Hz, 3H), 1.42 (sextet, J = 7.5 Hz, 2H), 1.64 (quint, J = 7.5 Hz, 2H), 1.70 (quint, J = 6.0 Hz, 2H), 1.84 (quint, J = 6.0 Hz, 2H), 2.53 (t, J = 6.0 Hz, 2H), 2.67 (t, J = 6.0 Hz, 2H), 3.99 (t, J = 7.8 Hz, 2H), 4.12 (dt, J = 6.0 Hz, 1.5 Hz, 2H), 4.46 (s, 2H), 5.20 (dq, J = 10.5 Hz, 1.8 Hz, 1H), 5.33 (dq, J = 17.1 Hz, 1.8 Hz, 1H), 5.91-6.05 (m, 1H), 7.19 (s, 1H). |
| 7-023 | ![structure with CHO group on bicyclic quinolinone with nBu] | 0.99 (t, J = 7.5 Hz, 3H), 1.46 (sextet, J = 7.5 Hz, 2H), 1.68 (quint, J = 7.5 Hz, 2H), 1.74 (quint, J = 6.0 Hz, 2H), 1.88 (quint, J = 6.0 Hz, 2H), 2.59 (t, J = 6.0 Hz, 2H), 2.76 (t, J = 6.0 Hz, 2H), 4.05 (t, J = 7.8 Hz, 2H), 7.76 (s, 1H), 10.34 (s, 1H). |

TABLE 45

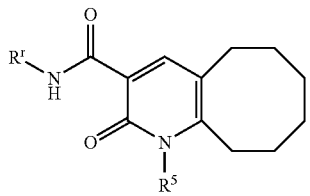

| Compound No. | Rʳ | R⁵ | ¹H-NMR (CDCl₃) |
|---|---|---|---|
| 10-001 | morpholinobutyl | nBu | 0.99 (d, J = 7.3 Hz, 3H), 1.22-1.53 (m, 6H), 1.62-1.86 (m, 6H), 2.36-2.42 (m, 6H), 2.64 (t, J = 6.0 Hz, 2H), 2.89 (t, J = 6.3 Hz, 2H), 3.48 (dt, J = 7.2, 6.9 Hz, 2H), 3.72 (t, J = 4.8 Hz, 4H), 4.05-4.14 (m, 2H), 8.29 (s, 1H), 10.1 (t, J = 5.4 Hz, 1H). |
| 10-002 | 2-pyridylethyl | nBu | 0.98 (d, J = 7.3 Hz, 3H), 1.34-1.54 (m, 6H), 1.62-1.83 (m, 6H), 2.65 (t, J = 6.0 Hz, 2H), 2.90 (t, J = 6.4 Hz, 2H), 4.05-4.20 (m, 2H), 4.80 (d, J = 5.5 Hz, 2H), 7.16 (m, 1H), 7.35 (d, J = 7.8 Hz, 1H), 7.64 (ddd, J = 7.8, 7.8, 1.8 Hz, 1H), 8.34 (s, 1H), 8.59 (dlike, 1H), 10.6 (t, J = 5.5 Hz, 1H). |
| 10-003 | 4-pyridylpropyl | nBu | 0.99 (d, J = 7.3 Hz, 3H), 1.34-1.53 (m, 6H), 1.60-1.90 (m, 6H), 2.64 (t, J = 6.0 Hz, 2H), 2.89 (t, J = 6.3 Hz, 2H), 2.94 (t, J = 7.5 Hz, 2H), 3.70 (dt, J = 7.5, 6.0 Hz, 2H), 4.03-4.14 (m, 2H), 7.18-7.20 (m, 2H), 8.29 (s, 1H), 8.50-8.52 (m, 2H), 10.1 (t, J = 6.0 Hz, 1H). |
| 10-004 | 4-pyridylethyl | nBu | 0.99 (d, J = 7.2 Hz, 3H), 1.34-1.54 (m, 6H), 1.62-1.85 (m, 6H), 2.66 (t, J = 6.0 Hz, 2H), 2.91 (t, J = 6.3 Hz, 2H), 4.12 (t, J = 7.3 Hz, 2H), 4.65 (d, J = 5.8 Hz, 2H), 7.28 (A2B2, J = 5.0 Hz, 2H), 8.53 (s, 1H), 8.54 (A2B2, J = 5.0 Hz, 2H), 10.5 (t, J = 5.8 Hz, 1H). |
| 10-005 | 3-pyridylpropyl | nBu | 0.99 (d, J = 7.3 Hz, 3H), 1.34-1.54 (m, 6H), 1.60-1.82 (m, 6H), 2.64 (t, J = 6.1 Hz, 2H), 2.89 (t, J = 6.4 Hz, 2H), 2.94 (t, J = 7.5 Hz, 2H), 3.68 (dt, J = 7.5, 6.3 Hz, 2H), 4.04-4.14 (m, 2H), 7.23 (dd, J = 7.8, 4.6 Hz, 1H), 7.59 (ddd, J = 7.8, 2.1, 1.5 Hz, 1H), 8.29 (s, 1H), 8.47 (dd, J = 7.8, 1.5 Hz, 1H), 8.50 (d, J = 2.1 Hz, 1H), 10.1 (t, J = 6.3 Hz, 1H) |

TABLE 45-continued

[Structure: R'-NH-C(=O)- attached to a bicyclic system consisting of a 2-oxo-pyridine fused with cyclooctane ring; N of pyridinone bears R⁵]

| Compound No. | R' | R⁵ | ¹H-NMR (CDCl₃) |
|---|---|---|---|
| 10-006 | 4-F-C₆H₄-CH₂-C(CH₃)₂-CH₂- | nBu | 0.98 (d, J = 7.3 Hz, 3H), 1.34-1.53 (m, 6H), 1.41 (s, 6H), 1.61-1.80 (m, 6H), 2.63 (t, J = 6.1 Hz, 2H), 2.88 (t, J = 6.4 Hz, 2H), 3.16 (s, 2H), 4.06 (br.s, 2H), 6.88-6.94 (m, 2H), 7.11-7.16 (m, 2H), 8.32 (s, 1H), 9.83 (br.s, 1H). |

TABLE 46

[Structure: R'-NH-C(=O)- attached to a bicyclic system consisting of a 2-oxo-pyridine fused with cyclooctane ring; N of pyridinone bears R⁵]

| Compound No. | R' | R⁵ | ¹H-NMR (CDCl₃) |
|---|---|---|---|
| 10-007 | 2-Cl-C₆H₄-CH₂- | nBu | 0.98 (d, J = 7.2 Hz, 3H), 1.38-1.49 (m, 6H), 1.51-1.80 (m, 6H), 2.64 (t, J = 6.4 Hz, 2H), 2.89 (t, J = 6.4 Hz, 2H), 4.10 (br.s, 2H), 4.73 (d, J = 5.8 Hz, 2H), 7.16-7.25 (m, 4H), 7.35 (m, 1H), 7.46 (m, 1H), 8.32 (s, 1H), 10.4 (br.s, 1H). |
| 10-008 | 2-OMe-C₆H₄-CH₂- | nBu | 0.98 (d, J = 7.3 Hz, 3H), 1.37-1.48 (m, 6H), 1.51-1.79 (m, 6H), 2.63 (t, J = 6.4 Hz, 2H), 2.87 (t, J = 6.4 Hz, 2H), 3.88 (s, 3H), 4.09 (m, 2H), 4.65 (d, J = 5.8 Hz, 2H), 6.85-6.93 (m, 2H), 7.22 (dt, J = 7.6, 1.8 Hz, 1H), 7.35 (dd, J = 7.6, 1.8 Hz, 1H), 8.32 (s, 1H), 10.3 (br.s, 1H). |
| 10-009 | 2-Me-C₆H₄-CH₂- | nBu | 0.97 (d, J = 7.3 Hz, 3H), 1.38-1.50 (m, 6H), 1.60-1.80 (m, 6H), 2.38 (s, 3H), 2.64 (t, J = 6.1 Hz, 2H), 2.88 (t, J = 6.4 Hz, 2H), 4.08 (m, 2H), 4.63 (d, J = 5.5 Hz, 2H), 7.15-7.20 (m, 3H), 7.33 (m, 1H), 8.33 (s, 1H), 10.2 (br.s, 1H). |
| 10-010 | 2,6-diF-C₆H₃-CH₂- | nBu | 0.97 (d, J = 7.3 Hz, 3H), 1.36-1.50 (m, 6H), 1.61-1.78 (m, 6H), 2.64 (t, J = 6.1 Hz, 2H), 2.87 (t, J = 6.7 Hz, 2H), 4.08 (br.s, 2H), 4.72 (d, J = 5.5 Hz, 2H), 6.84-6.92 (m, 2H), 7.20 (m, 1H), 8.32 (s, 1H), 10.2 (br.s, 1H). |
| 10-011 | C₆H₅-CH(CH₃)-CH(N₃)- | nBu | 0.99 (t, J = 7.2 Hz, 3H), 1.34-1.54 (m, 4H), 1.47 (sextet, J = 7.2 Hz, 2H), 1.65-1.81 (m, 6H), 2.63 (t, J = 6.3 Hz, 2H), 2.89 (t, J = 6.3 Hz, 2H), 3.71 (d, J = 6.3 Hz, 2H), 4.11 (br t, J = 7.2 Hz, 2H), 5.43 (dt, J = 8.1, 6.0 Hz, 1H), 7.26-7.70 (m, 5H), 8.23 (s, 1H), 10.74 (d, J = 8.1 Hz, 1H). |

TABLE 46-continued

| Compound No. | R$^r$ | R$^5$ | $^1$H-NMR (CDCl$_3$) |
|---|---|---|---|
| 10-012 | H$_2$N— (1-phenylethyl), CH$_3$CO$_2$H | nBu | 0.99 (t, J = 7.2 Hz, 3H), 1.34-1.56 (m, 4H), 1.47 (sextet, J = 7.2 Hz, 2H), 1.61-1.80 (m, 6H), 2.06 (s, 3H), 2.63 (t, J = 6.3 Hz, 2H), 2.89 (t, J = 6.3 Hz, 2H), 3.15 (d, J = 6.0 Hz, 2H), 4.12 (br t, J = 7.2 Hz, 2H), 5.25 (dt, J = 7.8 Hz, 6.0 Hz, 1H), 7.35-7.42 (m, 5H), 8.28 (s, 1H), 10.67 (d, J = 8.4 Hz, 1H). |

TABLE 47

| Compound No. | R$^r$ | R$^5$ | $^1$H-NMR (CDCl$_3$) |
|---|---|---|---|
| 10-013 | H$_2$N—CH$_2$-CH(CH$_3$)-CH$_2$CH$_2$-Ph, CH$_3$CO$_2$H | nBu | 1.00 (t, J = 7.5 Hz, 3H), 1.34-1.55 (m, 4H), 1.47 (sextet, J = 7.5 Hz, 2H), 1.62-1.80 (m, 6H), 2.01 (s, 3H), 2.63 (t, J = 6.0 Hz, 2H), 2.78-3.06 (m, 4H), 2.88 (t, J = 6.0 Hz, 2H), 4.10 (br t, J = 7.5 Hz, 2H), 4.35-4.45 (m, 1H), 7.18-7.30 (m, 5H), 8.24 (s, 1H), 10.25 (d, J = 7.8 Hz, 1H). |
| 10-014 | AcHN—CH$_2$-CH(CH$_3$)-Ph | nBu | 0.99 (t, J = 7.5 Hz, 3H), 1.36-1.55 (m, 4H), 1.46 (sextet, J = 7.5 Hz, 2H), 1.63-1.79 (m, 6H), 1.97 (s, 3H), 2.64 (t, J = 6.0 Hz, 2H), 2.89 (t, J = 6.0 Hz, 2H), 3.70-3.81 (m, 2H), 4.09 (br t, J = 7.5 Hz, 2H), 5.31-5.39 (m, 1H), 6.61 (br t, J = 4.5 Hz, 1H), 7.28-7.44 (m, 5H), 8.28 (s, 1H), 10.66 (d, J = 7.5 Hz, 1H). |
| 10-015 | MeO$_2$SHN—CH$_2$-CH(CH$_3$)-Ph | nBu | 0.99 (t, J = 7.2 Hz, 3H), 1.38-1.57 (m, 4H), 1.47 (sextet, J = 7.2 Hz, 2H), 1.62-1.80 (m, 6H), 2.64 (t, J = 6.0 Hz, 2H), 2.90 (s, 3H), 2.90 (t, J = 6.0 Hz, 2H), 3.60 (d, J = 6.6 Hz, 2H), 4.10 (br t, J = 7.2 Hz, 2H), 5.38 (dt, J = 7.5 Hz, 6.0 Hz, 1H), 7.35-7.43 (m, 5H), 8.29 (s, 1H), 10.75 (d, J = 9.0 Hz, 1H). |
| 10-016 | 2,5-dichlorobenzyl (Cl, Cl on phenyl with ethyl linker) | nBu | 0.99 (d, J = 7.3 Hz, 3H), 1.34-1.54 (m, 6H), 1.62-1.82 (m, 6H), 2.65 (t, J = 6.0 Hz, 2H), 2.90 (t, J = 6.3 Hz, 2H), 4.06-4.17 (m, 2H), 4.68 (d, J = 6.4 Hz, 2H), 7.16 (dd, J = 8.5, 2.4 Hz, 1H), 7.28 (d, J = 8.5 Hz, 1H), 7.41 (d, J = 2.4 Hz, 1H), 8.32 (s, 1H), 10.5 (t, J = 6.4 Hz, 1H). |

TABLE 47-continued

[Structure: R'-NH-C(=O)- attached to bicyclic pyridinone fused with cyclooctane, N-R5]

| Compound No. | R' | R5 | 1H-NMR (CDCl3) |
|---|---|---|---|
| 10-017 | 5-(furan-2-yl)-1H-pyrazol-3-yl (3-methyl) | nBu | 1.01 (t, J = 7.3 Hz, 3H), 1.35-1.57 (m, 6H), 1.65-1.85 (m, 6H), 2.69 (t, J = 6.0 Hz, 2H), 2.94 (t, J = 6.2 Hz, 2H), 4.08-4.20 (m, 2H), 6.33 (s, 1H), 6.48 (dd, J = 3.4, 1.8 Hz, 1H), 6.68 (d, J = 3.4 Hz, 1H), 7.46 (m, 1H), 8.35 (s, 1H), 12.8 (s, 1H). |

TABLE 48

[Structure: R'-NH-C(=O)- attached to bicyclic pyridinone fused with cyclooctane, N-R5]

| Compound No. | R' | R5 | 1H-NMR (CDCl3) |
|---|---|---|---|
| 10-018 | allyloxycarbonyl-NH-CH2-CH(CH3)-CH2-phenyl | nBu | 1.00 (t, J = 7.5 Hz, 3H), 1.37-1.57 (m, 4H), 1.47 (sextet, J = 7.5 Hz, 2H), 1.61-1.80 (m, 6H), 2.62 (t, J = 6.0 Hz, 2H), 2.88 (t, J = 6.0 Hz, 2H), 2.94 (t, J = 7.5 Hz, 2H), 3.23-3.33 (m, 1H), 3.45-3.55 (m, 1H), 4.09 (br t, J = 7.5 Hz, 2H), 4.40-4.50 (m, 1H), 4.53 (d, J = 6.0 Hz, 2H), 5.14-5.30 (m, 2H), 5.52 (br s, 1H), 5.82-5.96 (m,1H), 7.17-7.28 (m, 5H), 8.25 (s, 1H), 10.18 (d, J = 7.5 Hz, 1H). |
| 10-019 | tert-butoxycarbonyl-NH-CH2-CH(CH3)-CH2-phenyl | nBu | 1.00 (t, J = 7.5 Hz, 3H), 1.40 (s, 9H), 1.41-1.55 (m, 4H), 1.47 (sextet, J = 7.5 Hz, 2H), 1.64-1.80 (m, 6H), 2.62 (t, J = 6.0 Hz, 2H), 2.88 (t, J = 6.0 Hz, 2H), 2.88-3.00 (m, 2H), 3.18-3.28 (m, 1H), 3.38-3.48 (m, 1H), 4.09 (br t, J = 7.5 Hz, 2H), 4.37-4.47 (m, 1H), 5.11 (br s, 1H), 7.22-7.32 (m, 5H), 8.25 (s, 1H), 10.13 (d, J = 7.8 Hz, 1H). |
| 10-020 | allyl-NH-CH2-CH(CH3)-CH2-phenyl | nBu | 1.00 (t, J = 7.2 Hz, 3H), 1.36-1.81 (m, 12H), 2.62 (t, J = 6.0 Hz, 2H), 2.74-3.04 (m, 6H), 3.21-3.37 (m, 2H), 4.09 (br t, J = 7.2 Hz, 2H), 4.44-4.53 (m, 1H), 5.06-5.17 (m, 2H), 5.08-5.95 (m, 1H), 7.18-7.29 (m, 5H), 8.25 (s, 1H), 10.17 (br s, 1H). |
| 10-021 | benzoyl-NH-CH2-CH(CH3)-CH2-phenyl | nBu | 1.00 (t, J = 7.2 Hz, 3H), 1.36-1.52 (m, 4H), 1.47 (sextet, J = 7.2 Hz, 2H), 1.61-1.79 (m, 6H), 2.63 (t, J = 6.0 Hz, 2H), 2.88 (t, J = 6.0 Hz, 2H), 2.95-3.11 (m, 2H), 3.49-3.59 (m, 1H), 3.68-3.76 (m, 1H), 4.10 (br t, J = 7.2 Hz, 2H), 4.51-4.64 (m, 1H), 7.17-7.85 (m, 10H), 7.92 (br s, 1H), 8.27 (s, 1H), 10.45 (d, J = 7.5 Hz, 1H). |

TABLE 48-continued

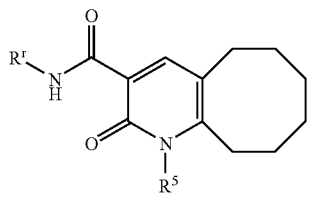

| Compound No. | R<sup>r</sup> | R<sup>5</sup> | <sup>1</sup>H-NMR (CDCl<sub>3</sub>) |
|---|---|---|---|
| 10-022 | 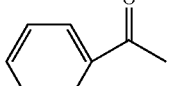 | nBu | 1.00 (t, J = 7.5 Hz, 3H), 1.36-1.57 (m, 4H), 1.48 (sextet, J = 7.5 Hz, 2H), 1.60-1.80 (m, 6H), 2.65 (t, J = 6.0 Hz, 2H), 2.89 (t, J = 6.0 Hz, 2H), 2.96-3.12 (m, 2H), 3.46-3.56 (m, 1H), 3.70-3.79 (m, 1H), 4.11 (br t, J = 7.5 Hz, 2H), 4.51-4.63 (m, 1H), 7.17-7.39 (m, 6H), 8.17 (d, J = 8.1 Hz, 1H), 8.28 (s, 1H), 8.37 (br s, 1H), 8.69 (d, J = 3.9 Hz,1H), 9.07 (br s, 1H), 10.52 (d, J = 7.2 Hz, 1H. |

TABLE 49

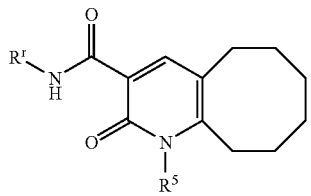

| Compound No. | R<sup>r</sup> | R<sup>5</sup> | <sup>1</sup>H-NMR (CDCl<sub>3</sub>) |
|---|---|---|---|
| 10-023 | 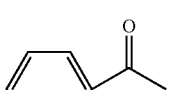 | nBu | 1.01 (t, J = 7.5 Hz, 3H), 1.39-1.59 (m, 4H), 1.50 (sextet, J = 7.5 Hz, 2H), 1.63-1.85 (m, 6H), 2.68 (t, J = 6.0 Hz, 2H), 2.94 (t, J = 6.0 Hz, 2H), 4.17 (br t, J = 7.5 Hz, 2H), 7.46-7.61 (m, 3H), 8.11 (d, J = 7.2 Hz, 2H), 8.42 (s, 1H), 13.76 (br s, 1H). |
| 10-021 | H— | nBu | 0.99 (t, J = 7.2 Hz, 3H), 1.37-1.56 (m, 4H), 1.47 (sextet, J = 7.2 Hz, 2H), 1.63-1.81 (m, 6H), 2.64 (t, J = 6.0 Hz, 2H), 2.90 (t, J = 6.0 Hz, 2H), 4.11 (t, J = 7.2 Hz, 2H), 5.69 (br s, 1H), 8.30 (s, 1H), 9.63 (br s, 1H). |
| 10-025 | 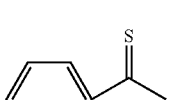 | nBu | 1.00 (t, J = 7.5 Hz, 3H), 1.37-1.84 (m, 12H), 2.69 (t, J = 6.0 Hz, 2H), 2.94 (t, J = 6.0 Hz, 2H), 4.13 (br t, J = 7.5 Hz, 2H), 7.50-7.53 (m, 3H), 8.00-8.08 (m, 2H), 8.37 (s, 1H), 13.04 (br s, 1H). |
| 10-026 | 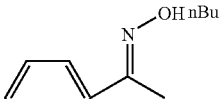 | nBu | 1.00 (t, J = 7.2 Hz, 3H), 1.38-1.57 (m, 4H), 1.48 (sextet, J = 7.2 Hz, 2H), 1.63-1.87 (m, 6H), 2.68 (t, J = 6.0 Hz, 2H), 2.94 (t, J = 6.0 Hz, 2H), 4.16 (br t, J = 7.2 Hz, 2H), 7.40-7.56 (m, 3H), 7.95 (d, J = 7.2 Hz, 2H), 8.42 (s, 1H), 14.37 (br s, 1H). |
| 10-027 |  | nBu | 0.99 (t, J = 7.2 Hz, 3H), 1.38-1.56 (m, 4H), 1.47 (sextet, J = 7.2 Hz, 2H), 1.63-1.82 (m, 6H), 2.62 (t, J = 6.0 Hz, 2H), 2.90 (t, J = 6.0 Hz, 2H), 4.11 (br t, J = 7.2 Hz, 2H), 6.12 (br s, 1H), 7.39-7.51 (m, 3H), 7.75-7.79 (m, 2H), 8.12 (s, 1H). |

TABLE 49-continued

[Structure: R'−NH−C(=O)− attached to a bicyclic pyridone fused with cyclooctane ring, with R⁵ on N]

| Compound No. | R' | R⁵ | ¹H-NMR (CDCl₃) |
|---|---|---|---|
| 10-028 | [PhC(=NOMe)CH₃ group, N−OMe] | nBu | 1.01 (t, J = 7.5 Hz, 3H), 1.37-1.58 (m, 4H), 1.48 (sextet, J = 7.2 Hz, 2H), 1.60-1.82 (m, 6H), 2.60 (t, J = 6.0 Hz, 2H), 2.91 (t, J = 6.0 Hz, 2H), 4.06 (s, 3H), 4.17 (br t, J = 7.5 Hz, 2H), 7.36-7.56 (m, 3H), 7.52-7.57 (m, 2H), 8.23 (s, 1H), 12.43 (br s, 1H). |
| 10-029 | [PhC(=NOEt)CH₃ group, N−OEt] | nBu | 1.01 (t, J = 7.5 Hz, 3H), 1.37-1.55 (m, 4H), 1.40 (t, J = 6.9 Hz, 3H), 1.48 (sextet, J = 7.5 Hz, 2H), 1.60-1.83 (m, 6H), 2.60 (t, J = 6.0 Hz, 2H), 2.91 (t, J = 6.0 Hz, 2H), 4.17 (br t, J = 7.5 Hz, 2H), 4.30 (q, J = 6.9 Hz, 2H), 7.32-7.40 (m, 3H), 7.51-7.61 (m, 2H), 8.23 (s, 1H), 12.44 (br s, 1H). |

TABLE 50

[Structure: R'−NH−C(=O)− attached to a bicyclic pyridone fused with cyclooctane ring, with R⁵ on N]

| Compound No. | R' | R⁵ | ¹H-NMR (CDCl₃) |
|---|---|---|---|
| 10-030 | [1-phenylethyl] | [4-pyridylmethyl-CH₂CH₂] | 1.37-1.53 (m, 4H), 1.56 (d, J = 7.2 Hz, 3H), 1.61-1.79 (m, 4H), 2.65 (t, J = 6.0 Hz, 2H), 2.72 (t, J = 6.3 Hz, 2H), 5.30 (quint, J = 6.9 Hz, 1H), 5.42 (br s, 2H), 6.98 (d, J = 5.1 Hz, 2H), 7.25-7.41 (m, 5H), 8.43 (s, 1H), 8.58 (br s, 2H), 10.11 (d, J = 7.8 Hz, 1H). |
| 10-031 | [2-hydroxy-1-phenylpropyl, HO−CH₂−] | [4-pyridylmethyl-CH₂CH₂] | 1.37-1.80 (m, 8H), 2.67 (t, J = 6.0 Hz, 2H), 2.74 (t, J = 6.0 Hz, 2H), 3.07 (br t, J = 6.0 Hz, 1H), 3.94 (t, J = 6.0 Hz, 2H), 5.30 (q, J = 6.9 Hz, 1H), 5.45 (br s, 2H), 6.99 (d, J = 5.4 Hz, 2H), 7.29-7.42 (m, 5H), 8.44 (s, 1H), 8.57 (d, J = 5.4 Hz, 2H), 10.50 (d, J = 7.5 Hz, 1H). |
| 10-032 | [(R)-1-indanyl] | nBu | 0.96 (t, J = 7.5 Hz, 3H), 1.37-1.58 (m, 6H), 1.60-1.80 (m, 6H), 1.92-2.05 (m, 1H), 2.62-2.73 (m, 1H), 2.66 (t, J = 6.0 Hz, 2H), 2.84-2.95 (m, 1H), 2.89 (t, J = 6.0 Hz, 2H), 2.99-3.09 (m, 1H), 3.95-4.16 (m, 2H), 5.68 (q, J = 7.5 Hz, 1H), 7.15-7.29 (m, 3H), 7.36-7.40 (m, 1H), 8.37 (s, 1H), 10.25 (d, J = 8.4 Hz, 1H). |
| 10-033 | [(S)-1-indanyl] | nBu | 0.96 (t, J = 7.5 Hz, 3H), 1.35-1.56 (m, 6H), 1.59-1.79 (m, 6H), 1.91-2.04 (m, 1H), 2.62-2.72 (m, 1H), 2.66 (t, J = 6.0 Hz, 2H), 2.84-2.95 (m, 1H), 2.89 (t, J = 6.0 Hz, 2H), 2.99-3.09 (m, 1H), 3.98-4.18 (m, 2H), 5.68 (q, J = 7.5 Hz, 1H), 7.15-7.26 (m, 3H), 7.36-7.40 (m, 1H), 8.37 (s, 1H), 10.25 (d, J = 8.1 Hz, 1H). |

TABLE 50-continued

[Structure: R'-NH-C(=O)- attached to a 2-oxo-1,2,5,6,7,8,9,10-octahydrocycloocta[b]pyridine-3-carboxamide scaffold with N-R⁵]

| Compound No. | R' | R⁵ | ¹H-NMR (CDCl₃) |
|---|---|---|---|
| 10-034 | 4-(N-methyl-N-methylamino)phenyl (N,N-dimethylaniline group, attached para) — [Me-N(Me)-C₆H₄-] | nBu | 1.00 (t, J = 7.5 Hz, 3H), 1.38-1.56 (m, 4H), 1.48 (sextet, J = 7.5 Hz, 2H), 1.63-1.83 (m, 6H), 2.65 (t, J = 6.0 Hz, 2H), 2.91 (t, J = 6.0 Hz, 2H), 3.29 (s, 3H), 4.13 (t, J = 7.5 Hz, 2H), 6.82 (t, J = 7.5 Hz, 1H), 6.90 (d, J = 8.7 Hz, 2H), 7.22-7.27 (m, 2H), 8.34 (s, 1H), 11.48 (br s, 1H). |
| 10-035 | cyclohexylmethyl | nBu | 0.99 (t, J = 7.2 Hz, 3H), 1.20-1.53 (m, 12H), 1.59-1.80 (m, 8H), 1.95-2.01 (m, 2H), 2.63 (t, J = 6.0 Hz, 2H), 2.88 (t, J = 6.0 Hz, 2H), 3.91-4.02 (m, 1H), 4.09 (br t, J = 7.2 Hz, 2H), 8.30 (s, 1H), 9.88 (d, J = 7.5 Hz, 1H). |
| 10-036 | 2-cyclohexylethyl | nBu | 0.99 (t, J = 7.2 Hz, 3H), 1.13-1.30 (m, 2H), 1.36-1.83 (m, 21H), 2.66 (t, J = 6.0 Hz, 2H), 2.88 (t, J = 6.0 Hz, 2H), 3.28 (t, J = 6.0 Hz, 2H), 4.10 (br t, J = 7.5 Hz, 2H), 8.31 (s, 1H), 9.98 (br s, 1H). |

TABLE 51

[Structure: R'-NH-C(=O)- attached to a 2-oxo-1,2,5,6,7,8,9,10-octahydrocycloocta[b]pyridine-3-carboxamide scaffold with N-R⁵]

| Compound No. | R' | R⁵ | ¹H-NMR(CDCl₃) |
|---|---|---|---|
| 10-037 | Me | nBu | 0.99(t, J=7.2Hz, 3H), 1.36-1.53(m, 6H), 1.62-1.81(m, 6H), 2.64(t, J=6.0Hz, 2H), 2.89(t, J=6.0Hz, 2H), 2.98(d, J=3.6Hz, 3H), 4.10(br t, J=7.2Hz, 2H), 8.31(s, 1H), 9.85(brs, 1H). |
| 10-038 | Et | nBu | 0.99(t, J=7.2Hz, 3H), 1.24(t, J=7.2Hz, 3H), 1.34-1.54(m, 4H), 1.47(sextet, J=7.2Hz, 2H), 1.63-1.80(m, 6H), 2.64(t, J=6.0Hz, 2H), 2.89(t, J=6.0Hz, 2H), 3.42-3.51(m, 2H), 4.10(br t, J=7.2Hz, 2H), 8.31(s, 1H), 9.90(br s, 1H). |
| 10-039 | iPr | nBu | 0.99(t, J=7.2Hz, 3H), 1.26(d, J=6.9Hz, 6H), 1.34-1.52(m, 4H), 1.47(sextet, J=7.2Hz, 2H), 1.60-1.80(m, 6H), 2.65(t, J=6.0Hz, 2H), 2.88(t, J=6.0Hz, 2H), 4.09(br t, J=7.2Hz, 2H), 4.25(sextet, J=6.6Hz, 1H), 8.31(s, 2H), 9.82(br s, 1H). |
| 10-040 | tBu | nBu | 0.99(t, J=7.5Hz, 3H), 1.35-1.56(m, 6H), 1.47(s, 9H), 1.61-1.79(m, 6H), 2.62(t, J=6.0Hz, 2H), 2.88(t, J=6.0Hz, 2H), 4.09(br t, J=7.5Hz, 2H), 8.30(s, 1H), 9.92(br s, 1H). |
| 10-041 | 1,1-dimethylpropyl (tert-amyl) | nBu | 0.99(t, J=7.5Hz, 3H), 1.01(s, 9H), 1.36-1.57(m, 6H), 1.62-1.80(m, 6H), 2.64(t, J=6.0Hz, 2H), 2.89(t, J=6.0Hz, 2H), 3.27(t, J=6.0Hz, 2H), 4.12(brt, J=7.5Hz, 2H), 8.32(s, 1H), 1010(br s, 1H). |

TABLE 51-continued

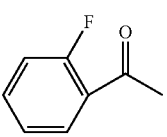

| Compound No. | R' | R⁵ | ¹H-NMR(CDCl₃) |
|---|---|---|---|
| 10-042 | 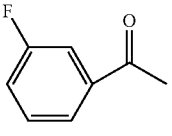 | nBu | 0.99(t, J=7.5Hz, 3H), 1.38-1.54(m, 6H), 1.62-1.83(m, 6H), 2.67(t, J=6.0Hz, 2H), 2.92(t, J=6.0Hz, 2H), 4.14(br t, J=7.5Hz, 2H), 7.15-7.30(m, 2H), 7.47-7.56(m, 1H), 7.96(td, J=7.8Hz, 1.5Hz, 1H), 8.38(s, 1H), 13.37(br s, 1H). |
| 10-043 | 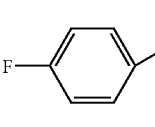 | nBu | 1.02(t, J=7.2Hz, 3H), 1.40-1.58(m, 6H), 1.67-1.85(m, 6H), 2.69(t, J=6.0Hz, 2H), 2.94(t, J=6.0Hz, 2H), 4.18(br t, J=7.2Hz, 2H), 7.25-7.32(m, 1H), 7.47-7.55(m, 1H), 7.80(dt, J=9.6Hz, 2.4Hz, 1H), 7.89(t, J=7.8Hz, 1H), 8.41(s, 1H), 13.84(br s, 1H). |
| 10-044 | 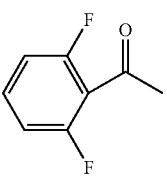 | nBu | 1.01(t, J=7.5Hz, 3H), 1.39-1.62(m, 6H), 1.65-1.89(m, 6H), 2.69(t, J=6.0Hz, 2H), 2.94(t, J=6.0Hz, 2H), 4.17(br t, J=7.5Hz, 2H), 7.20(t, J=9.0Hz, 2H), 8.11-8.16(m, 2H), 8.42(s, 1H), 13.79(br s, 1H). |

TABLE 52

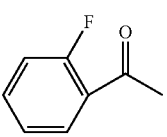

| Compound No. | R' | R⁵ | ¹H-NMR(CDCl₃) |
|---|---|---|---|
| 10-045 | 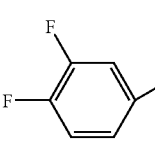 | nBu | 0.99(t, J=7.5Hz, 3H), 1.38-1.54(m, 6H), 1.62-1.83(m, 6H), 2.63(t, J=6.0Hz, 2H), 2.91(t, J=6.0Hz, 2H), 4.12(br t, J=7.5Hz, 2H), 6.96(t, J=7.8Hz, 2H), 7.34-7.44(m, 1H), 8.29(s, 1H), 13.18(br s, 1H). |
| 10-046 | 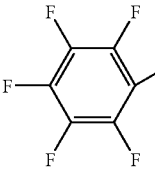 | nBu | 1.02(t, J=7.2Hz, 3H), 1.39-1.56(m, 6H), 1.67-1.85(m, 6H), 2.69(t, J=6.0Hz, 2H), 2.94(t, J=6.0Hz, 2H), 4.17(br t, J=7.2Hz, 2H), 7.32(dt, J=9.0Hz, 1.2Hz, 1H), 7.86-8.01(m, 2H), 8.41(s, 1H), 13.88(br s, 1H). |
| 10-047 |  | nBu | 1.02(t, J=7.2Hz, 3H), 1.42-1.57(m, 6H), 1.63-1.82(m, 6H), 2.66(t, J=6.0Hz, 2H), 2.95(t, J=6.0Hz, 2H), 4.15(br t, J=7.2Hz, 2H), 8.25(s, 1H), 13.37(br s, 1H). |

TABLE 52-continued

| Compound No. | R^r | R^5 | ^1H-NMR(CDCl_3) |
|---|---|---|---|
| 10-048 | 3,5-bis(trifluoromethyl)phenacyl | nBu | 1.03(t, J=7.5Hz, 3H), 1.40-1.55(m, 6H), 1.68-1.87(m, 6H), 2.70(t, J=6.0Hz, 2H), 2.96(t, J=6.0Hz, 2H), 4.20(br t, J=7.5Hz, 2H), 8.08(s, 1H), 8.41(s, 1H), 8.57(s, 2H), 14.30(br s, 1H). |
| 10-049 | (R)-1-cyclohexylethyl | nBu | 0.99(t, J=7.5Hz, 3H), 1.01-1.34(m, 6H), 1.18(d, J=6.9Hz, 3H), 1.37-1.57(m, 8H), 1.62-1.88(m, 9H), 2.63(t, J=6.0Hz, 2H), 2.88(t, J=6.0Hz, 2H), 3.99-4.10(m, 2H), 4.05-4.21(m, 1H), 8.30(s, 2H), 9.88(d, J=9.0Hz, 1H). |
| 10-050 | (S)-1-cyclohexylethyl | nBu | 0.99(t, J=7.5Hz, 3H), 1.01-1.32(m, 6H), 1.18(d, J=6.6Hz, 3H), 1.34-1.52(m, 8H), 1.62-1.86(m, 9H), 2.63(t, J=6.0Hz, 2H), 2.88(t, J=6.0Hz, 2H), 4.01-4.11(m, 2H), 4.05-4.22(m, 1H), 8.30(s, 1H), 9.88(d, J=8.4Hz, 1H). |
| 10-051 | phenacyl ethyl ketone | nBu | 0.99(t, J=7.2Hz, 3H), 1.36-1.55(m, 4H), 1.48(sextet, J=7.2Hz, 2H), 1.65-1.82(m, 6H), 2.65(t, J=6.0Hz, 2H), 2.90(t, J=6.0Hz, 2H), 4.16(br t, J=7.2Hz, 2H), 4.97(d, J=4.2Hz, 2H), 7.47-7.63(m, 3H), 8.02-8.06(m, 2H), 8.31(s, 1H), 10.81(br s, 1H). |
| 10-052 | 1-ethyl-1-hydroxycyclohexyl | nBu | 0.99(t, J=7.5Hz, 3H), 1.28-1.55(m, 12H), 1.59-1.80(m, 10H), 1.99(br s, 1H), 2.64(t, J=6.0Hz, 2H), 2.89(t, J=6.0Hz, 2H), 3.47(d, J=6.3Hz, 2H), 4.11(br t, J=7.5Hz, 2H), 8.30(s, 1H), 10.27(br s, 1H). |

TABLE 53

| Compound No. | R^r | R^5 | ^1H-NMR(CDCl_3) |
|---|---|---|---|
| 10-053 | cyclohexenylmethyl | nBu | 0.99(t, J=7.5Hz, 3H), 1.35-1.80(m, 14H), 1.46(sextet, J=7.5Hz, 2H), 2.00(br s, 4H), 2.64(t, J=6.0Hz, 2H), 2.88(t, J=6.0Hz, 2H), 3.94(d, J=6.0Hz, 2H), 4.10(br t, J=7.5Hz, 2H), 5.63(br s, 1H), 8.31(s, 1H), 9.97(br s, 1H). |
| 10-054 | 2-bromo-1-phenylpropyl | nBu | 1.00(t, J=7.2Hz, 3H), 1.35-1.79(m, 10H), 1.47(sextet, J=7.2Hz, 2H), 2.64(t, J=6.0Hz, 2H), 2.90(t, J=6.0Hz, 2H), 3.79(d, J=6.0Hz, 2H), 4.13(br t, J=7.2Hz, 2H), 5.52-5.59(m, 1H), 7.26-7.45(m, 5H), 8.32(br s, 1H), 10.80(br s, 1H). |

TABLE 53-continued

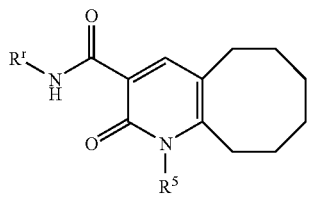

| Compound No. | R<sup>r</sup> | R<sup>5</sup> | <sup>1</sup>H-NMR(CDCl<sub>3</sub>) |
|---|---|---|---|
| 10-055 | (NC-CH2-CH(CH3)-phenyl) | nBu | 0.98(t, J=7.5Hz, 3H), 1.36-1.79(m, 10H), 1.45(sextet, J=7.5Hz, 2H), 2.64(t, J=6.0Hz, 2H), 2.89(t, J=6.0Hz, 2H), 3.03(dd, J=6.0Hz, 2.4Hz, 2H), 4.10(br t, J=7.5Hz, 2H), 5.47(q, J=6.6Hz, 1H), 7.31-7.50(m, 5H), 8.28(s, 1H), 10.82(d, J=7.5Hz, 1H). |
| 10-056 | (trans-2-hydroxy-1-methyl-indane) | nBu | 0.96(t, J=7.5Hz, 3H), 1.38-1.79(m, 12H), 2.66(t, J=6.0Hz, 2H), 2.89(t, J=6.0Hz, 2H), 3.04, 3.21(ABx, J=16.2Hz, 3.0Hz, 2H), 4.07(br t, J=7.5Hz, 2H), 4.74-4.80(m, 1H), 5.56(dd, J=7.2Hz, 5.1Hz, 1H), 7.20-7.30(m, 3H), 7.34-7.39(m, 1H), 8.35(s, 1H), 10.43(d, J=7.2Hz, 1H). |
| 10-057 | (cis-2-hydroxy-1-methyl-indane) | nBu | 0.96(t, J=7.5Hz, 3H), 1.35-1.81(m, 12H), 2.66(t, J=6.0Hz, 2H), 2.90(t, J=6.0Hz, 2H), 3.04, 3.21(ABx, J=16.2Hz, 3.0Hz, 2H), 4.07(br t, J=7.5Hz, 2H), 4.77(sextet, J=3.0Hz, 1H), 5.56(dd, J=7.2Hz, 5.1Hz, 1H), 7.23-7.32(m, 3H), 7.35-7.39(m, 1H), 8.35(s, 1H), 10.44(d, J=7.5Hz, 1H). |
| 10-058 | (1-phenylpropyl) | nBu | 0.96(t, J=7.5Hz, 3H), 0.99(t, J=7.5Hz, 3H), 1.35-1.53(m, 4H), 1.46(sextet, J=7.5Hz, 2H), 1.64-1.79(m, 6H), 1.85-1.98(m, 2H), 2.61(t, J=6.0Hz, 2H), 2.88(t, J=6.0Hz, 2H), 4.11(br t, J=7.5Hz, 2H), 5.08(q, J=7.5Hz, 1H), 7.18-7.40(m, 5H), 8.27(s, 1H), 10.40(d, J=7.8Hz, 1H). |

TABLE 54

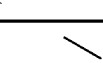

| Compound No. | R<sup>r</sup> | R<sup>5</sup> | <sup>1</sup>H-NMR(CDCl<sub>3</sub>) |
|---|---|---|---|
| 10-059 | 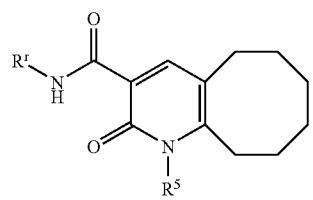 | nBu | 0.96(t, J=7.5Hz, 3H), 0.99(t, J=7.5Hz, 3H), 1.35-1.52(m, 4H), 1.46(sextet, J=7.5Hz, 2H), 1.61-1.79(m, 6H), 1.84-1.98(m, 2H), 2.61(t, J=6.0Hz, 2H), 2.88(t, J=6.0Hz, 2H), 4.10(br t, J=7.5Hz, 2H), 5.08(q, J=7.5Hz, 1H), 7.18-7.40(m, 5H), 8.27(s, 1H), 10.40(d, J=7.8Hz, 1H). |

TABLE 54-continued

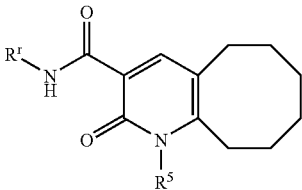

| Compound No. | R<sup>r</sup> | R<sup>5</sup> | <sup>1</sup>H-NMR(CDCl<sub>3</sub>) |
|---|---|---|---|
| 10-060 | 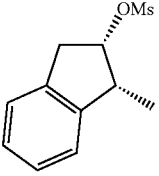 | nBu | 0.96(t, J=7.2Hz, 3H), 1.35-1.56(m, 4H), 1.42(sextet, J=7.2Hz, 2H), 1.59-1.80(m, 6H), 2.67(t, J=6.0Hz, 2H), 2.90(t, J=6.0Hz, 2H), 3.04(s, 3H), 3.28-3.43(m, 2H), 3.97-4.09(m, 2H), 5.58(td, J=4.5Hz, 1.5Hz, 1H), 5.90(dd, J=7.5Hz, 4.5Hz, 1H), 7.18-7.35(m, 4H), 8.35(s, 1H), 10.64(d, J=8.4Hz, 1H). |
| 10-061 | 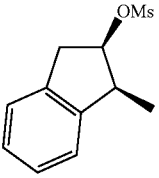 | nBu | 0.96(t, J=7.5Hz, 3H), 1.35-1.56(m, 4H), 1.42(sextet, J=7.5Hz, 2H), 1.61-1.81(m, 6H), 2.67(t, J=6.0Hz, 2H), 2.90(t, J=6.0Hz, 2H), 3.04(s, 3H), 3.28-3.44(m, 2H), 3.92-4.09(m, 2H), 5.58(td, J=4.5Hz, 1.5Hz, 1H), 5.90(dd, J=7.5Hz, 4.5Hz, 1H), 7.20-7.35(m, 4H), 8.35(s, 1H), 10.64(d, J=8.4Hz, 1H). |
| 10-062 |  | nBu | 0.97(t, J=7.2Hz, 3H), 1.36-1.54(m, 6H), 1.61-1.80(m, 6H), 2.66(t, J=6.0Hz, 1H), 2.90(t, J=6.0Hz, 2H), 2.95, 3.34(ABx, J=7.8Hz, 2H), 3.98-4.10(m, 2H), 4.23(q, J=7.2Hz, 1H), 5.65(t, J=7.2Hz, 1H), 7.19-7.32(m, 4H), 8.39(s, 1H), 10.36(d, J=8.4Hz, 1H). |
| 10-063 | 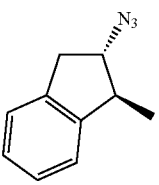 | nBu | 0.97(t, J=7.5Hz, 3H), 1.36-1.54(m, 6H), 1.61-1.81(m, 6H), 2.66(t, J=6.0Hz, 2H), 2.90(t, J=6.0Hz, 2H), 2.95, 3.34(ABx, J=7.5Hz, 2H), 3.98-4.10(m, 2H), 4.23(q, J=7.2Hz, 1H), 5.65(t, J=7.2Hz, 1H), 7.19-7.32(m, 4H), 8.39(s, 1H), 10.36(d, J=8.4Hz, 1H). |
| 10-064 | 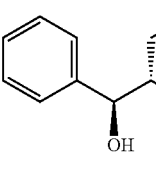 | nBu | 0.99(t, J=7.2Hz, 3H), 1.36-1.52(m, 6H), 1.63-1.80(m, 6H), 1.99(br s, 1H), 2.62(t, J=6.0Hz, 2H), 2.88(t, J=6.0Hz, 2H), 3.36(s, 3H), 3.45, 3.58(ABx, J=5.4Hz, 4.2Hz, 2H), 4.02-4.21(m, 2H), 4.33-4.41(m, 1H), 5.03(d, J=5.1Hz, 1H), 7.26-7.35(m, 3H), 7.42-7.46(m, 2H), 8.25(s, 1H), 10.62(d, J=7.8Hz, 1H). |

TABLE 55

[Structure: R^r-NH-C(=O)- attached to a bicyclic pyridinone fused with cyclooctane ring, with N-R^5]

| Compound No. | R^r | R^5 | ¹H-NMR(CDCl₃) |
|---|---|---|---|
| 10-065 | phenyl-CH(Cl)-CH(Me)-CH₂-OMe | Bu | 1.00(t, J=7.2Hz, 3H), 1.35-1.53(m, 6H), 1.61-1.80(m, 6H), 2.62(t, J=6.0Hz, 2H), 2.89(t, J=6.0Hz, 2H), 3.31, 3.57(ABx, J=5.4Hz, 4.2Hz, 2H), 3.34(s, 3H), 4.12(br t, J=7.2Hz, 2H), 4.76-4.85(m, 1H), 5.36(d, J=5.4Hz, 1H), 7.26-7.35(m, 3H), 7.45-7.49(m, 2H), 8.24(s, 1H), 10.53(d, J=8.1Hz, 1h). |
| 10-066 | Et₂CH- (3-pentyl) | Bu | 0.95(t, J=7.5Hz, 3H×2), 0.99(t, J=7.5Hz, 3H), 1.35-1.79(m, 16H), 2.63(t, J=6.0Hz, 2H), 2.88(t, J=6.0Hz, 2H), 3.92-4.05(m, 1H), 4.10(br t, J=7.2Hz, 2H), 8.31(s, 1H), 9.76(d, J=7.5Hz, 1H). |
| 10-067 | phenyl-C(=O)-CH(Me)-CH₂-OMe | Bu | 0.98(t, J=7.5Hz, 3H), 1.34-1.51(m, 6H), 1.61-1.79(m, 6H), 2.62(t, J=6.0Hz, 2H), 2.88(t, J=6.0Hz, 2H), 3.31, (s, 3H), 3.79-3.90(m, 2H), 4.11(br t, J=7.5Hz, 2H), 5.87-5.94(m, 1H), 7.45-7.62(m, 3H), 8.05-8.09(m, 2H), 8.26(s, 1H), 10.80(d, J=7.8Hz, 1H). |
| 10-068 | 1-phenylethyl | MeO-CH₂-CH₂- | 1.35(quint, J=6.0Hz, 2H), 1.48(quint, J=6.0Hz, 2H), 1.58(d, J=6.9Hz, 3H), 1.61-1.75(m, 4H), 2.64(t, J=6.0Hz, 2H), 3.04(t, J=6.0Hz, 2H), 3.31(s, 3H), 3.70(t, J=5.4Hz, 2H), 4.26-4.42(m, 2H), 5.31(quint, J=7.2Hz, 1H), 7.22-7.44(m, 5H), 8.32(s, 1H), 10.29(d, J=7.8Hz, 1H). |
| 10-069 | 1-cyclohexylethyl | MeO-CH₂-CH₂- | 0.98-1.54(m, 8H), 1.18(d, J=6.6Hz, 3H), 1.61-1.85(m, 11H), 2.65(t, J=6.0Hz, 2H), 3.04(t, J=6.0Hz, 2H), 3.31(s, 3H), 3.70(t, J=6.0Hz, 2H), 4.00-4.14(m, 1H), 4.25-4.43(m, 2H), 8.33(s, 1H), 9.81(d, J=8.7Hz, 1H). |
| 10-070 | phenyl-CH(OMs)-CH(Me)-CH₂-OMe | nBu | 1.00(t, J=7.2Hz, 3H), 1.34-1.53(m, 6H), 1.63-1.80(m, 6H), 2.62(t, J=6.0Hz, 2H), 2.83(s, 3H), 2.88(t, J=6.0Hz, 2H), 3.22, 3.50(ABx, J=4.8Hz, 2H), 3.32(s, 3H), 4.02-4.21(m, 2H), 4.68-4.78(m, 1H), 5.86(d, J=6.9Hz, 1H), 7.32-7.49(m, 5H), 8.23(s, 1H), 10.50(d, J=9.6Hz, 1H). |

TABLE 56

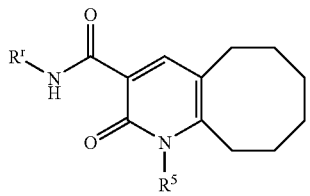

| Compound No. | R[r] | R[5] | $^1$H-NMR(CDCl$_3$) |
|---|---|---|---|
| 10-071 | 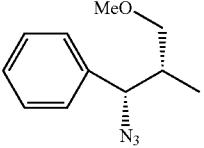 | nBu | 0.99(t, J=7.2Hz, 3H), 1.33-1.50(m, 6H), 1.62-1.79(m, 6H), 2.60(t, J=6.0Hz, 2H), 2.86(t, J=6.0Hz, 2H), 3.38, 3.68(ABx, J=4.8Hz, 2H), 3.36(s, 3H), 4.01-4.19(m, 2H), 4.60-4.69(m, 1H), 5.01(d, J=7.2Hz, 1H), 7.28-7.45(m, 5H), 8.20(s, 1H), 10.25(d, J=7.2Hz, 1H) |
| 10-072 | 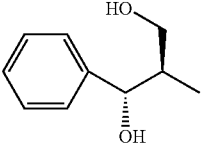 | nBu | 0.99(t, J=7.2Hz, 3H), 1.35-1.52(m, 6H), 1.62-1.80(m, 6H), 2.63(t, J=6.0Hz, 2H), 2.89(t, J=6.0Hz, 2H), 3.77, 3.87(ABx, J=6.6Hz, 4.8Hz, 2H), 4.11(br t, J=7.2Hz, 2H), 4.25(quint, J=4.8Hz, 1H), 5.07(d, J=6.0Hz, 1H), 7.26-7.36(m, 3H), 7.44-7.48(m, 2H), 8.27(s, 1H), 10.70(d, J=5.4Hz, 1H). |
| 10-073 | 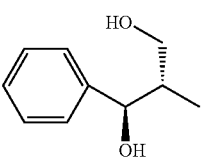 | nBu | 0.99(t, J=7.2Hz, 3H), 1.38-1.54(m, 6H), 1.61-1.80(m, 6H), 2.63(t, J=6.0Hz, 2H), 2.89(t, J=6.0Hz, 2H), 3.77, 3.87(ABx, J=6.6Hz, 4.5Hz, 2H), 4.08-4.16(m, 2H), 4.26(quint, J=6.0Hz, 1H), 5.07(d, J=5.4Hz, 1H), 7.23-7.36(m, 3H), 7.44-7.49(m, 2H), 8.28(s, 1H), 10.70(d, J=6.6Hz, 1H). |
| 10-074 | 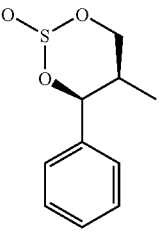 | nBu | 1.01(t, J=7.5Hz, 3H), 1.32-1.54(m, 4H), 1.46(sextet, J=7.5Hz, 2H), 1.61-1.78(m, 6H), 2.57(t, J=6.0Hz, 2H), 2.86(t, J=6.0Hz, 2H), 4.03-4.22(m, 2H), 4.12, 5.32(ABx, J=12.0Hz, 1.5Hz, 2H), 4.60(dd, J=9.0Hz, 1.5Hz, 1H), 6.32(d, J=1.5Hz, 1H), 7.24-7.32(m, 3H), 7.38-7.42(m, 2H), 8.09(s, 1H), 10.97(d, J=8.7Hz, 1H). |
| 10-075 | 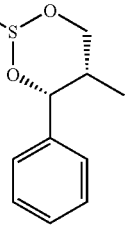 | nBu | 1.01(t, J=7.5Hz, 3H), 1.35-1.56(m, 4H), 1.45(sextet, J=7.5Hz, 2H), 1.61-1.79(m, 6H), 2.57(t, J=6.0Hz, 2H), 2.86(t, J=6.0Hz, 2H), 4.02-4.23(m, 2H), 4.12, 5.32(ABx, J=9.9Hz, 1.5Hz, 2H), 4.56-4.63(m, 1H), 6.32(d, J=1.8Hz, 1H), 7.24-7.32(m, 3H), 7.38-7.42(m, 2H), 8.09(s, 1H), 10.97(d, J=8.7Hz, 1H). |

TABLE 57

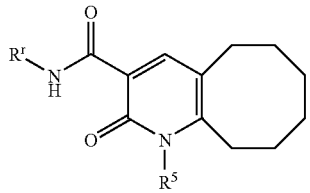

| Compound No. | R^r | R^5 | ^1H-NMR(CDCl_3) |
|---|---|---|---|
| 10-076 | 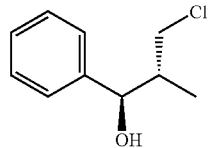 | nBu | 0.99(t, J=7.5Hz, 3H), 1.38-1.52(m, 4H), 1.45(sextet, J=7.5Hz, 2H), 1.63-1.79(m, 6H), 2.63(t, J=6.0Hz, 2H), 2.89(t, J=6.0Hz, 2H), 3.55, 3.77(ABx, J=6.0Hz, 5.1Hz, 2H), 3.73(br s, 1H), 4.03-4.19(m, 2H), 4.43-4.52(m, 1H), 5.10(d, J=6.0Hz, 1H), 7.26-7.37(m, 3H), 7.46-7.50(m, 2H), 8.25(s, 1H), 10.67(d, J=8.1Hz, 1H). |
| 10-077 | 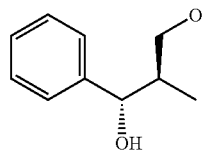 | nBu | 0.05(s, 3H), 0.06(s, 3H), 0.93(s, 9H), 0.98(t, J=7.5Hz, 3H), 1.33-1.51(m, 6H), 1.62-1.79(m, 6H), 1.90(br s, 1H), 2.61(t, J=6.0Hz, 2H), 2.88(t, J=6.0Hz, 2H), 3.73, 3.82(ABx, J=6.0Hz, 4.5Hz, 2H), 4.01-4.19(m, 2H), 4.26(sextet, J=4.5Hz, 1H), 5.10(d, J=5.4Hz, 1H), 7.24-7.33(m, 3H), 7.43-7.48(m, 2H), 8.22(s, 1H), 10.71(d, J=7.5Hz, 1H). |
| 10-078 | 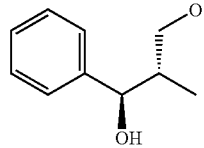 | nBu | 0.05(s, 3H), 0.06(s, 3H), 0.93(s, 9H), 0.99(t, J=7.5Hz, 3H), 1.33-1.50(m, 6H), 1.62-1.79(m, 6H), 2.05(br s, 1H), 2.61(t, J=6.0Hz, 2H), 2.88(t, J=6.0Hz, 2H), 3.73, 3.82(ABx, J=6.0Hz, 4.5Hz, 2H), 4.02-4.20(m, 2H), 4.27(sextet, J=4.5Hz, 1H), 5.10(d, J=4.8Hz, 1H), 7.22-7.34(m, 3H), 7.44-7.47(m, 2H), 8.22(s, 1H), 10.72(d, J=8.1Hz, 1H). |
| 10-079 | 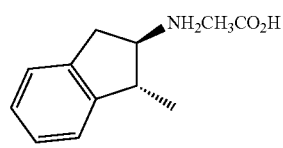 | nBu | 0.97(t, J=7.5Hz, 3H), 1.37-1.52(m, 6H), 1.61-1.80(m, 6H), 2.03(s, 3H), 2.67(t, J=6.0Hz, 2H), 2.91(t, J=6.0Hz, 2H), 3.06, 3.40(ABx, J=9.0Hz, 7.2Hz, 2H), 3.74(quint, J=7.5Hz, 1H), 3.99-4.21(m, 2H), 5.46(t, J=6.9Hz, 1H), 7.22-7.29(m, 3H), 7.33-7.38(m, 1H), 8.33(s, 1H), 10.60(d, J=6.3Hz, 1H). |
| 10-080 | 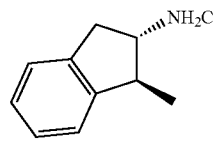 | nBu | 0.97(t, J=7.5Hz, 3H), 1.37-1.54(m, 6H), 1.61-1.78(m, 6H), 2.01(s, 3H), 2.67(t, J=6.0Hz, 2H), 2.91(t, J=6.0Hz, 2H), 3.11, 3.41(ABx, J=9.0Hz, 7.5Hz, 2H), 3.76(quint, J=7.5Hz, 1H), 3.99-4.23(m, 2H), 5.48(t, J=6.6Hz, 1H), 7.21-7.30(m, 3H), 7.34-7.38(m, 1H), 8.32(s, 1H), 10.64(d, J=6.0Hz, 1H). |

TABLE 58

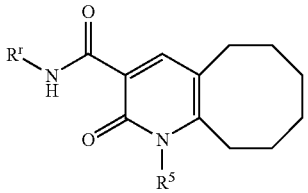

| Compound No. | R^r | R^5 | ^1H-NMR(CDCl_3) |
|---|---|---|---|
| 10-081 | 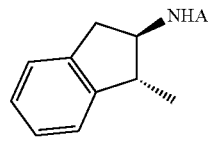 | nBu | 0.97(t, J=7.5Hz, 3H), 1.37-1.57(m, 6H), 1.62-1.81(m, 6H), 2.02(s, 3H), 2.67(t, J=6.0Hz, 2H), 2.71, 3.68(ABx, J=15.6Hz, 7.8Hz, 2H), 2.91(t, J=6.0Hz, 2H), 3.92-4.07(m, 1H), 4.11-4.27(m, 2H), 5.60(t, J=9.0Hz, 1H), 7.21-7.35(m, 5H), 8.31(s, 1H), 10.66(d, J=8.1Hz, 1H). |

TABLE 58-continued

| Compound No. | R<sup>r</sup> | R<sup>5</sup> | $^1$H-NMR(CDCl$_3$) |
|---|---|---|---|
| 10-082 | (2-methyl-1-indanyl with NHAc) | nBu | 0.97(t, J=7.5Hz, 3H), 1.38-1.58(m, 6H), 1.66-1.82(m, 6H), 2.02(s, 3H), 2.67(t, J=6.0Hz, 2H), 2.71, 3.68(ABx, J=15.6Hz, 7.8Hz, 2H), 2.91(t, J=6.0Hz, 2H), 3.92-4.06(m, 1H), 4.12-4.28(m, 2H), 5.60(t, J=9.0Hz, 1H), 7.20-7.34(m, 5H), 8.31(s, 1H), 10.66(d, J=7.8Hz, 1H). |
| 10-083 | (isobutyramide indanyl) | nBu | 0.98(t, J=7.5Hz, 3H), 1.17(t, J=7.5Hz, 6H), 1.37-1.56(m, 4H), 1.44(sextet, J=7.5Hz, 2H), 1.63-1.80(m, 6H), 2.43(quint, J=7.2Hz, 1H), 2.67(t, J=6.0Hz, 2H), 2.70, 3.71(ABx, J=15.6Hz, 7.8Hz, 2H), 2.91(t, J=6.0Hz, 2H), 3.98-4.06(m, 1H), 4.13-4.21(m, 2H), 5.60(t, J=9.0Hz, 1H), 7.22-7.37(m, 5H), 8.31(s, 1H), 10.65(d, J=7.5Hz, 1H). |
| 10-084 | (phenacyl with CH$_2$OH) | nBu | 0.98(t, J=7.2Hz, 3H), 1.38-1.52(m, 6H), 1.62-1.80(m, 6H), 2.64(t, J=6.0Hz, 2H), 2.90(t, J=6.0Hz, 2H), 3.94, 4.14(ABx, J=12.0Hz, 6.0Hz, 2H), 4.08-4.18(m, 2H), 5.76-5.82(m, 1H), 7.47-7.53(m, 2H), 7.57-7.63(m, 1H), 8.08-8.11(m, 2H), 8.29(s, 1H), 11.13(d, J=6.6Hz, 1H). |
| 10-085 | (phenacyl with CH$_2$OH) | nBu | 0.98(t, J=7.5Hz, 3H), 1.37-1.56(m, 6H), 1.61-1.80(m, 6H), 2.65(t, J=6.0Hz, 2H), 2.90(t, J=6.0Hz, 2H), 3.94, 4.14(ABx, J=12.0Hz, 6.0Hz, 2H), 4.08-4.18(m, 2H), 5.77-5.83(m, 1H), 7.48-7.53(m, 2H), 7.57-7.65(m, 1H), 8.08-8.12(m, 2H), 8.30(s, 1H), 11.14(d, J=6.6Hz, 1H). |
| 10-086 | (phenacyl with CH$_2$Cl) | nBu | 0.98(t, J=7.5Hz, 3H), 1.38-1.53(m, 6H), 1.65-1.81(m, 6H), 2.64(t, J=6.0Hz, 2H), 2.89(t, J=6.0Hz, 2H), 3.89, 4.11(ABx, J=11.4Hz, 5.1Hz, 2H), 4.08-4.19(m, 2H), 6.01-6.08(m, 1H), 7.45-7.53(m, 2H), 7.57-7.63(m, 1H), 8.04-8.08(m, 2H), 8.28(s, 1H), 10.92(d, J=7.5Hz, 1H) |

TABLE 59

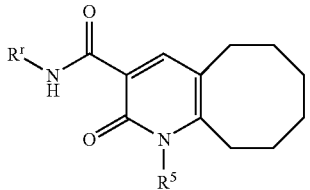

| Compound No. | R<sup>r</sup> | R<sup>5</sup> | <sup>1</sup>H-NMR(CDCl<sub>3</sub>) |
|---|---|---|---|
| 10-087 | 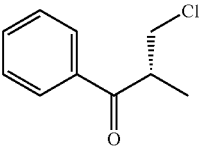 | nBu | 0.98(t, J=7.5Hz, 3H), 1.36-1.51(m, 6H), 1.62-1.79(m, 6H), 2.64(t, J=6.0Hz, 2H), 2.89(t, J=6.0Hz, 2H), 3.90, 4.11(ABx, J=11.4Hz, 5.1Hz, 2H), 4.08-4.19(m, 2H), 6.00-6.08(m, 1H), 7.45-7.53(m, 2H), 7.56-7.63(m, 1H), 8.03-8.07(m, 2H), 8.28(s, 1H), 10.92(d, J=7.8Hz, 1H). |
| 10-088 | 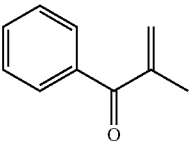 | nBu | 0.98(t, J=7.5Hz, 3H), 1.38-1.54(m, 6H), 1.64-1.80(m, 6H), 2.66(t, J=6.0Hz, 2H), 2.91(t, J=6.0Hz, 2H), 4.17(br t, J=7.5Hz, 2H), 5.58(s, 1H), 7.10(s, 1H), 7.42-7.49(m, 2H), 7.53-7.59(m, 1H), 7.77-7.82(m, 2H), 8.31(s, 1H), 12.52(br s, 1H). |
| 10-089 | 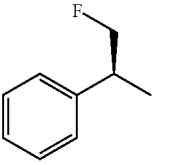 | nBu | 0.99(t, J=7.5Hz, 3H), 1.37-1.55(m, 6H), 1.60-1.81(m, 6H), 2.63(t, J=6.0Hz, 2H), 2.89(t, J=6.0Hz, 2H), 3.91(d, J=6.0Hz, 2H), 4.12(br t, J=7.5Hz, 2H), 5.51-5.58(m, 1H), 7.27-7.48(m, 5H), 8.29(s, 1H), 10.77(d, J=8.1Hz, 1H). |
| 10-090 | 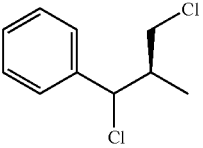 | nBu | 0.98(t, J=7.5Hz, 3H×2/5), 0.99(t, J=7.5Hz, 3H×3/5), 1.36-1.79(m, 12H), 2.61(t, J=6.0Hz, 2H×3/5), 2.62(t, J=6.0Hz, 2H×2/5), 2.87(t, J=6.0Hz, 2H×2/5), 2.88(t, J=6.0Hz, 2H×3/5), 3.52, 4.15(ABx, J=11.1Hz, 4.2Hz, 2H), 4.10-4.20(m, 2H), 4.83-4.91(m,1H×3/5), 4.98-5.08(m, 1H×2/5), 5.30(d, J=5.4Hz, 1H)×2/5), 5.44(d, J=5.4Hz, 1H×3/5), 7.28-7.38(m, 3H), 7.46-7.53(m, 2H), 8.16(s, 1H×2/5), 8.23(s, 1H×3/5), 10.46(d, J=8.4Hz, 1H×2/5), 10.72(d, J=8.4Hz, 1H×3/5). |
| 10-091 | 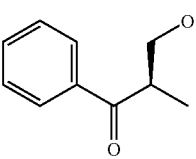 | nBu | −0.12(s, 3H), −0.11(s, 3H), 0.74(s, 9H), 0.98(t, J=7.5Hz, 3H), 1.36-1.53(m, 6H), 1.62-1.78(m, 6H), 2.62(t, J=6.0Hz, 2H), 2.88(t, J=6.0Hz, 2H), 3.96-4.10(m, 2H), 4.11-4.22(m, 2H), 5.80-5.88(m, 1H), 7.43-7.49(m, 2H), 7.53-7.61(m, 1H), 8.05-8.09(m, 2H), 8.26(s, 1H), 10.81(d, J=7.5Hz, 1H). |

TABLE 60

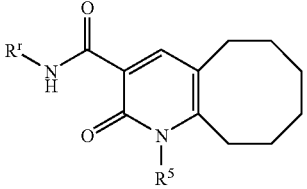

| Compound No. | R<sup>r</sup> | R<sup>5</sup> | ¹H-NMR(CDCl₃) |
|---|---|---|---|
| 10-092 | 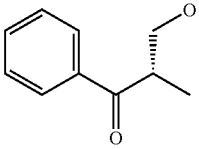 | nBu | −0.12(s, 3H), −0.11(s, 3H), 0.74(s, 9H), 0.98(t, J=7.5Hz, 3H), 1.37-1.52(m, 6H), 1.62-1.78(m, 6H), 2.62(t, J=6.0Hz, 2H), 2.88(t, J=6.0Hz, 2H), 3.96-4.10(m, 2H), 4.10-4.23(m, 2H), 5.80-4.87(m, 1H), 7.43-7.49(m, 2H), 7.53-7.61(m, 1H), 8.05-8.09(m, 2H), 8.26(s, 1H), 10.80(d, J=7.5Hz, 1H). |
| 10-093 | 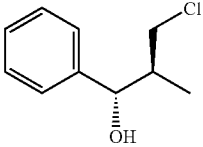 | nBu | 0.99(t, J=7.2Hz, 3H), 1.37-1.52(m, 6H), 1.63-1.81(m, 6H), 2.63(t, J=6.0Hz, 2H), 2.89(t, J=6.0Hz, 2H), 3.56, 3.77(ABx, J=11.1Hz, 5.1Hz, 2H), 4.08-4.18(m, 2H), 4.44-4.53(m, 1H), 5.10(d, J=6.0Hz, 1H), 7.25-7.37(m, 3H), 7.46-7.49(m, 2H), 8.28(s, 1H), 10.69(d, J=7.8Hz, 1H). |
| 10-094 | 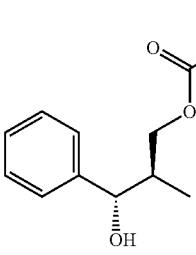 | nBu | 1.00(t, J=7.2Hz, 3H), 1.38-1.52(m, 6H), 1.63-1.80(m, 6H), 2.63(t, J=6.0Hz, 2H), 2.89(t, J=6.0Hz, 2H), 4.11(br t, J=7.2Hz, 2H), 4.34-4.42(m, 1H), 4.48-4.57(m, 2H), 5.03(d, J=4.8Hz, 1H), 7.26-7.37(m, 3H), 7.41-7.46(m, 2H), 8.26(s, 1H), 10.62(d, J=7.5Hz, 1H). |
| 10-095 | 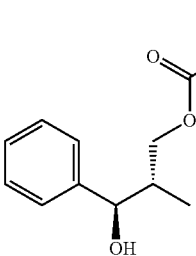 | nBu | 0.99(t,J=7.2Hz, 3H), 1.38-1.52(m, 6H), 1.62-1.79(m, 6H), 2.63(t, J=6.0Hz, 2H), 2.89(t, J=6.0Hz, 2H), 4.11(br t, J=7.2Hz, 2H), 4.34-4.42(m, 1H), 4.48-4.57(m, 2H), 5.03(d, J=4.5Hz, 1H), 7.26-7.37(m, 3H), 7.41-7.46(m, 2H), 8.24(s, 1H), 10.60(d, J=7.5Hz, 1H). |
| 10-096 | 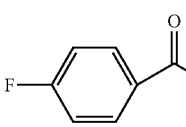 | nBu | 0.99(t, J=7.2Hz, 3H), 1.38-1.51(m, 6H), 1.64-1.78(m, 6H), 2.65(t, J=6.0Hz, 2H), 2.90(t, J=6.0Hz, 2H), 4.15(br t, J=7.2Hz, 2H), 4.93(d, J=4.5Hz, 2H), 7.14-7.21(m, 2H), 8.04-8.10(m, 2H), 8.30(s, 1H), 10.79(br s, 1H). |
| 10-097 | 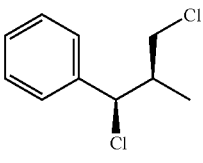 | nBu | 0.98(t, J=7.5Hz, 3H), 1.36-1.50(m, 6H), 1.62-1.78(m, 6H), 2.59(t, J=6.0Hz, 2H), 2.86(t, J=6.0Hz, 2H), 3.76, 4.15(ABx, J=11.7Hz, 4.5Hz, 2H), 4.00-4.13(m, 2H), 4.98-5.07(m, 1H), 5.30(d, J=8.1Hz, 1H), 7.24-7.37(m, 3H), 7.49-7.53(m, 2H), 8.16(s, 1H), 10.46(d, J=8.7Hz, 1H). |

TABLE 61

| Compound No. | Rʳ | R⁵ | ¹H-NMR (CDCl₃) |
|---|---|---|---|
| 10-098 | (S)-1-phenyl-2-methyl-3-chloropropyl with OCHO | nBu | 1.01 (t, J = 7.2 Hz, 3H), 1.38-1.52 (m, 6H), 1.63-1.81 (m, 6H), 2.62 (t, J = 6.0 Hz, 2H), 2.89 (t, J = 6.0 Hz, 2H), 3.47, 3.65 (ABx, J = 11.1 Hz, 5.1 Hz, 2H), 4.08-4.19 (m, 2H), 4.83-4.92 (m, 1H), 6.28 (d, J = 6.6 Hz, 1H), 7.29-7.39 (m, 3H), 7.44-7.53 (m, 2H), 8.17 (s, 1H), 8.23 (s, 1H), 10.64 (d, J = 8.7 Hz, 1H). |
| 10-099 | 1-phenyl-2-methyl-3-chloropropyl with Cl | nBu | 0.99 (t, J = 7.5 Hz, 3H), 1.38-1.52 (m, 6H), 1.62-1.79 (m, 6H), 2.59 (t, J = 6.0 Hz, 2H), 2.86 (t, J = 6.0 Hz, 2H), 3.76, 4.15 (ABx, J = 11.4 Hz, 4.5 Hz, 2H), 3.99-4.13 (m, 2H), 4.98-5.07 (m, 1H), 5.30 (d, J = 7.8 Hz, 1H), 7.24-7.41 (m, 3H), 7.50-7.53 (m, 2H), 8.16 (s, 1H), 10.46 (d, J = 8.4 Hz, 1H). |
| 10-100 | (S)-1-phenyl-2-methyl-3-chloropropyl with OCHO | nBu | 1.01 (t, J = 7.5 Hz, 3H), 1.40-1.53 (m, 6H), 1.64-1.80 (m, 6H), 2.62 (t, J = 6.0 Hz, 2H), 2.89 (t, J = 6.0 Hz, 2H), 3.47, 3.65 (ABx, J = 11.1 Hz, 5.1 Hz, 2H), 4.08-4.18 (m, 2H), 4.83-4.92 (m, 1H), 6.28 (d, J = 6.3 Hz, 1H), 7.30-7.38 (m, 3H), 7.45-7.49 (m, 2H), 8.17 (s, 1H), 8.23 (s, 1H), 10.64 (d, J = 9.0 Hz, 1H). |
| 10-101 | cyclohexylmethyl | CH₂=CH-O-(CH₂)₃- | 1.21-1.52 (m, 8H), 1.59-1.79 (m, 8H), 1.94-1.99 (m, 2H), 2.09 (quint, J = 6.0 Hz, 2H), 2.64 (t, J = 6.0 Hz, 2H), 2.92 (t, J = 6.0 Hz, 2H), 3.78 (t, J = 6.0 Hz, 2H), 3.93-4.03 (m, 1H), 4.05 (dd, J = 6.6 Hz, 2.1 Hz, 1H), 4.20 (dd, J = 14.1 Hz, 2.1 Hz, 1H), 4.25 (br t, J = 7.5 Hz, 2H), 6.49 (dd, J = 14.4 Hz, 6.9 Hz, 1H), 8.31 (s, 1H), 9.85 (d, J = 7.8 Hz, 1H). |
| 10-102 | cyclohexylmethyl | HO-(CH₂)₃- | 1.30-1.54 (m, 8H), 1.60-1.78 (m, 8H), 1.87-2.00 (m, 4H), 2.65 (t, J = 6.0 Hz, 2H), 2.93 (t, J = 6.0 Hz, 2H), 3.53 (t, J = 6.0 Hz, 2H), 3.91-4.02 (m, 1H), 4.34 (br t, J = 7.5 Hz, 2H), 8.37 (s, 1H), 9.77 (d, J = 7.2 Hz, 1H). |
| 10-103 | 2-(trifluoromethyl)benzyl | nBu | 0.99 (t, J = 7.5 Hz, 3H), 1.39-1.55 (m, 4H), 1.49 (sextet, J = 7.5 Hz, 2H), 1.68-1.83 (m, 6H), 2.67 (t, J = 6.0 Hz, 2H), 2.92 (t, J = 6.0 Hz, 2H), 4.18 (br t, J = 7.5 Hz, 2H), 7.21 (t, J = 7.5 Hz, 1H), 7.55 (t, J = 7.5 Hz, 1H), 7.64 (d, J = 8.1 Hz, 1H), 8.32 (d, J = 8.1 Hz, 1H), 8.36 (s, 1H), 12.41 (br s, 1H). |

TABLE 62

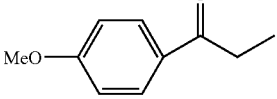

| Compound No. | $R^r$ | $R^5$ | $^1$H-NMR (CDCl$_3$) |
|---|---|---|---|
| 10-104 | 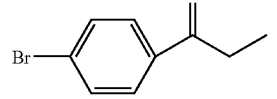 | nBu | 0.99 (t, J = 7.2 Hz, 3H), 1.38-1.52 (m, 6H), 1.63-1.80 (m, 6H), 2.65 (t, J = 6.0 Hz, 2H), 2.90 (t, J = 6.0 Hz, 2H), 3.88 (s, 3H), 4.14 (br t, J = 7.2 Hz, 2H), 4.91 (d, J = 4.5 Hz, 2H), 6.97 (d, J = 8.4 Hz, 2H), 8.03 (d, J = 8.4 Hz, 2H), 8.30 (s, 1H), 10.80 (br s, 1H). |
| 10-105 | 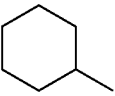 | nBu | 0.99 (t, J = 7.2 Hz, 3H), 1.36-1.53 (m, 4H), 1.47 (sextet, J = 7.2 Hz, 2H), 1.63-1.80 (m, 6H), 2.65 (t, J = 6.0 Hz, 2H), 2.90 (t, J = 6.0 Hz, 2H), 4.15 (br t, J = 7.2 Hz, 2H), 4.91 (d, J = 4.5 Hz, 2H), 7.64 (d, J = 8.7 Hz, 2H), 7.90 (d, J = 8.7 Hz, 2H), 8.29 (s, 1H), 10.79 (br s, 1H). |
| 10-106 | 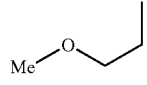 | 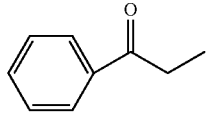 | 1.30-1.53 (m, 8H), 1.58-1.79 (m, 8H), 1.96-2.02 (m, 2H), 2.65 (t, J = 6.0 Hz, 2H), 3.03 (t, J = 6.0 Hz, 2H), 3.31 (s, 3H), 3.69 (t, J = 5.4 Hz, 2H), 3.92-4.03 (m, 1H), 4.33 (t, J = 5.4 Hz, 2H), 8.32 (s, 1H), 9.83 (d, J = 7.2 Hz, 1H). |
| 10-107 | 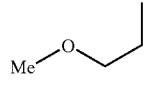 | 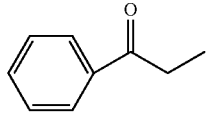 | 1.35-1.42 (m, 2H), 1.43-1.52 (m, 2H), 1.62-1.79 (m, 4H), 2.70 (t, J = 6.0 Hz, 2H), 3.06 (t, J = 6.0 Hz, 2H), 3.31 (s, 3H), 3.74 (t, J = 5.4 Hz, 2H), 4.40 (d, J = 5.4 Hz, 2H), 4.97 (d, J = 4.5 Hz, 2H), 7.50 (t, J = 7.5 Hz, 2H), 7.61 (t, J = 7.5 Hz, 1H), 8.05 (d, J = 7.5 Hz, 2H), 8.33 (s, 1H), 10.75 (br s, 1H). |
| 10-108 | 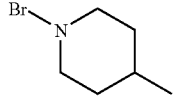 | nBu | 0.99 (t, J = 7.2 Hz, 3H), 1.38-1.52 (m, 6H), 1.63-1.79 (m, 8H), 1.95-2.07 (m, 2H), 2.20-2.33 (m, 2H), 2.63 (t, J = 6.0 Hz, 2H), 2.82-2.94 (m, 2H), 2.88 (t, J = 6.0 Hz, 2H), 3.55 (br s, 2H), 3.96-4.07 (m, 1H), 4.10 (br t, J = 7.2 Hz, 2H), 7.23-7.40 (m, 5H), 8.27 (s, 1H), 9.97 (br s, 1H). |
| 10-109 | 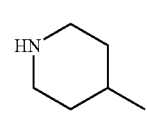<br>CH$_3$CO$_2$H | nBu | 1.00 (t, J = 7.5 Hz, 3H), 1.37-1.50 (m, 6H), 1.63-1.79 (m, 6H), 1.81-1.97 (m, 2H), 2.04 (s, 3H), 2.15-2.24 (m, 2H), 2.63 (t, J = 6.0 Hz, 2H), 2.89 (t, J = 6.0 Hz, 2H), 3.01 (t, J = 10.2 Hz, 2H), 3.33-3.41 (m, 2H), 4.09 (br t, J = 7.5 Hz, 2H), 4.10-4.25 (m, 1H), 8.26 (s, 1H), 10.21 (d, J = 7.2 Hz, 1H). |

TABLE 63

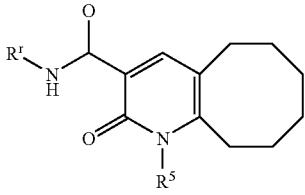

| Compound No. | R<sup>r</sup> | R<sup>5</sup> | <sup>1</sup>H-NMR (CDCl<sub>3</sub>) |
| --- | --- | --- | --- |
| 10-110 | 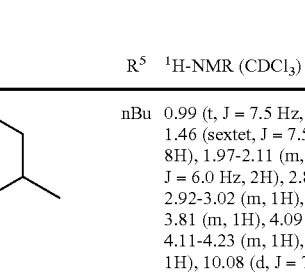 | nBu | 0.99 (t, J = 7.5 Hz, 3H), 1.36-1.58 (m, 4H), 1.46 (sextet, J = 7.5 Hz, 2H), 1.62-1.79 (m, 8H), 1.97-2.11 (m, 2H), 2.11 (s, 3H), 2.64 (t, J = 6.0 Hz, 2H), 2.89 (t, J = 6.0 Hz, 2H), 2.92-3.02 (m, 1H), 3.21-3.31 (m, 1H), 3.75-3.81 (m, 1H), 4.09 (br t, J = 7.5 Hz, 2H), 4.11-4.23 (m, 1H), 4.37-4.43 (m, 1H), 8.29 (s, 1H), 10.08 (d, J = 7.5 Hz, 1H). |
| 10-111 | 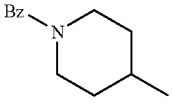 | nBu | 0.99 (t, J = 7.2 Hz, 3H), 1.36-1.57 (m, 4H), 1.46 (sextet, J = 7.2 Hz, 2H), 1.62-1.79 (m, 8H), 1.93-2.15 (m, 2H), 2.64 (t, J = 6.0 Hz, 2H), 2.89 (t, J = 6.0 Hz, 2H), 3.11-3.27 (m, 2H), 3.69-3.79 (m, 1H), 4.10 (br t, J = 7.2 Hz, 2H), 4.19-4.30 (m, 1H), 4.50-4.60 (m, 1H), 7.41 (s, 5H), 8.29 (s, 1H), 10.12 (d, J = 7.5 Hz, 1H). |
| 10-112 | 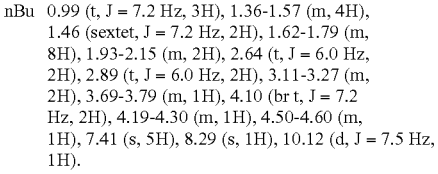 | nBu | 0.99 (t, J = 7.5 Hz, 3H), 1.29 (s, 9H), 1.35-1.79 (m, 14H), 2.00-2.09 (m, 2H), 2.65 (t, J = 6.0 Hz, 2H), 2.89 (t, J = 6.0 Hz, 2H), 3.09 (t, J = 11.4 Hz, 2H), 4.06-4.35 (m, 5H), 8.30 (s, 1H), 10.06 (d, J = 7.5 Hz, 1H). |
| 10-113 | 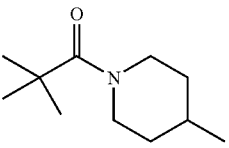 | nBu | 0.99 (t, J = 7.2 Hz, 3H), 1.28-1.81 (m, 24H), 1.98-2.10 (m, 2H), 2.44-2.53 (m, 1H), 2.65 (t, J = 6.0 Hz, 2H), 2.89 (t, J = 6.0 Hz, 2H), 2.89-2.99 (m, 1H), 3.15-3.28 (m, 1H), 3.85-3.93 (m, 1H), 4.09 (br t, J = 7.2 Hz, 2H), 4.10-4.25 (m, 1H), 4.40-4.48 (m, 1H), 8.30 (s, 1H), 10.06 (d, J = 6.9 Hz, 1H). |
| 10-114 | 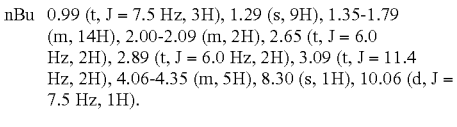 | nBu | 1.02 (t, J = 7.5 Hz, 3H), 1.38-1.78 (m, 14H), 2.07-2.20 (m, 2H), 2.65 (t, J = 6.0 Hz, 2H), 2.81 (s, 3H), 2.90 (t, J = 6.0 Hz, 2H), 2.94-3.01 (m, 2H), 3.70-3.79 (m, 2H), 4.11 (br t, J = 7.5 Hz, 2H), 4.11-4.23 (m, 1H), 8.29 (s, 1H), 10.11 (d, J = 7.2 Hz, 1H). |
| 10-115 | 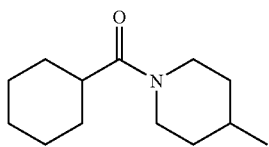 | nBu | 0.99 (t, J = 7.2 Hz, 3H), 1.37-1.51 (m, 6H), 1.62-1.78 (m, 8H), 2.03-2.09 (m, 2H), 2.53 (td, J = 11.4 Hz, 2.4 Hz, 2H), 2.62 (t, J = 6.0 Hz, 2H), 2.88 (t, J = 6.0 Hz, 2H), 3.71-3.77 (m, 2H), 3.82-3.94 (m, 1H), 4.07 (br t, J = 7.5 Hz, 2H), 7.52-7.65 (m, 3H), 7.76-7.71 (m, 2H), 8.25 (s, 1H), 10.00 (d, J = 6.9 Hz, 1H). |

TABLE 64

[Structure: bicyclic pyridone fused with cyclooctane ring, bearing C(=O)NH-R' group and N-R⁵]

| Compound No. | Rʳ | R⁵ | ¹H-NMR (CDCl₃) |
|---|---|---|---|
| 10-116 | Me-N-piperidin-4-ylmethyl | nBu | 0.99 (t, J = 7.2 Hz, 3H), 1.38-1.50 (m, 4H), 1.47 (quint, J = 7.2 Hz, 2H), 1.64-1.82 (m, 8H), 2.01-2.09 (m, 2H), 2.25-2.34 (m, 2H), 2.35 (s, 3H), 2.64 (t, J = 6.0 Hz, 2H), 2.82-2.90 (m, 2H), 2.88 (t, J = 6.0 Hz, 2H), 3.97-4.06 (m, 1H), 4.10 (br t, J = 7.2 Hz, 2H), 8.28 (s, 1H), 9.98 (d, J = 7.2 Hz, 1H). |
| 10-117 | cyclohexylmethyl | Cl(CH₂)₃ | 1.21-1.53 (m, 8H), 1.62-1.82 (m, 8H), 1.95-2.00 (m, 2H), 2.20 (dt, J = 15.0 Hz, 6.0 Hz, 2H), 2.65 (t, J = 6.0 Hz, 2H), 2.94 (t, J = 6.0 Hz, 2H), 3.69 (t, J = 6.0 Hz, 2H), 3.92-4.02 (m, 1H), 4.28 (t, J = 7.5 Hz, 2H), 8.33 (s, 1H), 9.80 (d, J = 6.9 Hz, 1H). |
| 10-118 | cyclohexylmethyl | MsO(CH₂)₃ | 1.26-1.52 (m, 8H), 1.60-1.80 (m, 8H), 1.94-2.00 (m, 2H), 2.19 (quint, J = 6.3 Hz, 2H), 2.64 (t, J = 6.0 Hz, 2H), 2.90 (t, J = 6.0 Hz, 2H), 3.06 (s, 3H), 3.92-4.01 (m, 1H), 4.27 (t, J = 7.5 Hz, 2H), 4.38 (t, J = 6.0 Hz, 2H), 8.33 (s, 1H), 9.78 (d, J = 8.1 Hz, 1H). |
| 10-119 | cyclohexylmethyl | AcS(CH₂)₃ | 1.25-1.52 (m, 8H), 1.59-1.79 (m, 8H), 1.93-2.05 (m, 4H), 2.32 (s, 3H), 2.63 (t, J = 6.0 Hz, 2H), 2.88 (t, J = 6.0 Hz, 2H), 2.98 (t, J = 6.9 Hz, 2H), 3.91-4.01 (m, 1H), 4.15 (t, J = 7.2 Hz, 2H), 8.30 (s, 1H), 9.82 (d, J = 7.5 Hz, 1H). |
| 10-120 | cyclohexylmethyl | N₃(CH₂)₃ | 1.25-1.52 (m, 8H), 1.58-1.80 (m, 8H), 1.93-2.03 (m, 4H), 2.64 (t, J = 6.0 Hz, 2H), 2.91 (t, J = 6.0 Hz, 2H), 3.48 (t, J = 6.0 Hz, 2H), 3.92-4.03 (m, 1H), 4.20 (t, J = 7.5 Hz, 2H), 8.32 (s, 1H), 9.81 (d, J = 6.9 Hz, 1H). |
| 10-121 | cyclohexylmethyl | H₂N(CH₂)₃ · CH₃CO₂H | 1.27-1.53 (m, 8H), 1.60-1.81 (m, 8H), 1.92-2.01 (m, 2H), 2.05 (s, 3H), 2.20-2.29 (m, 2H), 2.66 (t, J = 6.0 Hz, 2H), 2.90 (t, J = 6.0 Hz, 2H), 2.98 (br s, 2H), 3.90-4.00 (m, 1H), 4.27-4.35 (m, 2H), 8.40 (s, 1H), 9.50 (d, J = 7.5 Hz, 1H). |
| 10-122 | cyclohexylmethyl | AcHN(CH₂)₃ | 1.24-1.52 (m, 8H), 1.62-1.79 (m, 8H), 1.88-2.03 (m, 4H), 2.03 (s, 3H), 2.65 (t, J = 6.0 Hz, 2H), 2.89 (t, J = 6.0 Hz, 2H), 3.24-3.30 (m, 2H), 3.97-4.05 (m, 1H), 4.22 (br t, J = 7.5 Hz, 2H), 6.72 (br s, 1H), 8.35 (s, 1H), 9.81 (d, J = 7.8 Hz, 1H). |

TABLE 65

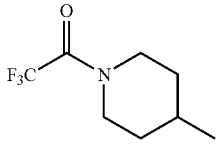

| Compound No. | R^r | R^5 | $^1$H-NMR (CDC$_3$) |
|---|---|---|---|
| 10-123 | 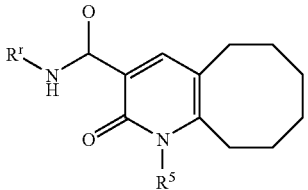 | nBu | 0.99 (t, J = 7.2 Hz, 3H), 1.37-1.52 (m, 6H), 1.60-1.72 (m, 6H), 1.71-1.80 (m, 2H), 2.07-2.17 (m, 2H), 2.65 (t, J = 6.0 Hz, 2H), 2.89 (t, J = 6.0 Hz, 2H), 3.17 (t, J =11.1 Hz, 1H), 3.37 (t, J = 11.1 Hz, 1H), 3.92-3.99 (m, 1H), 4.03-4.12 (m, 2H), 4.22-4.37 (m, 2H), 8.28 (s, 1H), 10.17 (d, J = 7.2 Hz, 1H). |
| 10-124 | 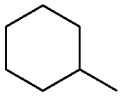 | 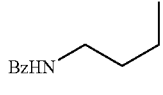 | 1.29-1.51 (m, 8H), 1.65-1.77 (m, 8H), 1.92-2.05 (m, 4H), 2.65 (t, J = 6.0 Hz, 2H), 2.93 (t, J = 6.0 Hz, 2H), 3.45 (br s, 2H), 3.97-4.05 (m, 1H), 4.32 (br t, J = 7.5 Hz, 2H), 7.42-7.55 (m, 3H), 7.89 (br s, 1H), 7.90-7.96 (m, 2H), 8.37 (s, 1H), 9.90 (d, J = 7.8 Hz, 1H). |
| 10-125 | 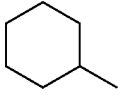 | 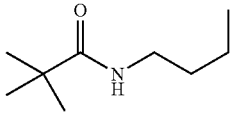 | 1.25 (s, 9H), 1.28-1.51 (m, 8H), 1.60-1.78 (m, 8H), 1.85-2.00 (m, 4H), 2.64 (t, J = 6.0 Hz, 2H), 2.90 (t, J = 6.0 Hz, 2H), 3.23 (br s, 2H), 3.95-4.04 (m, 1H), 4.22 (br t, J = 7.5 Hz, 2H), 7.12 (br s, 1H), 8.35 (s, 1H), 9.89 (d, J = 7.5 Hz, 1H). |
| 10-126 | 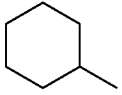 | 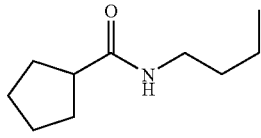 | 1.27-1.52 (m, 8H), 1.57-1.80 (m, 14H), 1.83-2.01 (m, 6H), 2.55-2.65 (m, 1H), 2.64 (t, J = 6.0 Hz, 2H), 2.89 (t, J = 6.0 Hz, 2H), 3.25-3.29 (m, 2H), 3.95-4.04 (m, 1H), 4.22 (br t, J = 7.5 Hz, 2H), 6.73 (br s, 1H), 8.34 (s, 1H), 9.85 (d, J = 8.1 Hz, 1H). |
| 10-127 | 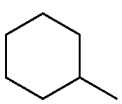 | 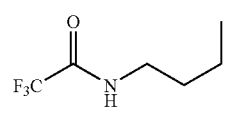 | 1.29-1.52 (m, 8H), 1.61-1.79 (m, 8H), 1.91-2.02 (m, 4H), 2.66 (t, J = 6.0 Hz, 2H), 2.91 (t, J = 6.0 Hz, 2H), 3.34 (br s, 2H), 3.97-4.04 (m, 1H), 4.27 (br t, J = 7.5 Hz, 2H), 8.39 (s, 1H), 8.67 (br s, 1H), 9.76 (d, J = 8.1 Hz, 1H). |
| 10-128 | 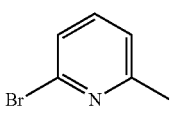 | nBu | 1.00 (t, J = 7.5 Hz, 3H), 1.40-1.54 (m, 6H), 1.68-1.81 (m, 6H), 2.67 (t, J = 6.0 Hz, 2H), 2.92 (t, J = 6.0 Hz, 2H), 4.15 (br t, J = 7.5 Hz, 2H), 7.18 (d, J = 7.5 Hz, 1H), 7.53 (t, J = 7.5 Hz, 1H), 8.33 (d, J = 7.5 Hz, 1H), 8.34 (s, 1H), 12.69 (br s, 1H). |

TABLE 66

| Compound No. | R^r | R^5 | $^1$H-NMR (CDCl$_3$) |
|---|---|---|---|
| 10-129 | 2-(OCHF$_2$)phenyl | nBu | 1.00 (t, J = 7.2 Hz, 3H), 1.37-1.54 (m, 6H), 1.65-1.81 (m, 6H), 2.67 (t, J = 6.0 Hz, 2H), 2.92 (t, J = 6.0 Hz, 2H), 4.17 (br t, J = 7.2 Hz, 2H), 6.22 (s, 1H × 1/5), 6.39 (s, 1H × 1/5), 6.47 (s, 1H × 1/5), 6.64 (s, 1H × 1/5), 6.88 (s, 1H × 1/5), 7.01-7.10 (m, 1H), 7.18-7.27 (m, 2H), 8.36 (s, 1H), 8.60 (dd, J = 7.8 Hz, 1.8 Hz, 1H), 12.59 (br s, 1H). |
| 10-130 | 2-(OCF$_3$)phenyl | nBu | 1.00 (t, J = 7.5 Hz, 3H), 1.37-1.53 (m, 4H), 1.47 (sextet, J = 7.5 Hz, 2H), 1.65-1.82 (m, 6H), 2.67 (t, J = 6.0 Hz, 2H), 2.92 (t, J = 6.0 Hz, 2H), 4.18 (br t, J = 7.5 Hz, 2H), 7.08 (td, J = 8.4 Hz, 1.8 Hz, 1H), 7.26-7.34 (m, 2H), 8.36 (s, 1H), 8.64 (dd, J = 9.0 Hz, 1.8 Hz, 1H), 12.76 (br s, 1H). |
| 10-131 | 5-bromo-2-methylthiazol-?-yl | nBu | 1.00 (t, J = 7.5 Hz, 3H), 1.38-1.54 (m, 4H), 1.47 (sextet, J = 7.5 Hz, 2H), 1.61-1.82 (m, 6H), 2.68 (t, J = 6.0 Hz, 2H), 2.93 (t, J = 6.0 Hz, 2H), 4.16 (br t, J = 7.5 Hz, 2H), 7.41 (s, 1H), 8.34 (s, 1H), 13.49 (br s, 1H). |
| 10-132 | 2-methyl-5-phenylthiazolyl | nBu | 1.01 (t, J = 7.5 Hz, 3H), 1.38-1.52 (m, 4H), 1.48 (sextet, J = 7.5 Hz, 2H), 1.63-1.85 (m, 6H), 2.68 (t, J = 6.0 Hz, 2H), 2.94 (t, J = 6.0 Hz, 2H), 4.17 (br t, J = 7.5 Hz, 2H), 7.27-7.32 (m, 1H), 7.36-7.42 (m, 2H), 7.57-7.61 (m, 2H), 7.71 (s, 1H), 8.37 (s, 1H), 13.52 (br s, 1H). |
| 10-133 | 6-methyl-2-phenylpyridinyl | nBu | 1.01 (t, J = 7.5 Hz, 3H), 1.40-1.55 (m, 4H), 1.49 (sextet, J = 7.5 Hz, 2H), 1.65-1.81 (m, 6H), 2.68 (t, J = 6.0 Hz, 2H), 2.93 (t, J = 6.0 Hz, 2H), 4.19 (br t, J = 7.5 Hz, 2H), 7.38-7.52 (m, 4H), 7.78 (t, J = 8.1 Hz, 1H), 8.09 (d, J = 8.1 Hz, 2H), 8.33 (d, J = 8.1 Hz, 1H), 8.40 (s, 1H), 12.61 (br s, 1H). |
| 10-134 | 2-(OCF$_3$)phenyl | MsHN(CH$_2$)$_3$- | 1.28-1.52 (m, 8H), 1.63-1.80 (m, 8H), 1.92-2.01 (m, 4H), 2.64 (t, J = 6.0 Hz, 2H), 2.90 (t, J = 6.0 Hz, 2H), 2.94 (s, 3H), 3.08 (q, J = 5.4 Hz, 2H), 3.94-4.02 (m, 1H), 4.29 (br t, J = 7.5 Hz, 2H), 5.84 (br t, J = 7.5 Hz, 1H), 8.35 (s, 1H), 9.72 (d, J = 7.5 Hz, 1H). |

TABLE 67

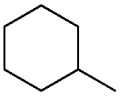

| Compound No. | R<sup>r</sup> | R<sup>5</sup> | $^1$H-NMR (CDCl$_3$) |
|---|---|---|---|
| 10-135 |  | 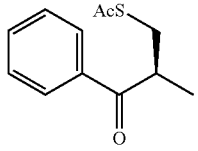 | 1.29-1.50 (m, 8H), 1.63-1.78 (m, 8H), 1.86-2.00 (m, 4H), 2.61 (t, J = 6.0 Hz, 2H), 2.79-2.90 (m, 2H), 2.85 (t, J = 6.0 Hz, 2H), 3.95-4.03 (m, 1H), 4.24 (br t, J = 7.5 Hz, 2H), 6.19 (br s, 1H), 7.44-7.58 (m, 3H), 7.82-7.87 (m, 2H), 8.34 (s, 1H), 9.75 (d, J = 7.5 Hz, 1H). |
| 10-136 | 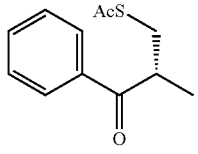 | nBu | 0.98 (t, J = 7.5 Hz, 3H), 1.36-1.53 (m, 4H), 1.45 (sextet, J = 7.5 Hz, 2H), 1.64-1.77 (m, 6H), 2.31 (s, 3H), 2.62 (t, J = 6.0 Hz, 2H), 2.88 (t, J = 6.0 Hz, 2H), 3.21, 3.66 (ABx, J = 13.8 Hz, 6.0 Hz, 2H), 4.10 (br t, J = 7.5 Hz, 2H), 5.92-6.00 (m, 1H), 7.46-7.52 (m, 2H), 7.55-7.62 (m, 1H), 8.12-8.16 (m, 2H), 8.27 (s, 1H), 10.76 (d, J = 8.4 Hz, 1H). |
| 10-137 | 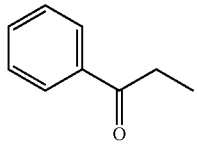 | nBu | 0.98 (t, J = 7.5 Hz, 3H), 1.36-1.52 (m, 4H), 1.45 (sextet, J = 7.5 Hz, 2H), 1.63-1.77 (m, 6H), 2.31 (s, 3H), 2.62 (t, J = 6.0 Hz, 2H), 2.88 (t, J = 6.0 Hz, 2H), 3.21, 3.66 (ABx, J = 13.8 Hz, 6.0 Hz, 2H), 4.11 (br t, J = 7.5 Hz, 2H), 5.92-6.00 (m, 1H), 7.46-7.62 (m, 3H), 8.12-8.16 (m, 2H), 8.27 (s, 1H), 10.75 (d, J = 7.8 Hz, 1H). |
| 10-138 | 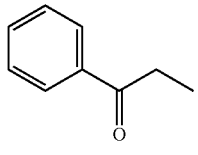 | 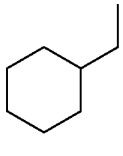 | 1.01 (d, J = 6.9 Hz, 6H), 1.38-1.52 (m, 4H), 1.60-1.73 (m, 5H), 1.78 (quint, J = 6.0 Hz, 2H), 2.65 (t, J = 6.0 Hz, 2H), 2.96 (t, J = 6.0 Hz, 2H), 4.16 (br t, J = 7.5 Hz, 2H), 4.97 (d, J = 4.8 Hz, 2H), 7.50 (t, J = 7.5 Hz, 2H), 7.61 (t, J = 7.5 Hz, 1H), 8.02-8.06 (m, 2H), 8.30 (s, 1H), 10.79 (br s, 1H). |
| 10-139 | 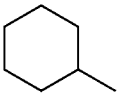 | 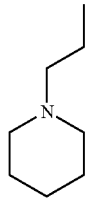 | 1.05-1.38 (m, 6H), 1.50 (br s, 2H), 1.63-1.77 (m, 10H), 1.82-1.93 (m, 1H), 2.65 (t, J = 6.0 Hz, 2H), 2.93 (t, J = 6.0 Hz, 2H), 4.04 (br s, 2H), 4.97 (d, J = 4.5 Hz, 2H), 7.50 (t, J = 7.5 Hz, 2H), 7.61 (t, J = 7.5 Hz, 1H), 8.02-8.06 (m, 2H), 8.31 (s, 1H), 10.79 (br s, 1H.). |
| 10-140 | | | 1.31-1.51 (m, 10H), 1.57-1.79 (m, 14H), 1.94-2.01 (m, 2H), 2.50-2.66 (m, 8H), 3.90-4.01 (m, 1H), 4.28 (br t, J = 7.5 2H), Hz, 8.30 (s, 1H), 9.84 (d, J = 7.8 Hz, 1H). |

TABLE 68

[Structure: bicyclic pyridone core with R^r-NH-C(O)- substituent and N-R^5]

| Compound No. | R^r | R^5 | $^1$H-NMR (CDCl$_3$) |
|---|---|---|---|
| 10-141 | Bn-N(piperidin-4-yl with Me) | CH(Me)CH$_2$CH(Me)Me | 1.01 (t, J = 6.3 Hz, 6H), 1.34-1.53 (m, 4H), 1.56-1.80 (m, 9H), 1.97-2.05 (m, 2H), 2.17-2.27 (m, 2H), 2.62 (t, J = 6.0 Hz, 2H), 2.81-2.89 (m, 2H), 2.87 (t, J = 6.0 Hz, 2H), 3.54 (s, 2H), 3.96-4.04 (m, 1H), 4.11 (br t, J = 7.5 Hz, 2H), 7.26-7.35 (m, 5H), 8.27 (s, 1H), 9.96 (d, J = 7.2 Hz, 1H). |
| 10-142 | Bn-N(piperidin-4-yl with Me) | cyclohexylmethyl | 1.05-1.36 (m, 8H), 1.48 (br s, 2H), 1.64-1.88 (m, 11H), 1.96-2.05 (m, 2H), 2.22 (t, J = 9.9 Hz, 2H), 2.63 (t, J = 6.0 Hz, 2H), 2.81-2.86 (m, 2H), 2.91 (t, J = 6.0 Hz, 2H), 3.54 (s, 2H), 3.93-4.02 (m, 3H), 7.23-7.36 (m, 5H), 8.29 (s, 1H), 9.96 (d, J = 7.8 Hz, 1H). |
| 10-143 | HN(piperidin-4-yl with Me) · CH$_3$CO$_2$H | CH(Me)CH$_2$CH(Me)Me | 1.02 (d, J = 6.6 Hz, 6H), 1.36-1.73 (m, 8H), 1.77 (quint, J = 6.0 Hz, 4H), 1.98-2.10 (m, 1H), 2.05 (s, 3H), 2.21-2.30 (m, 2H), 2.61-2.68 (m, 2H), 2.89 (t, J = 6.0 Hz, 2H), 3.09 (t, J = 9.9 Hz, 2H), 3.42-3.50 (m, 2H), 4.05-4.21 (m, 3H), 8.25 (s, 1H), 10.27 (d, J = 6.3 Hz, 1H). |
| 10-144 | Ac-N(piperidin-4-yl with Me) | CH(Me)CH$_2$CH(Me)Me | 1.01 (d, J = 6.6 Hz, 6H), 1.36-1.72 (m, 9H), 1.76 (quint, J = 6.0 Hz, 4H), 1.99-2.10 (m, 2H), 2.11 (s, 3H), 2.64 (t, J = 6.0 Hz, 2H), 2.88 (t, J = 6.0 Hz, 2H), 2.91-3.00 (m, 1H), 3.21-3.03 (m, 1H), 3.76-3.81 (m, 1H), 4.10 (br t, J = 7.5 Hz, 2H), 4.11-4.25 (m, 1H), 4.36-4.44 (m, 1H), 8.28 (s, 1H), 10.07 (d, J = 7.2 Hz, 1H). |
| 10-145 | Ms-N(piperidin-4-yl with Me) | CH(Me)CH$_2$CH(Me)Me | 1.01 (d, J = 6.3 Hz, 6H), 1.37-1.80 (m, 13H), 2.08-2.16 (m, 2H), 2.64 (t, J = 6.0 Hz, 2H), 2.81 (s, 3H), 2.88 (t, J = 6.0 Hz, 2H), 2.89-2.99 (m, 2H), 3.68-3.76 (m, 2H), 4.05-4.16 (m, 3H), 8.27 (s, 1H), 10.10 (d, J = 7.2 Hz, 1H). |
| 10-146 | F$_3$C-C(O)-N(piperidin-4-yl with Me) | CH(Me)CH$_2$CH(Me)Me | 1.01 (d, J = 6.3 Hz, 6H), 1.38-1.78 (m, 13H), 2.08-2.15 (m, 2H), 2.64 (t, J = 6.0 Hz, 2H), 2.89 (t, J = 6.0 Hz, 2H), 3.11-3.21 (m, 1H), 3.31-3.41 (m, 1H), 3.96 (t, J = 14.4 Hz, 1H), 4.14 (br t, J = 7.5 Hz, 2H), 4.21-4.38 (m, 2H), 8.28 (s, 1H), 10.16 (d, J = 7.5 Hz, 1H). |

TABLE 69

| Compound No. | R<sup>r</sup> | R<sup>5</sup> | $^1$H-NMR (CDCl$_3$) |
|---|---|---|---|
| 10-147 | 4-methylpiperidinyl (NH) · CH$_3$CO$_2$H | cyclohexyl | 1.06-1.40 (m, 8H), 1.49 (br s, 2H), 1.61-1.99 (m, 11H), 2.18-2.28 (m, 2H), 2.64 (t, J = 6.0 Hz, 2H), 2.92 (t, J = 6.0 Hz, 2H), 3.04 (t, J = 10.5 Hz, 2H), 3.38-3.44 (m, 2H), 4.05-4.20 (m, 3H), 8.26 (s, 1H), 10.23 (d, J = 7.2 Hz, 1H). |
| 10-148 | 1-Ac-4-methylpiperidinyl | cyclohexyl | 1.02-1.33 (m, 8H), 1.45-1.80 (m, 13H), 1.98-2.10 (m, 2H), 2.11 (s, 3H), 2.65 (t, J = 6.0 Hz, 2H), 2.92 (t, J = 6.0 Hz, 2H), 2.93-3.01 (m, 1H), 3.21-3.31 (m, 1H), 3.74-3.81 (m, 1H), 3.99 (br s, 1H), 4.10-4.23 (m, 2H), 4.37-4.43 (m, 1H), 8.29 (s, 1H), 10.08 (d, J = 7.8 Hz, 1H). |
| 10-149 | 1-Ms-4-methylpiperidinyl | cyclohexyl | 1.02-1.33 (m, 8H), 1.49 (br s, 2H), 1.60-1.81 (m, 11H), 2.08-2.15 (m, 2H), 2.65 (t, J = 6.0 Hz, 2H), 2.81 (s, 3H), 2.90-3.00 (m, 4H), 3.69-3.76 (m, 2H), 3.99 (br s, 1H), 4.06-4.12 (m, 2H), 8.28 (s, 1H), 10.10 (d, J = 7.2 Hz, 1H). |
| 10-150 | 1-(F$_3$C-CO)-4-methylpiperidinyl | cyclohexyl | 1.03-1.38 (m, 8H), 1.49 (br s, 2H), 1.60-1.85 (m, 11H), 2.07-2.17 (m, 2H), 2.65 (t, J = 6.0 Hz, 2H), 2.91 (t, J = 6.0 Hz, 2H), 3.11-3.21 (m, 1H), 3.31-3.41 (m, 1H), 3.96 (d, J = 14.4 Hz, 2H), 4.00 (br s, 1H), 4.22-4.38 (m, 2H), 8.29 (s, 1H), 10.17 (d, J = 7.5 Hz, 1H). |
| 10-151 | 2,6-dimethylpyridin-3-yl | nBu | 1.00 (t, J = 7.2 Hz, 3H), 1.37-1.54 (m, 4H), 1.47 (sextet, J = 7.2 Hz, 2H), 1.66-1.83 (m, 6H), 2.49 (s, 3H), 2.67 (t, J = 6.0 Hz, 2H), 2.92 (t, J = 6.0 Hz, 2H), 4.16 (br t, J = 7.2 Hz, 2H), 6.87 (d, J = 7.5 Hz, 1H), 7.59 (t, J = 7.5 Hz, 1H), 8.15 (d, J = 8.4 Hz, 1H), 8.37 (s, 1H), 12.55 (br s, 1H). |
| 10-152 | 6-methylpyridin-2-yl | nBu | 0.99 (t, J = 7.2 Hz, 3H), 1.38-1.54 (m, 4H), 1.46 (sextet, J = 7.2 Hz, 2H), 1.66-1.83 (m, 6H), 2.67 (t, J = 6.0 Hz, 2H), 2.92 (t, J = 6.0 Hz, 2H), 4.15 (t, J = 7.2 Hz, 2H), 6.99-7.04 (m, 1H), 7.67-7.74 (m, 1H), 8.33-8.37 (m, 2H), 8.36 (s, 1H), 12.77 (br s, 1H). |
| 10-153 | 6-bromo-2-methylpyridin-3-yl | MeOCH$_2$CH$_2$- | 1.36-1.43 (m, 2H), 1.47-1.55 (m, 2H), 1.65-1.80 (m, 4H), 2.69 (t, J = 6.0 Hz, 2H), 3.08 (t, J = 6.0 Hz, 2H), 3.31 (s, 3H), 3.74 (t, J = 5.1 Hz, 2H), 4.39 (t, J = 5.1 Hz, 2H), 7.18 (dd, J = 7.5 Hz, 0.9 Hz, 1H), 7.54 (t, J = 7.8 Hz, 1H), 8.33 (dd, J = 8.1 Hz, 0.9 Hz, 1H), 8.37 (s, 1H), 12.62 (br s, 1H). |

TABLE 70

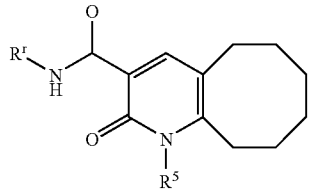

| Compound No. | R<sup>r</sup> | R<sup>5</sup> | ¹H-NMR (CDCl₃) |
|---|---|---|---|
| 10-154 | 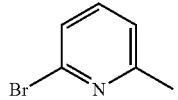 | 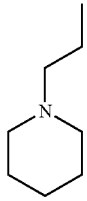 | 1.38-1.83 (m, 14H), 2.52-2.73 (m, 6H), 2.67 (t, J = 6.0 Hz, 2H), 3.02 (br t, J = 6.0 Hz, 2H), 4.39 (br t, J = 7.5 Hz, 2H, 7.19 (dd, J = 7.5 Hz, 0.6 Hz, 1H), 7.54 (t, J = 7.5 Hz, 1H), 8.33 (dd, J = 8.4 Hz, 0.6 Hz, 1H), 8.35 (s, 1H), 12.58 (br s, 1H). |
| 10-155 | 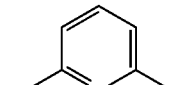 |  | 1.37-1.55 (m, 4H), 1.67-1.86 (m, 4H), 1.97 (quint, J = 6.0 Hz, 2H), 2.68 (t, J = 6.0 Hz, 2H), 2.97 (t, J = 6.0 Hz, 2H), 3.60 (t, J = 5.7 Hz, 2H), 4.39 (br t, J = 7.5 Hz, 2H), 7.20 (dd, J = 7.5 Hz, 0.6 Hz, 1H), 7.54 (t, J = 7.8 Hz, 1H), 8.33 (dd, J = 8.1 Hz, 0:6 Hz, 1H), 8.40 (s, 1H), 12.45 (br s, 1H). |
| 10-156 | 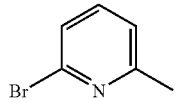 |  | 1.39-1.46 (m, 2H), 1.47-1.56 (m, 2H), 1.66-1.74 (m, 2H), 1.77-1.85 (m, 2H), 2.23 (quint, J = 6.0 Hz, 2H), 2.68 (t, J = 6.0 Hz, 2H), 2.94 (t, J = 6.0 Hz, 2H), 3.10 (s, 3H), 4.33 (t, J = 7.5 Hz, 2H), 4.40 (t, J = 6.0 Hz, 2H), 7.19 (dd, J = 7.5 Hz, 0.6 Hz, 1H), 7.55 (t, J = 7.8 Hz, 1H), 8.32 (dd, J = 8.4 Hz, 0.6 Hz, 1H, 8.37 (s, 1H), 12.56 (br s, 1H. |
| 10-157 | 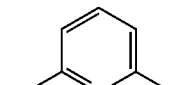 |  | 1.37-1.45 (m, 2H), 1.47-1.56 (m, 2H), 1.66-1.74 (m, 2H), 1.76-1.85 (m, 2H), 2.03 (quint, J = 7.5 Hz, 2H), 2.37 (s, 3H, 2.66 (t, J = 6.0 Hz, 2H), 2.92 (t, J = 6.0 Hz, 2H), 3.00 (t, J = 7.2 Hz, 2H), 4.21 (t, J = 7.5 Hz, 2H), 7.18 (d, J = 7.5 Hz, 1H), 7.54 (t, J = 7.5 Hz, 1H), 8.32 (d, J = 8.4 Hz, 1H), 8.35 (s, 1H), 12.59 (br s, 1H). |
| 10-158 | 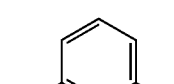 |  | 1.38-1.45 (m, 2H), 1.47-1.56 (m, 2H), 1.66-1.74 (m, 2H), 1.77-1.86 (m, 2H), 1.97-2.07 (m, 2H), 2.68 (t, J = 6.0 Hz, 2H), 2.95 (t, J = 6.0 Hz, 2H), 3.52 (t, J = 6.0 Hz, 2H), 4.25 (t, J = 7.5 Hz, 2H), 7.19 (dd, J = 7.5 Hz, 0.6 Hz, 1H), 7.54 (t, J = 7.8 Hz, 1H), 8.32 (dd, J = 8.4 Hz, 0.6 Hz, 1H), 8.36 (s, 1H), 12.58 (br s, 1H). |

TABLE 71

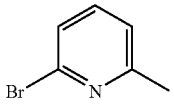

| Compound No. | R$^r$ | R$^5$ | $^1$H-NMR (CDCl$_3$) |
|---|---|---|---|
| 10-159 | 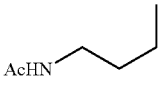 | 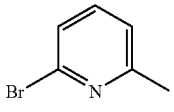 | 1.38-1.44 (m, 2H), 1.47-1.56 (m, 2H), 1.65-1.74 (m, 2H), 1.76-1.84 (m, 2H), 1.94 (quint, J = 6.6 Hz, 2H), 2.10 (s, 3H), 2.68 (t, J = 6.0 Hz, 2H), 2.93 (t, J = 6.0 Hz, 2H), 3.30 (q, J = 6.0 Hz, 2H), 4.26 (br t, J = 7.5 Hz, 2H), 6.63 (br t, J = 7.5 Hz, 1H), 7.21 (dd, J = 8.1 Hz, 0.6 Hz, 1H), 7.56 (t, J = 7.8 Hz, 1H), 8.34 (dd, J = 8.1 Hz, 0.6 Hz, 1H), 8.39 (s, 1H), 12.51 (br s, 1H). |
| 10-160 | 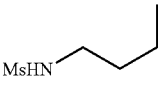 | 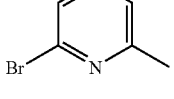 | 1.41-1.85 (m, 8H), 2.01-2.11 (m, 2H), 2.68 (t, J = 6.0 Hz, 2H), 2.94 (t, J = 6.0 Hz, 2H), 3.04 (s, 3H), 3.18 (q, J = 6.0 Hz, 2H), 4.34 (br t, J = 7.5 Hz, 2H), 5.58 (br t, J = 7.5 Hz, 1H), 7.20 (dd, J = 7.5 Hz, 0.6 Hz, 1H), 7.55 (t, J = 7.8 Hz, 1H), 8.31 (dd, J = 8.1 Hz, 0.6 Hz, 1H), 8.39 (s, 1H), 12.45 (br s, 1H). |
| 10-161 | 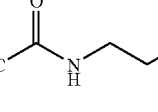 | 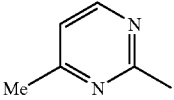 | 1.42-1.83 (m. 8H), 2.03 (quint, J = 6.0 Hz, 2H), 2.69 (t, J = 6.0 Hz, 2H), 2.93 (t, J = 6.0 Hz, 2H), 3.41 (q, J = 6.0 Hz, 2H), 4.30 (br t, J = 7.5 Hz, 2H), 7.22 (dd, J = 7.8 Hz, 0.6 Hz, 1H), 7.56 (t, J = 7.8 Hz, 1H), 8.13 (br s, 1H), 8.31 (dd, J = 7.8 Hz, 0.6 Hz, 1H), 8.42 (s, 1H), 12.40 (br s, 1H). |
| 10-162 | 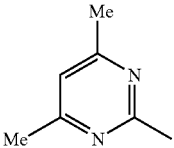 | nBu | 0.99 (t, J = 7.2 Hz, 3H), 1.39-1.57 (m, 4H), 1.47 (sextet, J = 7.2 Hz, 2H), 1.65-1.83 (m, 6H), 2.51 (s, 3H), 2.68 (t, J = 6.0 Hz, 2H), 2.92 (t, J = 6.0 Hz, 2H), 4.16 (br t, J = 7.2 Hz, 2H), 6.86 (d, J = 4.8 Hz, 1H), 8.41 (s, 1H), 8.54 (d, J = 4.8 Hz, 1H), 12.91 (br s, 1H). |
| 10-163 | 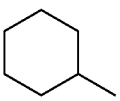 | nBu | 0.99 (t, J = 7.5 Hz, 3H), 1.39-1.53 (m, 4H), 1.46 (sextet, J = 7.5 Hz, 2H), 1.65-1.82 (m, 6H), 2.47 (s, 6H), 2.67 (t, J = 6.0 Hz, 2H), 2.91 (t, J = 6.0 Hz, 2H), 4.15 (br t, J = 7.5 Hz, 2H), 6.74 (s 1H), 8.41 (s, 1H), 12.75 (br s,1H). |
| 10-164 | 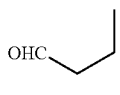 | OHC | 1.22-1.52 (m, 8H), 1.63-1.79 (m, 8H), 1.92-2.00 (m, 2H), 2.64 (t, J = 6.0 Hz, 2H), 2.89 (t, J = 6.0 Hz, 2H), 2.96 (t, J = 7.2 Hz, 2H), 3.92-4.03 (m, 1H), 4.42 (t, J = 7.2 Hz, 2H), 8.32 (s, 1H), 9.75 (d, J = 7.5 Hz, 1H), 9.84 (s, 1H). |

TABLE 72

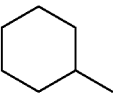

| Compound No. | R<sup>r</sup> | R<sup>5</sup> | <sup>1</sup>H-NMR (CDCl<sub>3</sub>) |
|---|---|---|---|
| 10-165 | 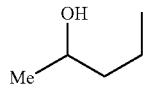 | 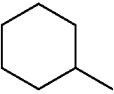 | 1.20 (d, J = 6.6 Hz, 3H), 1.21-1.87 (m, 18H), 1.90-2.01 (m, 2H), 2.55-2.73 (m, 2H), 2.85-3.02 (m, 2H), 3.62-3.70 (m, 1H), 3.92-4.01 (m, 2H), 4.65-4.78 (m, 1H), 8.36 (s, 1H), 9.77 (d, J = 7.5 Hz, 1H). |
| 10-166 | 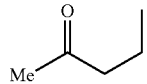 | 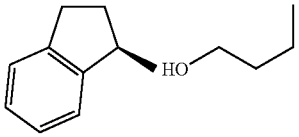 | 1.23-1.51 (m, 8H), 1.58-1.78 (m, 8H), 1.94-2.00 (m, 2H), 2.20 (s, 3H), 2.63 (t, J = 6.0 Hz, 2H), 2.88 (t, J = 6.0 Hz, 2H), 2.93 (t, J = 7.5 Hz, 2H), 3.92-4.01 (m, 1H), 4.36 (t, J = 7.5 Hz, 2H), 8.31 (s, 1H), 9.78 (d, J = 8.1 Hz, 1H). |
| 10-167 | 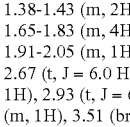 | 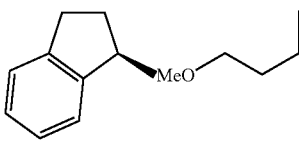 | 1.38-1.43 (m, 2H), 1.44-1.52 (m, 2H), 1.65-1.83 (m, 4H), 1.86-1.95 (m, 2H), 1.91-2.05 (m, 1H), 2.63-2.74 (m, 1H), 2.67 (t, J = 6.0 Hz, 2H), 2.85-2.96 (m, 1H), 2.93 (t, J = 6.0 Hz, 2H), 2.99-3.09 (m, 1H), 3.51 (br t, J = 4.5 Hz, 2H), 4.22-4.38 (m, 2H), 5.66 (q, J = 7.5 Hz, 1H), 7.19-7.38 (m, 4H), 8.43 (s, 1H), 10.11 (d, J = 6.9 Hz, 1H). |
| 10-168 | 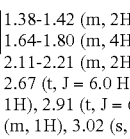 | | 1.38-1.42 (m, 2H), 1.44-1.52 (m, 2H), 1.64-1.80 (m, 4H), 1.91-2.08 (m, 1H), 2.11-2.21 (m, 2H), 2.62-2.73 (m, 1H), 2.67 (t, J = 6.0 Hz, 2H), 2.83-2.96 (m, 1H), 2.91 (t, J = 6.0 Hz, 2H), 2.99-3.06 (m, 1H), 3.02 (s, 3H), 4.25 (t, J = 6.9 Hz, 2H), 4.33 (t, J = 6.0 Hz, 2H), 5.67 (q, J = 7.8 Hz, 1H), 7.16-7.26 (m, 3H), 7.35-7.39 (m, 1H), 8.39 (s, 1H), 10.13 (d, J = 8.4 Hz, 1H). |
| 10-169 | 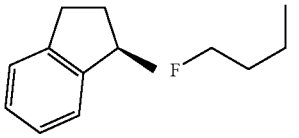 | 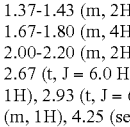 | 1.37-1.43 (m, 2H), 1.44-1.53 (m, 2H), 1.67-1.80 (m, 4H), 1.91-2.10 (m, 1H), 2.00-2.20 (m, 2H), 2.62-2.73 (m, 1H), 2.67 (t, J = 6.0 Hz, 2H), 2.84-2.96 (m, 1H), 2.93 (t, J = 6.0 Hz, 2H), 2.98-3.08 (m, 1H), 4.25 (sextet, J = 7.5 Hz, 2H), 4.45 (t, J = 7.8 Hz, 1H), 4.61 (t, J = 5.4 Hz, 1H), 5.67 (q, J = 7.5 Hz, 1H), 7.16-7.28 (m, 3H), 7.35-7.39 (m, 1H), 8.39 (s, 1H), 10.17 (d, J = 6.6 Hz, 1H). |

TABLE 73

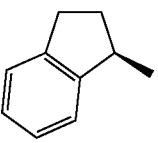

| Compound No. | R<sup>r</sup> | R<sup>5</sup> | <sup>1</sup>H-NMR (CDCl<sub>3</sub>) |
|---|---|---|---|
| 10-170 | 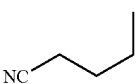 | 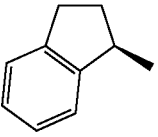 | 1.38-1.43 (m, 2H), 1.44-1.54 (m, 2H), 1.67-1.82 (m, 4H), 1.91-2.06 (m, 1H), 2.06 (quint, J = 7.5 Hz, 2H), 2.49 (t, J = 7.2 Hz, 2H), 2.62-2.74 (m, 1H), 2.67 (t, J = 6.0 Hz, 2H), 2.85-2.96 (m, 1H), 2.91 (t, J = 6.0 Hz, 2H), 2.99-3.09 (m, 1H), 4.21 (sextet, J = 7.2 Hz, 2H), 5.67 (q, J = 7.5 Hz, 1H), 7.19-7.26 (m, 3H), 7.35-7.39 (m, 1H), 8.40 (s, 1H), 10.08(d, J = 8.1 Hz, 1H). |
| 10-171 | 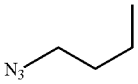 | 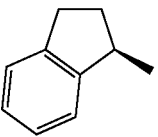 | 1.37-1.44 (m, 2H), 1.45-1.55 (m, 2H), 1.67-1.80 (m, 4H), 1.93-2.03 (m, 3H), 2.62-2.73 (m, 1H), 2.66 (t, J = 6.0 Hz, 2H), 2.84-2.96 (m, 1H), 2.91 (t, J = 6.0 Hz, 2H), 2.99-3.09 (m, 1H), 3.50 (t, J = 6.0 Hz, 2H), 4.17 (sextet, J = 7.5 Hz, 2H), 5.67 (q, J = 7.8 Hz, 1H), 7.18-7.26 (m, 3H), 7.35-7.39 (m, 1H), 8.39 (s, 1H), 10.16 (d, J = 8.4 Hz, 1H). |
| 10-172 | 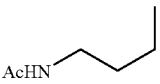 | 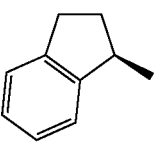 | 1.37-1.43 (m, 2H), 1.44-1.52 (m, 2H), 1.63-1.78 (m, 4H), 1.83-2.02 (m, 1H), 1.87 (quint, J = 6.0 Hz, 2H), 1.95 (s, 3H), 2.67 (t, J = 6.0 Hz, 2H), 2.69-2.76 (m, 1H), 2.88-2.95 (m, 1H), 2.90 (t, J = 6.0 Hz, 2H), 2.97-3.08 (m, 1H), 3.23 (quint, J = 6.0 Hz, 2H), 4.19 (br t, J = 7.5 Hz, 2H), 5.67 (q, J = 7.5 Hz, 1H), 6.65 (br t, J = 7.5 Hz, 1H), 7.18-7.28 (m,3H), 7.36-7.39 (m, 1H), 8.41 (s, 1H), 10.15 (d, J = 8.1 Hz, 1H). |
| 10-173 | 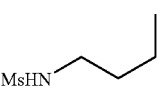 | 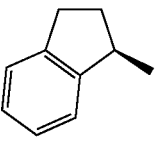 | 1.37-1.42 (m, 2H), 1.44-1.53 (m, 2H), 1.63-1.78 (m, 4H), 1.90-2.02 (m, 3H), 2.62-2.73 (m, 1H), 2.67 (t, J = 6.0 Hz, 2H), 2.84 (s, 3H), 2.85-2.97 (m, 1H), 2.90 (t, J = 6.0 Hz, 2H), 3.00-3.10 (m, 2H), 4.25 (br s, 2H), 5.67 (q, J = 7.5 Hz, 2H), 7.19-7.36 (m, 4H), 8.42 (s, 1H), 10.06 (d, J = 8.1 Hz, 1H). |
| 10-174 | 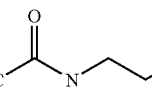 | | 1.38-1.43 (m, 2H), 1.44-1.52 (m, 2H), 1.65-1.80 (m, 4H), 1.88-2.00 (m, 3H), 2.68 (t, J = 6.0 Hz, 2H), 2.69-2.76 (m, 1H), 2.88-2.98 (m, 1H), 2.91 (t, J = 6.0 Hz, 2H), 3.00-3.10 (m, 1H), 3.25-3.37 (m, 2H), 4.24 (br s, 2H), 5.61 (q, J = 7.5 Hz, 1H), 7.18-7.39 (m, 4H), 8.42 (br s, 1H), 8.44 (s, 1H), 10.05 (d, J = 7.2 Hz, 1H). |

TABLE 74

| Compound No. | R' | R⁵ | ¹H-NMR (CDCl₃) |
|---|---|---|---|
| 10-175 | cyclohexyl-CH(OH)-CH₂CH₃ | nBu | 0.99 (t, J = 7.5 Hz, 3H), 1.02-1.28 (m, 6H), 1.36-1.52 (m, 8H); 1.62-1.80 (m, 8H), 1.92 (br d, J = 12.0 Hz, 1H), 2.64 (t, J = 6.0 Hz, 2H), 2.89 (t, J = 6.0 Hz, 2H), 3.45-3.62 (m, 3H), 4.07-4.15 (m, 2H), 8.30 (s, 1H), 10.28 (br s, 1H). |
| 10-176 | cyclohexyl-C(O)-CH₂CH₃ | nBu | 0.98 (t, J = 7.5 Hz, 3H), 1.20-1.51 (m, 14H), 1.58-1.91 (m, 8H), 2.41-2.50 (m, 1H), 2.63 (t, J = 6.0 Hz, 2H), 2.88 (t, J = 6.0 Hz, 2H), 4.12 (br t, J = 7.5 Hz, 2H), 4.36 (d, J = 5.4 Hz, 2H), 8.26 (s, 1H), 10.50 (br s, 1H). |
| 10-177 | Ph-CH(OH)-CH(CH₃)- | nBu | 0.98 (t, J = 7.5 Hz, 3H), 1.15 (d, J = 6.6 Hz, 3H), 1.37-1.53 (m, 4H), 1.44 (sextet, J = 7.5 Hz, 2H), 1.61-1.81 (m, 6H), 2.66 (t, J = 6.0 Hz, 2H), 2.90 (t, J = 6.0 Hz, 2H), 4.09 (br t, J = 7.5 Hz, 2H), 4.39-4.48 (m, 1H), 4.98 (d, J = 2.7 Hz, 1H), 7.23-7.39 (m, 5H), 8.33 (s, 1H), 10.10 (d, J = 7.5 Hz, 1H). |
| 10-178 | Ph-CH(OH)-CH(CH₃)- (enantiomer) | nBu | 0.98 (t, J = 7.2 Hz, 3H), 1.15 (d, J = 6.9 Hz, 3H), 1.37-1.53 (m, 4H), 1.44 (sextet, J = 7.2 Hz, 2H), 1.62-1.80 (m, 6H), 2.66 (t, J = 6.0 Hz, 2H), 2.90 (t, J = 6.0 Hz, 2H), 4.09 (br t, J = 7.2 Hz, 2H), 4.39-4.49 (m, 1H), 4.98 (d, J = 2.7 Hz, 1H), 7.23-7.40 (m, 5H), 8.33 (s, 1H), 10.10 (d, J = 6.9 Hz, 1H). |
| 10-179 | Ph-C(O)-CH(CH₃)- | nBu | 0.99 (t, J = 7.5 Hz, 3H), 1.37-1.50 (m, 4H), 1.43 (sextet, J = 7.5 Hz, 2H), 1.54 (d, J = 7.5 Hz, 3H), 1.63-1.80 (m, 6H), 2.63 (t, J = 6.0 Hz, 2H), 2.88 (t, J = 6.0 Hz, 2H), 4.12 (br t, J = 7.5 Hz, 2H), 5.69-5.79 (m, 1H), 7.45-7.51 (m, 2H), 7.55-7.61 (m, 1H), 8.05-8.09 (m, 2H), 8.28 (s, 1H), 10.73 (d, J = 6.9 Hz, 1H). |
| 10-180 | Ph-C(O)-CH(CH₃)- (enantiomer) | nBu | 0.99 (t, J = 7.5 Hz, 3H), 1.37-1.50 (m, 4H), 1.43 (sextet, J = 7.5 Hz, 2H), 1.54 (d, J = 6.9 Hz, 3H), 1.65-1.80 (m, 6H), 2.63 (t, J = 6.0 Hz, 2H), 2.89 (t, J = 6.0 Hz, 2H), 4.12 (br t, J = 7.5 Hz, 2H), 5.69-5.79 (m, 1H), 7.45-7.51 (m, 2H), 7.55-7.61 (m, 1H), 8.05-8.09 (m, 2H), 8.28 (s, 1H), 10.73 (d, J = 7.2 Hz, 1H). |

TABLE 75

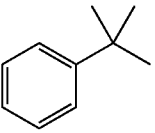

| Compound. No. | R<sup>r</sup> | R<sup>5</sup> | <sup>1</sup>H-NMR (CDCl<sub>3</sub>) |
|---|---|---|---|
| 11-001 | 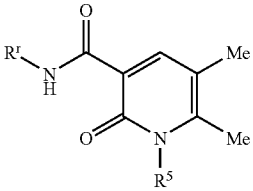 | nBu | 1.01 (t, J = 7.2 Hz, 3H), 1.42-1.54 (m, 2H), 1.65-1.79 (m, 2H), 1.79 (s, 6H), 2.13 (s, 3H), 2.41 (s, 3H), 4.13 (t, J = 7.8 Hz, 2H), 7.16-7.22 (m, 2H), 7.26-7.33 (m, 2H), 7.42-7.46 (m, 2H), 8.25 (s, 1H), 10.40 (br s, 1H). |
| 11-002 | 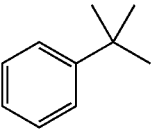 | Bu | 1.79 (s, 6H), 2.13 (s, 3H), 2.29 (s, 3H), 5.50(br s, 2H), 7.09-7.47 (m, 10H), 8.35 (s, 1H), 10.35 (br s, 1H) |
| 11-003 | 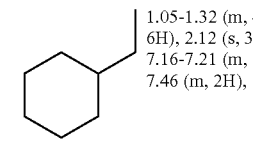 | 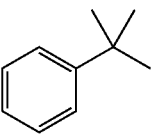 | 1.05-1.32 (m, 4H), 1.58-1.91 (m, 7H), 1.79 (s, 6H), 2.12 (s, 3H), 2.38 (s, 3H), 4.01 (br s, 2H), 7.16-7.21 (m, 1H), 7.26-7.32 (m, 2H), 7.43-7.46 (m, 2H), 8.24 (s, 1H), 10.39 (br s, 1H). |
| 11-004 | 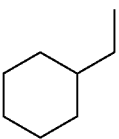 | 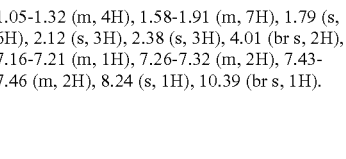 | 1.00-1.30 (m, 4H), 1.55-1.90 (m, 7H), 2.18 (s, 3H), 2.40 (s, 3H), 3.89-4.00 (m, 2H), 4.03 (br s, 2H), 5.26-5.32 (m, 1H), 7.26-7.43 (m, 5H), 8.33 (s, 1H), 10.72 (br d, J = 6.9 Hz, 1H). |
| 11-005 | 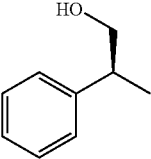 | 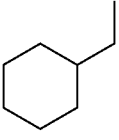 | 1.00-1.30 (m, 4H), 1.60-1.92 (m, 7H), 2.17 (s, 3H), 2.39 (s, 3H), 3.90 (d, J = 6.0 Hz, 2H), 4.04 (br s, 2H), 5.50-5.56 (m, 1H), 7.26-7.44 (m, 5H), 8.30 (s, 1H), 10.73 (d, J = 8.1 Hz, 1H). |
| 11-006 | 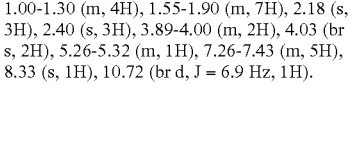 | 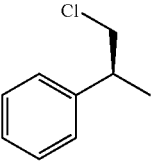 | 1.00-1.30 (m, 4H), 1.56-1.88 (m, 7H), 1.90-2.00 (m, 2H), 2.18 (s, 3H), 2.39 (s, 3H), 2.71 (t, J = 8.1 Hz, 2H), 3.46 (quint, J = 6.9 Hz, 2H), 4.03 (br s, 2H), 7.14-7.30 (m, 5H), 8.32 (s, 1H), 9.98 (br s, 1H). |
| 11-007 | 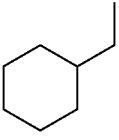 | nBu | 0.99 (t, J = 7.5 Hz, 3H), 1.39-1.51 (m, 2H), 1.62-1.73 (m, 2H), 2.18 (s, 3H), 2.42 (s, 3H), 3.89-4.00 (m, 2H), 4.12 (dd, J = 9.0 Hz, J = 5.1 Hz, 2H), 5.26-5.32 (m, 1H), 7.26-7.43 (m, 5H), 8.32 (s, 1H), 10.72 (br d, J = 6.9 Hz, 1H). |
| 11-008 | 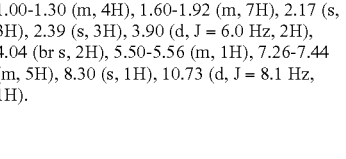 | nBu | 1.00 (t, J = 7.5 Hz, 3H), 1.41-1.53 (m, 2H), 1.64-1.74 (m, 2H), 2.16 (s, 3H), 2.41 (s, 3H), 3.91 (d, J = 5.7 Hz, 2H), 4.13 (t, J = 7.5 Hz, 2H), 5.50-5.57 (m, 1H), 7.28-7.45 (m, 5H), 8.30 (s, 1H), 10.73 (br d, J = 8.1 Hz, 1H) |

TABLE 75-continued
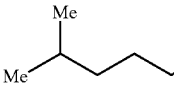
| Compound. No. | R^r | R^5 | $^1$H-NMR (CDCl$_3$) |
|---|---|---|---|
| 11-009 |  |  | 0.84 (d, J = 6.6 Hz, 6H), 1.06-1.85 (m, 21H), 2.17 (s, 3H), 2.38 (s, 3H), 4.00 (br s, 2H), 4.09-4.18 (m, 1H), 8.31 (s, 1H), 9.77 (d, J = 7.5 Hz, 1H). |
TABLE 76
| Compound No. | R^r | R^5 | $^1$H-NMR (CDCl$_3$) |
|---|---|---|---|
| 11-010 | 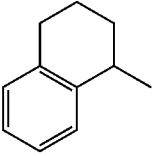 | 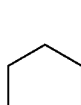 | 0.60-0.65 (m, 2H), 0.77-0.84 (m, 2H), 1.05-1.26 (m, 5H), 1.59-1.85 (m, 6H), 2.18 (s, 3H), 2.38 (s, 3H), 2.89-2.98 (m, 1H), 4.00 (br s, 2H), 8.32 (s, 1H), 9.89 (br s, 1H). |
| 11-011 | 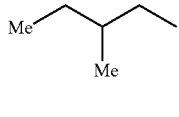 | 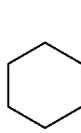 | 0.86-2.19 (m, 15H), 2.19 (s, 3H), 2.38 (s, 3H), 2.72-2.91 (m, 2H), 3.94 (br s, 2H), 5.37-5.44 (m, 1H), 7.06-7.16 (m, 3H), 7.34-7.37 (m, 1H), 8.38 (s, 1H), 10.22 (br d, J = 8.7 Hz, 1H). |
| 11-012 | 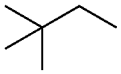 | | 0.92 (t, J = 7.5 Hz, 3H), 0.95 (d, J = 6.6 Hz, 3H), 1.06-1.85 (m, 14H), 2.18 (s, 3H), 2.39 (s, 3H), 3.20-3.29 (m, 1H), 3.34-3.42 (m, 1H), 4.03 (br s, 2H), 8.32 (s, 1H), 9.95 (br s, 1H). |
| 11-013 | 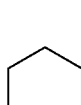 | 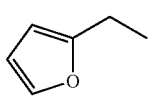 | 0.98 (s, 9H), 1.07-1.23 (m, 5H), 1.62-1.83 (m, 6H), 2.18 (s, 3H), 2.39 (s, 3H), 3.26 (d, J = 6.0 Hz, 2H). 4.03 (br s, 2H), 8.33 (s, 1H), 10.06 (br s, 1H) |
| 11-014 | 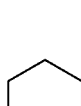 | | 1.05-1.23 (m, 5H), 1.62-1.87 (m, 6H), 2.18 (s, 3H), 2.39 (s, 3H), 4.00 (br s, 2H), 4.62 (d, J = 5.4 Hz, 2H), 6.25-6.31 (m, 2H), 7.35 (s, 1H), 8.34 (s, 1H), 10.23 (br s, 1H). |

TABLE 76-continued

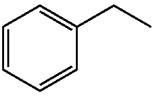

| Compound No. | R<sup>r</sup> | R<sup>5</sup> | <sup>1</sup>H-NMR (CDCl<sub>3</sub>) |
|---|---|---|---|
| 11-015 | 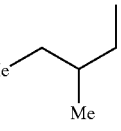 | 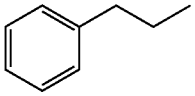 | 0.88 (d, J = 6.9 Hz, 3H), 0.93 (t, J = 7.5 Hz, 3H), 1.16-1.30 (m, 1H), 1.35-1.48 (m, 1H), 1.89-2.00 (m, 1H), 2.19 (s, 3H), 2.39 (s, 3H), 4.03 (br s, 1H), 4.64 (d, J = 6.0 Hz, 2H), 7.20-7.38 (m, 5H), 8.37 (s, 1H), 10.30 (br s, 1H). |
| 11-016 | 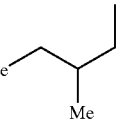 | 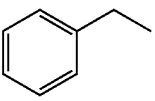 | 0.90 (t, J = 7.2 Hz, 3H), 0.95 (t, J = 7.5 Hz, 3H), 1.17-1.32 (m, 1H), 1.35-1.49 (m, 1H), 1.88-2.00 (m, 1H), 2.18 (s, 3H), 2.39 (s, 3H), 2.93 (t, J = 7.5 Hz, 2H), 3.62-3.69 (m, 2H), 4.06 (br s, 2H), 7.17-7.31 (m, 5H), 8.33 (s, 1H), 10.03 (br s, 1H). |
| 11-017 | 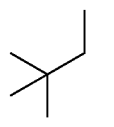 | 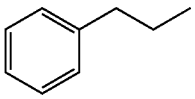 | 0.98 (s, 9H), 2.18 (s, 3H), 2.40 (s, 3H), 4.34 (br s, 2H), 7.20-7.37 (m, 5H), 8.34 (s, 1H), 10.31 (br s, 1H). |
| 11-018 | 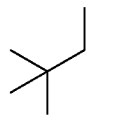 | 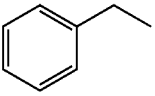 | 0.99 (s, 9H), 2.17 (s, 3H), 2.39 (s, 3H), 2.91 (t, J = 7.5 Hz, 2H), 3.63-3.70 (m, 2H), 7.16-7.31 (m, 5H), 8.30 (s, 1H), 10.01 (br s, 1H). |
| 11-019 | 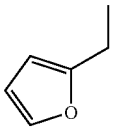 | 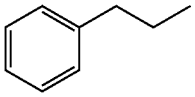 | 2.19 (s, 3H), 2.53 (s, 3H), 4.63 (d, J = 5.7 Hz, 2H), 5.34 (s, 2H), 6.33 (m, 2H), 7.21-7.37 (m, 6H), 8.38 (s, 1H), 10.18 (br s, 1H). |

TABLE 77

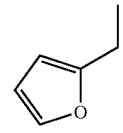

| Compound No. | R<sup>r</sup> | R<sup>5</sup> | <sup>1</sup>H-NMR (CDCl<sub>3</sub>) |
|---|---|---|---|
| 11-020 | 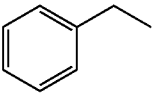 | 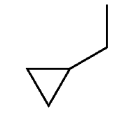 | 2.19 (s, 3H), 2.53 (s, 3H), 2.92 (t, J = 7.5 Hz, 2H), 3.62-3.69 (m, 2H), 5.34 (s, 2H), 6.35 (m, 2H), 7.17-7.32 (m, 5H), 7.35 (t, J = 1.5 Hz, 1H), 8.34 (s, 1H), 9.92 (br s, 1H) |
| 11-021 | | | 0.45-0.66 (m, 4H), 1.08-1.18 (m, 1H), 2.19 (s, 3H), 2.45 (s, 3H), 4.11 (d, J = 6.9 Hz, 2H), 4.64 (d, J = 5.7 Hz, 2H), 7.20-7.38 (m, 5H), 8.36 (s, 1H), 10.31 (br s, 1H). |

TABLE 77-continued

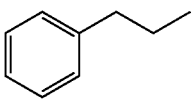

| Compound No. | R<sup>r</sup> | R<sup>5</sup> | <sup>1</sup>H-NMR (CDCl<sub>3</sub>) |
| --- | --- | --- | --- |
| 11-022 |  | 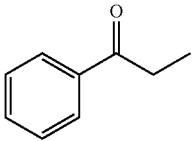 | 0.47-0.61 (m, 4H), 1.09-1.17 (m, 1H), 2.19 (s, 3H), 2.45 (s, 3H), 2.93 (t, J = 7.8 Hz, 2H), 3.63-6.70 (m, 2H), 4.12 (d, J = 6.9 Hz, 2H), 7.17-7.32 (m, 5H), 8.33 (s, 1H), 10.03 (br s, 1H). |
| 11-023 | H | nBu | 1.00 (t, J = 7.5 Hz, 3H), 1.40-1.53 (m, 2H), 1.63-1.73 (m, 2H), 2.18 (s, 3H), 2.42 (s, 3H), 4.13 (t, J = 8.1 Hz, 2H), 5.73 (br s, 1H), 8.31 (s, 1H), 9.62 (br s, 1H). |
| 11-024 | 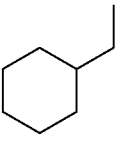 | 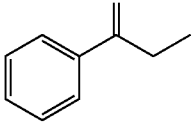 | 1.05-1.26 (m, 6H), 1.66-1.77 (m, 4H), 1.83-1.92 (m, 1H), 2.19 (s, 3H), 2.41 (s, 3H), 4.08 (br s, 2H), 4.97 (d, J = 4.5 Hz, 2H), 7.50 (t, J = 7.5 Hz, 2H), 7.61 (t, J = 7.5 Hz, 1H), 8.02-8.06 (m, 2H), 8.32 (s, 1H), 10.78 (br s, 1H). |
| 11-025 | 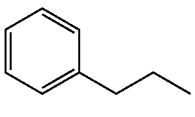 | Bn | 2.19 (s, 3H), 2.33. (s, 3H), 4.98 (d, J = 4.5 Hz, 2H), 5.52 (br s, 2H), 7.14 (d, J = 7.5 Hz, 2H), 7.29-7.36 (m, 3H), 7.50 (t, J = 7.5 Hz, 2H), 7.61 (t, J = 7.5 Hz, 1H), 8.03 (d, J = 7.5 Hz, 2H), 8.41 (s, 1H), 10.74 (br s, 1H). |

TABLE 78

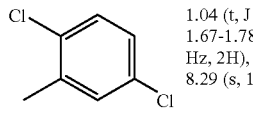

| Compound No. | R<sup>r</sup> | R<sup>3</sup> | <sup>1</sup>H-NMR (CDCl<sub>3</sub>) |
| --- | --- | --- | --- |
| 12-001 | 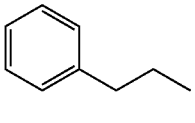 | 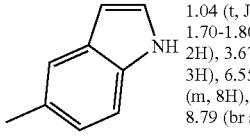 | 1.04 (t, J = 7.3 Hz, 3H), 1.42-1.54 (m, 2H), 1.67-1.78 (m, 2H), 2.28 (s, 3H), 2.94 (t, J = 7.3 Hz, 2H), 3.65-3.72 (m, 2H), 4.12-4.18 (m, 8H), 8.29 (s, 1H), 9.91 (t, J = 5.5 Hz, 1H). |
| 12-002 | 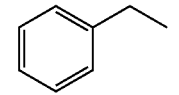 |  | 1.04 (t, J = 7.3 Hz, 3H), 1.43-1.55 (m, 2H), 1.70-1.80 (m, 2H), 2.44 (s, 3H), 2.97 (m, 2H), 3.67-3.74 (m, 2H), 4.18 (t, J = 7.9 Hz, 3H), 6.55 (m, 1H), 6.90-6.94 (m, 1H), 7.19-7.46 (m, 8H), 8.50 (s, 1H), 8.79 (br s, 1H), 10.14 (t, J = 5.8 Hz, 1H). |
| 12-003 |  | Et | 0.98 (t, J = 7.5 Hz, 3H), 1.16 (t, J = 7.5 Hz, 3H), 1.38-1.51 (m, 2H), 1.60-1.72 (m, 2H), 2.43 (s, 3H), 2.53 (quint, J = 7.5 Hz, 2H), 4.09 (t, J = 7.8 Hz, 2H), 4.64 (d, J = 6.0 Hz, 2H), 7.20-7.38 (m, 5H), 8.38 (s, 1H), 10.30 (br s, 1H). |

TABLE 78-continued

[Structure: R<sup>r</sup>-NH-C(=O)- attached to pyridinone with R<sup>3</sup>, Me, nBu substituents]

| Compound No. | R<sup>r</sup> | R<sup>3</sup> | <sup>1</sup>H-NMR (CDCl<sub>3</sub>) |
|---|---|---|---|
| 12-004 | phenethyl (–CH<sub>2</sub>CH<sub>2</sub>–Ph) | Et | 1.00 (t, J = 7.5 Hz, 3H), 1.16 (t, J = 7.5 Hz, 3H), 1.40-1.52 (m, 2H), 1.61-1.73 (m, 2H), 2.43 (s, 3H), 2.52 (quint, J = 7.5 Hz, 2H), 2.94 (t, J = 7.8 Hz, 2H), 3.63-3.70 (m, 2H), 4.11 (t, J = 7.8 Hz, 2H), 7.17-7.32 (m, 5H), 8.35 (s, 1H), 10.04 (br s, 1H). |

TABLE 79

| Compound No. | Structure | <sup>1</sup>H-NMR (CDCl<sub>3</sub>) |
|---|---|---|
| 13-0001 | [structure] | 0.99 (t, J = 7.5 Hz, 3H), 1.08 (t, J = 7.5 Hz, 3H), 1.19 (t, J = 7.5 Hz, 3H), 1.38-1.50 (m, 2H), 1.53-1.72 (m, 4H), 2.50 (quint, J = 7.5 Hz, 2H), 2.62-2.68 (m, 2H), 4.06 (m, 2H), 4.64 (t, J = 6.0 Hz, 2H), 7.23-7.37 (m, 5H), 8.40 (s, 1H), 10.32 (br s, 1H). |
| 13-0002 | [structure] | 1.01 (t, J = 7.2 Hz, 3H), 1.09 (t, J = 7.5 Hz, 3H), 1.19 (t, J = 7.5 Hz, 3H), 1.40-1.52 (m, 2H), 1.54-1.73 (m, 4H), 2.50 (quint, J = 7.5 Hz, 2H), 2.62-2.68 (m, 2H), 2.93 (t, J = 7.8 Hz, 2H), 3.63-3.70 (m, 2H), 4.04-4.10 (m, 2H), 7.18-7.32 (m, 5H), 8.37 (s, 1H), 10.06 (br s, 1H). |
| 13-0003 | [structure] | 0.98 (t, J = 7.2 Hz, 3H), 1.08 (t, J = 7.2 Hz, 3H), 1.38-1.50 (m, 2H), 1.53-1.72 (m, 4H), 2.19 (s, 3H), 2.62-2.68 (m, 2H), 4.04-4.10 (m, 2H), 4.64 (d, J = 5.7 Hz, 2H), 7.21-7.38 (m, 5H), 8.35 (s, 1H), 10.30 (br s, 1H). |
| 13-0004 | [structure] | 1.00 (t, J = 7.5 Hz, 3H), 1.08 (t, J = 7.5 Hz, 3H), 1.40-1.52 (m, 2H), 1.53-1.72 (m, 4H), 2.18 (s, 3H), 2.62-2.68 (m, 2H), 2.93 (t, J = 7.5 Hz, 2H), 3.63-3.70 (m, 2H), 4.04-4.10 (m, 2H), 7.18-7.32 (m, 5H), 8.31 (s, 1H), 10.03 (br s, 1H). |

TABLE 79-continued

| Compound No. | Structure | $^1$H-NMR (CDCl$_3$) |
|---|---|---|
| 13-0005 | 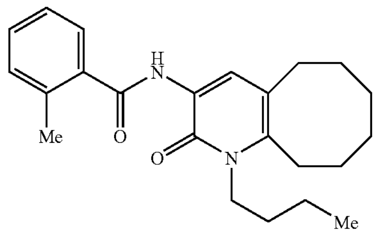 | 0.98 (t, J = 7.3 Hz, 3H), 1.38-1.53 (m, 6H), 1.62-1.72 (m, 6H), 2.54 (s, 3H), 2.62 (t, J = 6.1 Hz, 2H), 2.83 (t, J = 6.4 Hz, 2H), 4.10 (t, J = 7.9 Hz, 2H), 7.21-7.38 (m, 2H), 7.55 (d, J = 7.6 Hz, 1H), 8.38 (s, 1H), 8.79 (br s, 1H). |
| 13-0006 | 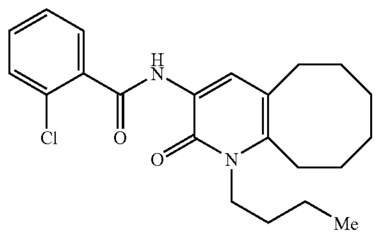 | 0.97 (t, J = 7.3 Hz, 3H), 1.38-1.53 (m, 6H), 1.62-1.75 (m, 6H), 2.62 (t, J = 6.1 Hz, 2H), 2.83 (t, J = 6.1 Hz, 2H), 4.10 (t, J = 7.9 Hz, 2H), 7.32-7.47 (m, 3H), 7.72-7.75 (m, 1H), 8.39 (s, 1H), 9.18 (br s, 1H). |
| 13-0007 | 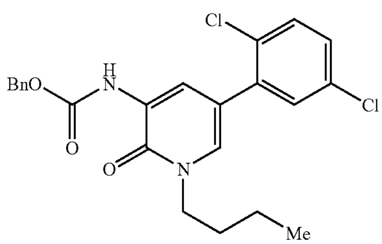 | 0.97 (t, J = 7.3 Hz, 3H), 1.34-1.46 (m, 2H), 1.72-1.82 (m, 2H), 4.03 (t, J = 7.3 Hz, 2H), 5.21 (s, 2H), 7.06 (d, J = 2.1 Hz, 1H), 7.23-7.40 (m, 8H), 7.95 (s, 1H), 8.15 (br s, 1H). |
| 13-0008 | 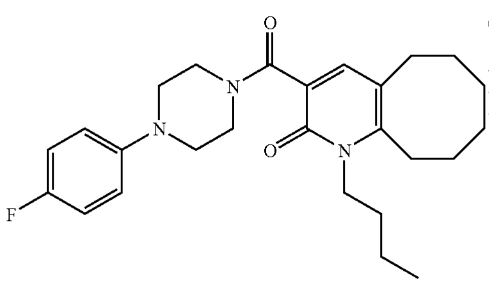 | 0.96 (d, J = 7.3 Hz, 3H), 1.36-1.56 (m, 6H), 1.58-1.71 (m, 4H), 1.71-1.81 (m, 2H), 2.57 (t, J = 6.0 Hz, 2H), 2.85 (t, J = 6.3 Hz, 2H), 3.08-3.20 (m, 2H), 3.18 (t, J = 5.0 Hz, 2H), 3.92 (t, J = 5.0 Hz, 2H), 4.06 (tlike, 2H), 6.87-7.00 (m, 5H). |
| 13-0009 | 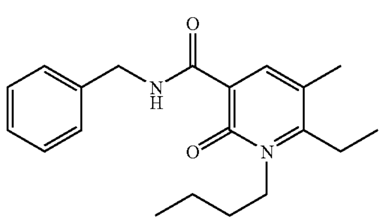 | 0.98 (t, J = 7.5 Hz, 3H), 1.22 (t, J = 7.5 Hz, 3H), 1.36-1.51 (m, 2H), 1.61-1.72 (m, 2H), 2.19 (s, 3H), 2.73 (quint, J = 7.5 Hz, 2H), 4.08 (t, J = 7.8 Hz, 2H), 4.64 (d, J = 6.0 Hz, 2H), 7.20-7.39 (m, 5H), 8.35 (s, 1H), 10.03 (brs, 1H). |

TABLE 80

| Compound No. | Structure | ¹H-NMR (CDCl₃) |
|---|---|---|
| 13-010 | 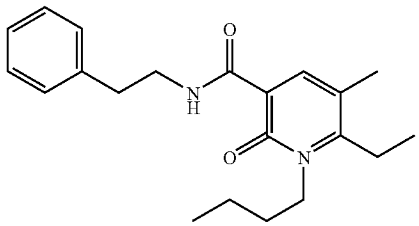 | 1.00 (t, J = 7.5 Hz, 3H), 1.23 (t, J = 7.5 Hz, 3H), 1.40-1.52 (m, 2H), 1.61-1.73 (m, 2H), 2.19 (s, 3H), 2.73 (quint, J = 7.5 Hz, 2H), 2.93 (t, J = 7.5 Hz, 2H), 3.63-3.70 (m, 2H), 4.08 (t, J = 7.5 Hz, 2H), 7.17-7.32 (m, 5H), 8.31 (s, 1H), 10.03 (br s, 1H). |
| 13-011 | 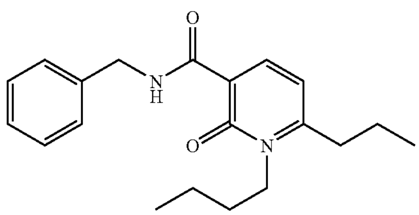 | 0.98 (t, J = 7.5 Hz, 3H), 1.06 (t, J = 7.5 Hz, 3H), 1.38-1.50 (m, 2H), 1.61-1.77 (m, 4H), 2.66 (t, J = 7.8 Hz, 2H), 4.05 (t, J = 7.8 Hz, 2H), 4.64 (d, J = 6.0 Hz, 2H), 6.28 (d, J = 7.8 Hz, 1H), 7.20-7.40 (m, 5H), 8.44 (d, J = 7.8 Hz, 1H), 10.21 (br s, 1H). |
| 13-012 | 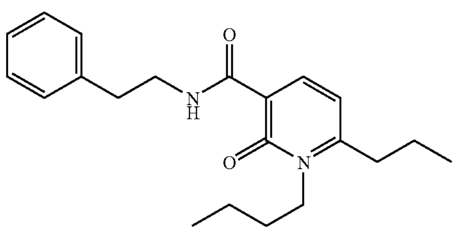 | 1.00 (t, J = 7.5 Hz, 3H), 1.06 (t, J = 7.5 Hz, 3H), 1.39-1.55 (m, 2H), 1.61-1.77 (m, 4H), 2.66 (t, J = 7.8 Hz, 2H), 2.93 (t, J = 7.8 Hz, 2H), 3.62-3.70 (m, 2H), 4.06 (t, J = 7.8 Hz, 2H), 6.27 (d, J = 7.5 Hz, 1H), 7.18-7.32 (m, 5H), 8.41 (d, J = 7.5 Hz, 1H), 9.95 (br s, 1H). |
| 13-013 | 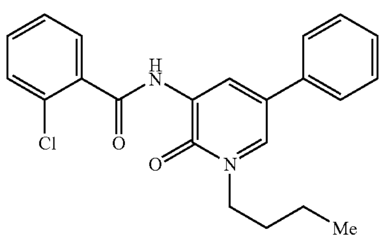 | 0.98 (t, J = 7.3 Hz, 3H), 1.37-1.49 (m, 2H), 1.76-1.86 (m, 2H), 4.08 (t, J = 7.3 Hz, 2H), 7.26 (d, J = 2.4 Hz, 1H), 7.32-7.54 (m, 8H), 7.76-7.79 (m, 1H), 8.92 (d, J = 2.4 Hz, 1H), 9.29 (s, 1H). |
| 13-014 | 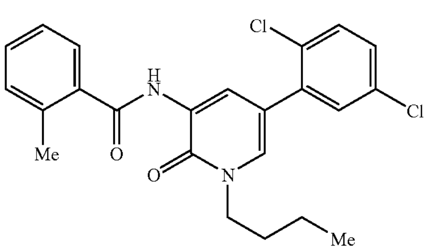 | 0.99 (t, J = 7.3 Hz, 3H), 1.38-1.50 (m, 2H), 1.60 (d, J = 7.0 Hz), 1.77-1.87 (m, 2H), 4.09 (dt, J = 7.1, 3.7 Hz, 2H), 5.32 (dt, J = 7.3, 7.0 Hz, 1H), 7.21-7.48 (m, 5H), 7.69 (d, J = 2.7 Hz, 1H), 8.83 (d, J = 2.7 Hz, 1H), 10.29 (d, J = 7.9 Hz). |
| 13-015 | 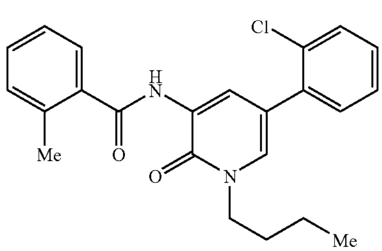 | 0.98 (t, J = 7.3 Hz, 3H), 1.37-1.49 (m, 2H), 1.76-1.86 (m, 2H), 2.54 (s, 3H), 4.06 (t, J = 7.3 Hz, 2H), 7.18-7.59 (m, 4H), 8.70 (d, J = 2.4 Hz, 1H), 8.84 (br s, 1H). |

TABLE 80-continued

| Compound No. | Structure | ¹H-NMR (CDCl₃) |
|---|---|---|
| 13-016 | 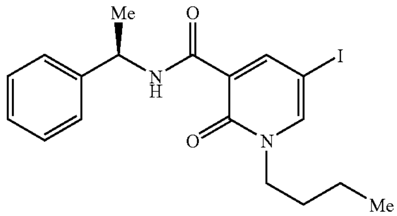 | 0.98 (t, J = 7.3 Hz, 3H), 1.38-1.46 (m, 2H), 1.57 (d, J = 7.0 Hz, 3H), 1.70-1.80 (m, 2H), 3.97 (dt, J = 4.3, 7.0 Hz, 2H), 5.29 (q, J = 7.3 Hz, 2H), 7.21-7.40 (m, 5H), 7.69 (d, J = 2.4 Hz, 1H), 8.62 (d, J = 2.4 Hz, 1H), 10.08 (d, J = 7.3 Hz, 1H). |
| 13-017 | 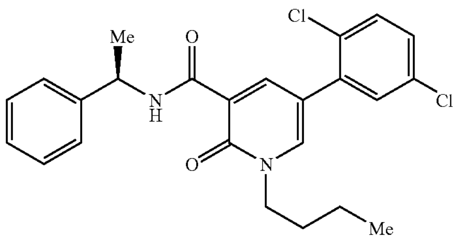 | 0.99 (t, J = 7.3 Hz, 3H), 1.37-1.49 (m, 2H), 1.59 (d, J = 7.0 Hz, 3H), 1.77-1.87 (m, 2H), 4.00-4.15 (m, 2H), 5.31 (dt, J = 7.6, 7.3 1H), 7.21-7.43 (m, 3H), 7.65 (d, J = 2.7 Hz, 1H), 8.61 (d, J = 2.7 Hz, 1H), 10.19 (d, J = 7.6 Hz, 1H). |
| 13-018 | 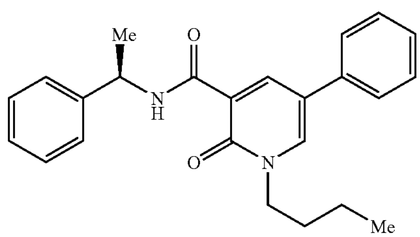 | 0.99 (t, J = 7.3 Hz, 3H), 1.38-1.50 (m, 2H), 1.60 (d, J = 7.0 Hz), 1.77-1.87 (m, 2H), 4.09 (dt, J = 7.1, 3.7 Hz, 2H), 5.32 (dt, J = 7.3, 7.0 Hz, 1H), 7.21-7.48 (m, 5H), 7.69 (d, J = 2.7 Hz, 1H), 8.83 (d, J = 2.7 Hz, 1H), 10.29 (d, J = 7.9 Hz). |

TABLE 81

| Compound No. | Structure | ¹H-NMR (CDCl₃) |
|---|---|---|
| 13-019 | 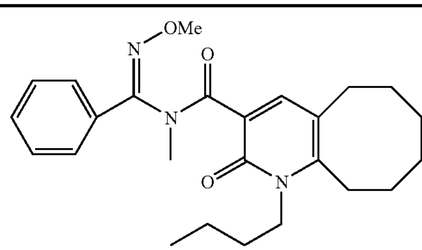 | 0.90 (t, J=7.2 Hz, 3H), 1.23-1.71 (m, 12H), 2.41 (br t, J=6.0 Hz, 2H), 2.68 (br t, J=6.0 Hz, 2H), 3.27 (s, 3H), 3.70-4.00 (m, 2H), 4.01 (s, 3H), 7.11-7.61 (m, 6H). |
| 13-020 | 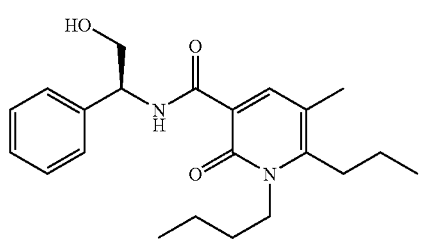 | 0.99 (t, J=7.2 Hz, 3H), 1.08 (t, J=7.5 Hz, 3H), 1.39-1.73 (m, 6H), 2.18 (s, 3H), 2.63-2.69 (m, 2H), 3.89-3.99 (m, 2H), 4.08 (s, 2H), 5.26-5.32 (m, 1H), 7.27-7.43 (m, 5H), 8.31 (s, 1H), 10.72 (d, J=5.7 Hz, 1H). |
| 13-021 | 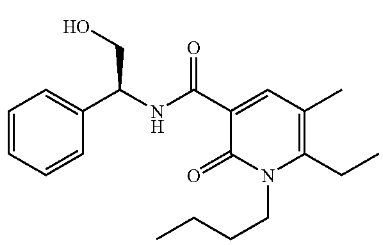 | 0.99 (t, J=7.5 Hz, 3H), 1.23 (t, J=7.5 Hz, 3H), 1.39-1.52 (m, 2H), 1.63-1.74 (m, 2H), 2.19 (s, 3H), 2.74 (q, J=7.5 Hz, 2H), 3.89-4.00 (m, 2H), 4.09 (s, 2H), 5.26-5.32 (m, 1H), 7.26-7.43 (m, 5H), 8.32 (s, 1H), 10.72 (d, J=7.2 Hz, 1H). |

TABLE 81-continued

| Compound No. | Structure | ¹H-NMR (CDCl₃) |
|---|---|---|
| 13-022 | 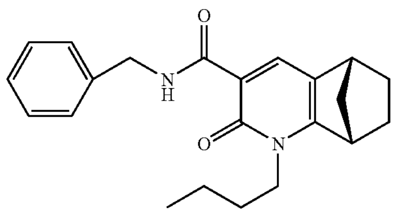 | 1.00 (t, J=7.5 Hz, 3H), 1.19-1.26 (m, 2H), 1.45 (sextet, J=7.5 Hz, 2H), 1.52-1.62 (m, 1H), 1.72 (quint, J=7.5 Hz, 2H), 1.81-1.87 (m, 1H), 1.92-2.07 (m, 2H), 3.40 (br s, 1H), 3.47 (br s, 1H), 3.89-3.99 (m, 1H), 4.17-4.26 (m, 1H), 4.57-4.71 (m, 2H), 7.20-7.38 (m, 5H), 8.44 (s, 1H), 10.30 (br s, 1H). |
| 13-023 | 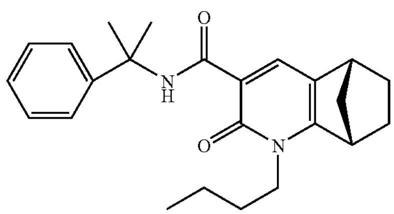 | 1.01 (t, J=7.5 Hz, 3H), 1.18-1.30 (m, 4H), 1.43- (m, 2H), 1.64-1.81 (m, 2H), 1.78 (s, 6H), 1.89-2.05 (m, 2H), 3.33 (br s, 1H), 3.47 (br s, 1H), 3.92-4.01 (m, 1H), 4.21-4.31 (m, 1H), 7.24-7.32 (m, 3H), 7.43-7.46 (m, 2H), 8.33 (s, 1H), 10.42 (br s, 1H). |
| 13-024 | 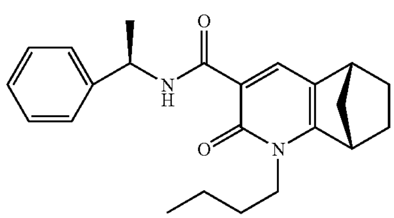 | 1.00 (t, J=7.5 Hz, 3H), 1.17-1.26 (m, 2H), 1.39-1.60 (m, 4H), 1.55 (d, J=3.0 Hz, 3H), 1.68-1.85 (m, 2H), 1.90-2.07 (m, 2H), 3.37 (br s, 1H), 3.47 (br s, 1H), 3.88-4.01 (m, 1H), 4.17-4.30 (m, 1H), 5.30 (quint, J=7.5 Hz, 1H), 7.18-7.41 (m, 5H), 8.40 (s, 1H), 10.34 (d, J=7.8 Hz, 1H). |
| 13-025 | 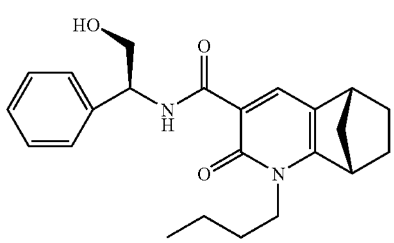 | 1.00 (t, J=7.2 Hz, 3H), 1.19-1.26 (m, 1H), 1.41-2.10 (m, 9H), 3.39 (br s, 1H), 3.49 (br s, 1H), 3.89-3.99 (m, 3H), 4.20-4.30 (m, 1H), 5.29 (q, J=6.0 Hz, 1H), 7.26-7.43 (m, 5H), 8.40 (s, 1H), 10.71 (d, J=7.2 Hz, 1H). |
| 13-026 | 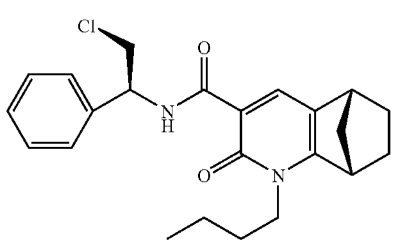 | 1.01 (t, J=7.5 Hz, 3H), 1.20-1.31 (m, 2H), 1.41-1.55 (m, 2H), 1.70-1.88 (m, 4H), 1.90-2.08 (m, 2H), 3.38 (br s, 1H), 3.48 (br s, 1H), 3.90 (d, J=4.8 Hz, 2H), 3.95-4.02 (m, 1H), 4.20-4.31 (m, 1H), 5.50-5.58 (m, 1H), 7.26-7.44 (m, 5H), 8.39 (s, 1H), 10.74 (d, J=7.8 Hz, 1H). |
| 13-027 | 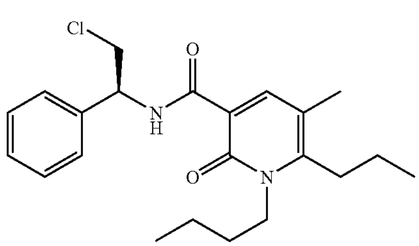 | 1.00 (t, J=7.5 Hz, 3H), 1.08 (t, J=7.5 Hz, 3H), 1.40-1.72 (m, 6H), 2.17 (s, 3H), 2.63-2.68 (m, 2H), 3.90 (d, J=5.7 Hz, 2H), 4.11 (br s, 2H), 5.54 (s, 1H), 7.26-7.44 (m, 5H), 8.30 (s, 1H), 10.74 (br d, J=7.8 Hz, 1H). |

TABLE 82

| Compound No. | Structure | ¹H-NMR (CDCl₃) |
| --- | --- | --- |
| 13-028 | 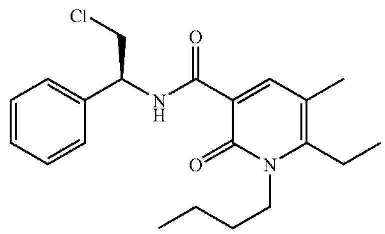 | 1.00 (t, J=7.5 Hz, 3H), 1.23 (t, J=7.5 Hz, 3H), 1.41-1.53 (m, 2H), 1.65-1.78 (m, 2H), 2.18 (s, 3H), 2.74 (quint, J=7.8 Hz, 2H), 3.90 (d, J=5.7 Hz, 2H), 4.11 (br s, 2H), 5.50-5.57 (m, 1H), 7.26-7.44 (m, 5H), 8.30 (s, 1H), 10.74 (br d, J=7.5 Hz, 1H). |
| 13-029 | 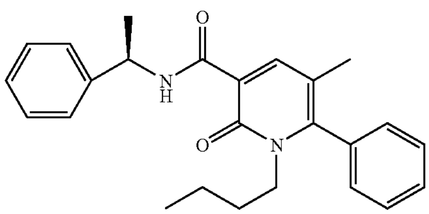 | 0.70 (t, J=7.2 Hz, 3H), 1.11 (sextet, J=7.2 Hz, 2H), 1.54 (quint, J=7.2 Hz, 2H), 1.61 (d, 3H), 1.81 (s, 3H), 3.70-3.86 (m, 2H), 5.34 (quint, J=7.2 Hz, 1H), 7.17-7.58 (m, 10H), 8.43 (s, 1H), 10.41 (d, J=7.8 Hz, 1H). |
| 13-030 | 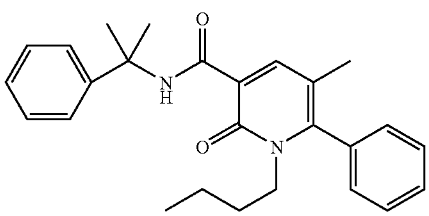 | 0.72 (t, J=7.5 Hz, 3H), 1.12 (sextet, J=7.5 Hz, 2H), 1.57 (quint, J=7.5 Hz, 2H), 1.78 (s, 3H), 1.82 (s, 6H), 3.81 (t, J=8.4 Hz, 2H), 7.16-7.57 (m, 10H), 8.37 (s, 1H), 10.49 (br s, 1H). |
| 13-031 | 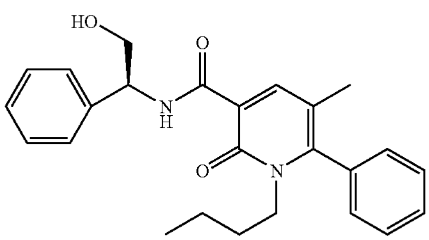 | 0.70 (t, J=7.2 Hz, 3H), 1.10 (sextet, J=7.2 Hz, 2H), 1.54 (quint, J=7.2 Hz, 2H), 1.83 (s, 3H), 3.76-3.86 (m, 2H), 3.91-4.03 (m, 2H), 5.29-5.36 (m, 1H), 7.16-7.57 (m, 10H), 8.48 (s, 1H), 10.82 (d, J=6.6 Hz, 1H). |
| 13-032 | 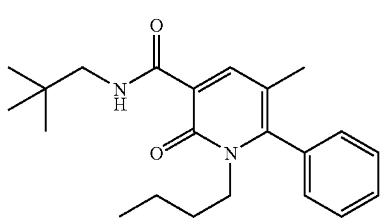 | 0.70 (t, J=7.2 Hz, 3H), 1.01 (s, 9H), 1.11 (sextet, J=7.2 Hz, 2H), 1.54 (quint, J=7.2 Hz, 2H), 1.83 (s, 3H), 3.29 (t, J=4.8 Hz, 2H), 3.80 (t, J=7.2 Hz, 2H), 7.20-7.67 (m, 2H), 7.50-7.60 (m, 3H), 8.46 (s, 1H), 10.15 (brs, 1H). |
| 13-033 | 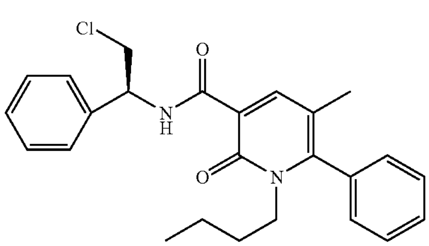 | 0.71 (t, J=7.5 Hz, 3H), 1.11 (sextet, J=7.5 Hz, 2H), 1.56 (quint, J=7.5 Hz, 2H), 1.82 (s, 3H), 3.81 (dd, J=6.0 Hz, 3.6 Hz, 2H), 3.93 (d, J=6.0 Hz, 2H), 5.53-5.61 (m, 1H), 7.19-7.57 (m, 10H), 8.44 (s, 1H), 10.83 (d, J=8.4 Hz, 1H). |

TABLE 82-continued

| Compound No. | Structure | $^1$H-NMR (CDCl$_3$) |
| --- | --- | --- |
| 13-034 | 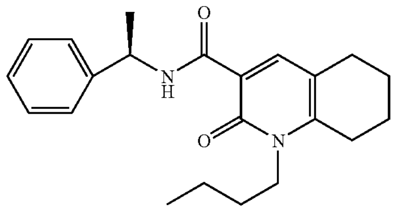 | 0.99 (t, J=7.2 Hz, 3H), 1.45 (sextet, J=7.2 Hz, 2H), 1.58 (d, J=7.2 Hz, 3H), 1.64-1.77 (m, 4H), 1.83-1.92 (m, 2H), 2.60 (t, J=6.0 Hz, 2H), 2.74 (t, J=6.0 Hz, 2H), 4.00-4.10 (m, 2H), 5.30 (quint, J=7.2 Hz, 1H), 7.19-7.42 (m, 5H), 8.23 (s, 1H), 10.34 (d, J=7.5 Hz, 1H). |
| 13-035 | 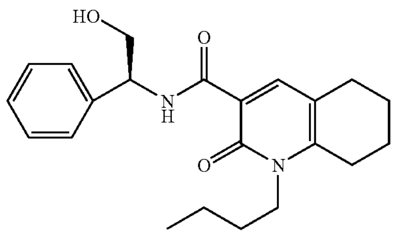 | 0.98 (t, J=7.5 Hz, 3H), 1.44 (sextet, J=7.5 Hz, 2H), 1.60-1.70 (m, 2H), 1.69-1.80 (m, 2H), 1.83-1.93 (m, 2H), 2.62 (t, J=6.0 Hz, 2H), 2.75 (t, J=6.0 Hz, 2H), 3.89-3.98 (m, 2H), 4.00-4.08 (m, 2H), 5.25-5.32 (m, 1H), 7.27-7.43 (m, 5H), 8.27 (s, 1H), 10.75 (d, J=5.4 Hz, 1H). |
| 13-036 | 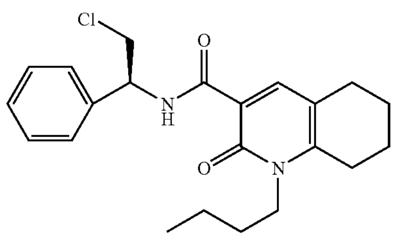 | 0.99 (t, J=7.2 Hz, 3H), 1.45 (sextet, J=7.2 Hz, 2H), 1.62-1.78 (m, 4H), 1.83-1.93 (m, 2H), 2.61 (t, J=6.0 Hz, 2H), 2.75 (t, J=6.0 Hz, 2H), 3.91 (d, J=6.0 Hz, 2H), 4.06 (t, J=7.2 Hz, 2H), 5.50-5.58 (m, 1H), 7.27-7.45 (m, 5H), 8.23 (s, 1H), 10.75 (t, J=7.5 Hz, 1H). |

TABLE 83

| Compound No. | Structure | $^1$H-NMR (CDCl$_3$) |
| --- | --- | --- |
| 13-037 | 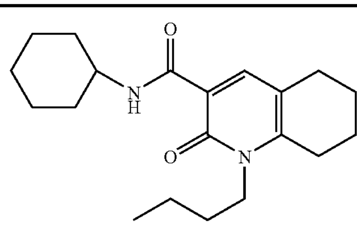 | 0.99 (t, J=7.2 Hz, 3H), 1.18-1.51 (m, 8H), 1.61-1.77 (m, 6H), 1.83-1.92 (m, 2H), 1.96-2.02 (m, 2H), 2.61 (t, J=6.0 Hz, 2H), 2.73 (t, J=6.0 Hz, 2H), 3.90-4.01 (m, 1H), 4.03 (t, J=7.2 Hz, 2H), 8.24 (s, 1H), 9.86 (d, J=7.5 Hz, 1H). |
| 13-038 | 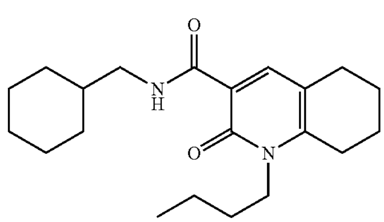 | 0.99 (t, J=7.5 Hz, 3H), 1.13-1.30 (m, 2H), 1.45 (sextet, J=7.5 Hz, 2H), 1.59-1.92 (m, 15H), 2.61 (t, J=6.0 Hz, 2H), 2.74 (t, J=6.0 Hz, 2H), 3.28 (t, J=6.0 Hz, 2H), 4.04 (t, J=7.5 Hz, 2H), 8.25 (s, 1H), 9.96 (br s, 1H). |
| 13-039 | 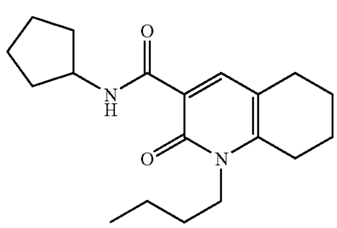 | 0.98 (t, J=7.5 Hz, 3H), 1.44 (sextet, J=7.5 Hz, 2H), 1.52-1.78 (m, 10H), 1.82-1.91 (m, 2H), 1.99-2.11 (m, 2H), 2.61 (t, J=6.0 Hz, 2H), 2.73 (t, J=6.0 Hz, 2H), 4.02 (t, J=7.5 Hz, 2H), 4.36 (sextet, J=6.6 Hz, 1H), 8.24 (s, 1H), 9.91 (d, J=6.9 Hz, 1H). |

TABLE 83-continued

| Compound No. | Structure | $^1$H-NMR (CDCl$_3$) |
| --- | --- | --- |
| 13-040 | 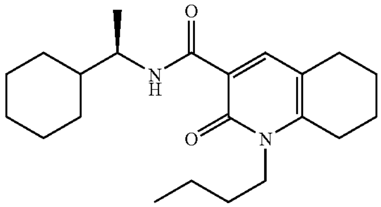 | 0.99 (t, J=7.2 Hz, 3H), 1.05-1.29 (m, 6H), 1.18 (d, J=6.6 Hz, 3H), 1.45 (sextet, J=7.2 Hz, 2H), 1.59-1.92 (m, 11H), 2.61 (t, J=6.0 Hz, 2H), 2.73 (t, J=6.0 Hz, 2H), 3.93-4.13 (m, 1H + 2H), 8.24 (s, 1H), 9.85 (d, J=8.7 Hz, 1H). |
| 13-041 | 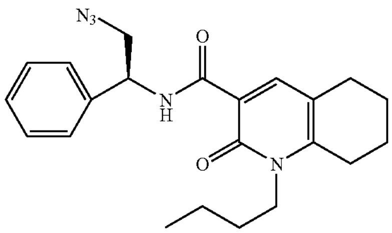 | 0.99 (t, J=7.2 Hz, 3H), 1.45 (sextet, J=7.2 Hz, 2H), 1.60-1.78 (m, 4H), 1.83-1.91 (m, 2H), 2.61 (t, J=6.0 Hz, 2H), 2.75 (t, J=6.0 Hz, 2H), 3.70 (d, J=6.0 Hz, 2H), 4.06 (t, J=7.2 Hz, 2H), 5.38-5.46 (m, 1H), 7.26-7.45 (m, 5H), 8.23 (s, 1H), 10.73 (t, J=8.7 Hz, 1H). |
| 13-042 | 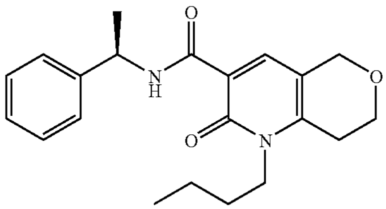 | 0.99 (t, J=7.5 Hz, 3H), 1.45 (sextet, J=7.5 Hz, 2H), 1.58 (d, J=7.2 Hz, 3H), 1.68 (quint, J=7.5 Hz, 2H), 2.82 (t, J=6.0 Hz, 2H), 4.00 (t, J=6.0 Hz, 2H), 4.05 (t, J=7.5 Hz, 2H), 4.58 (s, 2H), 5.29 (quint, J=7.2 Hz, 1H), 7.23-7.42 (m, 5H), 8.17 (s, 1H), 10.25 (d, J=7.5 Hz, 1H). |
| 13-043 | 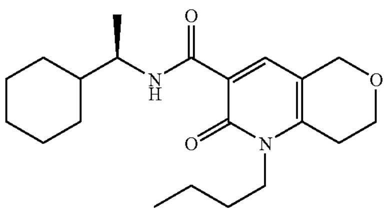 | 0.99 (t, J=7.2 Hz, 3H), 1.03-1.30 (m, 4H), 1.18 (d, J=6.6 Hz, 3H), 1.45 (sextet, J=7.2 Hz, 2H), 1.60-1.84 (m, 9H), 2.82 (t, J=6.0 Hz, 2H), 3.92-4.13 (m, 5H), 4.59 (s, 2H), 8.18 (s, 1H), 9.77 (d, J=8.1 Hz, 1H). |
| 13-044 | 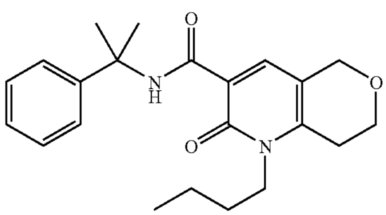 | 1.01 (t, J=7.5 Hz, 3H), 1.47 (sextet, J=7.5 Hz, 2H), 1.71 (quint, J=7.5 Hz, 2H), 1.79 (s, 6H), 2.82 (t, J=6.0 Hz, 2H), 4.00 (t, J=6.0 Hz, 2H), 4.05 (t, J=7.5 Hz, 2H), 4.54 (s, 2H), 7.26-7.34 (m, 3H), 7.42-7.46 (m, 2H), 8.11 (s, 1H), 10.34 (br s, 1H). |
| 13-045 | 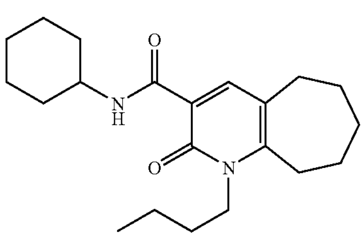 | 0.99 (t, J=7.5 Hz, 3H), 1.19-1.52 (m, 8H), 1.62-1.79 (m, 8H), 1.80-1.88 (m, 2H), 1.91-2.02 (m, 2H), 2.71 (t, J=6.0 Hz, 2H), 2.93 (t, J=6.0 Hz, 2H), 3.93-4.02 (m, 1H), 4.16 (br t, J=7.5 Hz, 2H), 8.29 (s, 1H), 9.86 (d, J=6.9 Hz, 1H). |

TABLE 84

| Compound No. | Structure | ¹H-NMR (CDCl₃) |
|---|---|---|
| 13-046 | 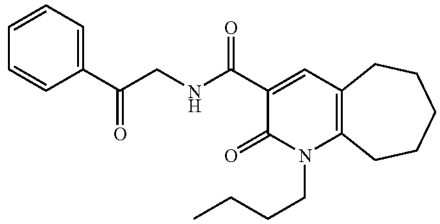 | 1.00 (t, J=7.2 Hz, 3H), 1.47 (sextet, J=7.2 Hz, 2H), 1.63-1.74 (m, 6H), 1.83-1.90 (m, 2H), 2.72 (t, J=6.0 Hz, 2H), 2.96 (t, J=6.0 Hz, 2H), 4.23 (br t, J=7.2 Hz, 2H), 4.96 (d, J=4.5 Hz, 2H), 7.50 (t, J=7.5 Hz, 2H), 7.61 (t, J=7.5 Hz, 1H), 8.04 (d, J=7.5 Hz, 2H), 8.29 (s, 1H), 10.79 (br s, 1H). |
| 13-047 | 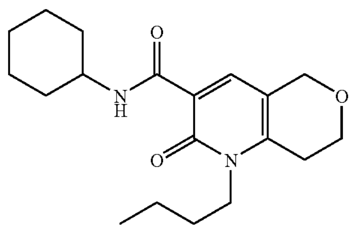 | 0.99 (t, J=7.2 Hz, 3H), 1.22-1.49 (m, 6H), 1.60-1.78 (m, 6H), 1.94-2.01 (m, 2H), 2.82 (t, J=6.0 Hz, 2H), 3.91-4.05 (m, 5H), 4.60 (s, 2H), 8.18 (s, 1H), 9.79 (d, J=6.3 Hz, 1H). |
| 13-048 | 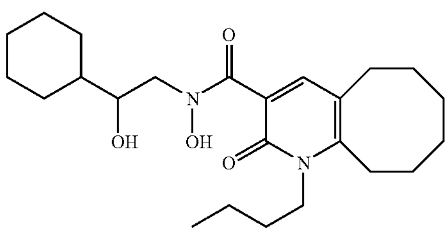 | 0.98 (t, J=7.2 Hz, 3H), 1.10-1.29 (m, 6H), 1.40-1.56 (m, 8H), 1.65-1.82 (m, 8H), 1.93 (br t, J=12.0 Hz, 1H), 2.66 (t, J=6.0 Hz, 2H), 2.93 (t, J=6.0 Hz, 2H), 3.78-3.87 (m, 2H), 4.00-4.12 (m, 1H), 4.16 (br t, J=7.2 Hz, 2H), 7.29 (br s, 1H), 8.00 (s, 1H). |
| 13-049 | 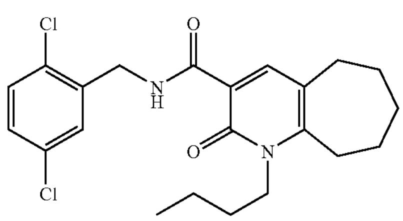 | 0.99 (t, J=7.2 Hz, 3H), 1.46 (sextet, J=7.2 Hz, 2H), 1.61-1.73 (m, 6H), 1.87 (sextet, J=6.0 Hz, 2H), 2.74 (t, J=6.0 Hz, 2H), 2.96 (t, J=6.0 Hz, 2H), 4.19 (br t, J=7.2 Hz, 2H), 4.68 (d, J=6.0 Hz, 2H), 7.15 (dd, J=8.4 Hz, 2.4 Hz, 1H), 7.23-7.29 (m, 1H), 7.39 (d, J=2.4 Hz, 1H), 8.31 (s, 1H), 10.43 (br s, 1H). |
| 13-050 | 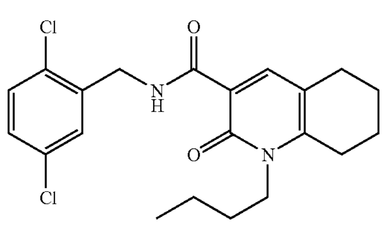 | 0.99 (t, J=7.2 Hz, 3H), 1.45 (sextet, J=7.2 Hz, 2H), 1.63-1.79 (m, 4H), 1.89 (quint, J=6.0 Hz, 2H), 2.63 (t, J=6.0 Hz, 2H), 2.76 (t, J=6.0 Hz, 2H), 4.05 (t, J=8.1 Hz, 2H), 4.68 (d, J=6.0 Hz, 2H), 7.15 (dd, J=8.7 Hz, 2.4 Hz, 1H), 7.25-7.29 (m, 1H), 7.38 (d, J=2.4 Hz, 1H), 8.27 (s, 1H), 10.44 (br s, 1H). |

TABLE 85

[Structure: R¹-NH-C(=O)- attached to pyridinone ring with R² at 5-position, Me at 6-position, and nBu on N]

| Compound No. | R¹ | R² |
|---|---|---|
| 3-031 | phenethyl (-CH₂CH₂-Ph) | Et |
| 3-032 | phenylpropyl (-CH₂CH₂CH₂-Ph) | Et |
| 3-041 | phenylpropyl (-CH₂CH₂CH₂-Ph) | 2,5-dichlorophenyl (with Cl at 2 and 5) |
| 3-042 | phenylpropyl (-CH₂CH₂CH₂-Ph) | 5-methyl-1H-indol-? |
| 3-043 | phenethyl (-CH₂CH₂-Ph) | CF₃ |

TABLE 86

| No. | Structure |
|---|---|
| 3-017 | PhCH₂-NH-C(=O)- pyridinone with Me, Me, and n-octyl on N |
| 3-018 | Ph-CH₂CH₂-NH-C(=O)- pyridinone with Me, Me, and n-octyl on N |

TABLE 86-continued

| No. | Structure |
|---|---|
| 3-019 | PhCH₂-NH-C(=O)- pyridinone with Me, Me, and cyclohexyl on N |
| 3-020 | Ph-CH₂CH₂-NH-C(=O)- pyridinone with Me, Me, and cyclohexyl on N |
| 5-021 | 2,5-dichlorobenzoyl-NH- pyridinone with Me, Me, nBu on N |
| 5-022 | 2-methylbenzoyl-NH- pyridinone with 5-phenyl and nBu on N |

TABLE 87

[Structure: quinolin-2(1H)-one with Y²-R¹' at 3-position and nBu on N]

| Compound No. | Y² | R¹' |
|---|---|---|
| 8-001 | —C(=O)—NH— | 4-methylphenyl (tolyl) |
| 8-002 | —C(=O)—NH— | 4-ethylphenyl |

TABLE 87-continued
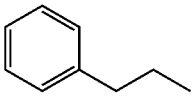
| Compound No. | Y² | Rʳ |
|---|---|---|
| 8-003 | —C(=O)—NH— | 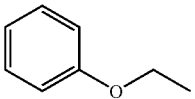 |
| 8-004 | —C(=O)—NH— | 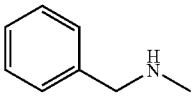 |
| 8-005 | —C(=O)—NH— | 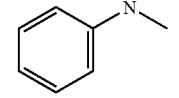 |
| 8-006 | —C(=O)—NH— | 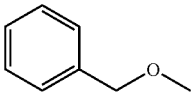 |
| 8-007 | —C(=O)—NH— | 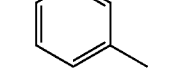 |
| 8-008 | —NH—C(=O)— | 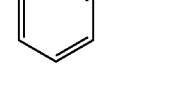 |
| 8-009 | —NH—C(=O)— | 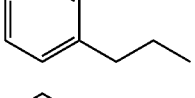 |
| 8-010 | —NH—C(=O)— | 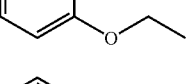 |
| 8-011 | —NH—C(=O)— | 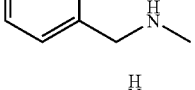 |
| 8-012 | —NH—C(=O)— | 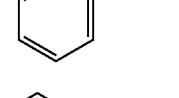 |
| 8-013 | —NH—C(=O)— | 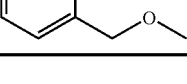 |
| 8-014 | —NH—C(=O)— | 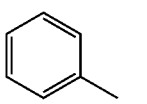 |
TABLE 88
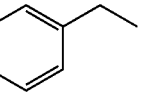
| Compound No. | Y² | Rʳ |
|---|---|---|
| 8-015 | —C(=O)—NH— | 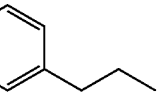 |
| 8-016 | —C(=O)—NH— | 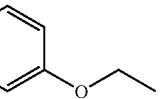 |
| 8-017 | —C(=O)—NH— | 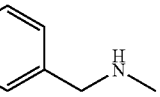 |
| 8-018 | —C(=O)—NH— | 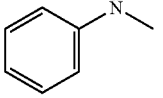 |
| 8-019 | —C(=O)—NH— | 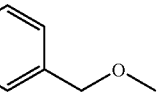 |
| 8-020 | —C(=O)—NH— | 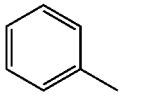 |
| 8-021 | —C(=O)—NH— | 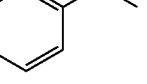 |
| 8-022 | —NH—C(=O)— | 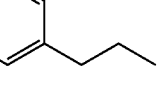 |
| 8-023 | —NH—C(=O)— | 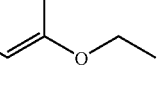 |
| 8-024 | —NH—C(=O)— | 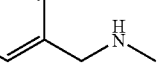 |
| 8-025 | —NH—C(=O)— | |
| 8-026 | —NH—C(=O)— | |

TABLE 88-continued

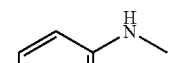

| Compound No. | Y² | Rʳ |
|---|---|---|
| 8-027 | —NH—C(=O)— | (N-methylanilino group shown) |
| 8-028 | —NH—C(=O)— | (benzyl methyl ether group shown) |

TABLE 89

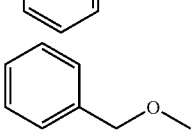

| Compound No. | R9 | R10 | n |
|---|---|---|---|
| 9-001 | (4-Cl)C6H4CH2— | n-Bu | 3 |
| 9-002 | (3-Cl)C6H4CH2— | n-Bu | 3 |
| 9-003 | (2-Cl)C6H4CH2— | n-Bu | 3 |
| 9-004 | (4-F)C6H4CH2— | n-Bu | 3 |
| 9-005 | (3-F)C6H4CH2— | n-Bu | 3 |
| 9-006 | (2-F)C6H4CH2— | n-Bu | 3 |
| 9-007 | (4-Me)C6H4CH2— | n-Bu | 3 |
| 9-008 | (3-Me)C6H4CH2— | n-Bu | 3 |
| 9-009 | (2-Me)C6H4CH2— | n-Bu | 3 |
| 9-010 | (4-MeO)C6H4CH2— | n-Bu | 3 |
| 9-011 | (3-MeO)C6H4CH2— | n-Bu | 3 |
| 9-012 | (2-MeO)C6H4CH2— | n-Bu | 3 |
| 9-013 | (4-Me2N)C6H4CH2— | n-Bu | 3 |
| 9-014 | (3-Me2N)C6H4CH2— | n-Bu | 3 |
| 9-015 | (2-Me2N)C6H4CH2— | n-Bu | 3 |
| 9-016 | (4-MeOCO)C6H4CH2— | n-Bu | 3 |
| 9-017 | (3-MeOCO)C6H4CH2— | n-Bu | 3 |
| 9-018 | (2-MeOCO)C6H4CH2— | n-Bu | 3 |
| 9-019 | (4-CN)C6H4CH2— | n-Bu | 3 |
| 9-020 | (3-CN)C6H4CH2— | n-Bu | 3 |
| 9-021 | (2CN)C6H4CH2— | n-Bu | 3 |
| 9-022 | (4NO2)C6H4CH2— | n-Bu | 3 |
| 9-023 | (3NO2)C6H4CH2— | n-Bu | 3 |
| 9-024 | (2NO2)C6H4CH2— | n-Bu | 3 |
| 9-025 | (4-Cl)C6H4CH2— | n-Bu | 4 |
| 9-026 | (3-Cl)C6H4CH2— | n-Bu | 4 |
| 9-027 | (2-Cl)C6H4CH2— | n-Bu | 4 |
| 9-028 | (4-F)C6H4CH2— | n-Bu | 4 |
| 9-029 | (3-F)C6H4CH2— | n-Bu | 4 |
| 9-030 | (2-F)C6H4CH2— | n-Bu | 4 |
| 9-031 | (4-Me)C6H4CH2— | n-Bu | 4 |
| 9-032 | (3-Me)C6H4CH2— | n-Bu | 4 |
| 9-033 | (2-Me)C6H4CH2— | n-Bu | 4 |
| 9-034 | (4-MeO)C6H4CH2— | n-Bu | 4 |
| 9-035 | (3-MeO)C6H4CH2— | n-Bu | 4 |
| 9-036 | (2-MeO)C6H4CH2— | n-Bu | 4 |
| 9-037 | (4-Me2N)C6H4CH2— | n-Bu | 4 |
| 9-038 | (3-Me2N)C6H4CH2— | n-Bu | 4 |
| 9-039 | (2-Me2N)C6H4CH2— | n-Bu | 4 |
| 9-040 | (4-MeOCO)C6H4CH2— | n-Bu | 4 |

TABLE 90

| Compound No. | R9 | R10 | n |
|---|---|---|---|
| 9-041 | (3-MeOCO)C6H4CH2— | n-Bu | 4 |
| 9-042 | (2-MeOCO)C6H4CH2— | n-Bu | 4 |
| 9-043 | (4-CN)C6H4CH2— | n-Bu | 4 |
| 9-044 | (3-CN)C6H4CH2— | n-Bu | 4 |
| 9-045 | (2CN)C6H4CH2— | n-Bu | 4 |
| 9-046 | (4NO2)C6H4CH2— | n-Bu | 4 |
| 9-047 | (3NO2)C6H4CH2— | n-Bu | 4 |
| 9-048 | (2NO2)C6H4CH2— | n-Bu | 4 |
| 9-049 | (4-Cl)C6H4CH2— | n-Bu | 5 |
| 9-050 | (3-Cl)C6H4CH2— | n-Bu | 5 |
| 9-051 | (2-Cl)C6H4CH2— | n-Bu | 5 |
| 9-052 | (4-F)C6H4CH2— | n-Bu | 5 |
| 9-053 | (3-F)C6H4CH2— | n-Bu | 5 |
| 9-054 | (2-F)C6H4CH2— | n-Bu | 5 |
| 9-055 | (4-Me)C6H4CH2— | n-Bu | 5 |
| 9-056 | (3-Me)C6H4CH2— | n-Bu | 5 |
| 9-057 | (2-Me)C6H4CH2— | n-Bu | 5 |
| 9-058 | (4-MeO)C6H4CH2— | n-Bu | 5 |
| 9-059 | (3-MeO)C6H4CH2— | n-Bu | 5 |
| 9-060 | (2-MeO)C6H4CH2— | n-Bu | 5 |
| 9-061 | (4-Me2N)C6H4CH2— | n-Bu | 5 |
| 9-062 | (3-Me2N)C6H4CH2— | n-Bu | 5 |
| 9-063 | (2-Me2N)C6H4CH2— | n-Bu | 5 |
| 9-064 | (4-MeOCO)C6H4CH2 | n-Bu | 5 |
| 9-065 | (3-MeOCO)C6H4CH2— | n-Bu | 5 |
| 9-066 | (2-MeOCO)C6H4CH2— | n-Bu | 5 |
| 9-067 | (4-CN)C6H4CH2— | n-Bu | 5 |
| 9-068 | (3-CN)C6H4CH2— | n-Bu | 5 |
| 9-069 | (2CN)C6H4CH2— | n-Bu | 5 |
| 9-070 | (4NO2)C6H4CH2— | n-Bu | 5 |
| 9-071 | (3NO2)C6H4CH2— | n-Bu | 5 |
| 9-072 | (2NO2)C6H4CH2— | n-Bu | 5 |
| 9-073 | (4-Cl)C6H4CH2— | n-Bu | 6 |
| 9-074 | (3-Cl)C6H4CH2— | n-Bu | 6 |
| 9-075 | (2-Cl)C6H4CH2— | n-Bu | 6 |
| 9-076 | (4-F)C6H4CH2— | n-Bu | 6 |
| 9-077 | (3-F)C6H4CH2— | n-Bu | 6 |
| 9-078 | (2-F)C6H4CH2— | n-Bu | 6 |
| 9-079 | (4-Me)C6H4CH2— | n-Bu | 6 |
| 9-080 | (3-Me)C6H4CH2— | n-Bu | 6 |

TABLE 91

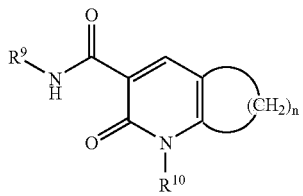

| Compound No. | R9 | R10 | n |
|---|---|---|---|
| 9-081 | (2-Me)C6H4CH2— | n-Bu | 6 |
| 9-082 | (4-MeO)C6H4CH2— | n-Bu | 6 |
| 9-083 | (3-MeO)C6H4CH2— | n-Bu | 6 |
| 9-084 | (2-MeO)C6H4CH2— | n-Bu | 6 |
| 9-085 | (4-Me2N)C6H4CH2— | n-Bu | 6 |
| 9-086 | (3-Me2N)C6H4CH2— | n-Bu | 6 |
| 9-087 | (2-Me2N)C6H4CH2— | n-Bu | 6 |
| 9-088 | (4-MeOCO)C6H4CH2— | n-Bu | 6 |
| 9-089 | (3-MeOCO)C6H4CH2— | n-Bu | 6 |
| 9-090 | (2-MeOCO)C6H4CH2— | n-Bu | 6 |
| 9-091 | (4-CN)C6H4CH2— | n-Bu | 6 |
| 9-092 | (3-CN)C6H4CH2— | n-Bu | 6 |
| 9-093 | (2CN)C6H4CH2— | n-Bu | 6 |
| 9-094 | (4NO2)C6H4CH2— | n-Bu | 6 |
| 9-095 | (3NO2)C6H4CH2— | n-Bu | 6 |
| 9-096 | (2NO2)C6H4CH2— | n-Bu | 6 |
| 9-097 | (4-Cl)C6H4CH2— | Bnzyl | 3 |
| 9-098 | (3-Cl)C6H4CH2— | Bnzyl | 3 |
| 9-099 | (2-Cl)C6H4CH2— | Bnzyl | 3 |
| 9-100 | (4-F)C6H4CH2— | Bnzyl | 3 |
| 9-101 | (3-F)C6H4CH2— | Bnzyl | 3 |
| 9-102 | (2-F)C6H4CH2— | Bnzyl | 3 |
| 9-103 | (4-Me)C6H4CH2— | Bnzyl | 3 |
| 9-104 | (3-Me)C6H4CH2— | Bnzyl | 3 |
| 9-105 | (2-Me)C6H4CH2— | Bnzyl | 3 |
| 9-106 | (4-MeO)C6H4CH2— | Bnzyl | 3 |
| 9-107 | (3-MeO)C6H4CH2— | Bnzyl | 3 |
| 9-108 | (2-MeO)C6H4CH2— | Bnzyl | 3 |
| 9-109 | (4-Me2N)C6H4CH2— | Bnzyl | 3 |
| 9-110 | (3-Me2N)C6H4CH2— | Bnzyl | 3 |
| 9-111 | (2-Me2N)C6H4CH2— | Bnzyl | 3 |
| 9-112 | (4-MeOCO)C6H4CH2— | Bnzyl | 3 |
| 9-113 | (3-MeOCO)C6H4CH2— | Bnzyl | 3 |
| 9-114 | (2-MeOCO)C6H4CH2— | Bnzyl | 3 |
| 9-115 | (4-CN)C6H4CH2— | Bnzyl | 3 |
| 9-116 | (3-CN)C6H4CH2— | Bnzyl | 3 |
| 9-117 | (2CN)C6H4CH2— | Bnzyl | 3 |
| 9-118 | (4NO2)C6H4CH2— | Bnzyl | 3 |
| 9-119 | (3NO2)C6H4CH2— | Bnzyl | 3 |
| 9-120 | (2NO2)C6H4CH2— | Bnzyl | 3 |

TABLE 92

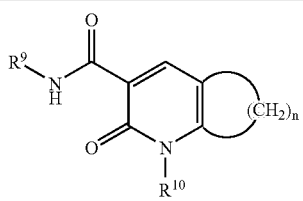

| Compound No. | R9 | R10 | n |
|---|---|---|---|
| 9-121 | (4-Cl)C6H4CH2— | Bnzyl | 4 |
| 9-122 | (3-Cl)C6H4CH2— | Bnzyl | 4 |
| 9-123 | (2-Cl)C6H4CH2— | Bnzyl | 4 |
| 9-124 | (4-F)C6H4CH2— | Bnzyl | 4 |
| 9-125 | (3-F)C6H4CH2— | Bnzyl | 4 |
| 9-126 | (2-F)C6H4CH2— | Bnzyl | 4 |
| 9-127 | (4-Me)C6H4CH2— | Bnzyl | 4 |
| 9-128 | (3-Me)C6H4CH2— | Bnzyl | 4 |
| 9-129 | (2-Me)C6H4CH2— | Bnzyl | 4 |

TABLE 92-continued

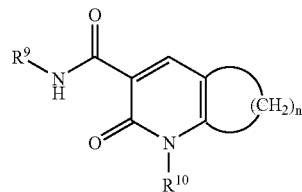

| Compound No. | R9 | R10 | n |
|---|---|---|---|
| 9-130 | (4-MeO)C6H4CH2— | Bnzyl | 4 |
| 9-131 | (3-MeO)C6H4CH2— | Bnzyl | 4 |
| 9-132 | (2-MeO)C6H4CH2— | Bnzyl | 4 |
| 9-133 | (4-Me2N)C6H4CH2— | Bnzyl | 4 |
| 9-134 | (3-Me2N)C6H4CH2— | Bnzyl | 4 |
| 9-135 | (2-Me2N)C6H4CH2— | Bnzyl | 4 |
| 9-136 | (4-MeOCO)C6H4CH2— | Bnzyl | 4 |
| 9-137 | (3-MeOCO)C6H4CH2— | Bnzyl | 4 |
| 9-138 | (2-MeOCO)C6H4CH2— | Bnzyl | 4 |
| 9-139 | (4-CN)C6H4CH2— | Bnzyl | 4 |
| 9-140 | (3-CN)C6H4CH2— | Bnzyl | 4 |
| 9-141 | (2CN)C6H4CH2— | Bnzyl | 4 |
| 9-142 | (4NO2)C6H4CH2— | Bnzyl | 4 |
| 9-143 | (3NO2)C6H4CH2— | Bnzyl | 4 |
| 9-144 | (2NO2)C6H4CH2— | Bnzyl | 4 |
| 9-145 | (4-Cl)C6H4CH2— | Bnzyl | 5 |
| 9-146 | (3-Cl)C6H4CH2— | Bnzyl | 5 |
| 9-147 | (2-Cl)C6H4CH2— | Bnzyl | 5 |
| 9-148 | (4-F)C6H4CH2— | Bnzyl | 5 |
| 9-149 | (3-F)C6H4CH2— | Bnzyl | 5 |
| 9-150 | (2-F)C6H4CH2— | Bnzyl | 5 |
| 9-151 | (4-Me)C6H4CH2— | Bnzyl | 5 |
| 9-152 | (3-Me)C6H4CH2— | Bnzyl | 5 |
| 9-153 | (2-Me)C6H4CH2— | Bnzyl | 5 |
| 9-154 | (4-MeO)C6H4CH2— | Bnzyl | 5 |
| 9-155 | (3-MeO)C6H4CH2— | Bnzyl | 5 |
| 9-156 | (2-MeO)C6H4CH2— | Bnzyl | 5 |
| 9-157 | (4-Me2N)C6H4CH2— | Bnzyl | 5 |
| 9-158 | (3-Me2N)C6H4CH2— | Bnzyl | 5 |
| 9-159 | (2-Me2N)C6H4CH2— | Bnzyl | 5 |
| 9-160 | (4-MeOCO)C6H4CH2— | Bnzyl | 5 |

TABLE 93

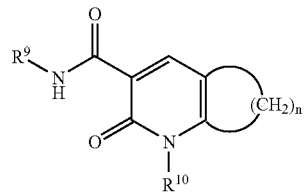

| Compound No. | R9 | R10 | n |
|---|---|---|---|
| 9-161 | (3-MeOCO)C6H4CH2— | Bnzyl | 5 |
| 9-162 | (2-MeOCO)C6H4CH2— | Bnzyl | 5 |
| 9-163 | (4-CN)C6H4CH2— | Bnzyl | 5 |
| 9-164 | (3-CN)C6H4CH2— | Bnzyl | 5 |
| 9-165 | (2CN)C6H4CH2— | Bnzyl | 5 |
| 9-166 | (4NO2)C6H4CH2— | Bnzyl | 5 |
| 9-167 | (3NO2)C6H4CH2— | Bnzyl | 5 |
| 9-168 | (2NO2)C6H4CH2— | Bnzyl | 5 |
| 9-169 | (4-Cl)C6H4CH2— | Bnzyl | 6 |
| 9-170 | (3-Cl)C6H4CH2— | Bnzyl | 6 |
| 9-171 | (2-Cl)C6H4CH2— | Bnzyl | 6 |
| 9-172 | (4-F)C6H4CH2— | Bnzyl | 6 |
| 9-173 | (3-F)C6H4CH2— | Bnzyl | 6 |
| 9-174 | (2-F)C6H4CH2— | Bnzyl | 6 |
| 9-175 | (4-Me)C6H4CH2— | Bnzyl | 6 |
| 9-176 | (3-Me)C6H4CH2— | Bnzyl | 6 |
| 9-177 | (2-Me)C6H4CH2— | Bnzyl | 6 |
| 9-178 | (4-MeO)C6H4CH2— | Bnzyl | 6 |

TABLE 93-continued

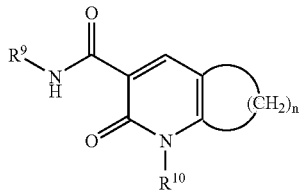

| Compound No. | R9 | R10 | n |
|---|---|---|---|
| 9-179 | (3-MeO)C6H4CH2— | Bnzyl | 6 |
| 9-180 | (2-MeO)C6H4CH2— | Bnzyl | 6 |
| 9-181 | (4-Me2N)C6H4CH2— | Bnzyl | 6 |
| 9-182 | (3-Me2N)C6H4CH2— | Bnzyl | 6 |
| 9-183 | (2-Me2N)C6H4CH2— | Bnzyl | 6 |
| 9-184 | (4-MeOCO)C6H4CH2— | Bnzyl | 6 |
| 9-185 | (3-MeOCO)C6H4CH2— | Bnzyl | 6 |
| 9-186 | (2-MeOCO)C6H4CH2— | Bnzyl | 6 |
| 9-187 | (4-CN)C6H4CH2— | Bnzyl | 6 |
| 9-188 | (3-CN)C6H4CH2— | Bnzyl | 6 |
| 9-189 | (2CN)C6H4CH2— | Bnzyl | 6 |
| 9-190 | (4NO2)C6H4CH2— | Bnzyl | 6 |
| 9-191 | (3NO2)C6H4CH2— | Bnzyl | 6 |
| 9-192 | (2NO2)C6H4CH2— | Bnzyl | 6 |
| 9-193 | (4-Cl)C6H4CH2— | 4-pyridyl-CH2— | 3 |
| 9-194 | (3-Cl)C6H4CH2— | 4-pyridyl-CH2— | 3 |
| 9-195 | (2-Cl)C6H4CH2— | 4-pyridyl-CH2— | 3 |
| 9-196 | (4-F)C6H4CH2— | 4-pyridyl-CH2— | 3 |
| 9-197 | (3-F)C6H4CH2— | 4-pyridyl-CH2— | 3 |
| 9-198 | (2-F)C6H4CH2— | 4-pyridyl-CH2— | 3 |
| 9-199 | (4-Me)C6H4CH2— | 4-pyridyl-CH2— | 3 |
| 9-200 | (3-Me)C6H4CH2— | 4-pyridyl-CH2— | 3 |

TABLE 94

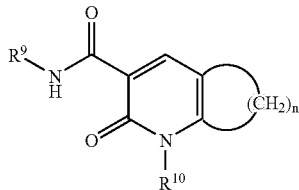

| Compound No. | R9 | R10 | n |
|---|---|---|---|
| 9-201 | (2-Me)C6H4CH2— | 4-pyridyl-CH2— | 3 |
| 9-202 | (4-MeO)C6H4CH2— | 4-pyridyl-CH2— | 3 |
| 9-203 | (3-MeO)C6H4CH2— | 4-pyridyl-CH2— | 3 |
| 9-204 | (2-MeO)C6H4CH2— | 4-pyridyl-CH2— | 3 |
| 9-205 | (4-Me2N)C6H4CH2— | 4-pyridyl-CH2— | 3 |
| 9-206 | (3-Me2N)C6H4CH2— | 4-pyridyl-CH2— | 3 |
| 9-207 | (2-Me2N)C6H4CH2— | 4-pyridyl-CH2— | 3 |
| 9-208 | (4-MeOCO)C6H4CH2— | 4-pyridyl-CH2— | 3 |
| 9-209 | (3-MeOCO)C6H4CH2— | 4-pyridyl-CH2— | 3 |
| 9-210 | (2-MeOCO)C6H4CH2— | 4-pyridyl-CH2— | 3 |
| 9-211 | (4-CN)C6H4CH2— | 4-pyridyl-CH2— | 3 |
| 9-212 | (3-CN)C6H4CH2— | 4-pyridyl-CH2— | 3 |
| 9-213 | (2CN)C6H4CH2— | 4-pyridyl-CH2— | 3 |
| 9-214 | (4NO2)C6H4CH2— | 4-pyridyl-CH2— | 3 |
| 9-215 | (3NO2)C6H4CH2— | 4-pyridyl-CH2— | 3 |
| 9-216 | (2NO2)C6H4CH2— | 4-pyridyl-CH2— | 3 |
| 9-217 | (4-Cl)C6H4CH2— | 4-pyridyl-CH2— | 4 |
| 9-218 | (3-Cl)C6H4CH2— | 4-pyridyl-CH2— | 4 |
| 9-219 | (2-Cl)C6H4CH2— | 4-pyridyl-CH2— | 4 |
| 9-220 | (4-F)C6H4CH2— | 4-pyridyl-CH2— | 4 |
| 9-221 | (3-F)C6H4CH2— | 4-pyridyl-CH2— | 4 |
| 9-222 | (2-F)C6H4CH2— | 4-pyridyl-CH2— | 4 |
| 9-223 | (4-Me)C6H4CH2— | 4-pyridyl-CH2— | 4 |
| 9-224 | (3-Me)C6H4CH2— | 4-pyridyl-CH2— | 4 |
| 9-225 | (2-Me)C6H4CH2— | 4-pyridyl-CH2— | 4 |
| 9-226 | (4-MeO)C6H4CH2— | 4-pyridyl-CH2— | 4 |
| 9-227 | (3-MeO)C6H4CH2— | 4-pyridyl-CH2— | 4 |

TABLE 94-continued

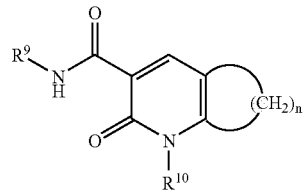

| Compound No. | R9 | R10 | n |
|---|---|---|---|
| 9-228 | (2-MeO)C6H4CH2— | 4-pyridyl-CH2— | 4 |
| 9-229 | (4-Me2N)C6H4CH2— | 4-pyridyl-CH2— | 4 |
| 9-230 | (3-Me2N)C6H4CH2— | 4-pyridyl-CH2— | 4 |
| 9-231 | (2-Me2N)C6H4CH2— | 4-pyridyl-CH2— | 4 |
| 9-232 | (4-MeOCO)C6H4CH2— | 4-pyridyl-CH2— | 4 |
| 9-233 | (3-MeOCO)C6H4CH2— | 4-pyridyl-CH2— | 4 |
| 9-234 | (2-MeOCO)C6H4CH2— | 4-pyridyl-CH2— | 4 |
| 9-235 | (4-CN)C6H4CH2— | 4-pyridyl-CH2— | 4 |
| 9-236 | (3-CN)C6H4CH2— | 4-pyridyl-CH2— | 4 |
| 9-237 | (2CN)C6H4CH2— | 4-pyridyl-CH2— | 4 |
| 9-238 | (4NO2)C6H4CH2— | 4-pyridyl-CH2— | 4 |
| 9-239 | (3NO2)C6H4CH2— | 4-pyridyl-CH2— | 4 |
| 9-240 | (2NO2)C6H4CH2— | 4-pyridyl-CH2— | 4 |

TABLE 95

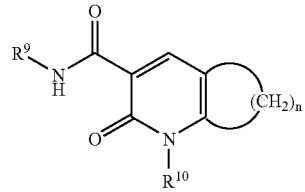

| Compound No. | R9 | R10 | n |
|---|---|---|---|
| 9-241 | (4-Cl)C6H4CH2— | 4-pyridyl-CH2— | 5 |
| 9-242 | (3-Cl)C6H4CH2— | 4-pyridyl-CH2— | 5 |
| 9-243 | (2-Cl)C6H4CH2— | 4-pyridyl-CH2— | 5 |
| 9-244 | (4-F)C6H4CH2— | 4-pyridyl-CH2— | 5 |
| 9-245 | (3-F)C6H4CH2— | 4-pyridyl-CH2— | 5 |
| 9-246 | (2-F)C6H4CH2— | 4-pyridyl-CH2— | 5 |
| 9-247 | (4-Me)C6H4CH2— | 4-pyridyl-CH2— | 5 |
| 9-248 | (3-Me)C6H4CH2— | 4-pyridyl-CH2— | 5 |
| 9-249 | (2-Me)C6H4CH2— | 4-pyridyl-CH2— | 5 |
| 9-250 | (4-MeO)C6H4CH2— | 4-pyridyl-CH2— | 5 |
| 9-251 | (3-MeO)C6H4CH2— | 4-pyridyl-CH2— | 5 |
| 9-252 | (2-MeO)C6H4CH2— | 4-pyridyl-CH2— | 5 |
| 9-253 | (4-Me2N)C6H4CH2— | 4-pyridyl-CH2— | 5 |
| 9-254 | (3-Me2N)C6H4CH2— | 4-pyridyl-CH2— | 5 |
| 9-255 | (2-Me2N)C6H4CH2— | 4-pyridyl-CH2— | 5 |
| 9-256 | (4-MeOCO)C6H4CH2— | 4-pyridyl-CH2— | 5 |
| 9-257 | (3-MeOCO)C6H4CH2— | 4-pyridyl-CH2— | 5 |
| 9-258 | (2-MeOCO)C6H4CH2— | 4-pyridyl-CH2— | 5 |
| 9-259 | (4-CN)C6H4CH2— | 4-pyridyl-CH2— | 5 |
| 9-260 | (3-CN)C6H4CH2— | 4-pyridyl-CH2— | 5 |
| 9-261 | (2CN)C6H4CH2— | 4-pyridyl-CH2— | 5 |
| 9-262 | (4NO2)C6H4CH2— | 4-pyridyl-CH2— | 5 |
| 9-263 | (3NO2)C6H4CH2— | 4-pyridyl-CH2— | 5 |
| 9-264 | (2NO2)C6H4CH2— | 4-pyridyl-CH2— | 5 |
| 9-265 | (4-Cl)C6H4CH2— | 4-pyridyl-CH2— | 6 |
| 9-266 | (3-Cl)C6H4CH2— | 4-pyridyl-CH2— | 6 |
| 9-267 | (2-Cl)C6H4CH2— | 4-pyridyl-CH2— | 6 |
| 9-268 | (4-F)C6H4CH2— | 4-pyridyl-CH2— | 6 |
| 9-269 | (3-F)C6H4CH2— | 4-pyridyl-CH2— | 6 |
| 9-270 | (2-F)C6H4CH2— | 4-pyridyl-CH2— | 6 |
| 9-271 | (4-Me)C6H4CH2— | 4-pyridyl-CH2— | 6 |
| 9-272 | (3-Me)C6H4CH2— | 4-pyridyl-CH2— | 6 |
| 9-273 | (2-Me)C6H4CH2— | 4-pyridyl-CH2— | 6 |
| 9-274 | (4-MeO)C6H4CH2— | 4-pyridyl-CH2— | 6 |
| 9-275 | (3-MeO)C6H4CH2— | 4-pyridyl-CH2— | 6 |
| 9-276 | (2-MeO)C6H4CH2— | 4-pyridyl-CH2— | 6 |

TABLE 95-continued

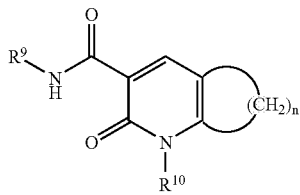

| Compound No. | R9 | R10 | n |
|---|---|---|---|
| 9-277 | (4-Me2N)C6H4CH2— | 4-pyridyl-CH2— | 6 |
| 9-278 | (3-Me2N)C6H4CH2— | 4-pyridyl-CH2— | 6 |
| 9-279 | (2-Me2N)C6H4CH2— | 4-pyridyl-CH2— | 6 |
| 9-280 | (4-MeOCO)C6H4CH2— | 4-pyridyl-CH2— | 6 |

TABLE 96

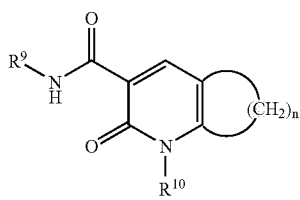

| Compound No. | R9 | R10 | n |
|---|---|---|---|
| 9-281 | (3-MeOCO)C6H4CH2— | 4-pyridyl-CH2— | 6 |
| 9-282 | (2-MeOCO)C6H4CH2— | 4-pyridyl-CH2— | 6 |
| 9-283 | (4-CN)C6H4CH2— | 4-pyridyl-CH2— | 6 |
| 9-284 | (3-CN)C6H4CH2— | 4-pyridyl-CH2— | 6 |
| 9-285 | (2CN)C6H4CH2— | 4-pyridyl-CH2— | 6 |
| 9-286 | (4NO2)C6H4CH2— | 4-pyridyl-CH2— | 6 |
| 9-287 | (3NO2)C6H4CH2— | 4-pyridyl-CH2— | 6 |
| 9-288 | (2NO2)C6H4CH2— | 4-pyridyl-CH2— | 6 |
| 9-289 | (4-Cl)C6H4CH2CH2— | n-Bu | 3 |
| 9-290 | (3-Cl)C6H4CH2CH2— | n-Bu | 3 |
| 9-291 | (2-Cl)C6H4CH2CH2— | n-Bu | 3 |
| 9-292 | (4-F)C6H4CH2CH2— | n-Bu | 3 |
| 9-293 | (3-F)C6H4CH2CH2— | n-Bu | 3 |
| 9-294 | (2-F)C6H4CH2CH2— | n-Bu | 3 |
| 9-295 | (4-Me)C6H4CH2CH2— | n-Bu | 3 |
| 9-296 | (3-Me)C6H4CH2CH2— | n-Bu | 3 |
| 9-297 | (2-Me)C6H4CH2CH2— | n-Bu | 3 |
| 9-298 | (4-MeO)C6H4CH2CH2— | n-Bu | 3 |
| 9-299 | (3-MeO)C6H4CH2CH2— | n-Bu | 3 |
| 9-300 | (2-MeO)C6H4CH2CH2— | n-Bu | 3 |
| 9-301 | (4-Me2N)C6H4CH2CH2— | n-Bu | 3 |
| 9-302 | (3-Me2N)C6H4CH2CH2— | n-Bu | 3 |
| 9-303 | (2-Me2N)C6H4CH2CH2— | n-Bu | 3 |
| 9-304 | (4-MeOCO)C6H4CH2CH2— | n-Bu | 3 |
| 9-305 | (3-MeOCO)C6H4CH2CH2— | n-Bu | 3 |
| 9-306 | (2-MeOCO)C6H4CH2CH2— | n-Bu | 3 |
| 9-307 | (4-CN)C6H4CH2CH2— | n-Bu | 3 |
| 9-308 | (3-CN)C6H4CH2CH2— | n-Bu | 3 |
| 9-309 | (2CN)C6H4CH2CH2— | n-Bu | 3 |
| 9-310 | (4NO2)C6H4CH2CH2— | n-Bu | 3 |
| 9-311 | (3NO2)C6H4CH2CH2— | n-Bu | 3 |
| 9-312 | (2NO2)C6H4CH2CH2— | n-Bu | 3 |
| 9-313 | (4-Cl)C6H4CH2CH2— | n-Bu | 4 |
| 9-314 | (3-Cl)C6H4CH2CH2— | n-Bu | 4 |
| 9-315 | (2-Cl)C6H4CH2CH2— | n-Bu | 4 |
| 9-316 | (4-F)C6H4CH2CH2— | n-Bu | 4 |
| 9-317 | (3-F)C6H4CH2CH2— | n-Bu | 4 |
| 9-318 | (2-F)C6H4CH2CH2— | n-Pu | 4 |
| 9-319 | (4-Me)C6H4CH2CH2— | n-Bu | 4 |
| 9-320 | (3-Me)C6H4CH2CH2— | n-Bu | 4 |

TABLE 97

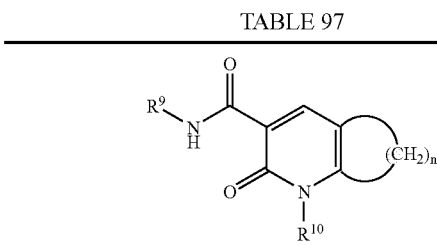

| Compound No. | R9 | R10 | n |
|---|---|---|---|
| 9-321 | (2-Me)C6H4CH2CH2— | n-Bu | 4 |
| 9-322 | (4-MeO)C6H4CH2CH2— | n-Bu | 4 |
| 9-323 | (3-MeO)C6H4CH2CH2— | n-Bu | 4 |
| 9-324 | (2-MeO)C6H4CH2CH2— | n-Bu | 4 |
| 9-325 | (4-Me2N)C6H4CH2CH2— | n-Bu | 4 |
| 9-326 | (3-Me2N)C6H4CH2CH2— | n-Bu | 4 |
| 9-327 | (2-Me2N)C6H4CH2CH2— | n-Bu | 4 |
| 9-328 | (4-MeOCO)C6H4CH2CH2— | n-Bu | 4 |
| 9-329 | (3-MeOCO)C6H4CH2CH2— | n-Bu | 4 |
| 9-330 | (2-MeOCO)C6H4CH2CH2— | n-Bu | 4 |
| 9-331 | (4-CN)C6H4CH2CH2— | n-Bu | 4 |
| 9-332 | (3-CN)C6H4CH2CH2— | n-Bu | 4 |
| 9-333 | (2CN)C6H4CH2CH2— | n-Bu | 4 |
| 9-334 | (4NO2)C6H4CH2CH2— | n-Bu | 4 |
| 9-335 | (3NO2)C6H4CH2CH2— | n-Bu | 4 |
| 9-336 | (2NO2)C6H4CH2CH2— | n-Bu | 4 |
| 9-337 | (4-Cl)C6H4CH2CH2— | n-Bu | 5 |
| 9-338 | (3-Cl)C6H4CH2CH2— | n-Bu | 5 |
| 9-339 | (2-Cl)C6H4CH2CH2— | n-Bu | 5 |
| 9-340 | (4-F)C6H4CH2CH2— | n-Bu | 5 |
| 9-341 | (3-F)C6H4CH2CH2— | n-Bu | 5 |
| 9-342 | (2-F)C6H4CH2CH2— | n-Bu | 5 |
| 9-343 | (4-Me)C6H4CH2CH2— | n-Bu | 5 |
| 9-344 | (3-Me)C6H4CH2CH2— | n-Bu | 5 |
| 9-345 | (2-Me)C6H4CH2CH2— | n-Bu | 5 |
| 9-346 | (4-MeO)C6H4CH2CH2— | n-Bu | 5 |
| 9-347 | (3-MeO)C6H4CH2CH2— | n-Bu | 5 |
| 9-348 | (2-MeO)C6H4CH2CH2— | n-Bu | 5 |
| 9-349 | (4-Me2N)C6H4CH2CH2— | n-Bu | 5 |
| 9-350 | (3-Me2N)C6H4CH2CH2— | n-Bu | 5 |
| 9-351 | (2-Me2N)C6H4CH2CH2— | n-Bu | 5 |
| 9-352 | (4-MeOCO)C6H4CH2CH2— | n-Bu | 5 |
| 9-353 | (3-MeOCO)C6H4CH2CH2— | n-Bu | 5 |
| 9-354 | (2-MeOCO)C6H4CH2CH2— | n-Bu | 5 |
| 9-355 | (4-CN)C6H4CH2CH2— | n-Bu | 5 |
| 9-356 | (3-CN)C6H4CH2CH2— | n-Bu | 5 |
| 9-357 | (2CN)C6H4CH2CH2— | n-Bu | 5 |
| 9-358 | (4NO2)C6H4CH2CH2— | n-Bu | 5 |
| 9-359 | (3NO2)C6H4CH2CH2— | n-Bu | 5 |
| 9-360 | (2NO2)C6H4CH2CH2— | n-Bu | 5 |

TABLE 98

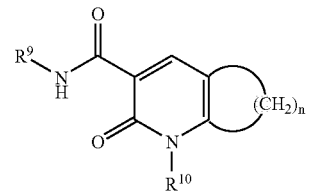

| Compound No. | R9 | R10 | n |
|---|---|---|---|
| 9-361 | (4-Cl)C6H4CH2CH2— | n-Bu | 6 |
| 9-362 | (3-Cl)C6H4CH2CH2— | n-Bu | 6 |
| 9-363 | (2-Cl)C6H4CH2CH2— | n-Bu | 6 |
| 9-364 | (4-F)C6H4CH2CH2— | n-Bu | 6 |
| 9-365 | (3-F)C6H4CH2CH2— | n-Bu | 6 |
| 9-366 | (2-F)C6H4CH2CH2— | n-Bu | 6 |
| 9-367 | (4-Me)C6H4CH2CH2— | n-Bu | 6 |
| 9-368 | (3-Me)C6H4CH2CH2— | n-Bu | 6 |
| 9-369 | (2-Me)C6H4CH2CH2— | n-Bu | 6 |

TABLE 98-continued

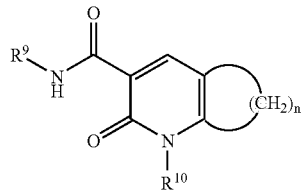

| Compound No. | R9 | R10 | n |
|---|---|---|---|
| 9-370 | (4-MeO)C6H4CH2CH2— | n-Bu | 6 |
| 9-371 | (3-MeO)C6H4CH2CH2— | n-Bu | 6 |
| 9-372 | (2-MeO)C6H4CH2CH2— | n-Bu | 6 |
| 9-373 | (4-Me2N)C6H4CH2CH2— | n-Bu | 6 |
| 9-374 | (3-Me2N)C6H4CH2CH2— | n-Bu | 6 |
| 9-375 | (2-Me2N)C6H4CH2CH2— | n-Bu | 6 |
| 9-376 | (4-MeOCO)C6H4CH2CH2— | n-Bu | 6 |
| 9-377 | (3-MeOCO)C6H4CH2CH2— | n-Bu | 6 |
| 9-378 | (2-MeOCO)C6H4CH2CH2— | n-Bu | 6 |
| 9-379 | (4-CN)C6H4CH2CH2— | n-Bu | 6 |
| 9-380 | (3-CN)C6H4CH2CH2— | n-Bu | 6 |
| 9-381 | (2CN)C6H4CH2CH2— | n-Bu | 6 |
| 9-382 | (4NO2)C6H4CH2CH2— | n-Bu | 6 |
| 9-383 | (3NO2)C6H4CH2CH2— | n-Bu | 6 |
| 9-384 | (2NO2)C6H4CH2CH2— | n-Bu | 6 |
| 9-385 | (4-Cl)C6H4CH2CH2— | Bnzyl | 3 |
| 9-386 | (3-Cl)C6H4CH2CH2— | Bnzyl | 3 |
| 9-387 | (2-Cl)C6H4CH2CH2— | Bnzyl | 3 |
| 9-388 | (4-F)C6H4CH2CH2— | Bnzyl | 3 |
| 9-389 | (3-F)C6H4CH2CH2— | Bnzyl | 3 |
| 9-390 | (2-F)C6H4CH2CH2— | Bnzyl | 3 |
| 9-391 | (4-Me)C6H4CH2CH2— | Bnzyl | 3 |
| 9-392 | (3-Me)C6H4CH2CH2— | Bnzyl | 3 |
| 9-393 | (2-Me)C6H4CH2CH2— | Bnzyl | 3 |
| 9-394 | (4-MeO)C6H4CH2CH2— | Bnzyl | 3 |
| 9-395 | (3-MeO)C6H4CH2CH2— | Bnzyl | 3 |
| 9-396 | (2-MeO)C6H4CH2CH2— | Bnzyl | 3 |
| 9-397 | (4-Me2N)C6H4CH2CH2— | Bnzyl | 3 |
| 9-398 | (3-Me2N)C6H4CH2CH2— | Bnzyl | 3 |
| 9-399 | (2-Me2N)C6H4CH2CH2— | Bnzyl | 3 |
| 9-400 | (4-MeOCO)C6H4CH2CH2— | Bnzyl | 3 |

TABLE 99

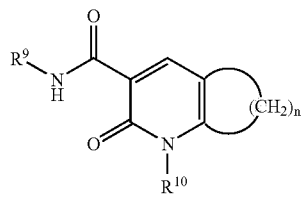

| Compound No. | R9 | R10 | n |
|---|---|---|---|
| 9-401 | (3-MeOCO)C6H4CH2CH2— | Bnzyl | 3 |
| 9-402 | (2-MeOCO)C6H4CH2CH2— | Bnzyl | 3 |
| 9-403 | (4-CN)C6H4CH2CH2— | Bnzyl | 3 |
| 9-404 | (3-CN)C6H4CH2CH2— | Bnzyl | 3 |
| 9-405 | (2CN)C6H4CH2CH2— | Bnzyl | 3 |
| 9-406 | (4NO2)C6H4CH2CH2— | Bnzyl | 3 |
| 9-407 | (3NO2)C6H4CH2CH2— | Bnzyl | 3 |
| 9-408 | (2NO2)C6H4CH2CH2— | Bnzyl | 3 |
| 9-409 | (4-Cl)C6H4CH2CH2— | Bnzyl | 4 |
| 9-410 | (3-Cl)C6H4CH2CH2— | Bnzyl | 4 |
| 9-411 | (2-Cl)C6H4CH2CH2— | Bnzyl | 4 |
| 9-412 | (4-F)C6H4CH2CH2— | Bnzyl | 4 |
| 9-413 | (3-F)C6H4CH2CH2— | Bnzyl | 4 |
| 9-414 | (2-F)C6H4CH2CH2— | Bnzyl | 4 |
| 9-415 | (4-Me)C6H4CH2CH2— | Bnzyl | 4 |
| 9-416 | (3-Me)C6H4CH2CH2— | Bnzyl | 4 |
| 9-417 | (2-Me)C6H4CH2CH2— | Bnzyl | 4 |
| 9-418 | (4-MeO)C6H4CH2CH2— | Bnzyl | 4 |

TABLE 99-continued

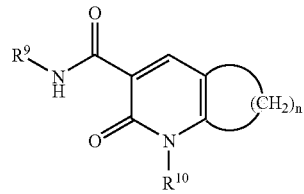

| Compound No. | R9 | R10 | n |
|---|---|---|---|
| 9-419 | (3-MeO)C6H4CH2CH2— | Bnzyl | 4 |
| 9-420 | (2-MeO)C6H4CH2CH2— | Bnzyl | 4 |
| 9-421 | (4-Me2N)C6H4CH2CH2— | Bnzyl | 4 |
| 9-422 | (3-Me2N)C6H4CH2CH2— | Bnzyl | 4 |
| 9-423 | (2-Me2N)C6H4CH2CH2— | Bnzyl | 4 |
| 9-424 | (4-MeOCO)C6H4CH2CH2— | Bnzyl | 4 |
| 9-425 | (3-MeOCO)C6H4CH2CH2— | Bnzyl | 4 |
| 9-426 | (2-MeOCO)C6H4CH2CH2— | Bnzyl | 4 |
| 9-427 | (4-CN)C6H4CH2CH2— | Bnzyl | 4 |
| 9-428 | (3-CN)C6H4CH2CH2— | Bnzyl | 4 |
| 9-429 | (2CN)C6H4CH2CH2— | Bnzyl | 4 |
| 9-430 | (4NO2)C6H4CH2CH2— | Bnzyl | 4 |
| 9-431 | (3NO2)C6H4CH2CH2— | Bnzyl | 4 |
| 9-432 | (2NO2)C6H4CH2CH2— | Bnzyl | 4 |
| 9-433 | (4-Cl)C6H4CH2CH2— | Bnzyl | 5 |
| 9-434 | (3-Cl)C6H4CH2CH2— | Bnzyl | 5 |
| 9-435 | (2-Cl)C6H4CH2CH2— | Bnzyl | 5 |
| 9-436 | (4-F)C6H4CH2CH2— | Bnzyl | 5 |
| 9-437 | (3-F)C6H4CH2CH2— | Bnzyl | 5 |
| 9-438 | (2-F)C6H4CH2CH2— | Bnzyl | 5 |
| 9-439 | (4-Me)C6H4CH2CH2— | Bnzyl | 5 |
| 9-440 | (3-Me)C6H4CH2CH2— | Bnzyl | 5 |

TABLE 100

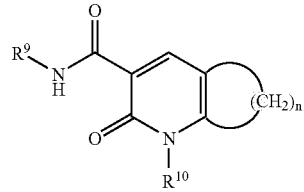

| Compound No. | R9 | R10 | n |
|---|---|---|---|
| 9-441 | (2-Me)C6H4CH2CH2— | Bnzyl | 5 |
| 9-442 | (4-MeO)C6H4CH2CH2— | Bnzyl | 5 |
| 9-443 | (3-MeO)C6H4CH2CH2— | Bnzyl | 5 |
| 9-444 | (2-MeO)C6H4CH2CH2— | Bnzyl | 5 |
| 9-445 | (4-Me2N)C6H4CH2CH2— | Bnzyl | 5 |
| 9-446 | (3-Me2N)C6H4CH2CH2— | Bnzyl | 5 |
| 9-447 | (2-Me2N)C6H4CH2CH2— | Bnzyl | 5 |
| 9-448 | (4-MeOCO)C6H4CH2CH2— | Bnzyl | 5 |
| 9-449 | (3-MeOCO)C6H4CH2CH2— | Bnzyl | 5 |
| 9-450 | (2-MeOCO)C6H4CH2CH2— | Bnzyl | 5 |
| 9-451 | (4-CN)C6H4CH2CH2— | Bnzyl | 5 |
| 9-452 | (3-CN)C6H4CH2CH2— | Bnzyl | 5 |
| 9-453 | (2CN)C6H4CH2CH2— | Bnzyl | 5 |
| 9-454 | (4NO2)C6H4CH2CH2— | Bnzyl | 5 |
| 9-455 | (3NO2)C6H4CH2CH2— | Bnzyl | 5 |
| 9-456 | (2NO2)C6H4CH2CH2— | Bnzyl | 5 |
| 9-457 | (4-Cl)C6H4CH2CH2— | Bnzyl | 6 |
| 9-458 | (3-Cl)C6H4CH2CH2— | Bnzyl | 6 |
| 9-459 | (2-Cl)C6H4CH2CH2— | Bnzyl | 6 |
| 9-460 | (4-F)C6H4CH2CH2— | Bnzyl | 6 |
| 9-461 | (3-F)C6H4CH2CH2— | Bnzyl | 6 |
| 9-462 | (2-F)C6H4CH2CH2— | Bnzyl | 6 |
| 9-463 | (4-Me)C6H4CH2CH2— | Bnzyl | 6 |
| 9-464 | (3-Me)C6H4CH2CH2— | Bnzyl | 6 |
| 9-465 | (2-Me)C6H4CH2CH2— | Bnzyl | 6 |
| 9-466 | (4-MeO)C6H4CH2CH2— | Bnzyl | 6 |
| 9-467 | (3-MeO)C6H4CH2CH2— | Bnzyl | 6 |

TABLE 100-continued

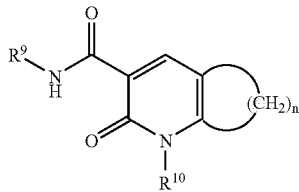

| Compound No. | R9 | R10 | n |
|---|---|---|---|
| 9-468 | (2-MeO)C6H4CH2CH2— | Bnzyl | 6 |
| 9-469 | (4-Me2N)C6H4CH2CH2— | Bnzyl | 6 |
| 9-470 | (3-Me2N)C6H4CH2CH2— | Bnzyl | 6 |
| 9-471 | (2-Me2N)C6H4CH2CH2— | Bnzyl | 6 |
| 9-472 | (4-MeOCO)C6H4CH2CH2— | Bnzyl | 6 |
| 9-473 | (3-MeOCO)C6H4CH2CH2— | Bnzyl | 6 |
| 9-474 | (2-MeOCO)C6H4CH2CH2— | Bnzyl | 6 |
| 9-475 | (4-CN)C6H4CH2CH2— | Bnzyl | 6 |
| 9-476 | (3-CN)C6H4CH2CH2— | Bnzyl | 6 |
| 9-477 | (2CN)C6H4CH2CH2— | Bnzyl | 6 |
| 9-478 | (4NO2)C6H4CH2CH2— | Bnzyl | 6 |
| 9-479 | (3NO2)C6H4CH2CH2— | Bnzyl | 6 |
| 9-480 | (2NO2)C6H4CH2CH2— | Bnzyl | 6 |

TABLE 101

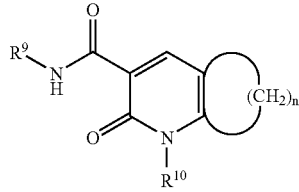

| Compound No. | R9 | R10 | n |
|---|---|---|---|
| 9-481 | (4-Cl)C6H4CH2CH2— | 4-pyridyl-CH2— | 3 |
| 9-482 | (3-Cl)C6H4CH2CH2— | 4-pyridyl-CH2— | 3 |
| 9-483 | (2-Cl)C6H4CH2CH2— | 4-pyridyl-CH2— | 3 |
| 9-484 | (4-F)C6H4CH2CH2— | 4-pyridyl-CH2— | 3 |
| 9-485 | (3-F)C6H4CH2CH2— | 4-pyridyl-CH2— | 3 |
| 9-486 | (2-F)C6H4CH2CH2— | 4-pyridyl-CH2— | 3 |
| 9-487 | (4-Me)C6H4CH2CH2— | 4-pyridyl-CH2— | 3 |
| 9-488 | (3-Me)C6H4CH2CH2— | 4-pyridyl-CH2— | 3 |
| 9-489 | (2-Me)C6H4CH2CH2— | 4-pyridyl-CH2— | 3 |
| 9-490 | (4-MeO)C6H4CH2CH2— | 4-pyridyl-CH2— | 3 |
| 9-491 | (3-MeO)C6H4CH2CH2— | 4-pyridyl-CH2— | 3 |
| 9-492 | (2-MeO)C6H4CH2CH2— | 4-pyridyl-CH2— | 3 |
| 9-493 | (4-Me2N)C6H4CH2CH2— | 4-pyridyl-CH2— | 3 |
| 9-494 | (3-Me2N)C6H4CH2CH2— | 4-pyridyl-CH2— | 3 |
| 9-495 | (2-Me2N)C6H4CH2CH2— | 4-pyridyl-CH2— | 3 |
| 9-496 | (4-MeOCO)C6H4CH2CH2— | 4-pyridyl-CH2— | 3 |
| 9-497 | (3-MeOCO)C6H4CH2CH2— | 4-pyridyl-CH2— | 3 |
| 9-498 | (2-MeOCO)C6H4CH2CH2— | 4-pyridyl-CH2— | 3 |
| 9-499 | (4-CN)C6H4CH2CH2— | 4-pyridyl-CH2— | 3 |
| 9-500 | (3-CN)C6H4CH2CH2— | 4-pyridyl-CH2— | 3 |
| 9-501 | (2CN)C6H4CH2CH2— | 4-pyridyl-CH2— | 3 |
| 9-502 | (4NO2)C6H4CH2CH2— | 4-pyridyl-CH2— | 3 |
| 9-503 | (3NO2)C6H4CH2CH2— | 4-pyridyl-CH2— | 3 |
| 9-504 | (2NO2)C6H4CH2CH2— | 4-pyridyl-CH2— | 3 |
| 9-505 | (4-Cl)C6H4CH2CH2— | 4-pyridyl-CH2— | 4 |
| 9-506 | (3-Cl)C6H4CH2CH2— | 4-pyridyl-CH2— | 4 |
| 9-507 | (2-Cl)C6H4CH2CH2— | 4-pyridyl-CH2— | 4 |
| 9-508 | (4-F)C6H4CH2CH2— | 4-pyridyl-CH2— | 4 |
| 9-509 | (3-F)C6H4CH2CH2— | 4-pyridyl-CH2— | 4 |
| 9-510 | (2-F)C6H4CH2CH2— | 4-pyridyl-CH2— | 4 |
| 9-511 | (4-Me)C6H4CH2CH2— | 4-pyridyl-CH2— | 4 |
| 9-512 | (3-Me)C6H4CH2CH2— | 4-pyridyl-CH2— | 4 |
| 9-513 | (2-Me)C6H4CH2CH2— | 4-pyridyl-CH2— | 4 |
| 9-514 | (4-MeO)C6H4CH2CH2— | 4-pyridyl-CH2— | 4 |
| 9-515 | (3-MeO)C6H4CH2CH2— | 4-pyridyl-CH2— | 4 |

TABLE 101-continued

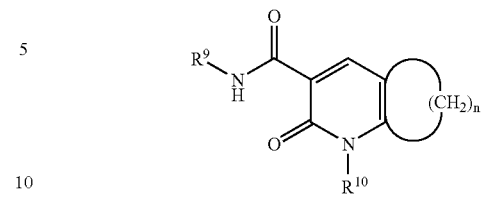

| Compound No. | R9 | R10 | n |
|---|---|---|---|
| 9-516 | (2-MeO)C6H4CH2CH2— | 4-pyridyl-CH2— | 4 |
| 9-517 | (4-Me2N)C6H4CH2CH2— | 4-pyridyl-CH2— | 4 |
| 9-518 | (3-Me2N)C6H4CH2CH2— | 4-pyridyl-CH2— | 4 |
| 9-519 | (2-Me2N)C6H4CH2CH2— | 4-pyridyl-CH2— | 4 |
| 9-520 | (4-MeOCO)C6H4CH2CH2— | 4-pyridyl-CH2— | 4 |

TABLE 102

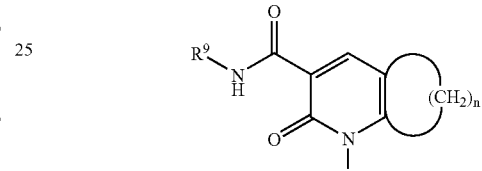

| Compound No. | R9 | R10 | n |
|---|---|---|---|
| 9-521 | (3-MeOCO)C6H4CH2CH2— | 4-pyridyl-CH2— | 4 |
| 9-522 | (2-MeOCO)C6H4CH2CH2— | 4-pyridyl-CH2— | 4 |
| 9-523 | (4-CN)C6H4CH2CH2— | 4-pyridyl-CH2— | 4 |
| 9-524 | (3-CN)C6H4CH2CH2— | 4-pyridyl-CH2— | 4 |
| 9-525 | (2CN)C6H4CH2CH2— | 4-pyridyl-CH2— | 4 |
| 9-526 | (4NO2)C6H4CH2CH2— | 4-pyridyl-CH2— | 4 |
| 9-527 | (3NO2)C6H4CH2CH2— | 4-pyridyl-CH2— | 4 |
| 9-528 | (2NO2)C6H4CH2CH2— | 4-pyridyl-CH2— | 4 |
| 9-529 | (4-Cl)C6H4CH2CH2— | 4-pyridyl-CH2— | 5 |
| 9-530 | (3-Cl)C6H4CH2CH2— | 4-pyridyl-CH2— | 5 |
| 9-531 | (2-Cl)C6H4CH2CH2— | 4-pyridyl-CH2— | 5 |
| 9-532 | (4-F)C6H4CH2CH2— | 4-pyridyl-CH2— | 5 |
| 9-533 | (3-F)C6H4CH2CH2— | 4-pyridyl-CH2— | 5 |
| 9-534 | (2-F)C6H4CH2CH2— | 4-pyridyl-CH2— | 5 |
| 9-535 | (4-Me)C6H4CH2CH2— | 4-pyridyl-CH2— | 5 |
| 9-536 | (3-Me)C6H4CH2CH2— | 4-pyridyl-CH2— | 5 |
| 9-537 | (2-Me)C6H4CH2CH2— | 4-pyridyl-CH2— | 5 |
| 9-538 | (4-MeO)C6H4CH2CH2— | 4-pyridyl-CH2— | 5 |
| 9-539 | (3-MeO)C6H4CH2CH2— | 4-pyridyl-CH2— | 5 |
| 9-540 | (2-MeO)C6H4CH2CH2— | 4-pyridyl-CH2— | 5 |
| 9-541 | (4-Me2N)C6H4CH2CH2— | 4-pyridyl-CH2— | 5 |
| 9-542 | (3-Me2N)C6H4CH2CH2— | 4-pyridyl-CH2— | 5 |
| 9-543 | (2-Me2N)C6H4CH2CH2— | 4-pyridyl-CH2— | 5 |
| 9-544 | (4-MeOCO)C6H4CH2CH2— | 4-pyridyl-CH2— | 5 |
| 9-545 | (3-MeOCO)C6H4CH2CH2— | 4-pyridyl-CH2— | 5 |
| 9-546 | (2-MeOCO)C6H4CH2CH2— | 4-pyridyl-CH2— | 5 |
| 9-547 | (4-CN)C6H4CH2CH2— | 4-pyridyl-CH2— | 5 |
| 9-548 | (3-CN)C6H4CH2CH2— | 4-pyridyl-CH2— | 5 |
| 9-549 | (2CN)C6H4CH2CH2— | 4-pyridyl-CH2— | 5 |
| 9-550 | (4NO2)C6H4CH2CH2— | 4-pyridyl-CH2— | 5 |
| 9-551 | (3NO2)C6H4CH2CH2— | 4-pyridyl-CH2— | 5 |
| 9-552 | (2NO2)C6H4CH2CH2— | 4-pyridyl-CH2— | 5 |
| 9-553 | (4-Cl)C6H4CH2CH2— | 4-pyridyl-CH2— | 6 |
| 9-554 | (3-Cl)C6H4CH2CH2— | 4-pyridyl-CH2— | 6 |
| 9-555 | (2-Cl)C6H4CH2CH2— | 4-pyridyl-CH2— | 6 |
| 9-556 | (4-F)C6H4CH2CH2— | 4-pyridyl-CH2— | 6 |
| 9-557 | (3-F)C6H4CH2CH2— | 4-pyridyl-CH2— | 6 |
| 9-558 | (2-F)C6H4CH2CH2— | 4-pyridyl-CH2— | 6 |
| 9-559 | (4-Me)C6H4CH2CH2— | 4-pyridyl-CH2— | 6 |
| 9-560 | (3-Me)C6H4CH2CH2— | 4-pyridyl-CH2— | 6 |

TABLE 103

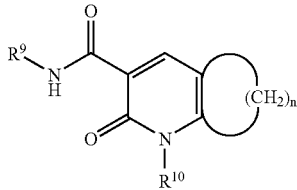

| Compound No. | R9 | R10 | n |
|---|---|---|---|
| 9-561 | (2-Me)C6H4CH2CH2— | 4-pyridyl-CH2— | 6 |
| 9-562 | (4-MeO)C6H4CH2CH2— | 4-pyridyl-CH2— | 6 |
| 9-563 | (3-MeO)C6H4CH2CH2— | 4-pyridyl-CH2— | 6 |
| 9-564 | (2-MeO)C6H4CH2CH2— | 4-pyridyl-CH2— | 6 |
| 9-565 | (4-Me2N)C6H4CH2CH2— | 4-pyridyl-CH2— | 6 |
| 9-566 | (3-Me2N)C6H4CH2CH2— | 4-pyridyl-CH2— | 6 |
| 9-567 | (2-Me2N)C6H4CH2CH2— | 4-pyridyl-CH2— | 6 |
| 9-568 | (4-MeOCO)C6H4CH2CH2— | 4-pyridyl-CH2— | 6 |
| 9-569 | (3-MeOCO)C6H4CH2CH2— | 4-pyridyl-CH2— | 6 |
| 9-570 | (2-MeOCO)C6H4CH2CH2— | 4-pyridyl-CH2— | 6 |
| 9-571 | (4-CN)C6H4CH2CH2— | 4-pyridyl-CH2— | 6 |
| 9-572 | (3-CN)C6H4CH2CH2— | 4-pyridyl-CH2— | 6 |
| 9-573 | (2CN)C6H4CH2CH2— | 4-pyridyl-CH2— | 6 |
| 9-574 | (4NO2)C6H4CH2CH2— | 4-pyridyl-CH2— | 6 |
| 9-575 | (3NO2)C6H4CH2CH2— | 4-pyridyl-CH2— | 6 |
| 9-576 | (2NO2)C6H4CH2CH2— | 4-pyridyl-CH2— | 6 |
| 9-577 | (4-Cl)C6H4CH(Me)— | n-Bu | 3 |
| 9-578 | (3-Cl)C6H4CH(Me)— | n-Bu | 3 |
| 9-579 | (2-Cl)C6H4CH(Me)— | n-Bu | 3 |
| 9-580 | (4-F)C6H4CH(Me)— | n-Bu | 3 |
| 9-581 | (3-F)C6H4CH(Me)— | n-Bu | 3 |
| 9-582 | (2-F)C6H4CH(Me)— | n-Bu | 3 |
| 9-583 | (4-Me)C6H4CH(Me)— | n-Bu | 3 |
| 9-584 | (3-Me)C6H4CH(Me)— | n-Bu | 3 |
| 9-585 | (2-Me)C6H4CH(Me)— | n-Bu | 3 |
| 9-586 | (4-MeO)C6H4CH(Me)— | n-Bu | 3 |
| 9-587 | (3-MeO)C6H4CH(Me)— | n-Bu | 3 |
| 9-588 | (2-MeO)C6H4CH(Me)— | n-Bu | 3 |
| 9-589 | (4-Me2N)C6H4CH(Me)— | n-Bu | 3 |
| 9-590 | (3-Me2N)C6H4CH(Me)— | n-Bu | 3 |
| 9-591 | (2-Me2N)C6H4CH(Me)— | n-Bu | 3 |
| 9-592 | (4-MeOCO)C6H4CH(Me)— | n-Bu | 3 |
| 9-593 | (3-MeOCO)C6H4CH(Me)— | n-Bu | 3 |
| 9-594 | (2-MeOCO)C6H4CH(Me)— | n-Bu | 3 |
| 9-595 | (4-CN)C6H4CH(Me)— | n-Bu | 3 |
| 9-596 | (3-CN)C6H4CH(Me)— | n-Bu | 3 |
| 9-597 | (2CN)C6H4CH(Me)— | n-Bu | 3 |
| 9-598 | (4NO2)C6H4CH(Me)— | n-Bu | 3 |
| 9-599 | (3NO2)C6H4CH(Me)— | n-Bu | 3 |
| 9-600 | (2NO2)C6H4CH(Me)— | n-Bu | 3 |

TABLE 104

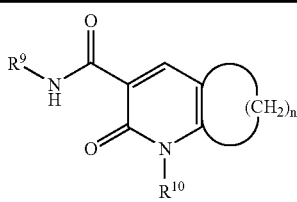

| Compound No. | R9 | R10 | n |
|---|---|---|---|
| 9-601 | (4-Cl)C6H4CH(Me)— | n-Bu | 4 |
| 9-602 | (3-Cl)C6H4CH(Me)— | n-Bu | 4 |
| 9-603 | (2-Cl)C6H4CH(Me)— | n-Bu | 4 |
| 9-604 | (4-F)C6H4CH(Me)— | n-Bu | 4 |
| 9-605 | (3-F)C6H4CH(Me)— | n-Bu | 4 |
| 9-606 | (2-F)C6H4CH(Me)— | n-Bu | 4 |
| 9-607 | (4-Me)C6H4CH(Me)— | n-Bu | 4 |

TABLE 104-continued

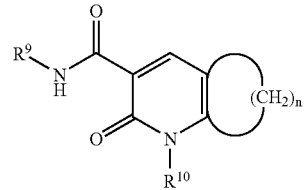

| Compound No. | R9 | R10 | n |
|---|---|---|---|
| 9-608 | (3-Me)C6H4CH(Me)— | n-Bu | 4 |
| 9-609 | (2-Me)C6H4CH(Me)— | n-Bu | 4 |
| 9-610 | (4-MeO)C6H4CH(Me)— | n-Bu | 4 |
| 9-611 | (3-MeO)C6H4CH(Me)— | n-Bu | 4 |
| 9-612 | (2-MeO)C6H4CH(Me)— | n-Bu | 4 |
| 9-613 | (4-Me2N)C6H4CH(Me)— | n-Bu | 4 |
| 9-614 | (3-Me2N)C6H4CH(Me)— | n-Bu | 4 |
| 9-615 | (2-Me2N)C6H4CH(Me)— | n-Bu | 4 |
| 9-616 | (4-MeOCO)C6H4CH(Me)— | n-Bu | 4 |
| 9-617 | (3-MeOCO)C6H4CH(Me)— | n-Bu | 4 |
| 9-618 | (2-MeOCO)C6H4CH(Me)— | n-Bu | 4 |
| 9-619 | (4-CN)C6H4CH(Me)— | n-Bu | 4 |
| 9-620 | (3-CN)C6H4CH(Me)— | n-Bu | 4 |
| 9-621 | (2CN)C6H4CH(Me)— | n-Bu | 4 |
| 9-622 | (4NO2)C6H4CH(Me)— | n-Bu | 4 |
| 9-623 | (3NO2)C6H4CH(Me)— | n-Bu | 4 |
| 9-624 | (2NO2)C6H4CH(Me)— | n-Bu | 4 |
| 9-625 | (4-Cl)C6H4CH(Me)— | n-Bu | 5 |
| 9-626 | (3-Cl)C6H4CH(Me)— | n-Bu | 5 |
| 9-627 | (2-Cl)C6H4CH(Me)— | n-Bu | 5 |
| 9-628 | (4-F)C6H4CH(Me)— | n-Bu | 5 |
| 9-629 | (3-F)C6H4CH(Me)— | n-Bu | 5 |
| 9-630 | (2-F)C6H4CH(Me)— | n-Bu | 5 |
| 9-631 | (4-Me)C6H4CH(Me)— | n-Bu | 5 |
| 9-632 | (3-Me)C6H4CH(Me)— | n-Bu | 5 |
| 9-633 | (2-Me)C6H4CH(Me)— | n.Bu | 5 |
| 9-634 | (4-MeO)C6H4CH(Me)— | n-Bu | 5 |
| 9-635 | (3-MeO)C6H4CH(Me)— | n-Bu | 5 |
| 9-636 | (2-MeO)C6H4CH(Me)— | n-Bu | 5 |
| 9-637 | (4-Me2N)C6H4CH(Me)— | n-Bu | 5 |
| 9-638 | (3-Me2N)C6H4CH(Me)— | n-Bu | 5 |
| 9-639 | (2-Me2N)C6H4CH(Me)— | n-Bu | 5 |
| 9-640 | (4-MeOCO)C6H4CH(Me)— | n-Bu | 5 |

TABLE 105

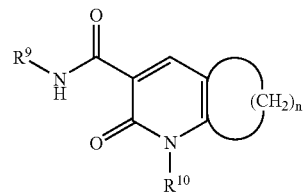

| Compound No. | R9 | R10 | n |
|---|---|---|---|
| 9-641 | (3-MeOCO)C6H4CH(Me)— | n-Bu | 5 |
| 9-642 | (2-MeOCO)C6H4CH(Me)— | n-Bu | 5 |
| 9-643 | (4-CN)C6H4CH(Me)— | n-Bu | 5 |
| 9-644 | (3-CN)C6H4CH(Me)— | n-Bu | 5 |
| 9-645 | (2CN)C6H4CH(Me)— | n-Bu | 5 |
| 9-646 | (4NO2)C6H4CH(Me)— | n-Bu | 5 |
| 9-647 | (3NO2)C6H4CH(Me)— | n-Bu | 5 |
| 9-648 | (2NO2)C6H4CH(Me)— | n-Bu | 5 |
| 9-649 | (4-Cl)C6H4CH(Me)— | n-Bu | 6 |
| 9-650 | (3-Cl)C6H4CH(Me)— | n-Bu | 6 |
| 9-651 | (2-Cl)C6H4CH(Me)— | n-Bu | 6 |
| 9-652 | (4-F)C6H4CH(Me)— | n-Bu | 6 |
| 9-653 | (3-F)C6H4CH(Me)— | n-Bu | 6 |
| 9-654 | (2-F)C6H4CH(Me)— | n-Bu | 6 |

TABLE 105-continued

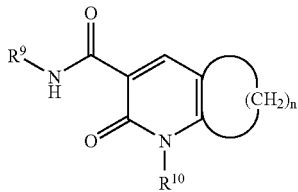

| Compound No. | R9 | R10 | n |
|---|---|---|---|
| 9-655 | (4-Me)C6H4CH(Me)— | n-Bu | 6 |
| 9-656 | (3-Me)C6H4CH(Me)— | n-Bu | 6 |
| 9-657 | (2-Me)C6H4CH(Me)— | n-Bu | 6 |
| 9-658 | (4-MeO)C6H4CH(Me)— | n-Bu | 6 |
| 9-659 | (3-MeO)C6H4CH(Me)— | n-Bu | 6 |
| 9-660 | (2-MeO)C6H4CH(Me)— | n-Bu | 6 |
| 9-661 | (4-Me2N)C6H4CH(Me)— | n-Bu | 6 |
| 9-662 | (3-Me2N)C6H4CH(Me)— | n-Bu | 6 |
| 9-663 | (2-Me2N)C6H4CH(Me)— | n-Bu | 6 |
| 9-664 | (4-MeOCO)C6H4CH(Me)— | n-Bu | 6 |
| 9-665 | (3-MeOCO)C6H4CH(Me)— | n-Bu | 6 |
| 9-666 | (2-MeOCO)C6H4CH(Me)— | n-Bu | 6 |
| 9-667 | (4-CN)C6H4CH(Me)— | n-Bu | 6 |
| 9-668 | (3-CN)C6H4CH(Me)— | n-Bu | 6 |
| 9-669 | (2CN)C6H4CH(Me)— | n-Bu | 6 |
| 9-670 | (4NO2)C6H4CH(Me)— | n-Bu | 6 |
| 9-671 | (3NO2)C6H4CH(Me)— | n-Bu | 6 |
| 9-672 | (2NO2)C6H4CH(Me)— | n-Bu | 6 |
| 9-673 | (4-Cl)C6H4CH(Me)— | Bnzyl | 3 |
| 9-674 | (3-Cl)C6H4CH(Me)— | Bnzyl | 3 |
| 9-675 | (2-Cl)C6H4CH(Me)— | Bnzyl | 3 |
| 9-676 | (4-F)C6H4CH(Me)— | Bnzyl | 3 |
| 9-677 | (3-F)C6H4CH(Me)— | Bnzyl | 3 |
| 9-678 | (2-F)C6H4CH(Me)— | Bnzyl | 3 |
| 9-679 | (4-Me)C6H4CH(Me)— | Bnzyl | 3 |
| 9-680 | (3-Me)C6H4CH(Me)— | Bnzyl | 3 |

TABLE 106

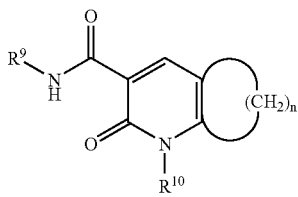

| Compound No. | R9 | R10 | n |
|---|---|---|---|
| 9-681 | (2-Me)C6H4CH(Me)— | Bnzyl | 3 |
| 9-682 | (4-MeO)C6H4CH(Me)— | Bnzyl | 3 |
| 9-683 | (3-MeO)C6H4CH(Me)— | Bnzyl | 3 |
| 9-684 | (2-MeO)C6H4CH(Me)— | Bnzyl | 3 |
| 9-685 | (4-Me2N)C6H4CH(Me)— | Bnzyl | 3 |
| 9-686 | (3-Me2N)C6H4CH(Me)— | Bnzyl | 3 |
| 9-687 | (2-Me2N)C6H4CH(Me)— | Bnzyl | 3 |
| 9-688 | (4-MeOCO)C6H4CH(Me)— | Bnzyl | 3 |
| 9-689 | (3-MeOCO)C6H4CH(Me)— | Bnzyl | 3 |
| 9-690 | (2-MeOCO)C6H4CH(Me)— | Bnzyl | 3 |
| 9-691 | (4-CN)C6H4CH(Me)— | Bnzyl | 3 |
| 9-692 | (3-CN)C6H4CH(Me)— | Bnzyl | 3 |
| 9-693 | (2CN)C6H4CH(Me)— | Bnzyl | 3 |
| 9-694 | (4NO2)C6H4CH(Me)— | Bnzyl | 3 |
| 9-695 | (3NO2)C6H4CH(Me)— | Bnzyl | 3 |
| 9-696 | (2NO2)C6H4CH(Me)— | Bnzyl | 3 |
| 9-697 | (4-Cl)C6H4CH(Me)— | Bnzyl | 4 |
| 9-698 | (3-Cl)C6H4CH(Me)— | Bnzyl | 4 |
| 9-699 | (2-Cl)C6H4CH(Me)— | Bnzyl | 4 |
| 9-700 | (4-F)C6H4CH(Me)— | Bnzyl | 4 |
| 9-701 | (3-F)C6H4CH(Me)— | Bnzyl | 4 |

TABLE 106-continued

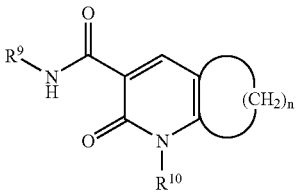

| Compound No. | R9 | R10 | n |
|---|---|---|---|
| 9-702 | (2-F)C6H4CH(Me)— | Bnzyl | 4 |
| 9-703 | (4-Me)C6H4CH(Me)— | Bnzyl | 4 |
| 9-704 | (3-Me)C6H4CH(Me)— | Bnzyl | 4 |
| 9-705 | (2-Me)C6H4CH(Me)— | Bnzyl | 4 |
| 9-706 | (4-MeO)C6H4CH(Me)— | Bnzyl | 4 |
| 9-707 | (3-MeO)C6H4CH(Me)— | Bnzyl | 4 |
| 9-708 | (2-MeO)C6H4CH(Me)— | Bnzyl | 4 |
| 9-709 | (4-Me2N)C6H4CH(Me)— | Bnzyl | 4 |
| 9-710 | (3-Me2N)C6H4CH(Me)— | Bnzyl | 4 |
| 9-711 | (2-Me2N)C6H4CH(Me)— | Bnzyl | 4 |
| 9-712 | (4-MeOCO)C6H4CH(Me)— | Bnzyl | 4 |
| 9-713 | (3-MeOCO)C6H4CH(Me)— | Bnzyl | 4 |
| 9-714 | (2-MeOCO)C6H4CH(Me)— | Bnzyl | 4 |
| 9-715 | (4-CN)C6H4CH(Me)— | Bnzyl | 4 |
| 9-716 | (3-CN)C6H4CH(Me)— | Bnzyl | 4 |
| 9-717 | (2CN)C6H4CH(Me)— | Bnzyl | 4 |
| 9-718 | (4NO2)C6H4CH(Me)— | Bnzyl | 4 |
| 9-719 | (3NO2)C6H4CH(Me)— | Bnzyl | 4 |
| 9-720 | (2NO2)C6H4CH(Me)— | Bnzyl | 4 |

TABLE 101

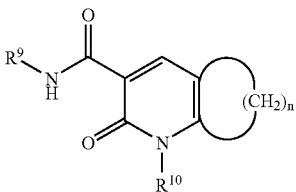

| Compound No. | R9 | R10 | n |
|---|---|---|---|
| 9-721 | (4-Cl)C6H4CH(Me)— | Bnzyl | 5 |
| 9-722 | (3-Cl)C6H4CH(Me)— | Bnzyl | 5 |
| 9-723 | (2-Cl)C6H4CH(Me)— | Bnzyl | 5 |
| 9-724 | (4-F)C6H4CH(Me)— | Bnzyl | 5 |
| 9-725 | (3-F)C6H4CH(Me)— | Bnzyl | 5 |
| 9-726 | (2-F)C6H4CH(Me)— | Bnzyl | 5 |
| 9-727 | (4-Me)C6H4CH(Me)— | Bnzyl | 5 |
| 9-728 | (3-Me)C6H4CH(Me)— | Bnzyl | 5 |
| 9-729 | (2-Me)C6H4CH(Me)— | Bnzyl | 5 |
| 9-730 | (4-MeO)C6H4CH(Me)— | Bnzyl | 5 |
| 9-731 | (3-MeO)C6H4CH(Me)— | Bnzyl | 5 |
| 9-732 | (2-MeO)C6H4CH(Me)— | Bnzyl | 5 |
| 9-733 | (4-Me2N)C6H4CH(Me)— | Bnzyl | 5 |
| 9-734 | (3-Me2N)C6H4CH(Me)— | Bnzyl | 5 |
| 9-735 | (2-Me2N)C6H4CH(Me)— | Bnzyl | 5 |
| 9-736 | (4-MeOCO)C6H4CH(Me)— | Bnzyl | 5 |
| 9-737 | (3-MeOCO)C6H4CH(Me)— | Bnzyl | 5 |
| 9-738 | (2-MeOCO)C6H4CH(Me)— | Bnzyl | 5 |
| 9-739 | (4-CN)C6H4CH(Me)— | Bnzyl | 5 |
| 9-740 | (3-CN)C6H4CH(Me)— | Bnzyl | 5 |
| 9-741 | (2CN)C6H4CH(Me)— | Bnzyl | 5 |
| 9-742 | (4NO2)C6H4CH(Me)— | Bnzyl | 5 |
| 9-743 | (3NO2)C6H4CH(Me)— | Bnzyl | 5 |
| 9-744 | (2NO2)C6H4CH(Me)— | Bnzyl | 5 |
| 9-745 | (4-Cl)C6H4CH(Me)— | Bnzyl | 6 |
| 9-746 | (3-Cl)C6H4CH(Me)— | Bnzyl | 6 |
| 9-747 | (2-Cl)C6H4CH(Me)— | Bnzyl | 6 |
| 9-748 | (4-F)C6H4CH(Me)— | Bnzyl | 6 |

TABLE 101-continued

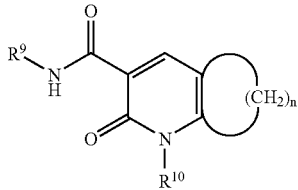

| Compound No. | R9 | R10 | n |
|---|---|---|---|
| 9-749 | (3-F)C6H4CH(Me)— | Bnzyl | 6 |
| 9-750 | (2-F)C6H4CH(Me)— | Bnzyl | 6 |
| 9-751 | (4-Me)C6H4CH(Me)— | Bnzyl | 6 |
| 9-752 | (3-Me)C6H4CH(Me)— | Bnzyl | 6 |
| 9-753 | (2-Me)C6H4CH(Me)— | Bnzyl | 6 |
| 9-754 | (4-MeO)C6H4CH(Me)— | Bnzyl | 6 |
| 9-755 | (3-MeO)C6H4CH(Me)— | Bnzyl | 6 |
| 9-756 | (2-MeO)C6H4CH(Me)— | Bnzyl | 6 |
| 9-757 | (4-Me2N)C6H4CH(Me)— | Bnzyl | 6 |
| 9-758 | (3-Me2N)C6H4CH(Me)— | Bnzyl | 6 |
| 9-759 | (2-Me2N)C6H4CH(Me)— | Bnzyl | 6 |
| 9-760 | (4-MeOCO)C6H4CH(Me)— | Bnzyl | 6 |

TABLE 108

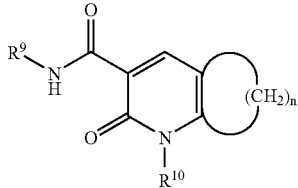

| Compound No. | R9 | R10 | n |
|---|---|---|---|
| 9-761 | (3-MeOCO)C6H4CH(Me)— | Bnzyl | 6 |
| 9-762 | (2-MeOCO)C6H4CH(Me)— | Bnzyl | 6 |
| 9-763 | (4-CN)C6H4CH(Me)— | Bnzyl | 6 |
| 9-764 | (3-CN)C6H4CH(Me)— | Bnzyl | 6 |
| 9-765 | (2CN)C6H4CH(Me)— | Bnzyl | 6 |
| 9-766 | (4NO2)C6H4CH(Me)— | Bnzyl | 6 |
| 9-767 | (3NO2)C6H4CH(Me)— | Bnzyl | 6 |
| 9-768 | (2NO2)C6H4CH(Me)— | Bnzyl | 6 |
| 9-769 | (4-Cl)C6H4CH(Me)— | 4-pyridyl-CH2— | 3 |
| 9-770 | (3-Cl)C6H4CH(Me)— | 4-pyridyl-CH2— | 3 |
| 9-771 | (2-Cl)C6H4CH(Me)— | 4-pyridyl-CH2— | 3 |
| 9-772 | (4-F)C6H4CH(Me)— | 4-pyridyl-CH2— | 3 |
| 9-773 | (3-F)C6H4CH(Me)— | 4-pyridyl-CH2— | 3 |
| 9-774 | (2-F)C6H4CH(Me)— | 4-pyridyl-CH2— | 3 |
| 9-775 | (4-Me)C6H4CH(Me)— | 4-pyridyl-CH2— | 3 |
| 9-776 | (3-Me)C6H4CH(Me)— | 4-pyridyl-CH2— | 3 |
| 9-777 | (2-Me)C6H4CH(Me)— | 4-pyridyl-CH2— | 3 |
| 9-778 | (4-MeO)C6H4CH(Me)— | 4-pyridyl-CH2— | 3 |
| 9-779 | (3-MeO)C6H4CH(Me)— | 4-pyridyl-CH2— | 3 |
| 9-780 | (2-MeO)C6H4CH(Me)— | 4-pyridyl-CH2— | 3 |
| 9-781 | (4-Me2N)C6H4CH(Me)— | 4-pyridyl-CH2— | 3 |
| 9-782 | (3-Me2N)C6H4CH(Me)— | 4-pyridyl-CH2— | 3 |
| 9-783 | (2-Me2N)C6H4CH(Me)— | 4-pyridyl-CH2— | 3 |
| 9-784 | (4-MeOCO)C6H4CH(Me)— | 4-pyridyl-CH2— | 3 |
| 9-785 | (3-MeOCO)C6H4CH(Me)— | 4-pyridyl-CH2— | 3 |
| 9-786 | (2-MeOCO)C6H4CH(Me)— | 4-pyridyl-CH2— | 3 |
| 9-787 | (4-CN)C6H4CH(Me)— | 4-pyridyl-CH2— | 3 |
| 9-788 | (3-CN)C6H4CH(Me)— | 4-pyridyl-CH2— | 3 |
| 9-789 | (2CN)C6H4CH(Me)— | 4-pyridyl-CH2— | 3 |
| 9-790 | (4NO2)C6H4CH(Me)— | 4-pyridyl-CH2— | 3 |
| 9-791 | (3NO2)C6H4CH(Me)— | 4-pyridyl-CH2— | 3 |
| 9-792 | (2NO2)C6H4CH(Me)— | 4-pyridyl-CH2— | 3 |
| 9-793 | (4-Cl)C6H4CH(Me)— | 4-pyridyl-CH2— | 4 |
| 9-794 | (3-Cl)C6H4CH(Me)— | 4-pyridyl-CH2— | 4 |
| 9-795 | (2-Cl)C6H4CH(Me)— | 4-pyridyl-CH2— | 4 |

TABLE 108-continued

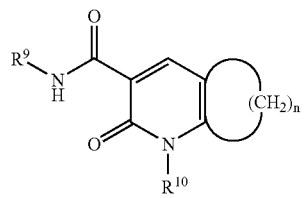

| Compound No. | R9 | R10 | n |
|---|---|---|---|
| 9-796 | (4-F)C6H4CH(Me)— | 4-pyridyl-CH2— | 4 |
| 9-797 | (3-F)C6H4CH(Me)— | 4-pyridyl-CH2— | 4 |
| 9-798 | (2-F)C6H4CH(Me)— | 4-pyridyl-CH2— | 4 |
| 9-799 | (4-Me)C6H4CH(Me)— | 4-pyridyl-CH2— | 4 |
| 9-800 | (3-Me)C6H4CH(Me)— | 4-pyridyl-CH2— | 4 |

TABLE 109

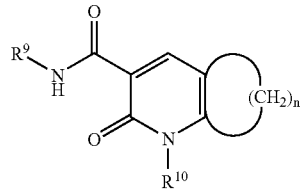

| Compound No. | R9 | R10 | n |
|---|---|---|---|
| 9-801 | (2-Me)C6H4CH(Me)— | 4-pyridyl-CH2— | 4 |
| 9-802 | (4-MeO)C6H4CH(Me)— | 4-pyridyl-CH2— | 4 |
| 9-803 | (3-MeO)C6H4CH(Me)— | 4-pyridyl-CH2— | 4 |
| 9-804 | (2-MeO)C6H4CH(Me)— | 4-pyridyl-CH2— | 4 |
| 9-805 | (4-Me2N)C6H4CH(Me)— | 4-pyridyl-CH2— | 4 |
| 9-806 | (3-Me2N)C6H4CH(Me)— | 4-pyridyl-CH2— | 4 |
| 9-807 | (2-Me2N)C6H4CH(Me)— | 4-pyridyl-CH2— | 4 |
| 9-808 | (4-MeOCO)C6H4CH(Me)— | 4-pyridyl-CH2— | 4 |
| 9-809 | (3-MeOCO)C6H4CH(Me)— | 4-pyridyl-CH2— | 4 |
| 9-810 | (2-MeOCO)C6H4CH(Me)— | 4-pyridyl-CH2— | 4 |
| 9-811 | (4-CN)C6H4CH(Me)— | 4-pyridyl-CH2— | 4 |
| 9-812 | (3-CN)C6H4CH(Me)— | 4-pyridyl-CH2— | 4 |
| 9-813 | (2CN)C6H4CH(Me)— | 4-pyridyl-CH2— | 4 |
| 9-814 | (4NO2)C6H4CH(Me)— | 4-pyridyl-CH2— | 4 |
| 9-815 | (3NO2)C6H4CH(Me)— | 4-pyridyl-CH2— | 4 |
| 9-816 | (2NO2)C6H4CH(Me)— | 4-pyridyl-CH2— | 4 |
| 9-817 | (4-Cl)C6H4CH(Me)— | 4-pyridyl-CH2— | 5 |
| 9-818 | (3-Cl)C6H4CH(Me)— | 4-pyridyl-CH2— | 5 |
| 9-819 | (2-Cl)C6H4CH(Me)— | 4-pyridyl-CH2— | 5 |
| 9-820 | (4-F)C6H4CH(Me)— | 4-pyridyl-CH2— | 5 |
| 9-821 | (3-F)C6H4CH(Me)— | 4-pyridyl-CH2— | 5 |
| 9-822 | (2-F)C6H4CH(Me)— | 4-pyridyl-CH2— | 5 |
| 9-823 | (4-Me)C6H4CH(Me)— | 4-pyridyl-CH2— | 5 |
| 9-824 | (3-Me)C6H4CH(Me)— | 4-pyridyl-CH2— | 5 |
| 9-825 | (2-Me)C6H4CH(Me)— | 4-pyridyl-CH2— | 5 |
| 9-826 | (4-MeO)C6H4CH(Me)— | 4-pyridyl-CH2— | 5 |
| 9-827 | (3-MeO)C6H4CH(Me)— | 4-pyridyl-CH2— | 5 |
| 9-828 | (2-MeO)C6H4CH(Me)— | 4-pyridyl-CH2— | 5 |
| 9-829 | (4-Me2N)C6H4CH(Me)— | 4-pyridyl-CH2— | 5 |
| 9-830 | (3-Me2N)C6H4CH(Me)— | 4-pyridyl-CH2— | 5 |
| 9-831 | (2-Me2N)C6H4CH(Me)— | 4-pyridyl-CH2— | 5 |
| 9-832 | (4-MeOCO)C6H4CH(Me)— | 4-pyridyl-CH2— | 5 |
| 9-833 | (3-MeOCO)C6H4CH(Me)— | 4-pyridyl-CH2— | 5 |
| 9-834 | (2-MeOCO)C6H4CH(Me)— | 4-pyridyl-CH2— | 5 |
| 9-835 | (4-CN)C6H4CH(Me)— | 4-pyridyl-CH2— | 5 |
| 9-836 | (3-CN)C6H4CH(Me)— | 4-pyridyl-CH2— | 5 |
| 9-837 | (2CN)C6H4CH(Me)— | 4-pyridyl-CH2— | 5 |
| 9-838 | (4NO2)C6H4CH(Me)— | 4-pyridyl-CH2— | 5 |
| 9-839 | (3NO2)C6H4CH(Me)— | 4-pyridyl-CH2— | 5 |
| 9-840 | (2NO2)C6H4CH(Me)— | 4-pyridyl-CH2— | 5 |

TABLE 110

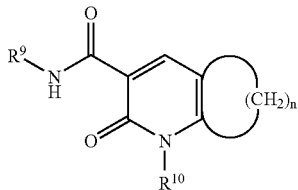

| Compound No. | R9 | R10 | n |
|---|---|---|---|
| 9-841 | (4-Cl)C6H4CH(Me)— | 4-pyridyl-CH2— | 6 |
| 9-842 | (3-Cl)C6H4CH(Me)— | 4-pyridyl-CH2— | 6 |
| 9-843 | (2-Cl)C6H4CH(Me)— | 4-pyridyl-CH2— | 6 |
| 9-844 | (4-F)C6H4CH(Me)— | 4-pyridyl-CH2— | 6 |
| 9-845 | (3-F)C6H4CH(Me)— | 4-pyridyl-CH2— | 6 |
| 9-846 | (2-F)C6H4CH(Me)— | 4-pyridyl-CH2— | 6 |
| 9-847 | (4-Me)C6H4CH(Me)— | 4-pyridyl-CH2— | 6 |
| 9-848 | (3-Me)C6H4CH(Me)— | 4-pyridyl-CH2— | 6 |
| 9-849 | (2-Me)C6H4CH(Me)— | 4-pyridyl-CH2— | 6 |
| 9-850 | (4-MeO)C6H4CH(Me)— | 4-pyridyl-CH2— | 6 |
| 9-851 | (3-MeO)C6H4CH(Me)— | 4-pyridyl-CH2— | 6 |
| 9-852 | (2-MeO)C6H4CH(Me)— | 4-pyridyl-CH2— | 6 |
| 9-853 | (4-Me2N)C6H4CH(Me)— | 4-pyridyl-CH2— | 6 |
| 9-854 | (3-Me2N)C6H4CH(Me)— | 4-pyridyl-CH2— | 6 |
| 9-855 | (2-Me2N)C6H4CH(Me)— | 4-pyridyl-CH2— | 6 |
| 9-856 | (4-MeOCO)C6H4CH(Me)— | 4-pyridyl-CH2— | 6 |
| 9-857 | (3-MeOCO)C6H4CH(Me)— | 4-pyridyl-CH2— | 6 |
| 9-858 | (2-MeOCO)C6H4CH(Me)— | 4-pyridyl-CH2— | 6 |
| 9-859 | (4-CN)C6H4CH(Me)— | 4-pyridyl-CH2— | 6 |
| 9-860 | (3-CN)C6H4CH(Me)— | 4-pyridyl-CH2— | 6 |
| 9-861 | (2CN)C6H4CH(Me)— | 4-pyridyl-CH2— | 6 |
| 9-862 | (4NO2)C6H4CH(Me)— | 4-pyridyl-CH2— | 6 |
| 9-863 | (3NO2)C6H4CH(Me)— | 4-pyridyl-CH2— | 6 |
| 9-864 | (2NO2)C6H4CH(Me)— | 4-pyridyl-CH2— | 6 |
| 9-865 | (4-Cl)C6H4C(Me2)— | n-Bu | 3 |
| 9-866 | (3-Cl)C6H4C(Me2)— | n-Bu | 3 |
| 9-867 | (2-Cl)C6H4C(Me2)— | n-Bu | 3 |
| 9-868 | (4-F)C6H4C(Me2)— | n-Bu | 3 |
| 9-869 | (3-F)C6H4C(Me2)— | n-Bu | 3 |
| 9-870 | (2-F)C6H4C(Me2)— | n-Bu | 3 |
| 9-871 | (4-Me)C6H4C(Me2)— | n-Bu | 3 |
| 9-872 | (3-Me)C6H4C(Me2)— | n-Bu | 3 |
| 9-873 | (2-Me)C6H4C(Me2)— | n-Bu | 3 |
| 9-874 | (4-MeO)C6H4C(Me2)— | n-Bu | 3 |
| 9-875 | (3-MeO)C6H4C(Me2)— | n-Bu | 3 |
| 9-876 | (2-MeO)C6H4C(Me2)— | n-Bu | 3 |
| 9-877 | (4-Me2N)C6H4C(Me2)— | n-Bu | 3 |
| 9-878 | (3-Me2N)C6H4C(Me2)— | n-Bu | 3 |
| 9-879 | (2-Me2N)C6H4C(Me2)— | n-Bu | 3 |
| 9-880 | (4-MeOCO)C6H4C(Me2)— | n-Bu | 3 |

TABLE 111

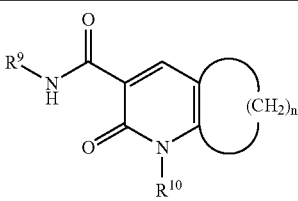

| Compound No. | R9 | R10 | n |
|---|---|---|---|
| 9-881 | (3-MeOCO)C6H4C(Me2)— | n-Bu | 3 |
| 9-882 | (2-MeOCO)C6H4C(Me2)— | n-Bu | 3 |
| 9-883 | (4-CN)C6H4C(Me2)— | n-Bu | 3 |
| 9-884 | (3-CN)C6H4C(Me2)— | n-Bu | 3 |
| 9-885 | (2CN)C6H4C(Me2)— | n-Bu | 3 |
| 9-886 | (4NO2)C6H4C(Me2)— | n-Bu | 3 |
| 9-887 | (3NO2)C6H4C(Me2)— | n-Bu | 3 |

TABLE 111-continued

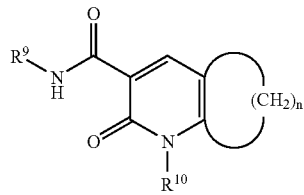

| Compound No. | R9 | R10 | n |
|---|---|---|---|
| 9-888 | (2NO2)C6H4C(Me2)— | n-Bu | 3 |
| 9-889 | (4-Cl)C6H4C(Me2)— | n-Bu | 4 |
| 9-890 | (3-Cl)C6H4C(Me2)— | n-Bu | 4 |
| 9-891 | (2-Cl)C6H4C(Me2)— | n-Bu | 4 |
| 9-892 | (4-F)C6H4C(Me2)— | n-Bu | 4 |
| 9-893 | (3-F)C6H4C(Me2)— | n-Bu | 4 |
| 9-894 | (2-F)C6H4C(Me2)— | n-Bu | 4 |
| 9-895 | (4-Me)C6H4C(Me2)— | n-Bu | 4 |
| 9-896 | (3-Me)C6H4C(Me2)— | n-Bu | 4 |
| 9-897 | (2-Me)C6H4C(Me2)— | n-Bu | 4 |
| 9-898 | (4-MeO)C6H4C(Me2)— | n-Bu | 4 |
| 9-899 | (3-MeO)C6H4C(Me2)— | n-Bu | 4 |
| 9-900 | (2-MeO)C6H4C(Me2)— | n-Bu | 4 |
| 9-901 | (4-Me2N)C6H4C(Me2)— | n-Bu | 4 |
| 9-902 | (3-Me2N)C6H4C(Me2)— | n-Bu | 4 |
| 9-903 | (2-Me2N)C6H4C(Me2)— | n-Bu | 4 |
| 9-904 | (4-MeOCO)C6H4C(Me2)— | n-Bu | 4 |
| 9-905 | (3-MeOCO)C6H4C(Me2)— | n-Bu | 4 |
| 9-906 | (2-MeOCO)C6H4C(Me2)— | n-Bu | 4 |
| 9-907 | (4-CN)C6H4C(Me2)— | n-Bu | 4 |
| 9-908 | (3-CN)C6H4C(Me2)— | n-Bu | 4 |
| 9-909 | (2CN)C6H4C(Me2)— | n-Bu | 4 |
| 9-910 | (4NO2)C6H4C(Me2)— | n-Bu | 4 |
| 9-911 | (3NO2)C6H4C(Me2)— | n-Bu | 4 |
| 9-912 | (2NO2)C6H4C(Me2)— | n-Bu | 4 |
| 9-913 | (4-Cl)C6H4C(Me2)— | n-Bu | 5 |
| 9-914 | (3-Cl)C6H4C(Me2)— | n-Bu | 5 |
| 9-915 | (2-Cl)C6H4C(Me2)— | n-Bu | 5 |
| 9-916 | (4-F)C6H4C(Me2)— | n-Bu | 5 |
| 9-917 | (3-F)C6H4C(Me2)— | n-Bu | 5 |
| 9-918 | (2-F)C6H4C(Me2)— | n-Bu | 5 |
| 9-919 | (4-Me)C6H4C(Me2)— | n-Bu | 5 |
| 9-920 | (3-Me)C6H4C(Me2)— | n-Bu | 5 |

TABLE 112

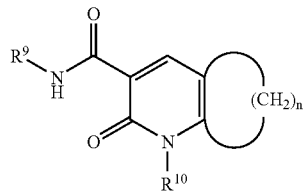

| Compound No. | R9 | R10 | n |
|---|---|---|---|
| 9-921 | (2-Me)C6H4C(Me2)— | n-Bu | 5 |
| 9-922 | (4-MeO)C6H4C(Me2)— | n-Bu | 5 |
| 9-923 | (3-MeO)C6H4C(Me2)— | n-Bu | 5 |
| 9-924 | (2-MeO)C6H4C(Me2)— | n-Bu | 5 |
| 9-925 | (4-Me2N)C6H4C(Me2)— | n-Bu | 5 |
| 9-926 | (3-Me2N)C6H4C(Me2)— | n-Bu | 5 |
| 9-927 | (2-Me2N)C6H4C(Me2)— | n-Bu | 5 |
| 9-928 | (4-MeOCO)C6H4C(Me2)— | n-Bu | 5 |
| 9-929 | (3-MeOCO)C6H4C(Me2)— | n-Bu | 5 |
| 9-930 | (2-MeOCO)C6H4C(Me2)— | n-Bu | 5 |
| 9-931 | (4-CN)C6H4C(Me2)— | n-Bu | 5 |
| 9-932 | (3-CN)C6H4C(Me2)— | n-Bu | 5 |
| 9-933 | (2CN)C6H4C(Me2)— | n-Bu | 5 |
| 9-934 | (4NO2)C6H4C(Me2)— | n-Bu | 5 |

TABLE 112-continued

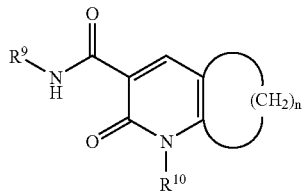

| Compound No. | R9 | R10 | n |
|---|---|---|---|
| 9-935 | (3NO2)C6H4C(Me2)— | n-Bu | 5 |
| 9-936 | (2NO2)C6H4C(Me2)— | n-Bu | 5 |
| 9-937 | (4-Cl)C6H4C(Me2)— | n-Bu | 6 |
| 9-938 | (3-Cl)C6H4C(Me2)— | n-Bu | 6 |
| 9-939 | (2-Cl)C6H4C(Me2)— | n-Bu | 6 |
| 9-940 | (4-F)C6H4C(Me2)— | n-Bu | 6 |
| 9-941 | (3-F)C6H4C(Me2)— | n-Bu | 6 |
| 9-942 | (2-F)C6H4C(Me2)— | n-Bu | 6 |
| 9-943 | (4-Me)C6H4C(Me2)— | n-Bu | 6 |
| 9-944 | (3-Me)C6H4C(Me2)— | n-Bu | 6 |
| 9-945 | (2-Me)C6H4C(Me2)— | n-Bu | 6 |
| 9-946 | (4-MeO)C6H4C(Me2)— | n-Bu | 6 |
| 9-947 | (3-MeO)C6H4C(Me2)— | n-Bu | 6 |
| 9-948 | (2-MeO)C6H4C(Me2)— | n-Bu | 6 |
| 9-949 | (4-Me2N)C6H4C(Me2)— | n-Bu | 6 |
| 9-950 | (3-Me2N)C6H4C(Me2)— | n-Bu | 6 |
| 9-951 | (2-Me2N)C6H4C(Me2)— | n-Bu | 6 |
| 9-952 | (4-MeOCO)C6H4C(Me2)— | n-Bu | 6 |
| 9-953 | (3-MeOCO)C6H4C(Me2)— | n-Bu | 6 |
| 9-954 | (2-MeOCO)C6H4C(Me2)— | n-Bu | 6 |
| 9-955 | (4-CN)C6H4C(Me2)— | n-Bu | 6 |
| 9-956 | (3-CN)C6H4C(Me2)— | n-Bu | 6 |
| 9-957 | (2CN)C6H4C(Me2)— | n-Bu | 6 |
| 9-958 | (4NO2)C6H4C(Me2)— | n-Bu | 6 |
| 9-959 | (3NO2)C6H4C(Me2)— | n-Bu | 6 |
| 9-960 | (2NO2)C6H4C(Me2)— | n-Bu | 6 |

TABLE 113

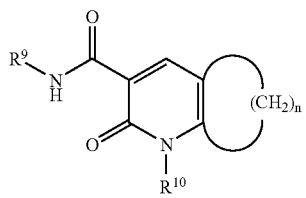

| Compound No. | R9 | R10 | n |
|---|---|---|---|
| 9-961 | (4-Cl)C6H4C(Me2)— | Bnzyl | 3 |
| 9-962 | (3-Cl)C6H4C(Me2)— | Bnzyl | 3 |
| 9-963 | (2-Cl)C6H4C(Me2)— | Bnzyl | 3 |
| 9-964 | (4-F)C6H4C(Me2)— | Bnzyl | 3 |
| 9-965 | (3-F)C6H4C(Me2)— | Bnzyl | 3 |
| 9-966 | (2-F)C6H4C(Me2)— | Bnzyl | 3 |
| 9-967 | (4-Me)C6H4C(Me2)— | Bnzyl | 3 |
| 9-968 | (3-Me)C6H4C(Me2)— | Bnzyl | 3 |
| 9-969 | (2-Me)C6H4C(Me2)— | Bnzyl | 3 |
| 9-970 | (4-MeO)C6H4C(Me2)— | Bnzyl | 3 |
| 9-971 | (3-MeO)C6H4C(Me2)— | Bnzyl | 3 |
| 9-972 | (2-MeO)C6H4C(Me2)— | Bnzyl | 3 |
| 9-973 | (4-Me2N)C6H4C(Me2)— | Bnzyl | 3 |
| 9-974 | (3-Me2N)C6H4C(Me2)— | Bnzyl | 3 |
| 9-975 | (2-Me2N)C6H4C(Me2)— | Bnzyl | 3 |
| 9-976 | (4-MeOCO)C6H4C(Me2)— | Bnzyl | 3 |
| 9-977 | (3-MeOCO)C6H4C(Me2)— | Bnzyl | 3 |
| 9-978 | (2-MeOCO)C6H4C(Me2)— | Bnzyl | 3 |
| 9-979 | (4-CN)C6H4C(Me2)— | Bnzyl | 3 |
| 9-980 | (3-CN)C6H4C(Me2)— | Bnzyl | 3 |
| 9-981 | (2CN)C6H4C(Me2)— | Bnzyl | 3 |

TABLE 113-continued

| Compound No. | R9 | R10 | n |
|---|---|---|---|
| 9-982 | (4NO2)C6H4C(Me2)— | Bnzyl | 3 |
| 9-983 | (3NO2)C6H4C(Me2)— | Bnzyl | 3 |
| 9-984 | (2NO2)C6H4C(Me2)— | Bnzyl | 3 |
| 9-985 | (4-Cl)C6H4C(Me2)— | Bnzyl | 4 |
| 9-986 | (3-Cl)C6H4C(Me2)— | Bnzyl | 4 |
| 9-987 | (2-Cl)C6H4C(Me2)— | Bnzyl | 4 |
| 9-988 | (4-F)C6H4C(Me2)— | Bnzyl | 4 |
| 9-989 | (3-F)C6H4C(Me2)— | Bnzyl | 4 |
| 9-990 | (2-F)C6H4C(Me2)— | Bnzyl | 4 |
| 9-991 | (4-Me)C6H4C(Me2)— | Bnzyl | 4 |
| 9-992 | (3-Me)C6H4C(Me2)— | Bnzyl | 4 |
| 9-993 | (2-Me)C6H4C(Me2)— | Bnzyl | 4 |
| 9-994 | (4-MeO)C6H4C(Me2)— | Bnzyl | 4 |
| 9-995 | (3-MeO)C6H4C(Me2)— | Bnzyl | 4 |
| 9-996 | (2-MeO)C6H4C(Me2)— | Bnzyl | 4 |
| 9-997 | (4-Me2N)C6H4C(Me2)— | Bnzyl | 4 |
| 9-998 | (3-Me2N)C6H4C(Me2)— | Bnzyl | 4 |
| 9-999 | (2-Me2N)C6H4C(Me2)— | Bnzyl | 4 |
| 9-1000 | (4-MeOCO)C6H4C(Me2)— | Bnzyl | 4 |

TABLE 114

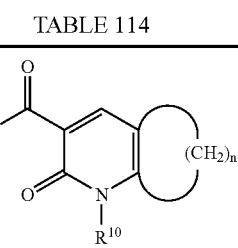

| Compound No. | R9 | R10 | n |
|---|---|---|---|
| 9-1001 | (3-MeOCO)C6H4C(Me2)— | Bnzyl | 4 |
| 9-1002 | (2-MeOCO)C6H4C(Me2)— | Bnzyl | 4 |
| 9-1003 | (4-CN)C6H4C(Me2)— | Bnzyl | 4 |
| 9-1004 | (3-CN)C6H4C(Me2)— | Bnzyl | 4 |
| 9-1005 | (2CN)C6H4C(Me2)— | Bnzyl | 4 |
| 9-1006 | (4NO2)C6H4C(Me2)— | Bnzyl | 4 |
| 9-1007 | (3NO2)C6H4C(Me2)— | Bnzyl | 4 |
| 9-1008 | (2NO2)C6H4C(Me2)— | Bnzyl | 4 |
| 9-1009 | (4-Cl)C6H4C(Me2)— | Bnzyl | 5 |
| 9-1010 | (3-Cl)C6H4C(Me2)— | Bnzyl | 5 |
| 9-1011 | (2-Cl)C6H4C(Me2)— | Bnzyl | 5 |
| 9-1012 | (4-F)C6H4C(Me2)— | Bnzyl | 5 |
| 9-1013 | (3-F)C6H4C(Me2)— | Bnzyl | 5 |
| 9-1014 | (2-F)C6H4C(Me2)— | Bnzyl | 5 |
| 9-1015 | (4-Me)C6H4C(Me2)— | Bnzyl | 5 |
| 9-1016 | (3-Me)C6H4C(Me2)— | Bnzyl | 5 |
| 9-1017 | (2-Me)C6H4C(Me2)— | Bnzyl | 5 |
| 9-1018 | (4-MeO)C6H4C(Me2)— | Bnzyl | 5 |
| 9-1019 | (3-MeO)C6H4C(Me2)— | Bnzyl | 5 |
| 9-1020 | (2-MeO)C6H4C(Me2)— | Bnzyl | 5 |
| 9-1021 | (4-Me2N)C6H4C(Me2)— | Bnzyl | 5 |
| 9-1022 | (3-Me2N)C6H4C(Me2)— | Bnzyl | 5 |
| 9-1023 | (2-Me2N)C6H4C(Me2)— | Bnzyl | 5 |
| 9-1024 | (4-MeOCO)C6H4C(Me2)— | Bnzyl | 5 |
| 9-1025 | (3-MeOCO)C6H4C(Me2)— | Bnzyl | 5 |
| 9-1026 | (2-MeOCO)C6H4C(Me2)— | Bnzyl | 5 |
| 9-1027 | (4-CN)C6H4C(Me2)— | Bnzyl | 5 |
| 9-1028 | (3-CN)C6H4C(Me2)— | Bnzyl | 5 |

TABLE 114-continued

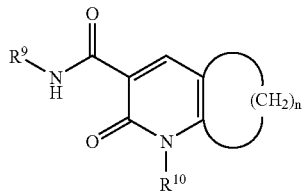

| Compound No. | R9 | R10 | n |
|---|---|---|---|
| 9-1029 | (2CN)C6H4C(Me2)— | Bnzyl | 5 |
| 9-1030 | (4NO2)C6H4C(Me2)— | Bnzyl | 5 |
| 9-1031 | (3NO2)C6H4C(Me2)— | Bnzyl | 5 |
| 9-1032 | (2NO2)C6H4C(Me2)— | Bnzyl | 5 |
| 9-1033 | (4-Cl)C6H4C(Me2)— | Bnzyl | 6 |
| 9-1034 | (3-Cl)C6H4C(Me2)— | Bnzyl | 6 |
| 9-1035 | (2-Cl)C6H4C(Me2)— | Bnzyl | 6 |
| 9-1036 | (4-F)C6H4C(Me2)— | Bnzyl | 6 |
| 9-1037 | (3-F)C6H4C(Me2)— | Bnzyl | 6 |
| 9-1038 | (2-F)C6H4C(Me2)— | Bnzyl | 6 |
| 9-1039 | (4-Me)C6H4C(Me2)— | Bnzyl | 6 |
| 9-1040 | (3-Me)C6H4C(Me2)— | Bnzyl | 6 |

TABLE 115

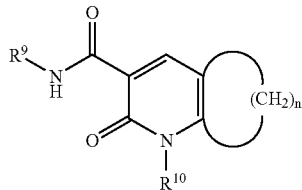

| Compound No. | R9 | R10 | n |
|---|---|---|---|
| 9-1041 | (2-Me)C6H4C(Me2)— | Bnzyl | 6 |
| 9-1042 | (4-MeO)C6H4C(Me2)— | Bnzyl | 6 |
| 9-1043 | (3-MeO)C6H4C(Me2)— | Bnzyl | 6 |
| 9-1044 | (2-MeO)6H4C(Me2)— | Bnzyl | 6 |
| 9-1045 | (4-Me2N)C6H4C(Me2)— | Bnzyl | 6 |
| 9-1046 | (3-Me2N)C6H4C(Me2)— | Bnzyl | 6 |
| 9-1047 | (2-Me2N)C6H4C(Me2)— | Bnzyl | 6 |
| 9-1048 | (4-MeOCO)C6H4C(Me2)— | Bnzyl | 6 |
| 9-1049 | (3-MeOCO)C6H4C(Me2)— | Bnzyl | 6 |
| 9-1050 | (2-MeOCO)C6H4C(Me2)— | Bnzyl | 6 |
| 9-1051 | (4-CN)C6H4C(Me2)— | Bnzyl | 6 |
| 9-1052 | (3-CN)C6H4C(Me2)— | Bnzyl | 6 |
| 9-1053 | (2CN)C6H4C(Me2)— | Bnzyl | 6 |
| 9-1054 | (4NO2)C6H4C(Me2)— | Bnzyl | 6 |
| 9-1055 | (3NO2)C6H4C(Me2)— | Bnzyl | 6 |
| 9-1056 | (2NO2)C6H4C(Me2)— | Bnzyl | 6 |
| 9-1057 | (4-Cl)C6H4C(Me2)— | 4-pyridyl-CH2— | 3 |
| 9-1058 | (3-Cl)C6H4C(Me2)— | 4-pyridyl-CH2— | 3 |
| 9-1059 | (2-Cl)C6H4C(Me2)— | 4-pyridyl-CH2— | 3 |
| 9-1060 | (4-F)C6H4C(Me2)— | 4-pyridyl-CH2— | 3 |
| 9-1061 | (3-F)C6H4C(Me2)— | 4-pyridyl-CH2— | 3 |
| 9-1062 | (2-F)C6H4C(Me2)— | 4-pyridyl-CH2— | 3 |
| 9-1063 | (4-Me)C6H4C(Me2)— | 4-pyridyl-CH2— | 3 |
| 9-1064 | (3-Me)C6H4C(Me2)— | 4-pyridyl-CH2— | 3 |
| 9-1065 | (2-Me)C6H4C(Me2)— | 4-pyridyl-CH2— | 3 |
| 9-1066 | (4-MeO)C6H4C(Me2)— | 4-pyridyl-CH2— | 3 |
| 9-1067 | (3-MeO)C6H4C(Me2)— | 4-pyridyl-CH2— | 3 |
| 9-1068 | (2-MeO)C6H4C(Me2)— | 4-pyridyl-CH2— | 3 |
| 9-1069 | (4-Me2N)C6H4C(Me2)— | 4-pyridyl-CH2— | 3 |
| 9-1070 | (3-Me2N)C6H4C(Me2)— | 4-pyridyl-CH2— | 3 |
| 9-1071 | (2-Me2N)C6H4C(Me2)— | 4-pyridyl-CH2— | 3 |
| 9-1072 | (4-MeOCO)C6H4C(Me2)— | 4-pyridyl-CH2— | 3 |
| 9-1073 | (3-MeOCO)C6H4C(Me2)— | 4-pyridyl-CH2— | 3 |
| 9-1074 | (2-MeOCO)C6H4C(Me2)— | 4-pyridyl-CH2— | 3 |
| 9-1075 | (4-CN)C6H4C(Me2)— | 4-pyridyl-CH2— | 3 |

TABLE 115-continued

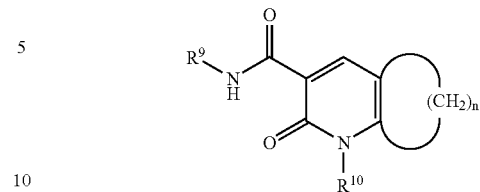

| Compound No. | R9 | R10 | n |
|---|---|---|---|
| 9-1076 | (3-CN)C6H4C(Me2)— | 4-pyridyl-CH2— | 3 |
| 9-1077 | (2CN)C6H4C(Me2)— | 4-pyridyl-CH2— | 3 |
| 9-1078 | (4NO2)C6H4C(Me2)— | 4-pyridyl-CH2— | 3 |
| 9-1079 | (3NO2)C6H4C(Me2)— | 4-pyridyl-CH2— | 3 |
| 9-1080 | (2NO2)C6H4C(Me2)— | 4-pyridyl-CH2— | 3 |

TABLE 116

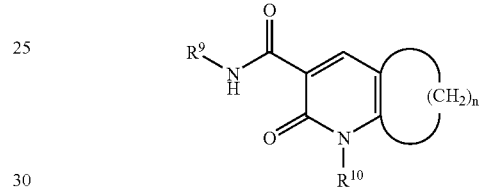

| Compound No. | R9 | R10 | n |
|---|---|---|---|
| 9-1081 | (4-Cl)C6H4C(Me2)— | 4-pyridyl-CH2— | 4 |
| 9-1082 | (3-Cl)C6H4C(Me2)— | 4-pyridyl-CH2— | 4 |
| 9-1083 | (2-Cl)C6H4C(Me2)— | 4-pyridyl-CH2— | 4 |
| 9-1084 | (4-F)C6H4C(Me2)— | 4-pyridyl-CH2— | 4 |
| 9-1085 | (3-F)C6H4C(Me2)— | 4-pyridyl-CH2— | 4 |
| 9-1086 | (2-F)C6H4C(Me2)— | 4-pyridyl-CH2— | 4 |
| 9-1087 | (4-Me)C6H4C(Me2)— | 4-pyridyl-CH2— | 4 |
| 9-1088 | (3-Me)C6H4C(Me2)— | 4-pyridyl-CH2— | 4 |
| 9-1089 | (2-Me)C6H4C(Me2)— | 4-pyridyl-CH2— | 4 |
| 9-1090 | (4-MeO)C6H4C(Me2)— | 4-pyridyl-CH2— | 4 |
| 9-1091 | (3-MeO)C6H4C(Me2)— | 4-pyridyl-CH2— | 4 |
| 9-1092 | (2-MeO)C6H4C(Me2)— | 4-pyridyl-CH2— | 4 |
| 9-1093 | (4-Me2N)C6H4C(Me2)— | 4-pyridyl-CH2— | 4 |
| 9-1094 | (3-Me2N)C6H4C(Me2)— | 4-pyridyl-CH2— | 4 |
| 9-1095 | (2-Me2N)C6H4C(Me2)— | 4-pyridyl-CH2— | 4 |
| 9-1096 | (4-MeOCO)C6H4C(Me2)— | 4-pyridyl-CH2— | 4 |
| 9-1097 | (3-MeOCO)C6H4C(Me2)— | 4-pyridyl-CH2— | 4 |
| 9-1098 | (2-MeOCO)C6H4C(Me2)— | 4-pyridyl-CH2— | 4 |
| 9-1099 | (4-CN)C6H4C(Me2)— | 4-pyridyl-CH2— | 4 |
| 9-1100 | (3-CN)C6H4C(Me2)— | 4-pyridyl-CH2— | 4 |
| 9-1101 | (2CN)C6H4C(Me2)— | 4-pyridyl-CH2— | 4 |
| 9-1102 | (4NO2)C6H4C(Me2)— | 4-pyridyl-CH2— | 4 |
| 9-1103 | (3NO2)C6H4C(Me2)— | 4-pyridyl-CH2— | 4 |
| 9-1104 | (2NO2)C6H4C(Me2)— | 4-pyridyl-CH2— | 4 |
| 9-1105 | (4-Cl)C6H4C(Me2)— | 4-pyridyl-CH2— | 5 |
| 9-1106 | (3-Cl)C6H4C(Me2)— | 4-pyridyl-CH2— | 5 |
| 9-1107 | (2-Cl)C6H4C(Me2)— | 4-pyridyl-CH2— | 5 |
| 9-1108 | (4-F)C6H4C(Me2)— | 4-pyridyl-CH2— | 5 |
| 9-1109 | (3-F)C6H4C(Me2)— | 4-pyridyl-CH2— | 5 |
| 9-1110 | (2-F)C6H4C(Me2)— | 4-pyridyl-CH2— | 5 |
| 9-1111 | (4-Me)C6H4C(Me2)— | 4-pyridyl-CH2— | 5 |
| 9-1112 | (3-Me)C6H4C(Me2)— | 4-pyridyl-CH2— | 5 |
| 9-1113 | (2-Me)C6H4C(Me2)— | 4-pyridyl-CH2— | 5 |
| 9-1114 | (4-MeO)C6H4C(Me2)— | 4-pyridyl-CH2— | 5 |
| 9-1115 | (3-MeO)C6H4C(Me2)— | 4-pyridyl-CH2— | 5 |
| 9-1116 | (2-MeO)C6H4C(Me2)— | 4-pyridyl-CH2— | 5 |
| 9-1117 | (4-Me2N)C6H4C(Me2)— | 4-pyridyl-CH2— | 5 |
| 9-1118 | (3-Me2N)C6H4C(Me2)— | 4-pyridyl-CH2— | 5 |
| 9-1119 | (2-Me2N)C6H4C(Me2)— | 4-pyridyl-CH2— | 5 |
| 9-1120 | (4-MeOCO)C6H4C(Me2)— | 4-pyridyl-CH2— | 5 |

TABLE 117

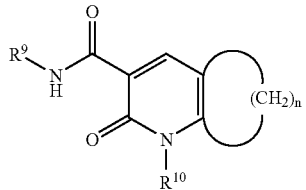

| Compound No. | R9 | R10 | n |
|---|---|---|---|
| 9-1121 | (3-MeOCO)C6H4C(Me2)— | 4-pyridyl-CH$_2$— | 5 |
| 9-1122 | (2-MeOCO)C6H4C(Me2)— | 4-pyridyl-CH$_2$— | 5 |
| 9-1123 | (4-CN)C6H4C(Me2)— | 4-pyridyl-CH$_2$— | 5 |
| 9-1124 | (3-CN)C6H4C(Me2)— | 4-pyridyl-CH$_2$— | 5 |
| 9-1125 | (2CN)C6H4C(Me2)— | 4-pyridyl-CH$_2$— | 5 |
| 9-1126 | (4NO2)C6H4C(Me2)— | 4-pyridyl-CH$_2$— | 5 |
| 9-1127 | (3NO2)C6H4C(Me2)— | 4-pyridyl-CH$_2$— | 5 |
| 9-1128 | (2NO2)C6H4C(Me2)— | 4-pyridyl-CH$_2$— | 5 |
| 9-1129 | (4-Cl)C6H4C(Me2)— | 4-pyridyl-CH$_2$— | 6 |
| 9-1130 | (3-Cl)C6H4C(Me2)— | 4-pyridyl-CH$_2$— | 6 |
| 9-1131 | (2-Cl)C6H4C(Me2)— | 4-pyridyl-CH$_2$— | 6 |
| 9-1132 | (4-F)C6H4C(Me2)— | 4-pyridyl-CH$_2$— | 6 |
| 9-1133 | (3-F)C6H4C(Me2)— | 4-pyridyl-CH$_2$— | 6 |
| 9-1134 | (2-F)C6H4C(Me2)— | 4-pyridyl-CH$_2$— | 6 |
| 9-1135 | (4-Me)C6H4C(Me2)— | 4-pyridyl-CH$_2$— | 6 |
| 9-1136 | (3-Me)C6H4C(Me2)— | 4-pyridyl-CH$_2$— | 6 |
| 9-1137 | (2-Me)C6H4C(Me2)— | 4-pyridyl-CH$_2$— | 6 |
| 9-1138 | (4-MeO)C6H4C(Me2)— | 4-pyridyl-CH$_2$— | 6 |
| 9-1139 | (3-MeO)C6H4C(Me2)— | 4-pyridyl-CH$_2$— | 6 |
| 9-1140 | (2-MeO)C6H4C(Me2)— | 4-pyridyl-CH$_2$— | 6 |
| 9-1141 | (4-Me2N)C6H4C(Me2)— | 4-pyridyl-CH$_2$— | 6 |
| 9-1142 | (3-Me2N)C6H4C(Me2)— | 4-pyridyl-CH$_2$— | 6 |
| 9-1143 | (2-Me2N)C6H4C(Me2)— | 4-pyridyl-CH$_2$— | 6 |
| 9-1144 | (4-MeOCO)C6H4C(Me2)— | 4-pyridyl-CH$_2$— | 6 |
| 9-1145 | (3-MeOCO)C6H4C(Me2)— | 4-pyridyl-CH$_2$— | 6 |
| 9-1146 | (2-MeOCO)C6H4C(Me2)— | 4-pyridyl-CH$_2$— | 6 |
| 9-1147 | (4-CN)C6H4C(Me2)— | 4-pyridyl-CH$_2$— | 6 |
| 9-1148 | (3-CN)C6H4C(Me2)— | 4-pyridyl-CH$_2$— | 6 |
| 9-1149 | (2CN)C6H4C(Me2)— | 4-pyridyl-CH$_2$— | 6 |
| 9-1150 | (4NO2)C6H4C(Me2)— | 4-pyridyl-CH$_2$— | 6 |
| 9-1151 | (3NO2)C6H4C(Me2)— | 4-pyridyl-CH$_2$— | 6 |
| 9-1152 | (2NO2)C6H4C(Me2)— | 4-pyridyl-CH$_2$— | 6 |
| 9-1153 | (4-Cl)C6H4CH2C(Me2)— | n-Bu | 3 |
| 9-1154 | (3-Cl)C6H4CH2C(Me2)— | n-Bu | 3 |
| 9-1155 | (2-Cl)C6H4CH2C(Me2)— | n-Bu | 3 |
| 9-1156 | (4-F)C6H4CH2C(Me2)— | n-Bu | 3 |
| 9-1157 | (3-F)C6H4CH2C(Me2)— | n-Bu | 3 |
| 9-1158 | (2-F)C6H4CH2C(Me2)— | n-Bu | 3 |
| 9-1159 | (4-Me)C6H4CH2C(Me2)— | n-Bu | 3 |
| 9-1160 | (3-Me)C6H4CH2C(Me2)— | n-Bu | 3 |

TABLE 118

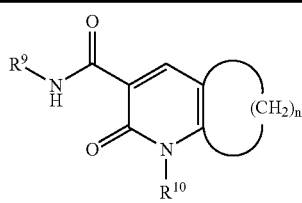

| Compound No. | R9 | R10 | n |
|---|---|---|---|
| 9-1161 | (2-Me)C6H4CH2C(Me2)— | n-Bu | 3 |
| 9-1162 | (4-MeO)C6H4CH2C(Me2)— | n-Bu | 3 |
| 9-1163 | (3-MeO)C6H4CH2C(Me2)— | n-Bu | 3 |
| 9-1164 | (2-MeO)C6H4CH2C(Me2)— | n-Bu | 3 |
| 9-1165 | (4-Me2N)C6H4CH2C(Me2)— | n-Bu | 3 |
| 9-1166 | (3-Me2N)C6H4CH2C(Me2)— | n-Bu | 3 |
| 9-1167 | (2-Me2N)C6H4CH2C(Me2)— | n-Bu | 3 |

TABLE 118-continued

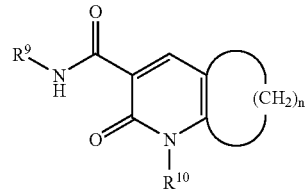

| Compound No. | R9 | R10 | n |
|---|---|---|---|
| 9-1168 | (4-MeOCO)C6H4CH2C(Me2)— | n-Bu | 3 |
| 9-1169 | (3-MeOCO)C6H4CH2C(Me2)— | n-Bu | 3 |
| 9-1170 | (2-MeOCO)C6H4CH2C(Me2)— | n-Bu | 3 |
| 9-1171 | (4-CN)C6H4CH2C(Me2)— | n-Bu | 3 |
| 9-1172 | (3-CN)C6H4CH2C(Me2)— | n-Bu | 3 |
| 9-1173 | (2CN)C6H4CH2C(Me2)— | n-Bu | 3 |
| 9-1174 | (4NO2)C6H4CH2C(Me2)— | n-Bu | 3 |
| 9-1175 | (3NO2)C6H4CH2C(Me2)— | n-Bu | 3 |
| 9-1176 | (2NO2)C6H4CH2C(Me2)— | n-Bu | 3 |
| 9-1177 | (4-Cl)C6H4CH2C(Me2)— | n-Bu | 4 |
| 9-1178 | (3-Cl)C6H4CH2C(Me2)— | n-Bu | 4 |
| 9-1179 | (2-Cl)C6H4CH2C(Me2)— | n-Bu | 4 |
| 9-1180 | (4-F)C6H4CH2C(Me2)— | n-Bu | 4 |
| 9-1181 | (3-F)C6H4CH2C(Me2)— | n-Bu | 4 |
| 9-1182 | (2-F)C6H4CH2C(Me2)— | n-Bu | 4 |
| 9-1183 | (4-Me)C6H4CH2C(Me2)— | n-Bu | 4 |
| 9-1184 | (3-Me)C6H4CH2C(Me2)— | n-Bu | 4 |
| 9-1185 | (2-Me)C6H4CH2C(Me2)— | n-Bu | 4 |
| 9-1186 | (4-MeO)C6H4CH2C(Me2)— | n-Bu | 4 |
| 9-1187 | (3-MeO)C6H4CH2C(Me2)— | n-Bu | 4 |
| 9-1188 | (2-MeO)C6H4CH2C(Me2)— | n-Bu | 4 |
| 9-1189 | (4-Me2N)C6H4CH2C(Me2)— | n-Bu | 4 |
| 9-1190 | (3-Me2N)C6H4CH2C(Me2)— | n-Bu | 4 |
| 9-1191 | (2-Me2N)C6H4CH2C(Me2)— | n-Bu | 4 |
| 9-1192 | (4-MeOCO)C6H4CH2C(Me2)— | n-Bu | 4 |
| 9-1193 | (3-MeOCO)C6H4CH2C(Me2)— | n-Bu | 4 |
| 9-1194 | (2-MeOCO)C6H4CH2C(Me2)— | n-Bu | 4 |
| 9-1195 | (4-CN)C6H4CH2C(Me2)— | n-Bu | 4 |
| 9-1196 | (3-CN)C6H4CH2C(Me2)— | n-Bu | 4 |
| 9-1197 | (2CN)C6H4CH2C(Me2)— | n-Bu | 4 |
| 9-1198 | (4NO2)C6H4CH2C(Me2)— | n-Bu | 4 |
| 9-1199 | (3NO2)C6H4CH2C(Me2)— | n-Bu | 4 |
| 9-1200 | (2NO2)C6H4CH2C(Me2)— | n-Bu | 4 |

TABLE 119

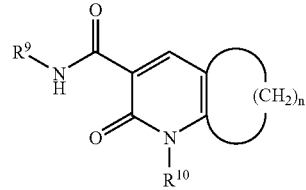

| Compound No. | R9 | R10 | n |
|---|---|---|---|
| 9-1201 | (4-Cl)C6H4CH2C(Me2)— | n-Bu | 5 |
| 9-1202 | (3-Cl)C6H4CH2C(Me2)— | n-Bu | 5 |
| 9-1203 | (2-Cl)C6H4CH2C(Me2)— | n-Bu | 5 |
| 9-1204 | (4-F)C6H4CH2C(Me2)— | n-Bu | 5 |
| 9-1205 | (3-F)C6H4CH2C(Me2)— | n-Bu | 5 |
| 9-1206 | (2-F)C6H4CH2C(Me2)— | n-Bu | 5 |
| 9-1207 | (4-Me)C6H4CH2C(Me2)— | n-Bu | 5 |
| 9-1208 | (3-Me)C6H4CH2C(Me2)— | n-Bu | 5 |
| 9-1209 | (2-Me)C6H4CH2C(Me2)— | n-Bu | 5 |
| 9-1210 | (4-MeO)C6H4CH2C(Me2)— | n-Bu | 5 |
| 9-1211 | (3-MeO)C6H4CH2C(Me2)— | n-Bu | 5 |
| 9-1212 | (2-MeO)C6H4CH2C(Me2)— | n-Bu | 5 |
| 9-1213 | (4-Me2N)C6H4CH2C(Me2)— | n-Bu | 5 |
| 9-1214 | (3-Me2N)C6H4CH2C(Me2)— | n-Bu | 5 |

TABLE 119-continued

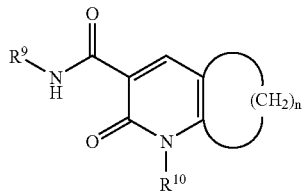

| Compound No. | R9 | R10 | n |
|---|---|---|---|
| 9-1215 | (2-Me2N)C6H4CH2C(Me2)— | n-Bu | 5 |
| 9-1216 | (4.MeOCO)C6H4CH2C(Me2)— | n-Bu | 5 |
| 9-1217 | (3-MeOCO)C6H4CH2C(Me2)— | n-Bu | 5 |
| 9-1218 | (2-MeOCO)C6H4CH2C(Me2)— | n-Bu | 5 |
| 9-1219 | (4-CN)C6H4CH2C(Me2)— | n-Bu | 5 |
| 9-1220 | (3-CN)C6H4CH2C(Me2)— | n-Bu | 5 |
| 9-1221 | (2CN)C6H4CH2C(Me2)— | n-Bu | 5 |
| 9-1222 | (4NO2)C6H4CH2C(Me2)— | n-Bu | 5 |
| 9-1223 | (3NO2)C6H4CH2C(Me2)— | n-Bu | 5 |
| 9-1224 | (2NO2)C6H4CH2C(Me2)— | n-Bu | 5 |
| 9-1225 | (4-Cl)C6H4CH2C(Me2)— | n-Bu | 6 |
| 9-1226 | (3-Cl)C6H4CH2C(Me2)— | n-Bu | 6 |
| 9-1227 | (2-Cl)C6H4CH2C(Me2)— | n-Bu | 6 |
| 9-1228 | (4-F)C6H4CH2C(Me2)— | n-Bu | 6 |
| 9-1229 | (3-F)C6H4CH2C(Me2)— | n-Bu | 6 |
| 9-1230 | (2-F)C6H4CH2C(Me2)— | n-Bu | 6 |
| 9-1231 | (4-Me)C6H4CH2C(Me2)— | n-Bu | 6 |
| 9-1232 | (3-Me)C6H4CH2C(Me2)— | n-Bu | 6 |
| 9-1233 | (2-Me)C6H4CH2C(Me2)— | n-Bu | 6 |
| 9-1234 | (4-MeO)C6H4CH2C(Me2)— | n-Bu | 6 |
| 9-1235 | (3-MeO)C6H4CH2C(Me2)— | n-Bu | 6 |
| 9-1236 | (2-MeO)C6H4CH2C(Me2)— | n-Bu | 6 |
| 9-1237 | (4-Me2N)C6H4CH2C(Me2)— | n-Bu | 6 |
| 9-1238 | (3-Me2N)C6H4CHC(Me2)— | n-Bu | 6 |
| 9-1239 | (2-Me2N)C6H4CH2C(Me2)— | n-Bu | 6 |
| 9-1240 | (4-MeOCO)C6H4CH2C(Me2)— | n-Bu | 6 |

TABLE 120

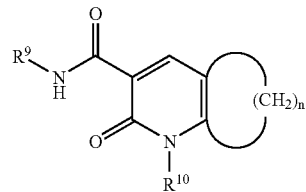

| Compound No. | R9 | R10 | n |
|---|---|---|---|
| 9-1241 | (3-MeOCO)C6H4CH2C(Me2)- | n-Bu | 6 |
| 9-1242 | (2-MeOCO)C6H4CH2C(Me2)- | n-Bu | 6 |
| 9-1243 | (4-CN)C6H4CH2C(Me2)- | n-Bu | 6 |
| 9-1244 | (3-CN)C6H4CH2C(Me2)- | n-Bu | 6 |
| 9-1245 | (2CN)C6H4CH2C(Me2)- | n-Bu | 6 |
| 9-1246 | (4NO2)C6H4CH2C(Me2)- | n-Bu | 6 |
| 9-1247 | (3NO2)C6H4CH2C(Me2)- | n-Bu | 6 |
| 9-1248 | (2NO2)C6H4CH2C(Me2)- | n-Bu | 6 |
| 9-1249 | (4-Cl)C6H4CH2C(Me2)- | Bnzyl | 3 |
| 9-1250 | (3-Cl)C6H4CH2C(Me2)- | Bnzyl | 3 |
| 9-1251 | (2-Cl)C6H4CH2C(Me2)- | Bnzyl | 3 |
| 9-1252 | (4-F)C6H4CH2C(Me2)- | Bnzyl | 3 |
| 9-1253 | (3-F)C6H4CH2C(Me2)- | Bnzyl | 3 |
| 9-1254 | (2-F)C6H4CH2C(Me2)- | Bnzyl | 3 |
| 9-1255 | (4-Me)C6H4CH2C(Me2)- | Bnzyl | 3 |
| 9-1256 | (3-Me)C6H4CH2C(Me2)- | Bnzyl | 3 |
| 9-1257 | (2-Me)C6H4CH2C(Me2)- | Bnzyl | 3 |
| 9-1258 | (4-MeO)C6H4CH2C(Me2)- | Bnzyl | 3 |
| 9-1259 | (3-MeO)C6H4CH2C(Me2)- | Bnzyl | 3 |
| 9-1260 | (2-MeO)C6H4CH2C(Me2)- | Bnzyl | 3 |
| 9-1261 | (4-Me2N)C6H4CH2C(Me2)- | Bnzyl | 3 |

TABLE 120-continued

| Compound No. | R9 | R10 | n |
|---|---|---|---|
| 9-1262 | (3-Me2N)C6H4CH2C(Me2)- | Bnzyl | 3 |
| 9-1263 | (2-Me2N)C6H4CH2C(Me2)- | Bnzyl | 3 |
| 9-1264 | (4-MeOCO)C6H4CH2C(Me2)- | Bnzyl | 3 |
| 9-1265 | (3-MeOCO)C6H4CH2C(Me2)- | Bnzyl | 3 |
| 9-1266 | (2-MeOCO)C6H4CH2C(Me2)- | Bnzyl | 3 |
| 9-1267 | (4-CN)C6H4CH2C(Me2)- | Bnzyl | 3 |
| 9-1268 | (3-CN)C6H4CH2C(Me2)- | Bnzyl | 3 |
| 9-1269 | (2CN)C6H4CH2C(Me2)- | Bnzyl | 3 |
| 9-1270 | (4NO2)C6H4CH2C(Me2)- | Bnzyl | 3 |
| 9-1271 | (3NO2)C6H4CH2C(Me2)- | Bnzyl | 3 |
| 9-1272 | (2NO2)C6H4CH2C(Me2)- | Bnzyl | 3 |
| 9-1273 | (4-Cl)C6H4CH2C(Me2)- | Bnzyl | 4 |
| 9-1274 | (3-Cl)C6H4CH2C(Me2)- | Bnzyl | 4 |
| 9-1275 | (2-Cl)C6H4CH2C(Me2)- | Bnzyl | 4 |
| 9-1276 | (4-F)C6H4CH2C(Me2)- | Bnzyl | 4 |
| 9-1277 | (3-F)C6H4CH2C(Me2)- | Bnzyl | 4 |
| 9-1278 | (2-F)C6H4CH2C(Me2)- | Bnzyl | 4 |
| 9-1279 | (4-Me)C6H4CH2C(Me2)- | Bnzyl | 4 |
| 9-1280 | (3-Me)C6H4CH2C(Me2)- | Bnzyl | 4 |

TABLE 121

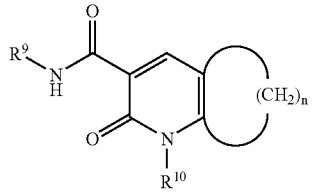

| Compound No. | R9 | R10 | n |
|---|---|---|---|
| 9-1281 | (2-Me)C6H4CH2C(Me2)— | Bnzyl | 4 |
| 9-1282 | (4-MeO)C6H4CH2C(Me2)— | Bnzyl | 4 |
| 9-1283 | (3-MeO)C6H4CH2C(Me2)— | Bnzyl | 4 |
| 9-1284 | (2-MeO)C6H4CH2C(Me2)— | Bnzyl | 4 |
| 9-1285 | (4-Me2N)C6H4CH2C(Me2)— | Bnzyl | 4 |
| 9-1286 | (3-Me2N)C6H4CH2C(Me2)— | Bnzyl | 4 |
| 9-1287 | (2-Me2N)C6H4CH2C(Me2)— | Bnzyl | 4 |
| 9-1288 | (4-MeOCO)C6H4CH2C(Me2)— | Bnzyl | 4 |
| 9-1289 | (3-MeOCO)C6H4CH2C(Me2)— | Bnzyl | 4 |
| 9-1290 | (2-MeOCO)C6H4CH2C(Me2)— | Bnzyl | 4 |
| 9-1291 | (4-CN)C6H4CH2C(Me2)— | Bnzyl | 4 |
| 9-1292 | (3-CN)C6H4CH2C(Me2)— | Bnzyl | 4 |
| 9-1293 | (2CN)C6H4CH2C(Me2)— | Bnzyl | 4 |
| 9-1294 | (4NO2)C6H4CH2C(Me2)— | Bnzyl | 4 |
| 9-1295 | (3NO2)C6H4CH2C(Me2)— | Bnzyl | 4 |
| 9-1296 | (2NO2)C6H4CH2C(Me2)— | Bnzyl | 4 |
| 9-1297 | (4-Cl)C6H4CH2C(Me2)— | Bnzyl | 5 |
| 9-1298 | (3-Cl)C6H4CH2C(Me2)— | Bnzyl | 5 |
| 9-1299 | (2-Cl)C6H4CH2C(Me2)— | Bnzyl | 5 |
| 9-1300 | (4-F)C6H4CH2C(Me2)— | Bnzyl | 5 |
| 9-1301 | (3-F)C6H4CH2C(Me2)— | Bnzyl | 5 |
| 9-1302 | (2-F)C6H4CH2C(Me2)— | Bnzyl | 5 |
| 9-1303 | (4-Me)C6H4CH2C(Me2)— | Bnzyl | 5 |
| 9-1304 | (3-Me)C6H4CH2C(Me2)— | Bnzyl | 5 |
| 9-1305 | (2-Me)C6H4CH2C(Me2)— | Bnzyl | 5 |
| 9-1306 | (4-MeO)C6H4CH2C(Me2)— | Bnzyl | 5 |
| 9-1307 | (3-MeO)C6H4CH2C(Me2)— | Bnzyl | 5 |
| 9-1308 | (2-MeO)C6H4CH2C(Me2)— | Bnzyl | 5 |

TABLE 121-continued

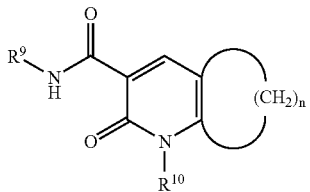

| Compound No. | R9 | R10 | n |
|---|---|---|---|
| 9-1309 | (4-Me2N)C6H4CH2C(Me2)— | Bnzyl | 5 |
| 9-1310 | (3-Me2N)C6H4CH2C(Me2)— | Bnzyl | 5 |
| 9-1311 | (2-Me2N)C6H4CH2C(Me2)— | Bnzyl | 5 |
| 9-1312 | (4-MeOCO)C6H4CH2C(Me2)— | Bnzyl | 5 |
| 9-1313 | (3-MeOCO)C6H4CH2C(Me2)— | Bnzyl | 5 |
| 9-1314 | (2-MeOCO)C6H4CH2C(Me2)— | Bnzyl | 5 |
| 9-1315 | (4-CN)C6H4CH2C(Me2)— | Bnzyl | 5 |
| 9-1316 | (3-CN)C6H4CH2C(Me2)— | Bnzyl | 5 |
| 9-1317 | (2CN)C6H4CH2C(Me2)— | Bnzyl | 5 |
| 9-1318 | (4NO2)C6H4CH2C(Me2)— | Bnzyl | 5 |
| 9-1319 | (3NO2)C6H4CH2C(Me2)— | Bnzyl | 5 |
| 9-1320 | (2NO2)C6H4CH2C(Me2)— | Bnzyl | 5 |

TABLE 122

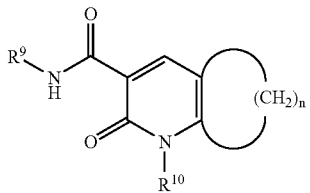

| Compound No. | R9 | R10 | n |
|---|---|---|---|
| 9-1321 | (4-Cl)C6H4CH2C(Me2)— | Bnzyl | 6 |
| 9-1322 | (3-Cl)C6H4CH2C(Me2)— | Bnzyl | 6 |
| 9-1323 | (2-Cl)C6H4CH2C(Me2)— | Bnzyl | 6 |
| 9-1324 | (4-F)C6H4CH2C(Me2)— | Bnzyl | 6 |
| 9-1325 | (3-F)C6H4CH2C(Me2)— | Bnzyl | 6 |
| 9-1326 | (2-F)C6H4CH2C(Me2)— | Bnzyl | 6 |
| 9-1327 | (4-Me)C6H4CH2C(Me2)— | Bnzyl | 6 |
| 9-1328 | (3-Me)C6H4CH2C(Me2)— | Bnzyl | 6 |
| 9-1329 | (2-Me)C6H4CH2C(Me2)— | Bnzyl | 6 |
| 9-1330 | (4-MeO)C6H4CH2C(Me2)— | Bnzyl | 6 |
| 9-1331 | (3-MeO)C6H4CH2C(Me2)— | Bnzyl | 6 |
| 9-1332 | (2-MeO)C6H4CH2C(Me2)— | Bnzyl | 6 |
| 9-1333 | (4-Me2N)C6H4CH2C(Me2)— | Bnzyl | 6 |
| 9-1334 | (3-Me2N)C6H4CH2C(Me2)— | Bnzyl | 6 |
| 9-1335 | (2-Me2N)C6H4CH2C(Me2)— | Bnzyl | 6 |
| 9-1336 | (4-MeOCO)C6H4CH2C(Me2)— | Bnzyl | 6 |
| 9-1337 | (3-MeOCO)C6H4CH2C(Me2)— | Bnzyl | 6 |
| 9-1338 | (2-MeOCO)C6H4CH2C(Me2)— | Bnzyl | 6 |
| 9-1339 | (4-CN)C6H4CH2C(Me2)— | Bnzyl | 6 |
| 9-1340 | (3-CN)C6H4CH2C(Me2)— | Bnzyl | 6 |
| 9-1341 | (2CN)C6H4CH2C(Me2)— | Bnzyl | 6 |
| 9-1342 | (4NO2)C6H4CH2C(Me2)— | Bnzyl | 6 |
| 9-1343 | (3NO2)C6H4CH2C(Me2)— | Bnzyl | 6 |
| 9-1344 | (2NO2)C6H4CH2C(Me2)— | Bnzyl | 6 |
| 9-1345 | (4-Cl)C6H4CH2C(Me2)— | 4-pyridyl-CH2— | 3 |
| 9-1346 | (3-Cl)C6H4CH2C(Me2)— | 4-pyridyl-CH2— | 3 |
| 9-1347 | (2-Cl)C6H4CH2C(Me2)— | 4-pyridyl-CH2— | 3 |
| 9-1348 | (4-F)C6H4CH2C(Me2)— | 4-pyridyl-CH2— | 3 |
| 9-1349 | (3-F)C6H4CH2C(Me2)— | 4-pyridyl-CH2— | 3 |
| 9-1350 | (2-F)C6H4CH2C(Me2)— | 4-pyridyl-CH2— | 3 |
| 9-1351 | (4-Me)C6H4CH2C(Me2)— | 4-pyridyl-CH2— | 3 |
| 9-1352 | (3-Me)C6H4CH2C(Me2)— | 4-pyridyl-CH2— | 3 |
| 9-1353 | (2-Me)C6H4CH2C(Me2)— | 4-pyridyl-CH2— | 3 |
| 9-1354 | (4-MeO)C6H4CH2C(Me2)— | 4-pyridyl-CH2— | 3 |
| 9-1355 | (3-MeO)C6H4CH2C(Me2)— | 4-pyridyl-CH2— | 3 |

TABLE 122-continued

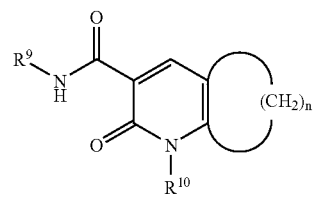

| Compound No. | R9 | R10 | n |
|---|---|---|---|
| 9-1356 | (2-MeO)C6H4CH2C(Me2)— | 4-pyridyl-CH2— | 3 |
| 9-1357 | (4-Me2N)C6H4CH2C(Me2)— | 4-pyridyl-CH2— | 3 |
| 9-1358 | (3-Me2N)C6H4CH2C(Me2)— | 4-pyridyl-CH2— | 3 |
| 9-1359 | (2-Me2N)C6H4CH2C(Me2)— | 4-pyridyl-CH2— | 3 |
| 9-1360 | (4-MeOCO)C6H4CH2C(Me2)— | 4-pyridyl-CH2— | 3 |

TABLE 123

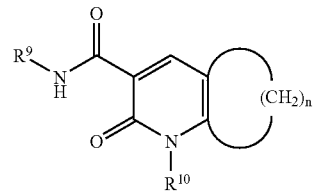

| Compound No- | R9 | R10 | n |
|---|---|---|---|
| 9-1361 | (3-MeOCO)C6H4CH2C(Me2)— | 4-pyridyl-CH2— | 3 |
| 9-1362 | (2-MeOCO)C6H4CH2C(Me2)— | 4-pyridyl-CH2— | 3 |
| 9-1363 | (4-CN)C6H4CH2C(Me2)— | 4-pyridyl-CH2— | 3 |
| 9-1364 | (3-CN)C6H4CH2C(Me2)— | 4-pyridyl-CH2— | 3 |
| 9-1365 | (2CN)C6H4CH2C(Me2)— | 4-pyridyl-CH2— | 3 |
| 9-1366 | (4NO2)C6H4CH2C(Me2)— | 4-pyridyl-CH2— | 3 |
| 9-1367 | (3NO2)C6H4CH2C(Me2)— | 4-pyridyl-CH2— | 3 |
| 9-1368 | (2NO2)C6H4CH2C(Me2)— | 4-pyridyl-CH2— | 3 |
| 9-1369 | (4-Cl)C6H4CH2C(Me2)— | 4-pyridyl-CH2— | 4 |
| 9-1370 | (3-Cl)C6H4CH2C(Me2)— | 4-pyridyl-CH2— | 4 |
| 9-1371 | (2-Cl)C6H4CH2C(Me2)— | 4-pyridyl-CH2— | 4 |
| 9-1372 | (4-F)C6H4CH2C(Me2)— | 4-pyridyl-CH2— | 4 |
| 9-1373 | (3-F)C6H4CH2C(Me2)— | 4-pyridyl-CH2— | 4 |
| 9-1374 | (2-F)C6H4CH2C(Me2)— | 4-pyridyl-CH2— | 4 |
| 9-1375 | (4-Me)C6H4CH2C(Me2)— | 4-pyridyl-CH2— | 4 |
| 9-1376 | (3-Me)C6H4CH2C(Me2)— | 4-pyridyl-CH2— | 4 |
| 9-1377 | (2-Me)C6H4CH2C(Me2)— | 4-pyridyl-CH2— | 4 |
| 9-1378 | (4-MeO)C6H4CH2C(Me2)— | 4-pyridyl-CH2— | 4 |
| 9-1379 | (3-MeO)C6H4CH2C(Me2)— | 4-pyridyl-CH2— | 4 |
| 9-1380 | (2-MeO)C6H4CH2C(Me2)— | 4-pyridyl-CH2— | 4 |
| 9-1381 | (4-Me2N)C6H4CH2C(Me2)— | 4-pyridyl-CH2— | 4 |
| 9-1382 | (3-Me2N)C6H4CH2C(Me2)— | 4-pyridyl-CH2— | 4 |
| 9-1383 | (2-Me2N)C6H4CH2C(Me2)— | 4-pyridyl-CH2— | 4 |
| 9-1384 | (4-MeOCO)C6H4CH2C(Me2)— | 4-pyridyl-CH2— | 4 |
| 9-1385 | (3-MeOCO)C6H4CH2C(Me2)— | 4-pyridyl-CH2— | 4 |
| 9-1386 | (2-MeOCO)C6H4CH2C(Me2)— | 4-pyridyl-CH2— | 4 |
| 9-1387 | (4-CN)C6H4CH2C(Me2)— | 4-pyridyl-CH2— | 4 |
| 9-1388 | (3-CN)C6H4CH2C(Me2)— | 4-pyridyl-CH2— | 4 |
| 9-1389 | (2CN)C6H4CH2C(Me2)— | 4-pyridyl-CH2— | 4 |
| 9-1390 | (4NO2)C6H4CH2C(Me2)— | 4-pyridyl-CH2— | 4 |
| 9-1391 | (3NO2)C6H4CH2C(Me2)— | 4-pyridyl-CH2— | 4 |
| 9-1392 | (2NO2)C6H4CH2C(Me2)— | 4-pyridyl-CH2— | 4 |
| 9-1393 | (4-Cl)C6H4CH2C(Me2)— | 4-pyridyl-CH2— | 5 |
| 9-1394 | (3-Cl)C6H4CH2C(Me2)— | 4-pyridyl-CH2— | 5 |
| 9-1395 | (2-Cl)C6H4CH2C(Me2)— | 4-pyridyl-CH2— | 5 |
| 9-1396 | (4-F)C6H4CH2C(Me2)— | 4-pyridyl-CH2— | 5 |
| 9-1397 | (3-F)C6H4CH2C(Me2)— | 4-pyridyl-CH2— | 5 |
| 9-1398 | (2-F)C6H4CH2C(Me2)— | 4-pyridyl-CH2— | 5 |
| 9-1399 | (4-Me)C6H4CH2C(Me2)— | 4-pyridyl-CH2— | 5 |
| 9-1400 | (3-Me)C6H4CH2C(Me2)— | 4-pyridyl-CH2— | 5 |

TABLE 124

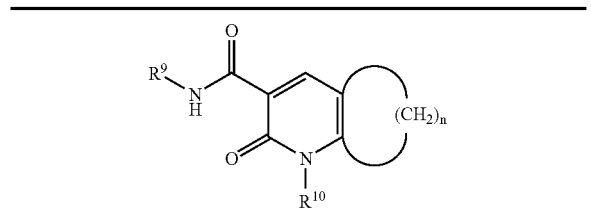

| Compound No- | R9 | R10 | n |
|---|---|---|---|
| 9-1401 | (2-Me)C6H4CH2C(Me2)— | 4-pyridyl-CH2— | 5 |
| 9-1402 | (4-MeO)C6H4CH2C(Me2)— | 4-pyridyl-CH2— | 5 |
| 9-1403 | (3-MeO)C6H4CH2C(Me2)— | 4-pyridyl-CH2— | 5 |
| 9-1404 | (2-MeO)C6H4CH2C(Me2)— | 4-pyridyl-CH2— | 5 |
| 9-1405 | (4-Me2N)C6H4CH2C(Me2)— | 4-pyridyl-CH2— | 5 |
| 9-1406 | (3-Me2N)C6H4CH2C(Me2)— | 4-pyridyl-CH2— | 5 |
| 9-1407 | (2-Me2N)C6H4CH2C(Me2)— | 4-pyridyl-CH2— | 5 |
| 9-1408 | (4-MeOCO)C6H4CH2C(Me2)— | 4-pyridyl-CH2— | 5 |
| 9-1409 | (3-MeOCO)C6H4CH2C(Me2)— | 4-pyridyl-CH2— | 5 |
| 9-1410 | (2-MeOCO)C6H4CH2C(Me2)— | 4-pyridyl-CH2— | 5 |
| 9-1411 | (4-CN)C6H4CH2C(Me2)— | 4-pyridyl-CH2— | 5 |
| 9-1412 | (3-CN)C6H4CH2C(Me2)— | 4-pyridyl-CH2— | 5 |
| 9-1413 | (2CN)C6H4CH2C(Me2)— | 4-pyridyl-CH2— | 5 |
| 9-1414 | (4NO2)C6H4CH2C(Me2)— | 4-pyridyl-CH2— | 5 |
| 9-1415 | (3NO2)C6H4CH2C(Me2)— | 4-pyridyl-CH2— | 5 |
| 9-1416 | (2NO2)C6H4CH2C(Me2)— | 4-pyridyl-CH2— | 5 |
| 9-1417 | (4-Cl)C6H4CH2C(Me2)— | 4-pyridyl-CH2— | 6 |
| 9-1418 | (3-Cl)C6H4CH2C(Me2)— | 4-pyridyl-CH2— | 6 |
| 9-1419 | (2-Cl)C6H4CH2C(Me2)— | 4-pyridyl-CH2— | 6 |
| 9-1420 | (4-F)C6H4CH2C(Me2)— | 4-pyridyl-CH2— | 6 |
| 9-1421 | (3-F)C6H4CH2C(Me2)— | 4-pyridyl-CH2— | 6 |
| 9-1422 | (2-F)C6H4CH2C(Me2)— | 4-pyridyl-CH2— | 6 |
| 9-1423 | (4-Me)C6H4CH2C(Me2)— | 4-pyridyl-CH2— | 6 |
| 9-1424 | (3-Me)C6H4CH2C(Me2)— | 4-pyridyl-CH2— | 6 |
| 9-1425 | (2-Me)C6H4CH2C(Me2)— | 4-pyridyl-CH2— | 6 |
| 9-1426 | (4-MeO)C6H4CH2C(Me2)— | 4-pyridyl-CH2— | 6 |

TABLE 124-continued

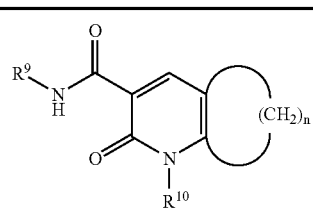

| Compound No- | R9 | R10 | n |
|---|---|---|---|
| 9-1427 | (3-MeO)C6H4CH2C(Me2)— | 4-pyridyl-CH2— | 6 |
| 9-1428 | (2-MeO)C6H4CH2C(Me2)— | 4-pyridyl-CH2— | 6 |
| 9-1429 | (4-Me2N)C6H4CH2C(Me2)— | 4-pyridyl-CH2— | 6 |
| 9-1430 | (3-Me2N)C6H4CH2C(Me2)— | 4-pyridyl-CH2— | 6 |
| 9-1431 | (2-Me2N)C6H4CH2C(Me2)— | 4-pyridyl-CH2— | 6 |
| 9-1432 | (4-MeOCO)C6H4CH2C(Me2)— | 4-pyridyl-CH2— | 6 |
| 9-1433 | (3-MeOCO)C6H4CH2C(Me2)— | 4-pyridyl-CH2— | 6 |
| 9-1434 | (2-MeOCO)C6H4CH2C(Me2)— | 4-pyridyl-CH2— | 6 |
| 9-1435 | (4-CN)C6H4CH2C(Me2)— | 4-pyridyl-CH2— | 6 |
| 9-1436 | (3-CN)C6H4CH2C(Me2)— | 4-pyridyl-CH2— | 6 |
| 9-1437 | (2CN)C6H4CH2C(Me2)— | 4-pyridyl-CH2— | 6 |
| 9-1438 | (4NO2)C6H4CH2C(Me2)— | 4-pyridyl-CH2— | 6 |
| 9-1439 | (3NO2)C6H4CH2C(Me2)— | 4-pyridyl-CH2— | 6 |
| 9-1440 | (2NO2)C6H4CH2C(Me2)— | 4-pyridyl-CH2— | 6 |

Furthermore, parallel syntheses of the compounds of the present invention were carried out using solid phase reaction as shown below. Moreover, the identification of the obtained compounds was performed by mass spectrum and those bioassay was carried out.

<Library A>
Combinatorial Preparation of 1-butyl-2-oxo-5-aryl-1,2-dihydropyridine-3-carboxylic acid qamide derivatives (Combi-A)

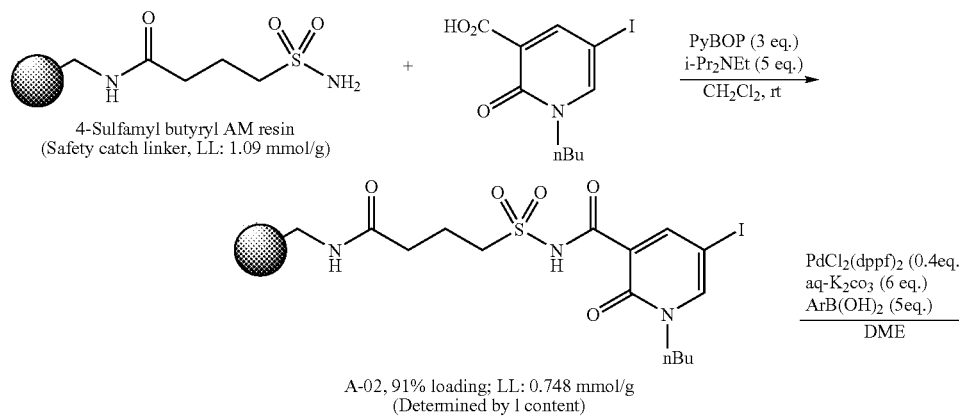

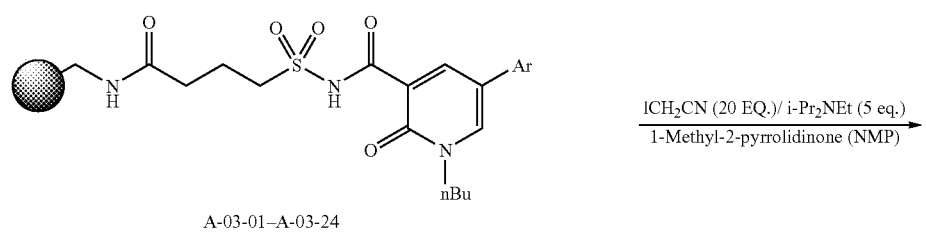

A-03-01–A-03-24

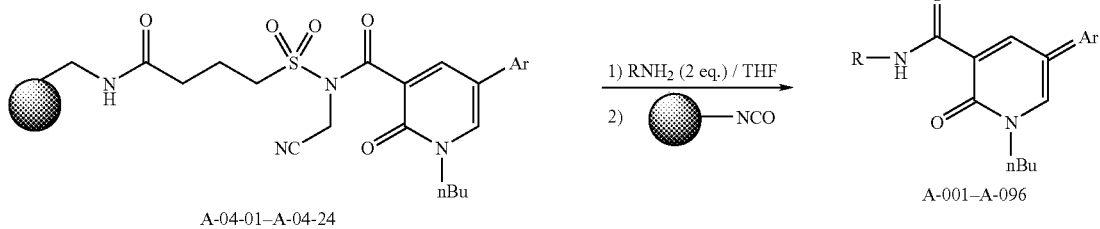

a) Preparation of Resin A-02

To a solution of 4-sulfamylbutyryl AM resin (3.9 g) in methylene chloride (80 mL) were added 1-butyl-5-iodo-2-oxo-1,2-dihydropyridine-3-carboxylic acid (A-01) (4.1 g) and N,N-diisopropylethylamine (3.7 mL) at room temperature. After stirring for 10 min, to the reaction mixture was added PyBOP (6.6 g) at room temperature, and the reaction mixture was stirred for additional 18 h. The resin was filtered off, washed with water, THF, methylene chloride, and diethyl ether one by one to give resin (A-02) [5.2 g, 92% determined by iodine elementary analysis].

b) Preparation of Resins (A-03-01 to A-03-24)

Resin A-02 (150 mg) was measured each in 24 flasks, and to each flasks were added DME (2.5 mL), PdCl$_2$(dppf) (35 mg), arylboronic acid (5 equivalent), and a 2 M aqueous solution of potassium carbonate (0.34 mL). After stirring at 80° C. for 18 h, the resin was filtered off, washed with water, THF, N-methylpyrrolidone, methylene chloride, and diethyl ether one by one to give resins A-03-01 to A-03-24, respectively.

c) Preparation of Resins A-04-01 to A-04-24

To resins A-03-01 to A-03-24 were added N-methylpyrrolidone (2.0 mL), iodoacetonitrile (0.16 mL), and 11N-diisopropylethylamine (0.1 mL) at room temperature. After stirring for 24 h, the resin was filtered off, washed with N-methylpyrrolidone, methylene chloride, and diethyl ether one by one to give resins A-04-01 to A-04-24, respectively.

d) Preparations of 1-butyl-2-oxo-5-aryl-1,2-dihydropyridine-3-carboxamide derivatives A-05-01 to A-05-96

Resins A-04-01 to A-04-24 were divided each into 4 portions, and measured into 96 hole plate. After THF was added to each hole, amine was added to each 24 kinds of resin. After shaking for 24 h, macromolecule-immobilized isocyanate was added, and the plate was shaken for additional 3 h. The resin was filtered off, washed methylene chloride, and the filtrate was evaporated under reduced to give 1-butyl-2-oxo-5-aryl-1,2-dihydropyridine-3-carboxamide derivatives A-001 to A-096.

The structures of A-001 to A-096 were described below.

TABLE 125

| No. | Structure |
|---|---|
| A-001 | 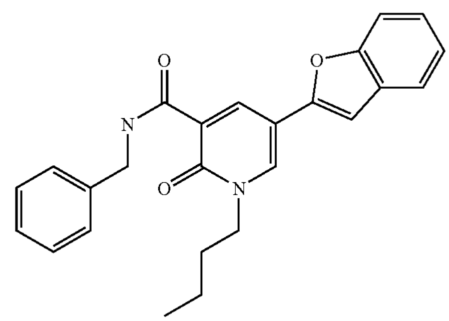 |
| A-002 | 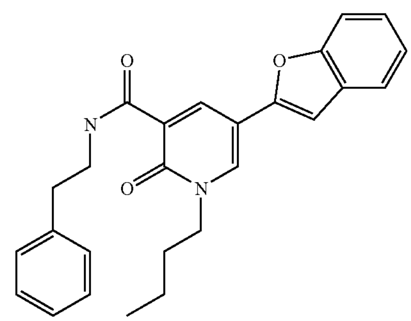 |
| A-003 | 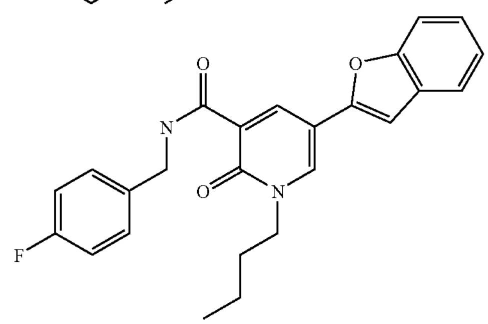 |
| A-004 | 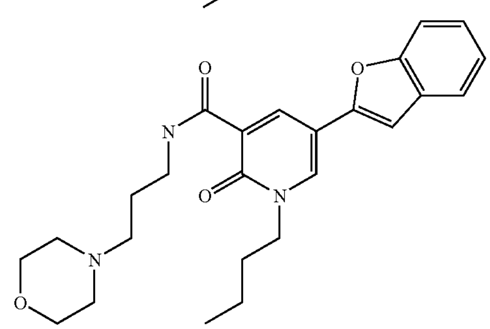 |

TABLE 125-continued

| No. | Structure |
|---|---|
| A-005 | 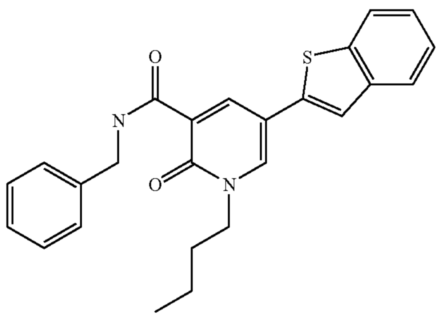 |
| A-006 | 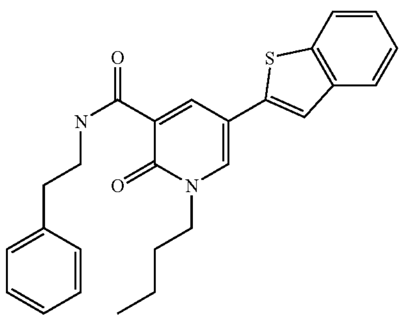 |
| A-007 | 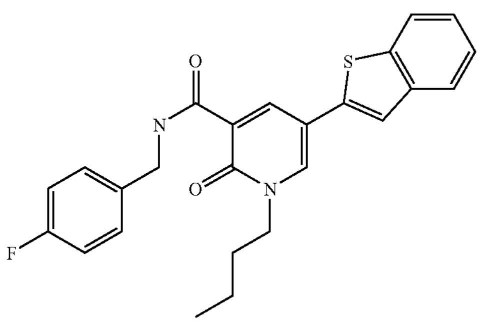 |
| A-008 | 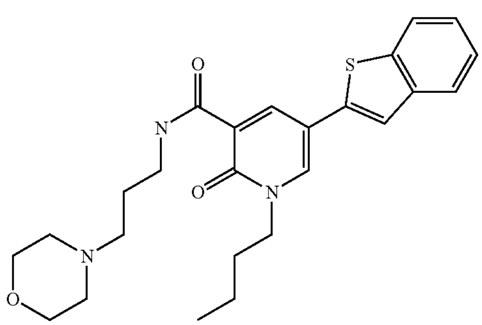 |
| A-009 | 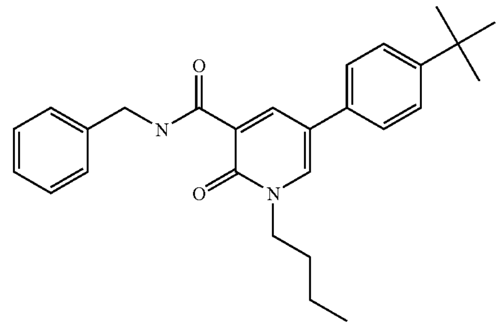 |
| A-010 | 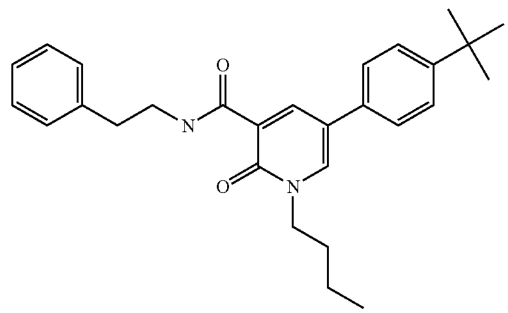 |
| A-011 | 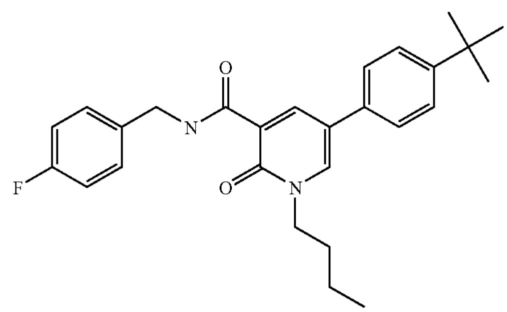 |
| A-012 | 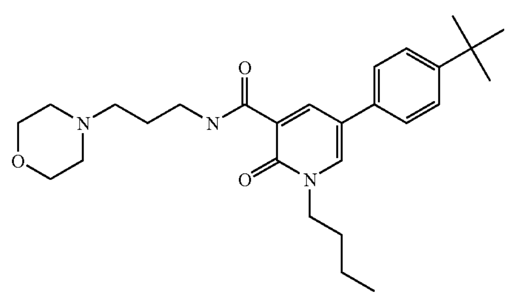 |
| A-013 | 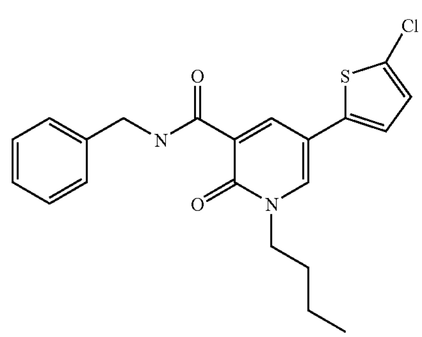 |

TABLE 125-continued

| No. | Structure |
|---|---|
| A-014 | (5-chlorothiophen-2-yl substituted 1-butyl-2-oxo-1,2-dihydropyridine-3-carboxamide with N-phenethyl) |

TABLE 126

| No. | Structure |
|---|---|
| A-015 | (5-chlorothiophen-2-yl substituted 1-butyl-2-oxo-1,2-dihydropyridine-3-carboxamide with N-(4-fluorobenzyl)) |
| A-016 | (5-chlorothiophen-2-yl substituted 1-butyl-2-oxo-1,2-dihydropyridine-3-carboxamide with N-(3-morpholinopropyl)) |
| A-017 | (5-(4-ethylphenyl) substituted 1-butyl-2-oxo-1,2-dihydropyridine-3-carboxamide with N-benzyl) |

TABLE 126-continued

| No. | Structure |
|---|---|
| A-018 | (5-(4-ethylphenyl) substituted 1-butyl-2-oxo-1,2-dihydropyridine-3-carboxamide with N-phenethyl) |
| A-019 | (5-(4-ethylphenyl) substituted 1-butyl-2-oxo-1,2-dihydropyridine-3-carboxamide with N-(4-fluorobenzyl)) |
| A-020 | (5-(4-ethylphenyl) substituted 1-butyl-2-oxo-1,2-dihydropyridine-3-carboxamide with N-(3-morpholinopropyl)) |
| A-021 | (5-(4-fluorophenyl) substituted 1-butyl-2-oxo-1,2-dihydropyridine-3-carboxamide with N-benzyl) |
| A-022 | (5-(4-fluorophenyl) substituted 1-butyl-2-oxo-1,2-dihydropyridine-3-carboxamide with N-phenethyl) |

TABLE 126-continued

| No. | Structure |
|---|---|
| A-023 | 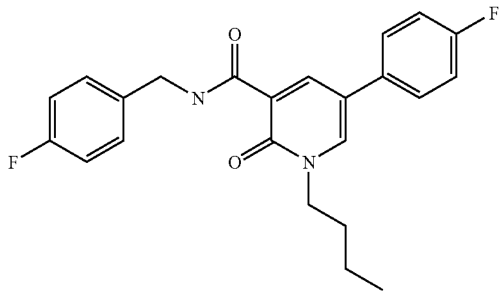 |
| A-024 | 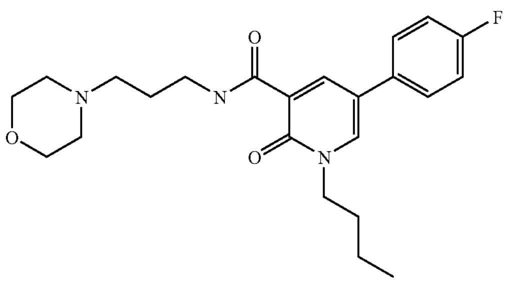 |
| A-025 | 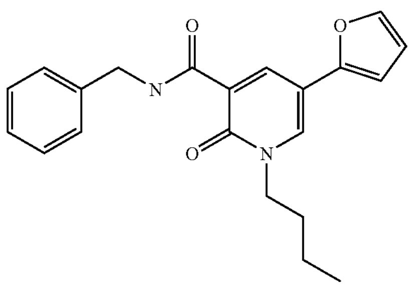 |
| A-026 | 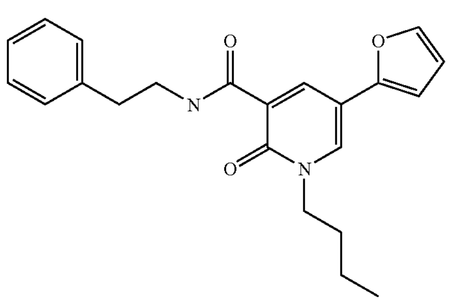 |
| A-027 | 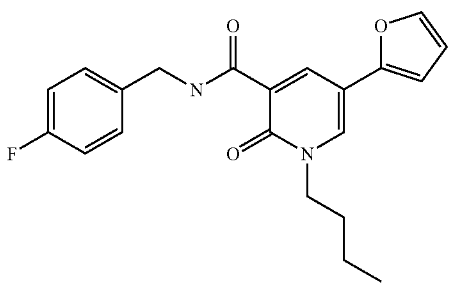 |

TABLE 126-continued

| No. | Structure |
|---|---|
| A-028 | |

TABLE 127

| No. | Structure |
|---|---|
| A-029 | 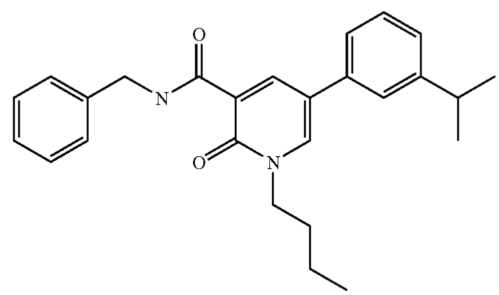 |
| A-030 | 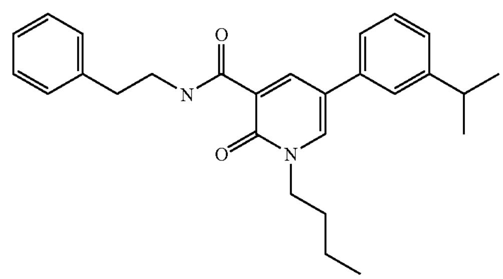 |
| A-031 | 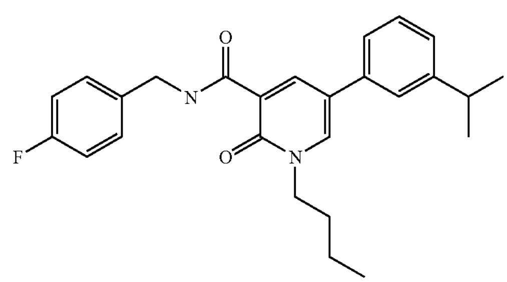 |
| A-032 | 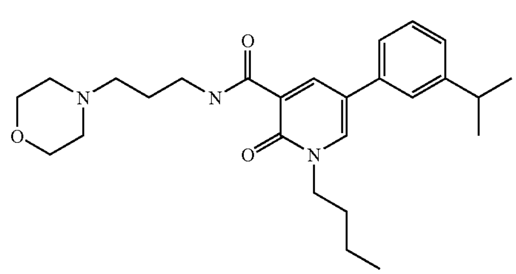 |

TABLE 127-continued

| No. | Structure |
|-----|-----------|
| A-033 | 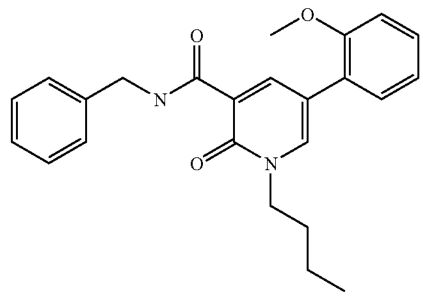 |
| A-034 | 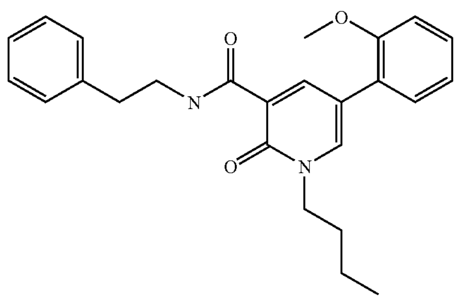 |
| A-035 | 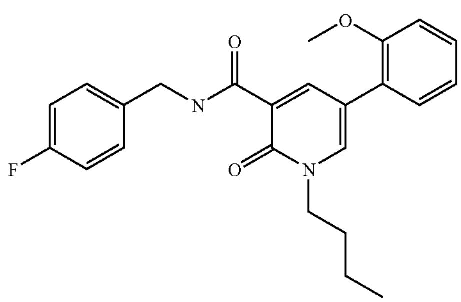 |
| A-036 | 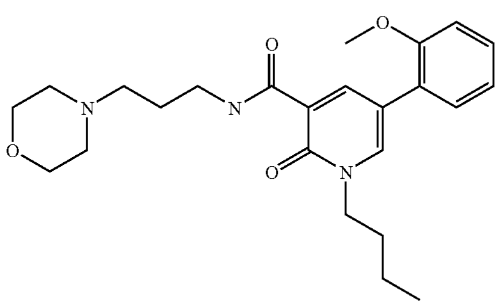 |
| A-037 | 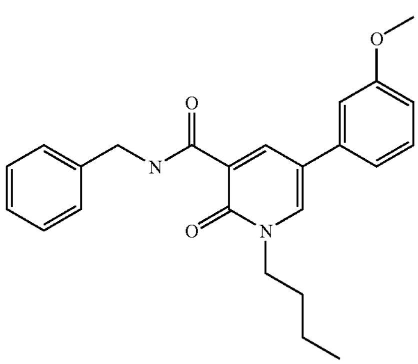 |

TABLE 127-continued

| No. | Structure |
|-----|-----------|
| A-038 | 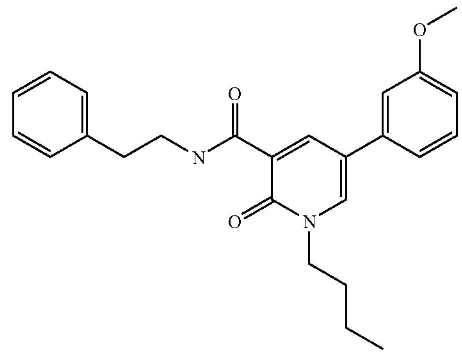 |
| A-039 | 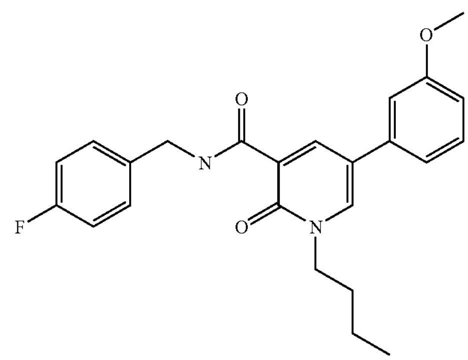 |
| A-040 | 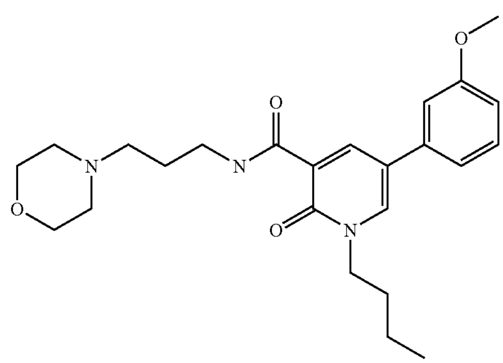 |
| A-041 | 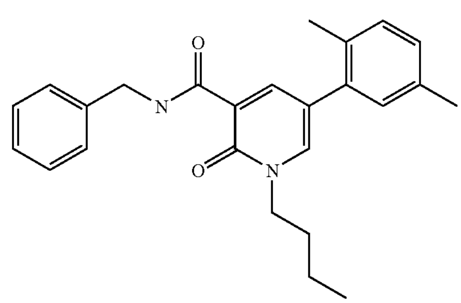 |

TABLE 127-continued

| No. | Structure |
|---|---|
| A-042 | 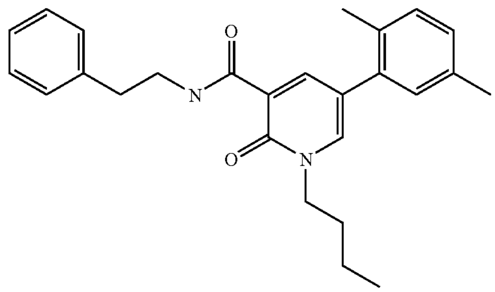 |

TABLE 128

| No. | Structure |
|---|---|
| A-043 | 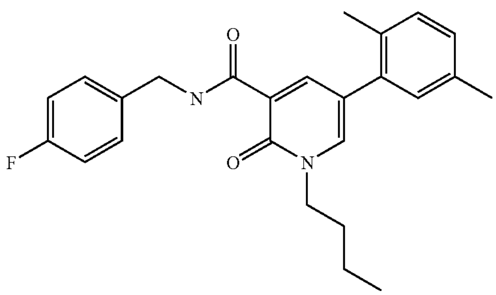 |
| A-044 | 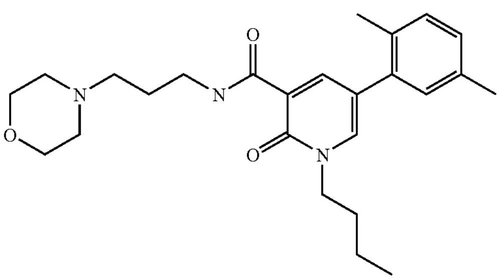 |
| A-045 | 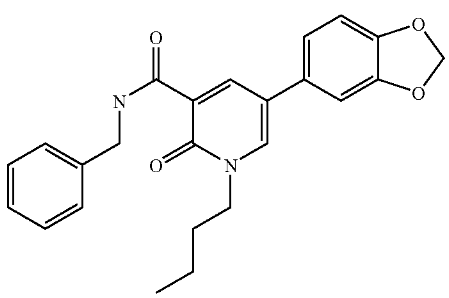 |
| A-046 | 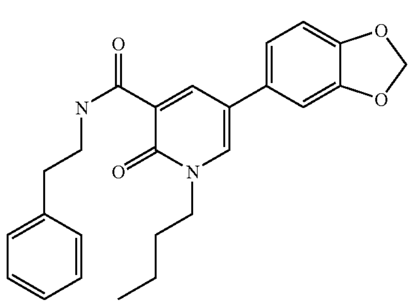 |

TABLE 128-continued

| No. | Structure |
|---|---|
| A-047 | 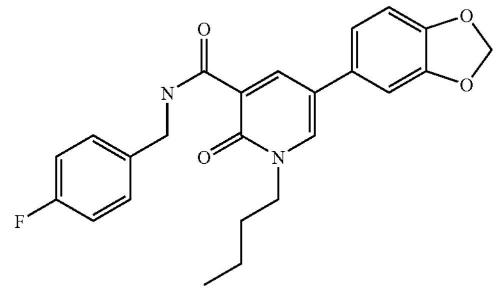 |
| A-048 | 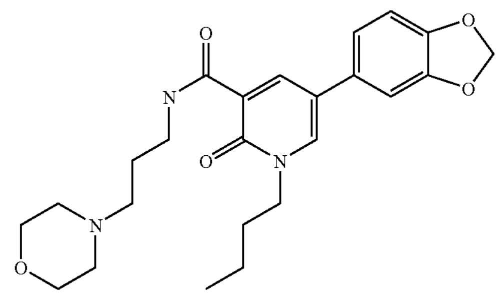 |
| A-049 | 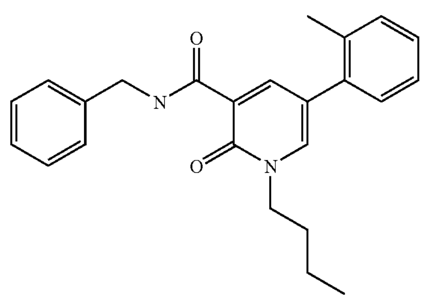 |
| A-050 | 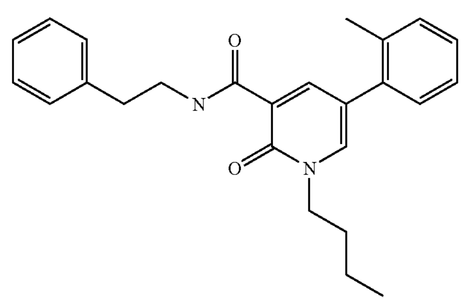 |
| A-051 | 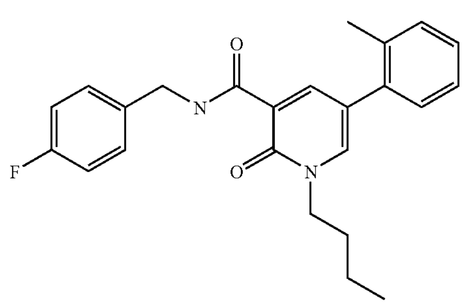 |

TABLE 128-continued

| No. | Structure |
|---|---|
| A-052 | (structure) |
| A-053 | (structure) |
| A-054 | (structure) |
| A-055 | (structure) |
| A-056 | (structure) |

TABLE 129

| No. | Structure |
|---|---|
| A-057 | (structure) |
| A-058 | (structure) |
| A-059 | (structure) |
| A-060 | (structure) |
| A-061 | (structure) |

TABLE 129-continued

| No. | Structure |
|---|---|
| A-062 | 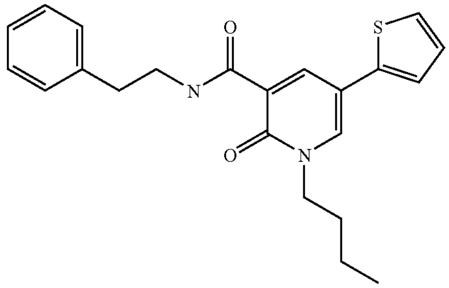 |
| A-063 | 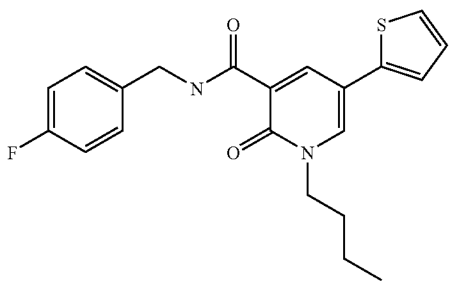 |
| A-064 | 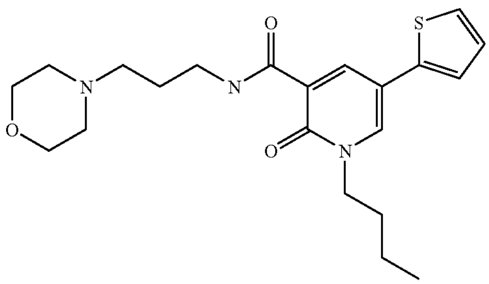 |
| A-065 | 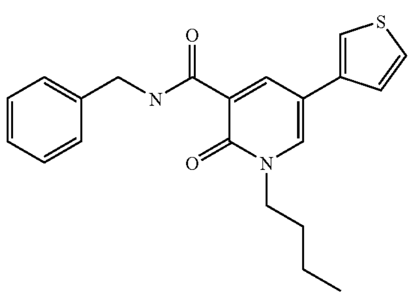 |
| A-066 | 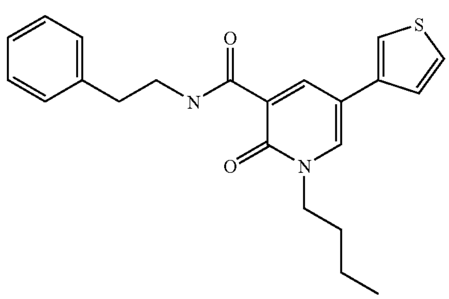 |
| A-067 | |
| A-068 | |
| A-069 | |
| A-070 | |

TABLE 130

| No. | Structure |
|---|---|
| A-071 | 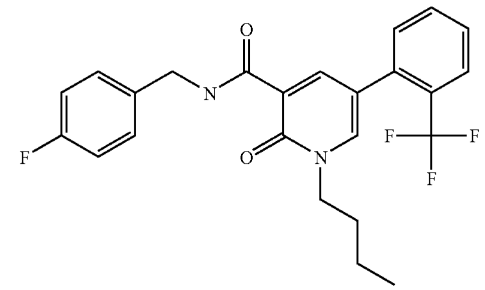 |
| A-072 | 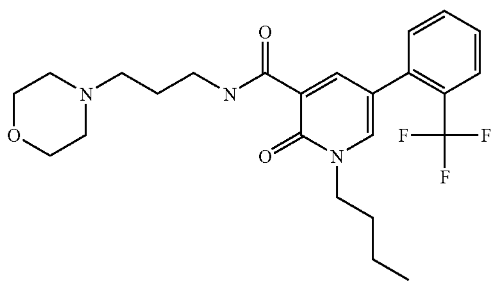 |
| A-073 | 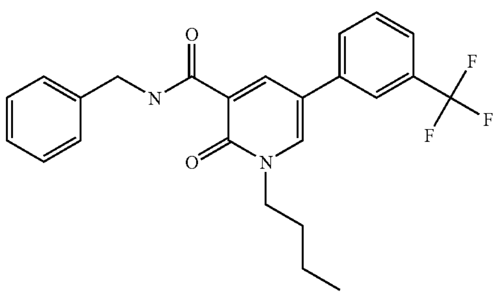 |
| A-074 | 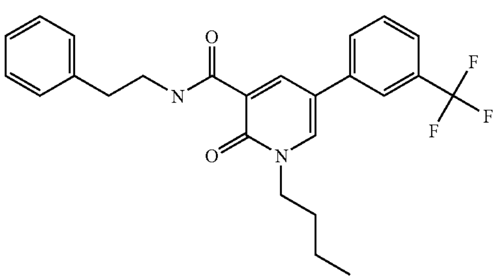 |
| A-075 | 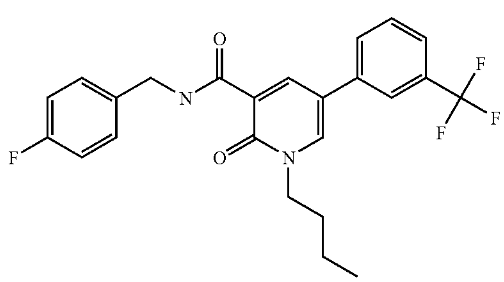 |

TABLE 130-continued

| No. | Structure |
|---|---|
| A-076 | 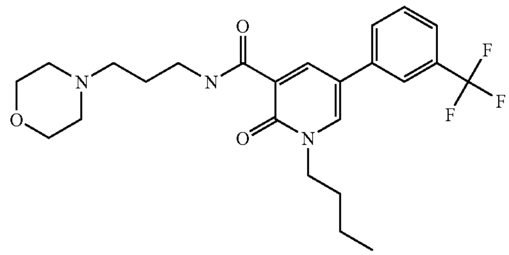 |
| A-077 | 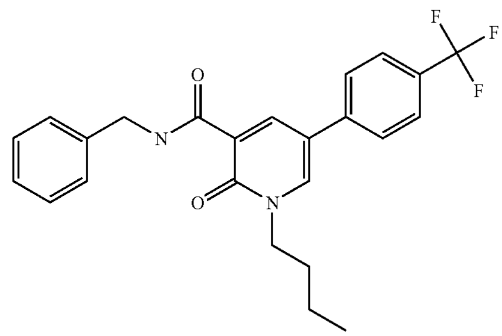 |
| A-078 | 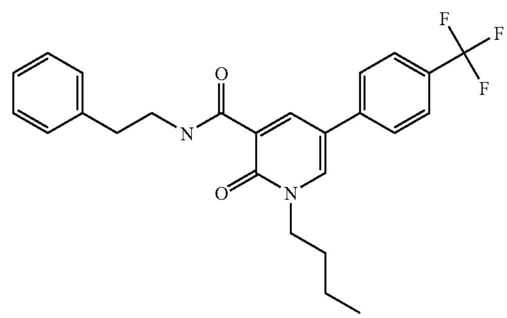 |
| A-079 | 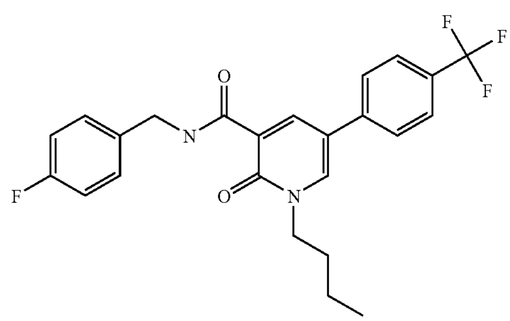 |
| A-080 | 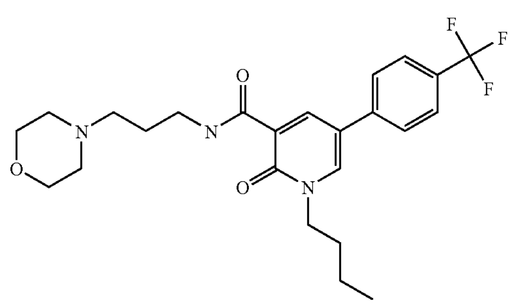 |

TABLE 130-continued

| No. | Structure |
|---|---|
| A-081 | 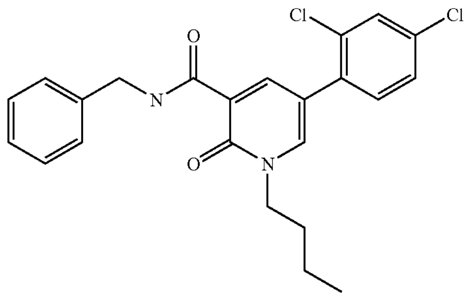 |
| A-082 | 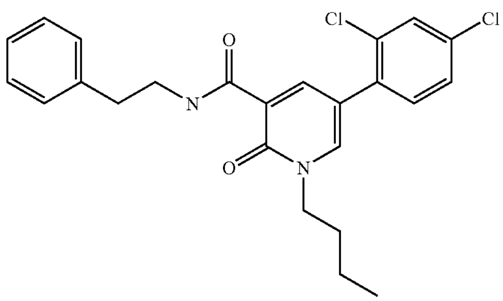 |
| A-083 | 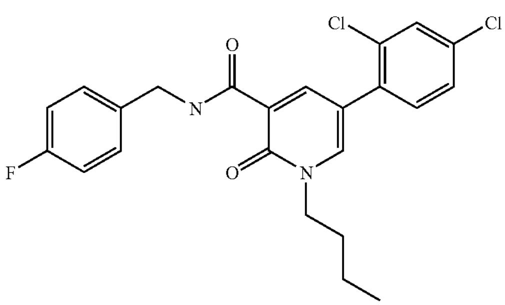 |
| A-084 | 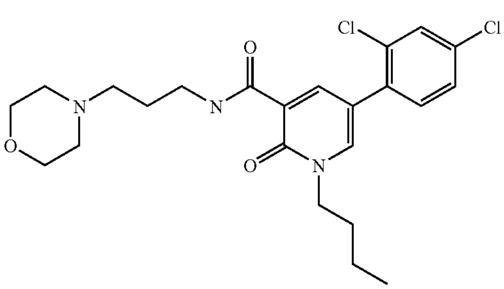 |

TABLE 131

| No. | Structure |
|---|---|
| A-085 | 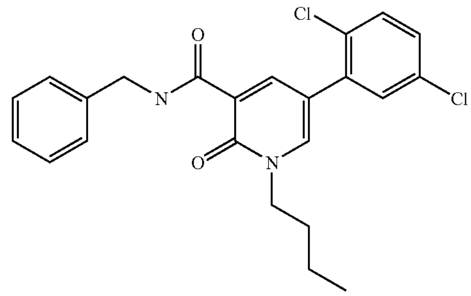 |
| A-086 | 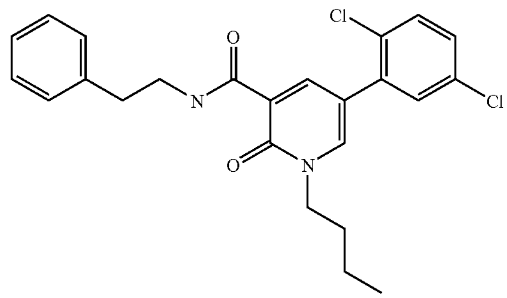 |
| A-087 | 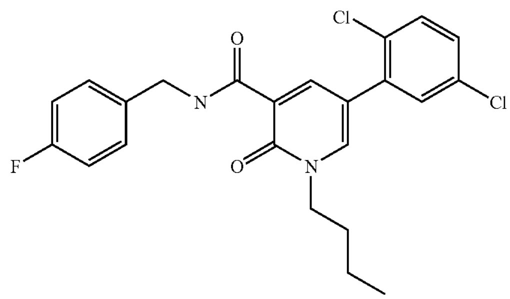 |
| A-088 | 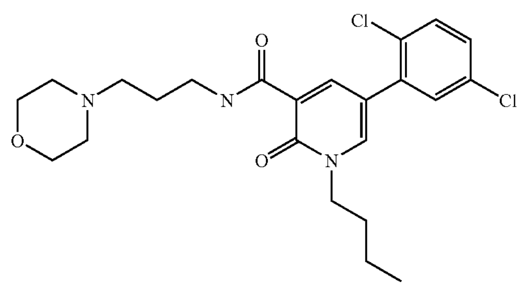 |
| A-089 | 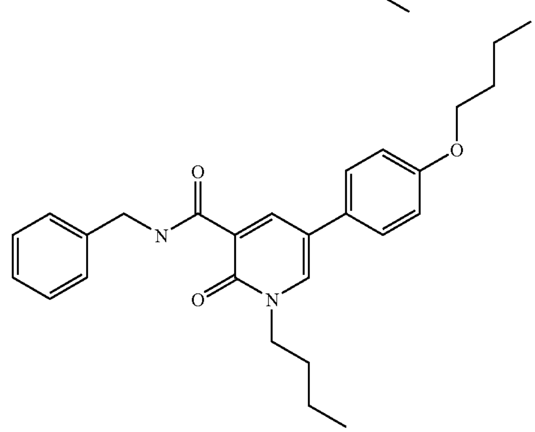 |

TABLE 131-continued
| No. | Structure |
|---|---|
| A-090 | 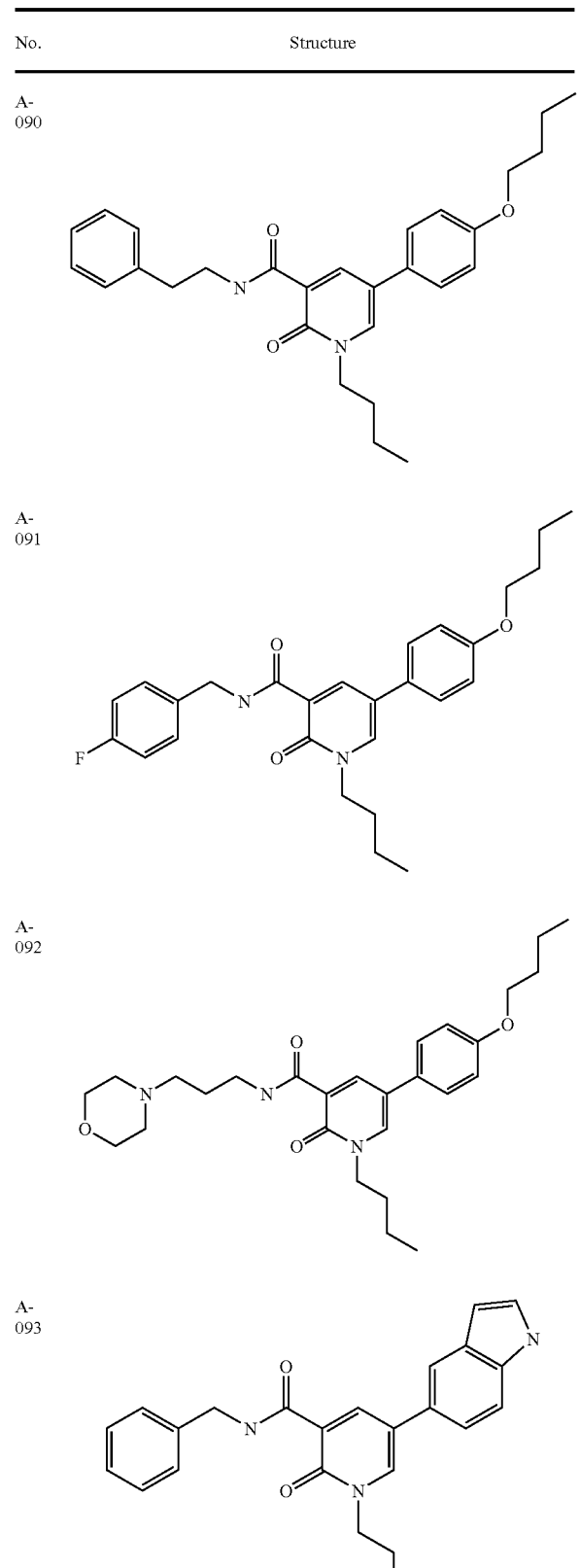 |
| A-091 | 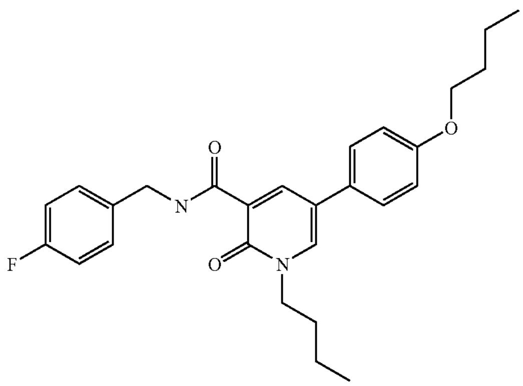 |
| A-092 | 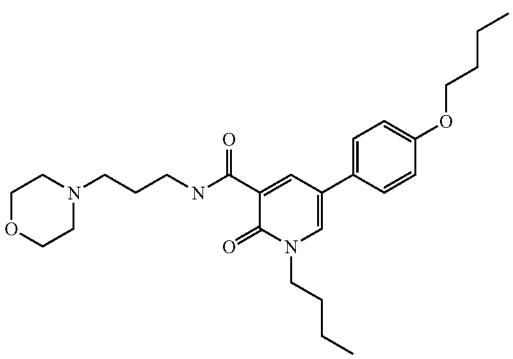 |
| A-093 | 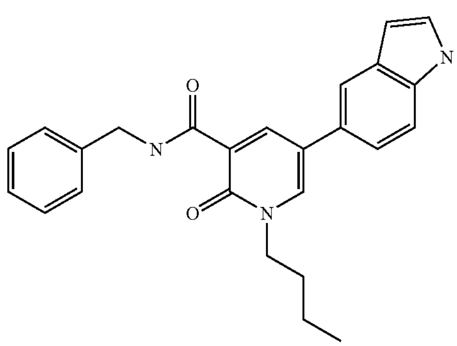 |
TABLE 131-continued
| No. | Structure |
|---|---|
| A-094 | 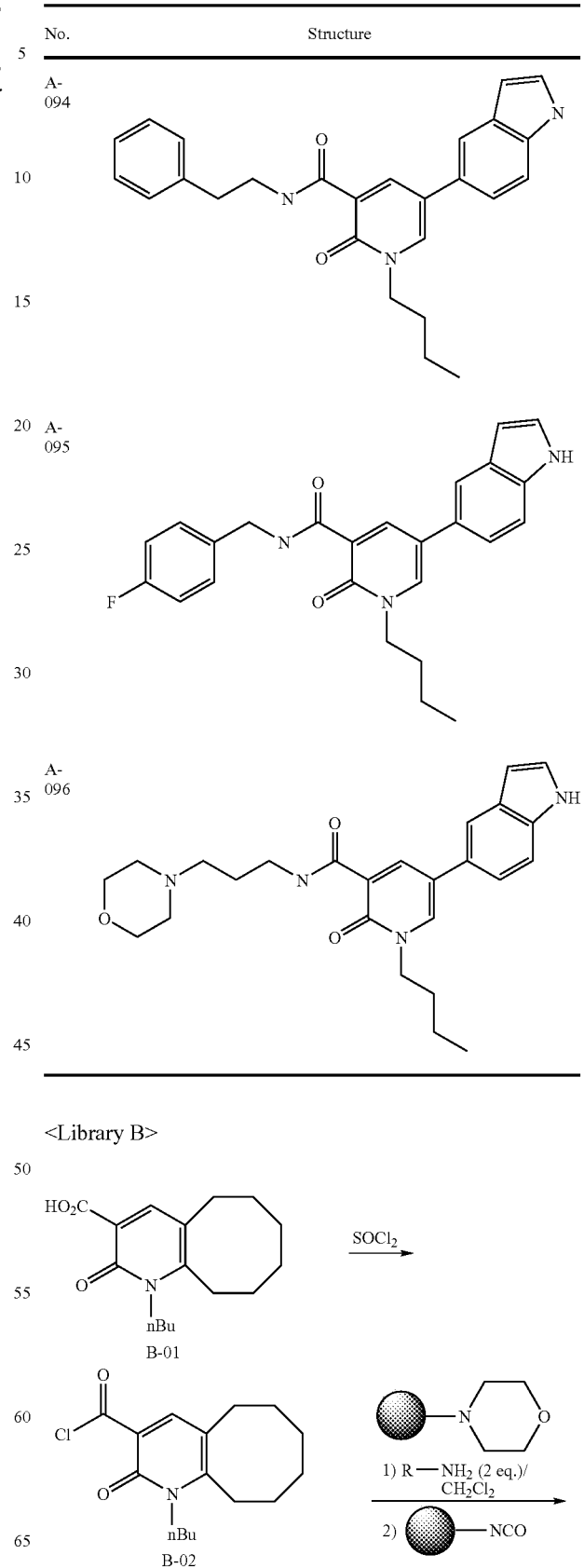 |
| A-095 | |
| A-096 | |
<Library B>

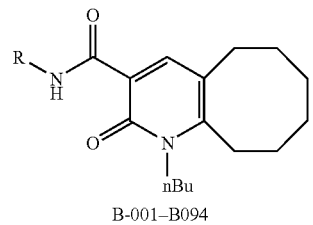

B-001–B094 a) Preparation of 1-butyl-2-oxo-1,2,5,6,7,8,9,10-octahydrocycloocta[b]pyridine-3-carbonyl chloride (B-02)

1-Butyl-2-oxo-1,2,5,6,7,8,9,10-octahydrocycloocta[b]pyridine-3-carboxylic acid (B-01) (416 mg, 1.50 mmol) was dissolved in toluene (15 ml), and to the reaction mixture was added thionyl chloride (328 μL, 4.50 mmol), and the reaction mixture was reacted at 65° C. for 20 min. The reaction mixture was evaporated under reduced pressure to give 1-butyl-2-oxo-1,2,5,6,7,8,9,10-octahydrocycloocta[b]pyridine-3-carbonyl chloride (B-02).

b) Preparation of 1-butyl-2-oxo-1,2,5,6,7,8,9,10-octahydrocycloocta[b]pyridine-3-carboxamide derivatives (B-03-01 to B-03-94)

After macromolecule-immobilized N-methylmorpholine resin (1.93 mmol/g) was measured each 15 mg to the 96 hole reaction plate, to the 96 hole reaction plate were each added 300 μL of 50 mM methylene chloride solution of amine R—NH$_2$), methylene chloride (700 μL), 100 μL of 30 mg/mL methylene chloride solution of 1-butyl-2-oxo-1,2,5,6,7,8,9,10-octahydrocycloocta[b]pyridine-3-carbonyl chloride (B-02).

After shaking at room temperature for 15 h, to the 96 hole reaction plate was added macromolecule-immobilized isocyanate resin, and the plate was shaken for 3 h. The resin was filtered off, washed with methylene chloride, and evaporated under reduced pressure to give B-001 to B-094.

The structures of B-001 to B-094 were described below.

TABLE 132-continued

| No. | Structure |
|---|---|
| B-007 | 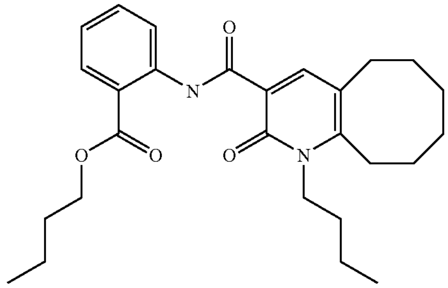 |
| B-008 | 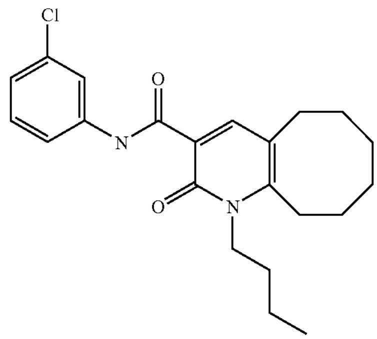 |
| B-009 | 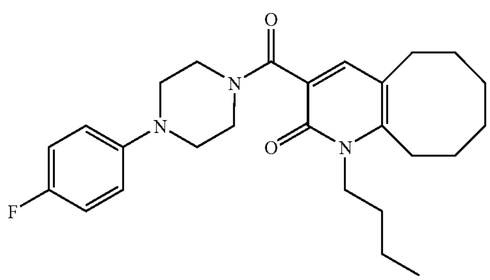 |
| B-010 | 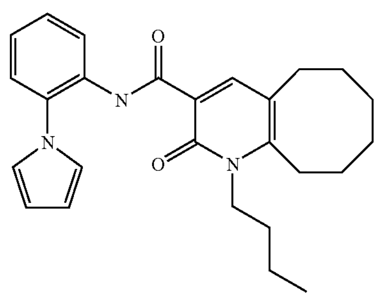 |
| B-011 | 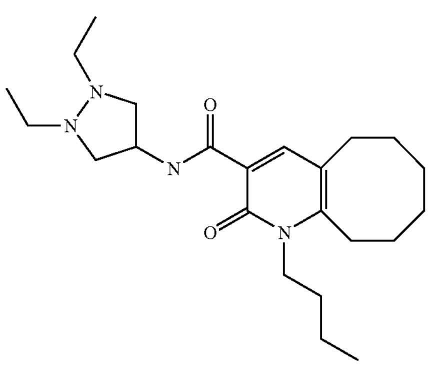 |
| B-012 | |
| B-013 | |
| B-014 | |

TABLE 133

| No. | Structure |
|---|---|
| B-015 | 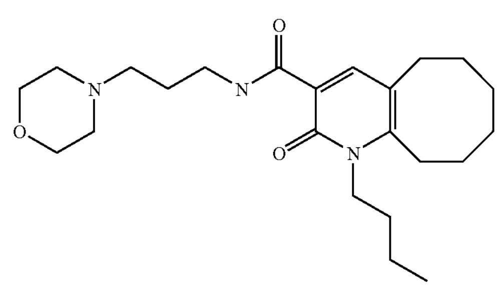 |

TABLE 133-continued
| No. | Structure |
|---|---|
| B-016 | 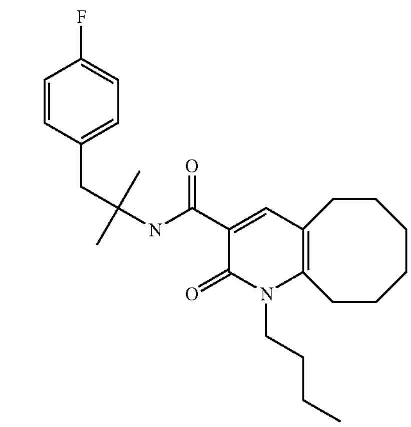 |
| B-017 | 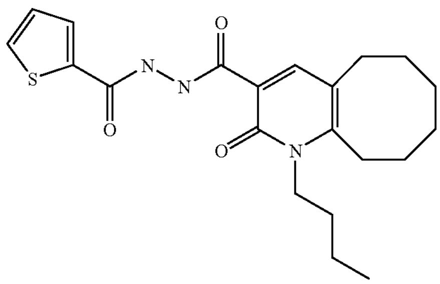 |
| B-018 | 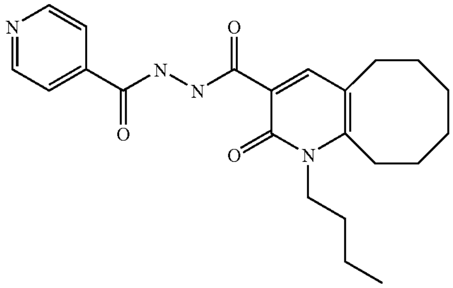 |
| B-019 | 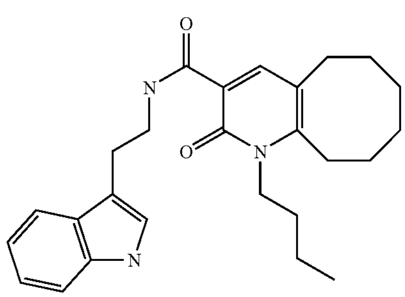 |
| B-020 | 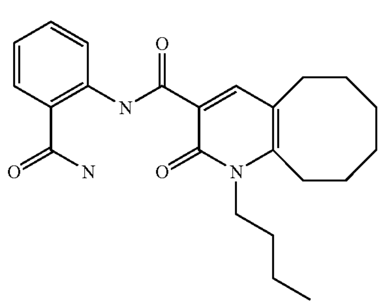 |
TABLE 133-continued
| No. | Structure |
|---|---|
| B-021 | 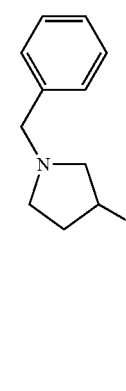 |
| B-022 | 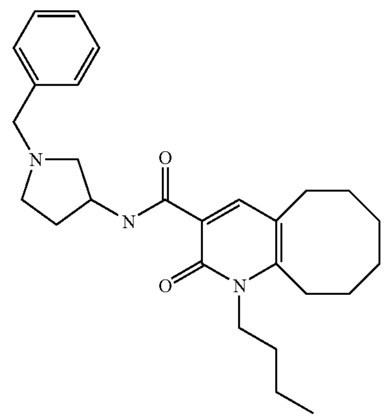 |
| B-023 | 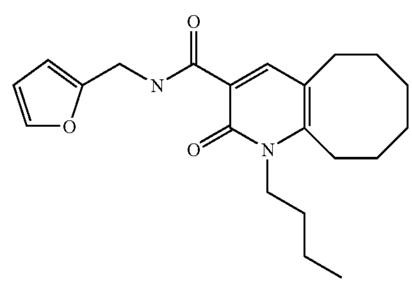 |
| B-024 | 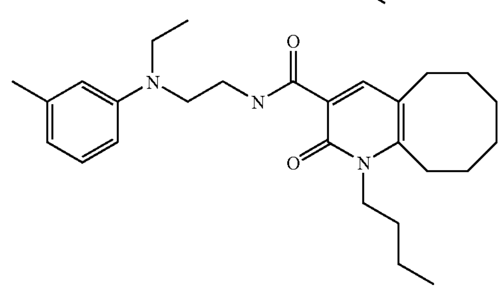 |
| B-025 | 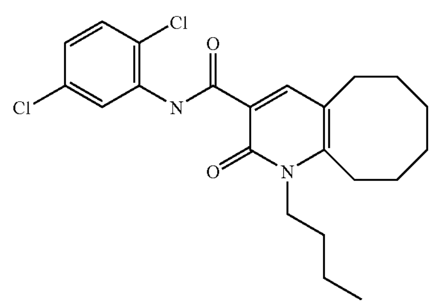 |

TABLE 133-continued
| No. | Structure |
|---|---|
| B-026 | 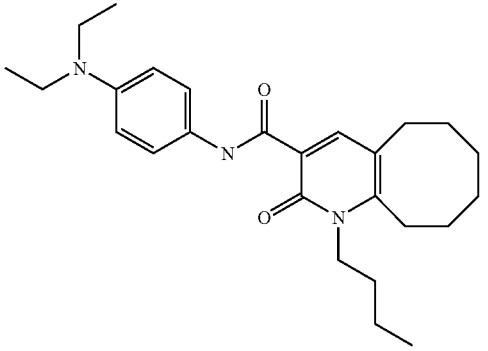 |
| B-027 | 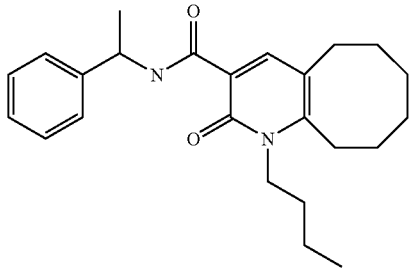 |
| B-028 | 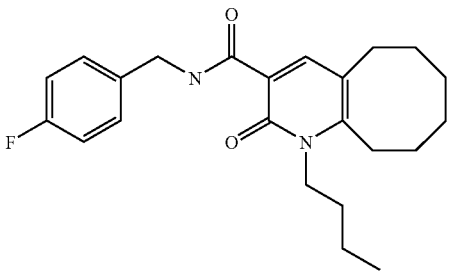 |
TABLE 134
| No. | Structure |
|---|---|
| B-029 | 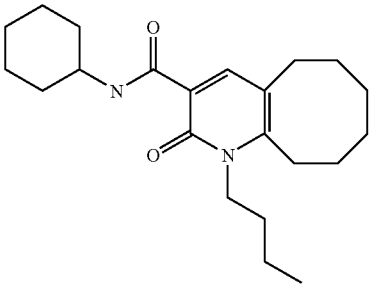 |
TABLE 134-continued
| No. | Structure |
|---|---|
| B-030 | 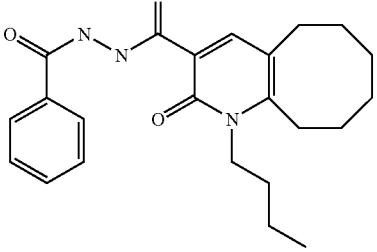 |
| B-031 | 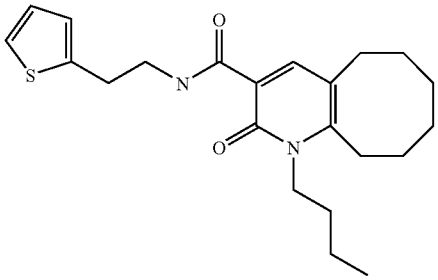 |
| B-032 | 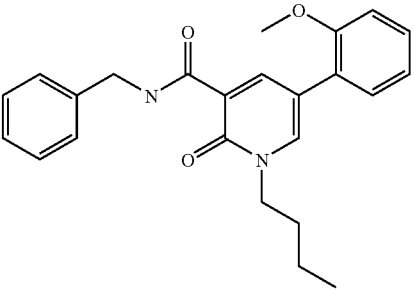 |
| B-033 | 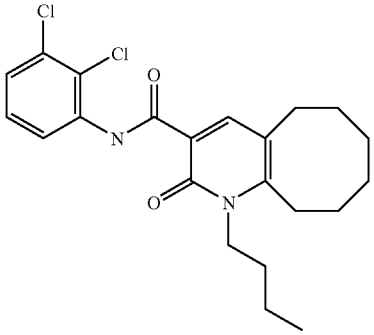 |
| B-034 | 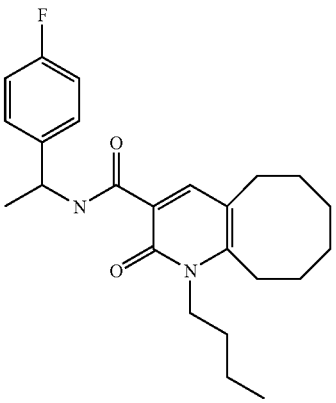 |

TABLE 134-continued

| No. | Structure |
|---|---|
| B-035 | 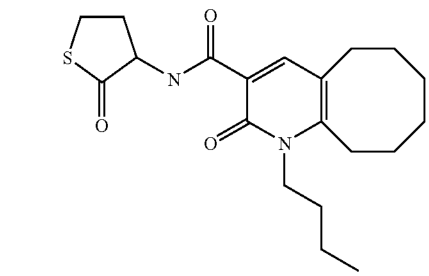 |
| B-036 | 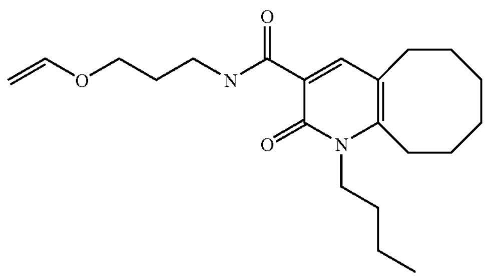 |
| B-037 | 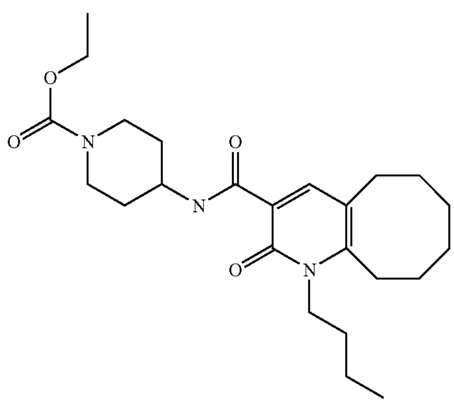 |
| B-038 | 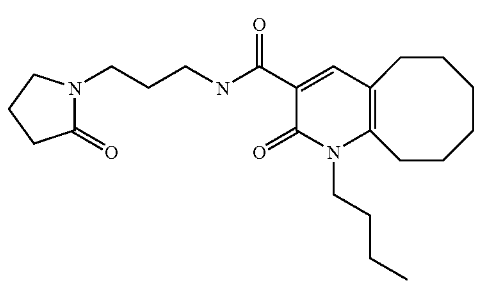 |
| B-039 | 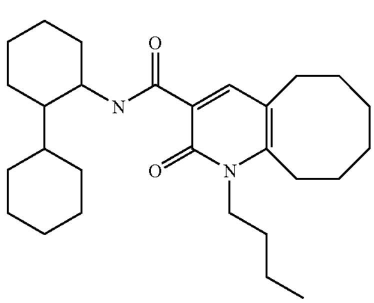 |
| B-040 | |
| B-041 | |
| B-042 | |

TABLE 135

| No. | Structure |
|---|---|
| B-043 | 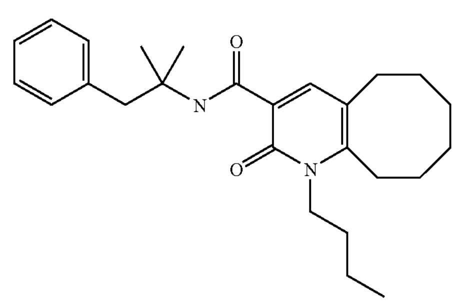 |

TABLE 135-continued

| No. | Structure |
|---|---|
| B-044 | 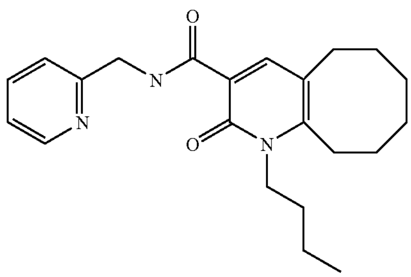 |
| B-045 | 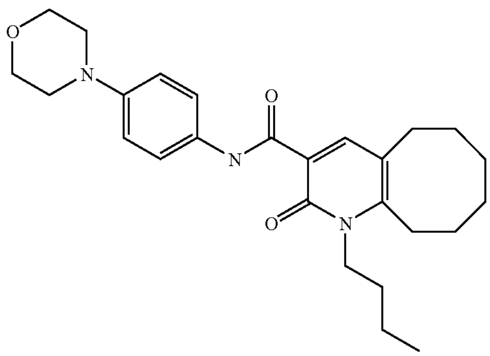 |
| B-046 | 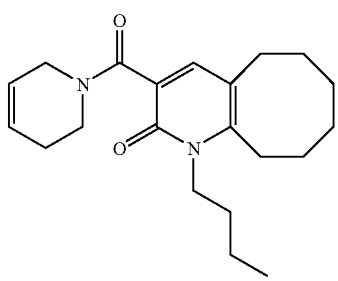 |
| B-047 | 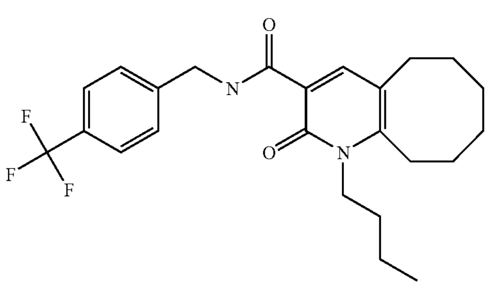 |
| B-048 | 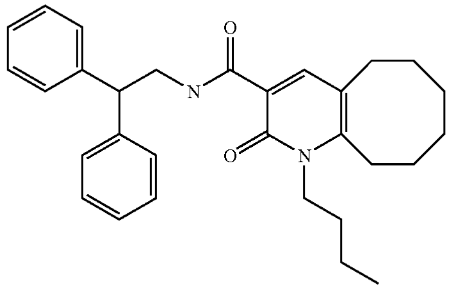 |
| B-049 | |
| B-050 | |
| B-051 | |
| B-052 | |

TABLE 135-continued

| No. | Structure |
|---|---|
| B-053 | 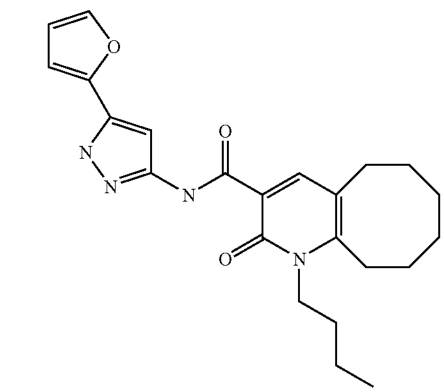 |
| B-054 | 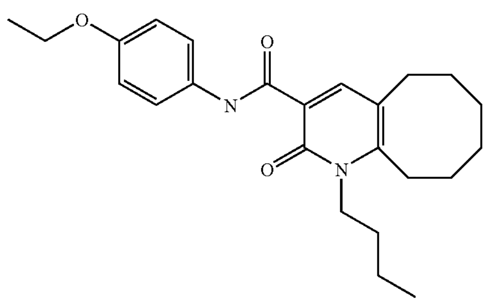 |
| B-055 | 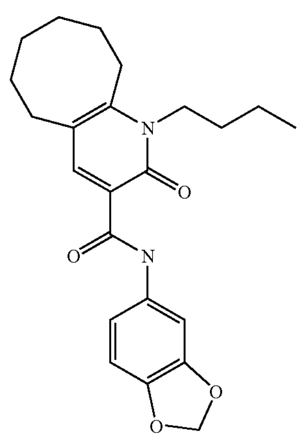 |
| B-056 | 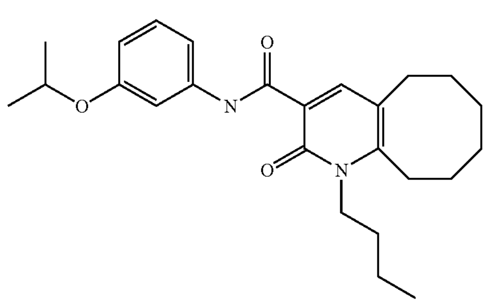 |

TABLE 137

| No. | Structure |
|---|---|
| B-071 | 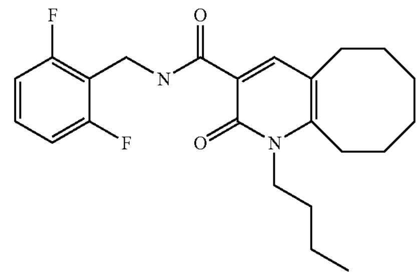 |
| B-072 | 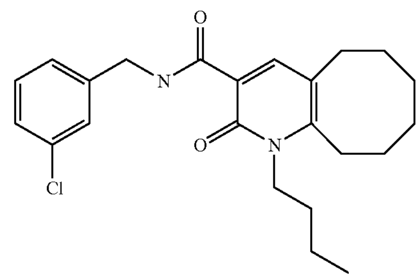 |
| B-073 | 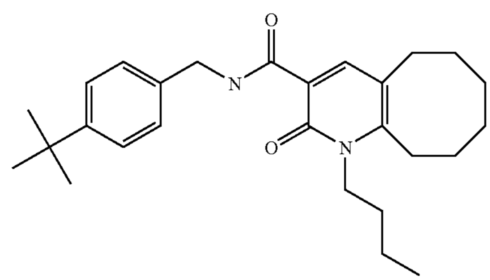 |
| B-074 | 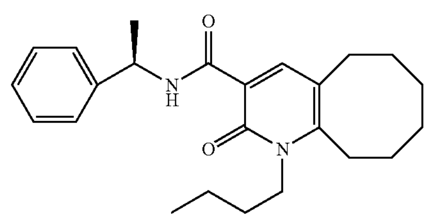 |
| B-075 | 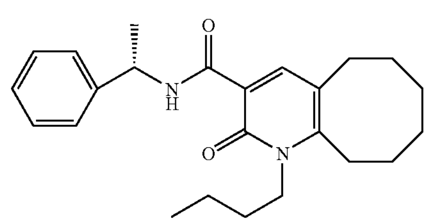 |
| B-076 | 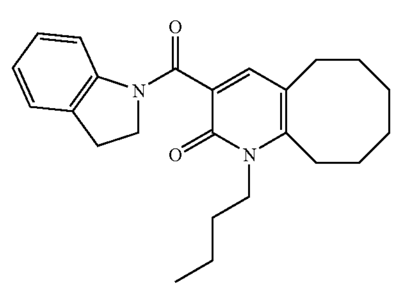 |

TABLE 137-continued
| No. | Structure |
|---|---|
| B-077 | 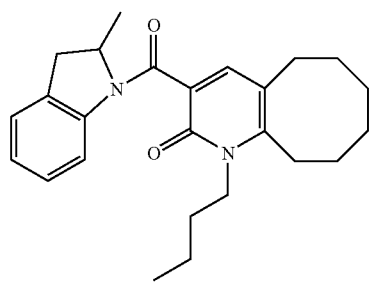 |
| B-078 | 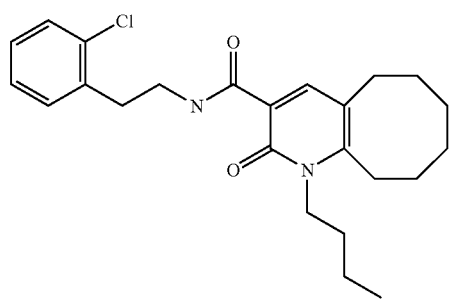 |
| B-079 | 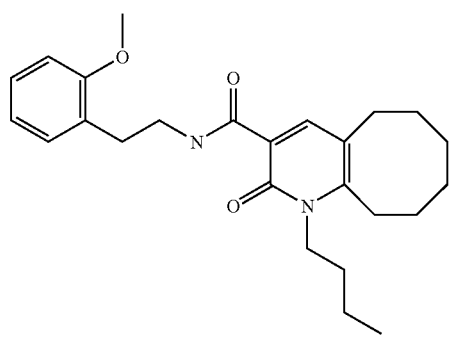 |
| B-080 | 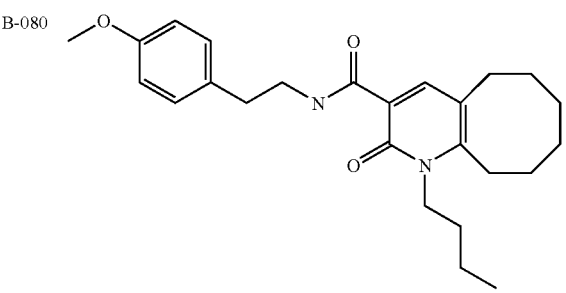 |
| B-081 | 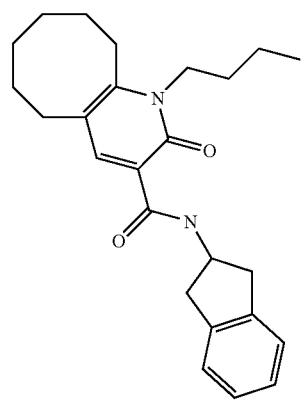 |
| B-082 | 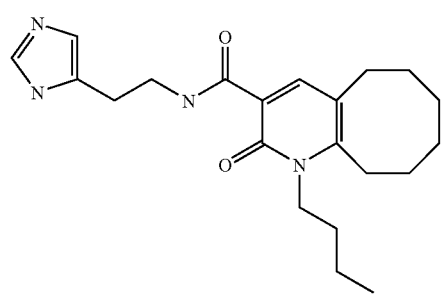 |
| B-083 | 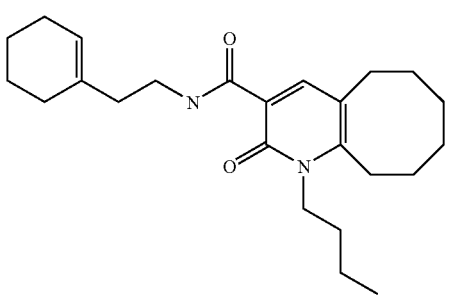 |
| B-084 | 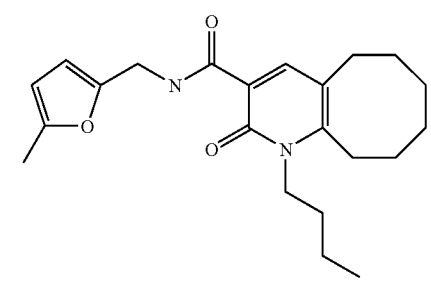 |

TABLE 136

| No. | Structure |
| --- | --- |
| B-057 | 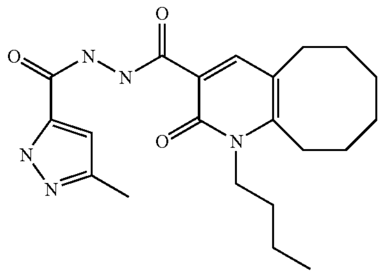 |
| B-058 | 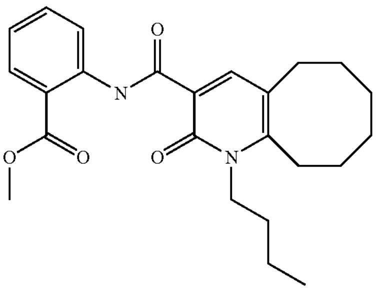 |
| B-059 | 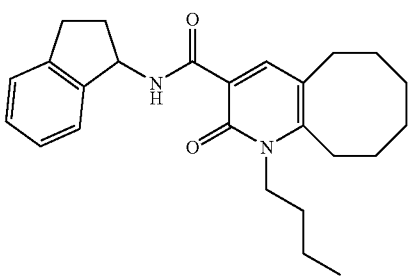 |
| B-060 | 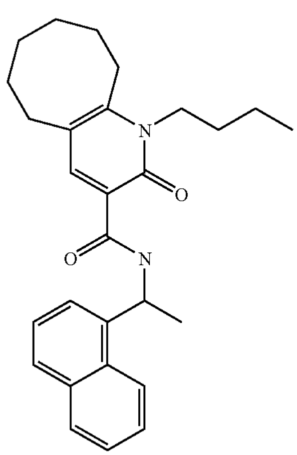 |

TABLE 136-continued

| No. | Structure |
| --- | --- |
| B-061 | 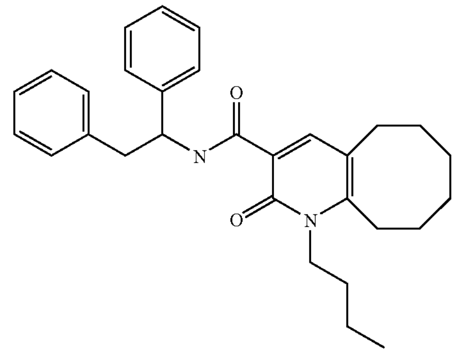 |
| B-062 | 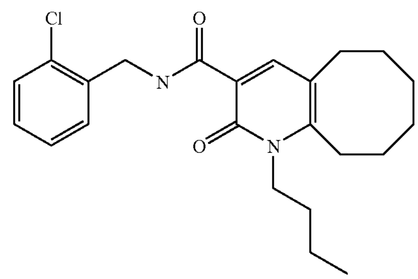 |
| B-063 | 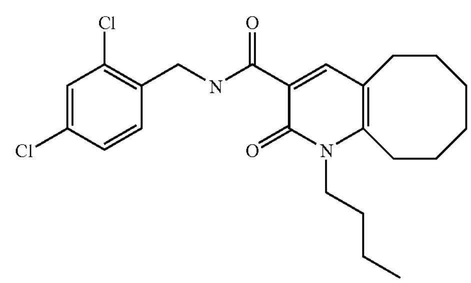 |
| B-064 | 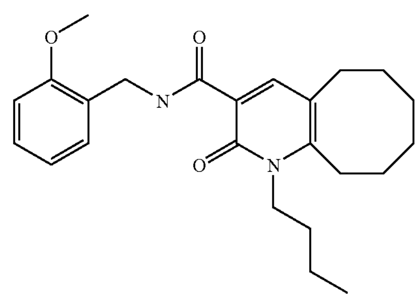 |
| B-065 | 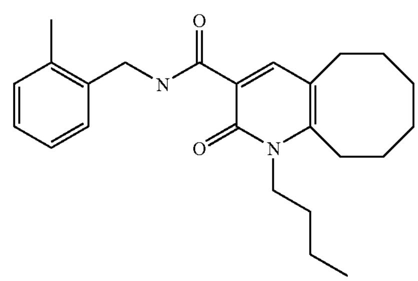 |

TABLE 136-continued
| No. | Structure |
|---|---|
| B-066 | 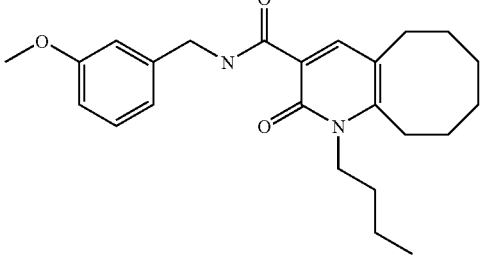 |
| B-067 | 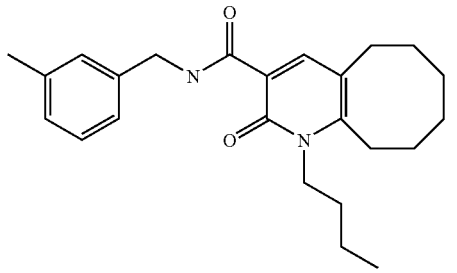 |
| B-068 | 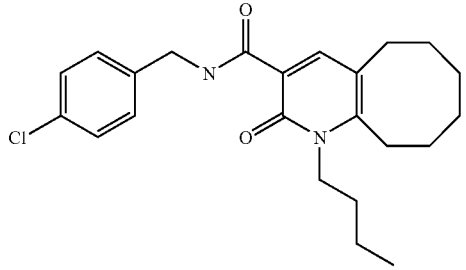 |
| B-069 | 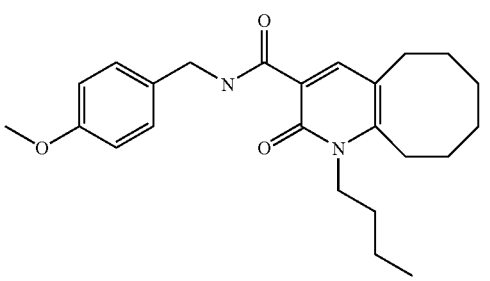 |
| B-070 | 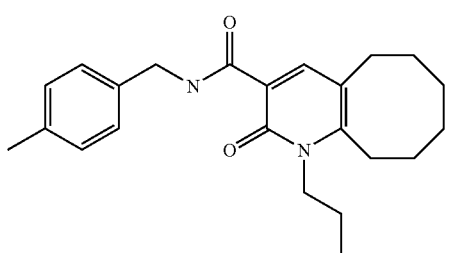 |
TABLE 138
| No. | Structure |
|---|---|
| B-085 | 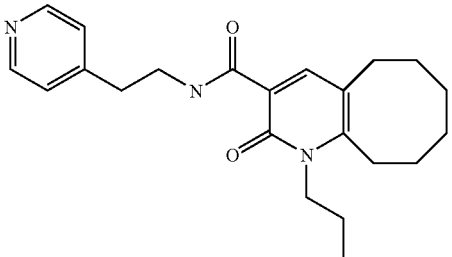 |
| B-086 | 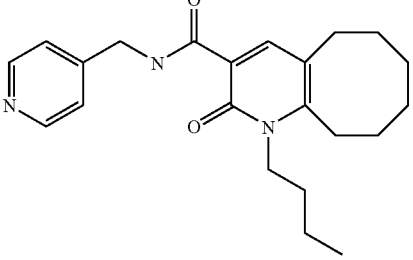 |
| B-087 | 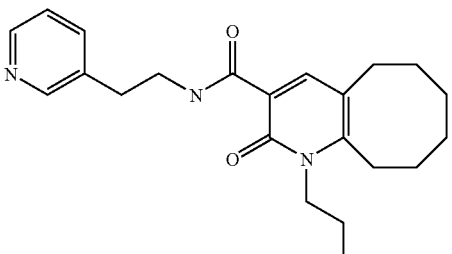 |
| B-088 | 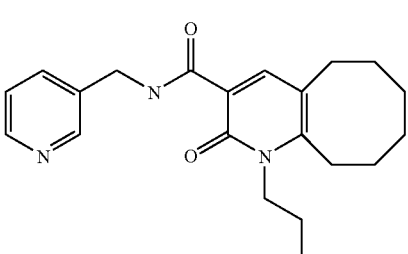 |
| B-089 | 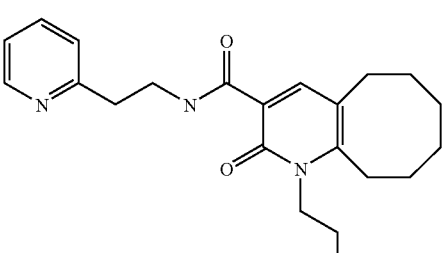 |

TABLE 138-continued

| No. | Structure |
|---|---|
| B-090 | 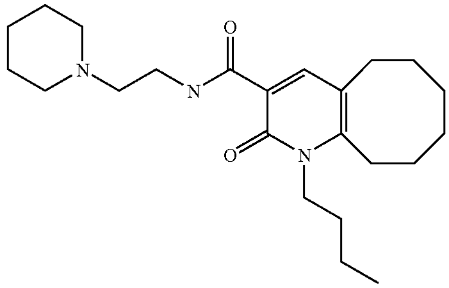 |
| B-091 | 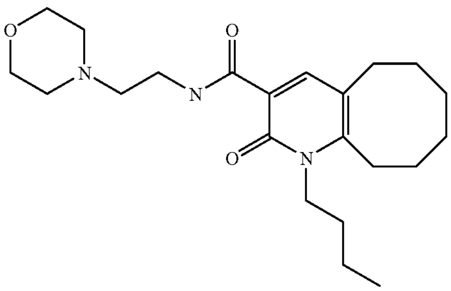 |
| B-092 | 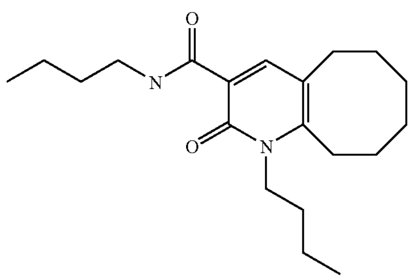 |
| B-093 | 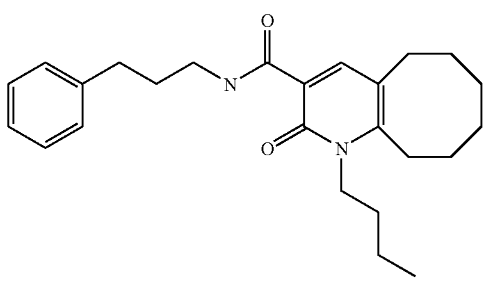 |
| B-094 | 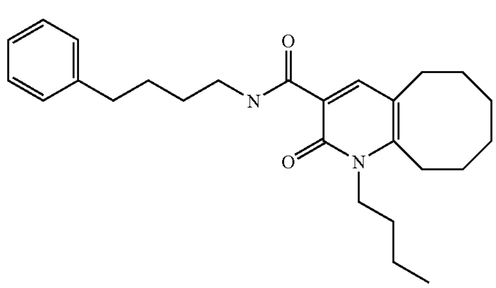 |

<Library C>

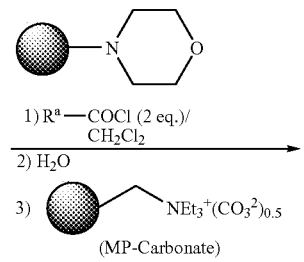

a) Preparation of N-(1-butyl-5,6-dimethyl-2-oxo-1,2-dihydropyridin-3-yl)alkylamide derivatives (C-02-01 to C-02-19)

After macromolecule-immobilized N-methylmorpholine resin (3.0 mmol/g) was measured each 50 mg to the 48 hole reaction plate, to the 48 hole reaction plate were each added 2 mL of 25 mM methylene chloride solution of 3-amino-1-butyl-5,6-dimethyl-1H-pyridine-2-one (C-01) and followed by acyl chloride (R—COCl, 0.10 mmol).

After shaking at room temperature for 15 h, to the 48 hole reaction plate was added macromolecule-immobilized carbonate resin (MP-Carbonate), and the plate was shaken for 12 h. The resin was filtered off, washed with methylene chloride, and evaporated

TABLE 139

| No. | Structure |
|---|---|
| C-001 | 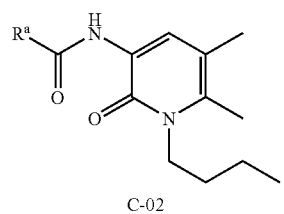 |

TABLE 139-continued

| No. | Structure |
|---|---|
| C-002 | |
| C-003 | |
| C-004 | |
| C-005 | |
| C-006 | |
| C-007 | 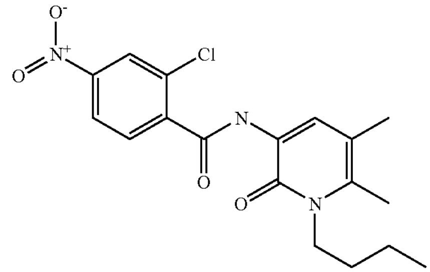 |
| C-008 | 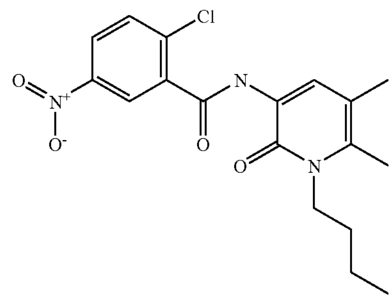 |
| C-009 | 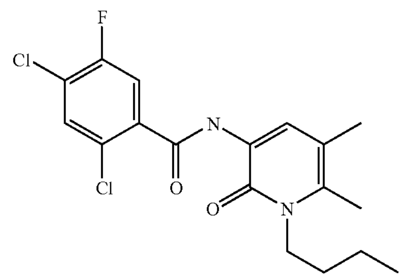 |
| C-010 | 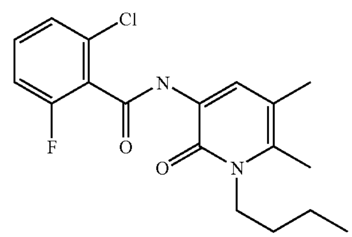 |
| C-011 | 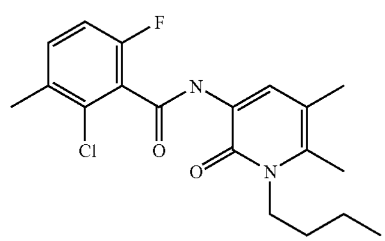 |
| C-012 | 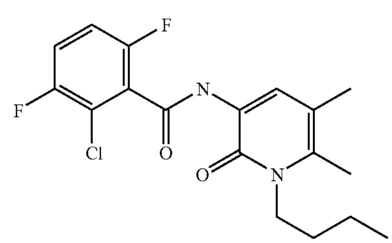 |

TABLE 139-continued

| No. | Structure |
|---|---|
| C-013 | (structure) |
| C-014 | (structure) |

TABLE 140

| No | Structure |
|---|---|
| C-015 | (structure) |
| C-016 | (structure) |
| C-017 | (structure) |

TABLE 140-continued

| No | Structure |
|---|---|
| C-018 | (structure) |
| C-019 | (structure) |

In Table 125 to 140, hydrogen on nitrogen atom of amide bond is abbreviated.

TEST EXAMPLE

Test-Examples of the above compounds of the present invention are shown as follows.

Test Example 1

Experiments for Human CB2 Receptor Binding Inhibition

The coding region of human CB2 receptor (CB2R) cDNA (Munro etc, Nature, 1993, 365, 61-65) was inserted into the mammalian expression vector, pSVL SV40 Late Promoter Expression Vector (Amersham Pharmacia Biotech Inc.). The prepared vector was transfected into Chinese Hamster Ovary (CHO) cells with LipofectAMINE reagent (Gibco BRL) according to the manufacture's protocol, and the stable CB2R-expressing clones were selected.

The crude membrane fractions were prepared from the CB2R-expressing CHO cells. Receptor binding assay was performed by incubating the membranes with each test compound and [$^3$H]CP55940 (at a final concentration of 0.5 nM: NEN Life Science Products) in the assay buffer (50 mM Tris-HCl, 1 mM EDTA, 3 mM MgCl$_2$, pH 7.4) containing 0.5% bovine serum albumin (BSA) for 2 h at 25° C. The incubation mixture was filtered through 1% polyethylenimine-treated GF/C glass filter and washed with 50 mM Tris-HCl (pH 7.4) containing 0.1% BSA. The radioactivity was then counted with a liquid scintillation counter. Non-specific binding was determined in the presence of 10 μM WIN55212-2 (a cannabinoid receptor agonist described in the U.S. Pat. No. 5,081,22, Research Biochemicals International), and the specific binding was calculated by subtracting the non-specific binding from the total binding. The IC$_{50}$ value for each test compound was determined as the concentration at which 50% of the specific binding was inhibited.

For the receptor binding assay of human CB1 receptor (CB1R), the stable CB1R-expressing CHO cells were prepared as described above, and the binding assay was performed using their membrane fractions. As a consequence of these studies, the Ki values of each test compound for both cannabinoid receptors were determined, which were presented in Table. As shown in this table, a series of compounds described in the present invention were found to block the binding of CP55940 (a cannabinoid receptor agonist described in the U.S. Pat. No. 4,371,720) to CB2R.

TABLE 141

| Compound | Ki (nM) | |
| --- | --- | --- |
|  | CB1 receptor | CB2 receptor |
| 2-004 | nt | 101 |
| 3-010 | nt | 57 |
| 3-038 | 1252 | 12 |
| 4-001 | 2851 | 28 |
| 4-002 | 746 | 17 |
| 4-003 | 680 | 44 |
| 4-052 | 1497 | 24 |
| 4-053 | 254 | 6 |
| 4-054 | 482 | 6 |
| 4-056 | 551 | 8 |
| 4-061 | 124 | 2.5 |
| 4-062 | >5000 | 4 |
| 4-101 | 890 | 1.5 |
| 4-102 | 908 | 1.6 |
| 4-104 | 54 | 6 |
| 4-105 | 91 | 2.1 |
| 4-301 | 1769 | 8 |
| 4-302 | >5000 | 10 |
| 4-310 | 512 | 9 |
| 5-005 | 391 | 16 |
| 5-006 | 390 | 14 | n.t.: not tested

Test Example 2

Inhibition Experiments for CB2 Receptor-Mediated Suppression of cAMP Synthesis

The CHO cells expressing human CB2R were incubated with test compounds for 15 min. After the incubation, forskolin (final concentration of 4 µM, Sigma) was added and the cells were incubated for 20 min at 37° C. The reaction was stopped by the addition of 1N HCl and the amount of cAMP in the cell supernatant was measured using an EIA kit (Amersham Pharmacia Biotech) according to the manufacture's protocol. The cAMP amount increased by forskolin compared to that in the absence of forskolin was defined as 100%, and the $IC_{50}$ value of each test compound was determined as the concentration at which 50% of the forskolin-stimulated cAMP synthesis was inhibited. As a consequence of these studies, the $IC_{50}$ value of each test compound was presented in Table. As shown in Table, the compounds described in the present invention were found to possess agonistic activity for CB2 receptor.

The antagonistic activity of each compound was also evaluated in this assay.

TABLE 142

| Compound | $IC_{50}$ (nM) |
| --- | --- |
| 3-038 | 28.6 |
| 4-001 | 64.2 |
| 4-053 | 7.9 |
| 4-054 | 4.2 |
| 4-056 | 4.3 |
| 4-061 | 2.3 |
| 4-062 | 1.3 |
| 4-101 | 1.4 |
| 4-102 | 1.7 |
| 4-104 | 9.8 |

On the otherhand, the compound of the present invention can be evaluated for its anti-inflammatory effecting by the following in vivo studies.

Test Example

Experiments for Sheep Red Blood Cell (SRBC)-Induced Delayed Type Hypersensitive (DTH) Reaction Female ddY mice (7 weeks old) were used, mice were sensitized by the intradermal injection of $10^7$ cells of SRBC into the left hind foot pad (40 µL). After 5 days, DTH reaction was induced by the intradermal injection of $10^8$ cells of SRBC in the right hind foot pad (40 µL). The compounds of the present invention having a binding activity to the cannabinoid type 2 receptor were administerd p.o. (10 ml/kg) at 1 h before and 5 h after the induction of DTH reaction. After 24 h of the injection of SRBC, the left and right foot pad volumes were measured by the water displacement method. The foot pad swelling was calculated as the differences in the volumes between the right and left hind foot pad, and used as an index of the DTH reaction.

Data are expressed as the inhibition percentage of each compound. Statistical analysis was performed with Welch's t-test, in which the value of P<0.05 is considered as a significant difference.

INDUSTRIAL APPLICABILITY

The compound of the present invention binds to the cannabinoid type 2 receptor to exhibit an antagonistic activity or agonistic activity to the cannabinoid type 2 receptor. Therefore, the compound of the present invention can be used for treating or preventing diseases related to the cannabinoid type 2 receptor.

The invention claimed is:
1. A compound of the formula:

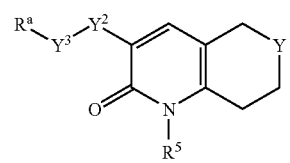

wherein Y is —NH—, —O—, or —$(CH_2)_{3-5}$—;
$Y^2$ is —C(=O)—NH— or —NH—C(=O)—;
$Y^3$ is single bond or optionally substituted alkylene;

$R^a$ is optionally substituted aryl, optionally substituted cycloalkyl, optionally substituted cycloalkenyl, optionally substituted heteroaryl or optionally substituted heterocycle;

$R^5$ is $C_3$ or more alkyl or a group represented by the formula: —$Y^6$—$R^e$— wherein $Y^6$ is alkylene; and $R^e$ is optionally substituted aryl, optionally substituted cycloalkyl, optionally substituted heteroaryl, or optionally substituted heterocycle;

or a pharmaceutically acceptable salt thereof.

2. The compound according to claim 1 wherein Y is —$(CH_2)_3$—;

or a pharmaceutically acceptable salt thereof.

3. The compound according to claim 1 wherein $Y^3$ is optionally substituted alkylene;

or a pharmaceutically acceptable salt thereof.

4. The compound according to claim 2 wherein $Y^3$ is optionally substituted alkylene;

or a pharmaceutically acceptable salt thereof.

5. A pharmaceutical composition which contains as an active ingredient a compound of claim 1.

6. A pharmaceutical composition which contains as an active ingredient a compound of claim 2.

7. A pharmaceutical composition which contains as an active ingredient a compound of claim 3.

* * * * *

UNITED STATES PATENT AND TRADEMARK OFFICE
CERTIFICATE OF CORRECTION

PATENT NO. : 7,652,141 B2
APPLICATION NO. : 11/168640
DATED : January 26, 2010
INVENTOR(S) : Tada et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 896 days.

Signed and Sealed this

Twenty-third Day of November, 2010

David J. Kappos
*Director of the United States Patent and Trademark Office*